US010710986B2

(12) United States Patent
Aktoudianakis et al.

(10) Patent No.: US 10,710,986 B2
(45) Date of Patent: Jul. 14, 2020

(54) PD-1/PD-L1 INHIBITORS

(71) Applicant: Gilead Sciences, Inc., Foster City, CA (US)

(72) Inventors: Evangelos Aktoudianakis, Redwood City, CA (US); Aesop Cho, Mountain View, CA (US); Zhimin Du, Belmont, CA (US); Michael Graupe, Pacifica, CA (US); Lateshkumar Thakorlal Lad, Belmont, CA (US); Paulo A. Machicao Tello, San Mateo, CA (US); Jonathan William Medley, San Mateo, CA (US); Samuel E. Metobo, Newark, CA (US); Prasenjit Kumar Mukherjee, South San Francisco, CA (US); Devan Naduthambi, San Bruno, CA (US); Eric Q. Parkhill, San Francisco, CA (US); Barton W. Phillips, San Mateo, CA (US); Scott Preston Simonovich, Oakland, CA (US); Neil H. Squires, San Francisco, CA (US); Peiyuan Wang, San Mateo, CA (US); William J. Watkins, Saratoga, CA (US); Jie Xu, Foster City, CA (US); Kin Shing Yang, San Mateo, CA (US); Christopher Allen Ziebenhaus, San Francisco, CA (US)

(73) Assignee: Gilead Sciences, Inc., Foster City, CA (US)

(*) Notice: Subject to any disclaimer, the term of this patent is extended or adjusted under 35 U.S.C. 154(b) by 0 days.

(21) Appl. No.: 16/274,106

(22) Filed: Feb. 12, 2019

(65) Prior Publication Data

US 2019/0270727 A1 Sep. 5, 2019

Related U.S. Application Data

(60) Provisional application No. 62/747,029, filed on Oct. 17, 2018, provisional application No. 62/763,116, filed on Apr. 19, 2018, provisional application No. 62/640,534, filed on Mar. 8, 2018, provisional application No. 62/630,187, filed on Feb. 13, 2018.

(51) Int. Cl.
| | |
|---|---|
| *C07D 403/14* | (2006.01) |
| *A61P 31/20* | (2006.01) |
| *A61P 35/02* | (2006.01) |
| *A61K 31/496* | (2006.01) |
| *C07D 519/00* | (2006.01) |
| *C07D 241/20* | (2006.01) |
| *C07D 487/10* | (2006.01) |
| *C07D 405/14* | (2006.01) |
| *C07D 487/08* | (2006.01) |
| *A61K 31/497* | (2006.01) |
| *C07D 491/107* | (2006.01) |
| *C07D 241/18* | (2006.01) |
| *A61P 35/00* | (2006.01) |
| *C07K 16/28* | (2006.01) |

(52) U.S. Cl.
CPC ......... *C07D 403/14* (2013.01); *A61K 31/496* (2013.01); *A61K 31/497* (2013.01); *A61P 31/20* (2018.01); *A61P 35/00* (2018.01); *A61P 35/02* (2018.01); *C07D 241/18* (2013.01); *C07D 241/20* (2013.01); *C07D 405/14* (2013.01); *C07D 487/08* (2013.01); *C07D 487/10* (2013.01); *C07D 491/107* (2013.01); *C07D 519/00* (2013.01); *C07K 16/2818* (2013.01); *C07K 16/2827* (2013.01)

(58) Field of Classification Search
USPC .......................................................... 514/247
See application file for complete search history.

(56) References Cited

U.S. PATENT DOCUMENTS

| | | | |
|---|---|---|---|
| 7,687,522 B2 | 3/2010 | Bellon et al. | |
| 7,750,048 B2 | 7/2010 | Kuo et al. | |
| 8,273,341 B2 | 9/2012 | Guo et al. | |
| 8,541,424 B2 | 9/2013 | Degoey et al. | |
| 8,835,451 B2 | 9/2014 | Serrano-Wu et al. | |
| 2002/0091116 A1 | 7/2002 | Zhu et al. | |
| 2003/0013028 A1 | 1/2003 | Kaoru et al. | |
| 2004/0209936 A1 | 10/2004 | Bratton et al. | |
| 2004/0235877 A1 | 11/2004 | Natsuki et al. | |
| 2006/0019967 A1 | 1/2006 | Wu et al. | |
| 2007/0155726 A1 | 7/2007 | Arnaiz et al. | |
| 2010/0249175 A1 | 9/2010 | Wilson et al. | |
| 2012/0225851 A1 | 6/2012 | Cardone et al. | |
| 2012/0189539 A1 | 7/2012 | Wang et al. | |
| 2012/0289558 A1 | 11/2012 | Kounnas et al. | |
| 2012/0309701 A1 | 12/2012 | Janetka et al. | |

(Continued)

FOREIGN PATENT DOCUMENTS

| | | |
|---|---|---|
| CN | 104876912 | 9/2015 |
| DE | 10104279 | 8/2002 |

(Continued)

OTHER PUBLICATIONS

Gura et. al. (Science, 1997, 278:1041-1042). (Year: 1997).*
Johnson et. al. (British Journal of Cancer, 2001, 84:1424-1431). (Year: 2001).*
Zarganes-Tzitzikas et. al. (Expert Opinion in therapeutic Patents (2016) 9:973-977). (Year: 2016).*
U.S. Appl. No. 16/388,517, filed Apr. 18, 2019, Aktoudianakis et al.
U.S. Appl. No. 16/510,647, filed Jul. 12, 2019, Aktoudianakis et al.
U.S. Appl. No. 16/551,550, filed Aug. 26, 2019, Aktoudianakis et al.
International Search Report and Written Opinion for International Application No. PCT/US2018/028386 dated Jun. 22, 2018. (14 pages).

(Continued)

*Primary Examiner* — Marcos L Sznaidman
(74) *Attorney, Agent, or Firm* — Sheppard Mullin Richter & Hampton LLP

(57) ABSTRACT

Compounds of Formula (I), methods of using said compounds singly or in combination with additional agents and compositions of said compounds for the treatment of cancer are disclosed.

5 Claims, 2 Drawing Sheets

(56) References Cited

U.S. PATENT DOCUMENTS

| | | |
|---|---|---|
| 2013/0023495 A1 | 1/2013 | Meyers et al. |
| 2013/0310379 A1 | 11/2013 | Albrecht et al. |
| 2014/0064053 A1 | 3/2014 | Tsuyama et al. |
| 2014/0073631 A1 | 3/2014 | Shetty |
| 2015/0197538 A1 | 7/2015 | Janetka et al. |
| 2015/0352206 A1 | 12/2015 | Gajewsi et al. |
| 2016/0145304 A1 | 5/2016 | Baumann et al. |
| 2016/0166592 A1 | 6/2016 | Bae et al. |
| 2016/0194307 A1 | 7/2016 | Chupak et al. |
| 2016/0207923 A1 | 7/2016 | Youngman et al. |
| 2017/0088532 A1 | 3/2017 | Cohen et al. |
| 2017/0100414 A1 | 4/2017 | Dunman et al. |
| 2017/0107202 A1 | 4/2017 | Yeung et al. |
| 2017/0107216 A1 | 4/2017 | Wu et al. |
| 2017/0145025 A1 | 5/2017 | Li et al. |
| 2017/0174679 A1 | 6/2017 | Lajkiewicz et al. |
| 2017/0210715 A1 | 7/2017 | Shao et al. |
| 2017/0252432 A1 | 9/2017 | Allen et al. |
| 2017/0266211 A1 | 9/2017 | David et al. |
| 2017/0283462 A1 | 10/2017 | Miller et al. |
| 2017/0283463 A1 | 10/2017 | Miller et al. |
| 2017/0320875 A1 | 11/2017 | Li et al. |
| 2017/0331067 A1 | 11/2017 | Park et al. |
| 2017/0362253 A1 | 12/2017 | Xiao et al. |
| 2018/0008554 A1 | 1/2018 | Lange et al. |
| 2018/0044303 A1 | 2/2018 | Sasikumar et al. |
| 2018/0044304 A1 | 2/2018 | Sasikumar et al. |
| 2018/0044305 A1 | 2/2018 | Sasikumar et al. |
| 2018/0044329 A1 | 2/2018 | Sasikumar et al. |
| 2018/0044350 A1 | 2/2018 | Sasikumar et al. |
| 2018/0057455 A1 | 3/2018 | Yeung et al. |
| 2018/0057486 A1 | 3/2018 | Wu et al. |
| 2018/0065917 A1 | 3/2018 | Webber et al. |
| 2018/0086793 A1 | 3/2018 | Gillman et al. |
| 2018/0273519 A1 | 9/2018 | Wu et al. |
| 2018/0305315 A1 | 10/2018 | Aktoudianakis et al. |
| 2019/0040082 A1 | 2/2019 | Xiao et al. |
| 2019/0062345 A1 | 2/2019 | Xiao et al. |
| 2019/0071439 A1 | 3/2019 | Li et al. |
| 2019/0135745 A1 | 5/2019 | Lange et al. |
| 2019/0144402 A1 | 5/2019 | Sasikumar et al. |
| 2019/0144439 A1 | 5/2019 | Wu et al. |
| 2019/0202824 A1 | 7/2019 | Wu et al. |
| 2019/0282555 A1 | 9/2019 | Lange et al. |
| 2019/0345131 A1 | 11/2019 | Aktoudianakis et al. |
| 2020/0017471 A1 | 1/2020 | Aktoudianakis et al. |

FOREIGN PATENT DOCUMENTS

| | | |
|---|---|---|
| EP | 2002838 | 12/2008 |
| EP | 3363790 | 8/2018 |
| JP | 2001002661 | 1/2001 |
| JP | 2001335476 | 12/2001 |
| JP | 2012036168 | 2/2012 |
| UY | 35733 A | 4/2016 |
| WO | WO 97/31910 | 9/1997 |
| WO | WO 2001/019798 | 3/2001 |
| WO | WO 2001/056989 | 8/2001 |
| WO | WO 2002/000647 | 1/2002 |
| WO | WO 2002/020436 | 3/2002 |
| WO | WO 2002/051775 | 7/2002 |
| WO | WO 2004/052848 | 6/2004 |
| WO | WO 2004/054582 | 7/2004 |
| WO | WO 2004/084824 | 10/2004 |
| WO | WO 2005/044797 | 5/2005 |
| WO | WO 2005/051890 | 6/2005 |
| WO | WO 2005/086808 | 9/2005 |
| WO | WO 2005/095338 | 10/2005 |
| WO | WO 2006/011615 | 2/2006 |
| WO | WO 2006/038738 | 4/2006 |
| WO | WO 2006/052566 | 5/2006 |
| WO | WO 2006/083612 | 8/2006 |
| WO | WO 2006/083781 | 8/2006 |
| WO | WO 2006/091394 | 8/2006 |
| WO | WO 2006/123257 | 11/2006 |
| WO | WO 2006/127503 | 11/2006 |
| WO | WO 2007/013689 | 2/2007 |
| WO | WO 2007/033002 | 3/2007 |
| WO | WO 2007/047591 | 4/2007 |
| WO | WO 2007/049050 | 5/2007 |
| WO | WO 2007/052466 | 5/2007 |
| WO | WO 2007/096142 | 8/2007 |
| WO | WO 2007/104560 | 9/2007 |
| WO | WO 2007/106469 | 9/2007 |
| WO | WO 2007/109376 | 9/2007 |
| WO | WO 2007/123225 | 11/2007 |
| WO | WO 2007/128460 | 11/2007 |
| WO | WO 2007/131619 | 11/2007 |
| WO | WO 2007/131620 | 11/2007 |
| WO | WO 2007/131621 | 11/2007 |
| WO | WO 2007/131622 | 11/2007 |
| WO | WO 2007/132307 | 11/2007 |
| WO | WO 2007/136572 | 11/2007 |
| WO | WO 2008/001931 | 1/2008 |
| WO | WO 2008/014236 | 1/2008 |
| WO | WO 2008/021936 | 2/2008 |
| WO | WO 2008/030520 | 3/2008 |
| WO | WO 2008/037266 | 4/2008 |
| WO | WO 2008/054674 | 5/2008 |
| WO | WO 2008/054675 | 5/2008 |
| WO | WO 2008/063768 | 5/2008 |
| WO | WO 2008/065409 | 6/2008 |
| WO | WO 2008/066097 | 6/2008 |
| WO | WO 2008/067644 | 6/2008 |
| WO | WO 2008/073865 | 6/2008 |
| WO | WO 2008/079965 | 7/2008 |
| WO | WO 2008/083027 | 7/2008 |
| WO | WO 2008/090327 | 7/2008 |
| WO | WO 2008/090356 | 7/2008 |
| WO | WO 2008/106202 | 9/2008 |
| WO | WO 2008/130514 | 10/2008 |
| WO | WO 2008/139987 | 11/2008 |
| WO | WO 2008/144925 | 12/2008 |
| WO | WO 2008/147852 | 12/2008 |
| WO | WO 2008/156656 | 12/2008 |
| WO | WO 2009/017822 | 2/2009 |
| WO | WO 2009/025983 | 2/2009 |
| WO | WO 2009/038204 | 3/2009 |
| WO | WO 2009/039942 | 4/2009 |
| WO | WO 2009/039943 | 4/2009 |
| WO | WO 2009/047798 | 4/2009 |
| WO | WO 2009/048527 | 4/2009 |
| WO | WO 2009/054390 | 4/2009 |
| WO | WO 2009/054468 | 4/2009 |
| WO | WO 2009/054479 | 4/2009 |
| WO | WO 2009/058237 | 5/2009 |
| WO | WO 2009/102568 | 8/2009 |
| WO | WO 2009/102633 | 8/2009 |
| WO | WO 2009/111056 | 9/2009 |
| WO | WO 2009/112445 | 9/2009 |
| WO | WO 2010/012650 | 2/2010 |
| WO | WO 2010/017870 | 2/2010 |
| WO | WO 2010/039238 | 4/2010 |
| WO | WO 2010/045258 | 4/2010 |
| WO | WO 2010/066682 | 6/2010 |
| WO | WO 2010/082563 | 7/2010 |
| WO | WO 2010/085522 | 7/2010 |
| WO | WO 2010/085525 | 7/2010 |
| WO | WO 2010/085528 | 7/2010 |
| WO | WO 2010/091176 | 8/2010 |
| WO | WO 2010/091413 | 8/2010 |
| WO | WO 2010/096462 | 8/2010 |
| WO | WO 2010/099527 | 9/2010 |
| WO | WO 2010/111534 | 9/2010 |
| WO | WO 2010/123016 | 10/2010 |
| WO | WO 2010/123017 | 10/2010 |
| WO | WO 2010/132601 | 11/2010 |
| WO | WO 2010/143733 | 12/2010 |
| WO | WO 2010/144646 | 12/2010 |
| WO | WO 2011/008709 | 1/2011 |
| WO | WO 2011/024001 | 3/2011 |
| WO | WO 2011/031934 | 3/2011 |
| WO | WO 2011/031965 | 3/2011 |
| WO | WO 2011/044073 | 4/2011 |

(56) References Cited

FOREIGN PATENT DOCUMENTS

| | | |
|---|---|---|
| WO | WO 2011/046851 | 4/2011 |
| WO | WO 2011/049825 | 4/2011 |
| WO | WO 2011/052756 | 5/2011 |
| WO | WO 2011/066183 | 6/2011 |
| WO | WO 2011/066241 | 6/2011 |
| WO | WO 2011/073376 | 6/2011 |
| WO | WO 2011/076732 | 6/2011 |
| WO | WO 2011/076734 | 6/2011 |
| WO | WO 2011/078371 | 6/2011 |
| WO | WO 2011/080755 | 7/2011 |
| WO | WO 2011/082400 | 7/2011 |
| WO | WO 2011/092284 | 8/2011 |
| WO | WO 2011/119858 | 9/2011 |
| WO | WO 2011/119870 | 9/2011 |
| WO | WO 2011/138665 | 11/2011 |
| WO | WO 2011/143208 | 11/2011 |
| WO | WO 2011/143466 | 11/2011 |
| WO | WO 2011/151436 | 12/2011 |
| WO | WO 2011/161030 | 12/2011 |
| WO | WO 2012/004269 | 1/2012 |
| WO | WO 2012/004270 | 1/2012 |
| WO | WO 2012/010413 | 1/2012 |
| WO | WO 2012/011124 | 1/2012 |
| WO | WO 2012/012627 | 1/2012 |
| WO | WO 2012/036168 | 3/2012 |
| WO | WO 2012/046869 | 4/2012 |
| WO | WO 2012/050918 | 4/2012 |
| WO | WO 2012/065904 | 5/2012 |
| WO | WO 2012/068234 | 5/2012 |
| WO | WO 2012/072691 | 6/2012 |
| WO | WO 2012/078802 | 6/2012 |
| WO | WO 2012/083043 | 6/2012 |
| WO | WO 2012/083048 | 6/2012 |
| WO | WO 2012/083053 | 6/2012 |
| WO | WO 2012/083059 | 6/2012 |
| WO | WO 2012/083061 | 6/2012 |
| WO | WO 2012/098033 | 7/2012 |
| WO | WO 2012/111849 | 8/2012 |
| WO | WO 2012/129562 | 9/2012 |
| WO | WO 2012/136221 | 10/2012 |
| WO | WO 2012/147518 | 11/2012 |
| WO | WO 2012/154608 | 11/2012 |
| WO | WO 2013/009259 | 1/2013 |
| WO | WO 2013/025424 | 2/2013 |
| WO | WO 2013/057743 | 4/2013 |
| WO | WO 2013/102626 | 7/2013 |
| WO | WO 2013/104257 | 7/2013 |
| WO | WO 2013/106520 | 7/2013 |
| WO | WO 2013/109521 | 7/2013 |
| WO | WO 2013/122028 | 8/2013 |
| WO | WO 2013/122029 | 8/2013 |
| WO | WO 2013/128378 | 9/2013 |
| WO | WO 2013/144097 | 10/2013 |
| WO | WO 2013/154163 | 10/2013 |
| WO | WO 2013/164292 | 11/2013 |
| WO | WO 2013/170113 | 11/2013 |
| WO | WO 2013/170115 | 11/2013 |
| WO | WO 2013/178575 | 12/2013 |
| WO | WO 2014/014129 | 1/2014 |
| WO | WO 2014/014530 | 1/2014 |
| WO | WO 2014/019186 | 2/2014 |
| WO | WO 2014/035827 | 3/2014 |
| WO | WO 2014/073904 | 5/2014 |
| WO | WO 2014/078608 | 5/2014 |
| WO | WO 2014/078609 | 5/2014 |
| WO | WO 2014/078610 | 5/2014 |
| WO | WO 2014/081689 | 5/2014 |
| WO | WO 2014/082918 | 6/2014 |
| WO | WO 2014/086712 | 6/2014 |
| WO | WO 2014/122067 | 8/2014 |
| WO | WO 2014/130608 | 8/2014 |
| WO | WO 2014/133361 | 9/2014 |
| WO | WO 2014/134243 | 9/2014 |
| WO | WO 2014/145817 | 9/2014 |
| WO | WO 2014/146604 | 9/2014 |
| WO | WO 2014/169817 | 10/2014 |
| WO | WO 2014/170842 | 10/2014 |
| WO | WO 2014/171762 | 10/2014 |
| WO | WO 2014/187343 | 11/2014 |
| WO | WO 2015/000412 | 1/2015 |
| WO | WO 2015/010655 | 1/2015 |
| WO | WO 2015/020184 | 2/2015 |
| WO | WO 2015/024448 | 2/2015 |
| WO | WO 2015/024526 | 2/2015 |
| WO | WO 2015/028960 | 3/2015 |
| WO | WO 2015/032328 | 3/2015 |
| WO | WO 2015/034820 | 3/2015 |
| WO | WO 2015/044073 | 4/2015 |
| WO | WO 2015/051496 | 4/2015 |
| WO | WO 2015/062486 | 5/2015 |
| WO | WO 2015/065621 | 5/2015 |
| WO | WO 2015/073342 | 5/2015 |
| WO | WO 2015/076800 | 5/2015 |
| WO | WO 2015/078802 | 6/2015 |
| WO | WO 2015/078949 | 6/2015 |
| WO | WO 2015/084692 | 6/2015 |
| WO | WO 2015/088868 | 6/2015 |
| WO | WO 2015/089809 | 6/2015 |
| WO | WO 2015/097713 | 7/2015 |
| WO | WO 2015/105779 | 7/2015 |
| WO | WO 2015/105786 | 7/2015 |
| WO | WO 2018/121560 | 7/2015 |
| WO | WO 2015/119899 | 8/2015 |
| WO | WO 2015/140717 | 9/2015 |
| WO | WO 2015/150097 | 10/2015 |
| WO | WO 2015/160641 | 10/2015 |
| WO | WO 2015/171722 | 11/2015 |
| WO | WO 2015/171733 | 11/2015 |
| WO | WO 2015/171757 | 11/2015 |
| WO | WO 2015/176267 | 11/2015 |
| WO | WO 2015/198045 | 12/2015 |
| WO | WO 2015/198046 | 12/2015 |
| WO | WO 2016/007714 | 1/2016 |
| WO | WO 2016/019587 | 2/2016 |
| WO | WO 2016/022446 | 2/2016 |
| WO | WO 2016/022448 | 2/2016 |
| WO | WO 2016/022742 | 2/2016 |
| WO | WO 2016/026772 | 2/2016 |
| WO | WO 2016/032120 | 3/2016 |
| WO | WO 2016/039749 | 3/2016 |
| WO | WO 2016/041511 | 3/2016 |
| WO | WO 2016/060517 | 4/2016 |
| WO | WO 2016/060963 | 4/2016 |
| WO | WO 2016/071283 | 5/2016 |
| WO | WO 2016/071293 | 5/2016 |
| WO | WO 2016/073774 | 5/2016 |
| WO | WO 2016/110821 | 7/2016 |
| WO | WO 2016/128908 | 8/2016 |
| WO | WO 2016/142833 | 9/2016 |
| WO | WO 2016/142835 | 9/2016 |
| WO | WO 2016/142852 | 9/2016 |
| WO | WO 2016/142886 | 9/2016 |
| WO | WO 2016/142894 | 9/2016 |
| WO | WO 2016/195776 | 12/2016 |
| WO | WO 2016/197987 | 12/2016 |
| WO | WO 2017/011279 | 1/2017 |
| WO | WO 2017/025368 | 2/2017 |
| WO | WO 2017/027309 | 2/2017 |
| WO | WO 2017/027310 | 2/2017 |
| WO | WO 2017/027312 | 2/2017 |
| WO | WO 2017/031392 | 2/2017 |
| WO | WO 2017/042121 | 3/2017 |
| WO | WO 2017/066227 | 4/2017 |
| WO | WO 2017/070089 | 4/2017 |
| WO | WO 2017/079669 | 5/2017 |
| WO | WO 2017/087777 | 5/2017 |
| WO | WO 2017/099034 | 6/2017 |
| WO | WO 2017/106634 | 6/2017 |
| WO | WO 2017/107979 | 6/2017 |
| WO | WO 2017/112730 | 6/2017 |
| WO | WO 2017/118762 | 7/2017 |
| WO | WO 2017/143220 | 8/2017 |
| WO | WO 2017/151830 | 9/2017 |
| WO | WO 2017/162284 | 9/2017 |

(56) References Cited

FOREIGN PATENT DOCUMENTS

| | | |
|---|---|---|
| WO | WO 2017/172505 | 10/2017 |
| WO | WO 2017/176608 | 10/2017 |
| WO | WO 2017/180457 | 10/2017 |
| WO | WO 2017/180571 | 10/2017 |
| WO | WO 2017/180769 | 10/2017 |
| WO | WO 2017/192961 | 11/2017 |
| WO | WO 2017/201683 | 11/2017 |
| WO | WO 2017/202273 | 11/2017 |
| WO | WO 2017/202274 | 11/2017 |
| WO | WO 2017/202275 | 11/2017 |
| WO | WO 2017/202276 | 11/2017 |
| WO | WO 2017/202744 | 11/2017 |
| WO | WO 2017/205464 | 11/2017 |
| WO | WO 2017/222976 | 12/2017 |
| WO | WO 2018/005374 | 1/2018 |
| WO | WO 2018/009505 | 1/2018 |
| WO | WO 2018/026971 | 2/2018 |
| WO | WO 2018/029150 | 2/2018 |
| WO | WO 2018/044783 | 3/2018 |
| WO | WO 2018/044963 | 3/2018 |
| WO | WO 2018/045142 | 3/2018 |
| WO | WO 2018/051254 | 3/2018 |
| WO | WO 2018/051255 | 3/2018 |
| WO | WO 2018/053302 | 3/2018 |
| WO | WO 2018/077699 | 5/2018 |
| WO | WO 2018/081047 | 5/2018 |
| WO | WO 2018/095877 | 5/2018 |
| WO | WO 2018/106518 | 6/2018 |
| WO | WO 2018/111012 | 6/2018 |
| WO | WO 2018/118664 | 6/2018 |
| WO | WO 2018/118670 | 6/2018 |
| WO | WO 2018/118848 | 6/2018 |
| WO | WO 2018/119221 | 6/2018 |
| WO | WO 2018/119224 | 6/2018 |
| WO | WO 2018/119236 | 6/2018 |
| WO | WO 2018/119263 | 6/2018 |
| WO | WO 2018/119266 | 6/2018 |
| WO | WO 2018/119286 | 6/2018 |
| WO | WO 2018/138026 | 8/2018 |
| WO | WO 2018/138027 | 8/2018 |
| WO | WO 2018/138028 | 8/2018 |
| WO | WO 2018/138029 | 8/2018 |
| WO | WO 2018/138030 | 8/2018 |
| WO | WO 2018/146008 | 8/2018 |
| WO | WO 2018/172727 | 9/2018 |
| WO | WO 2018/181847 | 10/2018 |
| WO | WO 2018/182050 | 10/2018 |
| WO | WO 2018/183171 | 10/2018 |
| WO | WO 2018/195321 | 10/2018 |
| WO | WO 2018/196768 | 11/2018 |
| WO | WO 2019/008156 | 1/2019 |
| WO | WO 2019/023575 | 1/2019 |
| WO | WO 2019/032547 | 2/2019 |
| WO | WO 2019/034172 | 2/2019 |
| WO | WO 2019/059411 | 3/2019 |
| WO | WO 2019/070643 | 4/2019 |
| WO | WO 2019/074241 | 4/2019 |
| WO | WO 2019/076343 | 4/2019 |
| WO | WO 2019/128918 | 7/2019 |
| WO | WO 2019/160882 | 8/2019 |
| WO | WO 2019/165043 | 8/2019 |
| WO | WO 2019/174533 | 9/2019 |
| WO | WO 2019/175897 | 9/2019 |
| WO | WO 2019/191624 A1 | 10/2019 |
| WO | WO 2019/191707 A1 | 10/2019 |
| WO | WO 2019/192506 A1 | 10/2019 |
| WO | WO 2019/204609 | 10/2019 |
| WO | WO 2019/217821 A1 | 11/2019 |
| WO | WO 2020/011246 | 1/2020 |
| WO | WO 2020/014643 | 1/2020 |

OTHER PUBLICATIONS

Tryfon Zarganes-Tzitzikas et al., "Inhibitors of programmed cell death 1 (PD-1), a patent review, 2010-2015", expert Opinion on Therapeutic Patents, vol. 26, No. 9, Sep. 19, 2016, pp. 973-977, XP055394015.

International Search Report and Written Opinion for International Application No. PCT/US2019/017721 dated Apr. 8, 2019. (15 pages).

Office Action dated Mar. 04, 2020 for Taiwan Application No. 108104664. 7 pages.

U.S. Appl. No. 16/660,219, filed Oct. 22, 2019, Du et al.

U.S. Appl. No. 16/840,217, filed Apr. 3, 2020, Aktoudianakis et al.

International Search Report and Written Opinion for International Application No. PCT/US2018/028382 dated Sep. 11, 2018. (17 pages).

International Search Report and Written Opinion for International Application No. PCT/US2019/028129 dated Jul. 22, 2019. (13 pages).

International Search Report and Written Opinion for International Application No. PCT/US2019/041657 dated Sep. 12, 2019. (12 pages).

* cited by examiner

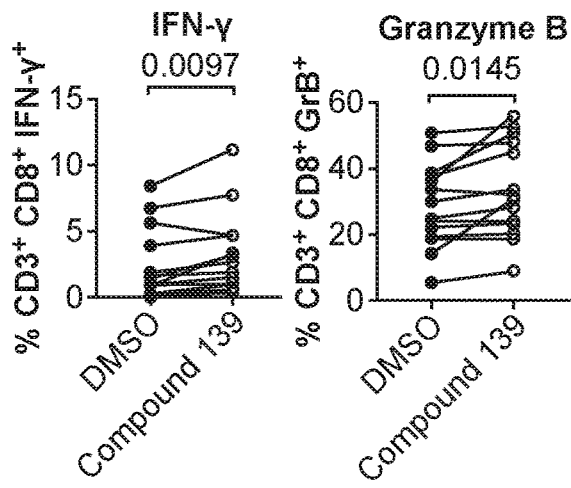
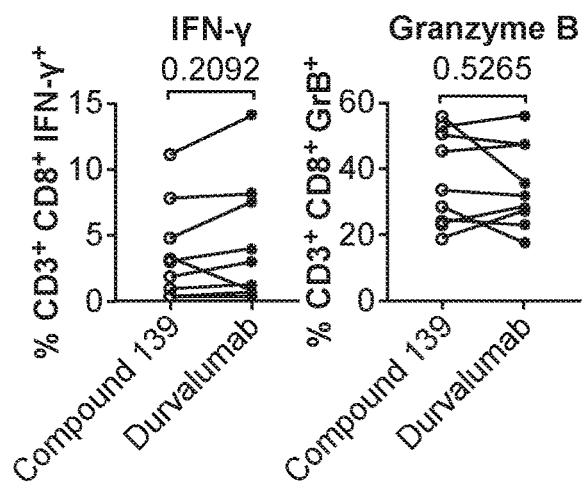
FIG. 1A          FIG. 1B
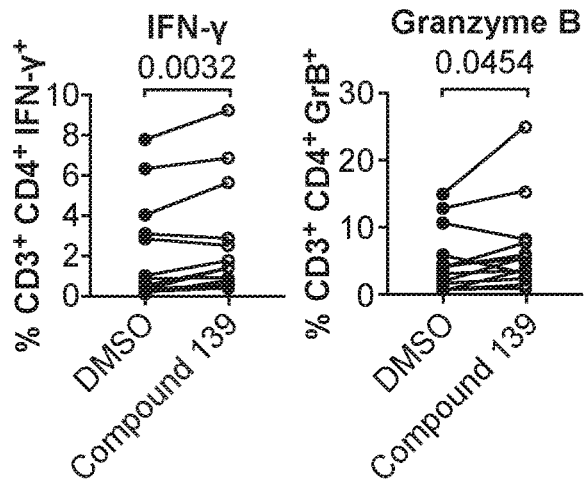
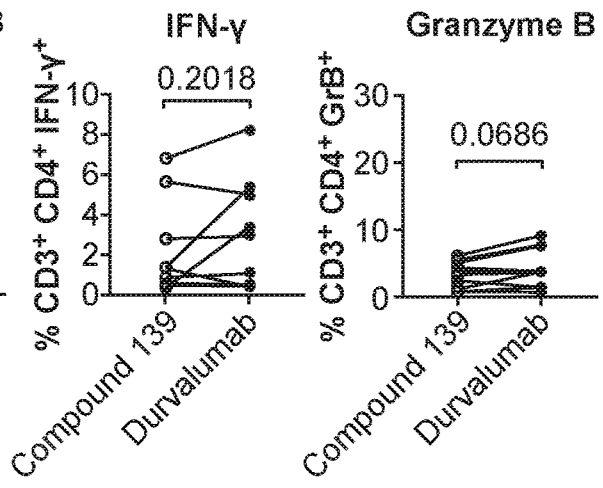
FIG. 2A          FIG. 2B
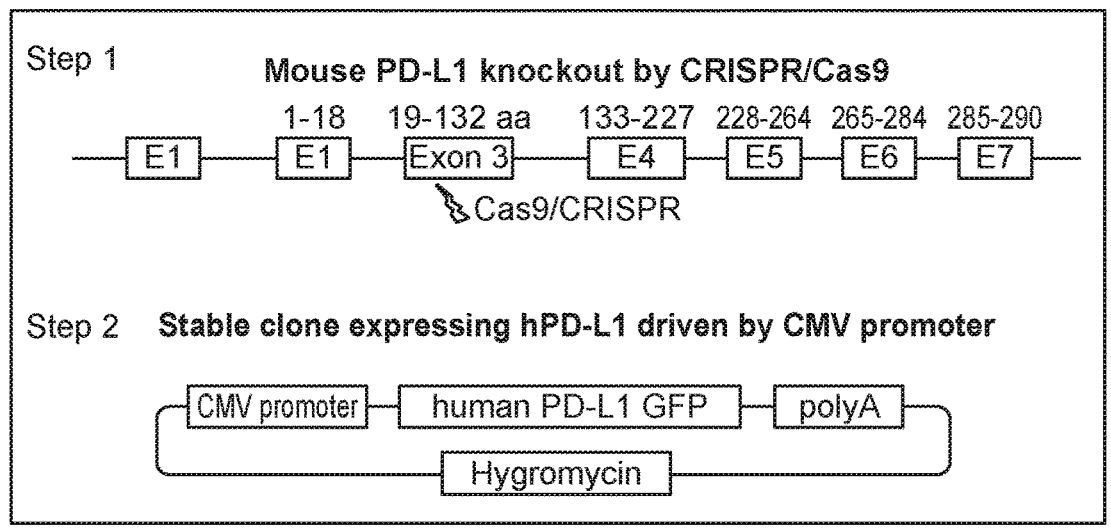
FIG. 3

PD-1/PD-L1 INHIBITORS

CROSS-REFERENCE TO RELATED APPLICATION

This application claims the benefit under 35 U.S.C. § 119(e) of United States Provisional Application Nos. 62/630,187, filed Feb. 13, 2018, 62/640,534, filed Mar. 8, 2018, 62/763,116, filed Apr. 19, 2018, and 62/747,029, filed Oct. 17, 2018, each of which are hereby incorporated by reference in their entirety.

FIELD

The present disclosure generally relates to compounds useful as inhibitors of PD-1, PD-L1 or the PD-1/PD-L1 interaction. Provided herein are compounds, compositions comprising such compounds, and methods for their use.

BACKGROUND

Programmed death-1 (CD279) is a receptor on T cells that has been shown to suppress activating signals from the T cell receptor when bound by either of its ligands, Programmed death-ligand 1 (PD-L1, CD274, B7-H1) or PD-L2 (CD273, B7-DC). When PD-1 expressing T cells contact cells expressing its ligands, functional activities in response to antigenic stimuli, including proliferation, cytokine secretion, and cytotoxicity are reduced. PD-1/PD-Ligand interactions down regulate immune responses during resolution of an infection or tumor, or during the development of self-tolerance. Chronic antigen stimulation, such as that which occurs during tumor disease or chronic infections, results in T cells that express elevated levels of PD-1 and are dysfunctional with respect to activity towards the chronic antigen. This is termed "T cell exhaustion." B cells also display PD-1/PD-ligand suppression and "exhaustion."

Blockade of the PD-1/PD-L1 ligation using antibodies to PD-L1 has been shown to restore and augment T cell activation in many systems. Patients with advanced cancer benefit from therapy with a monoclonal antibody to PD-L1. Preclinical animal models of tumors and chronic infections have shown that blockade of the PD-1/PD-L1 pathway by monoclonal antibodies can enhance the immune response and result in tumor rejection or control of infection. Antitumor immunotherapy via PD-1/PD-L1 blockade may augment therapeutic immune response to a number of histologically distinct tumors.

Interference with the PD-1/PD-L1 interaction has also shown enhanced T cell activity in chronic infection systems. Chronic lymphocytic chorio meningitis virus infection of mice also exhibits improved virus clearance and restored immunity with blockade of PD-L1. Humanized mice infected with HIV-1 show enhanced protection against viremia and viral depletion of CD4+ T cells. Blockade of PD-1/PD-L1 through monoclonal antibodies to PD-L1 can restore in vitro antigen-specific functionality to T cells from HIV patients, HCV patients or HBV patients.

Accordingly, agents that block PD-1, PD-L1 and/or the PD-1/PD-L1 interaction are desired. Small molecule agents that block or inhibit PD-1, PD-L1 and/or the PD-1/PD-L1 interaction are particularly desired. Applicants have discovered small molecule compounds that have activity as inhibitors of PD-1, PD-L1 or inhibitors of the interaction of PD-1 with PD-L1, and thus may be useful for treating patients having cancer, HIV, HCV and/or HBV.

SUMMARY

The present disclosure provides a compound of formula (I):

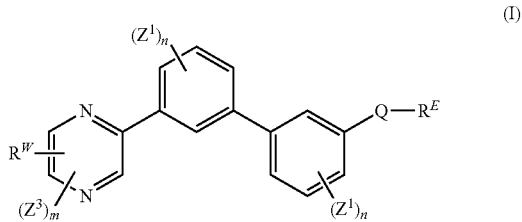

wherein:
each n is independently 0, 1, 2, 3 or 4;
each $Z^1$ is independently halo, —$OR^a$, —$NO_2$, —CN, —$NR^aR^b$, —$N_3$, —$S(O)_2R^a$, —$C_{1-6}$ alkyl, —$C_{1-6}$ haloalkyl, —$C_{2-6}$ alkenyl, —$C_{2-6}$ alkynyl, —O—$C_{1-6}$ alkyl, —O—$C_{1-6}$ haloalkyl, —$C_{3-8}$ cycloalkyl or —$C_{1-6}$ alkyl$C_{3-8}$ cycloalkyl;
  wherein each alkyl, alkenyl, alkynyl, and cycloalkyl group is optionally substituted with 1 to 4 groups independently selected from the group consisting of oxo, —$NO_2$, —$N_3$, —$OR^a$, halo, and cyano;
Q is aryl, heteroaryl or heterocyclyl, wherein the aryl, heteroaryl and heterocyclyl group is optionally substituted with 1 to 4 groups independently selected from the group consisting of halo, oxo, —$OR^a$, —$SR^a$, $N_3$, $NO_2$, —CN, —$NR^1R^2$, —$S(O)_2R^a$, —$S(O)_2NR^aR^b$, —$NR^aS(O)_2R^a$, —$NR^aC(O)R^a$, —$C(O)R^a$, —$C(O)OR^a$, —$C(O)NR^aR^b$, —$NR^aC(O)OR^a$, —$NR^aC(O)NR^1R^2$, —O—$C(O)NR^aR^b$, —$NR^aS(O)_2NR^aR^b$, —$C(O)NR^aS(O)_2NR^aR^b$, —$C_{1-6}$ alkyl, —$C_{2-6}$ alkenyl, —$C_{2-6}$ alkynyl, —O—$C_{1-6}$ alkyl, —$C_{3-8}$ cycloalkyl, —$C_{1-6}$ alkyl$C_{3-8}$ cycloalkyl, aryl, heteroaryl, heterocyclyl and $R^N$;
  wherein the alkyl, alkenyl, alkynyl, cycloalkyl, aryl, heteroaryl, or heterocyclyl group is optionally substituted with 1 to 4 groups independently selected from the group consisting of oxo, —$NO_2$, $N_3$, —$OR^a$, halo, cyano, —$NR^aR^b$, —$C(O)R^a$, —$C(O)OR^a$, —O—$C_{1-6}$ alkylCN, —$C(O)NR^aR^b$, $NR^aC(O)R^a$, —$NR^aC(O)OR^a$, —$S(O)_2R^a$, —$NR^aS(O)_2R^b$, —$S(O)_2NR^aR^b$, —$NR^aS(O)_2NR^aR^b$, —$C(O)NR^aS(O)_2NR^aR^b$ and —$C_{3-8}$ cycloalkyl; and wherein the heteroaryl or heterocyclyl group may be oxidized on a nitrogen atom to form an N-oxide or oxidized on a sulfur atom to form a sulfoxide or sulfone;
m is 0, 1 or 2;
each $Z^3$ is independently halo, oxo, —$OR^a$, $SR^a$, $N_3$, $NO_2$, —CN, —$NR^1R^2$, —$S(O)_2R^a$, —$S(O)_2NR^aR^b$, —$NR^aS(O)_2R^a$, —$NR^aC(O)R^a$, —$C(O)R^a$, —$C(O)OR^a$, —$C(O)NR^aR^b$, —$NR^aC(O)OR^a$, —$NR^aC(O)NR^1R^2$, —O—$C(O)NR^aR^b$, —$NR^aS(O)_2NR^aR^b$, —$C(O)NR^aS(O)_2NR^aR^b$, —$C_{1-6}$ alkyl, —$C_{2-6}$ alkenyl, —$C_{2-6}$ alkynyl, —O—$C_{1-6}$ alkyl, —$C_{3-8}$ cycloalkyl, —$C_{1-6}$ alkyl$C_{3-8}$ cycloalkyl, aryl, heteroaryl, heterocyclyl and $R^N$;
  wherein the alkyl, alkenyl, alkynyl, cycloalkyl, aryl, heteroaryl, or heterocyclyl group is optionally substituted with 1 to 4 groups independently selected from the group consisting of oxo, —$NO_2$, $N_3$, —$OR^a$, halo, cyano, —$NR^aR^b$, —$C(O)R^a$, —$C(O)OR^a$, —O—$C_{1-6}$ alkylCN, —$C(O)NR^aR^b$, $NR^aC(O)R^a$, —$NR^aC(O)OR^a$, —$S(O)_2R^a$, —$NR^aS(O)_2R^b$, —$S(O)_2NR^aR^b$, —$NR^aS(O)_2NR^aR^b$, —$C(O)NR^aS(O)_2NR^aR^b$ and —$C_{3-8}$ cycloalkyl;

each $R^N$ is independently —$C_{1-6}$ alkylNR$^1$R$^2$, —O—$C_{1-6}$ alkylNR$^1$R$^2$, —$C_{1-6}$ alkylOC$_{1-6}$ alkylNR$^1$R$^2$, —NR$^a$—$C_{1-6}$ alkylNR$^1$R$^2$, —$C_{1-6}$ alkylC(O)NR$^1$R$^2$, —O—$C_{1-6}$ alkylC(O)NR$^1$R$^2$, —O—$C_{1-6}$ alkylC(O)OR$^1$, —S—$C_{1-6}$ alkylNR$^1$R$^2$, —$C_{1-6}$ alkylOR$^a$, or $$L^1—V—L^2—\boxed{A};$$

wherein
$L^1$ is independently a bond, O, NR$^a$, S, S(O), or S(O)$_2$;
V is independently selected from the group consisting of a bond, $C_{1-6}$alkyl, $C_{2-6}$alkenyl, and $C_{2-6}$alkynyl;
   wherein the alkyl, alkenyl or alkynyl group is optionally independently substituted with —OR$^a$, halo, cyano, NR$^a$R$^b$ and —$C_{3-8}$ cycloalkyl;
$L^2$ is independently a bond, O, NR$^a$, S, S(O), or S(O)$_2$;
ring A is independently cycloalkyl, aryl, heteroaryl or heterocyclyl;
   wherein the cycloalkyl, aryl, heteroaryl, or heterocyclyl group is optionally substituted with 1 to 4 groups independently selected from the group consisting of oxo, —NO$_2$, N$_3$, —OR$^a$, halo, cyano, —$C_{1-6}$ alkyl, —$C_{1-6}$ haloalkyl, —$C_{2-6}$alkenyl, —$C_{2-6}$ alkynyl, —O—$C_{1-6}$ haloalkyl, NR$^a$R$^b$, —C(O)R$^a$, —C(O)OR$^a$, —O—$C_{1-6}$ alkylCN, —C(O)NR$^a$R$^b$, —NR$^a$C(O)R$^a$, —NR$^a$C(O)OR$^a$, —NR$^a$C(O)OR$^a$, —C(O)N(R$^a$)OR$^b$, —S(O)$_2$R$^a$, —S(O)$_2$NR$^a$R$^b$, —NR$^a$S(O)$_2$R$^b$, —NR$^a$S(O)$_2$NR$^a$R$^b$, —C(O)NR$^a$S(O)$_2$NR$^a$R$^b$, $C_{3-8}$cycloalkyl and $C_{1-6}$alkylC$_{3-8}$ cycloalkyl;
   wherein the alkyl, alkenyl or alkynyl group is optionally independently substituted with —OR$^a$, halo, cyano, NR$^a$R$^b$ and —$C_{3-8}$ cycloalkyl;
$R^E$ and $R^W$ are each independently —NR$^1$R$^2$, —$C_{1-6}$ alkylNR$^1$R$^2$, —O—$C_{1-6}$ alkylNR$^1$R$^2$, —$C_{1-6}$ alkylOC$_{1-6}$ alkylNR$^1$R$^2$, —NR$^a$—$C_{1-6}$ alkylNR$^1$R$^2$, —$C_{1-6}$ alkylN$^+$R$^1$R$^2$R$^3$, —S—$C_{1-6}$ alkylNR$^1$R$^2$, —C(O)NR$^1$R$^2$, —S(O)$_2$R$^a$, —(CH$_2$)$_u$S(O)$_2$NR$^1$R$^2$, —(CH$_2$)$_u$NR$^a$S(O)$_2$NR$^a$R$^b$, —S(O)$_2$NR$^a$C$_{1-6}$ alkylNR$^1$R$^2$, —NR$^a$S(O)$_2$C$_{1-6}$ alkylNR$^1$R$^2$, —(CH$_2$)$_u$C(O)NR$^a$S(O)$_2$NR$^a$R$^b$, —(CH$_2$)$_u$N$^+$R$^1$R$^2$O$^-$, —(CH$_2$)$_u$P$^+$R$^b$R$^c$R$^d$, —(CH$_2$)$_u$P$^+$R$^c$R$^d$O$^-$, —(CH$_2$)$_u$P$^+$O[NR$^a$R$^b$][NR$^c$R$^d$], —(CH$_2$)$_u$NR$^c$P(O)(OR$^c$)$_2$, —(CH$_2$)$_u$CH$_2$OP(O)(OR$^c$)(OR$^d$), —(CH$_2$)$_u$OP(O)(OR$^c$)(OR$^d$), —(CH$_2$)$_u$OP(O)NR$^a$R$^b$)(OR$^a$), or

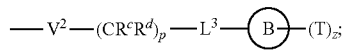

$$—V^2—(CR^cR^d)_p—L^3—\boxed{B}—(T)_z;$$

wherein:
$V^2$ is independently a bond, O, NR$^a$, S, S(O), S(O)$_2$, C(O)NR$^a$, NR$^a$C(O), S(O)$_2$NR$^1$, or NR$^a$S(O)$_2$;
$L^3$ is independently a bond, O, NR$^a$, S, S(O), S(O)$_2$, C(O)NR$^a$, NR$^a$C(O), S(O)$_2$NR$^1$, or NR$^a$S(O)$_2$;
ring B is independently cycloalkyl, aryl, heteroaryl or heterocyclyl;
T is independently H, —OR$^a$, (CH$_2$)$_q$NR$^1$R$^2$, (CH$_2$)$_q$NR$^a$C(O)R$^e$ or (CH$_2$)$_q$C(O)R$^e$;
p is independently 0, 1, 2, 3, 4, or 5;
q is independently 0, 1, 2, 3, 4, or 5;
u is 0, 1, 2, 3 or 4;
z is 0, 1, 2 or 3; and
wherein the alkyl, cycloalkyl, aryl, heteroaryl or heterocyclyl group of $R^E$ and $R^W$ is optionally substituted with 1 to 3 substituents independently selected from the group consisting of NR$^a$R$^b$, halo, cyano, oxo, —OR$^a$, —$C_{1-6}$ alkyl, —$C_{1-6}$ haloalkyl, —$C_{1-6}$ cyanoalkyl, —$C_{1-6}$ alkylNR$^a$R$^b$, —$C_{1-6}$ alkylOH, —$C_{3-8}$ cycloalkyl and —$C_{1-3}$ alkylC$_{3-8}$cycloalkyl;
provided that at least one of $V^2$, $L^3$, ring B and T contains a nitrogen atom;
each $R^1$ is independently selected from the group consisting of H, —$C_{1-8}$ alkyl, —$C_{2-6}$ alkenyl, —$C_{2-6}$ alkynyl, —$C_{3-6}$ cycloalkyl, aryl, heteroaryl, heterocyclyl, —$C_{1-6}$ alkylaryl, —$C_{1-6}$ alkylheteroaryl, —$C_{1-6}$ alkylheterocyclyl, —$C_{1-6}$ alkylC(O)OR$^a$, —$C_{2-6}$ alkenylC(O)OR$^a$, —S(O)$_2$R$^a$, —S(O)$_2$OR$^a$, —S(O)$_2$NR$^a$R$^b$, —C(O)NR$^a$S(O)$_2$R$^a$, and $C_{1-6}$ alkylC$_{3-8}$cycloalkyl;
   wherein each alkyl, alkenyl, cycloalkyl, aryl, heteroaryl or heterocyclyl group is optionally substituted with 1 to 4 groups independently selected from the group consisting of —OR$^a$, —CN, —NO$_2$, halo, $C_{1-6}$alkyl, —$C_{1-6}$ alkylOR$^a$, —$C_{1-6}$ cyanoalkyl, —$C_{1-6}$ haloalkyl, $C_{3-8}$ cycloalkyl, heteroaryl, heterocyclyl, —$C_{1-3}$ alkylC$_{3-8}$cycloalkyl, —C(O)R$^a$, —$C_{1-6}$ alkylC(O)R$^a$, —C(O)OR$^a$, —$C_{1-6}$ alkylC(O)OR$^a$, —NR$^a$R$^b$, —OC(O)NR$^a$R$^b$, —NR$^a$C(O)OR$^b$, —NR$^a$C(O)R$^b$, —$C_{1-6}$ alkylNR$^a$R$^b$, —C(O)NR$^a$R$^b$, —$C_{1-6}$ alkylC(O)NR$^a$R$^b$, —S(O)$_2$R$^a$, —S(O)$_2$OR$^a$, —$C_{1-6}$ alkylS(O)$_2$R$^a$, —S(O)$_2$NR$^a$R$^b$, —$C_{1-6}$ alkylS(O)$_2$NR$^a$R$^b$, —C(O)NR$^a$S(O)$_2$R$^b$, —NR$^a$C(O)NR$^b$, —$C_{1-6}$ alkylC(O)NR$^a$S(O)$_2$R$^b$, —NR$^a$C(O)R$^b$, and —$C_{1-6}$alkylNR$^a$C(O)R$^b$;
each $R^2$ is independently selected from the group consisting of H, —$C_{1-6}$ alkyl, —$C_{2-6}$ alkenyl, —$C_{2-6}$ alkynyl, —$C_{3-6}$ cycloalkyl, aryl, heteroaryl, heterocyclyl, —$C_{1-6}$ alkylaryl, —$C_{1-6}$ alkylheteroaryl, —$C_{1-6}$ alkylheterocyclyl, —$C_{2-6}$ alkyl-OR$^a$, —$C_{1-6}$ alkylC(O)OR$^a$, and —$C_{2-6}$ alkenylC(O)OR$^a$;
   wherein each alkyl, alkenyl, cycloalkyl, aryl, heteroaryl or heterocyclyl group is optionally substituted with 1 to 4 groups independently selected from the group consisting of —OR$^a$, —CN, halo, $C_{1-6}$alkyl, —$C_{1-6}$ alkylOR$^a$, —$C_{1-6}$ cyanoalkyl, —$C_{1-6}$ haloalkyl, —$C_{3-8}$ cycloalkyl, —$C_{1-3}$ alkylC$_{3-8}$cycloalkyl, —C(O)R$^a$, —$C_{1-6}$ alkylC(O)R$^a$, —C(O)OR$^a$, —$C_{1-6}$ alkylC(O)OR$^a$, —NR$^a$R$^b$, —$C_{1-6}$ alkylNR$^a$R$^b$, —C(O)NR$^a$R$^b$, $C_{1-6}$ alkylC(O)NR$^a$R$^b$, —S(O)$_2$R$^a$, —$C_{1-6}$ alkylS(O)$_2$R$^a$, —S(O)$_2$NR$^a$R$^b$, —$C_{1-6}$ alkylS(O)$_2$NR$^a$R$^b$, —C(O)NR$^a$S(O)$_2$R$^b$ and —NR$^a$C(O)R$^b$;
or $R^1$ and $R^2$ combine to form a heterocyclyl group optionally containing 1, 2, or 3 additional heteroatoms independently selected from oxygen, sulfur and nitrogen, and optionally substituted with 1 to 3 groups independently selected from the group consisting of oxo, —$C_{1-6}$ alkyl, —$C_{3-8}$ cycloalkyl, —$C_{2-6}$ alkenyl, —$C_{2-6}$ alkynyl, aryl, heteroaryl, heterocyclyl, —OR$^a$, —CN, halo, —C(O)OR$^a$, —$C_{1-6}$ cyanoalkyl, —$C_{1-6}$ alkylOR$^a$, —$C_{1-6}$ haloalkyl, —$C_{1-3}$ alkylC$_{3-8}$cycloalkyl, —C(O)R$^a$, $C_{1-6}$ alkylC(O)R$^a$, —$C_{1-6}$ alkylC(O)OR$^a$, —NR$^a$R$^b$, —$C_{1-6}$alkylNR$^a$R$^b$, —C(O)NR$^a$R$^b$, —NR$^a$C(O)OR$^b$, —NR$^a$C(O)NR$^a$R$^b$, —NR$^a$S(O)$_2$NR$^a$R$^b$, —NR$^a$S(O)$_2$R$^b$, —$C_{1-6}$ alkylC(O)NR$^a$R$^b$, —S(O)$_2$R$^a$, —$C_{1-6}$ alkylS(O)$_2$R$^a$, —S(O)$_2$NR$^a$R$^b$, and $C_{1-6}$ alkylS(O)$_2$NR$^a$R$^b$;
each $R^3$ is independently H, —$C_{1-6}$ alkyl, —$C_{2-6}$ alkenyl, —$C_{3-6}$ cycloalkyl, aryl, heteroaryl, heterocyclyl, —$C_{1-6}$ alkylaryl, —$C_{1-6}$ alkylheteroaryl, —$C_{1-6}$ alkylheterocyclyl, —$C_{2-6}$ alkyl-OR$^a$, —$C_{1-6}$ alkylC(O)OR$^a$, or —$C_{2-6}$ alkenyl-C(O)OR$^a$;
each $R^a$ is independently selected from the group consisting of H, —$C_{1-6}$ alkyl, —$C_{1-6}$ haloalkyl, —$C_{3-8}$ cycloalkyl, aryl, heteroaryl, heterocyclyl, —C$_{1-3}$ alkylC$_{3-8}$cycloalkyl, —C$_{1-6}$ alkylaryl, —C$_{1-6}$ alkylheteroaryl, and —C$_{1-6}$alkylheterocyclyl;

each R$^b$ is independently selected from the group consisting of H, —C$_{1-6}$ alkyl, —C$_{1-6}$ haloalkyl, —C$_{3-8}$ cycloalkyl, aryl, heteroaryl, heterocyclyl, —C$_{1-3}$ alkylC$_{3-8}$cycloalkyl, —C$_{1-6}$ alkylaryl, —C$_{1-6}$ alkylheteroaryl, and —C$_{1-6}$ alkylheterocyclyl;

or R$^a$ and R$^b$ may combine together to form a ring consisting of 3-8 ring atoms that are C, N, O, or S; wherein the ring is optionally substituted with 1 to 4 groups independently selected from the group consisting of —OR$^f$, —CN, halo, —C$_{1-6}$ alkylOR$^f$, —C$_{1-6}$ cyanoalkyl, —C$_{1-6}$ haloalkyl, —C$_{3-8}$ cycloalkyl, —C$_{1-3}$ alkylC$_{3-8}$cycloalkyl, —C(O)R$^f$, —C$_{1-6}$ alkylC(O)R$^f$, —C(O)OR$^f$, —C$_{1-6}$ alkylC(O)OR$^f$, —NR$^f$R$^g$, —C$_{1-6}$ alkylNR$^f$R$^g$, —C(O)NR$^f$R$^g$, C$_{1-6}$ alkylC(O)NR$^f$R$^g$, —S(O)$_2$R$^f$, —C$_{1-6}$ alkylS(O)$_2$R$^f$, —S(O)$_2$NR$^f$R$^g$, —C$_{1-6}$ alkylS(O)$_2$NR$^f$R$^g$, —C(O)NR$^f$S(O)$_2$R$^g$ and —NR$^f$C(O)R$^g$;

each R$^c$ is independently selected from the group consisting of H, OH, —C$_{1-6}$ alkyl, —C$_{3-8}$ cycloalkyl, aryl, heteroaryl, heterocyclyl, —C$_{1-3}$ alkylC$_{3-8}$ cycloalkyl, —C$_{1-6}$ alkylaryl, —C$_{1-6}$ alkylheteroaryl, and —C$_{1-6}$ alkylheterocyclyl; and each R$^d$ is independently selected from the group consisting of H, —C$_{1-6}$ alkyl, —C$_3$-C$_8$cycloalkyl, aryl, heteroaryl, heterocyclyl, —C$_{1-3}$ alkylC$_{3-8}$cycloalkyl, —C$_{1-6}$ alkylaryl, —C$_{1-6}$ alkylheteroaryl, and —C$_{1-6}$ alkylheterocyclyl;

each R$^e$ is independently selected from the group consisting of H, —C$_{1-6}$ alkyl, —O—C$_{1-6}$alkyl, —C$_{3-8}$ cycloalkyl, aryl, heteroaryl, heterocyclyl, —O—C$_{3-8}$ cycloalkyl, —O-aryl, —O-heteroaryl, —O-heterocyclyl, —C$_{1-3}$ alkylC$_{3-8}$cycloalkyl, —C$_{1-6}$ alkylaryl, —C$_{1-6}$alkylheteroaryl, —NR$^f$R$^g$, —C$_{1-6}$ alkylNR$^f$R$^g$, —C(O)NR$^f$R$^g$, —C$_{1-6}$ alkylC(O)NR$^f$R$^g$, —NHS(O)$_2$R$^f$, —C$_{1-6}$ alkylS(O)$_2$R$^f$, and —C$_{1-6}$ alkylS(O)$_2$NR$^f$R$^g$;

each R$^f$ is independently selected from the group consisting of H, —C$_{1-6}$ alkyl, —C$_{3-8}$ cycloalkyl, aryl, heteroaryl, heterocyclyl, —C$_{1-3}$ alkylC$_{3-8}$ cycloalkyl, —C$_{1-6}$ alkylaryl, —C$_{1-6}$ alkylheteroaryl, and —C$_{1-6}$ alkylheterocyclyl;

each R$^g$ is independently selected from the group consisting of H, —C$_{1-6}$ alkyl, —C$_{3-8}$ cycloalkyl, aryl, heteroaryl, heterocyclyl, —C$_{1-3}$ alkylC$_{3-8}$ cycloalkyl, —C$_{1-6}$ alkylaryl, —C$_{1-6}$ alkylheteroaryl, and —C$_{1-6}$ alkylheterocyclyl;

or a pharmaceutically acceptable salt, stereoisomer, mixture of stereoisomers, or tautomer thereof.

The present disclosure further provides a compound of formula (I):

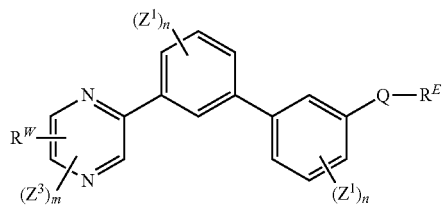

wherein:
each n is independently 0, 1, 2, 3 or 4;
each Z$^1$ is independently halo, —OR$^a$, —NO$_2$, —CN, —NR$^a$R$^b$, —N$_3$, —S(O)$_2$R$^a$, —C$_{1-6}$ alkyl, —C$_{1-6}$ haloalkyl, —C$_{2-6}$alkenyl, —C$_{2-6}$ alkynyl, —O—C$_{1-6}$ alkyl, —O—C$_{1-6}$ haloalkyl, —C$_{3-8}$ cycloalkyl or —C$_{1-6}$ alkylC$_{3-8}$ cycloalkyl;

wherein each alkyl, alkenyl, alkynyl, and cycloalkyl group is optionally substituted with 1 to 4 groups independently selected from the group consisting of oxo, —NO$_2$, —N$_3$, —OR$^a$, halo, and cyano;

Q is aryl, heteroaryl or heterocyclyl, wherein the aryl, heteroaryl and heterocyclyl group is optionally substituted with 1 to 4 groups independently selected from the group consisting of halo, oxo, —OR$^a$, N$_3$, NO$_2$, —CN, —NR$^1$R$^2$, —S(O)$_2$R$^a$, —S(O)$_2$NR$^a$R$^b$, —NR$^a$S(O)$_2$R$^a$, —NR$^a$C(O)R$^a$, —C(O)R$^a$, —C(O)OR$^a$, —C(O)NR$^a$R$^b$, —NR$^a$C(O)OR$^a$, —NR$^a$C(O)NR$^1$R$^2$, —OC(O)NR$^a$R$^b$, —NR$^a$S(O)$_2$NR$^a$R$^b$, —C(O)NR$^a$S(O)$_2$NR$^a$R$^b$, —C$_{1-6}$ alkyl, —C$_{2-6}$ alkenyl, —C$_{2-6}$ alkynyl, —O—C$_{1-6}$ alkyl, —C$_{3-8}$ cycloalkyl, —C$_{1-6}$ alkylC$_{3-8}$ cycloalkyl, aryl, heteroaryl, heterocyclyl and R$^N$;

wherein the alkyl, alkenyl, alkynyl, cycloalkyl, aryl, heteroaryl, or heterocyclyl group is optionally substituted with 1 to 4 groups independently selected from the group consisting of oxo, —NO$_2$, N$_3$, —OR$^a$, halo, cyano, —NR$^a$R$^b$, —C(O)R$^a$, —C(O)OR$^a$, —O—C$_{1-6}$ alkylCN, —C(O)NR$^a$R$^b$, NR$^a$C(O)R$^a$, —NR$^a$C(O)OR$^a$, —S(O)$_2$R$^a$, —NR$^a$S(O)$_2$R$^b$, —S(O)$_2$NR$^a$R$^b$, —NR$^a$S(O)$_2$NR$^a$R$^b$, —C(O)NR$^a$S(O)$_2$NR$^a$R$^b$ and —C$_{3-8}$ cycloalkyl; and wherein the heteroaryl or heterocyclyl group may be oxidized on a nitrogen atom to form an N-oxide or oxidized on a sulfur atom to form a sulfoxide or sulfone;

m is 0, 1 or 2;
each Z$^3$ is independently halo, oxo, —OR$^a$, N$_3$, NO$_2$, —CN, —NR$^1$R$^2$, —S(O)$_2$R$^a$, —S(O)$_2$NR$^a$R$^b$, —NR$^a$S(O)$_2$R$^a$, —NR$^a$C(O)R$^a$, —C(O)R$^a$, —C(O)OR$^a$, —C(O)NR$^a$R$^b$, —NR$^a$C(O)OR$^a$, —NR$^a$C(O)NR$^1$R$^2$, —OC(O)NR$^a$R$^b$, —NR$^a$S(O)$_2$NR$^a$R$^b$, —C(O)NR$^a$S(O)$_2$NR$^a$R$^b$, —C$_{1-6}$ alkyl, —C$_{2-6}$ alkenyl, —C$_{2-6}$ alkynyl, —O—C$_{1-6}$ alkyl, —C$_{3-8}$ cycloalkyl, —C$_{1-6}$ alkylC$_{3-8}$ cycloalkyl, aryl, heteroaryl, heterocyclyl and R$^N$;

wherein the alkyl, alkenyl, alkynyl, cycloalkyl, aryl, heteroaryl, or heterocyclyl group is optionally substituted with 1 to 4 groups independently selected from the group consisting of oxo, —NO$_2$, N$_3$, —OR$^a$, halo, cyano, —NR$^a$R$^b$, —C(O)R$^a$, —C(O)OR$^a$, —O—C$_{1-6}$ alkylCN, —C(O)NR$^a$R$^b$, NR$^a$C(O)R$^a$, —NR$^a$C(O)OR$^a$, —S(O)$_2$R$^a$, —NR$^a$S(O)$_2$R$^b$, —S(O)$_2$NR$^a$R$^b$, —NR$^a$S(O)$_2$NR$^a$R$^b$, —C(O)NR$^a$S(O)$_2$NR$^a$R$^b$ and —C$_{3-8}$ cycloalkyl;

each R$^N$ is independently —C$_{1-6}$ alkylNR$^1$R$^2$, —O—C$_{1-6}$ alkylNR$^1$R$^2$, —C$_{1-6}$ alkylOC$_{1-6}$ alkylNR$^1$R$^2$, —N—R$^a$C$_{1-6}$ alkylNR$^1$R$^2$, —C$_{1-6}$ alkylC(O)NR$^1$R$^2$, —O—C$_{1-6}$ alkylC(O)NR$^1$R$^2$, —O—C$_{1-6}$ alkylC(O)OR$^1$, —S—C$_{1-6}$ alkylNR$^1$R$^2$, —C$_{1-6}$ alkylOR$^a$, or

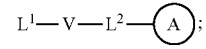

wherein
L$^1$ is independently a bond, O, NR$^a$, S, S(O), or S(O)$_2$;
V is independently selected from the group consisting of a bond, C$_{1-6}$alkyl, C$_{2-6}$alkenyl, and C$_{2-6}$alkynyl;

wherein the alkyl, alkenyl or alkynyl group is optionally independently substituted with —OR$^a$, halo, cyano, NR$^a$R$^b$ and —C$_{3-8}$ cycloalkyl;

L$^2$ is independently a bond, O, NR$^a$, S, S(O), or S(O)$_2$;
ring A is independently cycloalkyl, aryl, heteroaryl or heterocyclyl;

wherein the cycloalkyl, aryl, heteroaryl, or heterocyclyl group is optionally substituted with 1 to 4 groups independently selected from the group consisting of oxo, —NO₂, N₃, —OR$^a$, halo, cyano, —C$_{1-6}$ alkyl, —C$_{1-6}$ haloalkyl, —C$_{2-6}$alkenyl, —C$_{2-6}$ alkynyl, —O—C$_{1-6}$ haloalkyl, NR$^a$R$^b$, —C(O)R$^a$, —C(O)OR$^a$, —O—C$_{1-6}$ alkylCN, —C(O)NR$^a$R$^b$, —NR$^a$C(O)R$^a$, —NR$^a$C(O)OR$^a$, —NR$^a$C(O)OR$^a$, —C(O)N(R$^a$)OR$^b$, —S(O)$_2$R$^a$, —S(O)$_2$NR$^a$R$^b$, —NR$^a$S(O)$_2$R$^b$, —NR$^a$S(O)$_2$NR$^a$R$^b$, —C(O)NR$^a$S(O)$_2$NR$^a$R$^b$, C$_{3-8}$cycloalkyl and C$_{1-6}$alkylC$_{3-8}$ cycloalkyl;

wherein the alkyl, alkenyl or alkynyl group is optionally independently substituted with —OR$^a$, halo, cyano, NR$^a$R$^b$ and —C$_{3-8}$ cycloalkyl;

R$^E$ and R$^W$ are each independently —NR$^1$R$^2$, —C$_{1-6}$ alkylNR$^1$R$^2$, —O—C$_{1-6}$ alkylNR$^1$R$^2$, —C$_{1-6}$ alkylOC$_{1-6}$ alkylNR$^1$R$^2$, —NR$^a$—C$_{1-6}$ alkylNR$^1$R$^2$, —C$_{1-6}$ alkylN+R$^1$R$^2$R$^3$, —SC$_{1-6}$ alkylNR$^1$R$^2$, —C(O)NR$^1$R$^2$, —S(O)$_2$R$^a$, —(CH$_2$)$_u$S(O)$_2$NR$^1$R$^2$, —(CH$_2$)$_u$NR$^a$S(O)$_2$NR$^a$R$^b$, —S(O)$_2$ NR$^a$C$_{1-6}$ alkylNR$^1$R$^2$, —NR$^a$S(O)$_2$C$_{1-6}$ alkylNR$^1$R$^2$, —(CH$_2$)$_u$C(O)NR$^a$S(O)$_2$NR$^a$R$^b$, —(CH$_2$)$_u$N+R$^1$R$^2$O$^-$, —(CH$_2$)$_u$P+R$^b$R$^c$R$^d$, —(CH$_2$)$_u$P+R$^c$R$^d$O$^-$, —(CH$_2$)$_u$P+O[NR$^a$R$^b$][NR$^c$R$^d$], —(CH$_2$)$_u$NR$^a$P(O)(OR$^c$)$_2$, —(CH$_2$)$_u$CH$_2$OP(O)(OR$^c$)(OR$^d$), —(CH$_2$)$_u$OP(O)(OR$^c$)(OR$^d$), —(CH$_2$)$_u$OP(O)NR$^a$R$^b$)(OR$^a$), or

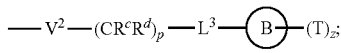

wherein:
V$^2$ is independently a bond, O, NR$^a$, S, S(O), S(O)$_2$, C(O)NR$^a$, NR$^a$C(O), S(O)$_2$NR$^1$, or NR$^a$S(O)$_2$;
L$^3$ is independently a bond, O, NR$^a$, S, S(O), S(O)$_2$, C(O)NR$^a$, NR$^a$C(O), S(O)$_2$NR$^1$, or NR$^a$S(O)$_2$;
ring B is independently cycloalkyl, aryl, heteroaryl or heterocyclyl;
T is independently H, —OR$^a$, (CH$_2$)$_q$NR$^1$R$^2$, (CH$_2$)$_q$NR$^a$C(O)R$^e$ or (CH$_2$)$_q$C(O)R$^e$;
p is independently 0, 1, 2, 3, 4, or 5;
q is independently 0, 1, 2, 3, 4, or 5;
u is 0, 1, 2, 3 or 4;
z is 0, 1, 2 or 3; and
wherein the alkyl, cycloalkyl, aryl, heteroaryl or heterocyclyl of R$^E$ or R$^W$ is optionally substituted with 1 to 3 substituents independently selected from the group consisting of NR$^a$R$^b$, halo, cyano, oxo, —OR$^a$, —C$_{1-6}$ alkyl, —C$_{1-6}$ haloalkyl, —C$_{1-6}$ cyanoalkyl, —C$_{1-6}$ alkylNR$^a$R$^b$, —C$_{1-6}$ alkylOH, —C$_{3-8}$ cycloalkyl and —C$_{1-3}$ alkylC$_{3-8}$cycloalkyl;
provided that at least one of V$^2$, L$^3$, ring B and T contains a nitrogen atom;

each R$^1$ is independently selected from the group consisting of H, —C$_{1-8}$ alkyl, —C$_{2-6}$ alkenyl, —C$_{2-6}$ alkynyl, —C$_{3-6}$ cycloalkyl, aryl, heteroaryl, heterocyclyl, —C$_{1-6}$ alkylaryl, —C$_{1-6}$ alkylheteroaryl, —C$_{1-6}$ alkylheterocyclyl, —C$_{1-6}$ alkylC(O)OR$^a$, —C$_{2-6}$ alkenylC(O)OR$^a$, —S(O)$_2$R$^a$, —S(O)$_2$NR$^a$R$^b$, —C(O)NR$^a$S(O)$_2$R$^a$, and C$_{1-6}$ alkylC$_{3-8}$cycloalkyl;
wherein each alkyl, alkenyl, cycloalkyl, aryl, heteroaryl or heterocyclyl group is optionally substituted with 1 to 4 groups independently selected from the group consisting of —OR$^a$, —CN, halo, C$_{1-6}$alkyl, —C$_{1-6}$ alkylOR$^a$, —C$_{1-6}$ cyanoalkyl, —C$_{1-6}$ haloalkyl, C$_{3-8}$ cycloalkyl, —C$_{1-3}$ alkylC$_{3-8}$cycloalkyl, —C(O)R$^a$, —C$_{1-6}$ alkylC(O)R$^a$, —C(O)OR$^a$, —C$_{1-6}$ alkylC(O)OR$^a$, —NR$^a$R$^b$, —OC(O)NR$^a$R$^b$, NR$^a$C(O)OR$^b$, —C$_{1-6}$ alkylNR$^a$R$^b$, —C(O)NR$^a$R$^b$, —C$_{1-6}$ alkylC(O)NR$^a$R$^b$, —S(O)$_2$R$^a$, —C$_{1-6}$ alkylS(O)$_2$R$^a$, —S(O)$_2$NR$^a$R$^b$, —C$_{1-6}$ alkylS(O)$_2$NR$^a$R$^b$, —C(O)NR$^a$S(O)$_2$R$^b$, —C$_{1-6}$ alkylC(O)NR$^a$S(O)$_2$R$^b$, —NR$^a$C(O)R$^b$, and —C$_{1-6}$alkylNR$^a$C(O)R$^b$;

each R$^2$ is independently selected from the group consisting of H, —C$_{1-6}$ alkyl, —C$_{2-6}$ alkenyl, —C$_{2-6}$ alkynyl, —C$_{3-6}$ cycloalkyl, aryl, heteroaryl, heterocyclyl, —C$_{1-6}$ alkylaryl, —C$_{1-6}$ alkylheteroaryl, —C$_{1-6}$ alkylheterocyclyl, —C$_{2-6}$ alkyl-OR$^a$, —C$_{1-6}$ alkylC(O)OR$^a$, and —C$_{2-6}$ alkenylC(O)OR$^a$;
wherein each alkyl, alkenyl, cycloalkyl, aryl, heteroaryl or heterocyclyl group is optionally substituted with 1 to 4 groups independently selected from the group consisting of —OR$^a$, —CN, halo, C$_{1-6}$alkyl, —C$_{1-6}$ alkylOR$^a$, —C$_{1-6}$ cyanoalkyl, —C$_{1-6}$ haloalkyl, —C$_{3-8}$ cycloalkyl, —C$_{1-3}$ alkylC$_{3-8}$cycloalkyl, —C(O)R$^a$, —C$_{1-6}$ alkylC(O)R$^a$, —C(O)OR$^a$, —C$_{1-6}$ alkylC(O)OR$^a$, —NR$^a$R$^b$, —C$_{1-6}$ alkylNR$^a$R$^b$, —C(O)NR$^a$R$^b$, C$_{1-6}$ alkylC(O)NR$^a$R$^b$, —S(O)$_2$R$^a$, —C$_{1-6}$ alkylS(O)$_2$R$^a$, —S(O)$_2$NR$^a$R$^b$, —C$_{1-6}$ alkylS(O)$_2$NR$^a$R$^b$, —C(O)NR$^a$S(O)$_2$R$^b$ and —NR$^a$C(O)R$^b$;

or R$^1$ and R$^2$ combine to form a heterocyclyl group optionally containing 1, 2, or 3 additional heteroatoms independently selected from oxygen, sulfur and nitrogen, and optionally substituted with 1 to 3 groups independently selected from the group consisting of oxo, —C$_{1-6}$ alkyl, —C$_{3-8}$ cycloalkyl, —C$_{2-6}$ alkenyl, —C$_{2-6}$ alkynyl, —OR$^a$, —C(O)OR$^a$, —C$_{1-6}$ cyanoalkyl, —C$_{1-6}$ alkylOR$^a$, haloalkyl, —C$_{1-3}$ alkylC$_{3-8}$cycloalkyl, —C(O)R$^a$, C$_{1-6}$ alkyl C(O)R$^a$, —C$_{1-6}$ alkylC(O)OR$^a$, —NR$^a$R$^b$, —C$_{1-6}$alkylNR$^a$R$^b$, —C(O)NR$^a$R$^b$, —C$_{1-6}$ alkylC(O)NR$^a$R$^b$, —S(O)$_2$R$^a$, —C$_{1-6}$ alkylS(O)$_2$R$^a$, —S(O)$_2$NR$^a$R$^b$, and C$_{1-6}$ alkylS(O)$_2$NR$^a$R$^b$;

each R$^3$ is independently H, —C$_{1-6}$ alkyl, —C$_{2-6}$ alkenyl, —C$_{3-6}$ cycloalkyl, aryl, heteroaryl, heterocyclyl, —C$_{1-6}$ alkylaryl, —C$_{1-6}$ alkylheteroaryl, —C$_{1-6}$ alkylheterocyclyl, —C$_{2-6}$ alkyl-OR$^a$, —C$_{1-6}$ alkylC(O)OR$^a$, or —C$_{2-6}$ alkenyl-C(O)OR$^a$;

each R$^a$ is independently selected from the group consisting of H, —C$_{1-6}$ alkyl, —C$_{3-8}$ cycloalkyl, aryl, heteroaryl, heterocyclyl, —C$_{1-3}$ alkylC$_{3-8}$cycloalkyl, —C$_{1-6}$ alkylaryl, —C$_{1-6}$ alkylheteroaryl, and —C$_{1-6}$alkylheterocyclyl;

each R$^b$ is independently selected from the group consisting of H, —C$_{1-6}$ alkyl, —C$_{3-8}$ cycloalkyl, aryl, heteroaryl, heterocyclyl, —C$_{1-3}$ alkylC$_{3-8}$cycloalkyl, —C$_{1-6}$ alkylaryl, —C$_{1-6}$ alkylheteroaryl, and —C$_{1-6}$ alkylheterocyclyl;

or R$^a$ and R$^b$ may combine together to form a ring consisting of 3-8 ring atoms that are C, N, O, or S; wherein the ring is optionally substituted with 1 to 4 groups independently selected from the group consisting of —OR$^f$, —CN, halo, —C$_{1-6}$ alkylOR$^f$, —C$_{1-6}$ cyanoalkyl, —C$_{1-6}$ haloalkyl, —C$_{3-8}$ cycloalkyl, —C$_{1-3}$ alkylC$_{3-8}$cycloalkyl, —C(O)R$^f$, —C$_{1-6}$ alkylC(O)R$^f$, —C(O)OR$^f$, —C$_{1-6}$ alkylC(O)OR$^f$, —NR$^f$R$^g$, —C$_{1-6}$ alkylNR$^f$R$^g$, —C(O)NR$^f$R$^g$, C$_{1-6}$ alkylC(O)NR$^f$R$^g$, —S(O)$_2$R$^f$, —C$_{1-6}$ alkylS(O)$_2$R$^f$, —S(O)$_2$NR$^f$R$^g$, —C$_{1-6}$ alkylS(O)$_2$NR$^f$R$^g$, —C(O)NR$^f$S(O)$_2$R$^g$ and —NR$^f$C(O)R$^g$;

each R$^c$ is independently selected from the group consisting of H, OH, —C$_{1-6}$ alkyl, —C$_{3-8}$ cycloalkyl, aryl, heteroaryl, heterocyclyl, —C$_{1-3}$ alkylC$_{3-8}$ cycloalkyl, —C$_{1-6}$ alkylaryl, —C$_{1-6}$ alkylheteroaryl, and —C$_{1-6}$ alkylheterocyclyl;

each R$^d$ is independently selected from the group consisting of H, —C$_{1-6}$ alkyl, —C$_3$-C$_8$cycloalkyl, aryl, heteroaryl, heterocyclyl, —C$_{1-3}$ alkylC$_{3-8}$cycloalkyl, —C$_{1-6}$ alkylaryl, —C$_{1-6}$ alkylheteroaryl, and —C$_{1-6}$ alkylheterocyclyl;

each R$^e$ is independently selected from the group consisting of H, —C$_{1-6}$ alkyl, —O—C$_{1-6}$alkyl, —C$_{3-8}$ cycloalkyl, aryl, heteroaryl, heterocyclyl, —O—C$_{3-8}$ cycloalkyl, —O-aryl, —O-heteroaryl, —O-heterocyclyl, —$C_{1-3}$ alkyl$C_{3-8}$cycloalkyl, —$C_{1-6}$ alkylaryl, —$C_{1-6}$alkylheteroaryl, —NR$^f$R$^g$, —$C_{1-6}$alkylNR$^f$R$^g$, —C(O)NR$^f$R$^g$, —$C_{1-6}$ alkylC(O)NR$^f$R$^g$, —NHS(O)$_2$R$^f$, —$C_{1-6}$ alkylS(O)$_2$R$^f$, and —$C_{1-6}$ alkylS(O)$_2$NR$^f$R$^g$;

each R$^f$ is independently selected from the group consisting of H, —$C_{1-6}$ alkyl, —$C_{3-8}$ cycloalkyl, aryl, heteroaryl, heterocyclyl, —$C_{1-3}$ alkyl$C_{3-8}$ cycloalkyl, —$C_{1-6}$ alkylaryl, —$C_{1-6}$ alkylheteroaryl, and —$C_{1-6}$ alkylheterocyclyl;

each R$^g$ is independently selected from the group consisting of H, —$C_{1-6}$ alkyl, —$C_{3-8}$ cycloalkyl, aryl, heteroaryl, heterocyclyl, —$C_{1-3}$ alkyl$C_{3-8}$ cycloalkyl, —$C_{1-6}$ alkylaryl, —$C_{1-6}$ alkylheteroaryl, and —$C_{1-6}$ alkylheterocyclyl;

or a pharmaceutically acceptable salt, stereoisomer, mixture of stereoisomers, or tautomer thereof.

Also provided herein are compounds of Table 1, or a pharmaceutically acceptable salt, stereoisomer, mixture of stereoisomers, or tautomer thereof.

The present disclosure provides a method of inhibiting PD-1, PD-L1 and/or the PD-1/PD-L1 interaction comprising administering a compound of formula (I) or a pharmaceutically acceptable salt, stereoisomer, mixture of stereoisomers or tautomer thereof, to a patient in need thereof.

The present disclosure provides a method of treating cancer comprising administering a therapeutically effective amount of a compound formula (I) or a pharmaceutically acceptable salt, stereoisomer, mixture of stereoisomers, or tautomer thereof, to a patient in need thereof.

One embodiment provides the use of a compound of formula (I) or a pharmaceutically acceptable salt, stereoisomer, mixture of stereoisomers or tautomer thereof, for the treatment of cancer or a condition in a patient that is amenable to treatment by inhibiting PD-1, PD-L1 or the PD-1/PD-L1 interaction comprising administering said compound of formula (I) to said patient in need thereof.

In one embodiment, provided is a method for treating a cancer wherein the cancer is pancreatic cancer, bladder cancer, colorectal cancer, breast cancer, prostate cancer, renal cancer, hepatocellular cancer, lung cancer, ovarian cancer, cervical cancer, gastric cancer, esophageal cancer, head and neck cancer, melanoma, neuroendocrine cancer, CNS cancer, brain cancer, bone cancer, soft tissue sarcoma, non-small cell lung cancer, small-cell lung cancer or colon cancer, comprising administering a therapeutically effective amount of formula (I) or a pharmaceutically acceptable salt, stereoisomer, mixture of stereoisomers, or tautomer thereof to a patient in need thereof.

In one embodiment, provided is a method for treating a cancer or a condition in a patient that is amenable to treatment by inhibiting PD-1, PD-L1 or the PD-1/PD-L1 interaction selected from pancreatic cancer, bladder cancer, colorectal cancer, breast cancer, prostate cancer, renal cancer, hepatocellular cancer, lung cancer, ovarian cancer, cervical cancer, gastric cancer, esophageal cancer, head and neck cancer, melanoma, neuroendocrine cancer, CNS cancer, brain cancer, bone cancer, soft tissue sarcoma, non-small cell lung cancer, small-cell lung cancer and colon cancer comprising administering a therapeutically effective amount of a compound of formula (I) or a pharmaceutically acceptable salt, stereoisomer, mixture of stereoisomers, or tautomer thereof to a patient in need thereof, further comprising administering at least one additional anticancer agent or therapy to a patient in need thereof. In certain embodiments, the additional anticancer agent or therapy is selected from nivolumab, pembrolizumab, atezolizumab, ipilimumab, chemotherapy, radiation therapy, and resection therapy, to a patient in need thereof.

In one embodiment, provided is a method for treating hepatitis B virus (HBV), comprising administering a therapeutically effective amount of formula (I) or a pharmaceutically acceptable salt, stereoisomer, mixture of stereoisomers, or tautomer thereof to a patient in need thereof.

In one embodiment, provided is a compound of formula (I) or a pharmaceutically acceptable salt, stereoisomer, mixture of stereoisomers or tautomer thereof, for the treatment of cancer or a condition in a patient selected from lymphoma, multiple myeloma, and leukemia. Additional diseases or conditions that may be treated include, but are not limited to acute lymphocytic leukemia (ALL), acute myeloid leukemia (AML), chronic lymphocytic leukemia (CLL), small lymphocytic lymphoma (SLL), myelodysplastic syndrome (MDS), myeloproliferative disease (MPD), chronic myeloid leukemia (CML), multiple myeloma (MM), non-Hodgkin's lymphoma (NHL), mantle cell lymphoma (MCL), follicular lymphoma, Waldestrom's macroglobulinemia (WM), T-cell lymphoma, B-cell lymphoma and diffuse large B-cell lymphoma (DLBCL).

In one embodiment, the present disclosure provides a compound of formula (I) or a pharmaceutically acceptable salt, stereoisomer, mixture of stereoisomers or tautomer thereof, in combination with at least one additional anti-cancer agent selected from rituxan, doxorubicin, gemcitabine, nivolumab, pembrolizumab, and ipilimumab.

In one embodiment, the present disclosure provides a compound of formula (I) or a pharmaceutically acceptable salt, stereoisomer, mixture of stereoisomers or tautomer thereof, in combination with at least one additional checkpoint inhibitor selected from nivolumab, pembrolizumab, atezolizumab, and ipilimumab.

In one embodiment, the present disclosure provides a pharmaceutical composition comprising a compound of formula (I) or a pharmaceutically acceptable salt, stereoisomer, mixture of stereoisomers or tautomer thereof, and a pharmaceutically acceptable carrier or excipient.

In one embodiment, the present disclosure provides a pharmaceutical composition comprising a compound of formula (I) or a pharmaceutically acceptable salt, stereoisomer, mixture of stereoisomers or tautomer thereof, and at least one additional anticancer agent and at least one pharmaceutically acceptable carrier or excipient.

In one embodiment, the present disclosure provides a pharmaceutical composition comprising a compound of formula (I) or a pharmaceutically acceptable salt, stereoisomer, mixture of stereoisomers or tautomer thereof, at least one additional therapeutic agent suitable for treating an HBV infection, and at least one pharmaceutically acceptable carrier or excipient.

In one embodiment, the present disclosure provides a kit that includes a compound of formula (I) or a pharmaceutically acceptable salt, stereoisomer, mixture of stereoisomers or tautomer thereof, a label and/or instructions for use of the compound in the treatment of cancer or a disease or condition mediated by PD-1, PD-L1 activity or the PD-1/PD-L1 interaction.

In one embodiment, the present disclosure provides a kit that includes a compound of formula (I) or a pharmaceutically acceptable salt, stereoisomer, mixture of stereoisomers or tautomer thereof, at least one additional anticancer agent, a label(s) and/or instructions for use of the compound(s) in the treatment of a disease or condition mediated by PD-1, PD-L1 activity or PD-1/PD-L1 interaction.

In one embodiment, the present disclosure provides articles of manufacture that include a compound of formula (I) or a pharmaceutically acceptable salt, or solvate thereof, and a container. In one embodiment, the container may be a vial, jar, ampoule, preloaded syringe, or an intravenous bag.

In one embodiment, the present disclosure provides a compound of formula (I) for use in therapy.

In another embodiment, the present disclosure provides a compound of formula (I) for use in the manufacture of a medicament for treating cancer.

DESCRIPTION OF THE FIGURES

FIG. 1, panels A (FIG. 1A) and B (FIG. 1B), show that compound 139 enhances IFN-γ and Granzyme B Production in chronic hepatitis B (CHB) CD8⁺ T Cells.

FIG. 2, panels A (FIG. 2A) and B (FIG. 2B), show that compound 139 enhances IFN-γ and Granzyme B Production in chronic hepatitis B (CHB) CD4⁺ T Cells.

FIG. 3 shows the experimental design for mouse PD-L1 knockout and replacement with human PD-L1 in MC38 mouse colorectal tumor cell line.

DETAILED DESCRIPTION

Definitions

Figure 4A:
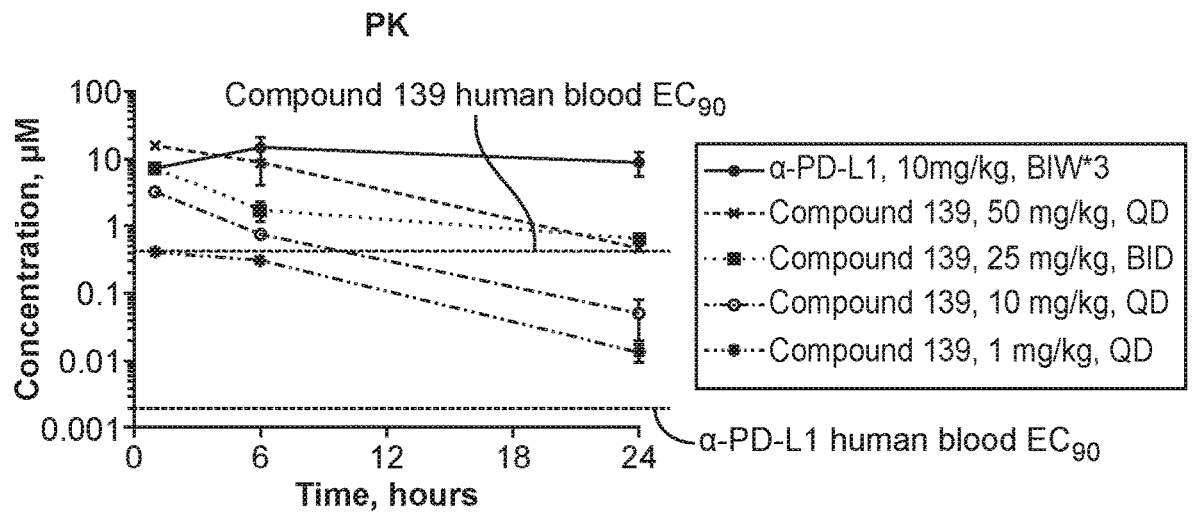
FIG. 4 shows the relationship between PK (FIG. 4A) and TO (FIG. 4B) for compound 139 on Day 6 in a human PD-L1 MC38 C57BL/6 mouse tumor model.

As used in the present disclosure, the following words and phrases are generally intended to have the meanings as set forth below unless expressly indicated otherwise or the context in which they are used indicates otherwise.

The following description sets forth exemplary methods, parameters and the like. It should be recognized, however, that such description is not intended as a limitation on the scope of the present disclosure but is instead provided as a description of exemplary embodiments.

As used in the present specification, the following words, phrases and symbols are generally intended to have the meanings as set forth below, except to the extent that the context in which they are used indicates otherwise.

A dash ("-") that is not between two letters or symbols is used to indicate a point of attachment for a substituent. For example, —C(O)NH₂ is attached through the carbon atom. A dash at the front or end of a chemical group is a matter of convenience; chemical groups may be depicted with or without one or more dashes without losing their ordinary meaning. Unless chemically or structurally required, no directionality is indicated or implied by the order in which a chemical group is written or named.

A squiggly line on a chemical group as shown below, for example,

indicates a point of attachment, i.e., it shows the broken bond by which the group is connected to another described group.

The prefix "$C_{u\text{-}v}$" indicates that the following group has from u to v carbon atoms. For example, "$C_{1\text{-}6}$ alkyl" indicates that the alkyl group has from 1 to 6 carbon atoms.

Reference to "about" a value or parameter herein includes (and describes) embodiments that are directed to that value or parameter per se. In certain embodiments, the term "about" includes the indicated amount ±10%. In other embodiments, the term "about" includes the indicated amount ±5%. In certain other embodiments, the term "about" includes the indicated amount ±1%. Also, to the term "about X" includes description of "X". Also, the singular forms "a" and "the" include plural references unless the context clearly dictates otherwise. Thus, e.g., reference to "the compound" includes a plurality of such compounds and reference to "the assay" includes reference to one or more assays and equivalents thereof known to those skilled in the art.

The term "substituted" means that any one or more (e.g., one to three, or one to five) hydrogen atoms on the designated atom or group is replaced with one or more (e.g., one to three, or one to five) substituents other than hydrogen, provided that the designated atom's normal valence is not exceeded. The one or more (e.g., one to three, or one to five) substituents include, but are not limited to, alkyl, alkenyl, alkynyl, alkoxy, acyl, amino, amido, amidino, aryl, azido, carbamoyl, carboxyl, carboxyl ester, cyano, guanidino, halo, haloalkyl, heteroalkyl, heteroaryl, heterocycloalkyl, hydroxy, hydrazino, imino, oxo, nitro, alkylsulfinyl, sulfonic acid, alkylsulfonyl, thiocyanate, thiol, thione, or combinations thereof. Polymers or similar indefinite structures arrived at by defining substituents with further substituents appended ad infinitum (e.g., a substituted aryl having a substituted alkyl which is itself substituted with a substituted aryl group, which is further substituted by a substituted heteroalkyl group, etc.) are not intended for inclusion herein, whether the substituents are the same or different. Unless otherwise noted, the maximum number of serial substitutions in compounds described herein is three. For example, serial substitutions of substituted aryl groups with two other substituted aryl groups are limited to ((substituted aryl) substituted aryl) substituted aryl. Similarly, the above definitions are not intended to include impermissible substitution patterns (e.g., methyl substituted with 5 fluorines or heteroaryl groups having two adjacent oxygen ring atoms). Such impermissible substitution patterns are well known to the skilled artisan. When used to modify a chemical group, the term "substituted" may describe other chemical groups defined herein. For example, the term "substituted aryl" includes, but is not limited to, "alkylaryl." Unless specified otherwise, where a group is described as optionally substituted, any substituents of the group are themselves unsubstituted.

A "substituted" group also includes embodiments in which a monoradical substituent is bound to a single atom of the substituted group (e.g., forming a branch), and also includes embodiments in which the substituent may be a diradical bridging group bound to two adjacent atoms of the substituted group, thereby forming a fused ring on the substituted group.

"Alkyl" refers to an unbranched or branched saturated hydrocarbon chain. As used herein, alkyl has 1 to 20 carbon atoms (i.e., $C_{1\text{-}20}$ alkyl), 1 to 8 carbon atoms (i.e., CL-s alkyl), 1 to 6 carbon atoms (i.e., $C_{1\text{-}6}$ alkyl), or 1 to 4 carbon atoms (i.e., $C_{1\text{-}4}$ alkyl). Examples of alkyl groups include methyl, ethyl, propyl, isopropyl, n-butyl, sec-butyl, isobutyl, tert-butyl, pentyl, 2-pentyl, isopentyl, neopentyl, hexyl, 2-hexyl, 3-hexyl, and 3-methylpentyl. When an alkyl residue having a specific number of carbons is named by chemical name or identified by molecular formula, all positional isomers having that number of carbons may be encompassed; thus, for example, "butyl" includes n-butyl (i.e., —$(CH_2)_3CH_3$), sec-butyl (i.e., —$CH(CH_3)CH_2CH_3$), isobutyl (i.e., —$CH_2CH(CH_3)_2$) and tert-butyl (i.e., —$C(CH_3)_3$); and "propyl" includes n-propyl (i.e., —$(CH_2)_2CH_3$) and isopropyl (i.e., —$CH(CH_3)_2$).

"Alkenyl" refers to an aliphatic group containing at least one carbon-carbon double bond and having from 2 to 20 carbon atoms (i.e., $C_{2-20}$ alkenyl), 2 to 8 carbon atoms (i.e., $C_{2-8}$ alkenyl), 2 to 6 carbon atoms (i.e., $C_{2-6}$ alkenyl), or 2 to 4 carbon atoms (i.e., $C_{2-4}$ alkenyl). Examples of alkenyl groups include ethenyl, propenyl, butadienyl (including 1,2-butadienyl, and 1,3-butadienyl).

"Alkynyl" refers to an aliphatic group containing at least one carbon-carbon triple bond and having from 2 to 20 carbon atoms (i.e., $C_{2-20}$ alkynyl), 2 to 8 carbon atoms (i.e., $C_{2-8}$ alkynyl), 2 to 6 carbon atoms (i.e., $C_{2-6}$ alkynyl), or 2 to 4 carbon atoms (i.e., $C_{2-4}$ alkynyl). The term "alkynyl" also includes those groups having one triple bond and one double bond.

"Alkoxy" refers to the group "alkyl-O—" or "—O-alkyl". Examples of alkoxy groups include methoxy, ethoxy, n-propoxy, iso-propoxy, n-butoxy, tert-butoxy, sec-butoxy, n-pentoxy, n-hexoxy, and 1,2-dimethylbutoxy.

"Haloalkoxy" refers to an alkoxy group as defined above, wherein one or more (e.g., one to three, or one to five) hydrogen atoms are replaced by a halogen.

"Amino" refers to the group —$NR^yR^z$ wherein $R^y$ and $R^z$ are independently selected from hydrogen, alkyl, haloalkyl, cycloalkyl, aryl, heterocyclyl, or heteroaryl; each of which may be optionally substituted.

"Aryl" refers to a monoradical or diradical aromatic carbocyclic group having a single ring (e.g., monocyclic) or multiple rings (e.g., bicyclic or tricyclic) including fused ring systems wherein one or more (e.g., one, two, or three) fused rings is/are fully or partially unsaturated. As used herein, aryl has 6 to 20 ring carbon atoms (i.e., $C_{6-20}$ aryl), 6 to 12 carbon ring atoms (i.e., $C_{6-12}$ aryl), or 6 to 10 carbon ring atoms (i.e., $C_{6-10}$ aryl). Non-limiting examples of aryl groups as used herein include phenyl, naphthyl, fluorenyl, indanyl, tetrahydroindanuyl, and anthryl. Aryl, however, does not encompass or overlap in any way with heteroaryl defined below. If one or more aryl groups are fused with a heteroaryl ring, the resulting ring system is heteroaryl. The classification of mono or diradical indicates whether the aryl group terminates the chain (monoradical) or is within a chain (diradical). The above definition does not preclude additional substituents on the aryl group. For example, as used herein, the aryl group in "A-aryl-B" is a diradical whereas the aryl group in "A-B-aryl" is monoradical, though additional substituents may be present on each aryl group.

The term "alkylsulfinyl" refers to the group —S(O)-alkyl, where alkyl is as defined above, and includes optionally substituted alkyl groups as also defined above.

The term "alkylsulfonyl" refers to the group —$S(O)_2$-alkyl, where alkyl is as defined above, and includes optionally substituted alkyl groups as also defined above.

"Cycloalkyl" refers to a saturated or partially saturated cyclic alkyl group having a single ring or multiple rings including fused, bridged, and spiro ring systems. As used herein, cycloalkyl has from 3 to 20 ring carbon atoms (i.e., $C_{3-20}$ cycloalkyl), 3 to 12 carbon ring atoms (i.e., $C_{3-12}$ cycloalkyl), 3 to 10 ring carbon atoms (i.e., $C_{3-10}$ cycloalkyl), 3 to 8 ring carbon atoms (i.e., $C_{3-8}$ cycloalkyl), or 3 to 6 ring carbon atoms (i.e., $C_{3-6}$ cycloalkyl). Examples of cycloalkyl groups include cyclopropyl, cyclobutyl, cyclopentyl, and cyclohexyl. As used herein the term "cycloalk-enyl" refers to the non-aromatic carbocyclic (partially saturated cyclic alkyl) group having at least one double bond.

"Cyanoalkyl" refers to an alkyl group substituted with cyano (CN).

"Halogen" or "halo" includes fluoro, chloro, bromo, and iodo.

The term "haloalkyl" refers to a monoradical or diradical having the indicated carbon atoms of the alkyl group wherein one or more (e.g., one to three, or one to five) hydrogen atoms have been substituted by a halogen. Examples of haloalkyl groups include —$CH_2F$, —$CHF_2$, —$CF_3$, —$CH_2CF_3$, —$CHFCH_2F$, —$CF_2$—, —$CHF$—, and the like. Similarly, the term "haloalkoxy", e.g., —O—$C_{1-3}$ haloalkyl, refers to an alkoxy group wherein one or more (e.g., one to three, or one to five) hydrogen atoms of the alkyl group have been substituted by a halogen. Examples of haloalkoxy groups include —$OCH_2F$, —$OCHF_2$, —$OCF_3$, —$OCH_2CF_3$, —$OCHFCH_2F$, and the like. One of skill in the art is aware that similar definitions apply for the alkenyl and alkynyl analogs (e.g., $C_{2-4}$haloalkenyl, —O—$C_{2-4}$haloalkynyl).

"Heteroalkyl" refers to an alkyl group in which one or more (e.g., one to three, or one to five) of the carbon atoms (and any associated hydrogen atoms) are each independently replaced with the same or different heteroatomic groups. The term "heteroalkyl" includes unbranched or branched saturated chain having carbon and heteroatoms. By way of example, 1, 2 or 3 carbon atoms may be independently replaced with the same or different heteroatomic group. Heteroatomic groups include, but are not limited to, —NR—, —O—, —S—, —S(O)—, —$S(O)_2$—, and the like, where R is H, alkyl, aryl, cycloalkyl, heteroalkyl, heteroaryl, or heterocycloalkyl, each of which may be optionally substituted. Examples of heteroalkyl groups include —$OCH_3$, —$CH_2OCH_3$, —$SCH_3$, —$CH_2SCH_3$, —$NRCH_3$, and —$CH_2NRCH_3$, where R is hydrogen, alkyl, cycloalkyl, aryl, arylalkyl, heteroalkyl, or heteroaryl, each of which may be optionally substituted. As used herein, heteroalkyl includes 1 to 10 carbon atoms, 1 to 8 carbon atoms, or 1 to 4 carbon atoms; and 1 to 3 heteroatoms, 1 to 2 heteroatoms, or 1 heteroatom.

"Heteroaryl" refers to a monoradical or diradical aromatic group having a single ring, multiple rings, or multiple fused rings, with one or more ring heteroatoms independently selected from nitrogen, oxygen, and sulfur. The term includes fused ring systems wherein one or more (e.g., one, two, or three) fused rings is/are fully or partially unsaturated. As used herein, heteroaryl include 1 to 20 ring carbon atoms (i.e., $C_{1-20}$ heteroaryl), 3 to 12 ring carbon atoms (i.e., $C_{3-12}$ heteroaryl), or 3 to 8 carbon ring atoms (i.e., $C_{3-8}$ heteroaryl); and 1 to 5 heteroatoms, 1 to 4 heteroatoms, 1 to 3 ring heteroatoms, 1 to 2 ring heteroatoms, or 1 ring heteroatom independently selected from nitrogen, oxygen, and sulfur. Non-limiting examples of heteroaryl groups include pyrimidinyl, purinyl, pyridyl, pyridazinyl, benzothiazolyl, benzodioxanyl, indolinyl, and pyrazolyl. The classification of mono or diradical indicates whether the heteroaryl group terminates the chain (monoradical) or is within a chain (diradical). The above definition does not preclude additional substituents on the heteroaryl group. For example, the heteroaryl group in "A-heteroaryl-B" is a diradical whereas the heteroaryl group in "A-B-heteroaryl" is monoradical, though additional substituents may be present on each heteroaryl group. Heteroaryl does not encompass or overlap with aryl as defined above.

"Heterocycloalkyl" refers to a saturated or unsaturated cyclic alkyl group, with one or more ring heteroatoms independently selected from nitrogen, oxygen and sulfur. A heterocycloalkyl may be a single ring or multiple rings wherein the multiple rings may be fused, bridged, or spiro. As used herein, heterocycloalkyl has 2 to 20 ring carbon atoms (i.e., $C_{2-20}$ heterocycloalkyl), 2 to 12 ring carbon atoms (i.e., $C_{2-12}$ heterocycloalkyl), 2 to 10 ring carbon atoms (i.e., $C_{2-10}$ heterocycloalkyl), 2 to 8 ring carbon atoms (i.e., $C_{2-8}$ heterocycloalkyl), 3 to 12 ring carbon atoms (i.e., $C_{3-12}$ heterocycloalkyl), 3 to 8 ring carbon atoms (i.e., $C_{3-8}$ heterocycloalkyl), or 3 to 6 ring carbon atoms (i.e., $C_{3-6}$ heterocycloalkyl); having 1 to 5 ring heteroatoms, 1 to 4 ring heteroatoms, 1 to 3 ring heteroatoms, 1 to 2 ring heteroatoms, or 1 ring heteroatom independently selected from nitrogen, sulfur or oxygen. Examples of heterocycloalkyl groups include pyrrolidinyl, piperidinyl, piperazinyl, oxetanyl, dioxolanyl, azetidinyl, and morpholinyl. As used herein, the term "bridged-heterocycloalkyl" refers to a four- to ten-membered cyclic moiety connected at two non-adjacent atoms of the heterocycloalkyl with one or more (e.g., 1 or 2) four- to ten-membered cyclic moiety having at least one heteroatom where each heteroatom is independently selected from nitrogen, oxygen, and sulfur. As used herein, bridged-heterocycloalkyl includes bicyclic and tricyclic ring systems. Also used herein, the term "spiro-heterocycloalkyl" refers to a ring system in which a three- to ten-membered heterocycloalkyl has one or more additional ring, wherein the one or more additional ring is three- to ten-membered cycloalkyl or three- to ten-membered heterocycloalkyl, where a single atom of the one or more additional ring is also an atom of the three- to ten-membered heterocycloalkyl. Examples of spiro-heterocycloalkyl include bicyclic and tricyclic ring systems, such as 2-oxa-7-azaspiro[3.5] nonanyl, 2-oxa-6-azaspiro[3.4]octanyl, and 6-oxa-1-azaspiro[3.3]heptanyl.

The term "heterocyclyl," "heterocycle," or "heterocyclic" refers to a monoradical or diradical saturated or unsaturated group having a single ring or multiple condensed rings, having from 3 to 12 carbon atoms, from 1 to 6 hetero atoms, or from 1 to 4 heteroatoms, selected from nitrogen, sulfur, phosphorus, and/or oxygen within the ring. Where the group does not terminate the molecule, it is a diradical and is construed as such i.e., also referred to as heterocyclylene or heterocyclene.

The term "heterocyclyl" includes heterocycloalkenyl groups (i.e., the heterocyclyl group having at least one double bond), bridged-heterocyclyl groups, fused-heterocyclyl groups, and spiro-heterocyclyl groups. A heterocyclyl may be a single ring or multiple rings wherein the multiple rings may be fused, bridged, or spiro. Any non-aromatic ring containing at least one heteroatom is considered a heterocyclyl, regardless of the attachment (i.e., can be bound through a carbon atom or a heteroatom). Further, the term heterocyclyl is intended to encompass any non-aromatic ring containing at least one heteroatom, which ring may be fused to an aryl or heteroaryl ring, regardless of the attachment to the remainder of the molecule. A heterocyclyl may contain one or more (e.g., one or two) oxo and/or thioxo groups.

Exemplary heterocyclic groups include, but are not limited to, 2,5-diazaspiro[3.4]octan-6-one (e.g., compound 1), azetidine (e.g., compound 2), 2,6-diazaspiro[3.3]heptane (e.g., compound 4), pyrrolidin-2-one (e.g., compound 6), tetrahydrofuran (e.g., compound 11), pyrrolidine (e.g., compound 17), piperidin-2-one (e.g., compound 36), piperazin-2-one (e.g., compound 41), 5-oxa-2,7-diazaspiro[3.4]octan-6-one (e.g., compound 50), 3-azabicyclo[3.1.0]hexane (e.g., compound 52), 2-azabicyclo[2.1.1]hexane (e.g., compound 53), tetrahydro-2H-pyran (e.g., compound 55), 2,6-diazaspiro[3.4]octan-7-one (e.g., compound 61), 4,5-dihydro-1H-imidazole (e.g., compound 114), 1,4,5,6-tetrahydropyrimidine (e.g., compound 119), piperidine (e.g., compound 158), 1,2,4-oxadiazol-5(2H)-one (e.g., compound 161), 2,5,7-triazaspiro[3.4]octan-6-one (e.g., compound 168), 2,7-diazaspiro[4.4]nonan-3-one (e.g., compound 193), 1,7-diazaspiro[4.4]nonan-2-one (e.g., compound 197), 2-azaspiro[4.4]nonan-3-one (e.g., compound 202), 1,8-diazaspiro[4.5]decan-2-one (e.g., compound 203), 2-azaspiro[3.3]heptane (e.g., compound 208), oxazolidin-2-one (e.g., compound 210), octahydrocyclopenta[b]pyrrole (e.g., compound 216), octahydrocyclopenta[c]pyrrole (e.g., compound 230), 2-oxa-7-azaspiro[4.4]nonan-1-one (e.g., compound 232), 6-oxa-2-azaspiro[3.4]octane (e.g., compound 234), piperazine (e.g., compound 250), 1,1-dioxotetrahydrothiophene (e.g., compound 286), hexahydropyrrolo[3,4-b]pyrrol-6(1H)-one (e.g., compound 287), 1,3,8-triazaspiro[4.5]decane-2,4-dione (e.g., compound 290), 2-methyl-1,3,7-triazaspiro[4.5]dec-2-en-4-one (e.g., compound 291), 1,3,7-triazaspiro[4.4]nonane-2,4-dione (e.g., compound 292), 1,3,7-triazaspiro[4.5]decane-2,4-dione (e.g., compound 293), 6-azaspiro[3.4]octane (e.g., compound 298), 1-thia-6-azaspiro[3.3]heptane 1,1-dioxide (e.g., compound 301), pyridin-2(1H)-one (e.g., compound 305), isothiazolidine 1,1-dioxide (e.g., compound 306), thietane 1,1-dioxide (e.g., compound 311), hexahydropyrrolo[3,4-b]pyrrol-2(1H)-one (e.g., compound 312), 2,5,7-triazaspiro[3.4]octane-6,8-dione (e.g., compound 313), 3-azabicyclo[3.1.0]hexan-2-one (e.g., compound 324), 5-azaspiro[2.4]heptan-4-one (e.g., compound 331), oxetane (e.g., compound 333), morpholine (e.g., compound 351), 2-thiaspiro[3.3]heptane 2,2-dioxide (e.g., compound 363), hexahydrocyclopenta[b]pyrrol-2(1H)-one (e.g., compound 388), pyrrolidine-2,5-dione (e.g., compound 403), 6,7-dihydro-5H-pyrrolo[3,4-b]pyridine (e.g., compound 414), and 1,3-dioxolane (e.g., compound 433).

"Acyl" refers to a group —C(=O)R, wherein R is hydrogen, alkyl, cycloalkyl, heterocycloalkyl, aryl, heteroalkyl, or heteroaryl; each of which may be optionally substituted, as defined herein. Examples of acyl include formyl, acetyl, cyclohexylcarbonyl, cyclohexylmethyl-carbonyl, and benzoyl.

The term "N-alkylated" means an alkyl group is substituted for one of the hydrogen atoms of a mono substituted amine, or a di-substituted amine group or a tri substituted amine group. When the alkylation is on a tri-substituted amine group an alkonium salt is generated i.e., a positive charge is generated on the nitrogen atom. N-alkylation is commonly associated with alkyl substitution on a ring nitrogen atom.

The term "cyano" refers to the group —CN.

The term "oxo" refers to a group =O.

The term "carboxy" refers to a group —C(O)OH.

The term "ester" or "carboxyl ester" refers to the group —C(O)OR, where R is alkyl, cycloalkyl, aryl, heteroaryl, or heterocyclyl, which may be optionally further substituted, for example, by alkyl, alkoxy, halogen, $CF_3$, amino, substituted amino, cyano or —S(O)$_y$R$^z$, in which R$^z$ is alkyl, aryl, or heteroaryl, and y is 0, 1 or 2.

The term "substituted amino" refers to the group —NRR, where each R is independently hydrogen, alkyl, cycloalkyl, aryl, heteroaryl, or heterocyclyl, each of which may be optionally substituted, or a group as described or exemplified herein, or where both R groups are joined to form a heterocyclic group (e.g., morpholino) as described or exemplified herein, which also may be optionally substituted.

The term "amido" refers to the group —C(O)NRR where each R is independently hydrogen, alkyl, cycloalkyl, aryl, heteroaryl, or heterocyclyl, each of which may be optionally substituted, or a group as described or exemplified herein, or where both R groups are joined to form a heterocyclic group (e.g., morpholino) as described or exemplified herein, which also may be optionally substituted.

The term "sulfoxide" refers to a group —S(O)R, in which R is alkyl, cycloalkyl, heterocyclyl, aryl, or heteroaryl, each of which may be optionally substituted.

The term "sulfone" refers to a group —S(O)$_2$R, in which R is alkyl, cycloalkyl, heterocyclyl, aryl, or heteroaryl, each of which may be optionally substituted.

As used herein, the terms "alkylcycloalkyl," "alkylaryl," "alkylheteroaryl" and "alkylheterocyclyl" are intended to refer to a cycloalkyl, aryl, heteroaryl or heterocyclyl group which is bound to the remainder of the molecule via an alkyl moiety, where the terms "alkyl," "cycloalkyl," "aryl," "heteroaryl" and "heterocyclyl" are as defined herein. Exemplary alkylaryl groups include benzyl, phenethyl, and the like.

"Optional" or "optionally" means that the subsequently described event or circumstance may or may not occur, and that the description includes instances where said event or circumstance occurs and instances in which it does not.

Certain commonly used alternative chemical names may be used. For example, a divalent group such as a divalent "alkyl" group, a divalent "aryl" group, etc., may also be referred to as an "alkylene" group or an "alkylenyl" group, an "arylene" group or an "arylenyl" group, respectively. Also, unless indicated explicitly otherwise, where combinations of groups are referred to herein as one moiety, e.g., arylalkyl, the last mentioned group contains the atom by which the moiety is attached to the rest of the molecule.

Where a group is represented by a bond, multiple adjacent groups whether the same or different, when represented by bonds, constitute a single bond. For example the group "-L$^1$-V$^1$-L$^2$-" constitutes a single bond if each of L$^1$, V$^1$ and L$^2$ is a bond.

Where a given group (moiety) is described herein as being attached to a second group and the site of attachment is not explicit, the given group may be attached at any available site of the given group or to any available site of the second group. For example, an "alkyl-substituted phenyl", where the attachment sites are not explicit, may have any available site of the alkyl group attached to any available site of the phenyl group. In this regard, an "available site" is a site of the group at which hydrogen of the group may be replaced with a substituent.

"Isomers" are different compounds that have the same molecular formula. Isomers include stereoisomers, enantiomers and diastereomers.

"Stereoisomers" are isomers that differ only in the way the atoms are arranged in space.

"Enantiomers" are a pair of stereoisomers that are non-superimposable mirror images of each other. A 1:1 mixture of a pair of enantiomers is a "racemic" mixture. The term "(±)" is used to designate a racemic mixture where appropriate.

"Diastereoisomers" are stereoisomers that have at least two asymmetric atoms, but which are not mirror-images of each other.

The compounds of the disclosure may possess one or more asymmetric centers and may be produced as a racemic mixture or as individual enantiomers or diastereoisomers. The number of stereoisomers present in any given compound of a given formula depends upon the number of asymmetric centers present (there are $2^n$ stereoisomers possible where n is the number of asymmetric centers). The individual stereoisomers may be obtained by resolving a racemic or non-racemic mixture of an intermediate at some appropriate stage of the synthesis or by resolution of the compound by conventional means. The individual stereoisomers (including individual enantiomers and diastereoisomers) as well as racemic and non-racemic mixture of stereoisomers are encompassed within the scope of the present disclosure, all of which are intended to be depicted by the structures of this specification unless otherwise specifically indicated.

The absolute stereochemistry is specified according to the Cahn Ingold Prelog R S system. When the compound is a pure enantiomer the stereochemistry at each chiral carbon may be specified by either R or S. A resolved compound whose absolute configuration is unknown may be designated (+) or (−) depending on the direction (dextro- or laevorotary) that it rotates the plane of polarized light at the wavelength of the sodium D line.

Some of the compounds exist as tautomeric isomers. Tautomeric isomers are in equilibrium with one another. For example, amide containing compounds may exist in equilibrium with imidic acid tautomers. Regardless of which tautomer is shown, and regardless of the nature of the equilibrium among tautomers, the compounds are understood by one of ordinary skill in the art to comprise both amide and imidic acid tautomers. Thus, the amide containing compounds are understood to include their imidic acid tautomers. Likewise, the imidic acid containing compounds are understood to include their amide tautomers.

The term "solvate" refers to a complex formed by combining a compound of formula (I), or any other formula as disclosed herein and a solvent.

The term "hydrate" refers to the complex formed by the combining of a compound of formula (I), or any formula disclosed herein, and water.

The term "prodrug" refers to compounds of formula (I), or derivatives of formula (I) disclosed herein, that include chemical groups which, in vivo, can be converted and/or can be split off from the remainder of the molecule to provide for the active drug. Pharmaceutically acceptable salts or biologically active metabolites thereof of the prodrug of a compound of formula (I) are also within the ambit of the present disclosure.

Any formula or structure given herein, including formula (I), or any formula disclosed herein, is intended to represent unlabeled forms as well as isotopically labeled forms of the compounds. Isotopically labeled compounds have structures depicted by the formulas given herein except that one or more (e.g., one to three, or one to five) atoms are replaced by an isotope having a selected atomic mass or mass number. Examples of isotopes that can be incorporated into compounds of the disclosure include isotopes of hydrogen, carbon, nitrogen, oxygen, phosphorus, fluorine and chlorine, such as, but not limited to $^2$H (deuterium, D), $^3$H (tritium), $^{11}$C, $^{13}$C, $^{14}$C, $^{15}$N, $^{18}$F, $^{31}$P, $^{32}$P, $^{35}$S, $^{36}$Cl, and $^{125}$I. Various isotopically labeled compounds of the present disclosure, for example those into which radioactive isotopes such as $^3$H, $^{13}$C and $^{14}$C are incorporated, are within the ambit of the present disclosure. Such isotopically labelled compounds may be useful in metabolic studies, reaction kinetic studies, detection or imaging techniques, such as positron emission tomography (PET) or single-photon emission computed tomography (SPECT) including drug or substrate tissue distribution assays or in treatment of patients. Such isotopically labeled analogs of compounds of the present disclosure may also be useful for treatment of diseases disclosed herein because they may provide improved pharmacokinetic and/or pharmacodynamic properties over the unlabeled forms of the same compounds. Such isotopically leveled forms of or analogs of compounds herein are within the ambit of the present disclosure. One of skill in the art is able to prepare and use such isotopically labeled forms following procedures for isotopically labeling compounds or aspects of compounds to arrive at isotopic or radiolabeled analogs of compounds disclosed herein.

The term "pharmaceutically acceptable salt" of a given compound refers to salts that retain the biological effectiveness and properties of the given compound, and which are not biologically or otherwise undesirable. Pharmaceutically acceptable base addition salts can be prepared from inorganic and organic bases. Salts derived from inorganic bases include, by way of example only, sodium, potassium, lithium, ammonium, calcium and magnesium salts. Salts derived from organic bases include, but are not limited to, salts of primary, secondary and tertiary amines, such as alkyl amines, dialkyl amines, trialkyl amines, substituted alkyl amines, di(substituted alkyl) amines, tri(substituted alkyl) amines, alkenyl amines, dialkenyl amines, trialkenyl amines, substituted alkenyl amines, di(substituted alkenyl) amines, tri(substituted alkenyl) amines, cycloalkyl amines, di(cycloalkyl) amines, tri(cycloalkyl) amines, substituted cycloalkyl amines, di-substituted cycloalkyl amine, tri-substituted cycloalkyl amines, cycloalkenyl amines, di(cycloalkenyl) amines, tri(cycloalkenyl) amines, substituted cycloalkenyl amines, di-substituted cycloalkenyl amine, tri-substituted cycloalkenyl amines, aryl amines, diaryl amines, triaryl amines, heteroaryl amines, diheteroaryl amines, triheteroaryl amines, heterocyclic amines, diheterocyclic amines, triheterocyclic amines, mixed di- and tri-amines where at least two of the substituents on the amine are different and are selected from alkyl, substituted alkyl, alkenyl, substituted alkenyl, cycloalkyl, substituted cycloalkyl, cycloalkenyl, substituted cycloalkenyl, aryl, heteroaryl, heterocyclic, and the like. Also included are amines where the two or three substituents, together with the amino nitrogen, form a heterocyclic or heteroaryl group. Amines are of general structure $N(R^{30})(R^{31})(R^{32})$, wherein mono-substituted amines have two of the three substituents on nitrogen ($R^{30}$, $R^{31}$, and $R^{32}$) as hydrogen, di-substituted amines have one of the three substituents on nitrogen ($R^{30}$, $R^{31}$, and $R^{32}$) as hydrogen, whereas tri-substituted amines have none of the three substituents on nitrogen ($R^{30}$, $R^{31}$, and $R^{32}$) as hydrogen. $R^{30}$, $R^{31}$, and $R^{32}$ are selected from a variety of substituents such as hydrogen, optionally substituted alkyl, aryl, heteroaryl, cycloalkyl, cycloalkenyl, heterocyclyl, and the like.

Specific examples of suitable amines include, by way of example only, isopropyl amine, trimethyl amine, diethyl amine, tri(iso-propyl) amine, tri(n-propyl) amine, ethanolamine, diethanolamine, 2-dimethylamino ethanol, lysine, arginine, histidine, caffeine, procaine, hydrabamine, choline, betaine, ethylenediamine, glucosamine, N-alkylglucamines, theobromine, purines, piperazine, piperidine, morpholine, N-ethylpiperidine, and the like.

Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

As used herein, "pharmaceutically acceptable carrier" or "pharmaceutically acceptable excipient" includes any and all solvents, dispersion media, coatings, antibacterial, and antifungal agents, isotonic and absorption delaying agents and the like. The use of such media and agents for pharmaceutically active substances is well known in the art. Except insofar as any conventional media or agent is incompatible with the active ingredient, or unless otherwise indicated herein, its use in the therapeutic compositions is contemplated. Supplementary active ingredients can also be incorporated into the compositions.

The term "anticancer agent" is any drug that is effective in the treatment of a malignant, or cancerous disease. Effectiveness may mean inhibition, partial, or full remission, prolongation of life, improvement in quality of life, or cure. There are several major classes of anticancer drugs including chemical compositions as disclosed herein or known to one of skill in the art e.g., PD-1, PD-L1, PD-1/PD-L1 interaction inhibitors, alkylating agents, antimetabolites, natural products, and hormones.

The term "additional anticancer agent" as used herein means the use or combination of a second, third, fourth, fifth, etc., anticancer agent(s) in addition to a compound according to formula (I) disclosed herein.

The term "anticancer therapy" means any currently known therapeutic methods for the treatment of cancer.

The term "blockade agent" or "check point inhibitors" are classes of immune oncology agents that inhibit PD-1, PD-L1, or the PD-1/PD-L1 interaction.

The term "treatment" or "treating" means any administration of a compound or compounds according to the present disclosure to a subject (e.g., a human) having or susceptible to a condition or disease disclosed herein for the purpose of: 1) preventing or protecting against the disease or condition, that is, causing the clinical symptoms not to develop; 2) inhibiting the disease or condition, that is, arresting or suppressing the development of clinical symptoms; or 3) relieving the disease or condition that is causing the regression of clinical symptoms. In some embodiments, the term "treatment" or "treating" refers to relieving the disease or condition or causing the regression of clinical symptoms.

As used herein, the term "preventing" refers to the prophylactic treatment of a patient in need thereof. The prophylactic treatment can be accomplished by providing an appropriate dose of a therapeutic agent to a subject at risk of suffering from an ailment, thereby substantially averting onset of the ailment. The presence of a genetic mutation or the predisposition to having a mutation may not be alterable. However, prophylactic treatment (prevention) as used herein has the potential to avoid/ameliorate the symptoms or clinical consequences of having the disease engendered by such genetic mutation or predisposition.

It will be understood by those of ordinary skill in the art that in human medicine, it is not always possible to distinguish between "preventing" and "suppressing" since the ultimate inductive event or events may be unknown, latent, or the patient is not ascertained until well after the occurrence of the event or events. Therefore, as used herein, the term "prophylaxis" is intended as an element of "treatment" to encompass both "preventing" and "suppressing" as defined herein. The term "protection," as used herein, is meant to include "prophylaxis."

The term "patient" typically refers to a "mammal" which includes, without limitation, human, monkeys, rabbits, mice, domestic animals, such as dogs and cats, farm animals, such as cows, horses, or pigs, and laboratory animals. In some embodiments, the term patient refers to a human in need of treatment as defined herein.

Compounds

Provided herein are compounds that function as PD-1 inhibitors, PD-L1 inhibitors, and/or PD-1/PD-L1 interaction inhibitors, methods of using such compounds and compositions comprising such compounds optionally in combination with one or more additional anticancer agents or therapies. In all embodiments discussed herein where there is more than one occurrence of a group or variable, it is intended that the group or variable is independently selected the list that follows. It is further contemplated that all embodiments directed to compounds include any pharmaceutically acceptable salt, stereoisomer, mixture of stereoisomers, solvate, prodrug or tautomer thereof.

In one embodiment, provided is a compound of formula (I):

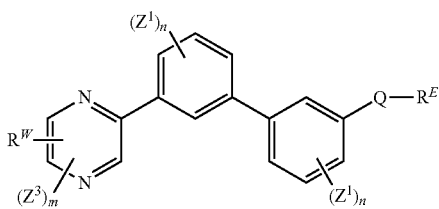

wherein:
each n is independently 0, 1, 2, 3 or 4;
each $Z^1$ is independently halo, —$OR^a$, —$NO_2$, —CN, —$NR^aR^b$, —$N_3$, —$S(O)_2R^a$, —$C_{1-6}$ alkyl, —$C_{1-6}$ haloalkyl, —$C_{2-6}$alkenyl, —$C_{2-6}$ alkynyl, —O—$C_{1-6}$ alkyl, —O—$C_{1-6}$ haloalkyl, —$C_{3-8}$ cycloalkyl or —$C_{1-6}$ alkyl$C_{3-8}$ cycloalkyl;
wherein each alkyl, alkenyl, alkynyl, and cycloalkyl group is optionally substituted with 1 to 4 groups independently selected from the group consisting of oxo, —$NO_2$, —$N_3$, —$OR^a$, halo, and cyano;
Q is aryl, heteroaryl or heterocyclyl, wherein the aryl, heteroaryl and heterocyclyl group is optionally substituted with 1 to 4 groups independently selected from the group consisting of halo, oxo, —$OR^a$, —$SR^a$, $N_3$, $NO_2$, —CN, —$NR^1R^2$, —$S(O)_2R^a$, —$S(O)_2NR^aR^b$, —$NR^aS(O)_2R^a$, —$NR^aC(O)R^a$, —$C(O)R^a$, —$C(O)OR^a$, —$C(O)NR^aR^b$, —$NR^aC(O)OR^a$, —$NR^aC(O)NR^1R^2$, —O—$C(O)NR^aR^b$, —$NR^aS(O)_2NR^aR^b$, —$C(O)NR^aS(O)_2NR^aR^b$, —$C_{1-6}$ alkyl, —$C_{2-6}$ alkenyl, —$C_{2-6}$ alkynyl, —O—$C_{1-6}$ alkyl, —$C_{3-8}$ cycloalkyl, —$C_{1-6}$ alkyl$C_{3-8}$ cycloalkyl, aryl, heteroaryl, heterocyclyl and $R^N$;
wherein the alkyl, alkenyl, alkynyl, cycloalkyl, aryl, heteroaryl, or heterocyclyl group is optionally substituted with 1 to 4 groups independently selected from the group consisting of oxo, —$NO_2$, $N_3$, —$OR^a$, halo, cyano, —$NR^aR^b$, —$C(O)R^a$, —$C(O)OR^a$, —O—$C_{1-6}$ alkylCN, —$C(O)NR^aR^b$, $NR^aC(O)R^a$, —$NR^aC(O)OR^a$, —$S(O)_2R^a$, —$NR^aS(O)_2R^b$, —$S(O)_2NR^aR^b$, —$NR^aS(O)_2NR^aR^b$, —$C(O)NR^aS(O)_2NR^aR^b$ and —$C_{3-8}$ cycloalkyl; and wherein the heteroaryl or heterocyclyl group may be oxidized on a nitrogen atom to form an N-oxide or oxidized on a sulfur atom to form a sulfoxide or sulfone;
m is 0, 1 or 2;
each $Z^3$ is independently halo, oxo, —$OR^a$, $SR^a$, $N_3$, $NO_2$, —CN, —$NR^1R^2$, —$S(O)_2R^a$, —$S(O)_2NR^aR^b$, —$NR^aS(O)_2R^a$, —$NR^aC(O)R^a$, —$C(O)R^a$, —$C(O)OR^a$, —$C(O)NR^aR^b$, —$NR^aC(O)OR^a$, —$NR^aC(O)NR^1R^2$, —O—$C(O)NR^aR^b$, —$NR^aS(O)_2NR^aR^b$, —$C(O)NR^aS(O)_2NR^aR^b$, —$C_{1-6}$ alkyl, —$C_{2-6}$ alkenyl, —$C_{2-6}$ alkynyl, —O—$C_{1-6}$ alkyl, —$C_{3-8}$ cycloalkyl, —$C_{1-6}$ alkyl$C_{3-8}$ cycloalkyl, aryl, heteroaryl, heterocyclyl and $R^N$;
wherein the alkyl, alkenyl, alkynyl, cycloalkyl, aryl, heteroaryl, or heterocyclyl group is optionally substituted with 1 to 4 groups independently selected from the group consisting of oxo, —$NO_2$, $N_3$, —$OR^a$, halo, cyano, —$NR^aR^b$, —$C(O)R^a$, —$C(O)OR^a$, —O—$C_{1-6}$ alkylCN, —$C(O)NR^aR^b$, $NR^aC(O)R^a$, —$NR^aC(O)OR^a$, —$S(O)_2R^a$, —$NR^aS(O)_2R^b$, —$S(O)_2NR^aR^b$, —$NR^aS(O)_2NR^aR^b$, —$C(O)NR^aS(O)_2NR^aR^b$ and —$C_{3-8}$ cycloalkyl;
each $R^N$ is independently —$C_{1-6}$ alkyl$NR^1R^2$, —O—$C_{1-6}$ alkyl$NR^1R^2$, —$C_{1-6}$ alkyl$OC_{1-6}$ alkyl$NR^1R^2$, —$NR^a$—$C_{1-6}$ alkyl$NR^1R^2$, —$C_{1-6}$ alkyl$C(O)NR^1R^2$, —O—$C_{1-6}$ alkyl$C(O)NR^1R^2$, —O—$C_{1-6}$ alkyl$C(O)OR^1$, —S—$C_{1-6}$ alkyl$NR^1R^2$, —$C_{1-6}$ alkyl$OR^a$, or

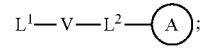

wherein
$L^1$ is independently a bond, O, $NR^a$, S, S(O), or $S(O)_2$;
V is independently selected from the group consisting of a bond, $C_{1-6}$alkyl, $C_{2-6}$alkenyl, and $C_{2-6}$alkynyl;
wherein the alkyl, alkenyl or alkynyl group is optionally independently substituted with —$OR^a$, halo, cyano, $NR^aR^b$ and —$C_{3-8}$ cycloalkyl;
$L^2$ is independently a bond, O, $NR^a$, S, S(O), or $S(O)_2$;
ring A is independently cycloalkyl, aryl, heteroaryl or heterocyclyl;
wherein the cycloalkyl, aryl, heteroaryl, or heterocyclyl group is optionally substituted with 1 to 4 groups independently selected from the group consisting of oxo, —$NO_2$, $N_3$, —$OR^a$, halo, cyano, —$C_{1-6}$ alkyl, —$C_{1-6}$ haloalkyl, —$C_{2-6}$alkenyl, —$C_{2-6}$ alkynyl, —O—$C_{1-6}$ haloalkyl, $NR^aR^b$, —$C(O)R^a$, —$C(O)OR^a$, —O—$C_{1-6}$ alkylCN, —$C(O)NR^aR^b$, —$NR^aC(O)R^a$, —$NR^aC(O)OR^a$, —$NR^aC(O)OR^a$, —$C(O)N(R^a)OR^b$, —$S(O)_2R^a$, —$S(O)_2NR^aR^b$, —$NR^aS(O)_2R^b$, —$NR^aS(O)_2NR^aR^b$, —$C(O)NR^aS(O)_2NR^aR^b$, $C_{3-8}$cycloalkyl and $C_{1-6}$alkyl$C_{3-8}$ cycloalkyl;
wherein the alkyl, alkenyl or alkynyl group is optionally independently substituted with —$OR^a$, halo, cyano, $NR^aR^b$ and —$C_{3-8}$ cycloalkyl;
$R^E$ and $R^W$ are each independently —$NR^1R^2$, —$C_{1-6}$ alkyl$NR^1R^2$, —O—$C_{1-6}$ alkyl$NR^1R^2$, —$C_{1-6}$ alkyl$OC_{1-6}$ alkyl$NR^1R^2$, —$NR^a$—$C_{1-6}$ alkyl$NR^1R^2$, —$C_{1-6}$ alkyl$N+R^1R^2R^3$, —S—$C_{1-6}$ alkyl$NR^1R^2$, —$C(O)NR^1R^2$, —$S(O)_2R^a$, —$(CH_2)_uS(O)_2NR^1R^2$, —$(CH_2)_uNR^aS(O)_2NR^aR^b$, —$S(O)_2NR^aC_{1-6}$ alkyl$NR^1R^2$, —$NR^aS(O)_2C_{1-6}$ alkyl$NR^1R^2$, —$(CH_2)_uC(O)NR^aS(O)_2NR^aR^b$, —$(CH_2)_uN+R^1R^2O^-$, —$(CH_2)_uP+R^bR^cR^d$, —$(CH_2)_uP+R^cR^dO^-$, —$(CH_2)_uP+O[NR^aR^b][NR^cR^d]$, —$(CH_2)_uNR^aP(o)(OR^c)_2$, —$(CH_2)_uCH_2OP(O)(OR^c)(OR^d)$, —$(CH_2)_uOP(O)(OR^c)(OR^d)$, —$(CH_2)_uOP(O)NR^aR^b)(OR^a)$, or

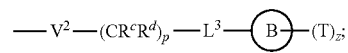

wherein:

$V^2$ is independently a bond, O, $NR^a$, S, S(O), $S(O)_2$, $C(O)NR^a$, $NR^aC(O)$, $S(O)_2NR^1$, or $NR^aS(O)_2$;

$L^3$ is independently a bond, O, $NR^a$, S, S(O), $S(O)_2$, $C(O)NR^a$, $NR^aC(O)$, $S(O)_2NR^1$, or $NR^aS(O)_2$;

ring B is independently cycloalkyl, aryl, heteroaryl or heterocyclyl;

T is independently H, $—OR^a$, $(CH_2)_qNR^1R^2$, $(CH_2)_qNR^aC(O)R^e$ or $(CH_2)_qC(O)R^e$;

p is independently 0, 1, 2, 3, 4, or 5;

q is independently 0, 1, 2, 3, 4, or 5;

u is 0, 1, 2, 3 or 4;

z is 0, 1, 2 or 3; and wherein the alkyl, cycloalkyl, aryl, heteroaryl or heterocyclyl group of $R^E$ and $R^W$ is optionally substituted with 1 to 3 substituents independently selected from the group consisting of $NR^aR^b$, halo, cyano, oxo, $—OR^a$, $—C_{1-6}$ alkyl, $—C_{1-6}$ haloalkyl, $—C_{1-6}$ cyanoalkyl, $—C_{1-6}$ alkyl$NR^aR^b$, $—C_{1-6}$ alkylOH, $—C_{3-8}$ cycloalkyl and $—C_{1-3}$ alkyl$C_{3-8}$cycloalkyl;

provided that at least one of $V^2$, $L^3$, ring B and T contains a nitrogen atom;

each $R^1$ is independently selected from the group consisting of H, $—C_{1-8}$ alkyl, $—C_{2-6}$ alkenyl, $—C_{2-6}$ alkynyl, $—C_{3-6}$ cycloalkyl, aryl, heteroaryl, heterocyclyl, $—C_{1-6}$ alkylaryl, $—C_{1-6}$ alkylheteroaryl, $—C_{1-6}$ alkylheterocyclyl, $—C_{1-6}$ alkylC(O)$OR^a$, $—C_{2-6}$ alkenylC(O)$OR^a$, $—S(O)_2R^a$, $—S(O)_2OR^a$, $—S(O)_2NR^aR^b$, $—C(O)NR^aS(O)_2R^a$, and $C_{1-6}$ alkyl$C_{3-8}$cycloalkyl;

wherein each alkyl, alkenyl, cycloalkyl, aryl, heteroaryl or heterocyclyl group is optionally substituted with 1 to 4 groups independently selected from the group consisting of $—OR^a$, $—CN$, $—NO_2$, halo, $C_{1-6}$alkyl, $—C_{1-6}$ alkyl$OR^a$, $—C_{1-6}$ cyanoalkyl, $—C_{1-6}$ haloalkyl, $C_{3-8}$ cycloalkyl, heteroaryl, heterocyclyl, $—C_{1-3}$ alkyl$C_{3-8}$ cycloalkyl, $—C(O)R^a$, $—C_{1-6}$ alkylC(O)$R^a$, $—C(O)OR^a$, $—C_{1-6}$ alkylC(O)$OR^a$, $—NR^aR^b$, $—OC(O)NR^aR^b$, $—NR^aC(O)OR^b$, $—NR^aC(O)R^b$, $—C_{1-6}$ alkyl$NR^aR^b$, $—C(O)NR^aR^b$, $—C_{1-6}$ alkylC(O)$NR^aR^b$, $—S(O)_2R^a$, $—S(O)_2OR^a$, $—C_{1-6}$ alkyl$S(O)_2R^a$, $—S(O)_2NR^aR^b$, $—C_{1-6}$ alkyl$S(O)_2NR^aR^b$, $—C(O)NR^aS(O)_2R^b$, $—NR^aC(O)NR^b$, $—C_{1-6}$ alkylC(O)$NR^aS(O)_2R^b$, $—NR^aC(O)R^b$, and $—C_{1-6}$alkyl$NR^aC(O)R^b$;

each $R^2$ is independently selected from the group consisting of H, $—C_{1-6}$ alkyl, $—C_{2-6}$ alkenyl, $—C_{2-6}$ alkynyl, $—C_{3-6}$ cycloalkyl, aryl, heteroaryl, heterocyclyl, $—C_{1-6}$ alkylaryl, $—C_{1-6}$ alkylheteroaryl, $—C_{1-6}$ alkylheterocyclyl, $—C_{2-6}$ alkyl-$OR^a$, $—C_{1-6}$ alkylC(O)$OR^a$, and $—C_{2-6}$ alkenylC(O)$OR^a$;

wherein each alkyl, alkenyl, cycloalkyl, aryl, heteroaryl or heterocyclyl group is optionally substituted with 1 to 4 groups independently selected from the group consisting of $—OR^a$, $—CN$, halo, $C_{1-6}$alkyl, $—C_{1-6}$ alkyl$OR^a$, $—C_{1-6}$ cyanoalkyl, $—C_{1-6}$ haloalkyl, $—C_{3-8}$ cycloalkyl, $—C_{1-3}$ alkyl$C_{3-8}$cycloalkyl, $—C(O)R^a$, $—C_{1-6}$ alkylC(O)$R^a$, $—C(O)OR^a$, $—C_{1-6}$ alkylC(O)$OR^a$, $—NR^aR^b$, $—C_{1-6}$ alkyl$NR^aR^b$, $—C(O)NR^aR^b$, $C_{1-6}$ alkylC(O)$NR^aR^b$, $—S(O)_2R^a$, $—C_{1-6}$ alkyl$S(O)_2R^a$, $—S(O)_2NR^aR^b$, $—C_{1-6}$ alkyl$S(O)_2NR^aR^b$, $—C(O)NR^aS(O)_2R^b$ and $—NR^aC(O)R^b$;

or $R^1$ and $R^2$ combine to form a heterocyclyl group optionally containing 1, 2, or 3 additional heteroatoms independently selected from oxygen, sulfur and nitrogen, and optionally substituted with 1 to 3 groups independently selected from the group consisting of oxo, $—C_{1-6}$ alkyl, $—C_{3-8}$ cycloalkyl, $—C_{2-6}$ alkenyl, $—C_{2-6}$ alkynyl, aryl, heteroaryl, heterocyclyl, $—OR^a$, $—CN$, halo, $—C(O)OR^a$, $—C_{1-6}$ cyanoalkyl, $—C_{1-6}$ alkyl$OR^a$, $—C_{1-6}$ haloalkyl, $—C_{1-3}$ alkyl$C_{3-8}$cycloalkyl, $—C(O)R^a$, $C_{1-6}$ alkylC(O)$R^a$, $—C_{1-6}$ alkylC(O)$OR^a$, $—NR^aR^b$, $—C_{1-6}$alkyl$NR^aR^b$, $—C(O)NR^aR^b$, $—NR^aC(O)OR^b$, $—NR^aC(O)NR^aR^b$, $—NR^aS(O)_2NR^aR^b$, $—NR^aS(O)_2R^b$, $—C_{1-6}$ alkylC(O)$NR^aR^b$, $—S(O)_2R^a$, $—C_{1-6}$ alkyl$S(O)_2R^a$, $—S(O)_2NR^aR^b$, and $C_{1-6}$ alkyl$S(O)_2NR^aR^b$;

each $R^3$ is independently H, $—C_{1-6}$ alkyl, $—C_{2-6}$ alkenyl, $—C_{3-6}$ cycloalkyl, aryl, heteroaryl, heterocyclyl, $—C_{1-6}$ alkylaryl, $—C_{1-6}$ alkylheteroaryl, $—C_{1-6}$ alkylheterocyclyl, $—C_{2-6}$ alkyl-$OR^a$, $—C_{1-6}$ alkylC(O)$OR^a$, or $—C_{2-6}$ alkenyl-C(O)$OR^a$;

each $R^a$ is independently selected from the group consisting of H, $—C_{1-6}$ alkyl, $—C_{1-6}$ haloalkyl, $—C_{3-8}$ cycloalkyl, aryl, heteroaryl, heterocyclyl, $—C_{1-3}$ alkyl$C_{3-8}$cycloalkyl, $—C_{1-6}$ alkylaryl, $—C_{1-6}$ alkylheteroaryl, and $—C_{1-6}$alkylheterocyclyl;

each $R^b$ is independently selected from the group consisting of H, $—C_{1-6}$ alkyl, $—C_{1-6}$ haloalkyl, $—C_{3-8}$ cycloalkyl, aryl, heteroaryl, heterocyclyl, $—C_{1-3}$ alkyl$C_{3-8}$cycloalkyl, $—C_{1-6}$ alkylaryl, $—C_{1-6}$ alkylheteroaryl, and $—C_{1-6}$ alkylheterocyclyl;

or $R^a$ and $R^b$ may combine together to form a ring consisting of 3-8 ring atoms that are C, N, O, or S; wherein the ring is optionally substituted with 1 to 4 groups independently selected from the group consisting of $—OR^f$, $—CN$, halo, $—C_{1-6}$ alkyl$OR^f$, $—C_{1-6}$ cyanoalkyl, $—C_{1-6}$ haloalkyl, $—C_{3-8}$ cycloalkyl, $—C_{1-3}$ alkyl$C_{3-8}$cycloalkyl, $—C(O)R^f$, $—C_{1-6}$ alkylC(O)$R^f$, $—C(O)OR^f$, $—C_{1-6}$ alkylC(O)$OR^f$, $—NR^fR^g$, $—C_{1-6}$ alkyl$NR^fR^g$, $—C(O)NR^fR^g$, $C_{1-6}$ alkylC(O)$NR^fR^g$, $—S(O)_2R^f$, $—C_{1-6}$ alkyl$S(O)_2R^f$, $—S(O)_2NR^fR^g$, $—C_{1-6}$ alkyl$S(O)_2NR^fR^g$, $—C(O)NR^fS(O)_2R^g$ and $—NR^fC(O)R^g$;

each $R^c$ is independently selected from the group consisting of H, OH, $—C_{1-6}$ alkyl, $—C_{3-8}$ cycloalkyl, aryl, heteroaryl, heterocyclyl, $—C_{1-3}$ alkyl$C_{3-8}$ cycloalkyl, $—C_{1-6}$ alkylaryl, $—C_{1-6}$ alkylheteroaryl, and $—C_{1-6}$ alkylheterocyclyl; and each $R^d$ is independently selected from the group consisting of H, $—C_{1-6}$ alkyl, $—C_3-C_8$cycloalkyl, aryl, heteroaryl, heterocyclyl, $—C_{1-3}$ alkyl$C_{3-8}$cycloalkyl, $—C_{1-6}$ alkylaryl, $—C_{1-6}$ alkylheteroaryl, and $—C_{1-6}$ alkylheterocyclyl;

each $R^e$ is independently selected from the group consisting of H, $—C_{1-6}$ alkyl, $—O—C_{1-6}$alkyl, $—C_{3-8}$ cycloalkyl, aryl, heteroaryl, heterocyclyl, $—O—C_{3-8}$ cycloalkyl, $—O$-aryl, $—O$-heteroaryl, $—O$-heterocyclyl, $—C_{1-3}$ alkyl$C_{3-8}$cycloalkyl, $—C_{1-6}$ alkylaryl, $—C_{1-6}$alkylheteroaryl, $—NR^fR^g$, $—C_{1-6}$ alkyl$NR^fR^g$, $—C(O)NR^fR^g$, $—C_{1-6}$ alkylC(O)$NR^fR^g$, $—NHS(O)_2R^f$, $—C_{1-6}$ alkyl$S(O)_2R^f$, and $—C_{1-6}$ alkyl$S(O)_2NR^fR^g$;

each $R^f$ is independently selected from the group consisting of H, $—C_{1-6}$ alkyl, $—C_{3-8}$ cycloalkyl, aryl, heteroaryl, heterocyclyl, $—C_{1-3}$ alkyl$C_{3-8}$ cycloalkyl, $—C_{1-6}$ alkylaryl, $—C_{1-6}$ alkylheteroaryl, and $—C_{1-6}$ alkylheterocyclyl;

each $R^g$ is independently selected from the group consisting of H, $—C_{1-6}$ alkyl, $—C_{3-8}$ cycloalkyl, aryl, heteroaryl, heterocyclyl, $—C_{1-3}$ alkyl$C_{3-8}$ cycloalkyl, $—C_{1-6}$ alkylaryl, $—C_{1-6}$ alkylheteroaryl, and $—C_{1-6}$ alkylheterocyclyl;

or a pharmaceutically acceptable salt, stereoisomer, mixture of stereoisomers, or tautomer thereof.

The present disclosure provides further a compound of formula (I):

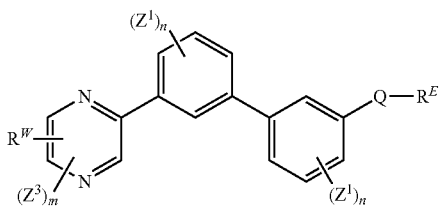

(I)

wherein:
each n is independently 0, 1, 2, 3 or 4;
each $Z^1$ is independently halo, —$OR^a$, —$NO_2$, —CN, —$NR^aR^b$, —$N_3$, —$S(O)_2R^a$, —$C_{1-6}$ alkyl, —$C_{1-6}$ haloalkyl, —$C_{2-6}$alkenyl, —$C_{2-6}$ alkynyl, —O—$C_{1-6}$ alkyl, —O—$C_{1-6}$ haloalkyl, —$C_{3-8}$ cycloalkyl or —$C_{1-6}$ alkyl$C_{3-8}$ cycloalkyl;
wherein each alkyl, alkenyl, alkynyl, and cycloalkyl group is optionally substituted with 1 to 4 groups independently selected from the group consisting of oxo, —$NO_2$, —$N_3$, —$OR^a$, halo, and cyano;
Q is aryl, heteroaryl or heterocyclyl, wherein the aryl, heteroaryl and heterocyclyl group is optionally substituted with 1 to 4 groups independently selected from the group consisting of halo, oxo, —$OR^a$, $N_3$, $NO_2$, —CN, —$NR^1R^2$, —$S(O)_2R^a$, —$S(O)_2NR^aR^b$, —$NR^aS(O)_2R^a$, —$NR^aC(O)R^a$, —$C(O)R^a$, —$C(O)OR^a$, —$C(O)NR^aR^b$, —$NR^aC(O)OR^a$, —$NR^aC(O)NR^1R^2$, —$OC(O)NR^aR^b$, —$NR^aS(O)_2NR^aR^b$, —$C(O)NR^aS(O)_2NR^aR^b$, —$C_{1-6}$ alkyl, —$C_{2-6}$ alkenyl, —$C_{2-6}$ alkynyl, —O—$C_{1-6}$ alkyl, —$C_{3-8}$ cycloalkyl, —$C_{1-6}$ alkyl$C_{3-8}$ cycloalkyl, aryl, heteroaryl, heterocyclyl and $R^N$;
wherein the alkyl, alkenyl, alkynyl, cycloalkyl, aryl, heteroaryl, or heterocyclyl group is optionally substituted with 1 to 4 groups independently selected from the group consisting of oxo, —$NO_2$, $N_3$, —$OR^a$, halo, cyano, —$NR^aR^b$, —$C(O)R^a$, —$C(O)OR^a$, —O—$C_{1-6}$ alkylCN, —$C(O)NR^aR^b$, $NR^aC(O)R^a$, —$NR^aC(O)OR^a$, —$S(O)_2R^a$, —$NR^aS(O)_2R^b$, —$S(O)_2NR^aR^b$, —$NR^aS(O)_2NR^aR^b$, —$C(O)NR^aS(O)_2NR^aR^b$ and —$C_{3-8}$ cycloalkyl; and wherein the heteroaryl or heterocyclyl group may be oxidized on a nitrogen atom to form an N-oxide or oxidized on a sulfur atom to form a sulfoxide or sulfone;
m is 0, 1 or 2;
each $Z^3$ is independently halo, oxo, —$OR^a$, $N_3$, $NO_2$, —CN, —$NR^1R^2$, —$S(O)_2R^a$, —$S(O)_2NR^aR^b$, —$NR^aS(O)_2R^a$, —$NR^aC(O)R^a$, —$C(O)R^a$, —$C(O)OR^a$, —$C(O)NR^aR^b$, —$NR^aC(O)OR^a$, —$NR^aC(O)NR^1R^2$, —$OC(O)NR^aR^b$, —$NR^aS(O)_2NR^aR^b$, —$C(O)NR^aS(O)_2NR^aR^b$, —$C_{1-6}$ alkyl, —$C_{2-6}$ alkenyl, —$C_{2-6}$ alkynyl, —O—$C_{1-6}$ alkyl, —$C_{3-8}$ cycloalkyl, —$C_{1-6}$ alkyl$C_{3-8}$ cycloalkyl, aryl, heteroaryl, heterocyclyl and $R^N$;
wherein the alkyl, alkenyl, alkynyl, cycloalkyl, aryl, heteroaryl, or heterocyclyl group is optionally substituted with 1 to 4 groups independently selected from the group consisting of oxo, —$NO_2$, $N_3$, —$OR^a$, halo, cyano, —$NR^aR^b$, —$C(O)R^a$, —$C(O)OR^a$, —O—$C_{1-6}$ alkylCN, —$C(O)NR^aR^b$, $NR^aC(O)R^a$, —$NR^aC(O)OR^a$, —$S(O)_2R^a$, —$NR^aS(O)_2R^b$, —$S(O)_2NR^aR^b$, —$NR^aS(O)_2NR^aR^b$, —$C(O)NR^aS(O)_2NR^aR^b$ and —$C_{3-8}$ cycloalkyl;
each $R^N$ is independently —$C_{1-6}$ alkylNR$^1$R$^2$, —O—$C_{1-6}$ alkylNR$^1$R$^2$, —$C_{1-6}$ alkylOC$_{1-6}$ alkylNR$^1$R$^2$, —NR$^a$—$C_{1-6}$ alkylNR$^1$R$^2$, —$C_{1-6}$ alkylC(O)NR$^1$R$^2$, —O—$C_{1-6}$ alkylC(O)NR$^1$R$^2$, —O—$C_{1-6}$ alkylC(O)OR$^1$, —S—$C_{1-6}$ alkylNR$^1$R$^2$, —$C_{1-6}$ alkylOR$^a$, or

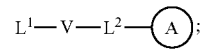

wherein
$L^1$ is independently a bond, O, NR$^a$, S, S(O), or S(O)$_2$;
V is independently selected from the group consisting of a bond, $C_{1-6}$alkyl, $C_{2-6}$alkenyl, and $C_{2-6}$alkynyl;
wherein the alkyl, alkenyl or alkynyl group is optionally independently substituted with —OR$^a$, halo, cyano, NR$^a$R$^b$ and —$C_{3-8}$ cycloalkyl;
$L^2$ is independently a bond, O, NR$^a$, S, S(O), or S(O)$_2$;
ring A is independently cycloalkyl, aryl, heteroaryl or heterocyclyl;
wherein the cycloalkyl, aryl, heteroaryl, or heterocyclyl group is optionally substituted with 1 to 4 groups independently selected from the group consisting of oxo, —$NO_2$, $N_3$, —$OR^a$, halo, cyano, —$C_{1-6}$ alkyl, —$C_{1-6}$ haloalkyl, —$C_{2-6}$alkenyl, —$C_{2-6}$ alkynyl, —O—$C_{1-6}$ haloalkyl, NR$^a$R$^b$, —C(O)R$^a$, —C(O)OR$^a$, —O—$C_{1-6}$ alkylCN, —C(O)NR$^a$R$^b$, —NR$^a$C(O)R$^a$, —NR$^a$C(O)OR$^a$, —NR$^a$C(O)OR$^a$, —C(O)N(R$^a$)OR$^b$, —S(O)$_2$R$^a$, —S(O)$_2$NR$^a$R$^b$, —NR$^a$S(O)$_2$R$^b$, —NR$^a$S(O)$_2$NR$^a$R$^b$, —C(O)NR$^a$S(O)$_2$NR$^a$R$^b$, $C_{3-8}$cycloalkyl and $C_{1-6}$alkyl$C_{3-8}$ cycloalkyl;
wherein the alkyl, alkenyl or alkynyl group is optionally independently substituted with —OR$^a$, halo, cyano, NR$^a$R$^b$ and —$C_{3-8}$ cycloalkyl;
R$^E$ and R$^W$ are each independently —NR$^1$R$^2$, —$C_{1-6}$ alkylNR$^1$R$^2$, —O—$C_{1-6}$ alkylNR$^1$R$^2$, —$C_{1-6}$ alkylOC$_{1-6}$ alkylNR$^1$R$^2$, —NR$^a$—$C_{1-6}$ alkylNR$^1$R$^2$, —$C_{1-6}$ alkylN+R$^1$R$^2$R$^3$, —S—$C_{1-6}$ alkylNR$^1$R$^2$, —C(O)NR$^1$R$^2$, —S(O)$_2$R$^a$, —(CH$_2$)$_u$S(O)$_2$NR$^1$R$^2$, —(CH$_2$)$_u$NR$^a$S(O)$_2$NR$^a$R$^b$, —S(O)$_2$NR$^a$C$_{1-6}$ alkylNR$^1$R$^2$, —NR$^a$S(O)$_2$C$_{1-6}$ alkylNR$^1$R$^2$, —(CH$_2$)$_u$C(O)NR$^a$S(O)$_2$NR$^a$R$^b$, —(CH$_2$)$_u$N+R$^1$R$^2$O$^-$, —(CH$_2$)$_u$P+R$^b$R$^c$R$^d$, —(CH$_2$)$_u$P+R$^c$R$^d$O$^-$, —(CH$_2$)$_u$P+O[NR$^a$R$^b$][NR$^c$R$^d$], —(CH$_2$)$_u$NR$^c$P(O)(OR$^c$)$_2$, —(CH$_2$)$_u$CH$_2$OP(O)(OR$^c$)(OR$^d$), —(CH$_2$)$_u$OP(O)(OR$^c$)(OR$^d$), —(CH$_2$)$_u$OP(O)NR$^a$R$^b$)(OR$^a$), or

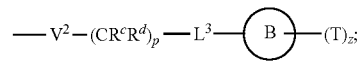

wherein:
$V^2$ is independently a bond, O, NR$^a$, S, S(O), S(O)$_2$, C(O)NR$^a$, NR$^a$C(O), S(O)$_2$NR$^1$, or NR$^a$S(O)$_2$;
$L^3$ is independently a bond, O, NR$^a$, S, S(O), S(O)$_2$, C(O)NR$^a$, NR$^a$C(O), S(O)$_2$NR$^1$, or NR$^a$S(O)$_2$;
ring B is independently cycloalkyl, aryl, heteroaryl or heterocyclyl;
T is independently H, —OR$^a$, (CH$_2$)$_q$NR$^1$R$^2$, (CH$_2$)$_q$NR$^a$C(O)R$^e$ or (CH$_2$)$_q$C(O)R$^e$;
p is independently 0, 1, 2, 3, 4, or 5;
q is independently 0, 1, 2, 3, 4, or 5;
u is 0, 1, 2, 3 or 4;
z is 0, 1, 2 or 3; and
wherein the alkyl, cycloalkyl, aryl, heteroaryl or heterocyclyl of R$^E$ or R$^W$ is optionally substituted with 1 to 3 substituents independently selected from the group consisting of NR$^a$R$^b$, halo, cyano, oxo, —OR$^a$, —$C_{1-6}$ alkyl, —$C_{1-6}$ haloalkyl, —$C_{1-6}$ cyanoalkyl, —$C_{1-6}$ alkylNR$^a$R$^b$, —$C_{1-6}$ alkylOH, —$C_{3-8}$ cycloalkyl and —$C_{1-3}$ alkyl$C_{3-8}$cycloalkyl;

provided that at least one of $V^2$, $L^3$, ring B and T contains a nitrogen atom;

each $R^1$ is independently selected from the group consisting of H, —$C_{1-8}$ alkyl, —$C_{2-6}$ alkenyl, —$C_{2-6}$ alkynyl, —$C_{3-6}$ cycloalkyl, aryl, heteroaryl, heterocyclyl, —$C_{1-6}$ alkylaryl, —$C_{1-6}$ alkylheteroaryl, —$C_{1-6}$ alkylheterocyclyl, —$C_{1-6}$ alkylC(O)OR$^a$, —$C_{2-6}$ alkenylC(O)OR$^a$, —S(O)$_2$R$^a$, —S(O)$_2$NR$^a$R$^b$, —C(O)NR$^a$S(O)$_2$R$^a$, and $C_{1-6}$ alkylC$_{3-8}$cycloalkyl;

wherein each alkyl, alkenyl, cycloalkyl, aryl, heteroaryl or heterocyclyl group is optionally substituted with 1 to 4 groups independently selected from the group consisting of —OR$^a$, —CN, halo, $C_{1-6}$alkyl, —$C_{1-6}$ alkylOR$^a$, —$C_{1-6}$ cyanoalkyl, —$C_{1-6}$ haloalkyl, $C_{3-8}$ cycloalkyl, —$C_{1-3}$ alkylC$_{3-8}$cycloalkyl, —C(O)R$^a$, —$C_{1-6}$ alkylC(O)R$^a$, —C(O)OR$^a$, —$C_{1-6}$ alkylC(O)OR$^a$, —NR$^a$R$^b$, —OC(O)NR$^a$R$^b$, NR$^a$C(O)OR$^b$, —$C_{1-6}$ alkylNR$^a$R$^b$, —C(O)NR$^a$R$^b$, —$C_{1-6}$ alkylC(O)NR$^a$R$^b$, —S(O)$_2$R$^a$, —$C_{1-6}$ alkylS(O)$_2$R$^a$, —S(O)$_2$NR$^a$R$^b$, —$C_{1-6}$ alkylS(O)$_2$NR$^a$R$^b$, —C(O)NR$^a$S(O)$_2$R$^b$, —$C_{1-6}$ alkylC(O)NR$^a$S(O)$_2$R$^b$, —NR$^a$C(O)R$^b$, and —$C_{1-6}$alkylNR$^a$C(O)R$^b$;

each $R^2$ is independently selected from the group consisting of H, —$C_{1-6}$ alkyl, —$C_{2-6}$ alkenyl, —$C_{2-6}$ alkynyl, —$C_{3-6}$ cycloalkyl, aryl, heteroaryl, heterocyclyl, —$C_{1-6}$ alkylaryl, —$C_{1-6}$ alkylheteroaryl, —$C_{1-6}$ alkylheterocyclyl, —$C_{2-6}$ alkyl-OR$^a$, —$C_{1-6}$ alkylC(O)OR$^a$, and —$C_{2-6}$ alkenylC(O)OR$^a$;

wherein each alkyl, alkenyl, cycloalkyl, aryl, heteroaryl or heterocyclyl group is optionally substituted with 1 to 4 groups independently selected from the group consisting of —OR$^a$, —CN, halo, $C_{1-6}$alkyl, —$C_{1-6}$ alkylOR$^a$, —$C_{1-6}$ cyanoalkyl, —$C_{1-6}$ haloalkyl, —$C_{3-8}$ cycloalkyl, —$C_{1-3}$ alkylC$_{3-8}$cycloalkyl, —C(O)R$^a$, —$C_{1-6}$ alkylC(O)R$^a$, —C(O)OR$^a$, —$C_{1-6}$ alkylC(O)OR$^a$, —NR$^a$R$^b$, —$C_{1-6}$ alkylNR$^a$R$^b$, —C(O)NR$^a$R$^b$, $C_{1-6}$ alkylC(O)NR$^a$R$^b$, —S(O)$_2$R$^a$, —$C_{1-6}$ alkylS(O)$_2$R$^a$, —S(O)$_2$NR$^a$R$^b$, —$C_{1-6}$ alkylS(O)$_2$NR$^a$R$^b$, —C(O)NR$^a$S(O)$_2$R$^b$ and —NR$^a$C(O)R$^b$;

or $R^1$ and $R^2$ combine to form a heterocyclyl group optionally containing 1, 2, or 3 additional heteroatoms independently selected from oxygen, sulfur and nitrogen, and optionally substituted with 1 to 3 groups independently selected from the group consisting of oxo, —$C_{1-6}$ alkyl, —$C_{3-8}$ cycloalkyl, —$C_{2-6}$ alkenyl, —$C_{2-6}$ alkynyl, —OR$^a$, —C(O)OR$^a$, —$C_{1-6}$ cyanoalkyl, —$C_{1-6}$ alkylOR$^a$, —$C_{1-6}$ haloalkyl, —$C_{1-3}$ alkylC$_{3-8}$cycloalkyl, —C(O)R$^a$, $C_{1-6}$ alkyl C(O)R$^a$, —$C_{1-6}$ alkylC(O)OR$^a$, —NR$^a$R$^b$, —$C_{1-6}$alkylNR$^a$R$^b$, —C(O)NR$^a$R$^b$, —$C_{1-6}$ alkylC(O)NR$^a$R$^b$, —S(O)$_2$R$^a$, —$C_{1-6}$ alkylS(O)$_2$R$^a$, —S(O)$_2$NR$^a$R$^b$, and $C_{1-6}$ alkylS(O)$_2$NR$^a$R$^b$;

each $R^3$ is independently H, —$C_{1-6}$ alkyl, —$C_{2-6}$ alkenyl, —$C_{3-6}$ cycloalkyl, aryl, heteroaryl, heterocyclyl, —$C_{1-6}$ alkylaryl, —$C_{1-6}$ alkylheteroaryl, —$C_{1-6}$ alkylheterocyclyl, —$C_{2-6}$ alkyl-OR$^a$, —$C_{1-6}$ alkylC(O)OR$^a$, or —$C_{2-6}$ alkenyl-C(O)OR$^a$;

each $R^a$ is independently selected from the group consisting of H, —$C_{1-6}$ alkyl, —$C_{3-8}$ cycloalkyl, aryl, heteroaryl, heterocyclyl, —$C_{1-3}$ alkylC$_{3-8}$cycloalkyl, —$C_{1-6}$ alkylaryl, —$C_{1-6}$ alkylheteroaryl, and —$C_{1-6}$alkylheterocyclyl;

each $R^b$ is independently selected from the group consisting of H, —$C_{1-6}$ alkyl, —$C_{3-8}$ cycloalkyl, aryl, heteroaryl, heterocyclyl, —$C_{1-3}$ alkylC$_{3-8}$cycloalkyl, —$C_{1-6}$ alkylaryl, —$C_{1-6}$ alkylheteroaryl, and —$C_{1-6}$ alkylheterocyclyl;

or $R^a$ and $R^b$ may combine together to form a ring consisting of 3-8 ring atoms that are C, N, O, or S; wherein the ring is optionally substituted with 1 to 4 groups independently selected from the group consisting of —OR$^f$, —CN, halo, —$C_{1-6}$ alkylOR$^f$, —$C_{1-6}$ cyanoalkyl, —$C_{1-6}$ haloalkyl, —$C_{3-8}$ cycloalkyl, —$C_{1-3}$ alkylC$_{3-8}$cycloalkyl, —C(O)R$^f$, —$C_{1-6}$ alkylC(O)R$^f$, —C(O)OR$^f$, —$C_{1-6}$ alkylC(O)OR$^f$, —NR$^f$R$^g$, —$C_{1-6}$ alkylNR$^f$R$^g$, —C(O)NR$^f$R$^g$, $C_{1-6}$ alkylC(O)NR$^f$R$^g$, —S(O)$_2$R$^f$, —$C_{1-6}$ alkylS(O)$_2$R$^f$, —S(O)$_2$NR$^f$R$^g$, —$C_{1-6}$ alkylS(O)$_2$NR$^f$R$^g$, —C(O)NR$^f$S(O)$_2$R$^g$ and —NR$^f$C(O)R$^g$;

each $R^c$ is independently selected from the group consisting of H, OH, —$C_{1-6}$ alkyl, —$C_{3-8}$ cycloalkyl, aryl, heteroaryl, heterocyclyl, —$C_{1-3}$ alkylC$_{3-8}$ cycloalkyl, —$C_{1-6}$ alkylaryl, —$C_{1-6}$ alkylheteroaryl, and —$C_{1-6}$ alkylheterocyclyl;

each $R^d$ is independently selected from the group consisting of H, —$C_{1-6}$ alkyl, —$C_3$-$C_8$cycloalkyl, aryl, heteroaryl, heterocyclyl, —$C_{1-3}$ alkylC$_{3-8}$cycloalkyl, —$C_{1-6}$ alkylaryl, —$C_{1-6}$ alkylheteroaryl, and —$C_{1-6}$ alkylheterocyclyl;

each $R^e$ is independently selected from the group consisting of H, —$C_{1-6}$ alkyl, —O—$C_{1-6}$alkyl, —$C_{3-8}$ cycloalkyl, aryl, heteroaryl, heterocyclyl, —O—$C_{3-8}$ cycloalkyl, —O-aryl, —O-heteroaryl, —O-heterocyclyl, —$C_{1-3}$ alkylC$_{3-8}$cycloalkyl, —$C_{1-6}$ alkylaryl, —$C_{1-6}$alkylheteroaryl, —NR$^f$R$^g$, —$C_{1-6}$ alkylNR$^f$R$^g$, —C(O)NR$^f$R$^g$, —$C_{1-6}$ alkylC(O)NR$^f$R$^g$, —NHS(O)$_2$R$^f$, —$C_{1-6}$ alkylS(O)$_2$R$^f$, and —$C_{1-6}$ alkylS(O)$_2$NR$^f$R$^g$;

each $R^f$ is independently selected from the group consisting of H, —$C_{1-6}$ alkyl, —$C_{3-8}$ cycloalkyl, aryl, heteroaryl, heterocyclyl, —$C_{1-3}$ alkylC$_{3-8}$ cycloalkyl, —$C_{1-6}$ alkylaryl, —$C_{1-6}$ alkylheteroaryl, and —$C_{1-6}$ alkylheterocyclyl;

each $R^g$ is independently selected from the group consisting of H, —$C_{1-6}$ alkyl, —$C_{3-8}$ cycloalkyl, aryl, heteroaryl, heterocyclyl, —$C_{1-3}$ alkylC$_{3-8}$ cycloalkyl, —$C_{1-6}$ alkylaryl, —$C_{1-6}$ alkylheteroaryl, and —$C_{1-6}$ alkylheterocyclyl;

or a pharmaceutically acceptable salt, stereoisomer, mixture of stereoisomers, or tautomer thereof.

In certain embodiments, provided is a compound of Formula (I):

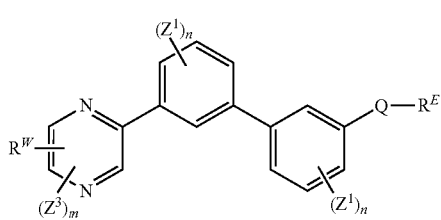

wherein:

each n is independently 0, 1, 2, 3 or 4;

each Z is independently halo, —OR$^a$, —NO$_2$, —CN, —NR$^a$R$^b$, —N$_3$, —S(O)$_2$R$^a$, —$C_{1-6}$ alkyl, —$C_{1-6}$ haloalkyl, —$C_{2-6}$alkenyl, —$C_{2-6}$ alkynyl, —O—$C_{1-6}$ alkyl, —O—$C_{1-6}$ haloalkyl, monocyclic —$C_{3-8}$ cycloalkyl or monocyclic —$C_{1-6}$ alkylC$_{3-8}$ cycloalkyl;

wherein each alkyl, alkenyl, alkynyl, and cycloalkyl group is optionally substituted with 1 to 4 groups independently selected from the group consisting of oxo, —NO$_2$, —N$_3$, —OR$^a$, halo, and cyano;

Q is monocyclic aryl, monocyclic heteroaryl or monocyclic heterocyclyl, wherein each Q is monocyclic group is optionally substituted with 1 to 4 groups independently selected from the group consisting of halo, oxo, —OR, N$_3$, NO$_2$, —CN, —NR$^1$R$^2$, —S(O)$_2$R$^a$, —S(O)$_2$NR$^a$R$^b$, —NR$^a$S(O)$_2$R$^a$, —NR$^a$C(O)R$^a$, —C(O)R$^a$, —C(O)OR$^a$, —C(O)NR$^a$R$^b$, —NR$^a$C(O)OR$^a$, —NR$^a$C(O)

NR$^1$R$^2$, —OC(O)NR$^a$R$^b$, —NR$^a$S(O)$_2$NR$^a$R$^b$, —C(O)NR$^a$S(O)$_2$NR$^a$R$^b$, —C$_{1-6}$ alkyl, —C$_{2-6}$ alkenyl, —C$_{2-6}$ alkynyl, —O—C$_{1-6}$ alkyl, monocyclic —C$_{3-8}$ cycloalkyl, monocyclic —C$_{1-6}$ alkylC$_{3-8}$ cycloalkyl, monocyclic aryl, and R$^N$;

wherein the alkyl, alkenyl, alkynyl, monocyclic C$_{3-8}$ cycloalkyl, or monocyclic aryl group is optionally substituted with 1 to 4 groups independently selected from the group consisting of oxo, —NO$_2$, N$_3$, —OR$^a$, halo, cyano, —NR$^a$R$^b$, —C(O)R$^a$, —C(O)OR$^a$, —O—C$_{1-6}$ alkylCN, —C(O)NR$^a$R$^b$, NR$^a$C(O)R$^a$, —NR$^a$C(O)OR$^a$, —S(O)$_2$R$^a$, —NR$^a$S(O)$_2$R$^b$, —S(O)$_2$NR$^a$R$^b$, —NR$^a$S(O)$_2$NR$^a$R$^b$, —C(O)NR$^a$S(O)$_2$ NR$^a$R$^b$ and monocyclic —C$_{3-8}$ cycloalkyl; and wherein the monocyclic heteroaryl or monocyclic heterocyclyl group may be oxidized on a nitrogen atom to form an N-oxide or oxidized on a sulfur atom to form a sulfoxide or sulfone;

m is 0, 10 or 2;

each Z$^3$ is independently halo, oxo, —OR$^a$, N$_3$, NO$_2$, —CN, —NR$^1$R$^2$, —S(O)$_2$R$^a$, —S(O)$_2$NR$^a$R$^b$, —NR$^a$S(O)$_2$R$^a$, —NR$^a$C(O)R$^a$, —C(O)R$^a$, —C(O)OR$^a$, —C(O)NR$^a$R$^b$, —NR$^a$C(O)OR$^a$, —NR$^a$C(O)NR$^1$R$^2$, —OC(O)NR$^a$R$^b$, —NR$^a$S(O)$_2$NR$^a$R$^b$, —C(O)NR$^a$S(O)$_2$NR$^a$R$^b$, —C$_{1-6}$ alkyl, —C$_{2-6}$ alkenyl, —C$_{2-6}$ alkynyl, —O—C$_{1-6}$ alkyl, monocyclic —C$_{3-8}$ cycloalkyl, monocyclic —C$_{1-6}$ alkylC$_{3-8}$ cycloalkyl, monocyclic aryl, and R$^N$;

wherein the alkyl, alkenyl, alkynyl, monocyclic C$_{3-8}$ cycloalkyl, or monocyclic aryl group is optionally substituted with 1 to 4 groups independently selected from the group consisting of oxo, —NO$_2$, N$_3$, —OR$^a$, halo, cyano, —NR$^a$R$^b$, —C(O)R$^a$, —C(O)OR$^a$, —O—C$_{1-6}$ alkylCN, —C(O)NR$^a$R$^b$, NR$^a$C(O)R$^a$, —NR$^a$C(O)OR$^a$, —S(O)$_2$R$^a$, —NR$^a$S(O)$_2$R$^b$, —S(O)$_2$NR$^a$R$^b$, —NR$^a$S(O)$_2$NR$^a$R$^b$, —C(O)NR$^a$S(O)$_2$ NR$^a$R$^b$ and monocyclic —C$_{3-8}$ cycloalkyl;

each R$^N$ is independently —C$_{1-6}$ alkylNR$^1$R$^2$, —O—C$_{1-6}$ alkylNR$^1$R$^2$, —C$_{1-6}$ alkylOC$_{1-6}$ alkylNR$^1$R$^2$, —NR$^a$—C$_{1-6}$ alkylNR$^1$R$^2$, —C$_{1-6}$ alkylC(O)NR$^1$R$^2$, —O—C$_{1-6}$ alkylC(O)NR$^1$R$^2$, —O—C$_{1-6}$ alkylC(O)OR$^1$, —S—C$_{1-6}$ alkylNR$^1$R$^2$, —C$_{1-6}$ alkylOR$^a$, or $$\text{L}^1\text{—V—L}^2\text{—}\boxed{A};$$

wherein

L$^1$ is independently a bond, O, NR$^a$, S, S(O), or S(O)$_2$;

V is independently selected from the group consisting of a bond, C$_{1-6}$alkyl, C$_{2-6}$alkenyl, and C$_{2-6}$alkynyl;

wherein the alkyl, alkenyl or alkynyl group is optionally independently substituted with —OR$^a$, halo, cyano, NR$^a$R$^b$ and monocyclic —C$_{3-8}$ cycloalkyl;

L$^2$ is independently a bond, O, NR$^a$, S, S(O), or S(O)$_2$;

ring A is independently monocyclic cycloalkyl, monocyclic aryl, monocyclic heteroaryl or monocyclic heterocyclyl;

wherein the monocyclic cycloalkyl, monocyclic aryl, monocyclic heteroaryl, or monocyclic heterocyclyl group is optionally substituted with 1 to 4 groups independently selected from the group consisting of oxo, —NO$_2$, N$_3$, —OR$^a$, halo, cyano, —C$_{1-6}$ alkyl, —C$_{1-6}$ haloalkyl, —C$_{2-6}$alkenyl, —C$_{2-6}$ alkynyl, —O—C$_{1-6}$ haloalkyl, NR$^a$R$^b$, —C(O)R$^a$, —C(O)OR$^a$, —O—C$_{1-6}$ alkylCN, —C(O)NR$^a$R$^b$, —NR$^a$C(O)R$^a$, —NR$^a$C(O)OR$^a$, —NR$^a$C(O)R$^a$, —C(O)N (R$^a$)OR$^b$, —S(O)$_2$R$^a$, —S(O)$_2$NR$^a$R$^b$, —NR$^a$S(O)$_2$R$^b$, —NR$^a$S(O)$_2$NR$^a$R$^b$, —C(O)NR$^a$S(O)$_2$NR$^a$R$^b$, monocyclic C$_{3-8}$cycloalkyl and monocyclic C$_{1-6}$alkylC$_{3-8}$ cycloalkyl;

wherein the alkyl, alkenyl or alkynyl group is optionally independently substituted with —OR$^a$, halo, cyano, NR$^a$R$^b$ and monocyclic —C$_{3-8}$ cycloalkyl;

R$^E$ and R$^W$ are each independently —NR$^1$R$^2$, —C$_{1-6}$ alkylNR$^1$R$^2$, —O—C$_{1-6}$ alkylNR$^1$R$^2$, —C$_{1-6}$ alkylOC$_{1-6}$ alkylNR$^1$R$^2$, —NR$^a$—C$_{1-6}$ alkylNR$^1$R$^2$, —C$_{1-6}$ alkylN+R$^1$R$^2$R$^3$, —S—C$_{1-6}$ alkylNR$^1$R$^2$, —C(O)NR$^1$R$^2$, —S(O)$_2$R$^a$, —(CH$_2$)$_u$S(O)$_2$NR$^1$R$^2$, —(CH$_2$)$_u$NR$^a$S(O)$_2$NR$^a$R$^b$, —S(O)$_2$NR$^a$C$_{1-6}$ alkylNR$^1$R$^2$, —NR$^a$S(O)$_2$C$_{1-6}$ alkylNR$^1$R$^2$, —(CH$_2$)$_u$C(O)NR$^a$S(O)$_2$NR$^a$R$^b$, —(CH$_2$)$_u$N+R$^1$R$^2$O$^-$, —(CH$_2$)$_u$P+R$^b$R$^c$R$^d$, —(CH$_2$)$_u$P+R$^c$R$^d$O$^-$, —(CH$_2$)$_u$P+O[NR$^a$R$^b$][NR$^c$R$^d$], —(CH$_2$)$_u$NR$^c$P(O)(OR$^c$)$_2$, —(CH$_2$)$_u$CH$_2$P(O)(OR$^c$)(OR$^d$), —(CH$_2$)$_u$OP(O)(OR$^c$)(OR$^d$), —(CH$_2$)$_u$OP(O)NR$^a$R$^b$)(OR$^a$), or $$\text{—V}^2\text{—(CR}^c\text{R}^d\text{)}_p\text{—L}^3\text{—}\boxed{B}\text{—(T)}_z;$$

wherein:

V$^2$ is independently a bond, O, NR$^a$, S, S(O), S(O)$_2$, C(O)NR$^a$, NR$^a$C(O), S(O)$_2$NR$^1$, or NR$^a$S(O)$_2$;

L$^3$ is independently a bond, O, NR$^a$, S, S(O), S(O)$_2$, C(O)NR$^a$, NR$^a$C(O), S(O)$_2$NR$^1$, or NR$^a$S(O)$_2$;

ring B is independently monocyclic cycloalkyl, monocyclic aryl, monocyclic heteroaryl, monocyclic heterocyclyl or spirocyclic heterocyclyl;

T is independently H, —OR$^a$, (CH$_2$)$_q$NR$^1$R$^2$, (CH$_2$)$_q$NR$^a$C(O)R$^e$ or (CH$_2$)$_q$C(O)R$^e$;

p is independently 0, 1, 2, 3, 4, or 5;

q is independently 0, 1, 2, 3, 4, or 5;

u is 0, 1, 2, 3 or 4;

z is 0, 1, 2 or 3; and wherein the alkyl, monocyclic cycloalkyl, monocyclic aryl, monocyclic heteroaryl, monocyclic heterocyclyl or spirocyclic heterocyclyl of R$^E$ or R$^W$ is optionally substituted with 1 to 3 substituents independently selected from the group consisting of NR$^a$R$^b$, halo, cyano, oxo, —OR$^a$, —C$_{1-6}$ alkyl, —C$_{1-6}$ haloalkyl, —C$_{1-6}$ cyanoalkyl, —C$_{1-6}$ alkylNR$^a$R$^b$, —C$_{1-6}$ alkyl OH, monocyclic —C$_{3-8}$ cycloalkyl and monocyclic —C$_{1-3}$ alkylC$_{3-8}$cycloalkyl;

provided that at least one of V$^2$, L$^3$, ring B and T contains a nitrogen atom;

each R$^1$ is independently selected from the group consisting of H, —C$_{1-8}$ alkyl, —C$_{2-6}$ alkenyl, —C$_{2-6}$ alkynyl, monocyclic —C$_{3-6}$ cycloalkyl, monocyclic aryl, monocyclic heteroaryl, monocyclic heterocyclyl, monocyclic —C$_{1-6}$ alkylaryl, monocyclic —C$_{1-6}$ alkylheteroaryl, monocyclic —C$_{1-6}$ alkylheterocyclyl, —C$_{1-6}$ alkylC(O)OR$^a$, —C$_{2-6}$ alkenylC(O)OR$^a$, —S(O)$_2$R$^a$, —S(O)$_2$NR$^a$R$^b$, —C(O)NR$^a$S(O)$_2$R$^a$, and monocyclic C$_{1-6}$ alkylC$_{3-8}$cycloalkyl;

wherein each alkyl, alkenyl, monocyclic cycloalkyl, monocyclic aryl, monocyclic heteroaryl or monocyclic heterocyclyl group is optionally substituted with 1 to 4 groups independently selected from the group consisting of —OR$^a$, —CN, halo, C$_{1-6}$alkyl, —C$_{1-6}$ alkylOR$^a$, —C$_{1-6}$ cyanoalkyl, —C$_{1-6}$ haloalkyl, monocyclic C$_{3-8}$ cycloalkyl, monocyclic —C$_{1-3}$ alkylC$_{3-8}$cycloalkyl, —C(O)R$^a$, —C$_{1-6}$ alkylC(O)R$^a$, —C(O)OR$^a$, —C$_{1-6}$ alkylC(O)OR$^a$, —NR$^a$R$^b$, —OC(O)NR$^a$R$^b$, NR$^a$C(O)OR$^b$, —C$_{1-6}$ alkylNR$^a$R$^b$, —C(O)NR$^a$R$^b$, —C$_{1-6}$ alkyl- C(O)NR$^a$R$^b$, —S(O)$_2$R$^a$, —C$_{1-6}$ alkylS(O)$_2$R$^a$, —S(O)$_2$ NR$^a$R$^b$, —C$_{1-6}$ alkylS(O)$_2$NR$^a$R$^b$, —C(O)NR$^a$S(O)$_2$ R$^b$, —C$_{1-6}$ alkylC(O)NR$^a$S(O)$_2$R$^b$, —NR$^a$C(O)R$^b$, and —C$_{1-6}$alkylNR$^a$C(O)R$^b$;

each R$^2$ is independently selected from the group consisting of H, —C$_{1-6}$ alkyl, —C$_{2-6}$ alkenyl, —C$_{2-6}$ alkynyl, monocyclic —C$_{3-6}$ cycloalkyl, monocyclic aryl, monocyclic heteroaryl, monocyclic heterocyclyl, monocyclic —C$_{1-6}$ alkylaryl, monocyclic —C$_{1-6}$ alkylheteroaryl, monocyclic —C$_{1-6}$ alkylheterocyclyl, —C$_{2-6}$ alkyl-OR$^a$, —C$_{1-6}$ alkylC(O)OR$^a$, and —C$_{2-6}$ alkenylC(O)OR$^a$;

wherein each alkyl, alkenyl, monocyclic cycloalkyl, monocyclic aryl, monocyclic heteroaryl or monocyclic heterocyclyl group is optionally substituted with 1 to 4 groups independently selected from the group consisting of —OR$^a$, —CN, halo, C$_{1-6}$alkyl, —C$_{1-6}$ alkylOR$^a$, —C$_{1-6}$ cyanoalkyl, —C$_{1-6}$ haloalkyl, monocyclic —C$_{3-8}$ cycloalkyl, monocyclic —C$_{1-3}$ alkylC$_{3-8}$cycloalkyl, —C(O)R$^a$, —C$_{1-6}$ alkylC(O)R$^a$, —C(O)OR$^a$, —C$_{1-6}$ alkylC(O)OR$^a$, —NR$^a$R$^b$, —C$_{1-6}$ alkylNR$^a$R$^b$, —C(O)NR$^a$R$^b$, C$_{1-6}$ alkylC(O)NR$^a$R$^b$, —S(O)$_2$R$^a$, —C$_{1-6}$ alkylS(O)$_2$R$^a$, —S(O)$_2$NR$^a$R$^b$, —C$_{1-6}$ alkylS(O)$_2$NR$^a$R$^b$, —C(O)NR$^a$S(O)$_2$R$^b$ and —NR$^a$C(O)R$^b$;

or R$^1$ and R$^2$, when bound to the same atom, may combine with the atom to which they are attached to form a monocyclic heterocyclyl group optionally containing 1, 2, or 3 additional heteroatoms independently selected from oxygen, sulfur and nitrogen, and optionally substituted with 1 to 3 groups independently selected from the group consisting of oxo, —C$_{1-6}$ alkyl, monocyclic —C$_{3-8}$ cycloalkyl, —C$_{2-6}$ alkenyl, —C$_{2-6}$ alkynyl, —OR$^a$, —C(O)OR$^a$, —C$_{1-6}$ cyanoalkyl, —C$_{1-6}$ alkylOR$^a$, —C$_{1-6}$ haloalkyl, monocyclic —C$_{1-3}$ alkylC$_{3-8}$cycloalkyl, —C(O)R$^a$, C$_{1-6}$ alkylC(O)R$^a$, —C$_{1-6}$ alkylC(O)OR$^a$, —NR$^a$R$^b$, —C$_{1-6}$alkylNR$^a$R$^b$, —C(O)NR$^a$R$^b$, —C$_{1-6}$ alkylC(O)NR$^a$R$^b$, —S(O)$_2$R$^a$, —C$_{1-6}$ alkylS(O)$_2$R$^a$, —S(O)$_2$NR$^a$R$^b$, and C$_{1-6}$ alkylS(O)$_2$NR$^a$R$^b$;

each R$^3$ is independently H, —C$_{1-6}$ alkyl, —C$_{2-6}$ alkenyl, monocyclic —C$_{3-6}$ cycloalkyl, monocyclic aryl, monocyclic heteroaryl, monocyclic heterocyclyl, —C$_{1-6}$ alkylaryl, monocyclic —C$_{1-6}$ alkylheteroaryl, monocyclic —C$_{1-6}$ alkylheterocyclyl, —C$_{2-6}$ alkyl-OR$^a$, —C$_{1-6}$ alkylC(O)OR$^a$, or —C$_{2-6}$ alkenylC(O)OR$^a$;

each R$^a$ is independently selected from the group consisting of H, —C$_{1-6}$ alkyl, monocyclic —C$_{3-8}$ cycloalkyl, monocyclic aryl, monocyclic heteroaryl, monocyclic heterocyclyl, monocyclic —C$_{1-3}$ alkylC$_{3-8}$cycloalkyl, monocyclic —C$_{1-6}$ alkylaryl, monocyclic —C$_{1-6}$ alkylheteroaryl, and monocyclic —C$_{1-6}$alkylheterocyclyl;

each R$^b$ is independently selected from the group consisting of H, —C$_{1-6}$ alkyl, monocyclic —C$_{3-8}$ cycloalkyl, monocyclic aryl, monocyclic heteroaryl, monocyclic heterocyclyl, monocyclic —C$_{1-3}$ alkylC$_{3-8}$cycloalkyl, monocyclic —C$_{1-6}$ alkylaryl, monocyclic —C$_{1-6}$ alkylheteroaryl, and monocyclic —C$_{1-6}$ alkylheterocyclyl;

or R$^a$ and R$^b$, when bound to the same atom, may combine together to form a monocyclic ring consisting of 3-8 ring atoms that are C, N, O, or S; wherein the ring is optionally substituted with 1 to 4 groups independently selected from the group consisting of —OR$^f$, —CN, halo, —C$_{1-6}$ alkyl OR$^f$, —C$_{1-6}$ cyanoalkyl, —C$_{1-6}$ haloalkyl, monocyclic —C$_{3-8}$ cycloalkyl, monocyclic —C$_{1-3}$ alkylC$_{3-8}$cycloalkyl, —C(O)R$^f$, —C$_{1-6}$ alkylC(O)R$^f$, —C(O)OR$^f$, —C$_{1-6}$ alkylC(O)OR$^f$, —NR$^f$R$^g$, —C$_{1-6}$ alkylNR$^f$R$^g$, —C(O)NR$^f$R$^g$, C$_{1-6}$ alkylC(O)NR$^f$R$^g$, —S(O)$_2$R$^f$, —C$_{1-6}$ alkylS(O)$_2$R$^f$, —S(O)$_2$NR$^f$R$^g$, —C$_{1-6}$ alkylS(O)$_2$NR$^f$R$^g$, —C(O)NR$^f$S(O)$_2$R$^g$ and —NR$^f$C(O)R$^g$;

each R$^c$ is independently selected from the group consisting of H, OH, —C$_{1-6}$ alkyl, monocyclic —C$_{3-8}$ cycloalkyl, monocyclic aryl, monocyclic heteroaryl, monocyclic heterocyclyl, monocyclic —C$_{1-3}$ alkylC$_{3-8}$ cycloalkyl, monocyclic —C$_{1-6}$ alkylaryl, monocyclic —C$_{1-6}$ alkylheteroaryl, and monocyclic —C$_{1-6}$ alkylheterocyclyl;

each R$^d$ is independently selected from the group consisting of H, —C$_{1-6}$ alkyl, monocyclic —C$_3$-C$_8$cycloalkyl, monocyclic aryl, monocyclic heteroaryl, monocyclic heterocyclyl, monocyclic —C$_{1-3}$ alkylC$_{3-8}$cycloalkyl, monocyclic —C$_{1-6}$ alkylaryl, monocyclic —C$_{1-6}$ alkylheteroaryl, and monocyclic —C$_{1-6}$ alkylheterocyclyl;

each R$^e$ is independently selected from the group consisting of H, —C$_{1-6}$ alkyl, —O—C$_{1-6}$alkyl, monocyclic —C$_{3-8}$ cycloalkyl, monocyclic aryl, monocyclic heteroaryl, monocyclic heterocyclyl, monocyclic —O—C$_{3-8}$ cycloalkyl, monocyclic —O-aryl, monocyclic —O-heteroaryl, monocyclic —O-heterocyclyl, monocyclic —C$_{1-3}$ alkylC$_{3-8}$cycloalkyl, monocyclic —C$_{1-6}$ alkylaryl, monocyclic —C$_{1-6}$ alkylheteroaryl, —NR$^f$R$^g$, —C$_{1-6}$ alkylNR$^f$R$^g$, —C(O)NR$^f$R$^g$, —C$_{1-6}$ alkylC(O)NR$^f$R$^g$, —NHS(O)$_2$R$^f$, —C$_{1-6}$ alkylS(O)$_2$R$^f$, and —C$_{1-6}$ alkylS(O)$_2$NR$^f$R$^g$;

each R$^f$ is independently selected from the group consisting of H, —C$_{1-6}$ alkyl, monocyclic —C$_{3-8}$ cycloalkyl, monocyclic aryl, monocyclic heteroaryl, monocyclic heterocyclyl, monocyclic —C$_{1-3}$ alkylC$_{3-8}$ cycloalkyl, monocyclic —C$_{1-6}$ alkylaryl, monocyclic —C$_{1-6}$ alkylheteroaryl, and monocyclic —C$_{1-6}$ alkylheterocyclyl;

each R$^g$ is independently selected from the group consisting of H, —C$_{1-6}$ alkyl, monocyclic —C$_{3-8}$ cycloalkyl, monocyclic aryl, monocyclic heteroaryl, monocyclic heterocyclyl, monocyclic —C$_{1-3}$ alkylC$_{3-8}$ cycloalkyl, monocyclic —C$_{1-6}$ alkylaryl, monocyclic —C$_{1-6}$ alkylheteroaryl, and monocyclic —C$_{1-6}$ alkylheterocyclyl;

or a pharmaceutically acceptable salt, stereoisomer, mixture of stereoisomers, or tautomer thereof.

Also provided are compounds of Formula (Ia):

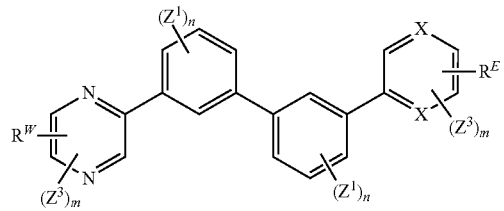

(Ia)

or a pharmaceutically acceptable salt, stereoisomer, mixture of stereoisomers, or tautomer thereof,
wherein:
each X is independently CH, CZ$^3$ or N;
each m is independently 0, 1 or 2; and
Z$^1$, Z$^3$, R$^E$, R$^W$ and n are as defined herein.

Also provided are compounds of Formula (Ib):

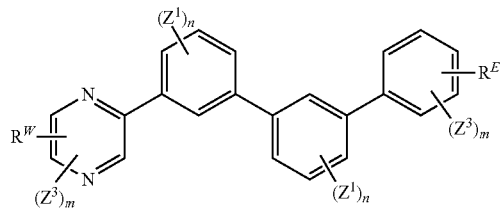

(Ib)

or a pharmaceutically acceptable salt, stereoisomer, mixture of stereoisomers, or tautomer thereof,
wherein:
each m is independently 0, 1 or 2; and
$Z^1$, $Z^3$, $R^E$, $R^W$ and n are as defined herein.
Also provided are compounds of Formula (Ic):

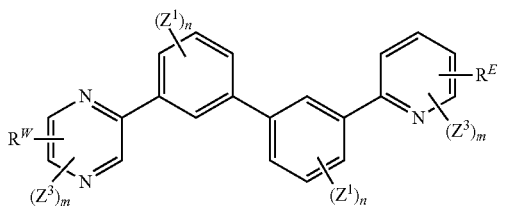

(Ic)

or a pharmaceutically acceptable salt, stereoisomer, mixture of stereoisomers, or tautomer thereof,
wherein:
each m is independently 0, 1 or 2; and
$Z^1$, $Z^3$, $R^E$, $R^W$ and n are as defined herein.
Also provided are compounds of Formula (Id):

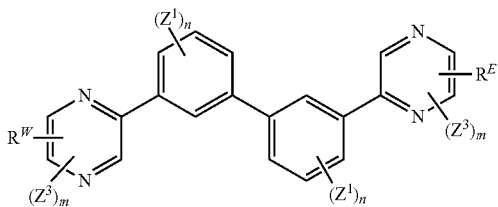

(Id)

or a pharmaceutically acceptable salt, stereoisomer, mixture of stereoisomers, or tautomer thereof,
wherein:
each m is independently 0, 1 or 2; and
$Z^1$, $Z^3$, $R^E$, $R^W$ and n are as defined herein.
Also provided are compounds of Formula (II):

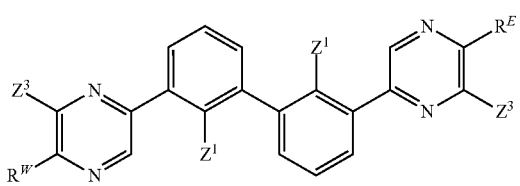

(II)

or a pharmaceutically acceptable salt, stereoisomer, mixture of stereoisomers, or tautomer thereof,
wherein:
$Z^1$, $Z^3$, $R^E$ and $R^W$ are as defined herein.
Also provided are compounds of formula (III):

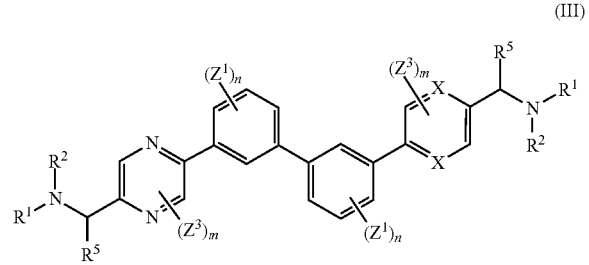

(III)

or a pharmaceutically acceptable salt, stereoisomer, mixture of stereoisomers, or tautomer thereof,
wherein:
each X is independently CH, $CZ^3$ or N;
each n is independently 0, 1, 2, 3 or 4;
each m is independently 0, 1 or 2;
each $R^5$ is independently selected from the group consisting of $NR^aR^b$, halo, cyano, —$OR^a$, —$C_{1-6}$ alkyl, —$C_{1-6}$ haloalkyl, —$C_{1-6}$ cyanoalkyl, —$C_{1-6}$ alkyl$NR^aR^b$, —$C_{1-6}$ alkylOH, —$C_{3-8}$ cycloalkyl and —$C_{1-3}$ alkyl$C_{3-8}$cycloalkyl; and
$R^1$, $R^2$, $Z^1$, $Z^3$, $R^E$ and $R^W$ are as defined herein.
The present disclosure provides a compound of formula (III):

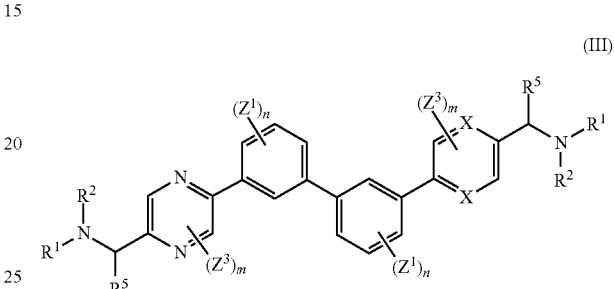

(III)

wherein:
each X is independently CH, $CZ^3$ or N;
each n is independently 0, 1, 2, 3 or 4;
each $Z^1$ is independently halo, —$OR^a$, —$NO_2$, —CN, —$NR^aR^b$, —$N_3$, —$S(O)_2R^a$, —$C_{1-6}$ alkyl, —$C_{1-6}$ haloalkyl, —$C_{2-6}$alkenyl, —$C_{2-6}$ alkynyl, —O—$C_{1-6}$ alkyl, —O—$C_{1-6}$ haloalkyl, —$C_{3-8}$ cycloalkyl or —$C_{1-6}$ alkyl$C_{3-8}$ cycloalkyl;
wherein each alkyl, alkenyl, alkynyl, and cycloalkyl group is optionally substituted with 1 to 4 groups independently selected from the group consisting of oxo, —$NO_2$, —$N_3$, —$OR^a$, halo, and cyano;
each m is independently 0, 1 or 2;
each $Z^3$ is independently halo, oxo, —$OR^a$, $SR^a$, $N_3$, $NO_2$, —CN, —$NR^1R^2$, —$S(O)_2R^a$, —$S(O)_2NR^aR^b$, —$NR^aS(O)_2R^a$, —$NR^aC(O)R^a$, —$C(O)R^a$, —$C(O)OR^a$, —$C(O)NR^aR^b$, —$NR^aC(O)OR^a$, —$NR^aC(O)NR^1R^2$, —O—$C(O)NR^aR^b$, —$NR^aS(O)_2NR^aR^b$, —$C(O)NR^aS(O)_2NR^aR^b$, —$C_{1-6}$ alkyl, —$C_{2-6}$ alkenyl, —$C_{2-6}$ alkynyl, —O—$C_{1-6}$ alkyl, —$C_{3-8}$ cycloalkyl, —$C_{1-6}$ alkyl$C_{3-8}$ cycloalkyl, aryl, heteroaryl, heterocyclyl and $R^N$;
wherein the alkyl, alkenyl, alkynyl, cycloalkyl, aryl, heteroaryl, or heterocyclyl group is optionally substituted with 1 to 4 groups independently selected from the group consisting of oxo, —$NO_2$, $N_3$, —$OR^a$, halo, cyano, —$NR^aR^b$, —$C(O)R^a$, —$C(O)OR^a$, —O—$C_{1-6}$ alkylCN, —$C(O)NR^aR^b$, $NR^aC(O)R^a$, —$NR^aC(O)OR^a$, —$S(O)_2R^a$, —$NR^aS(O)_2R^b$, —$S(O)_2NR^aR^b$, —$NR^aS(O)_2NR^aR^b$, —$C(O)NR^aS(O)_2NR^aR^b$ and —$C_{3-8}$ cycloalkyl;
each $R^N$ is independently —$C_{1-6}$ alkyl$NR^1R^2$, —O—$C_{1-6}$ alkyl$NR^1R^2$, —$C_{1-6}$ alkylO$C_{1-6}$ alkyl$NR^1R^2$, —$NR^a$—$C_{1-6}$ alkyl$NR^1R^2$, —$C_{1-6}$ alkylC(O)$NR^1R^2$, —O—$C_{1-6}$ alkylC(O)$NR^1R^2$, —O—$C_{1-6}$ alkylC(O)$OR^1$, —S—$C_{1-6}$ alkyl$NR^1R^2$, —$C_{1-6}$ alkyl$OR^a$, or

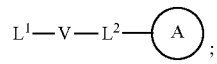

;

wherein $L^1$ is independently a bond, O, $NR^a$, S, S(O), or $S(O)_2$;

V is independently selected from the group consisting of a bond, $C_{1-6}$alkyl, $C_{2-6}$alkenyl, and $C_{2-6}$alkynyl;

wherein the alkyl, alkenyl or alkynyl group is optionally independently substituted with —$OR^a$, halo, cyano, $NR^aR^b$ and —$C_{3-8}$ cycloalkyl;

$L^2$ is independently a bond, O, $NR^a$, S, S(O), or $S(O)_2$;

ring A is independently cycloalkyl, aryl, heteroaryl or heterocyclyl;

wherein the cycloalkyl, aryl, heteroaryl, or heterocyclyl group is optionally substituted with 1 to 4 groups independently selected from the group consisting of oxo, —$NO_2$, $N_3$, —$OR^a$, halo, cyano, —$C_{1-6}$ alkyl, —$C_{1-6}$ haloalkyl, —$C_{2-6}$alkenyl, —$C_{2-6}$ alkynyl, —O—$C_{1-6}$ haloalkyl, $NR^aR^b$, —$C(O)R^a$, —$C(O)OR^a$, —O—$C_{1-6}$ alkylCN, —$C(O)NR^aR^b$, —$NR^aC(O)R^a$, —$NR^aC(O)OR^a$, —$NR^aC(O)OR^a$, —$C(O)N(R^a)OR^b$, —$S(O)_2R^a$, —$S(O)_2NR^aR^b$, —$NR^aS(O)_2R^b$, —$NR^aS(O)_2NR^aR^b$, —$C(O)NR^aS(O)_2NR^aR^b$, $C_{3-8}$cycloalkyl and $C_{1-6}$alkyl$C_{3-8}$ cycloalkyl;

wherein the alkyl, alkenyl or alkynyl group is optionally independently substituted with —$OR^a$, halo, cyano, $NR^aR^b$ and —$C_{3-8}$ cycloalkyl;

each $R^1$ is independently selected from the group consisting of H, —$C_{1-8}$ alkyl, —$C_{2-6}$ alkenyl, —$C_{2-6}$ alkynyl, —$C_{3-6}$ cycloalkyl, aryl, heteroaryl, heterocyclyl, —$C_{1-6}$ alkylaryl, —$C_{1-6}$ alkylheteroaryl, —$C_{1-6}$ alkylheterocyclyl, —$C_{1-6}$ alkylC(O)$OR^a$, —$C_{2-6}$ alkenylC(O)$OR^a$, —$S(O)_2R^a(O)_2(O)_2$ $OR^a$, —$S(O)_2NR^aR^b$, —$C(O)NR^aS(O)_2R^a$, and $C_{1-6}$ alkyl$C_{3-8}$cycloalkyl;

wherein each alkyl, alkenyl, cycloalkyl, aryl, heteroaryl or heterocyclyl group is optionally substituted with 1 to 4 groups independently selected from the group consisting of —$OR^a$, —CN, —$NO_2$, halo, $C_{1-6}$alkyl, —$C_{1-6}$ alkyl$OR^a$, —$C_{1-6}$ cyanoalkyl, —$C_{1-6}$ haloalkyl, $C_{3-8}$ cycloalkyl, heteroaryl, heterocyclyl, —$C_{1-3}$ alkyl$C_{3-8}$cycloalkyl, —$C(O)R^a$, —$C_{1-6}$ alkylC(O)$R^a$, —$C(O)OR^a$, —$C_{1-6}$ alkylC(O)$OR^a$, —$NR^aR^b$, —OC(O)$NR^aR^b$, —$NR^aC(O)OR^b$, —$NR^aC(O)R^b$, —$C_{1-6}$ alkylNR^aR^b$, —$C(O)NR^aR^b$, —$C_{1-6}$ alkylC(O)$NR^aR^b$, —$S(O)_2R^a$, —$S(O)_2OR^a$, —$C_{1-6}$ alkylS(O)$_2R^a$, —$S(O)_2NR^aR^b$, —$C_{1-6}$ alkylS(O)$_2NR^aR^b$, —$C(O)NR^aS(O)_2R^b$, —$NR^aC(O)NR^b$, —$C_{1-6}$ alkylC(O)$NR^aS(O)_2R^b$, —$NR^aC(O)R^b$, and —$C_{1-6}$alkylNR$^aC(O)R^b$;

each $R^2$ is independently selected from the group consisting of H, —$C_{1-6}$ alkyl, —$C_{2-6}$ alkenyl, —$C_{2-6}$ alkynyl, —$C_{3-6}$ cycloalkyl, aryl, heteroaryl, heterocyclyl, —$C_{1-6}$ alkylaryl, —$C_{1-6}$ alkylheteroaryl, —$C_{1-6}$ alkylheterocyclyl, —$C_{2-6}$ alkyl-$OR^a$, —$C_{1-6}$ alkylC(O)$OR^a$, and —$C_{2-6}$ alkenylC(O)$OR^a$;

wherein each alkyl, alkenyl, cycloalkyl, aryl, heteroaryl or heterocyclyl group is optionally substituted with 1 to 4 groups independently selected from the group consisting of —$OR^a$, —CN, halo, $C_{1-6}$alkyl, —$C_{1-6}$ alkyl$OR^a$, —$C_{1-6}$ cyanoalkyl, —$C_{1-6}$ haloalkyl, —$C_{3-8}$ cycloalkyl, —$C_{1-3}$ alkyl$C_{3-8}$cycloalkyl, —$C(O)R^a$, —$C_{1-6}$ alkylC(O)$R^a$, —$C(O)OR^a$, —$C_{1-6}$ alkylC(O)$OR^a$, —$NR^aR^b$, —$C_{1-6}$ alkylNR$^aR^b$, —$C(O)NR^aR^b$, $C_{1-6}$ alkylC(O)$NR^aR^b$, —$S(O)_2R^a$, —$C_{1-6}$ alkylS(O)$_2R^a$, —$S(O)_2NR^aR^b$, —$C_{1-6}$ alkylS(O)$_2NR^aR^b$, —$C(O)NR^aS(O)_2R^b$ and —$NR^aC(O)R^b$;

or $R^1$ and $R^2$ combine to form a heterocyclyl group optionally containing 1, 2, or 3 additional heteroatoms independently selected from oxygen, sulfur and nitrogen, and optionally substituted with 1 to 3 groups independently selected from the group consisting of oxo, —$C_{1-6}$ alkyl, —$C_{3-8}$ cycloalkyl, —$C_{2-6}$ alkenyl, —$C_{2-6}$ alkynyl, aryl, heteroaryl, heterocyclyl, —$OR^a$, —CN, halo, —$C(O)OR^a$, —$C_{1-6}$ cyanoalkyl, —$C_{1-6}$ alkyl$OR^a$, —$C_{1-6}$ haloalkyl, —$C_{1-3}$ alkyl$C_{3-8}$cycloalkyl, —$C(O)R^a$, $C_{1-6}$ alkylC(O)$R^a$, —$C_{1-6}$ alkylC(O)$OR^a$, —$NR^aR^b$, —$C_{1-6}$alkyl$NR^aR^b$, —$C(O)NR^aR^b$, —$NR^aC(O)OR^b$, —$NR^aC(O)NR^aR^b$, —$NR^aS(O)_2NR^aR^b$, —$NR^aS(O)_2R^b$, —$C_{1-6}$ alkylC(O)$NR^aR^b$, —$S(O)_2R^a$, —$C_{1-6}$ alkylS(O)$_2R^a$, —$S(O)_2NR^aR^b$, and $C_{1-6}$ alkylS(O)$_2NR^aR^b$;

each $R^3$ is independently H, —$C_{1-6}$ alkyl, —$C_{2-6}$ alkenyl, —$C_{3-6}$ cycloalkyl, aryl, heteroaryl, heterocyclyl, —$C_{1-6}$ alkylaryl, —$C_{1-6}$ alkylheteroaryl, —$C_{1-6}$ alkylheterocyclyl, —$C_{2-6}$ alkyl-$OR^a$, —$C_{1-6}$ alkylC(O)$OR^a$, or —$C_{2-6}$ alkenyl-C(O)$OR^a$;

each $R^5$ is independently selected from the group consisting of $NR^aR^b$, halo, cyano, —$OR^a$, —$C_{1-6}$ alkyl, —$C_{1-6}$ haloalkyl, —$C_{1-6}$ cyanoalkyl, —$C_{1-6}$ alkyl$NR^aR^b$, —$C_{1-6}$ alkylOH, —$C_{3-8}$ cycloalkyl and —$C_{1-3}$ alkyl$C_{3-8}$cycloalkyl;

each $R^a$ is independently selected from the group consisting of H, —$C_{1-6}$ alkyl, —$C_{1-6}$ haloalkyl, —$C_{3-8}$ cycloalkyl, aryl, heteroaryl, heterocyclyl, —$C_{1-3}$ alkyl$C_{3-8}$cycloalkyl, —$C_{1-6}$ alkylaryl, —$C_{1-6}$ alkylheteroaryl, and —$C_{1-6}$alkylheterocyclyl;

each $R^b$ is independently selected from the group consisting of H, —$C_{1-6}$ alkyl, —$C_{1-6}$ haloalkyl, —$C_{3-8}$ cycloalkyl, aryl, heteroaryl, heterocyclyl, —$C_{1-3}$ alkyl$C_{3-8}$cycloalkyl, —$C_{1-6}$ alkylaryl, —$C_{1-6}$ alkylheteroaryl, and —$C_{1-6}$ alkylheterocyclyl;

or $R^a$ and $R^b$ may combine together to form a ring consisting of 3-8 ring atoms that are C, N, O, or S; wherein the ring is optionally substituted with 1 to 4 groups independently selected from the group consisting of —$OR^f$, —CN, halo, —$C_{1-6}$ alkyl$OR^f$, —$C_{1-6}$ cyanoalkyl, —$C_{1-6}$ haloalkyl, —$C_{3-8}$ cycloalkyl, —$C_{1-3}$ alkyl$C_{3-8}$cycloalkyl, —$C(O)R^f$, —$C_{1-6}$ alkylC(O)$R^f$, —$C(O)OR^f$, —$C_{1-6}$ alkylC(O)$OR^f$, —$NR^fR^g$, —$C_{1-6}$ alkyl$NR^fR^g$, —$C(O)NR^fR^g$, $C_{1-6}$ alkylC(O)$NR^fR^g$, —$S(O)_2R^f$, —$C_{1-6}$ alkylS(O)$_2R^f$, —$S(O)_2NR^fR^g$, —$C_{1-6}$ alkylS(O)$_2NR^fR^g$, —$C(O)NR^fS(O)_2R^g$ and —$NR^fC(O)R^g$;

each $R^c$ is independently selected from the group consisting of H, OH, —$C_{1-6}$ alkyl, —$C_{3-8}$ cycloalkyl, aryl, heteroaryl, heterocyclyl, —$C_{1-3}$ alkyl$C_{3-8}$ cycloalkyl, —$C_{1-6}$ alkylaryl, —$C_{1-6}$ alkylheteroaryl, and —$C_{1-6}$ alkylheterocyclyl;

each $R^d$ is independently selected from the group consisting of H, —$C_{1-6}$ alkyl, —$C_3$-$C_8$cycloalkyl, aryl, heteroaryl, heterocyclyl, —$C_{1-3}$ alkyl$C_{3-8}$cycloalkyl, —$C_{1-6}$ alkylaryl, —$C_{1-6}$ alkylheteroaryl, and —$C_{1-6}$ alkylheterocyclyl;

each $R^f$ is independently selected from the group consisting of H, —$C_{1-6}$ alkyl, —$C_{3-8}$ cycloalkyl, aryl, heteroaryl, heterocyclyl, —$C_{1-3}$ alkyl$C_{3-8}$ cycloalkyl, —$C_{1-6}$ alkylaryl, —$C_{1-6}$ alkylheteroaryl, and —$C_{1-6}$ alkylheterocyclyl;

each $R^g$ is independently selected from the group consisting of H, —$C_{1-6}$ alkyl, —$C_{3-8}$ cycloalkyl, aryl, heteroaryl, heterocyclyl, —$C_{1-3}$ alkyl$C_{3-8}$ cycloalkyl, —$C_{1-6}$ alkylaryl, —$C_{1-6}$ alkylheteroaryl, and —$C_{1-6}$ alkylheterocyclyl;

or a pharmaceutically acceptable salt, stereoisomer, mixture of stereoisomers, or tautomer thereof.

(III)

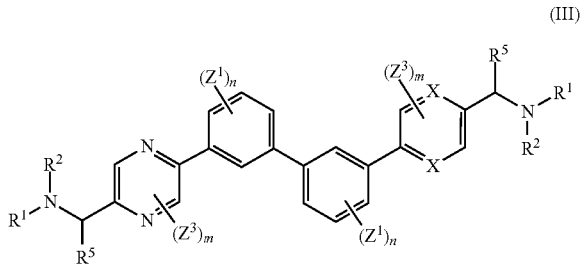

wherein:
each X is independently CH, CZ³ or N;
each $Z^1$ is independently halo or —$C_{1-6}$ alkyl;
each n is independently 0, 1, 2, 3 or 4;
each $Z^3$ is independently halo or —O—$C_{1-6}$ alkyl;
each m is independently 0, 1 or 2;
each $R^1$ is independently selected from the group consisting of H, —$C_{1-8}$ alkyl, —$C_{2-6}$ alkenyl, —$C_{2-6}$ alkynyl, —$C_{3-6}$ cycloalkyl, aryl, heteroaryl, heterocyclyl, —$C_{1-6}$ alkylaryl, —$C_{1-6}$ alkylheteroaryl, —$C_{1-6}$ alkylheterocyclyl, —$C_{1-6}$ alkylC(O)OR$^a$, —$C_{2-6}$ alkenylC(O)OR$^a$, —S(O)$_2$R$^a$, —S(O)$_2$NR$^a$R$^b$, —C(O)NR$^a$S(O)$_2$R$^a$, and $C_{1-6}$ alkylC$_{3-8}$cycloalkyl;

wherein each alkyl, alkenyl, cycloalkyl, aryl, heteroaryl or heterocyclyl group is optionally substituted with 1 to 4 groups independently selected from the group consisting of —OR$^a$, —CN, halo, $C_{1-6}$alkyl, —$C_{1-6}$ alkylOR$^a$, —$C_{1-6}$ cyanoalkyl, —$C_{1-6}$ haloalkyl, $C_{3-8}$ cycloalkyl, —$C_{1-3}$ alkylC$_{3-8}$cycloalkyl, —C(O)R$^a$, —$C_{1-6}$ alkylC(O)R$^a$, —C(O)OR$^a$, —$C_{1-6}$ alkylC(O)OR$^a$, —NR$^a$R$^b$, —OC(O)NR$^a$R$^b$, NR$^a$C(O)OR$^b$, —$C_{1-6}$ alkylNR$^a$R$^b$, —C(O)NR$^a$R$^b$, —$C_{1-6}$ alkylC(O)NR$^a$R$^b$, —S(O)$_2$R$^a$, —$C_{1-6}$ alkylS(O)$_2$R$^a$, —S(O)$_2$NR$^a$R$^b$, —$C_{1-6}$ alkylS(O)$_2$NR$^a$R$^b$, —C(O)NR$^a$S(O)$_2$R$^b$, —$C_{1-6}$ alkylC(O)NR$^a$S(O)$_2$R$^b$, —NR$^a$C(O)R$^b$, and —$C_{1-6}$alkylNR$^a$C(O)R$^b$;

each $R^2$ is independently selected from the group consisting of H, —$C_{1-6}$ alkyl, —$C_{2-6}$ alkenyl, —$C_{2-6}$ alkynyl, —$C_{3-6}$ cycloalkyl, aryl, heteroaryl, heterocyclyl, —$C_{1-6}$ alkylaryl, —$C_{1-6}$ alkylheteroaryl, —$C_{1-6}$ alkylheterocyclyl, —$C_{2-6}$ alkylOR$^a$, —$C_{1-6}$ alkylC(O)OR$^a$, and —$C_{2-6}$ alkenylC(O)OR$^a$;

wherein each alkyl, alkenyl, cycloalkyl, aryl, heteroaryl or heterocyclyl group is optionally substituted with 1 to 4 groups independently selected from the group consisting of —OR$^a$, —CN, halo, $C_{1-6}$alkyl, —$C_{1-6}$ alkylOR$^a$, —$C_{1-6}$ cyanoalkyl, —$C_{1-6}$ haloalkyl, —$C_{3-8}$ cycloalkyl, —$C_{1-3}$ alkylC$_{3-8}$cycloalkyl, —C(O)R$^a$, —$C_{1-6}$ alkylC(O)R$^a$, —C(O)OR$^a$, —$C_{1-6}$ alkylC(O)OR$^a$, —NR$^a$R$^b$, —$C_{1-6}$ alkylNR$^a$R$^b$, —C(O)NR$^a$R$^b$, $C_{1-6}$ alkylC(O)NR$^a$R$^b$, —S(O)$_2$R$^a$, —$C_{1-6}$ alkylS(O)$_2$R$^a$, —S(O)$_2$NR$^a$R$^b$, —$C_{1-6}$ alkylS(O)$_2$NR$^a$R$^b$, —C(O)NR$^a$S(O)$_2$R$^b$, and —NR$^a$C(O)R$^b$;

or $R^1$ and $R^2$ combine to form a heterocyclyl group optionally containing 1, 2, or 3 additional heteroatoms independently selected from oxygen, sulfur and nitrogen, and optionally substituted with 1 to 3 groups independently selected from the group consisting of oxo, —$C_{1-6}$ alkyl, —$C_{3-8}$ cycloalkyl, —$C_{2-6}$ alkenyl, —$C_{2-6}$ alkynyl, —OR$^a$, —C(O)OR$^a$, —$C_{1-6}$ cyanoalkyl, —$C_{1-6}$ alkylOR$^a$, —$C_{1-6}$ haloalkyl, —$C_{1-3}$ alkylC$_{3-8}$cycloalkyl, —C(O)R$^a$, $C_{1-6}$ alkyl C(O)R$^a$, —$C_{1-6}$ alkylC(O)OR$^a$, —NR$^a$R$^b$, —$C_{1-6}$alkylNR$^a$R$^b$, —C(O)NR$^a$R$^b$, —$C_{1-6}$ alkylC(O)NR$^a$R$^b$, —S(O)$_2$R$^a$, —$C_{1-6}$ alkylS(O)$_2$R$^a$, —S(O)$_2$NR$^a$R$^b$, and $C_{1-6}$ alkylS(O)$_2$NR$^a$R$^b$;

each $R^5$ is independently selected from the group consisting of NR$^a$R$^b$, halo, cyano, —OR$^a$, —$C_{1-6}$ alkyl, —$C_{1-6}$ haloalkyl, —$C_{1-6}$ cyanoalkyl, —$C_{1-6}$ alkylNR$^a$R$^b$, —$C_{1-6}$ alkylOH, —$C_{3-8}$ cycloalkyl and —$C_{1-3}$ alkylC$_{3-8}$cycloalkyl;

each $R^a$ is independently selected from the group consisting of H, —$C_{1-6}$ alkyl, —$C_{3-8}$ cycloalkyl, aryl, heteroaryl, heterocyclyl, —$C_{1-3}$ alkylC$_{3-8}$cycloalkyl, —$C_{1-6}$ alkylaryl, —$C_{1-6}$ alkylheteroaryl, and —$C_{1-6}$alkylheterocyclyl;

each $R^b$ is independently selected from the group consisting of H, —$C_{1-6}$ alkyl, —$C_{3-8}$ cycloalkyl, aryl, heteroaryl, heterocyclyl, —$C_{1-3}$ alkylC$_{3-8}$cycloalkyl, —$C_{1-6}$ alkylaryl, —$C_{1-6}$ alkylheteroaryl, and —$C_{1-6}$ alkylheterocyclyl;

or R$^a$ and R$^b$ may combine together to form a ring consisting of 3-8 ring atoms that are C, N, O, or S; wherein the ring is optionally substituted with 1 to 4 groups independently selected from the group consisting of —OR$^f$, —CN, halo, —$C_{1-6}$ alkylOR$^f$, —$C_{1-6}$ cyanoalkyl, —$C_{1-6}$ haloalkyl, —$C_{3-8}$ cycloalkyl, —$C_{1-3}$ alkylC$_{3-8}$cycloalkyl, —C(O)R$^f$, —$C_{1-6}$ alkylC(O)R$^f$, —C(O)OR$^f$, —$C_{1-6}$ alkylC(O)OR$^f$, —NR$^f$R$^g$, —$C_{1-6}$ alkylNR$^f$R$^g$, —C(O)NR$^f$R$^g$, $C_{1-6}$ alkylC(O)NR$^f$R$^g$, —S(O)$_2$R$^f$, —$C_{1-6}$ alkylS(O)$_2$R$^f$, —S(O)$_2$NR$^f$R$^g$, —$C_{1-6}$ alkylS(O)$_2$NR$^f$R$^g$, —C(O)NR$^f$S(O)$_2$R$^g$ and —NR$^f$C(O)R$^g$;

each $R^f$ is independently selected from the group consisting of H, —$C_{1-6}$ alkyl, —$C_{3-8}$ cycloalkyl, aryl, heteroaryl, heterocyclyl, —$C_{1-3}$ alkylC$_{3-8}$ cycloalkyl, —$C_{1-6}$ alkylaryl, —$C_{1-6}$ alkylheteroaryl, and —$C_{1-6}$ alkylheterocyclyl;

each $R^g$ is independently selected from the group consisting of H, —$C_{1-6}$ alkyl, —$C_{3-8}$ cycloalkyl, aryl, heteroaryl, heterocyclyl, —$C_{1-3}$ alkylC$_{3-8}$ cycloalkyl, —$C_{1-6}$ alkylaryl, —$C_{1-6}$ alkylheteroaryl, and —$C_{1-6}$ alkylheterocyclyl;

or a pharmaceutically acceptable salt, stereoisomer, mixture of stereoisomers, or tautomer thereof.

The present disclosure provides a compound of formula (IIIa):

(IIIa)

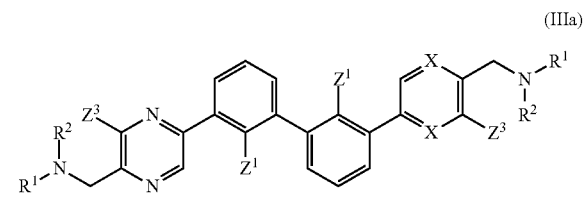

wherein:
each X is independently CH, CZ³ or N;
each $Z^1$ is independently halo or —$C_{1-6}$ alkyl;
each $Z^3$ is independently halo or —O—$C_{1-6}$ alkyl;
each $R^1$ is independently selected from the group consisting of H, —$C_{1-8}$ alkyl, —$C_{2-6}$ alkenyl, —$C_{2-6}$ alkynyl, —$C_{3-6}$ cycloalkyl, aryl, heteroaryl, heterocyclyl, —$C_{1-6}$ alkylaryl, —$C_{1-6}$ alkylheteroaryl, —$C_{1-6}$ alkylheterocyclyl, —$C_{1-6}$ alkylC(O)OR$^a$, —$C_{2-6}$ alkenylC(O)OR$^a$, —S(O)$_2$R$^a$, —S(O)$_2$OR$^a$, —S(O)$_2$NR$^a$R$^b$, —C(O)NR$^a$S(O)$_2$R$^a$, and $C_{1-6}$ alkylC$_{3-8}$cycloalkyl;

wherein each alkyl, alkenyl, cycloalkyl, aryl, heteroaryl or heterocyclyl group is optionally substituted with 1 to 4 groups independently selected from the group consisting of —OR$^a$, —CN, —NO$_2$, halo, $C_{1-6}$alkyl, —$C_{1-6}$ alkylOR$^a$, —$C_{1-6}$ cyanoalkyl, —$C_{1-6}$ haloalkyl, $C_{3-8}$ cycloalkyl, heteroaryl, heterocyclyl, —$C_{1-3}$ alkylC$_{3-8}$cycloalkyl, —C(O)R$^a$, —$C_{1-6}$ alkylC(O)R$^a$, —C(O)

OR$^a$, —C$_{1-6}$ alkylC(O)OR$^a$, —NR$^a$R$^b$, —OC(O) NR$^a$R$^b$, —NR$^a$C(O)OR$^b$, —NR$^a$C(O)R$^b$, —C$_{1-6}$ alkylNR$^a$R$^b$, —C(O)NR$^a$R$^b$, —C$_{1-6}$ alkylC(O)NR$^a$R$^b$, —S(O)$_2$R$^a$, —S(O)$_2$OR$^a$, —C$_{1-6}$ alkylS(O)$_2$R$^a$, —S(O)$_2$NR$^a$R$^b$, —C$_{1-6}$ alkylS(O)$_2$NR$^a$R$^b$, —C(O) NR$^a$S(O)$_2$R$^b$, —NR$^a$C(O)NR$^b$, —C$_{1-6}$ alkylC(O)NR$^a$S (O$_2$R$^b$, —NR$^a$C(O)R$^b$, and —C$_{1-6}$alkylNR$^a$C(O)R$^b$;

each R$^2$ is independently selected from the group consisting of H, —C$_{1-6}$ alkyl, —C$_{2-6}$ alkenyl, —C$_{2-6}$ alkynyl, —C$_{3-6}$ cycloalkyl, aryl, heteroaryl, heterocyclyl, —C$_{1-6}$ alkylaryl, —C$_{1-6}$ alkylheteroaryl, —C$_{1-6}$ alkylheterocyclyl, —C$_{2-6}$ alkylOR$^a$, —C$_{1-6}$ alkylC(O)OR$^a$, and —C$_{2-6}$ alkenylC(O) OR$^a$;

wherein each alkyl, alkenyl, cycloalkyl, aryl, heteroaryl or heterocyclyl group is optionally substituted with 1 to 4 groups independently selected from the group consisting of —OR$^a$, —CN, halo, C$_{1-6}$alkyl, —C$_{1-6}$ alkylOR$^a$, —C$_{1-6}$ cyanoalkyl, —C$_{1-6}$ haloalkyl, —C$_{3-8}$ cycloalkyl, —C$_{1-3}$ alkylC$_{3-8}$cycloalkyl, —C(O)R$^a$, —C$_{1-6}$ alkylC (O)R$^a$, —C(O)OR$^a$, —C$_{1-6}$ alkylC(O)OR$^a$, —NR$^a$R$^b$, —C$_{1-6}$ alkylNR$^a$R$^b$, —C(O)NR$^a$R$^b$, C$_{1-6}$ alkylC(O)-R$^a$R$^b$, —S(O)$_2$R$^a$, —C$_{1-6}$ alkylS(O)$_2$R$^a$, —S(O)$_2$ NR$^a$R$^b$, —C$_{1-6}$ alkylS(O)$_2$NR$^a$R$^b$, —C(O)NR$^a$S(O)$_2$ R$^b$ and —NR$^a$C(O)R$^b$;

or R$^1$ and R$^2$ combine to form a heterocyclyl group optionally containing 1, 2, or 3 additional heteroatoms independently selected from oxygen, sulfur and nitrogen, and optionally substituted with 1 to 3 groups independently selected from the group consisting of oxo, —C$_{1-6}$ alkyl, —C$_{3-8}$ cycloalkyl, —C$_{2-6}$ alkenyl, —C$_{2-6}$ alkynyl, aryl, heteroaryl, heterocyclyl, —OR$^a$, —CN, halo, —C(O)OR$^a$, —C$_{1-6}$ cyanoalkyl, —C$_{1-6}$ alkylOR$^a$, —C$_{1-6}$ haloalkyl, —C$_{1-3}$ alkylC$_{3-8}$cycloalkyl, —C(O)R$^a$, C$_{1-6}$ alkylC(O)R$^a$, —C$_{1-6}$ alkylC(O)OR$^a$, —NR$^a$R$^b$, —C$_{1-6}$alkylNR$^a$R$^b$, —C(O)NR$^a$R$^b$, —NR$^a$C(O)OR$^b$, —NR$^a$C(O)NR$^a$R$^b$, —NR$^a$S(O)$_2$NR$^a$R$^b$, —NR$^a$S(O)$_2$R$^a$, —C$_{1-6}$ alkylC(O)N-R$^a$R$^b$, —S(O)$_2$R$^a$, —C$_{1-6}$ alkylS(O)$_2$R$^a$, —S(O)$_2$NR$^a$R$^b$, and C$_{1-6}$ alkylS(O)$_2$NR$^a$R$^b$;

each R$^a$ is independently selected from the group consisting of H, —C$_{1-6}$ alkyl, —C$_{1-6}$ haloalkyl, —C$_{3-8}$ cycloalkyl, aryl, heteroaryl, heterocyclyl, —C$_{1-3}$ alkylC$_{3-8}$cycloalkyl, —C$_{1-6}$ alkylaryl, —C$_{1-6}$ alkylheteroaryl, and —C$_{1-6}$alkylheterocyclyl;

each R$^b$ is independently selected from the group consisting of H, —C$_{1-6}$ alkyl, —C$_{1-6}$ haloalkyl, —C$_{3-8}$ cycloalkyl, aryl, heteroaryl, heterocyclyl, —C$_{1-3}$ alkylC$_{3-8}$cycloalkyl, —C$_{1-6}$ alkylaryl, —C$_{1-6}$ alkylheteroaryl, and —C$_{1-6}$ alkylheterocyclyl;

or R$^a$ and R$^b$ may combine together to form a ring consisting of 3-8 ring atoms that are C, N, O, or S; wherein the ring is optionally substituted with 1 to 4 groups independently selected from the group consisting of —OR$^f$, —CN, halo, —C$_{1-6}$ alkylOR$^f$, —C$_{1-6}$ cyanoalkyl, —C$_{1-6}$ haloalkyl, —C$_{3-8}$ cycloalkyl, —C$_{1-3}$ alkylC$_{3-8}$cycloalkyl, —C(O)R$^f$, —C$_{1-6}$ alkylC(O)R$^f$, —C(O)OR$^f$, —C$_{1-6}$ alkylC(O)OR$^f$, —NR$^f$R$^g$, —C$_{1-6}$ alkylNR$^f$R$^g$, —C(O)NR$^f$R$^g$, C$_{1-6}$ alkylC (O)NR$^f$R$^g$, —S(O)$_2$R$^f$, —C$_{1-6}$ alkylS(O)$_2$R$^f$, —S(O)$_2$NR$^f$R$^g$, —C$_{1-6}$ alkylS(O)$_2$NR$^f$R$^g$, —C(O)NR$^f$S(O)$_2$R$^g$ and —NR$^f$C (O)R$^g$;

each R$^f$ is independently selected from the group consisting of H, —C$_{1-6}$ alkyl, —C$_{3-8}$ cycloalkyl, aryl, heteroaryl, heterocyclyl, —C$_{1-3}$ alkylC$_{3-8}$ cycloalkyl, —C$_{1-6}$ alkylaryl, —C$_{1-6}$ alkylheteroaryl, and —C$_{1-6}$ alkylheterocyclyl;

each R$^g$ is independently selected from the group consisting of H, —C$_{1-6}$ alkyl, —C$_{3-8}$ cycloalkyl, aryl, heteroaryl, heterocyclyl, —C$_{1-3}$ alkylC$_{3-8}$ cycloalkyl, —C$_{1-6}$ alkylaryl, —C$_{1-6}$ alkylheteroaryl, and —C$_{1-6}$ alkylheterocyclyl;

or a pharmaceutically acceptable salt, stereoisomer, mixture of stereoisomers, or tautomer thereof.

The present disclosure provides a compound of formula (IIIb):

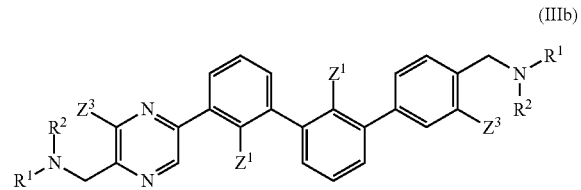

(IIIb)

or a pharmaceutically acceptable salt, stereoisomer, mixture of stereoisomers, or tautomer thereof, wherein:

Z$^1$, Z$^3$, R$^1$ and R$^2$ are as defined herein.

The present disclosure provides a compound of formula (IIIc):

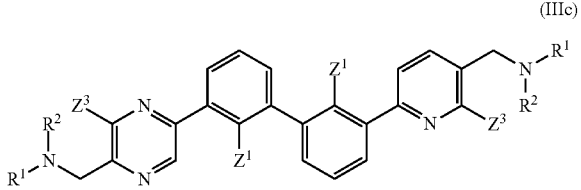

(IIIc)

or a pharmaceutically acceptable salt, stereoisomer, mixture of stereoisomers, or tautomer thereof, wherein:

Z$^1$, Z$^3$, R$^1$ and R$^2$ are as defined herein.

The present disclosure provides a compound of formula (IIId):

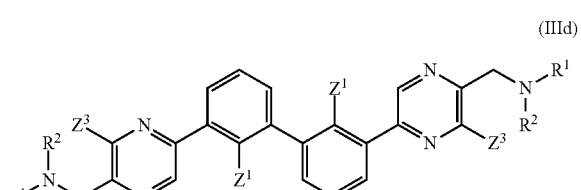

(IIId)

or a pharmaceutically acceptable salt, stereoisomer, mixture of stereoisomers, or tautomer thereof, wherein:

Z$^1$, Z$^3$, R$^1$ and R$^2$ are as defined herein.

In one embodiment, Q is selected from the group consisting of phenyl, pyridinyl, indazolyl, and thienyl each optionally substituted with 1 to 2 groups independently selected from the group consisting of halo, —OR$^a$, N$_3$, NO$_2$, —CN, —NR$^a$R$^b$, —S(O)$_2$R$^a$, —S(O)$_2$NR$^a$R$^b$, —NR$^a$S(O)$_2$ R$^a$, —NR$^a$C(O)R$^a$, —C(O)NR$^a$R$^b$, —C$_{1-6}$ alkyl, —O—C$_{1-6}$ alkyl, C$_{3-8}$ cycloalkyl, and —C$_{1-6}$alkylC$_{3-8}$ cycloalkyl.

In another embodiment, Q is selected from the group consisting of phenyl, pyridinyl and indanyl each optionally substituted with 1 to 3 groups independently selected from the group consisting of halo, —OR$^a$, N$_3$, NO$_2$, —CN, —NR$^a$R$^b$, —S(O)$_2$R$^a$, —S(O)$_2$NR$^a$R$^b$, —NR$^a$S(O)$_2$R$^a$, —NR$^a$C(O)R$^a$, —C(O)NR$^a$R$^b$, —C$_{1-6}$ alkyl, —O—C$_{1-6}$ alkyl, C$_{3-8}$ cycloalkyl, and —C$_{1-6}$alkylC$_{3-8}$ cycloalkyl.

In one embodiment, Q is optionally substituted aryl. In one embodiment, Q is optionally substituted phenyl.

In one embodiment, Q is optionally substituted heteroaryl. In one embodiment, Q is optionally substituted monocyclic heteroaryl. In one embodiment, Q is an optionally substituted 5- or 6-membered heteroaryl. In one embodiment, Q is an optionally substituted 5-membered heteroaryl. In one embodiment, Q is an optionally substituted 6-membered heteroaryl. In one embodiment, Q is optionally substituted pyridyl. In one embodiment, Q is optionally substituted pyrazinyl.

In certain embodiments, Q is

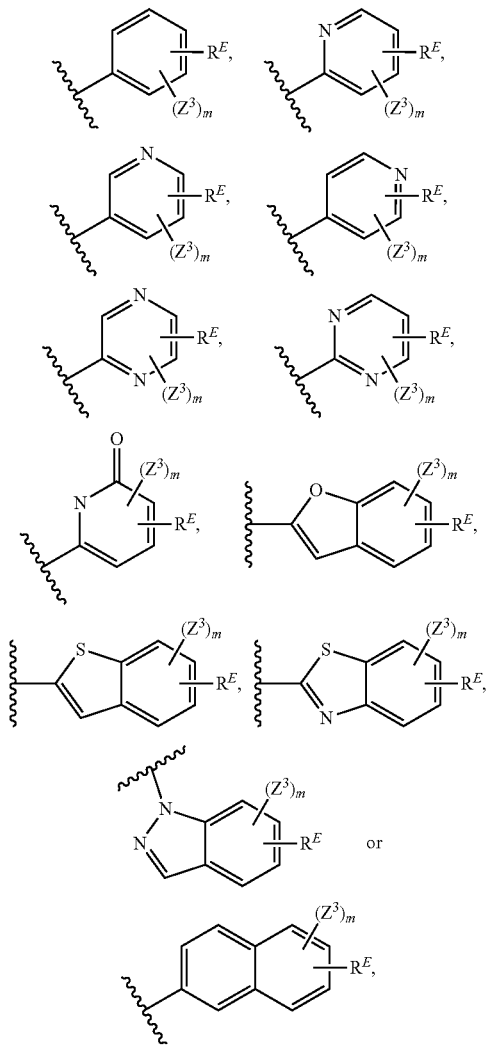

and m and $Z^3$ are as defined herein.

In certain embodiments, Q is

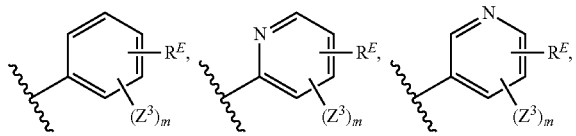

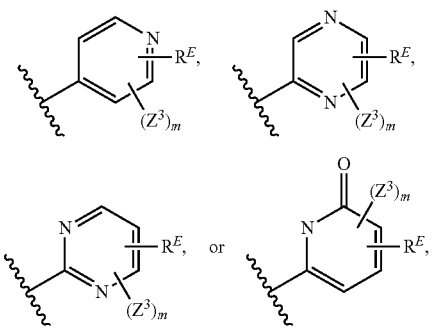

and m and $Z^3$ are as defined herein.

In one embodiment, substituents on Q are independently selected from the group consisting of OH, halo, CN, —$C_{1-6}$alkyl, —$C_{1-6}$haloalkyl, —O—$C_{1-6}$alkyl, —O—$C_{1-6}$haloalkyl, —$S(O)_2C_{1-6}$alkyl,

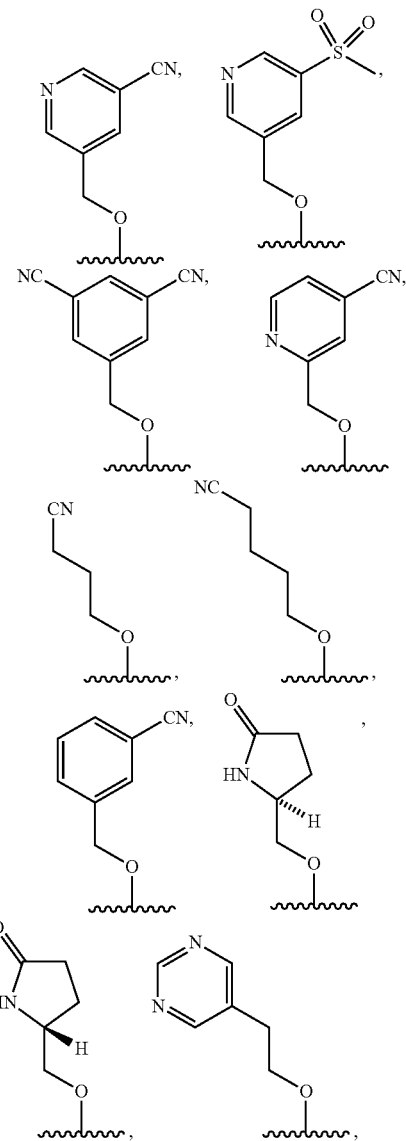

-continued

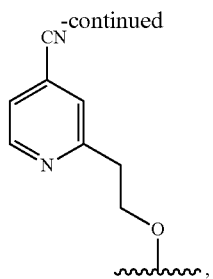

or a pharmaceutically acceptable salt thereof.

In one embodiment, Q is optionally substituted with 1 to 3 groups independently selected from the group consisting of OH, halo, CN, $S(O)_2R^a$, —$C_{1-6}$alkyl, and —O—$C_{1-6}$alkyl.

In one embodiment, Q is optionally substituted with 1 to 3 groups independently selected from the group consisting of OH, halo, CN, $S(O)_2R^a$, —$C_{1-6}$alkyl, and —O—$C_{1-6}$alkyl.

In one embodiment, $R^E$ and $R^W$ are each independently —$NR^1R^2$, —$C_{1-6}$ alkyl$NR^1R^2$, —O—$C_{1-6}$ alkyl$NR^1R^2$, —$C_{1-6}$ alkylO$C_{1-6}$alkyl$NR^1R^2$, —$NR^a$—$C_{1-6}$ alkyl$NR^1R^2$, —$C_{1-6}$ alkylN+$R^1R^2R^3$, —S—$C_{1-6}$ alkyl$NR^1R^2$, —$S(O)_2R^a$, —$(CH_2)_uS(O)_2NR^1R^2$, —$(CH_2)_uNR^aS(O)_2NR^aR^b$, —$S(O)_2NR^aC_{1-6}$ alkyl$NR^1R^2$, —$NR^aS(O)_2C_{1-6}$alkyl$NR^1R^2$, —$(CH_2)_uC(O)NR^aS(O)_2NR^aR^b$, —$(CH_2)_uN^+R^1R^2O^-$, —$(CH_2)_uP^+R^bR^cR^d$, —$(CH_2)_uP^+R^cR^dO^-$, —$(CH_2)_uP^+O[NR^aR^b][NR^cR^d]$, —$(CH_2)_uNR^cP(O)(OR^c)_2$, —$(CH_2)_uCH_2OP(O)(OR^c)(OR^d)$, —$(CH_2)_uOP(O)(OR^c)(OR^d)$, —$(CH_2)_uOP(O)NR^aR^b)(OR^a)$, or

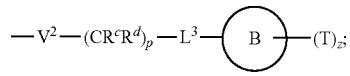

wherein:
$V^2$ is independently a bond, O, $NR^a$, S, S(O), $S(O)_2$, $S(O)_2NR$, or $NR^aS(O)_2$;
$L^3$ is independently a bond, O, $NR^a$, S, S(O), $S(O)_2$, $S(O)_2NR$, or $NR^aS(O)_2$;
ring B is independently cycloalkyl, aryl, heteroaryl or heterocyclyl;
T is independently H, —$OR^a$, $(CH_2)_qNR^1R^2$, $(CH_2)_qNR^aC(O)R^e$ or $(CH_2)_qC(O)R^e$;
p is independently 0, 1, 2, 3, 4, or 5;
q is independently 0, 1, 2, 3, 4, or 5;
u is 0, 1, 2, 3 or 4;
z is 0, 1, 2 or 3; and
wherein the alkyl, cycloalkyl, aryl, heteroaryl or heterocyclyl of $R^E$ or $R^W$ is optionally substituted with 1 to 3 substituents independently selected from the group consisting of $NR^aR^b$, halo, cyano, oxo, —$OR^a$, —$C_{1-6}$ alkyl, —$C_{1-6}$ haloalkyl, —$C_{1-6}$ cyanoalkyl, —$C_{1-6}$ alkyl$NR^aR^b$, —$C_{1-6}$ alkylOH, —$C_{3-8}$ cycloalkyl and —$C_{1-3}$ alkyl$C_{3-8}$cycloalkyl;
provided that at least one of $V^2$, $L^3$, ring B and T contains a nitrogen atom.

In one embodiment, $R^E$ and $R^W$ are independently selected from —$NR^1R^2$, —$C_{1-6}$ alkyl$NR^1R^2$, —O—$C_{1-6}$ alkyl$NR^1R^2$, —$C_{1-6}$ alkylO$C_{1-6}$alkyl$NR^1R^2$, —$NR^a$—$C_{1-6}$ alkyl$NR^1R^2$, —$C_{1-6}$ alkylN+$R^1R^2R^3$, —S—$C_{1-6}$ alkyl$NR^1R^2$, —$C(O)NR^1R^2$, —$S(O)_2R^a$, —$(CH_2)_uS(O)_2NR^1R^2$, —$(CH_2)_uNR^aS(O)_2NR^aR^b$, —$S(O)_2NR^aC_{1-6}$ alkyl$NR^1R^2$, —$NR^aS(O)_2C_{1-6}$ alkyl$NR^1R^2$, —$(CH_2)_uC(O)NR^aS(O)_2NR^aR^b$, —$(CH_2)_uN^+R^1R^2O^-$, —$(CH_2)_uP^+R^bR^cR^d$, —$(CH_2)_uP^+R^cR^dO^-$, —$(CH_2)_uP^+O[NR^aR^b][NR^cR^d]$, —$(CH_2)_uNR^cP(O)(OR^c)_2$, —$(CH_2)_uCH_2OP(O)(OR^c)(OR^d)$, —$(CH_2)_uOP(O)(OR^c)(OR^d)$, and —$(CH_2)_uOP(O)NR^aR^b)(OR^a)$; wherein
each $R^1$ is independently selected from H, —$C_{1-6}$alkyl, —$C_{3-6}$cycloalkyl, heterocyclyl, —$C_{2-6}$alkyl-$OR^a$, or —$C_{1-6}$alkylC(O)$OR^a$;
wherein each alkyl, cycloalkyl, or heterocyclyl is optionally substituted with 1 to 2 groups independently selected from —$OR^a$, —CN, halo, —$C_{1-6}$ alkyl$OR^a$, —$C_{1-6}$cyanoalkyl, —$C_{1-3}$haloalkyl, —C(O)$R^a$, —$C_{1-6}$alkylC(O)$R^a$, —C(O)$OR^a$, —$C_{1-6}$ alkylC(O)$OR^a$, —C(O)$NR^aR^b$, and —$C_{1-6}$ alkylC(O)$NR^aR^b$;
each $R^2$ is independently selected from —$C_{1-6}$ alkyl, —$C_{3-6}$ cycloalkyl, heterocyclyl, —$C_{2-6}$ alkyl-$OR^a$, and —$C_{1-6}$ alkylC(O)$OR^a$;
wherein each alkyl, cycloalkyl, or heterocyclyl is optionally substituted with 1 to 2 groups independently selected from —$OR^a$, —CN, —$C_{1-6}$alkyl$OR^a$, —$C_{1-6}$cyanoalkyl, —$C_{1-3}$haloalkyl, —$C_{3-8}$cycloalkyl, —$C_{1-3}$alkyl$C_{3-8}$cycloalkyl, —C(O)$R^a$, —$C_{1-6}$alkylC(O)$R^a$, —C(O)$OR^a$, —$C_{1-6}$ alkylC(O)$OR^a$, —C(O)$NR^aR^b$, and $C_{1-6}$ alkylC(O)$NR^aR^b$;
or $R^1$ and $R^2$ combine to form a heterocyclyl group optionally containing an additional heteroatom selected from oxygen, sulfur or nitrogen, and optionally substituted with 1 to 3 groups independently selected from oxo, —$C_{1-6}$alkyl, —$OR^a$, —C(O)$OR^a$, —C(O)$R^a$, $C_{1-6}$ alkylC(O)$R^a$, —$C_{1-6}$alkylC(O)$OR^a$, —$NR^aR^b$, —$C_{1-6}$ alkyl$NR^aR^b$, and —C(O)$NR^aR^b$;
each $R^3$ is independently H, —$C_{1-6}$ alkyl, —$C_{2-6}$ alkenyl, —$C_{3-6}$ cycloalkyl, aryl, heteroaryl, heterocyclyl, —$C_{1-6}$ alkylaryl;
each $R^a$ is independently H or —$C_{1-6}$ alkyl;
each $R^b$ is independently H or —$C_{1-6}$ alkyl;
each $R^c$ is independently selected from H, —$C_{1-6}$ alkyl, —$C_{3-8}$ cycloalkyl, and —$C_{1-3}$ alkyl$C_{3-8}$ cycloalkyl;
each $R^d$ is independently selected from H, —$C_{1-6}$ alkyl, —$C_3$-$C_8$cycloalkyl, and —$C_{1-3}$ alkyl$C_{3-8}$cycloalkyl; and
each u is independently 0, 1, 2, or 3.

In one embodiment, $R^E$ and $R^W$ are independently selected from —C(O)$NR^1R^2$, —$S(O)_2R^a$, —$(CH_2)_uS(O)_2NR^1R^2$, —$(CH_2)_uNR^aS(O)_2NR^aR^b$, —$S(O)_2NR^aC_{1-6}$ alkyl$NR^1R^2$, —$NR^aS(O)_2C_{1-6}$ alkyl$NR^1R^2$, and —$(CH_2)_uC(O)NR^aS(O)_2NR^aR^b$; wherein
each $R^1$ is independently selected from H, —$C_{1-6}$alkyl, —$C_{3-6}$cycloalkyl, heterocyclyl, —$C_{2-6}$alkyl-$OR^a$, or —$C_{1-6}$alkylC(O)$OR^a$;
wherein each alkyl, cycloalkyl, or heterocyclyl is optionally substituted with 1 to 2 groups independently selected from —$OR^a$, —CN, halo, —$C_{1-6}$ alkyl$OR^a$, —$C_{1-6}$cyanoalkyl, —$C_{1-3}$haloalkyl, —C(O)$R^a$, —$C_{1-6}$alkylC(O)$R^a$, —C(O)$OR^a$, —$C_{1-6}$ alkylC(O)$OR^a$, —C(O)$NR^aR^b$, and —$C_{1-6}$ alkylC(O)$NR^aR^b$;
each $R^2$ is independently selected from —$C_{1-6}$ alkyl, —$C_{3-6}$ cycloalkyl, heterocyclyl, —$C_{2-6}$ alkyl-$OR^a$, and —$C_{1-6}$ alkylC(O)$OR^a$;
wherein each alkyl, cycloalkyl, or heterocyclyl is optionally substituted with 1 to 2 groups independently selected from —$OR^a$, —CN, —$C_{1-6}$alkyl $R^a$, —$C_{1-6}$cyanoalkyl, —$C_{1-3}$haloalkyl, —$C_{3-8}$cycloalkyl, —$C_{1-3}$alkyl$C_{3-8}$cycloalkyl, —C(O)$R^a$, —$C_{1-6}$alkylC(O)$R^a$, —C(O)O$R^a$, —$C_{1-6}$ alkylC(O) O$R^a$, —C(O)N$R^aR^b$, and $C_{1-6}$ alkylC(O)N$R^aR^b$;
or $R^1$ and $R^2$ combine to form a heterocyclyl optionally containing an additional heteroatom selected from oxygen, sulfur or nitrogen, and optionally substituted with 1 to 3 groups independently selected from oxo, —$C_{1-6}$ alkyl, —O$R^a$, —C(O)O$R^a$, —C(O)$R^a$, $C_{1-6}$ alkylC(O) $R^a$, —$C_{1-6}$alkylC(O)O$R^a$, —N$R^aR^b$, —$C_{1-6}$ alkylN-$R^aR^b$, and —C(O)N$R^aR^b$;
each $R^a$ is independently H or —$C_{1-6}$ alkyl;
each $R^b$ is independently H or —$C_{1-6}$ alkyl; and
each u is independently 0, 1, 2, or 3.

In one embodiment, $R^E$ and $R^W$ are independently selected from —$(CH_2)_uN^+R^1R^2O^-$, —$(CH_2)_uP^+R^bR^cR^d$, —$(CH_2)_uP^+R^cR^dO^-$, —$(CH_2)_uP^+O[NR^aR^b][NR^cR^d]$, —$(CH_2)_uNR^cP(O)(OR^c)_2$, —$(CH_2)_uCH_2OP(O)(OR^c)(O)$ $(OR^d)$, —$(CH_2)_uOP(O)(OR^c)(OR^d)$, and —$(CH_2)_uOP(O)$ $NR^aR^b)(OR^a)$; wherein
each $R^1$ is independently selected from H, —$C_{1-6}$alkyl, —$C_{3-6}$cycloalkyl, heterocyclyl, —$C_{2-6}$alkyl-O$R^a$, and —$C_{1-6}$alkylC(O)O$R^a$;
wherein each alkyl, cycloalkyl, or heterocyclyl is optionally substituted with 1 to 2 groups independently selected from —O$R^a$, —CN, halo, —$C_{1-6}$ alkylO$R^a$, —$C_{1-6}$cyanoalkyl, —$C_{1-3}$haloalkyl, —C(O)$R^a$, —$C_{1-6}$alkylC(O)$R^a$, —C(O)O$R^a$, —$C_{1-6}$ alkylC(O)O$R^a$, —C(O)N$R^aR^b$, and —$C_{1-6}$ alkylC (O)N$R^aR^b$;
each $R^2$ is independently selected from —$C_{1-6}$ alkyl, —$C_{3-6}$ cycloalkyl, heterocyclyl, —$C_{2-6}$ alkyl-O$R^a$, and —$C_{1-6}$ alkylC(O)O$R^a$;
wherein each alkyl, cycloalkyl, or heterocyclyl is optionally substituted with 1 to 2 groups independently selected from —O$R^a$, —CN, —$C_{1-6}$alkyl O$R^a$, —$C_{1-6}$cyanoalkyl, —$C_{1-3}$haloalkyl, —$C_{3-8}$cycloalkyl, —$C_{1-3}$alkyl$C_{3-8}$cycloalkyl, —C(O)$R^a$, —$C_{1-6}$alkylC(O)$R^a$, —C(O)O$R^a$, —$C_{1-6}$ alkylC(O) O$R^a$, —C(O)N$R^aR^b$, and $C_{1-6}$ alkylC(O)N$R^aR^b$;
or $R^1$ and $R^2$ combine to form a heterocyclyl optionally containing an additional heteroatom selected from oxygen, sulfur or nitrogen, and optionally substituted with 1 to 3 groups independently selected from oxo, —$C_{1-6}$ alkyl, —O$R^a$, —C(O)O$R^a$, —C(O)$R^a$, $C_{1-6}$ alkylC(O) $R^a$, —$C_{1-6}$alkylC(O)O$R^a$, —N$R^aR^b$, —$C_{1-6}$ alkylN-$R^aR^b$, and —C(O)N$R^aR^b$;
each $R^a$ is independently H or —$C_{1-6}$ alkyl;
each $R^b$ is independently H or —$C_{1-6}$ alkyl;
each $R^c$ is independently selected from H, —$C_{1-6}$ alkyl, —$C_{3-8}$ cycloalkyl, and —$C_{1-3}$ alkyl$C_{3-8}$ cycloalkyl;
each $R^d$ is independently selected from H, —$C_{1-6}$ alkyl, —$C_3$-$C_8$cycloalkyl, and —$C_{1-3}$ alkyl$C_{3-8}$cycloalkyl; and
each u is independently 0, 1, 2 or 3.

In one embodiment, $R^E$ and $R^W$ are each independently —$NR^1R^2$, —$C_{1-6}$ alkylN$R^1R^2$, —O—$C_{1-6}$ alkylN$R^1R^2$, —$C_{1-6}$ alkylO$C_{1-6}$alkylN$R^1R^2$, —$NR^a$$C_{1-6}$ alkylN$R^1R^2$, or

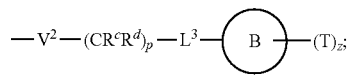

wherein
$V^2$ is independently a bond, O, $NR^a$, S, S(O) or S(O)$_2$;
$R^c$ is independently selected from H, OH, —$C_{1-6}$ alkyl, and —$C_{3-8}$ cycloalkyl;

$R^d$ is independently selected from H, —$C_{1-6}$ alkyl, and —$C_3$-$C_8$cycloalkyl;
$L^3$ is independently a bond, O, $NR^a$, S, S(O), or S(O)$_2$;
ring B is independently cycloalkyl, aryl, heteroaryl, or heterocyclyl;
T is independently H, —O$R^a$, $(CH_2)_qNR^1R^2$, $(CH_2)_qN-R^aC(O)R^e$ or $(CH_2)_qC(O)R^e$;
$R^e$ is independently selected from H, —$C_{1-6}$ alkyl, —O—$C_{1-6}$alkyl, —$C_{3-8}$ cycloalkyl, aryl, heteroaryl, heterocyclyl, —O—$C_{3-8}$ cycloalkyl, —O-aryl, —O-heteroaryl, —O-heterocyclyl, —$C_{1-3}$ alkyl$C_{3-8}$cycloalkyl, —$C_{1-6}$ alkylaryl, —$C_{1-6}$alkylheteroaryl, —$NR^fR^g$, —$C_{1-6}$ alkylN$R^fR^g$, —C(O)N$R^fR^g$, —$C_{1-6}$ alkylC(O)N$R^fR^g$, —NHS(O)$_2R^f$, —$C_{1-6}$ alkylS(O)$_2R^f$, and —$C_{1-6}$ alkylS(O)$_2NR^fR^g$;
p is independently 0, 1, 2, 3, 4, or 5;
q is independently 0, 1, 2, 3, 4, or 5; and
z is 0, 1, or 2;
and wherein the alkyl, cycloalkyl, aryl, heteroaryl, or heterocyclyl group is optionally substituted with 1 to 3 substituents independently selected from the group consisting of $NR^aR^b$, halo, cyano, —O$R^a$, —$C_{1-6}$ alkyl, —$C_{1-6}$ haloalkyl, —$C_{1-6}$ cyanoalkyl, —$C_{1-6}$ alkylN-$R^aR^b$, —$C_{1-6}$ alkylOH, —$C_{3-8}$ cycloalkyl, and —$C_{1-3}$ alkyl$C_{3-8}$cycloalkyl;
provided that at least one of $V^2$, $L^3$, ring B and T contains a nitrogen atom;
each $R^1$ is independently selected from H, —$C_{1-6}$alkyl, —$C_{3-6}$cycloalkyl, heterocyclyl, —$C_{2-6}$alkyl-O$R^a$, or —$C_{1-6}$ alkylC(O)O$R^a$;
wherein each alkyl, cycloalkyl, or heterocyclyl is optionally substituted with 1 to 2 groups independently selected from —O$R^a$, —CN, halo, —$C_{1-6}$alkylO$R^a$, —$C_{1-6}$cyanoalkyl, —$C_{1-3}$haloalkyl, —C(O)$R^a$, —$C_{1-6}$ alkylC(O)$R^a$, —C(O)O$R^a$, —$C_{1-6}$ alkylC(O)O$R^a$, —C(O)N$R^aR^b$, and —$C_{1-6}$ alkylC(O)N$R^aR^b$;
each $R^2$ is independently selected from —$C_{1-6}$ alkyl, —$C_{3-6}$ cycloalkyl, heterocyclyl, —$C_{2-6}$ alkyl-O$R^a$, and —$C_{1-6}$ alkyl C(O)O$R^a$;
wherein each alkyl, cycloalkyl, or heterocyclyl is optionally substituted with 1 to 2 groups independently selected from —O$R^a$, —CN, —$C_{1-6}$alkylO$R^a$, —$C_{1-6}$ cyanoalkyl, —$C_{1-3}$haloalkyl, —$C_{3-8}$cycloalkyl, —$C_{1-3}$ alkyl$C_{3-8}$cycloalkyl, —C(O)$R^a$, —$C_{1-6}$alkylC(O)$R^a$, —C(O)O$R^a$, —$C_{1-6}$ alkylC(O)O$R^a$, —C(O)N$R^aR^b$, and $C_{1-6}$ alkylC(O)N$R^aR^b$;
or $R^1$ and $R^2$ combine to form a heterocyclyl group optionally containing an additional heteroatom selected from oxygen, sulfur or nitrogen, and optionally substituted with 1 to 3 groups independently selected from oxo, —$C_{1-6}$alkyl, —O$R^a$, —C(O)O$R^a$, —C(O)$R^a$, $C_{1-6}$ alkylC(O)$R^a$, —$C_{1-6}$ alkylC(O)O$R^a$, —N$R^aR^b$, —$C_{1-6}$ alkylN$R^aR^b$, and —C(O) $NR^aR^b$;
each $R^a$ is independently H or —$C_{1-6}$ alkyl; and
each $R^b$ is independently H or —$C_{1-6}$ alkyl.

In one embodiment, $R^E$ and $R^W$ are each independently —$NR^1R^2$, —$C_{1-6}$ alkylN$R^1R^2$, —O—$C_{1-6}$ alkylN$R^1R^2$, —$C_{1-6}$ alkylO$C_{1-6}$alkylN$R^1R^2$, —$NR^a$—$C_{1-6}$ alkylN$R^1R^2$, or

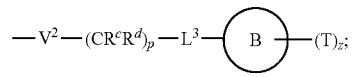

wherein
V² is independently a bond, O, NR$^a$, S, S(O) or S(O)$_2$;
L³ is independently a bond, O, NR$^a$, S, S(O), or S(O)$_2$;
ring B is independently cycloalkyl, aryl, heteroaryl, or heterocyclyl;
T is independently H, —OR$^a$, (CH$_2$)$_q$NR$^1$R$^2$, (CH$_2$)$_q$N-R$^a$C(O)R$^e$ or (CH$_2$)$_q$C(O)R$^e$;
p is independently 0, 1, 2, or 3;
q is independently 0, 1, 2, or 3;
z is 0, 1, 2, or 3;
and wherein the alkyl, cycloalkyl, aryl, heteroaryl, or heterocyclyl group is optionally substituted with 1 to 3 substituents independently selected from the group consisting of NR$^a$R$^b$, halo, cyano, —OR$^a$, —C$_{1-6}$ alkyl, —C$_{1-6}$ haloalkyl, —C$_{1-6}$ cyanoalkyl, —C$_{1-6}$ alkylNR$^a$R$^b$, —C$_{1-6}$ alkylOH, —C$_{3-8}$ cycloalkyl, and —C$_{1-3}$ alkylC$_{3-8}$cycloalkyl;
provided that at least one of V², L³, ring B and T contains a nitrogen atom;
each R$^1$ is independently selected from H, —C$_{1-6}$alkyl, —C$_{3-6}$cycloalkyl, heterocyclyl, —C$_{2-6}$alkyl-OR$^a$, or —C$_{1-6}$ alkylC(O)OR$^a$;
  wherein each alkyl, cycloalkyl, or heterocyclyl group is optionally substituted with 1 to 2 groups independently selected from —OR$^a$, —CN, halo, —C$_{1-6}$alkylOR$^a$, —C$_{1-6}$cyanoalkyl, —C$_{1-3}$haloalkyl, —C(O)R$^a$, —C$_{1-6}$ alkylC(O)R$^a$, —C(O)OR$^a$, —C$_{1-6}$ alkylC(O)OR$^a$, —C(O)NR$^a$R$^b$, and —C$_{1-6}$ alkylC(O)NR$^a$R$^b$;
each R$^2$ is independently selected from —C$_{1-6}$ alkyl, —C$_{3-6}$ cycloalkyl, heterocyclyl, —C$_{2-6}$ alkyl-OR$^a$, and —C$_{1-6}$ alkyl C(O)OR$^a$;
  wherein each alkyl, cycloalkyl, or heterocyclyl is optionally substituted with 1 to 2 groups independently selected from —OR$^a$, —CN, —C$_{1-6}$alkylOR$^a$, —C$_{1-6}$ cyanoalkyl, —C$_{1-3}$haloalkyl, —C$_{3-8}$cycloalkyl, —C$_{1-3}$alkylC$_{3-8}$cycloalkyl, —C(O)R$^a$, —C$_{1-6}$alkylC(O)R$^a$, —C(O)OR$^a$, —C$_{1-6}$ alkylC(O)OR$^a$, —C(O)NR$^a$R$^b$, and C$_{1-6}$ alkylC(O)NR$^a$R$^b$;
or R$^1$ and R$^2$ combine to form a heterocyclyl optionally containing an additional heteroatom selected from oxygen, sulfur or nitrogen, and optionally substituted with 1 to 3 groups independently selected from oxo, —C$_{1-6}$alkyl, —OR$^a$, —C(O)OR$^a$, —C(O)R$^a$, C$_{1-6}$ alkylC(O)R$^a$, —C$_{1-6}$ alkylC(O)OR$^a$, —NR$^a$R$^b$, —C$_{1-6}$ alkylNR$^a$R$^b$, and —C(O)NR$^a$R$^b$;
each R$^a$ is independently H or —C$_{1-6}$ alkyl;
each R$^b$ is independently H or —C$_{1-6}$ alkyl;
each R$^c$ is independently selected from H, OH, —C$_{1-6}$ alkyl, and —C$_{3-8}$ cycloalkyl;
each R$^d$ is independently selected from H, —C$_{1-6}$ alkyl, and —C$_3$-C$_8$cycloalkyl;
R$^e$ is selected from H, —C$_{1-6}$ alkyl, —O—C$_{1-6}$alkyl, —C$_{3-8}$ cycloalkyl, aryl, heteroaryl, heterocyclyl, —O—C$_{3-8}$ cycloalkyl, —O-aryl, —O-heteroaryl, —O-heterocyclyl, —C$_{1-3}$ alkylC$_{3-8}$cycloalkyl, —C$_{1-6}$ alkylaryl, —C$_{1-6}$alkylheteroaryl, —NR$^f$R$^g$, —C$_{1-6}$ alkylNR$^f$R$^g$, —C(O)NR$^f$R$^g$, —C$_{1-6}$ alkylC(O)NR$^f$R$^g$, —NHS(O)$_2$R$^f$, —C$_{1-6}$ alkylS(O)$_2$R$^f$, and —C$_{1-6}$ alkylS(O)$_2$NR$^f$R$^g$;
each R$^f$ is independently selected from H, —C$_{1-6}$ alkyl, and —C$_{3-8}$ cycloalkyl;
each R$^g$ is independently selected from H, —C$_{1-6}$ alkyl, and —C$_{3-8}$ cycloalkyl.
In one embodiment, R$^E$ and R$^W$ are each

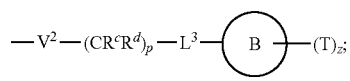

wherein
V² is independently a bond, O, NR$^a$, S, S(O) or S(O)$_2$;
R$^c$ is independently selected from H, OH, —C$_{1-6}$ alkyl, and —C$_{3-8}$ cycloalkyl;
R$^d$ is independently selected from H, —C$_{1-6}$ alkyl, and —C$_3$-C$_8$cycloalkyl;
L³ is independently a bond, O, NR$^a$, S, S(O), or S(O)$_2$;
ring B is independently cycloalkyl, aryl, heteroaryl, or heterocyclyl;
T is independently H, —OR$^a$, (CH$_2$)$_q$NR$^1$R$^2$, (CH$_2$)$_q$N-R$^a$C(O)R$^e$ or (CH$_2$)$_q$C(O)R$^e$;
R$^e$ is selected from H, —C$_{1-6}$ alkyl, —O—C$_{1-6}$alkyl, —C$_{3-8}$ cycloalkyl, aryl, heteroaryl, heterocyclyl, —O—C$_{3-8}$ cycloalkyl, —O-aryl, —O-heteroaryl, —O-heterocyclyl, —C$_{1-3}$ alkylC$_{3-8}$cycloalkyl, —C$_{1-6}$ alkylaryl, —C$_{1-6}$alkylheteroaryl, —NR$^f$R$^g$, —C$_{1-6}$ alkylNR$^f$R$^g$, —C(O)NR$^f$R$^g$, —C$_{1-6}$ alkylC(O)NR$^f$R$^g$, —NHS(O)$_2$R$^f$, —C$_{1-6}$ alkylS(O)$_2$R$^f$, and —C$_{1-6}$ alkylS(O)$_2$NR$^f$R$^g$;
R$^f$ is independently selected from H, —C$_{1-6}$ alkyl, and —C$_{3-8}$ cycloalkyl;
R$^g$ is independently selected from H, —C$_{1-6}$ alkyl, and —C$_{3-8}$ cycloalkyl;
p is independently 0, 1, 2, or 3;
q is independently 0, 1, 2, or 3;
z is 0, 1, 2, or 3;
and wherein the alkyl, cycloalkyl, aryl, heteroaryl, or heterocyclyl group is optionally substituted with 1 to 3 substituents independently selected from the group consisting of NR$^a$R$^b$, halo, cyano, —OR$^a$, —C$_{1-6}$ alkyl, —C$_{1-6}$ haloalkyl, —C$_{1-6}$ cyanoalkyl, —C$_{1-6}$ alkylNR$^a$R$^b$, —C$_{1-6}$ alkylOH, —C$_{3-8}$ cycloalkyl, and —C$_{1-3}$ alkylC$_{3-8}$cycloalkyl;
provided that at least one of V², L³, ring B and T contains a nitrogen atom.
In one embodiment, R$^E$ and R$^W$ are each independently —NR$^1$R$^2$, —C$_{1-6}$ alkylNR$^1$R$^2$, or —O—C$_{1-6}$ alkylNR$^1$R$^2$;
each R$^1$ is independently selected from H, —C$_{1-6}$alkyl, —C$_{3-6}$cycloalkyl, heterocyclyl, —C$_{2-6}$alkyl-OR$^a$, or —C$_{1-6}$ alkylC(O)OR$^a$;
  wherein each alkyl, cycloalkyl, or heterocyclyl is optionally substituted with 1 to 2 groups independently selected from —OR$^a$, —CN, halo, —C$_{1-6}$alkylOR$^a$, —C$_{1-6}$cyanoalkyl, —C$_{1-3}$haloalkyl, —C(O)R$^a$, —C$_{1-6}$ alkylC(O)R$^a$, —C(O)OR$^a$, —C$_{1-6}$ alkylC(O)OR$^a$, —C(O)NR$^a$R$^b$, and —C$_{1-6}$ alkylC(O)NR$^a$R$^b$;
each R$^2$ is independently selected from —C$_{1-6}$ alkyl, —C$_{3-6}$ cycloalkyl, heterocyclyl, —C$_{2-6}$ alkyl-OR$^a$, and —C$_{1-6}$ alkyl C(O)OR$^a$;
  wherein each alkyl, cycloalkyl, or heterocyclyl is optionally substituted with 1 to 2 groups independently selected from —OR$^a$, —CN, —C$_{1-6}$alkylOR$^a$, —C$_{1-6}$ cyanoalkyl, —C$_{1-3}$haloalkyl, —C$_{3-8}$cycloalkyl, —C$_{1-3}$alkylC$_{3-8}$cycloalkyl, —C(O)R$^a$, —C$_{1-6}$alkylC(O)R$^a$, —C(O)OR$^a$, —C$_{1-6}$ alkylC(O)OR$^a$, —C(O)NR$^a$R$^b$, and C$_{1-6}$ alkylC(O)NR$^a$R$^b$;
or R$^1$ and R$^2$ combine to form a heterocyclyl optionally containing 1 or 2 additional heteroatoms independently selected from oxygen, sulfur or nitrogen, and optionally substituted with 1 to 3 groups independently selected from oxo, —C$_{1-6}$alkyl, —OR$^a$, —C(O)OR$^a$, —C(O)R$^a$, C$_{1-6}$ alkylC(O)R$^a$, —C$_{1-6}$alkylC(O)OR$^a$, —NR$^a$R$^b$, —C$_{1-6}$ alkyl NR$^a$R$^b$, and —C(O)NR$^a$R$^b$;
each R$^a$ is independently H or —C$_{1-6}$ alkyl;
each R$^b$ is independently H or —C$_{1-6}$ alkyl.
In one embodiment, R$^E$ and R$^W$ are each —C$_{1-6}$alkyl OC$_{1-6}$ alkylNR$^1$R$^2$;

each $R^1$ is selected from H, —$C_{1-6}$alkyl, —$C_{3-6}$cycloalkyl, heterocyclyl, —$C_{2-6}$alkyl-$OR^a$, and —$C_{1-6}$alkylC(O)$OR^a$;
  wherein each alkyl, cycloalkyl, or heterocyclyl is optionally substituted with 1 to 2 groups independently selected from —$OR^a$, —CN, halo, —$C_{1-6}$alkyl$OR^a$, —$C_{1-6}$cyanoalkyl, —$C_{1-3}$haloalkyl, —C(O)$R^a$, —$C_{1-6}$alkylC(O)$R^a$, —C(O)$OR^a$, —$C_{1-6}$alkylC(O)$OR^a$, —C(O)$NR^aR^b$, and —$C_{1-6}$alkylC(O)$NR^aR^b$;
each $R^2$ is selected from —$C_{1-6}$alkyl, —$C_{3-6}$cycloalkyl, heterocyclyl, —$C_{2-6}$alkyl-$OR^a$, and —$C_{1-6}$alkylC(O)$OR^a$;
  wherein each alkyl, cycloalkyl, or heterocyclyl is optionally substituted with 1 to 2 groups independently selected from —$OR^a$, —CN, —$C_{1-6}$alkyl$OR^a$, —$C_{1-6}$cyanoalkyl, —$C_{1-3}$haloalkyl, —$C_{3-8}$cycloalkyl, —$C_{1-3}$alkyl$C_{3-8}$cycloalkyl, —C(O)$R^a$, —$C_{1-6}$alkylC(O)$R^a$, —C(O)$OR^a$, —$C_{1-6}$alkylC(O)$OR^a$, —C(O)$NR^aR^b$, and $C_{1-6}$alkylC(O)$NR^aR^b$; or
$R^1$ and $R^2$ combine to form a heterocyclyl optionally containing 1 or 2 additional heteroatoms independently selected from oxygen, sulfur or nitrogen, and optionally substituted with 1 to 3 groups independently selected from oxo, —$C_{1-6}$alkyl, —$OR^a$, —C(O)$OR^a$, —C(O)$R^a$, $C_{1-6}$alkylC(O)$R^a$, —$C_{1-6}$alkylC(O)$OR^a$, —$NR^aR^b$, —$C_{1-6}$alkyl$NR^aR^b$, and —C(O)$NR^aR^b$;
each $R^a$ is independently H or —$C_{1-6}$alkyl; and
each $R^b$ is independently H or —$C_{1-6}$alkyl.

In one embodiment, provided is a compound of formula (I), wherein $R^E$ and $R^W$ are each —O—$C_{1-6}$alkyl$NR^1R^2$;
$R^1$ is selected from H, —$C_{1-6}$alkyl, —$C_{3-6}$cycloalkyl, heterocyclyl, —$C_{2-6}$alkyl-$OR^a$, and —$C_{1-6}$alkylC(O)$OR^a$;
  wherein each alkyl, cycloalkyl, or heterocyclyl is optionally substituted with 1 to 2 groups independently selected from —$OR^a$, —CN, halo, —$C_{1-6}$alkyl$OR^a$, —$C_{1-6}$cyanoalkyl, —$C_{1-3}$haloalkyl, —C(O)$R^a$, —$C_{1-6}$alkylC(O)$R^a$, —C(O)$OR^a$, —$C_{1-6}$alkylC(O)$OR^a$, —C(O)$NR^aR^b$, and —$C_{1-6}$alkylC(O)$NR^aR^b$;
$R^2$ is selected from —$C_{1-6}$alkyl, —$C_{3-6}$cycloalkyl, heterocyclyl, —$C_{2-6}$alkyl-$OR^a$, and —$C_{1-6}$alkylC(O)$OR^a$;
  wherein each alkyl, cycloalkyl, or heterocyclyl is optionally substituted with 1 to 2 groups independently selected from —$OR^a$, —CN, —$C_{1-6}$alkyl$OR^a$, —$C_{1-6}$cyanoalkyl, —$C_{1-3}$haloalkyl, —$C_{3-8}$cycloalkyl, —$C_{1-3}$alkyl$C_{3-8}$cycloalkyl, —C(O)$R^a$, —$C_{1-6}$alkylC(O)$R^a$, —C(O)$OR^a$, —$C_{1-6}$alkylC(O)$OR^a$, —C(O)$NR^aR^b$, and —$C_{1-6}$alkylC(O)$NR^aR^b$; or
$R^1$ and $R^2$ combine to form a heterocyclyl group optionally containing 1 or 2 additional heteroatoms independently selected from oxygen, sulfur or nitrogen, and optionally substituted with 1 to 3 groups independently selected from oxo, —$C_{1-6}$alkyl, —$OR^a$, —C(O)$OR^a$, —C(O)$R^a$, $C_{1-6}$alkylC(O)$R^a$, —$C_{1-6}$alkylC(O)$OR^a$, —$NR^aR^b$, —$C_{1-6}$alkyl$NR^aR^b$, and —C(O)$NR^aR^b$;
$R^a$ is independently H or —$C_{1-6}$alkyl; and
$R^b$ is independently H or —$C_{1-6}$alkyl.

In one embodiment, $R^E$ and $R^W$ are each —$NR^1R^2$;
$R^1$ is selected from H, —$C_{1-6}$alkyl, —$C_{3-6}$cycloalkyl, heterocyclyl, —$C_{2-6}$alkyl-$OR^a$, and —$C_{1-6}$alkylC(O)$OR^a$;
  wherein each alkyl, cycloalkyl, or heterocyclyl is optionally substituted with 1 to 2 groups independently selected from —$OR^a$, —CN, halo, —$C_{1-6}$alkyl$OR^a$, —$C_{1-6}$cyanoalkyl, —$C_{1-3}$haloalkyl, —C(O)$R^a$, —$C_{1-6}$alkylC(O)$R^a$, —C(O)$OR^a$, —$C_{1-6}$alkylC(O)$OR^a$, —C(O)$NR^aR^b$, and —$C_{1-6}$alkylC(O)$NR^aR^b$;
$R^2$ is selected from —$C_{1-6}$alkyl, —$C_{3-6}$cycloalkyl, heterocyclyl, —$C_{2-6}$alkyl-$OR^a$, and —$C_{1-6}$alkylC(O)$OR^a$;
  wherein each alkyl, cycloalkyl, or heterocyclyl group is optionally substituted with 1 to 2 groups independently selected from —$OR^a$, —CN, —$C_{1-6}$alkyl$OR^a$, —$C_{1-6}$cyanoalkyl, —$C_{1-3}$haloalkyl, —$C_{3-8}$cycloalkyl, —$C_{1-3}$alkyl$C_{3-8}$cycloalkyl, —C(O)$R^a$, —$C_{1-6}$alkylC(O)$R^a$, —C(O)$OR^a$, —$C_{1-6}$alkylC(O)$OR^a$, —C(O)$NR^aR^b$, and $C_{1-6}$alkylC(O)$NR^aR^b$;
or $R^1$ and $R^2$ combine to form a heterocyclyl group optionally containing an additional heteroatom selected from oxygen, sulfur or nitrogen, and optionally substituted with 1 to 3 groups independently selected from oxo, —$C_{1-6}$alkyl, —$OR^a$, —C(O)$OR^a$, —C(O)$R^a$, $C_{1-6}$alkylC(O)$R^a$, —$C_{1-6}$alkylC(O)$OR^a$, —$NR^aR^b$, —$C_{1-6}$alkyl$NR^aR^b$, and —C(O)$NR^aR^b$;
$R^a$ is independently H or —$C_{1-6}$alkyl; and
$R^b$ is independently H or —$C_{1-6}$alkyl.

In one embodiment, $R^E$ and $R^W$ do not contain an amide group (i.e., —NC(O)— or —C(O)N—). In one embodiment, at least one on $R^E$ and $R^W$ contains a heterocyclyl moiety which optionally comprises an oxo.

In one embodiment, $R^E$ and $R^W$ are each independently —$NR^1R^2$, —$C_{1-6}$alkyl$NR^1R^2$, —O—$C_{1-6}$alkyl$NR^1R^2$, —$C_{1-6}$alkylO$C_{1-6}$alkyl$NR^1R^2$, —$NR^a$—$C_{1-6}$alkyl$NR^1R^2$, —$C_{1-6}$alkylN+$R^1R^2R^3$, —S—$C_{1-6}$alkyl$NR^1R^2$, —C(O)$NR^1R^2$, —S(O)$_2R^a$, —(CH$_2$)$_u$S(O)$_2NR^1R^2$, —(CH$_2$)$_u$$NR^a$S(O)$_2NR^aR^b$, —S(O)$_2NR^aC_{1-6}$alkyl$NR^1R^2$, —$NR^a$S(O)$_2C_{1-6}$alkyl$NR^1R^2$;
each $R^1$ is independently —$C_{1-6}$alkylheterocyclyl;
  wherein each heterocyclyl is independently 2,5-diazaspiro[3.4]octan-6-one, azetidine, 2,6-diazaspiro[3.3]heptane, pyrrolidin-2-one, tetrahydrofuran, pyrrolidine, piperidin-2-one (36), piperazin-2-one, 5-oxa-2,7-diazaspiro[3.4]octan-6-one, 3-azabicyclo[3.1.0]hexane, 2-azabicyclo[2.1.1]hexane, tetrahydro-2H-pyran, 2,6-diazaspiro[3.4]octan-7-one, 4,5-dihydro-1H-imidazole, 1,4,5,6-tetrahydropyrimidine, piperidine, 1,2,4-oxadiazol-5(2H)-one, 2,5,7-triazaspiro[3.4]octan-6-one, 2,7-diazaspiro[4.4]nonan-3-one, 1,7-diazaspiro[4.4]nonan-2-one, 2-azaspiro[4.4]nonan-3-one, 1,8-diazaspiro[4.5]decan-2-one, 2-azaspiro[3.3]heptane, oxazolidin-2-one, octahydrocyclopenta[b]pyrrole, octahydrocyclopenta[c]pyrrole, 2-oxa-7-azaspiro[4.4]nonan-1-one, 6-oxa-2-azaspiro[3.4]octane, piperazine, 1,1-dioxotetrahydrothiophene, hexahydropyrrolo[3,4-b]pyrrol-6(1H)-one, 1,3,8-triazaspiro[4.5]decane-2,4-dione, 2-methyl-1,3,7-triazaspiro[4.5]dec-2-en-4-one, 1,3,7-triazaspiro[4.4]nonane-2,4-dione, 1,3,7-triazaspiro[4.5]decane-2,4-dione, 6-azaspiro[3.4]octane, 1-thia-6-azaspiro[3.3]heptane 1,1-dioxide, pyridin-2(1H)-one, isothiazolidine 1,1-dioxide, thietane 1,1-dioxide, hexahydropyrrolo[3,4-b]pyrrol-2(1H)-one, 2,5,7-triazaspiro[3.4]octane-6,8-dione, 3-azabicyclo[3.1.0]hexan-2-one, 5-azaspiro[2.4]heptan-4-one, oxetane, morpholine, 2-thiaspiro[3.3]heptane 2,2-dioxide, hexahydrocyclopenta[b]pyrrol-2(1H)-one, pyrrolidine-2,5-dione, 6,7-dihydro-5H-pyrrolo[3,4-b]pyridine, or 1,3-dioxolane, and each is optionally substituted with 1 to 4 groups independently selected from the group consisting of —$OR^a$, —CN, halo, $C_{1-6}$alkyl, —$C_{1-6}$alkyl$OR^a$, —$C_{1-6}$cyanoalkyl, —$C_{1-6}$haloalkyl, $C_{3-8}$cycloalkyl, —$C_{1-3}$alkyl$C_{3-8}$cycloalkyl, —C(O)$R^a$, —$C_{1-6}$alkylC(O)$R^a$, —C(O)$OR^a$, —$C_{1-6}$alkylC(O)$OR^a$, —$NR^aR^b$, —OC(O)$NR^aR^b$, $NR^aC(O)OR^b$, —$C_{1-6}$alkyl$NR^aR^b$, —C(O)$NR^aR^b$, —$C_{1-6}$alkylC(O)$NR^aR^b$, —S(O)$_2R^a$, —$C_{1-6}$alkylS(O)$_2R^a$, —S(O)$_2NR^aR^b$, —$C_{1-6}$alkylS(O)$_2NR^aR^b$, —C(O)$NR^aS(O)_2R^b$, —$C_{1-6}$alkylC(O)$NR^aS(O)_2R^b$, —$NR^aC(O)R^b$, and —$C_{1-6}$alkyl$NR^aC(O)R^b$; and
each $R^2$ is H.

In one embodiment, $R^W$ and $R^E$ are each independently selected from:
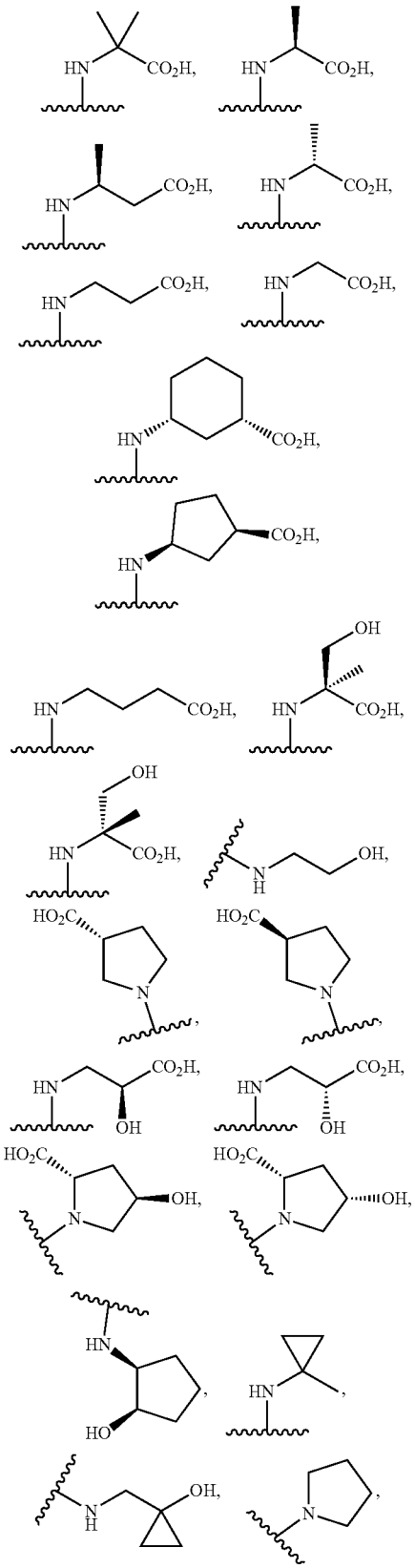
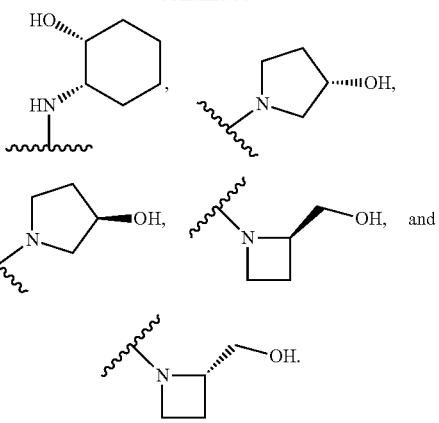
In one embodiment, each $R^W$ and $R^E$ is independently selected from:
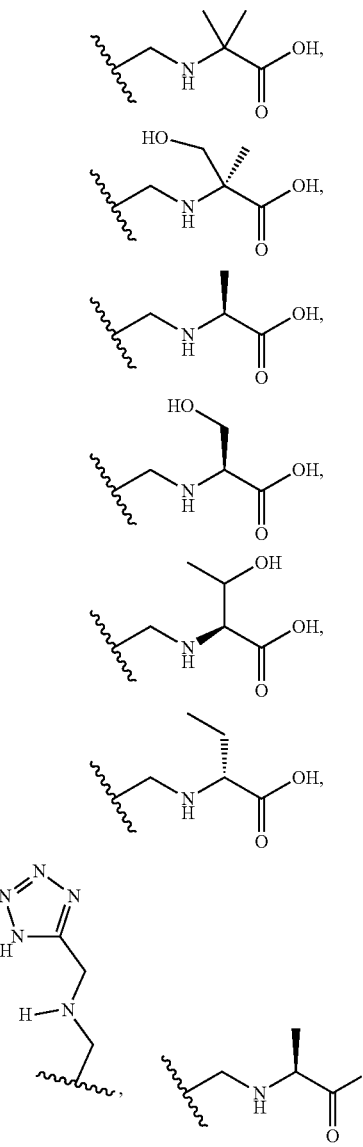

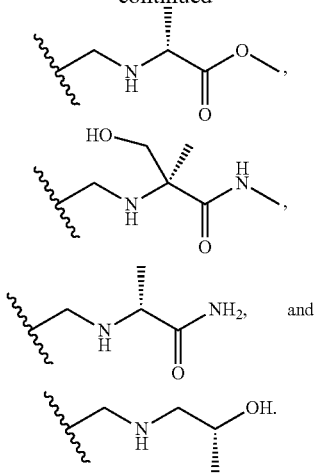
In one embodiment, each $R^W$ and $R^E$ is independently selected from:
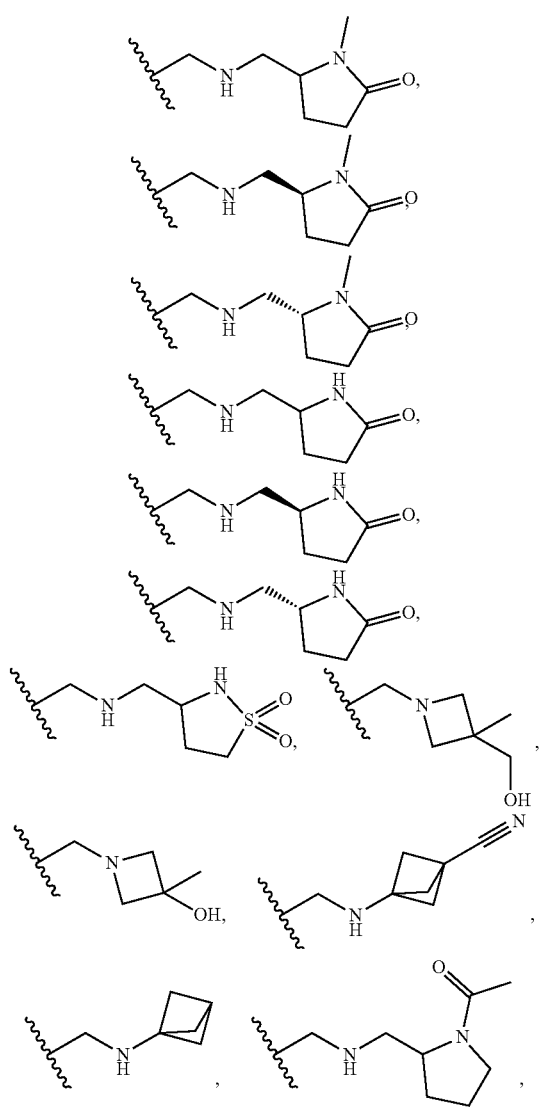
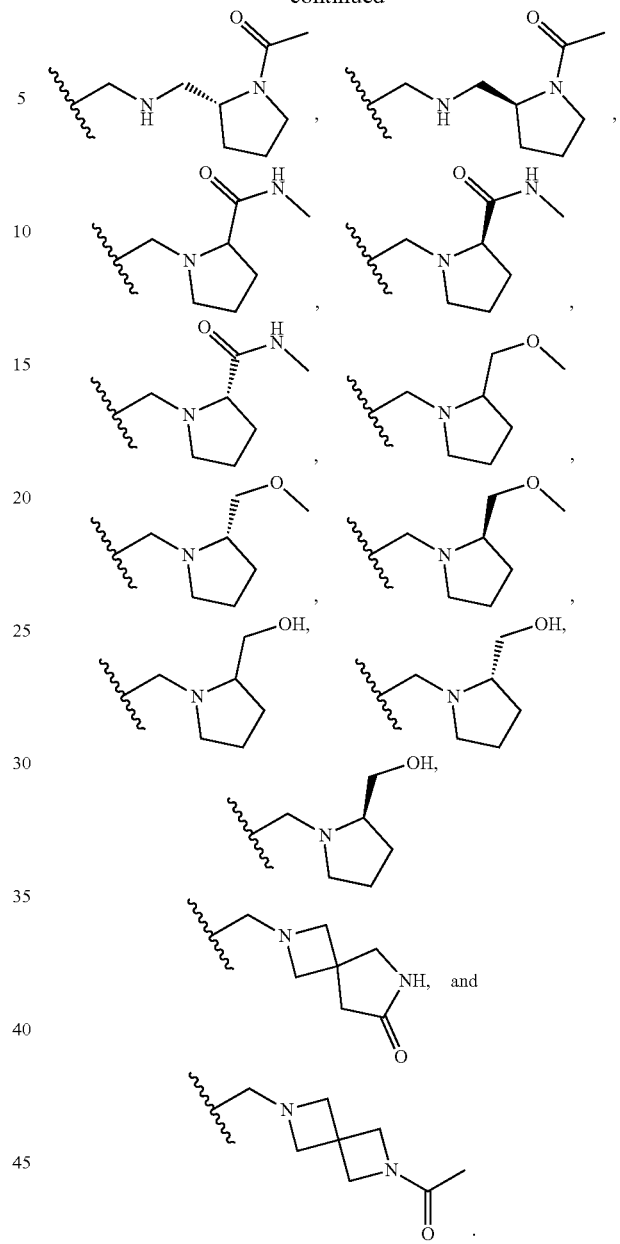
In one embodiment, each $R^W$ and $R^E$ is independently selected from:
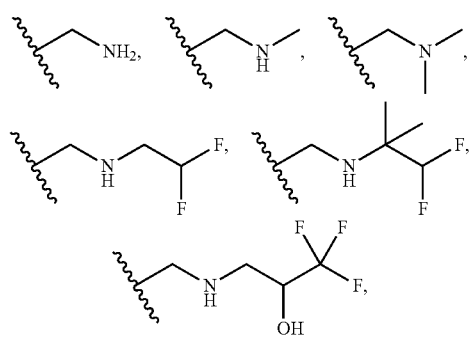

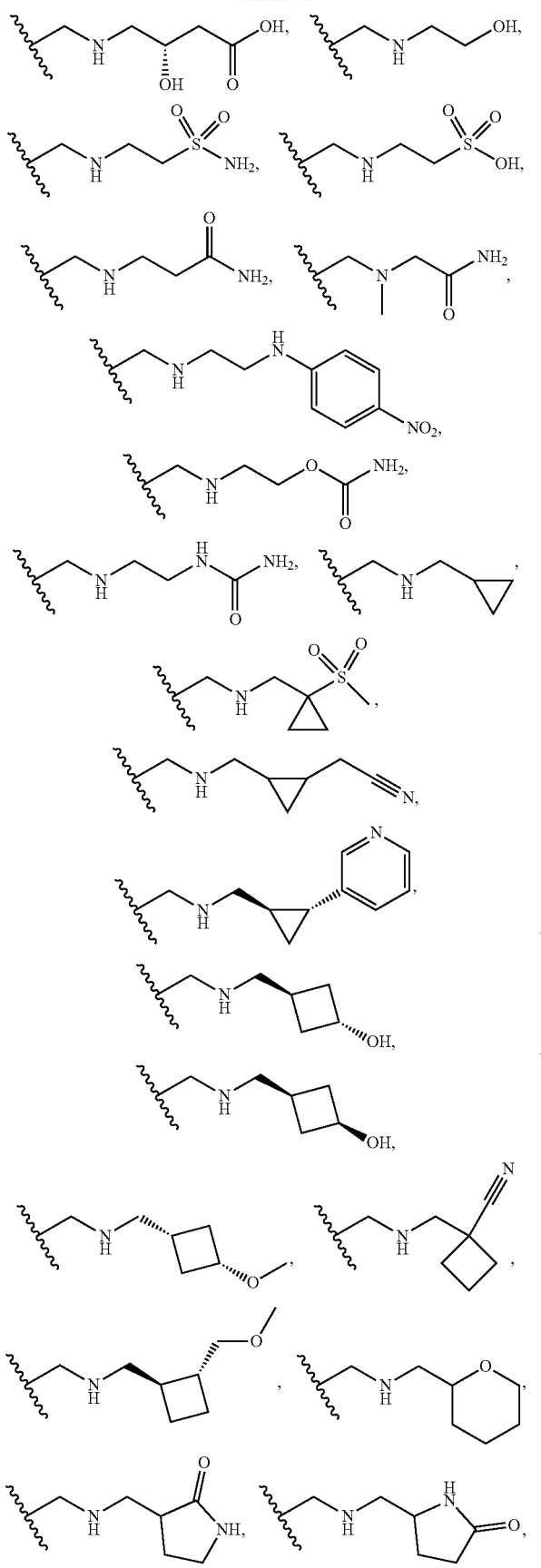
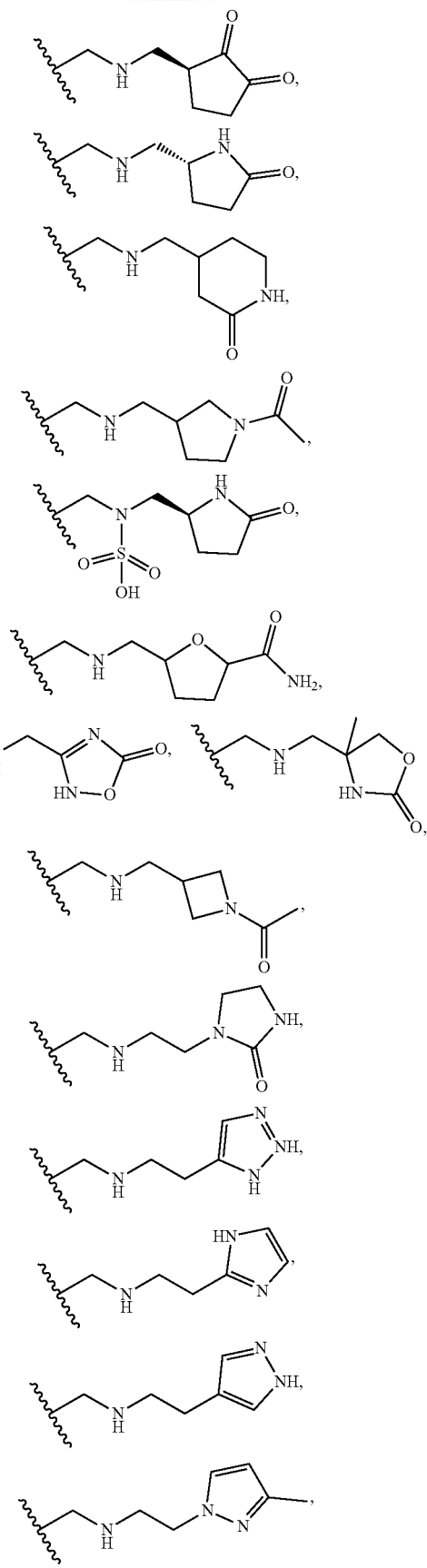

57
-continued
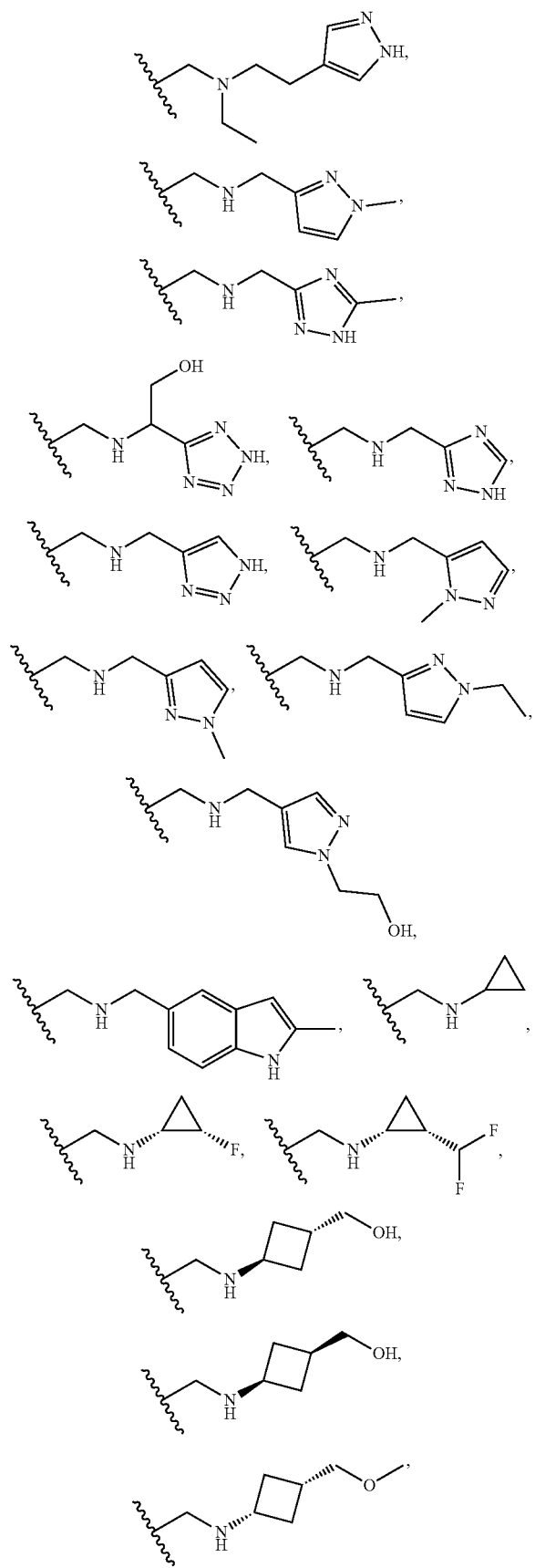
58
-continued
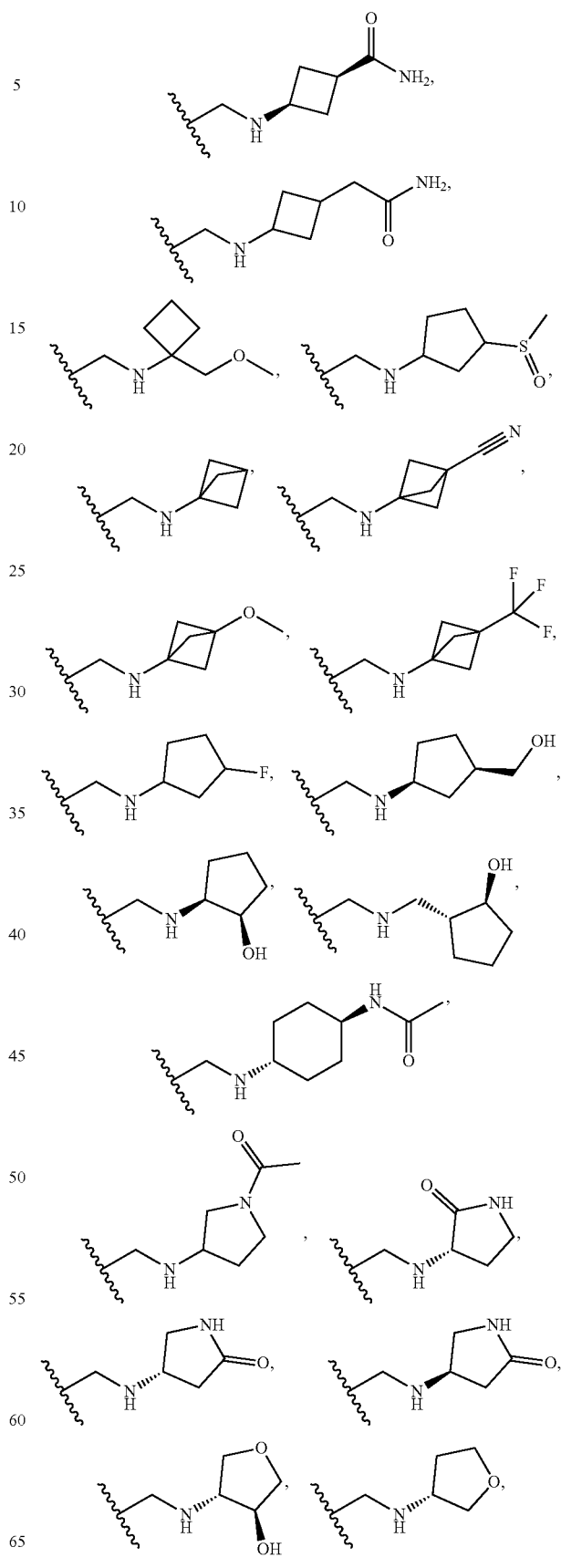

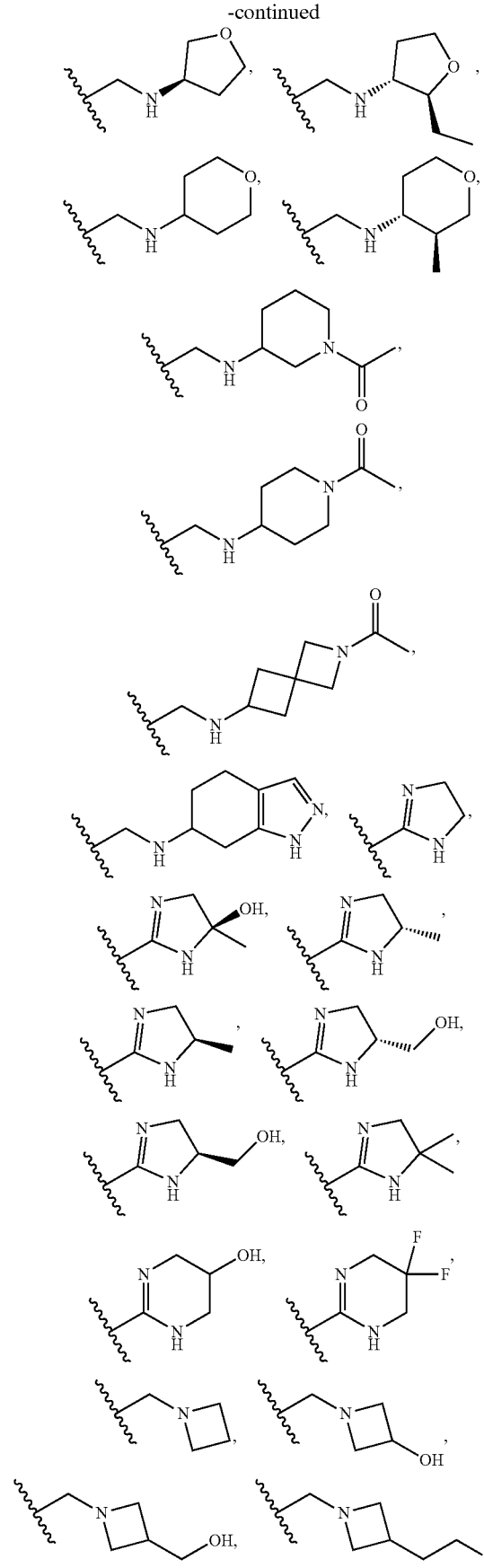
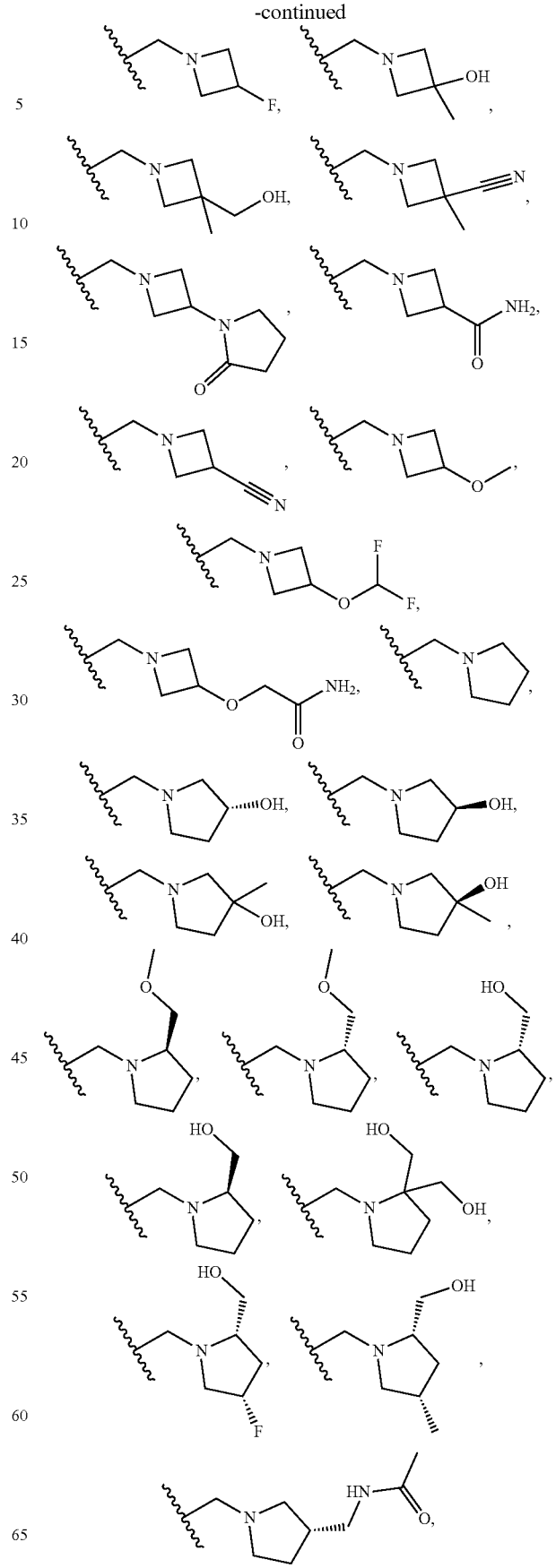

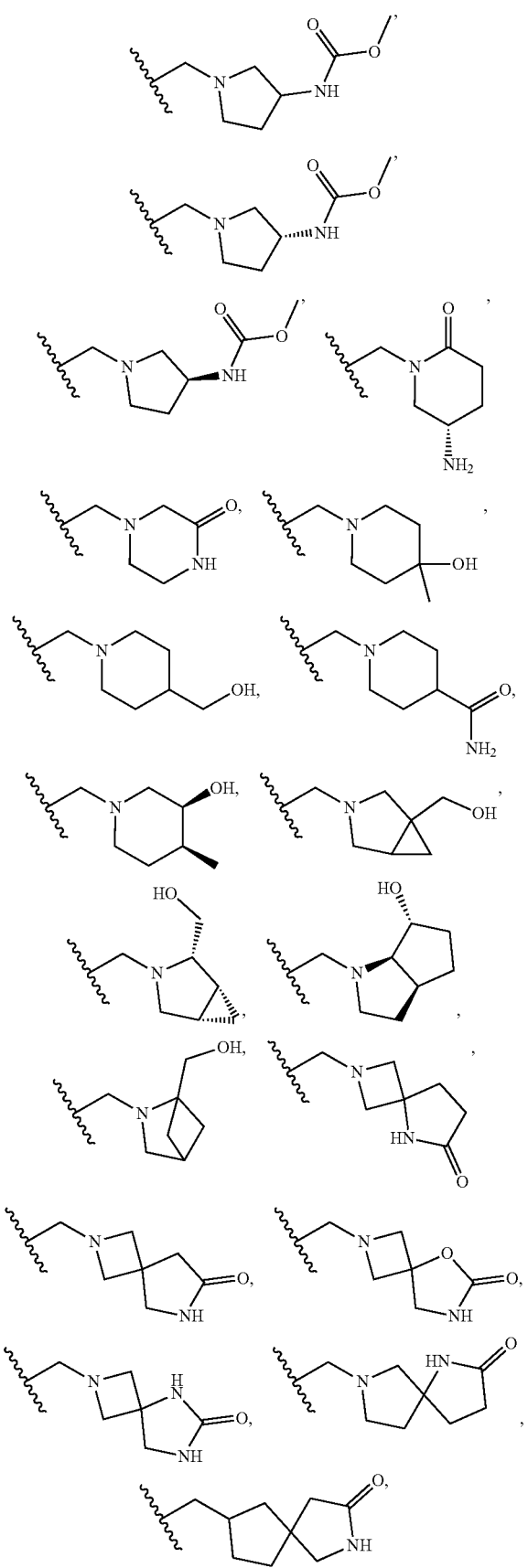
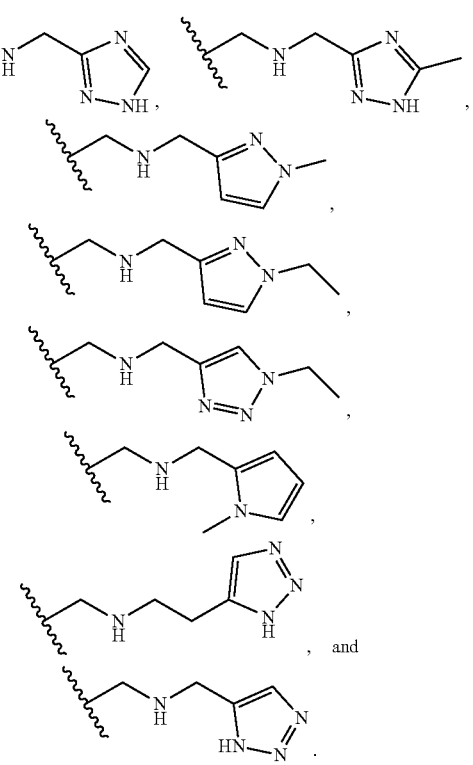

In one embodiment, each $R^W$ and $R^E$ is independently selected from:

In certain embodiments, each $Z^1$ is independently halo or —$C_{1-6}$ alkyl. In certain embodiments, each $Z^1$ is fluoro, chloro, or methyl.

In certain embodiments, each $Z^1$ is independently halo. In certain embodiments, each $Z^1$ is chloro.

In certain embodiments, each $Z^3$ is independently —$C_{1-6}$ alkyl, —O—$C_{1-6}$ alkyl, or —O—$C_{3-8}$ cycloalkyl. In certain embodiments, each $Z^3$ is methyl, methoxy, or cyclopropoxy.

In certain embodiments, each $Z^3$ is independently $C_{1-6}$ alkoxy. In certain embodiments, each $Z^3$ is methoxy.

In certain embodiments, neither of $R^E$ or $R^W$ is an optionally substituted fused 5,6-aromatic or 5,6-heteromatic ring. In certain embodiments, none of $Z^1$, $Z^3$, $R^N$, $R^E$ or $R^W$ is an optionally substituted fused 5,6-aromatic or 5,6-heteromatic ring.

In certain embodiments, provided is a compound as shown in Table 1, or a pharmaceutically acceptable salt, stereoisomer, mixture of stereoisomers, or tautomer thereof.

In certain embodiments, the compound as provided herein has a molecular weight of less than about 850 g/mol, or less than about 800 g/mol, or less than about 750 g/mol, or less than about 700 g/mol, or between about 500 to about 850 g/mol, or between about 500 to about 600 g/mol, or between about 550 to about 650 g/mol, or between about 600 to about 700 g/mol, or between about 650 to about 750 g/mol, or between about 700 to about 800 g/mol, or between about 750 to about 850 g/mol.

One of skill in the art is aware that each and every embodiment of a group (e.g., $R^E$) disclosed herein may be combined with any other embodiment of each of the remaining groups (e.g., $R^W$, $Z^1$, $Z^3$, etc.) to generate a complete compound of formula (I) as disclosed herein; each of which is deemed within the ambit of the present disclosure.

Formulations and Methods

PD-1 and its ligand, PD-L1, are monomeric type I transmembrane proteins that play critical roles in T cell inhibition and exhaustion. PD-L1 is composed of two extracellular immunoglobulin (Ig)-like domains whereas PD-1 is composed of a single extracellular Ig like domain and an intracellular tail. The crystal structure of the PD-1/PD-L1 complex reveals that PD-1 binds to PD-L1 with a 1:1 stoichiometry to form a monomeric complex (see, e.g., Cheng et al. *J Biol Chem*, 2013; 288(17); 11771-85, Lin et al. *Proc Natl Acad Sci USA*, 2008; 105(8); 3011-6, Zak et al. *Structure*, 2015; 23(12); 2341-8). This arrangement represents a distinct ligand-binding mode and signaling mechanism that differs from other co-inhibitory receptor/ligand interactions such as CTLA-4/B7, where oligomerization plays an important role in signaling (see, e.g., Schwartz et al. *Nature*, 2001; 410(6828); 604-8). Engagement of PD-1 to PD-L1, along with TCR signaling, leads to phosphorylation of the cytoplasmic domain tyrosines on PD-1 and recruitment of Src-homology 2-containing tyrosine phosphatases (SHP-1 and SHP-2). These phosphatases dephosphorylate TCR-associated proteins, resulting in alteration of downstream signaling including blocking phosphoinositide 3 kinase (PI3K) and Akt kinase activation, disrupting glucose metabolism, and inhibiting IL-2 and IFN-γ secretion (see, e.g., Hofmeyer et al. *J Biomed Biotechnol*, 2011; 2011; 451694, Latchman et al. *Nature immunology*, 2001; 2(3); 261-8).

Monoclonal antibodies developed for cancer immunotherapy binding to either PD-1 or PD-L1 have demonstrated significant response rates in patients, particularly for melanoma, non-small cell lung cancer (NSCLC), renal cell carcinoma (RCC) and bladder cancer. Many of these studies have shown that blockade of the PD-1/PD-L1 axis leads to an enhancement in T cell cytotoxic activity at the tumor site (see, e.g., Wherry E J. *Nat Immunol*, 2011; 12(6); 492-9). In addition to cancer, inhibition of this pathway has also shown promise for the control or elimination of chronic viral infections, such as HBV (see, e.g., Bengsch et al. *J Hepatol*, 2014; 61(6); 1212-9, Fisicaro et al. *Gastroenterology*, 2010; 138(2), 682-93, 93 e1-4, Fisicaro et al. *Gastroenterology*, 2012; 143(6), 1576-85 e4).

Methods

In one embodiment, the present disclosure provides a compound of formula (I) useful as an inhibitor of PD-1, PD-L1 and/or the PD-1/PD-L1 interaction. In some embodiments, compounds disclosed herein inhibit the PD-1/PD-L1 interaction by dimerizing PD-L1, or by inducing or stabilizing PD-L1 dimer formation.

In one embodiment, the present disclosure provides a pharmaceutical composition comprising a compound of formula (I) and a pharmaceutically acceptable carrier.

The present disclosure provides a compound of formula (I) for use in therapy.

In one embodiment, provided is a compound of formula (I) or a pharmaceutically acceptable salt, stereoisomer, mixture of stereoisomers or tautomer thereof, useful for treating an HBV infection or a condition in a patient that is amenable to treatment by inhibiting PD-1, PD-L1 or the PD-1/PD-L1 interaction.

In one embodiment, the present disclosure provides a pharmaceutical composition comprising a compound of formula (I) or a pharmaceutically acceptable salt, stereoisomer, mixture of stereoisomers or tautomer thereof, at least one additional therapeutic agent suitable for treating an HBV infection, and at least one pharmaceutically acceptable carrier or excipient.

In another embodiment, the present disclosure provides a compound of formula (I) for use in the manufacture of a medicament for treating or eliminating HBV. Elimination of HBV during acute infection is associated with the emergence of functional HBV-specific $CD8^+$ T cells. In contrast, chronic infection is marked by the presence of dysfunctional HBV-specific $CD8^+$ T cells that are unable to control viral infection (see, e.g., Boni et al. *J Virol*, 2007; 81(8); 4215-4225, Ferrari, *Liver Int*, 2015; 35; Suppl 1:121-8, Fisicaro et al., *Gastroenterology*, 2010; 138(2); 682-693, 93 e1-4, Guidotti et al. *Cell*, 2015; 161(3); 486-500). Mechanisms that may contribute to the dysfunction of HBV-specific T cells in CHB include upregulation of inhibitory T cell receptors (e.g. PD-1, CTLA-4 and TIM-3), due to persistent high viral load and antigen levels (see, e.g., Boni et al. *J Virol*, 2007; 81(8); 4215-4225, Franzese et al. *J Virol*, 2005; 79(6); 3322-3328, Peppa et al. *J Exp Med*, 2013; 210(1); 99-114, Wherry E J. *Nature immunology* 2011; 12(6); 492-499). Among all inhibitory immune receptors, PD-1 is most frequently upregulated on HBV-specific T cells. Furthermore, multiple studies have confirmed that the majority of circulating and intrahepatic HBV-specific $CD8^+$ T cells in CHB patients are exhausted and express high levels of PD-1 (see, e.g., Bengsch et al. *J Hepatol*, 2014; 61(6); 1212-1219, Fisicaro et al., *Gastroenterology*, 2010; 138(2); 682-693, 93 e1-4). Notably, the defects in effector cytokine production by HBV-specific $CD4^+$ and $CD8^+$ T cells were partially reversed by blocking the PD-1/PD-L1 interaction with an anti-PD-L1 antibody in PBMCs isolated from CHB patients (see, e.g., Bengsch et al. *J Hepatol*, 2014; 61(6); 1212-1219, Fisicaro et al., *Gastroenterology*, 2010; 138(2); 682-693, 93 e1-4, Fisicaro et al. *Gastroenterology*, 2012; 143(6); 1576-1585 e4). Consistent with these pre-clinical data, a clinical study evaluating α-PD-1 therapy in CHB subjects showed significant reductions in HBsAg levels in the majority of subjects which includes three out of twenty patients with reduction in HBsAg levels of over 0.5 $\log_{10}$ and one subject that experienced a functional cure (sustained HBsAg loss and appearance of anti-HBsAb) (see, e.g., Gane et al. "A phase1 study evaluating anti-PD-1 treatment with or without GS-4774 in HBeAg negative chronic hepatitis B patients", Abstract PS-044, European Association for the Study of the Liver (EASL); 2017 Apr. 19-23; Amsterdam, The Netherlands). Taken together, these findings demonstrate that inhibiting the PD-1/PD-L1 axis may improve T cell function in CHB patients and increase the rates of functional cure. Disclosed herein are selective and potent PD-L1 small molecule inhibitors that bind specifically to PD-L1 and inhibit the PD-1/PD-L1 interaction by inducing PD-L1 dimerization (see, e.g., Biological Example 2).

In one embodiment, the present disclosure provides a pharmaceutical composition comprising a compound of formula (I) or a pharmaceutically acceptable salt, stereoisomer, mixture of stereoisomers or tautomer thereof, and at least one additional anticancer agent and at least one pharmaceutically acceptable excipient.

In one embodiment, the present disclosure provides a method of treating cancer in a patient in need thereof, comprising administering a compound of formula (I) in combination with one or more check-point inhibitors selected from nivolumab, pembrolizumab, and atezolizumab.

In another embodiment, the present disclosure provides a compound of formula (I) for use in the manufacture of a medicament for treating cancer.

In one embodiment, provided is a compound of formula (I) or a pharmaceutically acceptable salt, stereoisomer, mixture of stereoisomers or tautomer thereof, useful for the treatment of cancer or a condition in a patient that is amenable to treatment by inhibiting PD-1, PD-L1 or the PD-1/PD-L1 interaction. Cancers that may be treated with the compounds of formula (I) disclosed herein include pancreatic cancer, bladder cancer, colorectal cancer, breast cancer, prostate cancer, renal cancer, hepatocellular cancer, lung cancer, ovarian cancer, cervical cancer, gastric cancer, esophageal cancer, head and neck cancer, melanoma, neuroendocrine cancer, CNS cancer, brain cancer, bone cancer, soft tissue sarcoma, non-small cell lung cancer, small-cell lung cancer and colon cancer.

In one embodiment, provided is a compound of formula (I) or a pharmaceutically acceptable salt, stereoisomer, mixture of stereoisomers or tautomer thereof, useful for the treatment of cancer or a condition in a patient that is amenable to treatment by inhibiting PD-1, PD-L1 or the PD-1/PD-L1 interaction including, but not limited to, lymphoma, multiple myeloma, and leukemia. Additional diseases or conditions that may be treated include, but are not limited to acute lymphocytic leukemia (ALL), acute myeloid leukemia (AML), chronic lymphocytic leukemia (CLL), small lymphocytic lymphoma (SLL), myelodysplastic syndrome (MDS), myeloproliferative disease (MPD), chronic myeloid leukemia (CML), multiple myeloma (MM), non-Hodgkin's lymphoma (NHL), mantle cell lymphoma (MCL), follicular lymphoma, Waldestrom's macroglobulinemia (WM), T-cell lymphoma, B-cell lymphoma and diffuse large B-cell lymphoma (DLBCL).

"Administering" or "administration" refers to the delivery of one or more therapeutic agents to a patient. In one embodiment, the administration is a monotherapy wherein a compound of formula (I) is the only active ingredient administered to the patient in need of therapy. In another embodiment, the administration is co-administration such that two or more therapeutic agents are delivered together during the course of the treatment. In one embodiment, two or more therapeutic agents may be co-formulated into a single dosage form or "combined dosage unit", or formulated separately and subsequently combined into a combined dosage unit, as is typically for intravenous administration or oral administration as a mono or bilayer tablet or capsule.

In one embodiment, the compound of formula (I) or a pharmaceutically acceptable salt thereof is administered to a human patient in need thereof in an effective amount, such as, from about 0.1 mg to about 1000 mg per day of said compound. In one embodiment, the effective amount is from about 0.1 mg to about 200 mg per day. In one embodiment, the effective amount is from about 1 mg to about 100 mg per day. In other embodiments, the effective amount is about 1 mg, about 3 mg, about 5 mg, about 10 mg, about 15 mg, about 18 mg, about 20 mg, about 30 mg, about 40 mg, about 60 mg, about 80 mg, or about 100 mg per day.

In one embodiment, the compound of formula (I) or a pharmaceutically acceptable salt thereof and at least one additional anticancer agent is administered to a human patient in need thereof in an effective amount of each agent, independently from about 0.1 mg to about 1000 mg per compound or formulation per day per compounds. In one embodiment, the effective amount of the combination treatment of a compound of formula (I) and an additional compound is independently from about 0.1 mg to about 200 mg per compound per day. In one embodiment, the effective amount of the combination treatment of a compound of formula (I) and an additional compound is independently from about 1 mg to about 100 mg per compound per day. In other embodiments, the effective amount of the combination treatment of a compound of formula (I) and an additional compound is for each component, about 1 mg, about 3 mg, about 5 mg, about 10 mg, about 15 mg, about 18 mg, about 20 mg, about 30 mg, about 40 mg, about 60 mg, about 80 mg, about 100 mg, about 200 mg, or about 500 mg each per day.

In one embodiment, the compound of formula (I) and/or a combination of the compound of formula (I) and an additional anticancer agent or a pharmaceutically acceptable salt thereof is administered once a day. In yet another embodiment, the compound of formula (I) and/or an additional anticancer agent or a pharmaceutically acceptable salt thereof is administered as a loading dose of from about 10 mg to about 500 mg per compound on the first day and each day or on alternate days or weekly for up to a month followed by a regular regimen of a compound of formula (I) and/or one or more additional anticancer agents or therapies. The maintenance dose may be 1-500 mg daily or weekly for each component of a multi component drug regimen. A qualified care giver or treating physician is aware of what dose regimen is best for a particular patient or particular presenting conditions and will make appropriate treating regimen decisions for that patient. Thus, in another embodiment, the qualified caregiver is able to tailor a dose regimen of the compound of formula (I) and/or an additional agent(s) as disclosed herein to fit with the particular needs of the patient. Thus, it will be understood that the amount of the compound of formula (I), or a pharmaceutically acceptable salt thereof and the amount of an additional agent actually administered will usually be determined by a physician, in light of the relevant circumstances, including the condition(s) to be treated, the chosen route of administration, the actual compound (e.g., salt or free base) administered and its relative activity, the age, weight, and response of the individual patient, the severity of the patient's symptoms, and the like.

Co-administration may also include administering component drugs e.g., one on more compounds of formula (I) and one or more additional (e.g., a second, third, fourth or fifth) anticancer or other therapeutic agent(s). Such combination of one on more compounds of formula (I) and one or more additional anticancer or other therapeutic agent(s) may be administered simultaneously or in sequence (one after the other) within a reasonable period of time of each administration (e.g., about 1 minute to 24 hours) depending on the pharmacokinetic and/or pharmacodynamics properties of each agent or the combination. Co-administration may also involve treatment with a fixed combination wherein agents of the treatment regimen are combinable in a fixed dosage or combined dosage medium e.g., solid, liquid or aerosol. In one embodiment, a kit may be used to administer the drug or drug components.

Thus, one embodiment of the present disclosure is a method of treating a disease amenable to treatment with a PD-1, PD-L1 inhibitor or a PD-1/PD-L1 interaction inhibitor e.g., cancer, comprising administering therapeutically effective amounts of formulations of one on more compounds of formula (I) and one or more additional anticancer agents, including for example, via a kit to a patient in need thereof. It will be understood that a qualified care giver will administer or direct the administration of a therapeutically effective amount of any of the compound(s) or combinations of compounds of the present disclosure.

"Intravenous administration" is the administration of substances directly into a vein, or "intravenously." Compared with other routes of administration, the intravenous (IV) route is a faster way to deliver fluids and medications throughout the body. An infusion pump can allow precise control over the flow rate and total amount of medication delivered. However, in cases where a change in the flow rate would not have serious consequences, or if pumps are not available, the drip is often left to flow simply by placing the bag above the level of the patient and using the clamp to regulate the rate. Alternatively, a rapid infuser can be used if the patient requires a high flow rate and the IV access device is of a large enough diameter to accommodate it. This is either an inflatable cuff placed around the fluid bag to force the fluid into the patient or a similar electrical device that may also heat the fluid being infused. When a patient requires medications only at certain times, intermittent infusion is used which does not require additional fluid. It can use the same techniques as an intravenous drip (pump or gravity drip), but after the complete dose of medication has been given, the tubing is disconnected from the IV access device. Some medications are also given by IV push or bolus, meaning that a syringe is connected to the IV access device and the medication is injected directly (slowly, if it might irritate the vein or cause a too-rapid effect). Once a medicine has been injected into the fluid stream of the IV tubing there must be some means of ensuring that it gets from the tubing to the patient. Usually this is accomplished by allowing the fluid stream to flow normally and thereby carry the medicine into the bloodstream; however, a second fluid injection is sometimes used, as a "flush", following the injection to push the medicine into the bloodstream more quickly. Thus in one embodiment, compound(s) or combination of compounds described herein may be administered by IV administration alone or in combination with administration of certain components of the treatment regimen by oral or parenteral routes.

"Oral administration" is a route of administration where a substance is taken through the mouth, and includes buccal, sub labial, and sublingual administration, as well as enteral administration and that through the respiratory tract, unless made through e.g., tubing so the medication is not in direct contact with any of the oral mucosa. Typical form for the oral administration of therapeutic agents includes the use of tablets or capsules. Thus in one embodiment, compound(s) or combination of compounds described herein may be administered by oral route alone or in combination with administration of certain components of the treatment regimen by IV or parenteral routes.

Pharmaceutical Formulations

The compound(s) of formula (I) or a pharmaceutically acceptable salt thereof may be administered in a pharmaceutical formulation. Pharmaceutical formulations/compositions contemplated by the present disclosure comprise, in addition to a carrier, the compound of formula (I), or a pharmaceutically acceptable salt thereof, or a combination of compound of formula (I), or a pharmaceutically acceptable salt thereof, optionally in combination with an additional agent such as for example, ipilimumab, or a pharmaceutically acceptable salt thereof.

Pharmaceutical formulations/compositions contemplated by the present disclosure may also be intended for administration by injection and include aqueous solutions, oil suspensions, emulsions (with sesame oil, corn oil, cottonseed oil, or peanut oil) as well as elixirs, mannitol, dextrose, or a sterile aqueous solution, and similar pharmaceutical vehicles. Aqueous solutions in saline are also conventionally used for injection. Ethanol, glycerol, propylene glycol, liquid polyethylene glycol, and the like (and suitable mixtures thereof), cyclodextrin derivatives, and vegetable oils may also be employed. The proper fluidity can be maintained, for example, by the use of a coating, such as lecithin, by the maintenance of the required particle size in the case of dispersion and/or by the use of surfactants. The prevention of the action of microorganisms can be brought about by various antibacterial and antifungal agents, for example, parabens, chlorobutanol, phenol, sorbic acid, thimerosal, and the like.

Sterile injectable solutions are prepared by incorporating the component compound(s) in the required amount in the appropriate solvent with various other ingredients as enumerated above or as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient(s) plus any additional desired ingredient from a previously sterile-filtered solution thereof.

In making pharmaceutical compositions that comprise compound of formula (I), or a pharmaceutically acceptable salt thereof, optionally in combination with an additional agent/therapy useful for the purpose or pharmaceutically acceptable salt thereof, the active ingredient is usually diluted by an excipient or carrier and/or enclosed or mixed with such a carrier that may be in the form of a capsule, sachet, paper or other container. When the excipient serves as a diluent, it can be a solid, semi-solid, or liquid material (as above), which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 20% by weight of the active compounds, soft and hard gelatin capsules, sterile injectable solutions, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents.

The compositions of the disclosure may be formulated so as to provide quick, sustained or delayed release of the active ingredient after administration to the patient by employing procedures known in the art. In one embodiment, sustained release formulations are used. Controlled release drug delivery systems for oral administration include osmotic pump systems and dissolutional systems containing polymer-coated reservoirs or drug-polymer matrix formulations.

Certain compositions are preferably formulated in a unit dosage form. The term "unit dosage forms" or "combined dosage unit" refers to physically discrete units suitable as unitary dosages for human subjects and other mammals, each unit containing a predetermined quantity of one or more of the active materials (e.g., compound (I), optionally in combination with an additional agent calculated to produce the desired effect, in association with a suitable pharmaceutical excipient in for example, a tablet, capsule, ampoule or vial for injection. It will be understood, however, that the amount of each active agent actually administered will be determined by a physician, in the light of the relevant circumstances, including the condition to be treated, the chosen route of administration, the actual compounds administered and their relative activity, the age, weight, and response of the individual patient, the severity of the patient's symptoms, and the like.

For preparing solid compositions such as tablets, the principal active ingredient(s) is/are mixed with a pharmaceutical excipient to form a solid pre-formulation composition containing a homogeneous mixture of a compound of the present disclosure. When referring to these pre-formulation compositions as homogeneous, it is meant that the active ingredient(s) are dispersed evenly throughout the composition so that the composition may be readily subdivided into equally effective unit dosage forms such as tablets, pills and capsules.

The tablets or pills comprising compound of formula (I) or a pharmaceutically acceptable salt thereof of the present disclosure optionally in combination with the second agent may be coated or otherwise compounded to provide a dosage form affording the advantage of prolonged action, or to protect from the acidic conditions of the stomach. For example, the tablet or pill can comprise an inner dosage and an outer dosage element, the latter being in the form of an envelope over the former. In one embodiment, the inner dosage element may comprise the compound (I) and the outer dosage element may comprise the second or additional agent or vice versa. Alternatively, the combined dosage unit may be side by side configuration as in a capsule or tablet where one portion or half of the tablet or capsule is filled with a formulation of the compound of formula (I) while the other portion or half of the table or capsule comprises the additional agent A variety of materials may be used for such enteric layers or coatings, such materials including a number of polymeric acids and mixtures of polymeric acids with such materials as shellac, cetyl alcohol, and cellulose acetate. One of ordinary skill in the art is aware of techniques and materials used in the manufacture of dosages of formulations disclosed herein.

A "sustained release formulation" or "extended release formulation" is a formulation which is designed to slowly release a therapeutic agent into the body over an extended period of time, whereas an "immediate release formulation" is a formulation which is designed to quickly release a therapeutic agent into the body over a shortened period of time. In some cases the immediate release formulation may be coated such that the therapeutic agent is only released once it reaches the desired target in the body (e.g., the stomach). One of ordinary skill in the art is able to develop sustained release formulations of the presently disclosed compounds without undue experimentation. Thus in one embodiment, compound(s) or combination of compounds described herein may be delivered via sustained released formulations alone or in combination with administration of certain components of the treatment regimen by oral, IV or parenteral routes.

A lyophilized formulation may also be used to administer a compound of formula (I) singly or in combination with an additional anticancer agent. One of skill in the art is aware of how to make and use lyophilized formulations of drug substances amenable to lyophilization.

Spray-dried formulation may also be used to administer a compound of formula (I) singly or in combination with an additional anti-cancer agent. One of skill in the art is aware of how to make and use spray-dried formulations of drug substances amenable to spray-drying. Other known formulation techniques may also be employed to formulate a compound or combination of compounds disclosed herein.

Articles of Manufacture

Articles of manufacture comprising a container in which a compound of formula (I) or a pharmaceutically acceptable salt thereof, and at least one pharmaceutically acceptable carrier are contained are provided. The article of manufacture may be a bottle, vial, ampoule, single-use disposable applicator, or the like, containing the pharmaceutical composition provided in the present disclosure. The container may be formed from a variety of materials, such as glass or plastic and in one aspect also contains a label on, or associated with, the container which indicates directions for use in the treatment of cancer or inflammatory conditions.

It should be understood that the active ingredient may be packaged in any material capable of providing reasonable chemical and physical stability, such as an aluminum foil bag.

Unit dosage forms of the pharmaceutical composition comprising a compound of formula (I), or a pharmaceutically acceptable salt thereof, and at least one pharmaceutically acceptable carrier are also provided.

Any pharmaceutical composition provided in the present disclosure may be used in the articles of manufacture, the same as if each and every composition were specifically and individually listed for use an article of manufacture.

Also provided is a kit that includes a compound of formula (I) or a pharmaceutically acceptable salt, stereoisomer, mixture of stereoisomers or tautomer thereof; a label, and/or instructions for use of the compound in the treatment of a disease or condition mediated by PD-1, PD-L1 activity or PD-1/PD-L1 interaction.

In one embodiment, the instructions are directed to use of the pharmaceutical composition for the treatment of cancer, including for example, leukemia or lymphoma. In specific embodiments, the cancer is acute lymphocytic leukemia (ALL), acute myeloid leukemia (AML), chronic lymphocytic leukemia (CLL), small lymphocytic lymphoma (SLL), myelodysplastic syndrome (MDS), myeloproliferative disease (MPD), chronic myeloid leukemia (CML), multiple myeloma (MM), indolent non-Hodgkin's lymphoma (iNHL), refractory iNHL, non-Hodgkin's lymphoma (NHL), mantle cell lymphoma (MCL), follicular lymphoma, Waldestrom's macroglobulinemia (WM), T-cell lymphoma, B-cell lymphoma, and diffuse large B-cell lymphoma (DLBCL). In one embodiment, the cancer is T-cell acute lymphoblastic leukemia (T-ALL), or B-cell acute lymphoblastic leukemia (B-ALL). The non-Hodgkin lymphoma encompasses the indolent B-cell diseases that include, for example, follicular lymphoma, lymphoplamacytic lymphoma, Waldestrom macroglobulinemia, and marginal zone lymphoma, as well as the aggressive lymphomas that include, for example, Burkitt lymphoma, diffuse large B-cell lymphoma (DLBCL) and mantle cell lymphoma (MCL). In one embodiment, the cancer is indolent non-Hodgkin's lymphoma (iNHL)

In a particular variation, the instructions are directed to use of the pharmaceutical composition for the treatment of an autoimmune disease. Specific embodiments of an autoimmune disease include asthma, rheumatoid arthritis, multiple sclerosis, and lupus.

Also provided is an article of manufacture which includes a compound of formula (I) or a pharmaceutically acceptable salt, prodrug, or solvate thereof, and a container. In one embodiment, the container may be a vial, jar, ampoule, preloaded syringe, or an intravenous bag.

Formulations of compound(s) of the present disclosure i.e., a compound of formula (I) or the combination of a compound of formula (I) and an additional agent may be accomplished by admixing said compounds or salt thereof with one or more non-toxic, pharmaceutically acceptable vehicles, carriers and/or diluents and/or adjuvants collectively referred to herein as excipients or carrier materials. The compounds of the disclosure may be administered by any suitable route, preferably in the form of a pharmaceutical composition adapted to such route, and in a therapeutically effective dose. The compounds or the combination of compounds for the disclosure may be delivered orally, mucosally, parenterally, including intravascularly, intravenously, intraperitoneally, subcutaneously, intramuscularly, and intranasally in dosage formulations containing conventional pharmaceutical excipients.

In one embodiment, the combination of a compound formula (I), or a pharmaceutically acceptable salt thereof, and an additional agent useful for the treatment of cancer may be formulated in a fixed dose or combined dose formulation in a tablet, capsule or premixed IV solution. In another embodiment, the fixed dose combination preferably comprises of compound formula (I), and an additional anticancer agent. Other fixed dose formulations may include premixed liquids, suspensions, elixirs, aerosolized sprays or patch presentations. As used herein fixed dose or combined dose formulations are synonymous with simultaneous co-administration of the active ingredients of the compound (I) and at least one additional agent.

Combination Therapy

Also provided are methods of treatment in which a compound of formula (I) or a pharmaceutically acceptable salt thereof, is given to a patient in combination with one or more additional active agents or therapy. The compound described herein may be used or combined with one or more of the additional therapeutic agents. The one or more therapeutic agents include, but are not limited to, an inhibitor, agonist, antagonist, ligand, modulator, stimulator, blocker, activator or suppressor of a gene, ligand, receptor, protein, factor such as Abelson murine leukemia viral oncogene homolog 1 gene (ABL, such as ABL1), Acetyl-CoA carboxylase (such as ACC1/2), activated CDC kinase (ACK, such as ACK1), Adenosine deaminase, adenosine receptor (such as A2B, A2a, A3), Adenylate cyclase, ADP ribosyl cyclase-1, adrenocorticotropic hormone receptor (ACTH), Aerolysin, AKT1 gene, Alk-5 protein kinase, Alkaline phosphatase, Alpha 1 adrenoceptor, Alpha 2 adrenoceptor, Alpha-ketoglutarate dehydrogenase (KGDH), Aminopeptidase N, AMP activated protein kinase, anaplastic lymphoma kinase (ALK, such as ALK1), Androgen receptor, Angiopoietin (such as ligand-1, ligand-2), Angiotensinogen (AGT) gene, murine thymoma viral oncogene homolog 1 (AKT) protein kinase (such as AKT1, AKT2, AKT3), apolipoprotein A-I (APOA1) gene, Apoptosis inducing factor, apoptosis protein (such as 1, 2), apoptosis signal-regulating kinase (ASK, such as ASK1), Arginase (I), Arginine deiminase, Aromatase, Asteroid homolog 1 (ASTE1) gene, ataxia telangiectasia and Rad 3 related (ATR) serine/threonine protein kinase, Aurora protein kinase (such as 1, 2), Axl tyrosine kinase receptor, Baculoviral IAP repeat containing 5 (BIRC5) gene, Basigin, B-cell lymphoma 2 (BCL2) gene, Bcl2 binding component 3, Bcl2 protein, BCL2L11 gene, BCR (breakpoint cluster region) protein and gene, Beta adrenoceptor, Beta-catenin, B-lymphocyte antigen CD19, B-lymphocyte antigen CD20, B-lymphocyte cell adhesion molecule, B-lymphocyte stimulator ligand, Bone morphogenetic protein-10 ligand, Bone morphogenetic protein-9 ligand modulator, Brachyury protein, Bradykinin receptor, B-Raf proto-oncogene (BRAF), Brc-Abl tyrosine kinase, Bromodomain and external domain (BET) bromodomain containing protein (such as BRD2, BRD3, BRD4), Bruton's tyrosine kinase (BTK), Calmodulin, calmodulin-dependent protein kinase (CaMK, such as CAMKII), Cancer testis antigen 2, Cancer testis antigen NY-ESO-1, cancer/testis antigen 1B (CTAG1) gene, Cannabinoid receptor (such as CB1, CB2), Carbonic anhydrase, casein kinase (CK, such as CKI, CKII), Caspase (such as caspase-3, caspase-7, Caspase-9), caspase 8 apoptosis-related cysteine peptidase CASP8-FADD-like regulator, Caspase recruitment domain protein-15, Cathepsin G, CCR5 gene, CDK-activating kinase (CAK), Checkpoint kinase (such as CHK1, CHK2), chemokine (C-C motif) receptor (such as CCR2, CCR4, CCR5, CCR8), chemokine (C-X-C motif) receptor (such as CXCR4, CXCR1 and CXCR2), Chemokine CC21 ligand, Cholecystokinin CCK2 receptor, Chorionic gonadotropin, c-Kit (tyrosine-protein kinase Kit or CD117), Claudin (such as 6, 18), cluster of differentiation (CD) such as CD4, CD27, CD29, CD30, CD33, CD37, CD40, CD40 ligand receptor, CD40 ligand, CD40LG gene, CD44, CD45, CD47, CD49b, CD51, CD52, CD55, CD58, CD66e, CD70 gene, CD74, CD79, CD79b, CD79B gene, CD80, CD95, CD99, CD117, CD122, CDw123, CD134, CDw137, CD158a, CD158b1, CD158b2, CD223, CD276 antigen; clusterin (CLU) gene, Clusterin, c-Met (hepatocyte growth factor receptor (HGFR)), Complement C3, Connective tissue growth factor, COP9 signalosome subunit 5, CSF-1 (colony-stimulating factor 1 receptor), CSF2 gene, CTLA-4 (cytotoxic T-lymphocyte protein 4) receptor, Cyclin D1, Cyclin G1, cyclin-dependent kinases (CDK, such as CDK1, CDK1B, CDK2-9), cyclooxygenase (such as 1, 2), CYP2B1 gene, Cysteine palmitoyltransferase porcupine, Cytochrome P450 11B2, Cytochrome P450 17, cytochrome P450 17A1, Cytochrome P450 2D6, cytochrome P450 3A4, Cytochrome P450 reductase, cytokine signalling-1, cytokine signalling-3, Cytoplasmic isocitrate dehydrogenase, Cytosine deaminase, cytosine DNA methyltransferase, cytotoxic T-lymphocyte protein-4, DDR2 gene, Delta-like protein ligand (such as 3, 4), Deoxyribonuclease, Dickkopf-1 ligand, dihydrofolate reductase (DHFR), Dihydropyrimidine dehydrogenase, Dipeptidyl peptidase IV, discoidin domain receptor (DDR, such as DDR1), DNA binding protein (such as HU-beta), DNA dependent protein kinase, DNA gyrase, DNA methyltransferase, DNA polymerase (such as alpha), DNA primase, dUTP pyrophosphatase, L-dopachrome tautomerase, echinoderm microtubule like protein 4, EGFR tyrosine kinase receptor, Elastase, Elongation factor 1 alpha 2, Elongation factor 2, Endoglin, Endonuclease, Endoplasmin, Endosialin, Endostatin, endothelin (such as ET-A, ET-B), Enhancer of zeste homolog 2 (EZH2), Ephrin (EPH) tyrosine kinase (such as Epha3, Ephb4), Ephrin B2 ligand, epidermal growth factor, epidermal growth factor receptors (EGFR), epidermal growth factor receptor (EGFR) gene, Epigen, Epithelial cell adhesion molecule (EpCAM), Erb-b2 (v-erb-b2 avian erythroblastic leukemia viral oncogene homolog 2) tyrosine kinase receptor, Erb-b3 tyrosine kinase receptor, Erb-b4 tyrosine kinase receptor, E-selectin, Estradiol 17 beta dehydrogenase, Estrogen receptor (such as alpha, beta), Estrogen related receptor, Eukaryotic translation initiation factor 5A (EIF5A) gene, Exportin 1, Extracellular signal related kinase (such as 1, 2), Extracellular signal-regulated kinases (ERK), Factor (such as Xa, VIIa), farnesoid x receptor (FXR), Fas ligand, Fatty acid synthase (FASN), Ferritin, FGF-2 ligand, FGF-5 ligand, fibroblast growth factor (FGF, such as FGF1, FGF2, FGF4), Fibronectin, Fms-related tyrosine kinase 3 (Flt3), FMS-like tyrosine kinase-3 ligand (FLT3L), focal adhesion kinase (FAK, such as FAK2), folate hydrolase prostate-specific membrane antigen 1 (FOLH1), Folate receptor (such as alpha), Folate, Folate transporter 1, FYN tyrosine kinase, paired basic amino acid cleaving enzyme (FURIN), Beta-glucuronidase, Galactosyltransferase, Galectin-3, Ganglioside GD2, Glucocorticoid, glucocorticoid-induced TNFR-related protein GITR receptor, Glutamate carboxypeptidase II, glutaminase, Glutathione S-transferase P, glycogen synthase kinase (GSK, such as 3-beta), Glypican 3 (GPC3), gonadotropin-releasing hormone (GNRH), Granulocyte macrophage colony stimulating factor (GM-CSF) receptor, Granulocyte-colony stimulating factor (GCSF) ligand, growth factor receptor-bound protein 2 (GRB2), Grp78 (78 kDa glucose-regulated protein) calcium binding protein, molecular chaperone groEL2 gene, Heme oxygenase 1 (HO1), Heat shock protein (such as 27, 70, 90 alpha, beta), Heat shock protein gene, Heat stable enterotoxin receptor, Hedgehog protein, Heparanase, Hepatocyte growth factor, HERV-H LTR associating protein 2, Hexose kinase, Histamine H2 receptor, Histone methyltransferase (DOT1L), histone deacetylase (HDAC, such as 1, 2, 3, 6, 10, 11), Histone H1, Histone H3, HLA class I antigen (A-2 alpha), HLA class II antigen, Homeobox protein NANOG, HSPB1 gene, Human leukocyte antigen (HLA), Human papillomavirus (such as E6, E7) protein, Hyaluronic acid, Hyaluronidase, Hypoxia inducible factor-1 alpha (HIF1α), Imprinted Maternally Expressed Transcript (H19) gene, mitogen-activated protein kinase kinase kinase kinase 1 (MAP4K1), tyrosine-protein kinase HCK, I-Kappa-B kinase (IKK, such as IKKbe), IL-1 alpha, IL-1 beta, IL-12, IL-12 gene, IL-15, IL-17, IL-2 gene, IL-2 receptor alpha subunit, IL-2, IL-3 receptor, IL-4, IL-6, IL-7, IL-8, immunoglobulin (such as G, G1, G2, K, M), Immunoglobulin Fc receptor, Immunoglobulin gamma Fc receptor (such as I, III, IIIA), indoleamine 2,3-dioxygenase (IDO, such as IDO1), indoleamine pyrrole 2,3-dioxygenase 1 inhibitor, insulin receptor, Insulin-like growth factor (such as 1, 2), Integrin alpha-4/beta-1, integrin alpha-4/beta-7, Integrin alpha-5/beta-1, Integrin alpha-V/beta-3, Integrin alpha-V/beta-5, Integrin alpha-V/beta-6, Intercellular adhesion molecule 1 (ICAM-1), interferon (such as alpha, alpha 2, beta, gamma), Interferon inducible protein absent in melanoma 2 (AIM2), interferon type I receptor, Interleukin 1 ligand, Interleukin 13 receptor alpha 2, interleukin 2 ligand, interleukin-1 receptor-associated kinase 4 (IRAK4), Interleukin-2, Interleukin-29 ligand, isocitrate dehydrogenase (such as IDH1, IDH2), Janus kinase (JAK, such as JAK1, JAK2), Jun N terminal kinase, kallikrein-related peptidase 3 (KLK3) gene, Killer cell Ig like receptor, Kinase insert domain receptor (KDR), Kinesin-like protein KIF11, Kirsten rat sarcoma viral oncogene homolog (KRAS) gene, Kisspeptin (KiSS-1) receptor, KIT gene, v-kit Hardy-Zuckerman 4 feline sarcoma viral oncogene homolog (KIT) tyrosine kinase, lactoferrin, Lanosterol-14 demethylase, LDL receptor related protein-1, Leukotriene A4 hydrolase, Listeriolysin, L-Selectin, Luteinizing hormone receptor, Lyase, lymphocyte activation gene 3 protein (LAG-3), Lymphocyte antigen 75, Lymphocyte function antigen-3 receptor, lymphocyte-specific protein tyrosine kinase (LCK), Lymphotactin, Lyn (Lck/Yes novel) tyrosine kinase, lysine demethylases (such as KDM1, KDM2, KDM4, KDM5, KDM6, A/B/C/D), Lysophosphatidate-1 receptor, lysosomal-associated membrane protein family (LAMP) gene, Lysyl oxidase homolog 2, lysyl oxidase protein (LOX), lysyl oxidase-like protein (LOXL, such as LOXL2), Hematopoietic Progenitor Kinase 1 (HPK1), Hepatocyte growth factor receptor (MET) gene, macrophage colony-stimulating factor (MCSF) ligand, Macrophage migration inhibitory fact, MAGEC1 gene, MAGEC2 gene, Major vault protein, MAPK-activated protein kinase (such as MK2), Mas-related G-protein coupled receptor, matrix metalloprotease (MMP, such as MMP2, MMP9), Mcl-1 differentiation protein, Mdm2 p53-binding protein, Mdm4 protein, Melan-A (MART-1) melanoma antigen, Melanocyte protein Pmel 17, melanocyte stimulating hormone ligand, melanoma antigen family A3 (MAGEA3) gene, Melanoma associated antigen (such as 1, 2, 3, 6), Membrane copper amine oxidase, Mesothelin, MET tyrosine kinase, Metabotropic glutamate receptor 1, Metalloreductase STEAP1 (six transmembrane epithelial antigen of the prostate 1), Metastin, methionine aminopeptidase-2, Methyltransferase, Mitochondrial 3 ketoacyl CoA thiolase, mitogen-activate protein kinase (MAPK), mitogen-activated protein kinase (MEK, such as MEK1, MEK2), mTOR (mechanistic target of rapamycin (serine/threonine kinase), mTOR complex (such as 1,2), mucin (such as 1, 5A, 16), mut T homolog (MTH, such as MTH1), Myc proto-oncogene protein, myeloid cell leukemia 1 (MCL1) gene, myristoylated alanine-rich protein kinase C substrate (MARCKS) protein, NAD ADP ribosyltransferase, natriuretic peptide receptor C, Neural cell adhesion molecule 1, Neurokinin 1 (NK1) receptor, Neurokinin receptor, Neuropilin 2, NF kappa B activating protein, NIMA-related kinase 9 (NEK9), Nitric oxide synthase, NK cell receptor, NK3 receptor, NKG2 A B activating NK receptor, Noradrenaline transporter, Notch (such as Notch-2 receptor, Notch-3 receptor, Notch-4 receptor), Nuclear erythroid 2-related factor 2, Nuclear Factor (NF) kappa B, Nucleolin, Nucleophosmin, nucleophosmin-anaplastic lymphoma kinase (NPM-ALK), 2 oxoglutarate dehydrogenase, 2,5-oligoadenylate synthetase, O-methylguanine DNA methyltransferase, Opioid receptor (such as delta), Ornithine decarboxylase, Orotate phosphoribosyltransferase, orphan nuclear hormone receptor NR4A1, Osteocalcin, Osteoclast differentiation factor, Osteopontin, OX-40 (tumor necrosis factor receptor superfamily member 4 TNFRSF4, or CD134) receptor, P3 protein, p38 kinase, p38 MAP kinase, p53 tumor suppressor protein, Parathyroid hormone ligand, peroxisome proliferator-activated receptors (PPAR, such as alpha, delta, gamma), P-Glycoprotein (such as 1), phosphatase and tensin homolog (PTEN), phosphatidylinositol 3-kinase (PI3K), phosphoinositide-3 kinase (PI3K such as alpha, delta, gamma), phosphorylase kinase (PK), PKN3 gene, placenta growth factor, platelet-derived growth factor (PDGF, such as alpha, beta), Platelet-derived growth factor (PDGF, such as alpha, beta), Pleiotropic drug resistance transporter, Plexin B1, PLK1 gene, polo-like kinase (PLK), Polo-like kinase 1, Poly ADP ribose polymerase (PARP, such as PARP1, 2 and 3), Preferentially expressed antigen in melanoma (PRAME) gene, Prenyl-binding protein (PrPB), Probable transcription factor PML, Progesterone receptor, Programmed cell death 1 (PD-1), Programmed cell death ligand 1 inhibitor (PD-L1), Prosaposin (PSAP) gene, Prostanoid receptor (EP4), prostate specific antigen, Prostatic acid phosphatase, proteasome, Protein E7, Protein farnesyltransferase, protein kinase (PK, such as A, B, C), protein tyrosine kinase, Protein tyrosine phosphatase beta, Proto-oncogene serine/threonine-protein kinase (PIM, such as PIM-1, PIM-2, PIM-3), P-Selectin, Purine nucleoside phosphorylase, purinergic receptor P2X ligand gated ion channel 7 (P2X7), Pyruvate dehydrogenase (PDH), Pyruvate dehydrogenase kinase, Pyruvate kinase (PYK), 5-Alpha-reductase, Raf protein kinase (such as 1, B), RAF1 gene, Ras gene, Ras GTPase, RET gene, Ret tyrosine kinase receptor, retinoblastoma associated protein, retinoic acid receptor (such as gamma), Retinoid X receptor, Rheb (Ras homolog enriched in brain) GTPase, Rho (Ras homolog) associated protein kinase 2, ribonuclease, Ribonucleotide reductase (such as M2 subunit), Ribosomal protein S6 kinase, RNA polymerase (such as I, II), Ron (Recepteur d'Origine Nantais) tyrosine kinase, ROS1 (ROS proto-oncogene 1, receptor tyrosine kinase)gene, Ros1 tyrosine kinase, Runt-related transcription factor 3, Gamma-secretase, S100 calcium binding protein A9, Sarco endoplasmic calcium ATPase, Second mitochondria-derived activator of caspases (SMAC) protein, Secreted frizzled related protein-2, Semaphorin-4D, Serine protease, serine/threonine kinase (STK), serine/threonine-protein kinase (TBK, such as TBK1), signal transduction and transcription (STAT, such as STAT-1, STAT-3, STAT-5), Signaling lymphocytic activation molecule (SLAM) family member 7, six-transmembrane epithelial antigen of the prostate (STEAP) gene, SL cytokine ligand, smoothened (SMO) receptor, Sodium iodide cotransporter, Sodium phosphate cotransporter 2B, Somatostatin receptor (such as 1, 2, 3, 4, 5), Sonic hedgehog protein, Son of sevenless (SOS), Specific protein 1 (Sp1) transcription factor, Sphingomyelin synthase, Sphingosine kinase (such as 1, 2), Sphingosine-1-phosphate receptor-1, spleen tyrosine kinase (SYK), SRC gene, Src tyrosine kinase, STAT3 gene, Steroid sulfatase, Stimulator of interferon genes (STING) receptor, stimulator of interferon genes protein, Stromal cell-derived factor 1 ligand, SUMO (small ubiquitin-like modifier), Superoxide dismutase, Survivin protein, Synapsin 3, Syndecan-1, Synuclein alpha, T cell surface glycoprotein CD28, tank-binding kinase (TBK), TATA box-binding protein-associated factor RNA polymerase I subunit B (TAF1B) gene, T-cell CD3 glycoprotein zeta chain, T-cell differentiation antigen CD6, T-cell immunoglobulin and mucin-domain containing-3 (TIM-3), T-cell surface glycoprotein CD8, Tec protein tyrosine kinase, Tek tyrosine kinase receptor, telomerase, Telomerase reverse transcriptase (TERT) gene, Tenascin, TGF beta 2 ligand, Thrombopoietin receptor, Thymidine kinase, Thymidine phosphorylase, Thymidylate synthase, Thymosin (such as alpha 1), Thyroid hormone receptor, Thyroid stimulating hormone receptor, Tissue factor, TNF related apoptosis inducing ligand, TNFR1 associated death domain protein, TNF-related apoptosis-inducing ligand (TRAIL) receptor, TNFSF11 gene, TNFSF9 gene, Toll-like receptor (TLR such as 1-13), topoisomerase (such as I, II, III), Transcription factor, Transferase, Transferrin, Transforming growth factor (TGF, such as beta) kinase, Transforming growth factor TGF-β receptor kinase, Transglutaminase, Translocation associated protein, Transmembrane glycoprotein NMB, Trop-2 calcium signal transducer, trophoblast glycoprotein (TPBG) gene, Trophoblast glycoprotein, Tropomyosin receptor kinase (Trk) receptor (such as TrkA, TrkB, TrkC), Tryptophan 5-hydroxylase, Tubulin, Tumor necrosis factor (TNF, such as alpha, beta), Tumor necrosis factor 13C receptor, tumor progression locus 2 (TPL2), Tumor protein 53 (TP53) gene, Tumor suppressor candidate 2 (TUSC2) gene, Tyrosinase, Tyrosine hydroxylase, tyrosine kinase (TK), Tyrosine kinase receptor, Tyrosine kinase with immunoglobulin-like and EGF-like domains (TIE) receptor, Tyrosine protein kinase ABL1 inhibitor, Ubiquitin, Ubiquitin carboxyl hydrolase isozyme L5, Ubiquitin thioesterase-14, Ubiquitin-conjugating enzyme E2I (UBE2I, UBC9), Urease, Urokinase plasminogen activator, Uteroglobin, Vanilloid VR1, Vascular cell adhesion protein 1, vascular endothelial growth factor receptor (VEGFR), V-domain Ig suppressor of T-cell activation (VISTA), VEGF-1 receptor, VEGF-2 receptor, VEGF-3 receptor, VEGF-A, VEGF-B, Vimentin, Vitamin D3 receptor, Proto-oncogene tyrosine-protein kinase Yes, Wee-1 protein kinase, Wilms' tumor antigen 1, Wilms' tumor protein, X-linked inhibitor of apoptosis protein, Zinc finger protein transcription factor or any combination thereof.

Thus, in one embodiment, a method of treating cancer and/or diseases or symptoms that co-present or are exacerbated or triggered by the cancer e.g., an allergic disorder and/or an autoimmune and/or inflammatory disease, and/or an acute inflammatory reaction, comprises administering to a patient in need thereof an effective amount of a compound of formula (I) or a pharmaceutically acceptable salt thereof, optionally in combination with an additional agent (e.g., a second, third, fourth or fifth active agent) which can be useful for treating a cancer, an allergic disorder and/or an autoimmune and/or inflammatory disease, and/or an acute inflammatory reaction incident to or co-presenting with a cancer. Treatment with the second, third, fourth or fifth active agent may be prior to, concomitant with, or following treatment with a compound of formula (I) or a pharmaceutically acceptable salt thereof. In one embodiment, a compound of formula (I) or a pharmaceutically acceptable salt thereof is combined with another active agent in a single dosage form. Suitable antitumor or anticancer therapeutics that may be used in combination with a compound of formula (I) or a pharmaceutically acceptable salt thereof include, but are not limited to, chemotherapeutic agents, for example mitomycin C, carboplatin, taxol, cisplatin, paclitaxel, etoposide, doxorubicin, or a combination comprising at least one of the foregoing chemotherapeutic agents. Radiotherapeutic antitumor agents may also be used, alone or in combination with chemotherapeutic agents.

A compound of formula (I) or a pharmaceutically acceptable salt thereof can be useful as chemo-sensitizing agents, and thus, can be useful in combination with other chemotherapeutic drugs, in particular, drugs that induce apoptosis. Thus, in one embodiment, the present disclosure provides a method for increasing sensitivity of cancer cells to chemotherapy, comprising administering to a patient in need of or undergoing chemotherapy, a chemotherapeutic agent together with a compound of formula (I), or a pharmaceutically acceptable salt thereof in an amount sufficient to increase the sensitivity of cancer cells to the chemotherapeutic agent.

Anti-Cancer Combination Therapy

The compounds described herein may be used or combined with one or more of a chemotherapeutic agent, an anti-cancer agent, an anti-angiogenic agent, an anti-fibrotic agent, an immunotherapeutic agent, a therapeutic antibody, a bispecific antibody and "antibody-like" therapeutic protein (such as DARTs®, Duobodies®, Bites®, XmAbs®, TandAbs®, Fab derivatives), an antibody-drug conjugate (ADC), a radiotherapeutic agent, an anti-neoplastic agent, an anti-proliferation agent, an oncolytic virus, a gene modifier or editor (such as CRISPR/Cas9, zinc finger nucleases or synthetic nucleases, TALENs), a CAR (chimeric antigen receptor) T-cell immunotherapeutic agent, an engineered T cell receptor (TCR-T), or any combination thereof. These therapeutic agents may be in the forms of compounds, antibodies, polypeptides, or polynucleotides. In one embodiment, the application provides a product comprising a compound described herein and an additional therapeutic agent as a combined preparation for simultaneous, separate, or sequential use in therapy.

As used herein, the term "chemotherapeutic agent" or "chemotherapeutic" (or "chemotherapy" in the case of treatment with a chemotherapeutic agent) is meant to encompass any non-proteinaceous (i.e., non-peptidic) chemical compound useful in the treatment of cancer. Examples of chemotherapeutic agents include but not limited to: alkylating agents such as thiotepa and cyclophosphamide (CYTOXAN®); alkyl sulfonates such as busulfan, improsulfan, and piposulfan; aziridines such as benzodepa, carboquone, meturedepa, and uredepa; ethylenimines and methylamelamines including altretamine, triethylenemelamine, triethylenephosphoramide, triethylenethiophosphoramide, and trimemylolomelamine; acetogenins, especially bullatacin and bullatacinone; a camptothecin, including synthetic analog topotecan; bryostatin, callystatin; CC-1065, including its adozelesin, carzelesin, and bizelesin synthetic analogs; cryptophycins, particularly cryptophycin 1 and cryptophycin 8; dolastatin; duocarmycin, including the synthetic analogs KW-2189 and CBI-TMI; eleutherobin; 5-azacytidine; pancratistatin; a sarcodictyin; spongistatin; nitrogen mustards such as chlorambucil, chlornaphazine, cyclophosphamide, glufosfamide, evofosfamide, bendamustine, estramustine, ifosfamide, mechlorethamine, mechlorethamine oxide hydrochloride, melphalan, novembichin, phenesterine, prednimustine, trofosfamide, and uracil mustard; nitrosoureas such as carmustine, chlorozotocin, foremustine, lomustine, nimustine, and ranimustine; antibiotics such as the enediyne antibiotics (e.g., calicheamicin, especially calicheamicin gammaII and calicheamicin phiII), dynemicin including dynemicin A, bisphosphonates such as clodronate, an esperamicin, neocarzinostatin chromophore and related chromoprotein enediyne antibiotic chrommomophores, aclacinomycins, actinomycin, authramycin, azaserine, bleomycins, cactinomycin, carabicin, carrninomycin, carzinophilin, chromomycins, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin, and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, and zorubicin; anti-metabolites such as methotrexate and 5-fluorouracil (5-FU); folic acid analogs such as demopterin, methotrexate, pteropterin, and trimetrexate; purine analogs such as fludarabine, 6-mercaptopurine, thiamiprine, and thioguanine; pyrimidine analogs such as ancitabine, azacitidine, 6-azauridine, carmofur, cytarabine, dideoxyuridine, doxifluridine, enocitabine, and floxuridine; androgens such as calusterone, dromostanolone propionate, epitiostanol, mepitiostane, and testolactone; anti-adrenals such as aminoglutethimide, mitotane, and trilostane; folic acid replinishers such as frolinic acid; radiotherapeutic agents such as Radium-223; trichothecenes, especially T-2 toxin, verracurin A, roridin A, and anguidine; taxoids such as paclitaxel (TAXOL®), abraxane, docetaxel (TAXOTERE®), cabazitaxel, BIND-014, tesetaxel; platinum analogs such as cisplatin and carboplatin, NC-6004 nanoplatin; aceglatone; aldophosphamide glycoside; aminolevulinic acid; eniluracil; amsacrine; hestrabucil; bisantrene; edatraxate; defofamine; demecolcine; diaziquone; elformthine; elliptinium acetate; an epothilone; etoglucid; gallium nitrate; hydroxyurea; lentinan; leucovorin; lonidamine; maytansinoids such as maytansine and ansamitocins; mitoguazone; mitoxantrone; mopidamol; nitracrine; pentostatin; phenamet; pirarubicin; losoxantrone; fluoropyrimidine; folinic acid; podophyllinic acid; 2-ethylhydrazide; procarbazine; polysaccharide-K (PSK); razoxane; rhizoxin; sizofiran; spirogermanium; tenuazonic acid; trabectedin, triaziquone; 2,2',2"-tricUorotriemylamine; urethane; vindesine; dacarbazine; mannomustine; mitobronitol; mitolactol; pipobroman; gacytosine; arabinoside ("Ara-C"); cyclophosphamide; thiopeta; chlorambucil; gemcitabine (GEMZAR®); 6-thioguanine; mercaptopurine; methotrexate; vinblastine; platinum; etoposide (VP-16); ifosfamide; mitroxantrone; vancristine; vinorelbine (NAVELBINE®); novantrone; teniposide; edatrexate; daunomycin; aminopterin; xeoloda; ibandronate; CPT-11; topoisomerase inhibitor RFS 2000; difluoromethylornithine (DFMO); retinoids such as retinoic acid; capecitabine; NUC-1031; FOLFIRI (fluorouracil, leucovorin, and irinotecan); and pharmaceutically acceptable salts, acids, or derivatives of any of the above.

The compound described herein may be used or combined with one or more of the additional therapeutic agents. Therapeutic agents may be categorized by their mechanism of action into, for example, the following groups:

anti-metabolites/anti-cancer agents, such as pyrimidine analogs floxuridine, capecitabine, cytarabine, CPX-351 (liposomal cytarabine, daunorubicin), and TAS-118;

purine analogs, folate antagonists (such as pralatrexate), and related inhibitors;

antiproliferative/antimitotic agents including natural products, such as vinca alkaloids (vinblastine, vincristine) and microtubule disruptors such as taxane (paclitaxel, docetaxel), vinblastin, nocodazole, epothilones, vinorelbine (NAVELBINE®), and epipodophyllotoxins (etoposide, teniposide);

DNA damaging agents, such as actinomycin, amsacrine, busulfan, carboplatin, chlorambucil, cisplatin, cyclophosphamide (CYTOXAN®), dactinomycin, daunorubicin, doxorubicin, epirubicin, iphosphamide, melphalan, merchlorethamine, mitomycin C, mitoxantrone, nitrosourea, procarbazine, taxol, Taxotere, teniposide, etoposide, and triethylenethiophosphoramide;

DNA-hypomethylating agents, such as guadecitabine (SGI-110), ASTX727;

antibiotics such as dactinomycin, daunorubicin, doxorubicin, idarubicin, anthracyclines, mitoxantrone, bleomycins, plicamycin (mithramycin);

enzymes such as L-asparaginase which systemically metabolizes L-asparagine and deprives cells which do not have the capacity to synthesize their own asparagine;

antiplatelet agents;

DNAi oligonucleotides targeting Bcl-2, such as PNT2258;

agents that activate or reactivate latent human immunodeficiency virus (HIV), such as panobinostat and romidepsin;

asparaginase stimulators, such as crisantaspase (Erwinase®) and GRASPA (ERY-001, ERY-ASP), calaspargase pegol;

pan-Trk, ROS1 and ALK inhibitors, such as entrectinib, TPX-0005;

anaplastic lymphoma kinase (ALK) inhibitors, such as alectinib, ceritinib;

antiproliferative/antimitotic alkylating agents, such as nitrogen mustard cyclophosphamide and analogs (melphalan, chlorambucil, hexamethylmelamine, thiotepa), alkyl nitrosoureas (carmustine) and analogs, streptozocin, and triazenes (dacarbazine);

antiproliferative/antimitotic antimetabolites, such as folic acid analogs (methotrexate);

platinum coordination complexes (cisplatin, oxiloplatinim, and carboplatin), procarbazine, hydroxyurea, mitotane, and aminoglutethimide;

hormones, hormone analogs (estrogen, tamoxifen, goserelin, bicalutamide, and nilutamide), and aromatase inhibitors (letrozole and anastrozole);

anticoagulants such as heparin, synthetic heparin salts, and other inhibitors of thrombin;

fibrinolytic agents such as tissue plasminogen activator, streptokinase, urokinase, aspirin, dipyridamole, ticlopidine, and clopidogrel;

antimigratory agents;

antisecretory agents (breveldin);

immunosuppressives, such as tacrolimus, sirolimus, azathioprine, and mycophenolate;

growth factor inhibitors, and vascular endothelial growth factor inhibitors;

fibroblast growth factor inhibitors, such as FPA14;

anti-VEGFR antibodies, such as IMC-3C5, GNR-011, tanibirumab;

anti-VEGF/DDL4 antibodies, such as ABT-165;

anti-cadherins antibodies, such as HKT-288;

anti-CD70 antibodies, such as AMG-172;

anti-leucine-rich repeat containing 15 (LRRC15) antibodies, such as ABBV-085, and ARGX-110;

angiotensin receptor blockers, nitric oxide donors;

antisense oligonucleotides, such as AEG35156, IONIS-KRAS-2.5Rx, EZN-3042, RX-0201, IONIS-AR-2.5Rx, BP-100 (prexigebersen), IONIS-STAT3-2.5Rx; DNA interference oligonucleotides, such as PNT2258, AZD-9150;

anti-ANG-2 antibodies, such as MEDI3617, and LY3127804;

anti-ANG-1/ANG-2 antibodies, such as AMG-780;

anti-MET/EGFR antibodies, such as LY3164530;

anti-EGFR antibodies, such as ABT-414, AMG-595, necitumumab, ABBV-221, depatuxizumab mafodotin (ABT-414), tomuzotuximab, ABT-806, vectibix, modotuximab, RM-1929;

anti-CSF1R antibodies, such as emactuzumab, LY3022855, AMG-820, FPA-008 (cabiralizumab);

anti-CD40 antibodies, such as RG7876, SEA-CD40, APX-005M, ABBV-428;

anti-endoglin antibodies, such as TRC 105 (carotuximab);

anti-CD45 antibodies, such as 131I-BC8 (lomab-B);

anti-HER3 antibodies, such as LJM716, GSK2849330;

anti-HER2 antibodies, such as margetuximab, MEDI4276, BAT-8001;

anti-HLA-DR antibodies, such as IMMU-114;

anti-IL-3 antibodies, such as JNJ-56022473;

anti-OX40 antibodies, such as MEDI6469, MEDI6383, MEDI0562 (tavolixizumab), MOXR0916, PF-04518600, RG-7888, GSK-3174998, INCAGN1949, BMS-986178, GBR-8383, ABBV-368;

anti-EphA3 antibodies, such as KB-004;

anti-CD20 antibodies, such as obinutuzumab, IGN-002;

anti-CD20/CD3 antibodies, such as RG7828;

anti-CD37 antibodies, such as AGS67E, otlertuzumab (TRU-016);

anti-ENPP3 antibodies, such as AGS-16C3F;

anti-FGFR-3 antibodies, such as LY3076226, B-701;

anti-FGFR-2 antibodies, such as GAL-F2;

anti-C5 antibodies, such as ALXN-1210;

anti-CD27 antibodies, such as varlilumab (CDX-1127);

anti-TROP-2 antibodies, such as IMMU-132 anti-NKG2a antibodies, such as monalizumab;

anti-VISTA antibodies, such as HMBD-002;

anti-PVRIG antibodies, such as COM-701;

anti-EpCAM antibodies, such as VB4-845;

anti-BCMA antibodies, such as GSK-2857916 anti-CEA antibodies, such as RG-7813;

anti-cluster of differentiation 3 (CD3) antibodies, such as MGD015;

anti-folate receptor alpha antibodies, such as IMGN853;

MCL-1 inhibitors, such as AMG-176, AMG-397, S-64315, and AZD-5991, 483-LM, A-1210477, UMI-77, JKY-5-037;

epha2 inhibitors, such as MM-310;

anti LAG-3 antibodies, such as relatlimab (ONO-4482), LAG-525, MK-4280, REGN-3767;

raf kinase/VEGFR inhibitors, such as RAF-265;

polycomb protein (EED) inhibitors, such as MAK683;

anti-fibroblast activation protein (FAP)/IL-2R antibodies, such as RG7461;

anti-fibroblast activation protein (FAP)/TRAIL-R2 antibodies, such as RG7386;

anti-fucosyl-GM1 antibodies, such as BMS-986012;

p38 MAP kinase inhibitors, such as ralimetinib;

PRMT1 inhibitors, such as MS203;

Sphingosine kinase 2 (SK2) inhibitors, such as opaganib;

FLT3-ITD inhibitors, such as BCI-332;

Nuclear erythroid 2-related factor 2 stimulators, such as omaveloxolone (RTA-408);

Tropomyosin receptor kinase (TRK) inhibitors, such as LOXO-195, ONO-7579;

anti-ICOS antibodies, such as JTX-2011, GSK3359609;

anti-DR5 (TRAIL2) antibodies, such as DS-8273;

anti-GD2 antibodies, such as APN-301;

anti-interleukin-17 (IL-17) antibodies, such as CJM-112;

anti-carbonic anhydrase IX antibodies, such as TX-250;

anti-CD38-attenukine, such as TAK573;

anti-Mucin 1 antibodies, such as gatipotuzumab;

Mucin 1 inhibitors, such as GO-203-2C;

MARCKS protein inhibitors, such as BIO-11006;

Folate antagonists, such as arfolitixorin;

Galectin-3 inhibitors, such as GR-MD-02;

Phosphorylated P68 inhibitors, such as RX-5902;

CD95/TNF modulators, such as ofranergene obadenovec;

PI3K/Akt/mTOR inhibitors, such as ABTL-0812;

pan-PIM kinase inhibitors, such as INCB-053914;

IL-12 gene stimulators, such as EGEN-001, tavokinogene telseplasmid;

Heat shock protein HSP90 inhibitors, such as TAS-116, PEN-866;

VEGF/HGF antagonists, such as MP-0250;

SYK tyrosine kinase/FLT3 tyrosine kinase inhibitors, such as TAK-659;

SYK tyrosine kinase/JAK tyrosine kinase inhibitors, such as ASN-002;

FLT3 tyrosine kinase, such as FF-10101;

FMS-like tyrosine kinase-3 ligand (FLT3L), such as CDX-301;

FLT3/MEK1 inhibitors, such as E-6201;

IL-24 antagonist, such as AD-IL24;

RIG-I agonists, such as RGT-100;

Aerolysin stimulators, such as topsalysin;

P-Glycoprotein 1 inhibitors, such as HM-30181A;

CSF-1 antagonists, such as ARRY-382, BLZ-945;

CCR8 inhibitors, such as 1-309, SB-649701, HG-1013, RAP-310;

anti-Mesothelin antibodies, such as SEL-403;

Thymidine kinase stimulators, such as aglatimagene besadenovec;

Polo-like kinase 1 inhibitors, such as PCM-075;

TLR-7 agonists, such as TMX-101 (imiquimod);

NEDD8 inhibitors, such as pevonedistat (MLN-4924), TAS-4464;

Pleiotropic pathway modulators, such as avadomide (CC-122);

FoxM1 inhibitors, such as thiostrepton;

Anti-MUC1 antibodies, such as Mab-AR-20.5;

anti-CD38 antibodies, such as isatuximab, MOR-202;

UBA1 inhibitors, such as TAK-243;

Src tyrosine kinase inhibitors, such as VAL-201;

VDAC/HK inhibitors, such as VDA-1102;

BRAF/PI3K inhibitors, such as ASN-003;

Elf4a inhibitors, such as rohinitib, eFT226;

TP53 gene stimulators, such as ad-p53;

PD-L1/EGFR inhibitors, such as GNS-1480;

Retinoic acid receptor alpha (RARα) inhibitors, such as SY-1425;

SIRT3 inhibitors, such as YC8-02;

Stromal cell-derived factor 1 ligand inhibitors, such as olaptesed pegol (NOX-A12);

IL-4 receptor modulators, such as MDNA-55;

Arginase-I stimulators, such as pegzilarginase;

Topoisomerase I inhibitor/hypoxia inducible factor-1 alpha inhibitors, such as PEG-SN38 (firtecan pegol);

Hypoxia inducible factor-1 alpha inhibitors, such as PT-2977, PT-2385;

CD122 agonists such as NKTR-214;

p53 tumor suppressor protein stimulators such as kevetrin;

Mdm4/Mdm2 p53-binding protein inhibitors, such as ALRN-6924;

kinesin spindle protein (KSP) inhibitors, such as filanesib (ARRY-520);

CD80-fc fusion protein inhibitors, such as FPT-155;

Menin and mixed lineage leukemia (MLL) inhibitors such as KO-539;

Liver x receptor agonists, such as RGX-104;

IL-10 agonists, such as AM-0010;

EGFR/ErbB-2 inhibitors, such as varlitinib;

VEGFR/PDGFR inhibitors, such as vorolanib;

IRAK4 inhibitors, such as CA-4948;

anti-TLR-2 antibodies, such as OPN-305;

Calmodulin modulators, such as CBP-501;

Glucocorticoid receptor antagonists, such as relacorilant (CORT-125134);

Second mitochondria-derived activator of caspases (SMAC) protein inhibitors, such as BI-891065;

Lactoferrin modulators, such as LTX-315;

Kit tyrosine kinase/PDGF receptor alpha antagonists such as DCC-2618;

KIT inhibitors, such as PLX-9486;

Exportin 1 inhibitors, such as eltanexor;

EGFR/ErbB2/Ephb4 inhibitors, such as tesevatinib;

anti-CD33 antibodies, such as IMGN-779;

anti-KMA antibodies, such as MDX-1097;

anti-TIM-3 antibodies, such as TSR-022, LY-3321367, MBG-453;

anti-CD55 antibodies, such as PAT-SC1;

anti-PSMA antibodies, such as ATL-101;

anti-CD100 antibodies, such as VX-15;

anti-EPHA3 antibodies, such as fibatuzumab;

anti-Erbb antibodies, such as CDX-3379, HLX-02, seribantumab;

anti-APRIL antibodies, such as BION-1301;

Anti-Tigit antibodies, such as BMS-986207, RG-6058;

CHST15 gene inhibitors, such as STNM-01;

RAS inhibitors, such as NEO-100;

Somatostatin receptor antagonist, such as OPS-201;

CEBPA gene stimulators, such as MTL-501;

DKK3 gene modulators, such as MTG-201;

p70s6k inhibitors, such as MSC2363318A;

methionine aminopeptidase 2 (MetAP2) inhibitors, such as M8891, APL-1202;

arginine N-methyltransferase 5 inhibitors, such as GSK-3326595;

anti-programmed cell death protein 1 (anti-PD-1) antibodies, such as nivolumab (OPDIVO®, BMS-936558, MDX-1106), pembrolizumab (KEYTRUDA®, MK-3477, SCH-900475, lambrolizumab, CAS Reg. No. 1374853-91-4), pidilizumab, PF-06801591, BGB-A317, GLS-010 (WBP-3055), AK-103 (HX-008), MGA-012, BI-754091, REGN-2810 (cemiplimab), AGEN-2034, JS-001, JNJ-63723283, genolimzumab (CBT-501), LZM-009, BCD-100, LY-3300054, SHR-1201, BAT-1306, and anti-programmed death-ligand 1 (anti-PD-L1) antibodies such as BMS-936559, atezolizumab (MPDL3280A), durvalumab (MEDI4736), avelumab, CK-301, (MSB0010718C), MEDI0680, CX-072, CBT-502, PDR-001 (spartalizumab), TSR-042 (dostarlimab), JTX-4014, BGB-A333, SHR-1316, CS-1001 (WBP-3155, KN-035, IBI-308, FAZ-053, and MDX1105-01; PD-L1/VISTA antagonists such as CA-170;

anti-PD-L1/TGFβ antibodies, such as M7824;

anti-transferrin antibodies, such as CX-2029;

anti-IL-8 (Interleukin-8) antibodies, such as HuMax-Inflam;

ATM (ataxia telangiectasia) inhibitors, such as AZD0156;

CHK1 inhibitors, such as GDC-0575, LY2606368 (prexasertib), SRA737, RG7741 (CHK1/2);

CXCR4 antagonists, such as BL-8040, LY2510924, burixafor (TG-0054), X4P-002, X4P-001-IO;

EXH2 inhibitors, such as GSK2816126;

HER2 inhibitors, such as neratinib, tucatinib (ONT-380);

KDM1 inhibitors, such as ORY-1001, IMG-7289, INCB-59872, GSK-2879552;

CXCR2 antagonists, such as AZD-5069;

GM-CSF antibodies, such as lenzilumab;

DNA dependent protein kinase inhibitors, such as MSC2490484A (nedisertib), VX-984, AsiDNA (DT-01);

protein kinase C (PKC) inhibitors, such as LXS-196, and sotrastaurin;

Selective estrogen receptor downregulators (SERD), such as fulvestrant (Faslodex®), RG6046, RG6047, elacestrant (RAD-1901) and AZD9496;

Selective estrogen receptor covalent antagonists (SERCAs), such as H3B-6545;

selective androgen receptor modulator (SARM), such as GTX-024, and darolutamide;

transforming growth factor-beta (TGF-beta) kinase antagonists, such as galunisertib;

anti-transforming growth factor-beta (TGF-beta) antibodies, such as LY3022859, NIS793, and XOMA 089;

bispecific antibodies, such as MM-141 (IGF-1/ErbB3), MM-111 (Erb2/Erb3), JNJ-64052781 (CD19/CD3), PRS-343 (CD-137/HER2), AFM26 (BCMA/CD16A), JNJ-61186372 (EGFR/cMET), AMG-211 (CEA/CD3), RG7802 (CEA/CD3), ERY-974 (CD3/GPC3) vancizumab (angiopoietins/VEGF), PF-06671008 (Cadherins/CD3), AFM-13 (CD16/CD30), APVO436 (CD123/CD3), flotetuzumab (CD123/CD3), REGN-1979 (CD20/CD3), MCLA-117 (CD3/CLEC12A), MCLA-128 (HER2/HER3), JNJ-0819, JNJ-7564 (CD3/heme), AMG-757 (DLL3-CD3), MGD-013 (PD-1/LAG-3), AK-104 (CTLA-4/PD-1), AMG-330 (CD33/CD3), AMG-420 (BCMA/CD3), BI-836880 (VEFG/ANG2), JNJ-63709178 (CD123/CD3), MGD-007 (CD3/gpA33), and MGD-009 (CD3/B7H3);

mutant selective EGFR inhibitors, such as PF-06747775, EGF816 (nazartinib), ASP8273, ACEA-0010, and BI-1482694;

anti-GITR (glucocorticoid-induced tumor necrosis factor receptor-related protein) antibodies, such as MEDI1873, FPA-154, INCAGN-1876, TRX-518, BMS-986156, MK-1248, and GWN-323;

anti-delta-like protein ligand 3 (DDL3) antibodies, such as rovalpituzumab tesirine;

anti-clusterin antibodies, such as AB-16B5;

anti-Ephrin-A4 (EFNA4) antibodies, such as PF-06647263;

anti-RANKL antibodies, such as denosumab;

anti-mesothelin antibodies, such as BMS-986148, and anti-MSLN-MMAE;

anti-sodium phosphate cotransporter 2B (NaP2B) antibodies, such as lifastuzumab anti-c-Met antibodies, such as ABBV-399;

adenosine A2A receptor antagonists, such as CPI-444, AZD-4635, preladenant, and PBF-509;

alpha-ketoglutarate dehydrogenase (KGDH) inhibitors, such as CPI-613;

XPO1 inhibitors, such as selinexor (KPT-330);

isocitrate dehydrogenase 2 (IDH2) inhibitors, such as enasidenib (AG-221);

IDH1 inhibitors such as AG-120, and AG-881 (IDH1 and IDH2), IDH-305, and BAY-1436032;

interleukin-3 receptor (IL-3R) modulators, such as SL-401;

Arginine deiminase stimulators, such as pegargiminase (ADI-PEG-20);

antibody-drug conjugates, such as MLN0264 (anti-GCC, guanylyl cyclase C), T-DM1 (trastuzumab emtansine, Kadcycla), milatuzumab-doxorubicin (hCD74-DOX), brentuximab vedotin, DCDT2980S, polatuzumab vedotin, SGN-CD70A, SGN-CD19A, inotuzumab ozogamicin, lorvotuzumab mertansine, SAR3419, isactuzumab govitecan, enfortumab vedotin (ASG-22ME), ASG-15ME, DS-8201 ((trastuzumab deruxtecan), 225Ac-lintuzumab, U3-1402, 177Lu-tetraxetan-tetuloma, tisotumab vedotin, anetumab ravtansine, CX-2009, SAR-566658, W-0101, polatuzumab vedotin, and ABBV-085;

claudin-18 inhibitors, such as claudiximab;

β-catenin inhibitors, such as CWP-291;

anti-CD73 antibodies, such as MEDI-9447 (oleclumab), CPX-006, IPH-53, BMS-986179, and NZV-930;

CD73 antagonists, such as AB-680, PSB-12379, PSB-12441, PSB-12425, and CB-708;

CD39/CD73 antagonists, such as PBF-1662;

chemokine receptor 2 (CCR) inhibitors, such as PF-04136309, CCX-872, and BMS-813160 (CCR2/CCR5)

thymidylate synthase inhibitors, such as ONX-0801;

ALK/ROS1 inhibitors, such as lorlatinib;

tankyrase inhibitors, such as G007-LK;

Mdm2 p53-binding protein inhibitors, such as CMG-097, and HDM-201;

c-PIM inhibitors, such as PIM447;

BRAF inhibitors, such as dabrafenib, vemurafenib, encorafenib (LGX818), and PLX8394;

sphingosine kinase-2 (SK2) inhibitors, such as Yeliva® (ABC294640);

cell cycle inhibitors, such as selumetinib (MEK1/2), and sapacitabine;

AKT inhibitors such as MK-2206, ipatasertib, afuresertib, AZD5363, and ARQ-092, capivasertib, and triciribine;

anti-CTLA-4 (cytotoxic T-lymphocyte protein-4) inhibitors, such as tremelimumab, AGEN-1884, and BMS-986218;

c-MET inhibitors, such as AMG-337, savolitinib, tivantinib (ARQ-197), capmatinib, and tepotinib, ABT-700, AG213, AMG-208, JNJ-38877618 (OMO-1), merestinib, and HQP-8361;

c-Met/VEGFR inhibitors, such as BMS-817378, and TAS-115;

c-Met/RON inhibitors, such as BMS-777607;

BRAF/EGFR inhibitors, such as BGB-283;

bcr/abl inhibitors, such as rebastinib, asciminib;

MNK1/MNK2 inhibitors, such as eFT-508;

mTOR inhibitor/cytochrome P450 3A4 stimulators, such as TYME-88 lysine-specific demethylase-1 (LSD1) inhibitors, such as CC-90011;

Pan-RAF inhibitors, such as LY3009120, LXH254, and TAK-580;

Raf/MEK inhibitors, such as RG7304;

CSF1R/KIT and FLT3 inhibitors, such as pexidartinib (PLX3397);

kinase inhibitors, such as vandetanib;

E selectin antagonists, such as GMI-1271;

differentiation inducers, such as tretinoin;

epidermal growth factor receptor (EGFR) inhibitors, such as osimertinib (AZD-9291);

topoisomerase inhibitors, such as doxorubicin, daunorubicin, dactinomycin, eniposide, epirubicin, etoposide, idarubicin, irinotecan, mitoxantrone, pixantrone, sobuzoxane, topotecan, irinotecan, MM-398 (liposomal irinotecan), vosaroxin and GPX-150, aldoxorubicin, AR-67, mavelertinib, AST-2818, avitinib (ACEA-0010), and irofulven (MGI-114);

corticosteroids, such as cortisone, dexamethasone, hydrocortisone, methylprednisolone, prednisone, and prednisolone;

growth factor signal transduction kinase inhibitors;

nucleoside analogs, such as DFP-10917;

Axl inhibitors, such as BGB-324 (bemcentinib), and SLC-0211;

BET inhibitors, such as INCB-054329, INCB057643, TEN-010, AZD-5153, ABT-767, BMS-986158, CC-90010, GSK525762 (molibresib), NHWD-870, ODM-207, GSK- 2820151, GSK-1210151A, ZBC246, ZBC260, ZEN3694, FT-1101, RG-6146, CC-90010, mivebresib, BI-894999, PLX-2853, PLX-51107, CPI-0610, and GS-5829;

PARP inhibitors, such as olaparib, rucaparib, veliparib, talazoparib, ABT-767, and BGB-290;

proteasome inhibitors, such as ixazomib, carfilzomib (Kyprolis®), marizomib;

glutaminase inhibitors, such as CB-839;

vaccines, such as peptide vaccine TG-01 (RAS), GALE-301, GALE-302, nelipepimut-s, SurVaxM, DSP-7888, TPIV-200, PVX-410, VXL-100, DPX-E7, ISA-101, 6MHP, OSE-2101, galinpepimut-S, SVN53-67/M57-KLH, IMU-131; bacterial vector vaccines such as CRS-207/GVAX, axalimogene filolisbac (ADXS11-001); adenovirus vector vaccines such as nadofaragene firadenovec; autologous Gp96 vaccine; dendritic cells vaccines, such as CVactm, stapuldencel-T, eltrapuldencel-T, SL-701, BSK01™, rocapuldencel-T (AGS-003), DCVAC, CVac™, stapuldencel-T, eltrapuldencel-T, SL-701, BSK01™, ADXS31-142; oncolytic vaccines such as, talimogene laherparepvec, pexastimogene devacirepvec, GL-ONC1, MG1-MA3, parvovirus H-1, ProstAtak, enadenotucirev, MG1MA3, ASN-002 (TG-1042); therapeutic vaccines, such as CVAC-301, CMP-001, PF-06753512, VBI-1901, TG-4010, ProscaVax™; tumor cell vaccines, such as Vigil® (IND-14205), Oncoquest-L vaccine; live attenuated, recombinant, serotype 1 poliovirus vaccine, such as PVS-RIPO; Adagloxad simolenin; MEDI-0457; DPV-001 a tumor-derived, autophagosome enriched cancer vaccine; RNA vaccines such as, CV-9209, LV-305; DNA vaccines, such as MEDI-0457, MVI-816, INO-5401; modified vaccinia virus Ankara vaccine expressing p53, such as MVA-p53; DPX-Survivac; BriaVax™; GI-6301; GI-6207; and GI-4000;

anti-DLL4 (delta like ligand 4) antibodies, such as demcizumab;

STAT-3 inhibitors, such as napabucasin (BBI-608);

ATPase p97 inhibitors, such as CB-5083;

smoothened (SMO) receptor inhibitors, such as Odomzo® (sonidegib, formerly LDE-225), LEQ506, vismodegib (GDC-0449), BMS-833923, glasdegib (PF-04449913), LY2940680, and itraconazole;

interferon alpha ligand modulators, such as interferon alpha-2b, interferon alpha-2a biosimilar (Biogenomics), ropeginterferon alfa-2b (AOP-2014, P-1101, PEG IFN alpha-2b), Multiferon (Alfanative, Viragen), interferon alpha 1b, Roferon-A (Canferon, Ro-25-3036), interferon alfa-2a follow-on biologic (Biosidus)(Inmutag, Inter 2A), interferon alfa-2b follow-on biologic (Biosidus—Bioferon, Citopheron, Ganapar, Beijing Kawin Technology—Kaferon), Alfaferone, pegylated interferon alpha-1b, peginterferon alfa-2b follow-on biologic (Amega), recombinant human interferon alpha-1b, recombinant human interferon alpha-2a, recombinant human interferon alpha-2b, veltuzumab-IFN alpha 2b conjugate, Dynavax (SD-101), and interferon alfa-n1 (Humoferon, SM-10500, Sumiferon);

interferon gamma ligand modulators, such as interferon gamma (OH-6000, Ogamma 100);

IL-6 receptor modulators, such as tocilizumab, siltuximab, and AS-101 (CB-06-02, IVX-Q-101);

Telomerase modulators, such as, tertomotide (GV-1001, HR-2802, Riavax) and imetelstat (GRN-163, JNJ-63935937);

DNA methyltransferases inhibitors, such as temozolomide (CCRG-81045), decitabine, guadecitabine (S-110, SGI-110), KRX-0402, RX-3117, RRx-001, and azacitidine;

DNA gyrase inhibitors, such as pixantrone and sobuzoxane;

Bcl-2 family protein inhibitors, such as ABT-263, venetoclax (ABT-199), ABT-737, and AT-101;

Notch inhibitors, such as LY3039478 (crenigacestat), tarextumab (anti-Notch2/3), and BMS-906024;

anti-myostatin inhibitors, such as landogrozumab;

hyaluronidase stimulators, such as PEGPH-20;

Wnt pathway inhibitors, such as SM-04755, PRI-724, and WNT-974;

gamma-secretase inhibitors, such as PF-03084014, MK-0752, and RO-4929097;

Grb-2 (growth factor receptor bound protein-2) inhibitors, such as BP1001;

TRAIL pathway-inducing compounds, such as ONC201, and ABBV-621;

Focal adhesion kinase inhibitors, such as VS-4718, defactinib, and GSK2256098;

hedgehog inhibitors, such as saridegib, sonidegib (LDE225), glasdegib and vismodegib;

Aurora kinase inhibitors, such as alisertib (MLN-8237), and AZD-2811, AMG-900, barasertib, and ENMD-2076;

HSPB1 modulators (heat shock protein 27, HSP27), such as brivudine, and apatorsen;

ATR inhibitors, such as BAY-937, AZD6738, AZD6783, VX-803, VX-970 (berzosertib) and VX-970;

mTOR inhibitors, such as sapanisertib and vistusertib (AZD2014), and ME-344;

mTOR/PI3K inhibitors, such as gedatolisib, GSK2141795, omipalisib, and RG6114;

Hsp90 inhibitors, such as AUY922, onalespib (AT13387), SNX-2112, SNX5422;

murine double minute (mdm2) oncogene inhibitors, such as DS-3032b, RG7775, AMG-232, HDM201, and idasanutlin (RG7388);

CD137 agonists, such as urelumab, utomilumab (PF-05082566);

STING agonists, such as ADU-S100 (MIW-815), SB-11285, MK-1454, SR-8291, AdVCA0848, GSK-532, SYN-STING, MSA-1, SR-8291;

FGFR inhibitors, such as FGF-401, INCB-054828, BAY-1163877, AZD4547, JNJ-42756493, LY2874455, and Debio-1347;

fatty acid synthase (FASN) inhibitors, such as TVB-2640;

anti-KIR monoclonal antibodies, such as lirilumab (IPH-2102), and IPH-4102;

antigen CD19 inhibitors, such as MOR208, MEDI-551, AFM-11, and inebilizumab;

CD44 binders, such as A6;

protein phosphatease 2A (PP2A) inhibitors, such as LB-100;

CYP17 inhibitors, such as seviteronel (VT-464), ASN-001, ODM-204, CFG920, and abiraterone acetate;

RXR agonists, such as IRX4204;

hedgehog/smoothened (hh/Smo) antagonists, such as taladegib, and patidegib;

complement C3 modulators, such as Imprime PGG;

IL-15 agonists, such as ALT-803, NKTR-255, and hetIL-15;

EZH2 (enhancer of zeste homolog 2) inhibitors, such as tazemetostat, CPI-1205, GSK-2816126;

oncolytic viruses, such as pelareorep, CG-0070, MV-NIS therapy, HSV-1716, DS-1647, VCN-01, ONCOS-102, TBI-1401, tasadenoturev (DNX-2401), vocimagene amiretrorepvec, RP-1, CVA21, Celyvir, LOAd-703, and OBP-301;

DOT1L (histone methyltransferase) inhibitors, such as pinometostat (EPZ-5676);

toxins such as Cholera toxin, ricin, *Pseudomonas* exotoxin, *Bordetella pertussis* adenylate cyclase toxin, diphtheria toxin, and caspase activators;

DNA plasmids, such as BC-819;

PLK inhibitors of PLK 1, 2, and 3, such as volasertib (PLK1);

WEE1 inhibitors, such as AZD1775 (adavosertib);

Rho kinase (ROCK) inhibitors, such as AT13148, and KD025;

ERK inhibitors, such as GDC-0994, LY3214996, and MK-8353;

IAP inhibitors, such as ASTX660, debio-1143, birinapant, APG-1387, and LCL-161;

RNA polymerase inhibitors, such has lurbinectedin (PM-1183), and CX-5461;

tubulin inhibitors, such as PM-184, BAL-101553 (lisavanbulin), OXI-4503, fluorapacin (AC-0001), and plinabulin;

Toll-like receptor 4 (TL4) agonists, such as G100, GSK1795091, and PEPA-10;

elongation factor 1 alpha 2 inhibitors, such as plitidepsin;

CD95 inhibitors, such as APG-101, APO-010, and asunercept;

WT1 inhibitors, such as DSP-7888;

splicing factor 3B subunitl (SF3B1) inhibitors, such as H3B-8800

PDGFR alpha/KIT mutant-specific inhibitors such as BLU-285;

SHP-2 inhibitors, such as TNO155 (SHP-099), RMC-4550, JAB-3068, and RMC-4630; or retinoid Z receptor gamma (RORγ) agonists, such as LYC-55716.

Examples of other chemotherapeutic drugs that can be used in combination with compounds of formula (I), or a pharmaceutically acceptable salt thereof include topoisomerase I inhibitors (camptothesin or topotecan), topoisomerase II inhibitors (e.g., daunomycin and etoposide), alkylating agents (e.g., cyclophosphamide, melphalan and BCNU), tubulin directed agents (e.g., taxol and vinblastine), and biological agents (e.g., antibodies such as anti CD20 antibody, IDEC 8, immunotoxins, and cytokines).

In some embodiments, the compound(s) of formula (I), or a pharmaceutically acceptable salt thereof is used in combination with Rituxan® (Rituximab) and/or other agents that work by selectively depleting CD20+ B-cells.

Included herein are methods of treatment in which a compound of formula (I), or a pharmaceutically acceptable salt thereof is administered in combination with an anti-inflammatory agent. Anti-inflammatory agents include but are not limited to NSAIDs, non-specific and COX-2 specific cyclooxgenase enzyme inhibitors, gold compounds, corticosteroids, methotrexate, tumor necrosis factor receptor (TNF) receptors antagonists, immunosuppressants and methotrexate.

Examples of NSAIDs include, but are not limited to ibuprofen, flurbiprofen, naproxen and naproxen sodium, diclofenac, combinations of diclofenac sodium and misoprostol, sulindac, oxaprozin, diflunisal, piroxicam, indomethacin, etodolac, fenoprofen calcium, ketoprofen, sodium nabumetone, sulfasalazine, tolmetin sodium, and hydroxychloroquine. Examples of NSAIDs also include COX-2 specific inhibitors (i.e., a compound that inhibits COX-2 with an $IC_{50}$ that is at least 50-fold lower than the $IC_{50}$ for COX-1) such as celecoxib, valdecoxib, lumiracoxib, etoricoxib and/or rofecoxib.

In a further embodiment, the anti-inflammatory agent is a salicylate. Salicylates include but are not limited to acetylsalicylic acid or aspirin, sodium salicylate, and choline and magnesium salicylates.

The anti-inflammatory agent may also be a corticosteroid. For example, the corticosteroid may be chosen from cortisone, dexamethasone, methylprednisolone, prednisolone, prednisolone sodium phosphate, and prednisone.

In some embodiments, the anti-inflammatory therapeutic agent is a gold compound such as gold sodium thiomalate or auranofin.

In some embodiments, the anti-inflammatory agent is a metabolic inhibitor such as a dihydrofolate reductase inhibitor, such as methotrexate or a dihydroorotate dehydrogenase inhibitor, such as leflunomide.

In one embodiment, the compound(s) of formula (I), or a pharmaceutically acceptable salt thereof is used in combination with at least one anti-inflammatory compound that is an anti-C5 monoclonal antibody (such as eculizumab or pexelizumab), a TNF antagonist, such as entanercept, or infliximab, which is an anti-TNF alpha monoclonal antibody.

In one embodiment, the compound(s) of formula (I), or a pharmaceutically acceptable salt thereof is used in combination with at least one active agent that is an immunosuppressant compound such as methotrexate, leflunomide, cyclosporine, tacrolimus, azathioprine, or mycophenolate mofetil.

In other embodiments, the compound(s) of formula (I), or a pharmaceutically acceptable salt thereof is used in combination with one or more phosphatidylinositol 3-kinase (PI3K) inhibitors, including for example, Compounds A, B and C (whose structures are provided below), or a pharmaceutically acceptable salt thereof.

Compound A

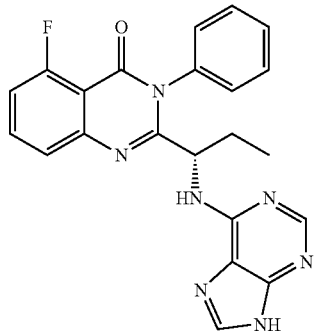

Compound B

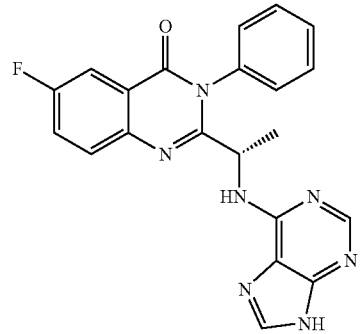

Compound C

[Chemical structure of Compound C]

Compounds A, B and C are disclosed in WO2015/017460 and WO2015/100217. PI3K inhibitors include inhibitors of PI3Kγ, PI3Kδ, PI3Kβ, PI3Kα, and/or pan-PI3K. Additional examples of PI3K inhibitors include, but are not limited to, ACP-319, AEZA-129, AMG-319, AS252424, AZD8186, BAY 10824391, BEZ235, buparlisib (BKM120), BYL719 (alpelisib), CH5132799, copanlisib (BAY 80-6946), duvelisib, GDC-0941, GDC-0980, GSK2636771, GSK2269557, idelalisib (Zydelig®), IPI-145, IPI-443, IPI-549, KAR4141, LY294002, LY3023414, MLN1117, OXY111A, PA799, PX-866, RG7604, rigosertib, RP5090, taselisib, TG100115, TGR-1202 (umbralisib), TGX221, WX-037, X-339, X-414, XL147 (SAR245408), XL499, XL756, wortmannin, ZSTK474, and the compounds described in WO 2005/113556 (ICOS), WO 2013/052699 (Gilead Calistoga), WO 2013/116562 (Gilead Calistoga), WO 2014/100765 (Gilead Calistoga), WO 2014/100767 (Gilead Calistoga), and WO 2014/201409 (Gilead Sciences). Further examples of PI3K inhibitors include, but are not limited to, GDC-0032, GDC-0077, INCB50465, RP6530, and SRX3177.

In yet another embodiment, the compound(s) of formula (I) may be used in combination with Spleen Tyrosine Kinase (SYK) Inhibitors. Examples of SYK inhibitors include, but are not limited to, 6-(1H-indazol-6-yl)-N-(4-morpholinophenyl)imidazo[1,2-a]pyrazin-8-amine, BAY-61-3606, cerdulatinib (PRT-062607), entospletinib, fostamatinib (R788), HMPL-523, NVP-QAB 205 AA, R112, R343, tamatinib (R406), and those described in U.S. Pat. No. 8,450,321 (Gilead Conn.) and those described in U.S. 2015/0175616.

In yet another embodiment, the compounds of formula (I) may be used in combination with Tyrosine-kinase Inhibitors (TKIs). TKIs may target epidermal growth factor receptors (EGFRs) and receptors for fibroblast growth factor (FGF), platelet-derived growth factor (PDGF), and vascular endothelial growth factor (VEGF). Examples of TKIs include, but are not limited to, afatinib, ARQ-087, asp5878, AZD3759, AZD4547, bosutinib, brigatinib, cabozantinib, cediranib, crenolanib, dacomitinib, dasatinib, dovitinib, E-6201, erdafitinib, erlotinib, gefitinib, gilteritinib (ASP-2215), FP-1039, HM61713, icotinib, imatinib, KX2-391 (Src), lapatinib, lestaurtinib, midostaurin, nintedanib, ODM-203, osimertinib (AZD-9291), ponatinib, poziotinib, quizartinib, radotinib, rociletinib, sulfatinib (HMPL-012), sunitinib, and TH-4000. In certain embodiments, TKIs include, but are not limited to, afatinib, ARQ-087 (derazantinib), asp5878, AZD3759, AZD4547, bosutinib, brigatinib, cabozantinib, cediranib, crenolanib, dacomitinib, dasatinib, dovitinib, E-6201, erdafitinib, erlotinib, gefitinib, gilteritinib (ASP-2215), FP-1039, HM61713, icotinib, imatinib, KX2-391 (Src), lapatinib, lestaurtinib, lenvatinib, midostaurin, nintedanib, ODM-203, osimertinib (AZD-9291), ponatinib, poziotinib, quizartinib, radotinib, rociletinib, sulfatinib (HMPL-012), sunitinib, tivoanib, TH-4000, and MEDI-575 (anti-PDGFR antibody).

In yet other embodiments, the compound(s) of formula (I), or a pharmaceutically acceptable salt thereof is used in combination with one or more inhibitors of lysyl oxidase-like 2 (LOXL) or a substance that binds to LOXL, including for example, a humanized monoclonal antibody (mAb) with an immunoglobulin IgG4 isotype directed against human LOXL2. LOXL inhibitors include inhibitors of LOXL1, LOXL2, LOXL3, LOXL4, and/or LOXL5. Examples of LOXL inhibitors include, but are not limited to, the antibodies described in WO 2009/017833 (Arresto Biosciences). Examples of LOXL2 inhibitors include, but are not limited to, the antibodies described in WO 2009/017833 (Arresto Biosciences), WO 2009/035791 (Arresto Biosciences), and WO 2011/097513 (Gilead Biologics).

In yet another embodiment, the compounds of formula (I) may be used in combination with Toll-like receptor 8 (TLR8) inhibitors. Examples of TLR8 inhibitors include, but are not limited to, E-6887, IMO-4200, IMO-8400, IMO-9200, MCT-465, MEDI-9197, motolimod, resiquimod, VTX-1463, and VTX-763.

In yet another embodiment, the compounds of formula (I) may be used in combination with Toll-like receptor (TLR9) inhibitors. Examples of TLR9 inhibitors include, but are not limited to, AST-008, IMO-2055, IMO-2125, lefitolimod, litenimod, MGN-1601, and PUL-042.

In one embodiment, the compound of formula (I) is useful for the treatment of cancer in combination with a BTK (Bruting's Tyrosine kinase) inhibitor. An example of such BTK inhibitor is a compound disclosed in U.S. Pat. No. 7,405,295. Additional examples of BTK inhibitors include, but are not limited to, (S)-6-amino-9-(1-(but-2-ynoyl)pyrrolidin-3-yl)-7-(4-phenoxyphenyl)-7H-purin-8(9H)-one, acalabrutinib (ACP-196), BGB-3111, HM71224, ibrutinib, M-2951 (evobrutinib), tirabrutinib (ONO-4059), PRN-1008, spebrutinib (CC-292), and TAK-020. Further examples of BTK inhibitors include, but are not limited to, CB988, M7583, vecabrutinib, ARQ-531, SHR-1459, DTRM-WXHS-12, and TAS-5315.

In one embodiment, the compound of formula (I) is useful for the treatment of cancer in combination with a BET inhibitor. An example of such BET inhibitor is a compound disclosed in WO2014/182929, the entire contents of which are incorporated herein by reference.

In one embodiment, the compound of formula (I) is useful for the treatment of cancer in combination with a TBK (Tank Binding kinase) inhibitor. An example of such TBK inhibitor is a compound disclosed in WO2016/049211.

In one embodiment, the compound of formula (I) is useful for the treatment of cancer in combination with a MMP inhibitor. Exemplary MMP inhibitors include inhibitors of MMP1 through 10. Additional examples of MMP9 inhibitors include, but are not limited to, marimastat (BB-2516), cipemastat (Ro 32-3555), GS-5745 (andecaliximab) and those described in WO 2012/027721 (Gilead Biologics).

In one embodiment, the compound of formula (I) is useful for the treatment of cancer in combination with a OX40 inhibitor. An example of such OX40 inhibitor is a compound disclosed in U.S. Pat. No. 8,450,460, the entire contents of which are incorporated herein by reference.

In one embodiment, the compound of formula (I) is useful for the treatment of cancer in combination with a JAK-1 inhibitor. An example of such JAK-1 inhibitor is a compound disclosed in WO2008/109943. Examples of other JAK inhibitors include, but are not limited to, AT9283, AZD1480, baricitinib, BMS-911543, fedratinib, filgotinib (GLPG0634), gandotinib (LY2784544), INCB039110 (itacitinib), lestaurtinib, momelotinib (CYT0387), NS-018, pacritinib (SB 1518), peficitinib (ASP015K), ruxolitinib, tofacitinib (formerly tasocitinib), INCB052793, and XL019.

In one embodiment, the compound of formula (I) is useful for the treatment of cancer in combination with an Indoleamine-pyrrole-2,3-dioxygenase (IDO) inhibitors. An example of such IDO inhibitor is a compound disclosed in WO2016/186967. In one embodiment, the compounds of formula (I) are useful for the treatment of cancer in combination with IDO1 inhibitors including but not limited to BLV-0801, epacadostat, F-001287, GBV-1012, GBV-1028, GDC-0919, indoximod, NKTR-218, NLG-919-based vaccine, PF-06840003, pyranonaphthoquinone derivatives (SN-35837), resminostat, SBLK-200802, and shIDO-ST. Other examples of IDO1 inhibitors include, but are not limited to, BMS-986205, EOS-200271, KHK-2455, LY-3381916.

In one embodiment, the compound of formula (I) is useful for the treatment of cancer in combination with a Mitogen-activated Protein Kinase (MEK) Inhibitors. MEK inhibitors useful for combination treatment with a compound(s) of formula (I) includes antroquinonol, binimetinib, cobimetinib (GDC-0973, XL-518), MT-144, selumetinib (AZD6244), sorafenib, trametinib (GSK1120212), uprosertib and trametinib. Other exemplary MEK inhibitors include PD-0325901, pimasertib, LTT462, AS703988, CC-90003, and refametinib.

In one embodiment, the compound of formula (I) is useful for the treatment of cancer in combination with an Apoptosis Signal-Regulating Kinase (ASK) Inhibitors: ASK inhibitors include but are not limited to those described in WO 2011/008709 (Gilead Sciences) and WO 2013/112741 (Gilead Sciences) including, for example, selonsertib.

In one embodiment, the compounds of formula (I) may be combined with Cluster of Differentiation 47 (CD47) inhibitors.

Examples of CD47 inhibitors include, but are not limited to anti-CD47 mAbs (Vx-1004), anti-human CD47 mAbs (CNTO-7108), CC-90002, CC-90002-ST-001, humanized anti-CD47 antibody (Hu5F9-G4), NI-1701, NI-1801, RCT-1938, and TTI-621.

In one embodiment, the compounds of formula (I) may be combined with Cyclin-dependent Kinase (CDK) Inhibitors. CDK inhibitors include inhibitors of CDK 1, 2, 3, 4, 6 and 9, such as abemaciclib, alvocidib (HMR-1275, flavopiridol), AT-7519, FLX-925, LEE001, palbociclib, ribociclib, rigosertib, selinexor, UCN-01, and TG-02. Other exemplary CDK inhibitors include dinaciclib, ibrance, SY1365, CT-7001, SY-1365, G1T38, milciclib, and trilaciclib.

In one embodiment, the compounds of formula (I) may be combined with Discoidin Domain Receptor (DDR) Inhibitors for the treatment of cancer. DDR inhibitors include inhibitors of DDR1 and/or DDR2. Examples of DDR inhibitors include, but are not limited to, those disclosed in WO 2014/047624 (Gilead Sciences), US 2009-0142345 (Takeda Pharmaceutical), US 2011-0287011 (Oncomed Pharmaceuticals), WO 2013/027802 (Chugai Pharmaceutical), and WO 2013/034933 (Imperial Innovations).

In one embodiment, the compounds of formula (I) may be combined with Histone Deacetylase (HDAC) Inhibitors such as those disclosed in U.S. Pat. No. 8,575,353 and equivalents thereof. Additional examples of HDAC inhibitors include, but are not limited to, abexinostat, ACY-241, AR-42, BEBT-908, belinostat, CKD-581, CS-055 (HBI-8000), CUDC-907 (fimepinostat), entinostat, givinostat, mocetinostat, panobinostat, pracinostat, quisinostat (JNJ-26481585), resminostat, ricolinostat, SHP-141, valproic acid (VAL-001), vorinostat. Further examples of HDAC inhibitors include, but are not limited to, tinostamustine, remetinostat, entinostat.

In one embodiment, the compounds of formula (I) may be combined with a Hematopoietic Progenitor Kinase 1 (HPK1) inhibitor. Examples of Hematopoietic Progenitor Kinase 1 (HPK1) inhibitors include, but are not limited to, those described in WO18183956, WO18183964, WO18167147, and WO16090300.

Anti-Hormonal Agents:

Also included in the definition of "chemotherapeutic agent" are anti-hormonal agents such as anti-estrogens and selective estrogen receptor modulators (SERMs), inhibitors of the enzyme aromatase, anti-androgens, and pharmaceutically acceptable salts, acids or derivatives of any of the above that act to regulate or inhibit hormone action on tumors.

Examples of anti-estrogens and SERMs include, for example, tamoxifen (including NOLVADEX), raloxifene, droloxifene, 4-hydroxytamoxifen, trioxifene, keoxifene, LY117018, onapristone, and toremifene (FARESTON®).

Inhibitors of the enzyme aromatase regulate estrogen production in the adrenal glands. Examples include 4(5)-imidazoles, aminoglutethimide, megestrol acetate (MEGACE®), exemestane, formestane, fadrozole, vorozole (RIVISOR®), letrozole (FEMARA®), and anastrozole (ARIMIDEX®).

Examples of anti-androgens include apalutamide, abiraterone, enzalutamide, flutamide, galeterone, nilutamide, bicalutamide, leuprolide, goserelin, ODM-201, APC-100, ODM-204.

Examples of progesterone receptor antagonist include onapristone.

Anti-Angiogenic Agents:

Anti-angiogenic agents include, but are not limited to, retinoid acid and derivatives thereof, 2-methoxyestradiol, ANGIOSTATIN®, ENDOSTATIN®, regorafenib, necuparanib, suramin, squalamine, tissue inhibitor of metalloproteinase-1, tissue inhibitor of metalloproteinase-2, plasminogen activator inhibitor-1, plasminogen activator inhibitor-2, cartilage-derived inhibitor, paclitaxel (nab-paclitaxel), platelet factor 4, protamine sulphate (clupeine), sulphated chitin derivatives (prepared from queen crab shells), sulphated polysaccharide peptidoglycan complex (sp-pg), staurosporine, modulators of matrix metabolism including proline analogs such as 1-azetidine-2-carboxylic acid (LACA), cis-hydroxyproline, d,I-3,4-dehydroproline, thiaproline, $\alpha,\alpha'$-dipyridyl, beta-aminopropionitrile fumarate, 4-propyl-5-(4-pyridinyl)-2(3h)-oxazolone, methotrexate, mitoxantrone, heparin, interferons, 2 macroglobulin-serum, chicken inhibitor of metalloproteinase-3 (ChIMP-3), chymostatin, beta-cyclodextrin tetradecasulfate, eponemycin, fumagillin, gold sodium thiomalate, d-penicillamine, beta-1-anticollagenase-serum, alpha-2-antiplasmin, bisantrene, lobenzarit disodium, n-2-carboxyphenyl-4-chloroanthronilic acid disodium or "CCA", thalidomide, angiostatic steroid, carboxy aminoimidazole, metalloproteinase inhibitors such as BB-94, inhibitors of S100A9 such as tasquinimod. Other anti-angiogenesis agents include antibodies, preferably monoclonal antibodies against these angiogenic growth factors: beta-FGF, alpha-FGF, FGF-5, VEGF isoforms, VEGF-C, HGF/SF, and Ang-1/Ang-2.

Anti-Fibrotic Agents:

Anti-fibrotic agents include, but are not limited to, the compounds such as beta-aminopropionitrile (BAPN), as well as the compounds disclosed in U.S. Pat. No. 4,965,288 relating to inhibitors of lysyl oxidase and their use in the treatment of diseases and conditions associated with the abnormal deposition of collagen and U.S. Pat. No. 4,997,854 relating to compounds which inhibit LOX for the treatment of various pathological fibrotic states, which are herein incorporated by reference. Further exemplary inhibitors are described in U.S. Pat. No. 4,943,593 relating to compounds such as 2-isobutyl-3-fluoro-, chloro-, or bromo-allylamine, U.S. Pat. Nos. 5,021,456, 5,059,714, 5,120,764, 5,182,297, 5,252,608 relating to 2-(1-naphthyloxymemyl)-3-fluoroallylamine, and US 2004-0248871, which are herein incorporated by reference.

Exemplary anti-fibrotic agents also include the primary amines reacting with the carbonyl group of the active site of the lysyl oxidases, and more particularly those which produce, after binding with the carbonyl, a product stabilized by resonance, such as the following primary amines: emylenemamine, hydrazine, phenylhydrazine, and their derivatives; semicarbazide and urea derivatives; aminonitriles such as BAPN or 2-nitroethylamine; unsaturated or saturated haloamines such as 2-bromo-ethylamine, 2-chloroethylamine, 2-trifluoroethylamine, 3-bromopropylamine, and p-halobenzylamines; and selenohomocysteine lactone.

Other anti-fibrotic agents are copper chelating agents penetrating or not penetrating the cells. Exemplary compounds include indirect inhibitors which block the aldehyde derivatives originating from the oxidative deamination of the lysyl and hydroxylysyl residues by the lysyl oxidases. Examples include the thiolamines, particularly D-penicillamine, and its analogs such as 2-amino-5-mercapto-5-methylhexanoic acid, D-2-amino-3-methyl-3-((2-acetamidoethyl)dithio)butanoic acid, p-2-amino-3-methyl-3-((2-aminoethyl)dithio)butanoic acid, sodium-4-((p-1-dimethyl-2-amino-2-carboxyethyl)dithio)butane sulphurate, 2-acetamidoethyl-2-acetamidoethanethiol sulphanate, and sodium-4-mercaptobutanesulphinate trihydrate.

Immunotherapeutic Agents:

The immunotherapeutic agents include and are not limited to therapeutic antibodies suitable for treating patients. Some examples of therapeutic antibodies include abagovomab, ABP-980, adecatumumab, afutuzumab, alemtuzumab, altumomab, amatuximab, anatumomab, arcitumomab, bavituximab, bectumomab, bevacizumab, bivatuzumab, blinatumomab, brentuximab, cantuzumab, catumaxomab, CC49, cetuximab, citatuzumab, cixutumumab, clivatuzumab, conatumumab, dacetuzumab, dalotuzumab, daratumumab, detumomab, dinutuximab, drozitumab, duligotumab, dusigitumab, ecromeximab, elotuzumab, emibetuzumab, ensituximab, ertumaxomab, etaracizumab, farletuzumab, ficlatuzumab, figitumumab, flanvotumab, futuximab, ganitumab, gemtuzumab, girentuximab, glembatumumab, ibritumomab, igovomab, imgatuzumab, indatuximab, inotuzumab, intetumumab, ipilimumab (YERVOY®, MDX-010, BMS-734016, and MDX-101), iratumumab, labetuzumab, lexatumumab, lintuzumab, lorvotuzumab, lucatumumab, mapatumumab, matuzumab, milatuzumab, minretumomab, mitumomab, mogamulizumab, moxetumomab, naptumomab, narnatumab, necitumumab, nimotuzumab, nofetumomab, OBI-833, obinutuzumab, ocaratuzumab, ofatumumab, olaratumab, onartuzumab, oportuzumab, oregovomab, panitumumab, parsatuzumab, pasudotox, patritumab, pemtumomab, pertuzumab, pintumomab, pritumumab, racotumomab, radretumab, ramucirumab (Cyramza®), rilotumumab, rituximab, robatumumab, samalizumab, satumomab, sibrotuzumab, siltuximab, solitomab, simtuzumab, tacatuzumab, taplitumomab, tenatumomab, teprotumumab, tigatuzumab, tositumomab, trastuzumab, tucotuzumab, ublituximab, veltuzumab, vorsetuzumab, votumumab, zalutumumab, and 3F8. Rituximab can be used for treating indolent B-cell cancers, including marginal-zone lymphoma, WM, CLL and small lymphocytic lymphoma. A combination of Rituximab and chemotherapy agents is especially effective.

The exemplified therapeutic antibodies may be further labeled or combined with a radioisotope particle such as indium-111, yttrium-90 (90Y-clivatuzumab), or iodine-131.

Cancer Gene Therapy and Cell Therapy:

Cancer Gene Therapy and Cell Therapy including the insertion of a normal gene into cancer cells to replace a mutated or altered gene; genetic modification to silence a mutated gene; genetic approaches to directly kill the cancer cells; including the infusion of immune cells designed to replace most of the patient's own immune system to enhance the immune response to cancer cells, or activate the patient's own immune system (T cells or Natural Killer cells) to kill cancer cells, or find and kill the cancer cells; genetic approaches to modify cellular activity to further alter endogenous immune responsiveness against cancer.

Gene Editors:

The genome editing system is selected from the group consisting of: a CRISPR/Cas9 system, a zinc finger nuclease system, a TALEN system, a homing endonucleases system, and a meganuclease system.

CAR-T Cell Therapy and TCR-T Cell Therapy:

A population of immune effector cells engineered to express a chimeric antigen receptor (CAR), wherein the CAR comprises a tumor antigen-binding domain. The immune effector cell is a T cell or an NK cell. TCR-T cells are engineered to target tumor derived peptides present on the surface of tumor cells. Cells can be autologous or allogeneic.

In some embodiments, the CAR comprises an antigen binding domain, a transmembrane domain, and an intracellular signaling domain. In some embodiments, the intracellular domain comprises a primary signaling domain, a costimulatory domain, or both of a primary signaling domain and a costimulatory domain. In some embodiments, the primary signaling domain comprises a functional signaling domain of one or more proteins selected from the group consisting of CD3 zeta, CD3 gamma, CD3 delta, CD3 epsilon, common FcR gamma (FCERIG), FcR beta (Fc Epsilon RIb), CD79a, CD79b, Fcgamma RIIa, DAP10, and DAP12.

In some embodiments, the costimulatory domain comprises a functional domain of one or more proteins selected from the group consisting of CD27, CD28, 4-1BB(CD137), OX40, CD30, CD40, PD-1, ICOS, lymphocyte function-associated antigen-1 (LFA-I), CD2, CD7, LIGHT, NKG2C, B7-H3, a ligand that specifically binds with CD83, CDS, ICAM-1, GITR, BAFFR, HVEM (LIGHTR), SLAMF7, NKp80 (KLRFI), CD160, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD 1 1d, ITGAE, CD103, ITGAL, CD 1 1a, LFA-1, ITGAM, CD1 1b, ITGAX, CD1 1c, ITGB1, CD29, ITGB2, CD18, LFA-1, ITGB7, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF, CD150, IPO-3), BLAME (SLAMF8), SELPLG (CD162), LTBR, LAT, GADS, SLP-76, PAG/Cbp, NKp44, NKp30, NKp46, and NKG2D.

In some embodiments, the transmembrane domain comprises a transmembrane domain of a protein selected from the group consisting of the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137, CD154, KIRDS2, OX40, CD2, CD27, LFA-1 (CD1 1a, CD18), ICOS (CD278), 4-1BB (CD137), GITR, CD40, BAFFR, HVEM (LIGHTR), SLAMF7, NKp80 (KLRF1), CD160, CD19, IL2R beta, IL2R gamma, IL7R u, ITGA1, VLA1, CD49a, ITGA4, IA4, CD49D, ITGA6, VLA-6, CD49f, ITGAD, CD1 1d, ITGAE, CD103, ITGAL, CD1 1a, LFA-1, ITGAM, CD1 1b, ITGAX, CD1 1c, ITGB1, CD29, ITGB2, CD18, LFA-1, ITGB7, TNFR2, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), SLAMF6 (NTB-A, Lyl08), SLAM (SLAMF1, CD150, IPO-3), BLAME (SLAMF8), SELPLG (CD162), LTBR, PAG/Cbp, NKp44, NKp30, NKp46, NKG2D, and NKG2C.

In some embodiments, the antigen binding domain binds a tumor antigen. In some embodiments, the tumor antigen is selected from the group consisting of: CD19; CD123; CD22; CD30; CD171; CS-1 (also referred to as CD2 subset 1, CRACC, SLAMF7, CD319, and 19A24); C-type lectin-like molecule-1 (CLL-1 or CLECLI); CD33; epidermal growth factor receptor variant III (EGFRvlll); ganglioside G2 (GD2); ganglioside GD3 (aNeuSAc(2-8)aNeuSAc(2-3)bD-Gaip(1-4)bDGlcp(1-1)Cer); TNF receptor family member B cell maturation (BCMA); Tn antigen ((Tn μg) or (GaINAcu-Ser/Thr)); prostate-specific membrane antigen (PSMA); Receptor tyrosine kinase-like orphan receptor 1 (RORI); Fms-Like, Tyrosine Kinase 3 (FLT3); Tumor-associated glycoprotein 72 (TAG72); CD38; CD44v6; Carcinoembryonic antigen (CEA); Epithelial cell adhesion molecule (EP-CAM); B7H3 (CD276); KIT (CD117); Interleukin-13 receptor subunit alpha-2 (IL-13Ra2 or CD213A2); Mesothelin; Interleukin 11 receptor alpha (IL-11Ra); prostate stem cell antigen (PSCA); Protease Serine 21 (Testisin or PRSS21); vascular endothelial growth factor receptor 2 (VEGFR2); Lewis(Y)antigen; CD24; Platelet-derived growth factor receptor beta (PDGFR-beta); Stage-specific embryonic antigen-4 (SSEA-4); CD20; delta like 3 (DLL3); Folate receptor alpha; Receptor tyrosine-protein kinase, ERBB2 (Her2/neu); Mucin 1, cell surface associated (MUC1); epidermal growth factor receptor (EGFR); neural cell adhesion molecule (NCAM); Prostase; prostatic acid phosphatase (PAP); elongation factor 2 mutated (ELF2M); Ephrin B2; fibroblast activation protein alpha (FAP); insulin-like growth factor 1 receptor (IGF-I receptor), carbonic anhydrase IX (CAIX); Proteasome (Prosome, Macropain) Subunit, Beta Type, 9 (LMP2); glycoprotein 100 (gp100); oncogene fusion protein consisting of breakpoint cluster region (BCR) and Abelson murineleukemia viral oncogene homolog 1 (Ab1) (bcr-ab1); tyrosinase; ephrin type-A receptor 2(EphA2); Fucosyl GM1; sialyl Lewis adhesion molecule (sLe); ganglioside GM3 (aNeuSAc(2-3)bDGalp(1-4)bDGlcp(1-1)Cer); transglutaminase 5 (TGS5); high molecular weight-melanomaassociatedantigen (HMWMAA); o-acetyl-GD2 ganglioside (OAcGD2); Folate receptor beta; tumor endothelial marker 1 (TEM1/CD248); tumor endothelial marker 7-related (TEM7R); six transmembrane epithelial antigen of the prostate I (STEAP1); claudin 6 (CLDN6); thyroid stimulating hormone receptor (TSHR); G protein-coupled receptor class C group 5, member D (GPRCSD); chromosome X open reading frame 61 (CXORF61); CD97; CD179a; anaplastic lymphoma kinase (ALK); Polysialic acid; placenta-specific 1 (PLAC 1); hexasaccharide portion of globoH glycoceramide (GloboH); mammary gland differentiation antigen (NY-BR-1); uroplakin 2 (UPK2); Hepatitis A virus cellular receptor 1 (HAVCR1); adrenoceptor beta 3 (ADRB3); pannexin 3 (PANX3); G protein-coupled receptor 20 (GPR20); lymphocyte antigen 6 complex, locus K 9 (LY6K); Olfactory receptor 51E2 (ORS IE2); TCR Gamma Alternate Reading Frame Protein (TARP); Wilms tumor protein (WT1); Cancer/testis antigen 1 (NY-ESO-1); Cancer/testis antigen 2 (LAGE-la); Melanomaassociated antigen 1 (MAGE-A1); ETS translocation-variant gene 6, located on chromosome 12p (ETV6-AML); sperm protein 17 (SPA17); X Antigen Family, Member 1A (XAGE1); angiopoietin-binding cell surface receptor 2 (Tie 2); melanoma cancer testis antigen-1 (MADCT-1); melanoma cancer testis antigen-2 (MAD-CT-2); Fos-related antigen 1; tumor protein p53, (p53); p53 mutant; prostein; survivin; telomerase; prostate carcinoma tumor antigen-1 (PCTA-1 or Galectin 8), melanoma antigen recognized by T cells 1 (MelanA or MARTI); Rat sarcoma (Ras) mutant; human Telomerase reverse transcriptase (hTERT); sarcoma translocation breakpoints; melanoma inhibitor of apoptosis (ML-IAP); ERG (transmembrane protease, serine 2 (TMPRSS2) ETS fusion gene); N-Acetyl glucosaminyl-transferase V (NA17); paired box protein Pax-3 (PAX3); Androgen receptor; Cyclin B1; v-myc avian myelocytomatosis viral oncogene neuroblastoma derived homolog (MYCN); Ras Homolog Family Member C (RhoC); Tyrosinase-related protein 2 (TRP-2); Cytochrome P450 1B1(CYP IBI); CCCTC-Binding Factor (Zinc Finger Protein)-Like (BORIS or Brother of the Regulator of Imprinted Sites), Squamous Cell Carcinoma Antigen Recognized By T Cells 3 (SART3); Paired box protein Pax-5 (PAX5); proacrosin binding protein sp32 (OY-TES I); lymphocyte-specific protein tyrosine kinase (LCK); A kinase anchor protein 4 (AKAP-4); synovial sarcoma, X breakpoint 2 (SSX2); Receptor for Advanced Glycation Endproducts (RAGE-I); renal ubiquitous 1 (RUI); renal ubiquitous 2 (RU2); legumain; human papilloma virus E6 (HPV E6); human papilloma virus E7 (HPV E7); intestinal carboxyl esterase; heat shock protein 70-2 mutated (mut hsp70-2); CD79a; CD79b; CD72; Leukocyte-associated immunoglobulin-like receptor 1 (LAIRI); Fc fragment of IgA receptor (FCAR or CD89); Leukocyte immunoglobulin-like receptor subfamily A member 2 (LILRA2); CD300 molecule-like family member f (CD300LF); C-type lectin domain family 12 member A (CLEC12A); bone marrow stromal cell antigen 2 (BST2); EGF-like module containing mucin-like hormone receptor-like 2 (EMR2); lymphocyte antigen 75 (LY75); Glypican-3 (GPC3); Fc receptor-like 5 (FCRL5); and immunoglobulin lambda-like polypeptide 1 (IGLL1).

In some embodiments, the tumor antigen is selected from CD150, 5T4, ActRIIA, B7, BMCA, CA-125, CCNA1, CD123, CD126, CD138, CD14, CD148, CD15, CD19, CD20, CD200, CD21, CD22, CD23, CD24, CD25, CD26, CD261, CD262, CD30, CD33, CD362, CD37, CD38, CD4, CD40, CD40L, CD44, CD46, CD5, CD52, CD53, CD54, CD56, CD66a-d, CD74, CD8, CD80, CD92, CE7, CS-1, CSPG4, ED-B fibronectin, EGFR, EGFRvIII, EGP-2, EGP-4, EPHa2, ErbB2, ErbB3, ErbB4, FBP, GD2, GD3, HER1-HER2 in combination, HER2-HER3 in combination, HERV-K, HIV-1 envelope glycoprotein gp120, HIV-1 envelope glycoprotein gp41, HLA-DR, HM1.24, HMW-MAA, Her2, Her2/neu, IGF-1R, IL-11Ralpha, IL-13R-alpha2, IL-2, IL-22R-alpha, IL-6, IL-6R, Ia, Ii, L1-CAM, L1-cell adhesion molecule, Lewis Y, L1-CAM, MAGE A3, MAGE-A1, MART-1, MUC1, NKG2C ligands, NKG2D Ligands, NYESO-1, OEPHa2, PIGF, PSCA, PSMA, ROR1, T101, TAC, TAG72, TIM-3, TRAIL-R1, TRAIL-R1 (DR4), TRAIL-R2 (DR5), VEGF, VEGFR2, WT-I, a G-protein coupled receptor, alphafetoprotein (AFP), an angiogenesis factor, an exogenous cognate binding molecule (ExoCBM), oncogene product, anti-folate receptor, c-Met, carcinoembryonic antigen (CEA), cyclin (D 1), ephrinB2, epithelial tumor antigen, estrogen receptor, fetal acethycholine e receptor, folate binding protein, gp100, hepatitis B surface antigen, kappa chain, kappa light chain, kdr, lambda chain, livin, melanoma-associated antigen, mesothelin, mouse double minute 2 homolog (MDM2), mucin 16 (MUC16), mutated p53, mutated ras, necrosis antigens, oncofetal antigen, ROR2, progesterone receptor, prostate specific antigen, tEGFR, tenascin, P2-Microgiobuiin, and Fc Receptor-like 5 (FcRL5).

Non limiting examples of cell therapies include Algenpantucel-L, Sipuleucel-T, (BPX-501) rivogenlecleucel U.S. Pat. No. 9,089,520, WO2016100236, AU-105, ACTR-087, activated allogeneic natural killer cells CNDO-109-AANK, MG-4101, AU-101, BPX-601, FATE-NK100, LFU-835 hematopoietic stem cells, Imilecleucel-T, baltaleucel-T, PNK-007, UCARTCS1, ET-1504, ET-1501, ET-1502, ET-190, CD19-ARTEMIS, ProHema, FT-1050-treated bone marrow stem cell therapy, CD4CARNK-92 cells, CryoStim, AlloStim, lentiviral transduced huCART-meso cells, CART-22 cells, EGFRt/19-28z/4-1BBL CAR T cells, autologous 4H11-28z/flL-12/EFGRt T cell, CCR5-SBC-728-HSPC, CAR4-1BBZ, CH-296, dnTGFbRII-NY-ESOc259T, Ad-RTS-IL-12, IMA-101, IMA-201, CARMA-0508, TT-18, CMD-501, CMD-503, CMD-504, CMD-502, CMD-601, CMD-602, and CSG-005.

Additional agents include those where the tumor targeting antigen is:

Alpha-fetoprotein, such as ET-1402, and AFP-TCR;

Anthrax toxin receptor 1, such as anti-TEM8 CAR T-cell therapy;

B cell maturation antigens (BCMA), such as bb-2121, UCART-BCMA, ET-140, KITE-585, MCM-998, LCAR-B38M, CART-BCMA, SEA-BCMA, BB212, UCART-BCMA, ET-140, P-BCMA-101, and AUTO-2 (APRIL-CAR);

Anti-CLL-1 antibodies, such as KITE-796;

B7 homolog 6, such as CAR-NKp30 and CAR-B7H6;

B-lymphocyte antigen CD19, such as TBI-1501, CTL-119 huCART-19 T cells, JCAR-015 U.S. Pat. No. 7,446,190, JCAR-014, JCAR-017, (WO2016196388, WO2016033570, WO2015157386), axicabtagene ciloleucel (KTE-C19), U.S. Pat. Nos. 7,741,465, 6,319,494, UCART-19, EBV-CTL, T tisagenlecleucel-T (CTL019), WO2012079000, WO2017049166, CD19CAR-CD28-CD3zeta-EGFRt-expressing T cells, CD19/4-1BBL armored CAR T cell therapy, C-CAR-011, CIK-CAR.CD19, CD19CAR-28-zeta T cells, PCAR-019, MatchCART, DSCAR-01, and IM19 CAR-T;

B-lymphocyte antigen CD20, such as ATTCK-20;

B-lymphocyte cell adhesion, such as UCART-22, and JCAR-018 (WO2016090190);

NY-ESO-1, such as GSK-3377794, and TBI-1301;

Carbonic anhydrase, such as DC-Ad-GMCAIX;

Caspase 9 suicide gene, such as CaspaCIDe DLI, and BPX-501;

CCR5, such as SB-728;

CDw123, such as MB-102, and UCART-123;

CD20m such as CBM-C20.1;

CD4, such as ICG-122;

CD30, such as CART30 (CBM-C30.1;

CD33, such as CIK-CAR.CD33;

CD38, such as T-007, UCART-38;

CD40 ligand, such as BPX-201;

CEACAM protein 4 modulators, such as MG7-CART;

Claudin 6, such as CSG-002;

EBV targeted, such as CMD-003;

EGFR, such as autologous 4H11-28z/flL-12/EFGRt T cell;

Endonuclease, such as PGN-514, PGN-201;

Epstein-Barr virus specific T-lymphocytes, such as TT-10;

Erbb2, such as CST-102, CIDeCAR;

Ganglioside (GD2), such as 4SCAR-GD2;

Glutamate carboxypeptidase II, such as CIK-CAR.PSMA, CART-PSMA-TGFBRDN, and P-PSMA-101;

Glypican-3(GPC3), such as TT-16, and GLYCAR;

Hemoglobin, such as PGN-236;

Hepatocyte growth factor receptor, such as anti-cMet RNA CAR T;

Human papillomavirus E7 protein, such as KITE-439;

Immunoglobulin gamma Fc receptor III, such as ACTR087;

IL-12, such as DC-RTS-IL-12;

IL-12 agonist/mucin 16, such as JCAR-020;

IL-13 alpha 2, such as MB-101;

IL-2, such as CST-101;

K-Ras GTPase, such as anti-KRAS G12V mTCR cell therapy;

Neural cell adhesion molecule L1 L1CAM (CD171), such as JCAR-023;

Latent membrane protein 1/Latent membrane protein 2, such as Ad5f35-LMPd1-2-transduced autologous dendritic cells;

Melanoma associated antigen 10, such as MAGE-A10C796T MAGE-A10 TCR;

Melanoma associated antigen 3/Melanoma associated antigen 6 (MAGE A3/A6) such as KITE-718;

Mesothelin, such as CSG-MESO, and TC-210;

NKG2D, such as NKR-2;

Ntrkr1 tyrosine kinase receptor, such as JCAR-024;

T cell receptors, such as BPX-701, and IMCgp 100;

T-lymphocyte, such as TT-12;

Tumor infiltrating lymphocytes, such as LN-144, and LN-145;

Wilms tumor protein, such as JTCR-016, and WT1-CTL;

Subjects

Any of the methods of treatment provided may be used to treat a subject (e.g., human) who has been diagnosed with or is suspected of having cancer. As used herein, a subject refers to a mammal, including, for example, a human.

In some embodiments, the subject may be a human who exhibits one or more symptoms associated with cancer or hyperproliferative disease. In some embodiments, the subject may be a human who exhibits one or more symptoms associated with cancer. In some embodiments, the subject is at an early stage of a cancer. In other embodiments, the subject is at an advanced stage of cancer.

In certain, the subject may be a human who is at risk, or genetically or otherwise predisposed (e.g., risk factor) to developing cancer or hyperproliferative disease who has or has not been diagnosed. As used herein, an "at risk" subject is a subject who is at risk of developing cancer. The subject may or may not have detectable disease, and may or may not have displayed detectable disease prior to the treatment methods described herein. An at risk subject may have one or more so-called risk factors, which are measurable parameters that correlate with development of cancer, which are described herein. A subject having one or more of these risk factors has a higher probability of developing cancer than an individual without these risk factor(s). These risk factors may include, for example, age, sex, race, diet, history of previous disease, presence of precursor disease, genetic (e.g., hereditary) considerations, and environmental exposure. In some embodiments, the subjects at risk for cancer include, for example, those having relatives who have experienced the disease, and those whose risk is determined by analysis of genetic or biochemical markers.

In addition, the subject may be a human who is undergoing one or more standard therapies, such as chemotherapy, radiotherapy, immunotherapy, surgery, or combination thereof. Accordingly, one or more kinase inhibitors may be administered before, during, or after administration of chemotherapy, radiotherapy, immunotherapy, surgery or combination thereof.

In certain embodiments, the subject may be a human who is (i) substantially refractory to at least one chemotherapy treatment, or (ii) is in relapse after treatment with chemotherapy, or both (i) and (ii). In some of embodiments, the subject is refractory to at least two, at least three, or at least four chemotherapy treatments (including standard or experimental chemotherapies).

As used herein, a "therapeutically effective amount" means an amount sufficient to modulate a specific pathway, and thereby treat a subject (such as a human) suffering an indication, or to alleviate the existing symptoms of the indication. Determination of a therapeutically effective amount is within the capability of those skilled in the art, especially in light of the detailed disclosure provided herein. In some embodiments, a therapeutically effective amount of a JAK inhibitor, such as Compound A or ruxolitinib or pharmaceutically acceptable salt thereof, and a therapeutically effective amount of PI3K inhibitor, such as Compound B, Compound C, Compound D, or Compound E and pharmaceutically acceptable salt thereof, may (i) reduce the number of diseased cells; (ii) reduce tumor size; (iii) inhibit, retard, slow to some extent, and preferably stop the diseased cell infiltration into peripheral organs; (iv) inhibit (e.g., slow to some extent and preferably stop) tumor metastasis; (v) inhibit tumor growth; (vi) prevent or delay occurrence and/or recurrence of a tumor; and/or (vii) relieve to some extent one or more of the symptoms associated with cancer or myeloproliferative disease. In other embodiments, a therapeutically effective amount of Compound B or Compound C and a therapeutically effective amount of obinutuzumab may (i) reduce the number of cancer cells; (ii) reduce tumor size; (iii) inhibit, retard, slow to some extent, and preferably stop cancer cell infiltration into peripheral organs; (iv) inhibit (e.g., slow to some extent and preferably stop) tumor metastasis; (v) inhibit tumor growth; (vi) prevent or delay occurrence and/or recurrence of a tumor; and/or (vii) relieve to some extent one or more of the symptoms associated with the cancer. In various embodiments, the amount is sufficient to ameliorate, palliate, lessen, and/or delay one or more of symptoms of cancer.

In some embodiments, the cancer is Burkitt's lymphoma, Hodgkin's lymphoma, non-Hodgkin's lymphoma (NHL), indolent non-Hodgkin's lymphoma (iNHL), refractory iNHL, multiple myeloma (MM), chronic myeloid leukemia (CML), acute lymphocytic leukemia (ALL), B-cell ALL, acute myeloid leukemia (AML), chronic lymphocytic leukemia (CLL), small lymphocytic lymphoma (SLL), myelodysplastic syndrome (MDS), myeloproliferative disease (MPD), mantle cell lymphoma (MCL), follicular lymphoma (FL), Waldestrom's macroglobulinemia (WM), T-cell lymphoma, B-cell lymphoma, diffuse large B-cell lymphoma (DLBCL), or marginal zone lymphoma (MZL). In one embodiment, the cancer is minimal residual disease (MRD). In additional embodiment, the cancer is selected from Hodgkin's lymphoma, non-Hodgkin's lymphoma (NHL), indolent non-Hodgkin's lymphoma (iNHL), and refractory iNHL. In certain embodiment, the cancer is indolent non-Hodgkin's lymphoma (iNHL). In some embodiment, the cancer is refractory iNHL. In one embodiment, the cancer is chronic lymphocytic leukemia (CLL). In other embodiment, the cancer is diffuse large B-cell lymphoma (DLBCL).

In certain embodiments, the cancer is a solid tumor is selected from the group consisting of pancreatic cancer; bladder cancer; colorectal cancer; breast cancer, including metastatic breast cancer; prostate cancer, including androgen-dependent and androgen-independent prostate cancer; kidney or renal cancer, including, e.g., metastatic renal cell carcinoma; hepatocellular cancer; lung cancer, including, e.g., non-small cell lung cancer (NSCLC), bronchioloalveolar carcinoma (BAC), and adenocarcinoma of the lung; ovarian cancer, including, e.g., progressive epithelial or primary peritoneal cancer; cervical cancer; gastric cancer; esophageal cancer; head and neck cancer, including, e.g., squamous cell carcinoma of the head and neck; melanoma; neuroendocrine cancer, including metastatic neuroendocrine tumors; brain tumors, including, e.g., glioma, anaplastic oligodendroglioma, adult glioblastoma multiforme, and adult anaplastic astrocytoma; bone cancer; and soft tissue sarcoma, hepatic carcinoma, rectal cancer, penile carcinoma, vulval cancer, thyroid cancer, salivary gland carcinoma, endometrial or uterine carcinoma, hepatoma, hepatocellular cancer, liver cancer, gastric or stomach cancer including gastrointestinal cancer, cancer of the peritoneum, squamous carcinoma of the lung, gastroesophageal cancer, biliary tract cancer, gall bladder cancer, colorectal/appendiceal cancer, squamous cell cancer (e.g., epithelial squamous cell cancer).

Any of the methods of treatment provided may be used to treat cancer at various stages. By way of example, the cancer stage includes but is not limited to early, advanced, locally advanced, remission, refractory, reoccurred after remission and progressive.

Lymphoma or Leukemia Combination Therapy:

Some chemotherapy agents are suitable for treating lymphoma or leukemia. These agents include aldesleukin, alvocidib, amifostine trihydrate, aminocamptothecin, antineoplaston A10, antineoplaston AS2-1, anti-thymocyte globulin, arsenic trioxide, Bcl-2 family protein inhibitor ABT-263, beta alethine, BMS-345541, bortezomib (VELCADE®), bortezomib (VELCADE®, PS-341), bryostatin 1, bulsulfan, campath-1H, carboplatin, carfilzomib (Kyprolis®), carmustine, caspofungin acetate, CC-5103, chlorambucil, CHOP (cyclophosphamide, doxorubicin, vincristine, and prednisone), cisplatin, cladribine, clofarabine, curcumin, CVP (cyclophosphamide, vincristine, and prednisone), cyclophosphamide, cyclosporine, cytarabine, denileukin diftitox, dexamethasone, docetaxel, dolastatin 10, doxorubicin, doxorubicin hydrochloride, DT-PACE (dexamethasone, thalidomide, cisplatin, doxorubicin, cyclophosphamide, and etoposide), enzastaurin, epoetin alfa, etoposide, everolimus (RAD001), FCM (fludarabine, cyclophosphamide, and mitoxantrone), FCR (fludarabine, cyclophosphamide, and rituximab), fenretinide, filgrastim, flavopiridol, fludarabine, FR (fludarabine and rituximab), geldanamycin (17-AAG), hyperCVAD (hyperfractionated cyclophosphamide, vincristine, doxorubicin, dexamethasone, methotrexate, and cytarabine), ICE (iphosphamide, carboplatin, and etoposide), ifosfamide, irinotecan hydrochloride, interferon alpha-2b, ixabepilone, lenalidomide (REVLIMID®, CC-5013), lymphokine-activated killer cells, MCP (mitoxantrone, chlorambucil, and prednisolone), melphalan, mesna, methotrexate, mitoxantrone hydrochloride, motexafin gadolinium, mycophenolate mofetil, nelarabine, obatoclax (GX15-070), oblimersen, octreotide acetate, omega-3 fatty acids, Omr-IgG-am (WNIG, Omrix), oxaliplatin, paclitaxel, palbociclib (PD0332991), pegfilgrastim, PEGylated liposomal doxorubicin hydrochloride, perifosin, prednisolone, prednisone, recombinant flt3 ligand, recombinant human thrombopoietin, recombinant interferon alfa, recombinant interleukin-11, recombinant interleukin-12, rituximab, R-CHOP (rituximab and CHOP), R-CVP (rituximab and CVP), R-FCM (rituximab and FCM), R-ICE (rituximab and ICE), and R-MCP (rituximab and MCP), R-roscovitine (seliciclib, CYC202), sargramostim, sildenafil citrate, simvastatin, sirolimus, styryl sulphones, tacrolimus, tanespimycin, temsirolimus (CCI-779), thalidomide, therapeutic allogeneic lymphocytes, thiotepa, tipifarnib, vincristine, vincristine sulfate, vinorelbine ditartrate, SAHA (suberanilohydroxamic acid, or suberoyl, anilide, and hydroxamic acid), vemurafenib (Zelboraf®), venetoclax (ABT-199).

One modified approach is radioimmunotherapy, wherein a monoclonal antibody is combined with a radioisotope particle, such as indium-111, yttrium-90, and iodine-131. Examples of combination therapies include, but are not limited to, iodine-131 tositumomab (BEXXAR®), yttrium-90 ibritumomab tiuxetan (ZEVALIN®), and BEXXAR® with CHOP.

The abovementioned therapies can be supplemented or combined with stem cell transplantation or treatment. Therapeutic procedures include peripheral blood stem cell transplantation, autologous hematopoietic stem cell transplantation, autologous bone marrow transplantation, antibody therapy, biological therapy, enzyme inhibitor therapy, total body irradiation, infusion of stem cells, bone marrow ablation with stem cell support, in vitro-treated peripheral blood stem cell transplantation, umbilical cord blood transplantation, immunoenzyme technique, low-LET cobalt-60 gamma ray therapy, bleomycin, conventional surgery, radiation therapy, and nonmyeloablative allogeneic hematopoietic stem cell transplantation.

Non-Hodgkin's Lymphomas Combination Therapy:

Treatment of non-Hodgkin's lymphomas (NHL), especially those of B cell origin, includes using monoclonal antibodies, standard chemotherapy approaches (e.g., CHOP, CVP, FCM, MCP, and the like), radioimmunotherapy, and combinations thereof, especially integration of an antibody therapy with chemotherapy.

Examples of unconjugated monoclonal antibodies for the treatment of NHL/B-cell cancers include rituximab, alemtuzumab, human or humanized anti-CD20 antibodies, lumiliximab, anti-TNF-related apoptosis-inducing ligand (anti-TRAIL), bevacizumab, galiximab, epratuzumab, SGN-40, and anti-CD74.

Examples of experimental antibody agents used in treatment of NHL/B-cell cancers include ofatumumab, ha20, PRO 131921, alemtuzumab, galiximab, SGN-40, CHIR-12.12, epratuzumab, lumiliximab, apolizumab, milatuzumab, and bevacizumab.

Examples of standard regimens of chemotherapy for NHL/B-cell cancers include CHOP, FCM, CVP, MCP, R-CHOP, R-FCM, R-CVP, and R-MCP.

Examples of radioimmunotherapy for NHL/B-cell cancers include yttrium-90 ibritumomab tiuxetan (ZEVALIN®) and iodine-131 tositumomab (BEXXAR®).

Mantle Cell Lymphoma Combination Therapy:

Therapeutic treatments for mantle cell lymphoma (MCL) include combination chemotherapies such as CHOP, hyper-CVAD, and FCM. These regimens can also be supplemented with the monoclonal antibody rituximab to form combination therapies R-CHOP, hyperCVAD-R, and R-FCM. Any of the abovementioned therapies may be combined with stem cell transplantation or ICE in order to treat MCL.

An alternative approach to treating MCL is immunotherapy. One immunotherapy uses monoclonal antibodies like rituximab. Another uses cancer vaccines, such as GTOP-99, which are based on the genetic makeup of an individual patient's tumor.

A modified approach to treat MCL is radioimmunotherapy, wherein a monoclonal antibody is combined with a radioisotope particle, such as iodine-131 tositumomab (BEXXAR®) and yttrium-90 ibritumomab tiuxetan (ZEVALIN®). In another example, BEXXAR® is used in sequential treatment with CHOP.

Other approaches to treating MCL include autologous stem cell transplantation coupled with high-dose chemotherapy, administering proteasome inhibitors such as bortezomib (VELCADE® or PS-341), or administering antiangiogenesis agents such as thalidomide, especially in combination with rituximab.

Another treatment approach is administering drugs that lead to the degradation of Bcl-2 protein and increase cancer cell sensitivity to chemotherapy, such as oblimersen, in combination with other chemotherapeutic agents.

A further treatment approach includes administering mTOR inhibitors, which can lead to inhibition of cell growth and even cell death. Non-limiting examples are sirolimus, temsirolimus (TORISEL®, CCI-779), CC-115, CC-223, SF-1126, PQR-309 (bimiralisib), voxtalisib, GSK-2126458, and temsirolimus in combination with RITUXAN®, VELCADE®, or other chemotherapeutic agents.

Other recent therapies for MCL have been disclosed. Such examples include flavopiridol, palbociclib (PD0332991), R-roscovitine (seliciclib, CYC202), styryl sulphones, obatoclax (GX15-070), TRAIL, Anti-TRAIL death receptors DR4 and DR5 antibodies, temsirolimus (TORISEL®, CCI-779), everolimus (RAD001), BMS-345541, curcumin, SAHA, thalidomide, lenalidomide (REVLIMID®, CC-5013), and geldanamycin (17-AAG).

Waldestrom's Macroglobulinemia Combination Therapy:

Therapeutic agents used to treat Waldestrom's Macroglobulinemia (WM) include aldesleukin, alemtuzumab, alvocidib, amifostine trihydrate, aminocamptothecin, antineoplaston A10, antineoplaston AS2-1, anti-thymocyte globulin, arsenic trioxide, autologous human tumor-derived HSPPC-96, Bcl-2 family protein inhibitor ABT-263, beta alethine, bortezomib (VELCADE®), bryostatin 1, busulfan, campath-1H, carboplatin, carmustine, caspofungin acetate, CC-5103, cisplatin, clofarabine, cyclophosphamide, cyclosporine, cytarabine, denileukin diftitox, dexamethasone, docetaxel, dolastatin 10, doxorubicin hydrochloride, DT-PACE, enzastaurin, epoetin alfa, epratuzumab (hLL2-anti-CD22 humanized antibody), etoposide, everolimus, fenretinide, filgrastim, fludarabine, ifosfamide, indium-111 monoclonal antibody MN-14, iodine-131 tositumomab, irinotecan hydrochloride, ixabepilone, lymphokine-activated killer cells, melphalan, mesna, methotrexate, mitoxantrone hydrochloride, monoclonal antibody CD19 (such as tisagenlecleucel-T, CART-19, CTL-019), monoclonal antibody CD20, motexafin gadolinium, mycophenolate mofetil, nelarabine, oblimersen, octreotide acetate, omega-3 fatty acids, oxaliplatin, paclitaxel, pegfilgrastim, PEGylated liposomal doxorubicin hydrochloride, pentostatin, perifosine, prednisone, recombinant flt3 ligand, recombinant human thrombopoietin, recombinant interferon alfa, recombinant interleukin-11, recombinant interleukin-12, rituximab, sargramostim, sildenafil citrate (VIAGRA), simvastatin, sirolimus, tacrolimus, tanespimycin, thalidomide, therapeutic allogeneic lymphocytes, thiotepa, tipifarnib, tositumomab, veltuzumab, vincristine sulfate, vinorelbine ditartrate, vorinostat, WT1 126-134 peptide vaccine, WT-1 analog peptide vaccine, yttrium-90 ibritumomab tiuxetan, yttrium-90 humanized epratuzumab, and any combination thereof.

Examples of therapeutic procedures used to treat WM include peripheral blood stem cell transplantation, autologous hematopoietic stem cell transplantation, autologous bone marrow transplantation, antibody therapy, biological therapy, enzyme inhibitor therapy, total body irradiation, infusion of stem cells, bone marrow ablation with stem cell support, in vitro-treated peripheral blood stem cell transplantation, umbilical cord blood transplantation, immunoenzyme techniques, low-LET cobalt-60 gamma ray therapy, bleomycin, conventional surgery, radiation therapy, and nonmyeloablative allogeneic hematopoietic stem cell transplantation.

Diffuse Large B-cell Lymphoma Combination Therapy:
Therapeutic agents used to treat diffuse large B-cell lymphoma (DLBCL) include cyclophosphamide, doxorubicin, vincristine, prednisone, anti-CD20 monoclonal antibodies, etoposide, bleomycin, many of the agents listed for WM, and any combination thereof, such as ICE and R-ICE.

Chronic Lymphocytic Leukemia Combination Therapy:
Examples of therapeutic agents used to treat chronic lymphocytic leukemia (CLL) include chlorambucil, cyclophosphamide, fludarabine, pentostatin, cladribine, doxorubicin, vincristine, prednisone, prednisolone, alemtuzumab, many of the agents listed for WM, and combination chemotherapy and chemoimmunotherapy, including the following common combination regimens: CVP, R-CVP, ICE, R-ICE, FCR, and FR.

Myelofibrosis Combination Therapy:
Myelofibrosis inhibiting agents include, but are not limited to, hedgehog inhibitors, histone deacetylase (HDAC) inhibitors, and tyrosine kinase inhibitors. Non-limiting examples of hedgehog inhibitors are saridegib and vismodegib. Examples of HDAC inhibitors include, but are not limited to, pracinostat and panobinostat. Non-limiting examples of tyrosine kinase inhibitors are lestaurtinib, bosutinib, imatinib, gilteritinib, radotinib, and cabozantinib.

Hyperproliferative Disorder Combination Therapy:
Gemcitabine, nab-paclitaxel, and gemcitabine/nab-paclitaxel may be used with a JAK inhibitor and/or PI3K8 inhibitor to treat hyperproliferative disorders.

Bladder Cancer Combination Therapy:
Therapeutic agents used to treat bladder cancer include atezolizumab, carboplatin, cisplatin, docetaxel, doxorubicin, fluorouracil (5-FU), gemcitabine, ifosfamide, Interferon alfa-2b, methotrexate, mitomycin, nab-paclitaxel, paclitaxel, pemetrexed, thiotepa, vinblastine, and any combination thereof.

Breast Cancer Combination Therapy:
Therapeutic agents used to treat breast cancer include albumin-bound paclitaxel, anastrozole, capecitabine, carboplatin, cisplatin, cyclophosphamide, docetaxel, doxorubicin, epirubicin, everolimus, exemestane, fluorouracil, fulvestrant, gemcitabine, Ixabepilone, lapatinib, Letrozole, methotrexate, mitoxantrone, paclitaxel, pegylated liposomal doxorubicin, pertuzumab, tamoxifen, toremifene, trastuzumab, vinorelbine, and any combinations thereof.

Triple Negative Breast Cancer Combination Therapy:
Therapeutic agents used to treat triple negative breast cancer include cyclophosphamide, docetaxel, doxorubicin, epirubicin, fluorouracil, paclitaxel, and combinations thereof.

Colorectal Cancer Combination Therapy:
Therapeutic agents used to treat colorectal cancer include bevacizumab, capecitabine, cetuximab, fluorouracil, irinotecan, leucovorin, oxaliplatin, panitumumab, ziv-aflibercept, and any combinations thereof.

Castration-Resistant Prostate Cancer Combination Therapy:
Therapeutic agents used to treat castration-resistant prostate cancer include abiraterone, cabazitaxel, docetaxel, enzalutamide, prednisone, sipuleucel-T, and any combinations thereof.

Esophageal and Esophagogastric Junction Cancer Combination Therapy:
Therapeutic agents used to treat esophageal and esophagogastric junction cancer include capecitabine, carboplatin, cisplatin, docetaxel, epirubicin, fluoropyrimidine, fluorouracil, irinotecan, leucovorin, oxaliplatin, paclitaxel, ramucirumab, trastuzumab, and any combinations thereof.

Gastric Cancer Combination Therapy:
Therapeutic agents used to treat gastric cancer include capecitabine, carboplatin, cisplatin, docetaxel, epirubicin, fluoropyrimidine, fluorouracil, Irinotecan, leucovorin, mitomycin, oxaliplatin, paclitaxel, ramucirumab, trastuzumab, and any combinations thereof.

Head & Neck Cancer Combination Therapy:
Therapeutic agents used to treat head & neck cancer include afatinib, bleomycin, capecitabine, carboplatin, cetuximab, cisplatin, docetaxel, fluorouracil, gemcitabine, hydroxyurea, methotrexate, nivolumab, paclitaxel, pembrolizumab, vinorelbine, and any combinations thereof.

Hepatobiliary Cancer Combination Therapy:
Therapeutic agents used to treat hepatobiliary cancer include capecitabine, cisplatin, fluoropyrimidine, 5-fluorourcil, gemecitabine, oxaliplatin, sorafenib, and any combinations thereof.

Hepatocellular Carcinoma Combination Therapy:
Therapeutic agents used to treat hepatocellular carcinoma include capecitabine, doxorubicin, gemcitabine, sorafenib, and any combinations thereof.

Non-Small Cell Lung Cancer Combination Therapy:
Therapeutic agents used to treat non-small cell lung cancer (NSCLC) include afatinib, albumin-bound paclitaxel, alectinib, bevacizumab, bevacizumab, cabozantinib, carboplatin, cisplatin, crizotinib, dabrafenib, docetaxel, erlotinib, etoposide, gemcitabine, nivolumab, paclitaxel, pembrolizumab, pemetrexed, ramucirumab, trametinib, trastuzumab, vandetanib, vemurafenib, vinblastine, vinorelbine, and any combinations thereof.

Small Cell Lung Cancer Combination Therapy:
Therapeutic agents used to treat small cell lung cancer (SCLC) include bendamustime, carboplatin, cisplatin, cyclophosphamide, docetaxel, doxorubicin, etoposide, gemcitabine, ipillimumab, irinotecan, nivolumab, paclitaxel, temozolomide, topotecan, vincristine, vinorelbine, and any combinations thereof.

Melanoma Combination Therapy:
Therapeutic agents used to treat melanoma cancer include albumin bound paclitaxel, carboplatin, cisplatin, cobiemtinib, dabrafenib, dacrabazine, IL-2, imatinib, interferon alfa-2b, ipilimumab, nitrosourea, nivolumab, paclitaxel, pembrolizumab, pilimumab, temozolomide, trametinib, vemurafenib, vinblastine, and any combinations thereof.

Ovarian Cancer Combination Therapy:

Therapeutic agents used to treat ovarian cancer include 5-flourouracil, albumin bound paclitaxel, altretamine, anastrozole, bevacizumab, capecitabine, carboplatin, cisplatin, cyclophosphamide, docetaxel, doxorubicin, etoposide, exemestane, gemcibabine, ifosfamide, irinotecan, letrozole, leuprolide acetate, liposomal doxorubicin, megestrol acetate, melphalan, olaparib, oxaliplatin, paclitaxel, Pazopanib, pemetrexed, tamoxifen, topotecan, vinorelbine, and any combinations thereof.

Pancreatic Cancer Combination Therapy:

Therapeutic agents used to treat pancreatic cancer include 5-fluorourcil, albumin-bound paclitaxel, capecitabine, cisplatin, docetaxel, erlotinib, fluoropyrimidine, gemcitabine, irinotecan, leucovorin, oxaliplatin, paclitaxel, and any combinations thereof.

Renal Cell Carcinoma Combination Therapy:

Therapeutic agents used to treat renal cell carcinoma include axitinib, bevacizumab, cabozantinib, erlotinib, everolimus, levantinib, nivolumab, pazopanib, sorafenib, sunitinib, temsirolimus, and any combinations thereof.

In one embodiment, the compound of formula (I) is useful for the treatment of cancer in combination with a standard of care in the treatment of the respective cancer. One of skill in the art is aware of the standard of care as of a given date in the particular field of cancer therapy or with respect to a given cancer.

Certain embodiments of the present application include or use one or more additional therapeutic agent. The one or more additional therapeutic agent may be an agent useful for the treatment of cancer, inflammation, autoimmune disease and/or related conditions. The one or more additional therapeutic agent may be a chemotherapeutic agent, an anti-angiogenic agent, an antifibrotic agent, an anti-inflammatory agent, an immune modulating agent, an immunotherapeutic agent, a therapeutic antibody, a radiotherapeutic agent, an anti-neoplastic agent, an anti-cancer agent, an anti-proliferation agent, or any combination thereof. In some embodiments, the compound(s) described herein may be used or combined with a chemotherapeutic agent, an anti-angiogenic agent, an anti-fibrotic agent, an anti-inflammatory agent, an immune modulating agent, an immunotherapeutic agent, a therapeutic antibody, a radiotherapeutic agent, an antineoplastic agent or an anti-cancer agent, an anti-proliferation agent, or any combination thereof.

In one embodiment, a compound(s) of formula (I) optionally in combination with an additional anticancer agent described herein, may be used or combined with an anti-neoplastic agent or an anti-cancer agent, anti-fibrotic agent, an anti-anti-inflammatory agent, or an immune modulating agent.

In one embodiment, provided are kits comprising a pharmaceutical composition comprising a compound of formula (I) or a pharmaceutically acceptable salt, or a compound of formula (I) and at least one additional anticancer agent, or a pharmaceutically acceptable salt thereof, and at least one pharmaceutically acceptable carrier. In one embodiment, the kit comprises instructions for use in the treatment of cancer or inflammatory conditions. In one embodiment, the instructions in the kit are directed to use of the pharmaceutical composition for the treatment of cancer selected from pancreatic cancer, bladder cancer, colorectal cancer, breast cancer, prostate cancer, renal cancer, hepatocellular cancer, lung cancer, ovarian cancer, cervical cancer, gastric cancer, esophageal cancer, head and neck cancer, melanoma, neuroendocrine cancer, CNS cancer, brain cancer, bone cancer, soft tissue sarcoma, non-small cell lung cancer, small-cell lung cancer and colon cancer.

The application also provides method for treating a subject who is undergoing one or more standard therapies, such as chemotherapy, radiotherapy, immunotherapy, surgery, or combination thereof comprising administering or co-administering a compound of formula (I) to said subject. Accordingly, one or more compound(S) of formula (I), or pharmaceutically acceptable salt thereof, may be administered before, during, or after administration of a chemotherapy, radiotherapy, immunotherapy, surgery or combination thereof.

In one embodiment, the subject may be a human who is (i) substantially refractory to at least one chemotherapy treatment, or (ii) in relapse after treatment with chemotherapy, or both (i) and (ii). In some of embodiments, the subject is refractory to at least two, at least three, or at least four chemotherapy treatments (including standard or experimental chemotherapies).

In one embodiment, the subject is refractory to at least one, at least two, at least three, or at least four chemotherapy treatment (including standard or experimental chemotherapy) selected from fludarabine, rituximab, obinutuzumab, alkylating agents, alemtuzumab and other chemotherapy treatments such as CHOP (cyclophosphamide, doxorubicin, vincristine, prednisone); R-CHOP (rituximab-CHOP); hyperCVAD (hyperfractionated cyclophosphamide, vincristine, doxorubicin, dexamethasone, methotrexate, cytarabine); R-hyperCVAD (rituximab-hyperCVAD); FCM (fludarabine, cyclophosphamide, mitoxantrone); R-FCM (rituximab, fludarabine, cyclophosphamide, mitoxantrone); bortezomib and rituximab; temsirolimus and rituximab; temsirolimus and Velcade®; Iodine-131 tositumomab (Bexxar®) and CHOP; CVP (cyclophosphamide, vincristine, prednisone); R-CVP (rituximab-CVP); ICE (iphosphamide, carboplatin, etoposide); R-ICE (rituximab-ICE); FCR (fludarabine, cyclophosphamide, rituximab); FR (fludarabine, rituximab); and D.T. PACE (dexamethasone, thalidomide, cisplatin, Adriamycin®, cyclophosphamide, etoposide).

Other examples of chemotherapy treatments (including standard or experimental chemotherapies) are described below. In addition, treatment of certain lymphomas is reviewed in Cheson, B. D., Leonard, J. P., "Monoclonal Antibody Therapy for B-Cell Non-Hodgkin's Lymphoma" *The New England Journal of Medicine* 2008, 359(6), p. 613-626; and Wierda, W. G., "Current and Investigational Therapies for Patients with CLL" *Hematology* 2006, p. 285-294. Lymphoma incidence patterns in the United States is profiled in Morton, L. M., et al. "Lymphoma Incidence Patterns by WHO Subtype in the United States, 1992-2001" *Blood* 2006, 107(1), p. 265-276.

Examples of immunotherapeutic agents treating lymphoma or leukemia include, but are not limited to, rituximab (such as Rituxan), alemtuzumab (such as Campath, MabCampath), anti-CD19 antibodies, anti-CD20 antibodies, anti-MN-14 antibodies, anti-TRAIL, Anti-TRAIL DR4 and DR5 antibodies, anti-CD74 antibodies, apolizumab, bevacizumab, CHIR-12.12, epratuzumab (hLL2-anti-CD22 humanized antibody), galiximab, ha20, ibritumomab tiuxetan, lumiliximab, milatuzumab, ofatumumab, PRO 131921, SGN-40, WT-1 analog peptide vaccine, WT1 126-134 peptide vaccine, tositumomab, autologous human tumor-derived HSPPC-96, and veltuzumab. Additional immunotherapy agents includes using cancer vaccines based upon the genetic makeup of an individual patient's tumor, such as lymphoma vaccine example is GTOP-99 (MyVax®).

Examples of chemotherapy agents for treating lymphoma or leukemia include aldesleukin, alvocidib, antineoplaston AS2-1, antineoplaston A10, anti-thymocyte globulin, amifostine trihydrate, aminocamptothecin, arsenic trioxide, beta alethine, Bcl-2 family protein inhibitor ABT-263, BMS-345541, bortezomib (Velcade®), bryostatin 1, busulfan, carboplatin, campath-1H, CC-5103, carmustine, caspofungin acetate, clofarabine, cisplatin, Cladribine (Leustarin), Chlorambucil (Leukeran), Curcumin, cyclosporine, Cyclophosphamide (Cyloxan, Endoxan, Endoxana, Cyclostin), cytarabine, denileukin diftitox, dexamethasone, DT PACE, docetaxel, dolastatin 10, Doxorubicin (Adriamycin®, Adriblastine), doxorubicin hydrochloride, enzastaurin, epoetin alfa, etoposide, Everolimus (RAD001), fenretinide, filgrastim, melphalan, mesna, Flavopiridol, Fludarabine (Fludara), Geldanamycin (17-AAG), ifosfamide, irinotecan hydrochloride, ixabepilone, Lenalidomide (Revlimid®, CC-5013), lymphokine-activated killer cells, melphalan, methotrexate, mitoxantrone hydrochloride, motexafin gadolinium, mycophenolate mofetil, nelarabine, oblimersen (Genasense) Obatoclax (GX15-070), oblimersen, octreotide acetate, omega-3 fatty acids, oxaliplatin, paclitaxel, PD0332991, PEGylated liposomal doxorubicin hydrochloride, pegfilgrastim, Pentstatin (Nipent), perifosine, Prednisolone, Prednisone, R-roscovitine (Selicilib, CYC202), recombinant interferon alfa, recombinant interleukin-12, recombinant interleukin-11, recombinant flt3 ligand, recombinant human thrombopoietin, rituximab, sargramostim, sildenafil citrate, simvastatin, sirolimus, Styryl sulphones, tacrolimus, tanespimycin, Temsirolimus (CCI-779), Thalidomide, therapeutic allogeneic lymphocytes, thiotepa, tipifarnib, Velcade® (bortezomib or PS-341), Vincristine (Oncovin), vincristine sulfate, vinorelbine ditartrate, Vorinostat (SAHA), vorinostat, and FR (fludarabine, rituximab), CHOP (cyclophosphamide, doxorubicin, vincristine, prednisone), CVP (cyclophosphamide, vincristine and prednisone), FCM (fludarabine, cyclophosphamide, mitoxantrone), FCR (fludarabine, cyclophosphamide, rituximab), hyperCVAD (hyperfractionated cyclophosphamide, vincristine, doxorubicin, dexamethasone, methotrexate, cytarabine), ICE (iphosphamide, carboplatin and etoposide), MCP (mitoxantrone, chlorambucil, and prednisolone), R-CHOP (rituximab plus CHOP), R-CVP (rituximab plus CVP), R-FCM (rituximab plus FCM), R-ICE (rituximab-ICE), and R-MCP (Rituximab-MCP).

In some embodiments, the cancer is melanoma. Suitable agents for use in combination with the compounds described herein include, without limitation, dacarbazine (DTIC), optionally, along with other chemotherapy drugs such as carmustine (BCNU) and cisplatin; the "Dartmouth regimen," which consists of DTIC, BCNU, cisplatin and tamoxifen; a combination of cisplatin, vinblastine, and DTIC, temozolomide or YERVOY™. Compounds disclosed herein may also be combined with immunotherapy drugs, including cytokines such as interferon alpha, interleukin 2, and tumor necrosis factor (TNF) in the treatment of melanoma.

Compounds described here may also be used in combination with vaccine therapy in the treatment of melanoma. Anti-melanoma vaccines are, in some ways, similar to the anti-virus vaccines which are used to prevent diseases caused by viruses such as polio, measles, and mumps. Weakened melanoma cells or parts of melanoma cells called antigens may be injected into a patient to stimulate the body's immune system to destroy melanoma cells.

Melanomas that are confined to the arms or legs may also be treated with a combination of agents including one or more compounds described herein, using for example, a hyperthermic isolated limb perfusion technique. This treatment protocol temporarily separates the circulation of the involved limb from the rest of the body and injects high doses of chemotherapy into the artery feeding the limb, thus providing high doses to the area of the tumor without exposing internal organs to these doses that might otherwise cause severe side effects. Usually the fluid is warmed to 102° to 104° F. Melphalan is the drug most often used in this chemotherapy procedure. This can be given with another agent called tumor necrosis factor (TNF) and optionally in combination with a compound of formula (I).

The therapeutic treatments can be supplemented or combined with any of the aforementioned therapies with stem cell transplantation or treatment. One example of modified approach is radioimmunotherapy, wherein a monoclonal antibody is combined with a radioisotope particle, such as indium In 111, yttrium Y 90, iodine I-131. Examples of combination therapies include, but are not limited to, Iodine-131 tositumomab (Bexxar®), Yttrium-90 ibritumomab tiuxetan (Zevalin®), Bexxar® with CHOP.

Other therapeutic procedures useful in combination with treatment with a compound of formula (I) include peripheral blood stem cell transplantation, autologous hematopoietic stem cell transplantation, autologous bone marrow transplantation, antibody therapy, biological therapy, enzyme inhibitor therapy, total body irradiation, infusion of stem cells, bone marrow ablation with stem cell support, in vitro-treated peripheral blood stem cell transplantation, umbilical cord blood transplantation, immunoenzyme technique, pharmacological study, low-LET cobalt-60 gamma ray therapy, bleomycin, conventional surgery, radiation therapy, and nonmyeloablative allogeneic hematopoietic stem cell transplantation.

In some embodiments, the application provides pharmaceutical compositions comprising a compound of formula (I) in combination with an MMP9 binding protein and/or one or more additional therapeutic agent, and a pharmaceutically acceptable diluent, carrier or excipient. In one embodiment, the pharmaceutical compositions comprise an MMP9 binding protein, one or more additional therapeutic agent, and a pharmaceutically acceptable excipient, carrier or diluent. In some embodiments, the pharmaceutical compositions comprise the compound of formula (I) and anti-MMP9 antibody AB0045.

In one embodiment, the pharmaceutical compositions comprise the compound of formula (I), anti-MMP9 antibody AB0045, at least one additional therapeutic agent that is an immunomodulating agent, and a pharmaceutically acceptable diluent, carrier or excipient. In certain other embodiments, the pharmaceutical compositions comprise the anti-MMP9 antibody AB0045, at least one additional therapeutic agent that is an anti-inflammatory agent, and a pharmaceutically acceptable diluent, carrier or excipient. In certain other embodiments, the pharmaceutical compositions comprise compound of formula (I), the anti-MMP9 antibody AB0045, at least one additional therapeutic agent that is an antineoplastic agent or anti-cancer agent, and a pharmaceutically acceptable diluent, carrier or excipient. In one embodiment, MMP9 compounds useful for combination treatment with a compound of formula (I) include but are not limited to marimastat (BB-2516), cipemastat (Ro 32-3555) and those described in WO 2012/027721 (Gilead Biologics).

In one embodiment, the one or more additional therapeutic agent is an immune modulating agent, e.g., an immunostimulant or an immunosuppressant. In certain other embodiments, an immune modulating agent is an agent capable of altering the function of immune checkpoints, including the CTLA-4, LAG-3, B7-H3, B7-H4, Tim3, BTLA, KIR, A2aR, CD200 and/or PD-1 pathways. In other embodiments, the immune modulating agent is immune checkpoint modulating agents. Exemplary immune checkpoint modulating agents include anti-CTLA-4 antibody (e.g., ipilimumab), anti-LAG-3 antibody, anti-B7-H3 antibody, anti-B7-H4 antibody, anti-Tim3 antibody, anti-BTLA antibody, anti-KIR antibody, anti-A2aR antibody, anti CD200 antibody, anti-PD-1 antibody, anti-PD-L1 antibody, anti-CD28 antibody, anti-CD80 or -CD86 antibody, anti-B7RP1 antibody, anti-B7-H3 antibody, anti-HVEM antibody, anti-CD137 or -CD137L antibody, anti-OX40 or -OX40L antibody, anti-CD40 or -CD40L antibody, anti-GAL9 antibody, anti-IL-10 antibody and A2aR drug. For certain such immune pathway gene products, the use of either antagonists or agonists of such gene products is contemplated, as are small molecule modulators of such gene products. In one embodiment, the immune modulatory agent is an anti-PD-1 or anti-PD-L1 antibody. In some embodiments, immune modulating agents include those agents capable of altering the function of mediators in cytokine mediated signaling pathways.

In some embodiments, the one or more additional therapy or anti-cancer agent is cancer gene therapy or cell therapy. Cancer gene therapy and cell therapy include the insertion of a normal gene into cancer cells to replace a mutated or altered gene; genetic modification to silence a mutated gene; genetic approaches to directly kill the cancer cells; including the infusion of immune cells designed to replace most of the patient's own immune system to enhance the immune response to cancer cells, or activate the patient's own immune system (T cells or Natural Killer cells) to kill cancer cells, or find and kill the cancer cells; genetic approaches to modify cellular activity to further alter endogenous immune responsiveness against cancer. Non limiting examples are Algenpantucel-L (2 pancreatic cell lines), Sipuleucel-T, SGT-53 liposomal nanodelivery (scL) of gene p53; T-cell therapy, such as CD19 CAR-T tisagenlecleucel-T (CTL019) WO2012079000, WO2017049166, axicabtagene ciloleucel (KTE-C19) U.S. Pat. Nos. 7,741,465, 6,319,494, JCAR-015 U.S. Pat. No. 7,446,190, JCAR-014, JCAR-020, JCAR-024, JCAR-023, JTCR-016, JCAR-018 WO2016090190, JCAR-017, (WO2016196388, WO2016033570, WO2015157386), BPX-501 U.S. Pat. No. 9,089,520, WO2016100236, AU-105, UCART-22, ACTR-087, P-BCMA-101; activated allogeneic natural killer cells CNDO-109-AANK, FATE-NK100, LFU-835 hematopoietic stem cells.

In one embodiment, the one or more additional therapeutic agent is an immune checkpoint inhibitor. Tumors subvert the immune system by taking advantage of a mechanism known as T-cell exhaustion, which results from chronic exposure to antigens and is characterized by the up-regulation of inhibitory receptors. These inhibitory receptors serve as immune checkpoints in order to prevent uncontrolled immune reactions.

PD-1 and co-inhibitory receptors such as cytotoxic T-lymphocyte antigen 4 (CTLA-4, B and T Lymphocyte Attenuator (BTLA; CD272), T cell Immunoglobulin and Mucin domain-3 (Tim-3), Lymphocyte Activation Gene-3 (Lag-3; CD223), and others are often referred to as a checkpoint regulators. They act as molecular determinants to influence whether cell cycle progression and other intracellular signaling processes should proceed based upon extracellular information.

In addition to specific antigen recognition through the T-cell receptor (TCR), T-cell activation is regulated through a balance of positive and negative signals provided by costimulatory receptors. These surface proteins are typically members of either the TNF receptor or B7 superfamilies. Agonistic antibodies directed against activating co-stimulatory molecules and blocking antibodies against negative co-stimulatory molecules may enhance T-cell stimulation to promote tumor destruction.

Programmed Cell Death Protein 1, (PD-1 or CD279), a 55-kD type 1 transmembrane protein, is a member of the CD28 family of T cell co-stimulatory receptors that include immunoglobulin superfamily member CD28, CTLA-4, inducible co-stimulator (ICOS), and BTLA. PD-1 is highly expressed on activated T cells and B cells. PD-1 expression can also be detected on memory T-cell subsets with variable levels of expression. Two ligands specific for PD-1 have been identified: programmed death-ligand 1 (PD-L1, also known as B7-H1 or CD274) and PD-L2 (also known as B7-DC or CD273). PD-L1 and PD-L2 have been shown to down-regulate T cell activation upon binding to PD-1 in both mouse and human systems (Okazaki et al., *Int. Immunol.*, 2007; 19: 813-824). The interaction of PD-1 with its ligands, PD-L1 and PD-L2, which are expressed on antigen-presenting, cells (APCs) and dendritic cells (DCs), transmits negative regulatory stimuli to down-modulate the activated T cell immune response. Blockade of PD-1 suppresses this negative signal and amplifies T cell responses. Numerous studies indicate that the cancer microenvironment manipulates the PD-L1/PD-1 signaling pathway and that induction of PD-L1 expression is associated with inhibition of immune responses against cancer, thus permitting cancer progression and metastasis. The PD-L1/PD-1 signaling pathway is a primary mechanism of cancer immune evasion for several reasons. This pathway is involved in negative regulation of immune responses of activated T effector cells found in the periphery. PD-L1 is up-regulated in cancer microenvironments, while PD-1 is also up-regulated on activated tumor infiltrating T cells, thus possibly potentiating a vicious cycle of inhibition. This pathway is also intricately involved in both innate and adaptive immune regulation through bi-directional signaling. These factors make the PD-1/PD-L1 complex a central point through which cancer can manipulate immune responses and promote its own progression.

The first immune-checkpoint inhibitor to be tested in a clinical trial was ipilimumab (Yervoy, Bristol-Myers Squibb), a CTLA-4 mAb. CTLA-4 belongs to the immunoglobulin superfamily of receptors, which also includes PD-1, BTLA, TIM-3, and V-domain immunoglobulin suppressor of T cell activation (VISTA). Anti-CTLA-4 mAb is a powerful checkpoint inhibitor which removes "the break" from both naive and antigen-experienced cells.

Therapy enhances the antitumor function of CD8+ T cells, increases the ratio of CD8+ T cells to Foxp3+ T regulatory cells, and inhibits the suppressive function of T regulatory cells. TIM-3 has been identified as another important inhibitory receptor expressed by exhausted CD8+ T cells. In mouse models of cancer, it has been shown that the most dysfunctional tumor-infiltrating CD8+ T cells actually co-express PD-1 and LAG-3. LAG-3 is another recently identified inhibitory receptor that acts to limit effector T-cell function and augment the suppressive activity of T regulatory cells. It has recently been revealed that PD-1 and LAG-3 are extensively co-expressed by tumor-infiltrating T cells in mice, and that combined blockade of PD-1 and LAG-3 provokes potent synergistic antitumor immune responses in mouse models of cancer.

Thus in one embodiment, the present disclosure provides the use of immune checkpoint inhibitors of formula (I) disclosed herein in combination with one or more additional immune checkpoint inhibitors. In one embodiment, the present disclosure provides the use of immune checkpoint inhibitors of formula (I) disclosed herein in combination with one or more additional immune checkpoint inhibitors and an anti-MMP9 antibody or antigen binding fragment thereof to treat or prevent cancer. In some embodiments, the immune checkpoint inhibitors may be an anti-PD-1 and/or an anti-PD-L1 antibody or an anti PD-1/PD-L1 interaction inhibitor. In some embodiments, the anti-PD-L1 antibody may be B7-H1 antibody, BMS 936559 antibody, MPDL3280A (atezolizumab) antibody, MEDI-4736 antibody, MSB0010718C antibody or combinations thereof. According to another embodiment, the anti-PD-1 antibody may be nivolumab antibody, pembrolizumab antibody, pidilizumab antibody or combinations thereof.

In addition, PD-1 may also be targeted with AMP-224, which is a PD-L2-IgG recombinant fusion protein. Additional antagonists of inhibitory pathways in the immune response include IMP321, a soluble LAG-3 Ig fusion protein and MHC class II agonist, which is used to increase an immune response to tumors. Lirilumab is an antagonist to the KIR receptor and BMS 986016 is an antagonist of LAG3. The TIM-3-Galectin-9 pathway is another inhibitory checkpoint pathway that is also a promising target for checkpoint inhibition. RX518 targets and activates the glucocorticoid-induced tumor necrosis factor receptor (GITR), a member of the TNF receptor superfamily that is expressed on the surface of multiple types of immune cells, including regulatory T cells, effector T cells, B cells, natural killer (NK) cells, and activated dendritic cells. Thus. in one embodiment, the compound(s) of formula (I) may be used in combination with IMP321, Lirilumab and/or BMS 986016.

Anti-PD-1 antibodies that may be used in the compositions and methods described herein include but are not limited to: Nivolumab/MDX-1106/BMS-936558/ONO1152, a fully human 1gG4 anti-PD-1 monoclonal antibody; pidilizumab (MDV9300/CT-011), a humanized 1gG1 monoclonal antibody; pembrolizumab (MK-3475/pembrolizumab/lambrolizumab), a humanized monoclonal IgG4 antibody; durvalumab (MEDI-4736) and atezolizumab. Anti-PD-L1 antibodies that may be used in compositions and methods described herein include but are not limited to: avelumab; BMS-936559, a fully human IgG4 antibody; atezolizumab (MPDL3280A/RG-7446), a human monoclonal antibody; MEDI4736; MSB0010718C, and MDX1105-01.

In one embodiment, the compound of formula (I) is administered in combination with the anti-PD-1 antibody nivolumab, pembrolizumab, and/or pidilizumab to a patient in need thereof. In one embodiment, the anti-PD-L1 antibody useful for combination treatment with a compound of formula (I) is BMS-936559, atezolizumab, or avelumab. In one embodiment, the immune modulating agent inhibits an immune checkpoint pathway. In another embodiment, the immune checkpoint pathway is selected from CTLA-4, LAG-3, B7-H3, B7-H4, Tim3, BTLA, KIR, A2aR, CD200 and PD-1. Additional antibodies that may be used in combination with a compound of formula (I) in compositions and methods described herein include the anti-PD-1 and anti-PD-L1 antibodies disclosed in U.S. Pat. Nos. 8,008,449 and 7,943,743, respectively.

In one embodiment, the one or more additional therapeutic agent is an anti-inflammatory agent. In certain other embodiments, the anti-inflammatory agent is a tumor necrosis factor alpha (TNF-α) inhibitor. As used herein, the terms "TNF alpha," "TNF-α," and "TNFα," are interchangeable. TNF-α is a pro-inflammatory cytokine secreted primarily by macrophages but also by a variety of other cell types including lymphoid cells, mast cells, endothelial cells, cardiac myocytes, adipose tissue, fibroblasts, and neuronal tissue. TNF-α is also known as endotoxin-induced factor in serum, cachectin, and differentiation inducing factor. The tumor necrosis factor (TNF) family includes TNF alpha, TNF beta, CD40 ligand (CD40L), Fas ligand (FasL), TNF-related apoptosis inducing ligand (TRAIL), and LIGHT (homologous to lymphotoxins, exhibits inducible expression, and competes with HSV glycoprotein D for HVEM, a receptor expressed by T lymphocytes), some of the most important cytokines involved in, among other physiological processes, systematic inflammation, tumor lysis, apoptosis and initiation of the acute phase reaction.

The above therapeutic agents when employed in combination with a compound(s) disclosed herein, may be used, for example, in those amounts indicated in the referenced manuals e.g., Physicians Desk Reference or in amounts generally known to a qualified care giver, i.e., one of ordinary skill in the art. In the methods of the present disclosure, such other therapeutic agent(s) may be administered prior to, simultaneously with, or following the administration of the compound(s) of formula (I). Certain other therapeutic agents may be combined into a single formulation or kit when amenable to such. For example, tablet, capsule or liquid formulations may be combined with other tablet, capsule or liquid formulations into one fixed or combined dose formulation or regimen. Other combinations may be given separately, contemporaneously or otherwise.

Combination Therapy for HBV

In certain embodiments, a method for treating or preventing an HBV infection in a human having or at risk of having the infection is provided, comprising administering to the human a therapeutically effective amount of a compound disclosed herein, or a pharmaceutically acceptable salt thereof, in combination with a therapeutically effective amount of one or more (e.g., one, two, three, four, one or two, one to three, or one to four) additional therapeutic agents. In one embodiment, a method for treating an HBV infection in a human having or at risk of having the infection is provided, comprising administering to the human a therapeutically effective amount of a compound disclosed herein, or a pharmaceutically acceptable salt thereof, in combination with a therapeutically effective amount of one or more (e.g., one, two, three, four, one or two, one to three, or one to four) additional therapeutic agents.

In certain embodiments, the present disclosure provides a method for treating an HBV infection, comprising administering to a patient in need thereof a therapeutically effective amount of a compound disclosed herein or a pharmaceutically acceptable salt thereof, in combination with a therapeutically effective amount of one or more (e.g., one, two, three, four, one or two, one to three, or one to four) additional therapeutic agents which are suitable for treating an HBV infection.

In certain embodiments, a compound disclosed herein, or a pharmaceutically acceptable salt thereof, is combined with one, two, three, four, or more additional therapeutic agents. In certain embodiments, a compound disclosed herein, or a pharmaceutically acceptable salt thereof, is combined with two additional therapeutic agents. In other embodiments, a compound disclosed herein, or a pharmaceutically acceptable salt thereof, is combined with three additional therapeutic agents. In further embodiments, a compound disclosed herein, or a pharmaceutically acceptable salt thereof, is combined with four additional therapeutic agents. The one, two, three, four, or more additional therapeutic agents can be different therapeutic agents selected from the same class of therapeutic agents, and/or they can be selected from different classes of therapeutic agents.

Administration of HBV Combination Therapy

In certain embodiments, when a compound disclosed herein is combined with one or more additional therapeutic agents as described above, the components of the composition are administered as a simultaneous or sequential regimen. When administered sequentially, the combination may be administered in two or more administrations.

Co-administration of a compound disclosed herein with one or more additional therapeutic agents generally refers to simultaneous or sequential administration of a compound disclosed herein and one or more additional therapeutic agents, such that therapeutically effective amounts of each agent are present in the body of the patient.

Co-administration includes administration of unit dosages of the compounds disclosed herein before or after administration of unit dosages of one or more additional therapeutic agents. The compound disclosed herein may be administered within seconds, minutes, or hours of the administration of one or more additional therapeutic agents. For example, in some embodiments, a unit dose of a compound disclosed herein is administered first, followed within seconds or minutes by administration of a unit dose of one or more additional therapeutic agents. Alternatively, in other embodiments, a unit dose of one or more additional therapeutic agents is administered first, followed by administration of a unit dose of a compound disclosed herein within seconds or minutes. In some embodiments, a unit dose of a compound disclosed herein is administered first, followed, after a period of hours (e.g., 1-12 hours), by administration of a unit dose of one or more additional therapeutic agents. In other embodiments, a unit dose of one or more additional therapeutic agents is administered first, followed, after a period of hours (e.g., 1-12 hours), by administration of a unit dose of a compound disclosed herein.

In certain embodiments, a compound disclosed herein is combined with one or more additional therapeutic agents in a unitary dosage form for simultaneous administration to a patient, for example as a solid dosage form for oral administration.

In certain embodiments a compound of Formula (I) is formulated as a tablet, which may optionally contain one or more other compounds useful for treating hepatitis B virus (HBV). In certain embodiments, the tablet can contain another active ingredient for treating hepatitis B virus (HBV).

In certain embodiments, such tablets are suitable for once daily dosing.

The compounds described herein may be used or combined with one or more of a chemotherapeutic agent, an immunomodulator, an immunotherapeutic agent, a therapeutic antibody, a therapeutic vaccine, a bispecific antibody and "antibody-like" therapeutic protein (such as DARTs®, Duobodies®, Bites®, XmAbs®, TandAbs®, Fab derivatives), an antibody-drug conjugate (ADC), gene modifiers or gene editors (such as CRISPR Cas9, zinc finger nucleases, homing endonucleases, synthetic nucleases, TALENs), cell therapies such as CAR-T (chimeric antigen receptor T-cell), and TCR-T (an engineered T cell receptor) agent or any combination thereof.

In the above embodiments, the additional therapeutic agent may be an anti-HBV agent. For example, the additional therapeutic agent may be selected from the group consisting of HBV combination drugs, other drugs for treating hepatitis B virus (HBV), 3-dioxygenase (IDO) inhibitors, antisense oligonucleotide targeting viral mRNA, Apolipoprotein A1 modulator, arginase inhibitors, B- and T-lymphocyte attenuator inhibitors, Bruton's tyrosine kinase (BTK) inhibitors, CCR2 chemokine antagonist, CD137 inhibitors, CD160 inhibitors, CD305 inhibitors, CD4 agonist and modulator, compounds targeting HBcAg, compounds targeting hepatitis B core antigen (HBcAg), covalently closed circular DNA (cccDNA) inhibitors, cyclophilin inhibitors, cytokines, cytotoxic T-lymphocyte-associated protein 4 (ipi4) inhibitors, DNA polymerase inhibitor, Endonuclease modulator, epigenetic modifiers, Farnesoid X receptor agonist, gene modifiers or editors, HBsAg inhibitors, HBsAg secretion or assembly inhibitors, HBV antibodies, HBV DNA polymerase inhibitors, HBV replication inhibitors, HBV RNAse inhibitors, HBV vaccines, HBV viral entry inhibitors, HBx inhibitors, Hepatitis B large envelope protein modulator, Hepatitis B large envelope protein stimulator, Hepatitis B structural protein modulator, hepatitis B surface antigen (HBsAg) inhibitors, hepatitis B surface antigen (HBsAg) secretion or assembly inhibitors, hepatitis B virus E antigen inhibitors, hepatitis B virus replication inhibitors, Hepatitis virus structural protein inhibitor, HIV-1 reverse transcriptase inhibitor, Hyaluronidase inhibitor, IAPs inhibitors, IL-2 agonist, IL-7 agonist, Immunoglobulin agonist, Immunoglobulin G modulator, immunomodulators, indoleamine-2, inhibitors of ribonucleotide reductase, Interferon agonist, Interferon alpha 1 ligand, Interferon alpha 2 ligand, Interferon alpha 5 ligand modulator, Interferon alpha ligand, Interferon alpha ligand modulator, interferon alpha receptor ligands, Interferon beta ligand, Interferon ligand, Interferon receptor modulator, Interleukin-2 ligand, ipi4 inhibitors, lysine demethylase inhibitors, histone demethylase inhibitors, KDM5 inhibitors, KDM1 inhibitors, killer cell lectin-like receptor subfamily G member 1 inhibitors, lymphocyte-activation gene 3 inhibitors, lymphotoxin beta receptor activators, microRNA (miRNA) gene therapy agents, modulators of Ax1, modulators of B7-H3, modulators of B7-H4, modulators of CD160, modulators of CD161, modulators of CD27, modulators of CD47, modulators of CD70, modulators of GITR, modulators of HEVEM, modulators of ICOS, modulators of Mer, modulators of NKG2A, modulators of NKG2D, modulators of OX40, modulators of SIRPalpha, modulators of TIGIT, modulators of Tim-4, modulators of Tyro, Na+-taurocholate cotransporting polypeptide (NTCP) inhibitors, natural killer cell receptor 2B4 inhibitors, NOD2 gene stimulator, Nucleoprotein inhibitor, nucleoprotein modulators, PD-1 inhibitors, PD-L1 inhibitors, PEG-Interferon Lambda, Peptidylprolyl isomerase inhibitor, phosphatidylinositol-3 kinase (PI3K) inhibitors, recombinant scavenger receptor A (SRA) proteins, recombinant thymosin alpha-1, Retinoic acid-inducible gene 1 stimulator, Reverse transcriptase inhibitor, Ribonuclease inhibitor, RNA DNA polymerase inhibitor, short interfering RNAs (siRNA), short synthetic hairpin RNAs (sshRNAs), SLC10A1 gene inhibitor, SMAC mimetics, Src tyrosine kinase inhibitor, stimulator of interferon gene (STING) agonists, stimulators of NOD1, T cell surface glycoprotein CD28 inhibitor, T-cell surface glycoprotein CD8 modulator, Thymosin agonist, Thymosin alpha 1 ligand, Tim-3 inhibitors, TLR-3 agonist, TLR-7 agonist, TLR-9 agonist, TLR9 gene stimulator, toll-like receptor (TLR) modulators, Viral ribonucleotide reductase inhibitor, zinc finger nucleases or synthetic nucleases (TALENs), and combinations thereof.

In some embodiments, provided herein is a method for treating hepatitis B virus (HBV) in a patient in need thereof, comprising administering an effective amount of a compound described herein in combination with an effective amount of one or more anti-HCV agents, such as a NS5A inhibitor, a NS5B inhibitor, a NS3 inhibitor, or a combination thereof.

In some embodiments, provided is a method of treating hepatitis B virus (HBV) infection in a human in need thereof, comprising administering to the patient an effective amount of a compound described herein in combination with an effective amount of a NS5A inhibitor. In some embodiments, the NS5A inhibitor is ledipasvir or velpatasvir. In some embodiments, is provided a method of treating hepatitis B virus (HBV) infection in a human in need thereof, comprising administering to the patient an effective amount of a compound described herein in combination with an effective amount of a NS5B inhibitor. In some embodiments, the NS5B inhibitor is sofosbuvir or mericitabine. In some embodiments, is provided a method of treating hepatitis B virus (HBV) infection in a human in need thereof, comprising administering to the patient an effective amount of a compound described herein in combination with an effective amount of a NS3 inhibitor. In some embodiments, the NS3 inhibitor is voxilaprevir.

In some embodiments, the patient is administered an effective amount of a compound described herein in combination with an effective amount of both an effective amount of a NS5A inhibitor and an effective amount of a NS5B inhibitor. In some embodiments, the NS5A inhibitor is ledipasvir and the NS5B inhibitor is sofosbuvir. In some embodiments, the patient is administered an effective amount of a compound described herein in combination with an effective amount of a fixed dose combination of a NS5A inhibitor and a NS5B inhibitor. In some embodiments, the patient is administered an effective amount of a compound described herein in combination with an effective amount of a fixed dose combination of ledipasvir and sofosbuvir.

In some embodiments, the patient is administered an effective amount of a compound of Table 1 in combination with an effective amount of both an effective amount of a NS5A inhibitor and an effective amount of a NS5B inhibitor. In some embodiments, the NS5A inhibitor is ledipasvir and the NS5B inhibitor is sofosbuvir. In some embodiments, the patient is administered an effective amount of a compound of Table 1 in combination with an effective amount of a fixed dose combination of a NS5A inhibitor and a NS5B inhibitor. In some embodiments, the patient is administered an effective amount of a compound of Table 1 in combination with an effective amount of a fixed dose combination of ledipasvir and sofosbuvir (e.g., ledipasvir 90 mg/sofosbuvir 400 mg). In some embodiments, the patient is administered an effective amount of a compound of Table 1 in combination with an effective amount of Harvoni®. In some embodiments, the patient is administered an effective amount of a compound of Table 1 in combination with an effective amount of a fixed dose combination of velpatasvir and sofosbuvir (e.g., velpatasvir 100 mg/sofosbuvir 400 mg). In some embodiments, the patient is administered an effective amount of a compound of Table 1 in combination with an effective amount of Epclusa®.

In some embodiments, the patient is administered an effective amount of compound 139 in combination with an effective amount of both an effective amount of a NS5A inhibitor and an effective amount of a NS5B inhibitor. In some embodiments, the NS5A inhibitor is ledipasvir and the NS5B inhibitor is sofosbuvir. In some embodiments, the patient is administered an effective amount of compound 139 in combination with an effective amount of a fixed dose combination of a NS5A inhibitor and a NS5B inhibitor. In some embodiments, the patient is administered an effective amount of compound 139 in combination with an effective amount of a fixed dose combination of ledipasvir and sofosbuvir (e.g., ledipasvir 90 mg/sofosbuvir 400 mg). In some embodiments, the patient is administered an effective amount of compound 139 in combination with an effective amount of Harvoni®. In some embodiments, the patient is administered an effective amount of compound 139 in combination with an effective amount of a fixed dose combination of velpatasvir and sofosbuvir (e.g., velpatasvir 100 mg/sofosbuvir 400 mg). In some embodiments, the patient is administered an effective amount of compound 139 in combination with an effective amount of Epclusa®.

In some embodiments, the patient is administered an effective amount of a compound described herein in combination with an effective amount of both an effective amount of a NS5A inhibitor and an effective amount of a NS5B inhibitor, and optionally a NS3 inhibitor. In some embodiments, the patient is administered an effective amount of a compound described herein in combination with an effective amount of sofosbuvir, velpatasvir, and voxilaprevir (e.g., sofosbuvir 400 mg/velpatasvir 100 mg/voxilaprevir 100 mg). In some embodiments, the patient is administered an effective amount of a compound described herein (e.g., compound 139) in combination with an effective amount of Vosevi™ In certain embodiments, a compound of Formula (I) is formulated as a tablet, which may optionally contain one or more other compounds useful for treating hepatitis B virus (HBV). In certain embodiments, the tablet can contain another active ingredient for treating hepatitis B virus (HBV), such as 3-dioxygenase (IDO) inhibitors, Apolipoprotein A1 modulator, arginase inhibitors, B- and T-lymphocyte attenuator inhibitors, Bruton's tyrosine kinase (BTK) inhibitors, CCR2 chemokine antagonist, CD137 inhibitors, CD160 inhibitors, CD305 inhibitors, CD4 agonist and modulator, compounds targeting HBcAg, compounds targeting hepatitis B core antigen (HBcAg), core protein allosteric modulators, covalently closed circular DNA (cccDNA) inhibitors, cyclophilin inhibitors, cytotoxic T-lymphocyte-associated protein 4 (ipi4) inhibitors, DNA polymerase inhibitor, Endonuclease modulator, epigenetic modifiers, Farnesoid X receptor agonist, HBsAg inhibitors, HBsAg secretion or assembly inhibitors, HBV DNA polymerase inhibitors, HBV replication inhibitors, HBV RNAse inhibitors, HBV viral entry inhibitors, HBx inhibitors, Hepatitis B large envelope protein modulator, Hepatitis B large envelope protein stimulator, Hepatitis B structural protein modulator, hepatitis B surface antigen (HBsAg) inhibitors, hepatitis B surface antigen (HBsAg) secretion or assembly inhibitors, hepatitis B virus E antigen inhibitors, hepatitis B virus replication inhibitors, Hepatitis virus structural protein inhibitor, HIV-1 reverse transcriptase inhibitor, Hyaluronidase inhibitor, IAPs inhibitors, IL-2 agonist, IL-7 agonist, immunomodulators, indoleamine-2 inhibitors, inhibitors of ribonucleotide reductase, Interleukin-2 ligand, ipi4 inhibitors, lysine demethylase inhibitors, histone demethylase inhibitors, KDM1 inhibitors, KDM5 inhibitors, killer cell lectin-like receptor subfamily G member 1 inhibitors, lymphocyte-activation gene 3 inhibitors, lymphotoxin beta receptor activators, modulators of Ax1, modulators of B7-H3, modulators of B7-H4, modulators of CD160, modulators of CD161, modulators of CD27, modulators of CD47, modulators of CD70, modulators of GITR, modulators of HEVEM, modulators of ICOS, modulators of Mer, modulators of NKG2A, modulators of NKG2D, modulators of OX40, modulators of SIRPalpha, modulators of TIGIT, modulators of Tim-4, modulators of Tyro, Na+-taurocholate cotransporting polypeptide (NTCP) inhibitors, natural killer cell receptor 2B4 inhibitors, NOD2 gene stimulator, Nucleoprotein inhibitor, nucleoprotein modulators, PD-1 inhibitors, PD-L1 inhibitors, Peptidylprolyl isomerase inhibitor, phosphatidylinositol-3 kinase (PI3K) inhibitors, Retinoic acid-inducible gene 1 stimulator, Reverse transcriptase inhibitor, Ribonuclease inhibitor, RNA DNA polymerase inhibitor, SLC10A1 gene inhibitor, SMAC mimetics, Src tyrosine kinase inhibitor, stimulator of interferon gene (STING) agonists, stimulators of NOD1, T cell surface glycoprotein CD28 inhibitor, T-cell surface glycoprotein CD8 modulator, Thymosin agonist, Thymosin alpha 1 ligand, Tim-3 inhibitors, TLR-3 agonist, TLR-7 agonist, TLR-9 agonist, TLR9 gene stimulator, toll-like receptor (TLR) modulators, Viral ribonucleotide reductase inhibitor, and combinations thereof.

In certain embodiments, a compound of the present disclosure, or a pharmaceutically acceptable salt thereof, is combined with one, two, three, four or more additional therapeutic agents selected from HBV combination drugs, HBV vaccines, HBV DNA polymerase inhibitors, immunomodulators toll-like receptor (TLR) modulators, interferon alpha receptor ligands, hyaluronidase inhibitors, hepatitis b surface antigen (HBsAg) inhibitors, cytotoxic T-lymphocyte-associated protein 4 (ipi4) inhibitors, cyclophilin inhibitors, HBV viral entry inhibitors, antisense oligonucleotide targeting viral mRNA, short interfering RNAs (siRNA) and ddRNAi endonuclease modulators, ribonucleotide reductase inhibitors, HBV E antigen inhibitors, covalently closed circular DNA (cccDNA) inhibitors, farnesoid X receptor agonists, HBV antibodies, CCR2 chemokine antagonists, thymosin agonists, cytokines, nucleoprotein modulators, retinoic acid-inducible gene 1 stimulators, NOD2 stimulators, phosphatidylinositol 3-kinase (PI3K) inhibitors, indoleamine-2,3-dioxygenase (IDO) pathway inhibitors, PD-1 inhibitors, PD-L1 inhibitors, recombinant thymosin alpha-1, bruton's tyrosine kinase (BTK) inhibitors, KDM inhibitors, HBV replication inhibitors, arginase inhibitors, and other HBV drugs.

HBV Combination Drugs

Examples of combination drugs for the treatment of HBV include TRUVADA® (tenofovir disoproxil fumarate and emtricitabine); ABX-203, lamivudine, and PEG-IFN-alpha; ABX-203 adefovir, and PEG-IFNalpha; and INO-1800 (INO-9112 and RG7944).

Other HBV Drugs

Examples of other drugs for the treatment of HBV include alpha-hydroxytropolones, amdoxovir, beta-hydroxycytosine nucleosides, AL-034, CCC-0975, elvucitabine, ezetimibe, cyclosporin A, gentiopicrin (gentiopicroside), JNJ-56136379, nitazoxanide, birinapant, NJK14047, NOV-205 (molixan, BAM-205), oligotide, mivotilate, feron, GST-HG-131, levamisole, Ka Shu Ning, alloferon, WS-007, Y-101 (Ti Fen Tai), rSIFN-co, PEG-IIFNm, KW-3, BP-Inter-014, oleanolic acid, HepB-nRNA, cTP-5 (rTP-5), HSK-II-2, HEISCO-106-1, HEISCO-106, Hepbarna, IBPB-006IA, Hepuyinfen, DasKloster 0014-01, ISA-204, Jiangantai (Ganxikang), MIV-210, OB-AI-004, PF-06, picroside, DasKloster-0039, hepulantai, IMB-2613, TCM-800B, reduced glutathione, RO-6864018, RG-7834, UB-551, and ZH-2N, and the compounds disclosed in US20150210682, (Roche), US 2016/0122344 (Roche), WO2015173164, WO2016023877, US2015252057A (Roche), WO16128335A1 (Roche), WO16120186A1 (Roche), US2016237090A (Roche), WO16107833A1 (Roche), WO16107832A1 (Roche), US2016176899A (Roche), WO16102438A1 (Roche), WO16012470A1 (Roche), US2016220586A (Roche), and US2015031687A (Roche).

HBV Vaccines

HBV vaccines include both prophylactic and therapeutic vaccines. Examples of HBV prophylactic vaccines include Vaxelis, Hexaxim, Heplisav, Mosquirix, DTwP-HBV vaccine, Bio-Hep-B, D/T/P/HBV/M (LBVP-0101; LBVW-0101), DTwP-Hepb-Hib-IPV vaccine, Heberpenta L, DTwP-HepB-Hib, V-419, CVI-HBV-001, Tetrabhay, hepatitis B prophylactic vaccine (Advax Super D), Hepatrol-07, GSK-223192A, ENGERIX B®, recombinant hepatitis B vaccine (intramuscular, Kangtai Biological Products), recombinant hepatitis B vaccine (Hansenual polymorpha yeast, intramuscular, Hualan Biological Engineering), recombinant hepatitis B surface antigen vaccine, Bimmugen, Euforavac, Eutravac, anrix-DTaP-IPV-Hep B, HBAI-20, Infanrix-DTaP-IPV-Hep B-Hib, Pentabio Vaksin DTP—HB-Hib, Comvac 4, Twinrix, Euvax-B, Tritanrix HB, Infanrix Hep B, Comvax, DTP-Hib-HBV vaccine, DTP-HBV vaccine, Yi Tai, Heberbiovac HB, Trivac HB, GerVax, DTwP-Hep B-Hib vaccine, Bilive, Hepavax-Gene, SUPERVAX, Comvac5, Shanvac-B, Hebsulin, Recombivax HB, Revac B mcf, Revac B+, Fendrix, DTwP-HepB-Hib, DNA-001, Shan5, Shan6, rhHBsAG vaccine, HBI pentavalent vaccine, LBVD, Infanrix HeXa, and DTaP-rHB-Hib vaccine.

Examples of HBV therapeutic vaccines include HBsAG-HBIG complex, ARB-1598, Bio-Hep-B, NASVAC, abi-HB (intravenous), ABX-203, Tetrabhay, GX-110E, GS-4774, peptide vaccine (epsilonPA-44), Hepatrol-07, NASVAC (NASTERAP), IMP-321, BEVAC, Revac B mcf, Revac B+, MGN-1333, KW-2, CVI-HBV-002, AltraHepB, VGX-6200, FP-02, FP-02.2, TG-1050, NU-500, HBVax, im/TriGrid/antigen vaccine, Mega-CD40L-adjuvanted vaccine, HepB-v, RG7944 (INO-1800), recombinant VLP-based therapeutic vaccine (HBV infection, VLP Biotech), AdTG-17909, AdTG-17910 AdTG-18202, ChronVac-B, TG-1050, and Lm HBV.

HBV DNA Polymerase Inhibitors

Examples of HBV DNA polymerase inhibitors include adefovir (HEPSERA®), emtricitabine (EMTRIVA®), tenofovir disoproxil fumarate (VIREAD®), tenofovir alafenamide, tenofovir, tenofovir disoproxil, tenofovir alafenamide fumarate, tenofovir alafenamide hemifumarate, tenofovir dipivoxil, tenofovir dipivoxil fumarate, tenofovir octadecyloxyethyl ester, CMX-157, besifovir, entecavir (BARACLUDE®), entecavir maleate, telbivudine (TYZEKA®), pradefovir, clevudine, ribavirin, lamivudine (EPIVIR-HBV®), phosphazide, famciclovir, fusolin, metacavir, SNC-019754, FMCA, AGX-1009, AR-II-04-26, HIP-1302, tenofovir disoproxil aspartate, tenofovir disoproxil orotate, and HS-10234.

Immunomodulators

Examples of immunomodulators include rintatolimod, imidol hydrochloride, ingaron, dermaVir, plaquenil (hydroxychloroquine), proleukin, hydroxyurea, mycophenolate mofetil (MPA) and its ester derivative mycophenolate mofetil (MMF), WF-10, ribavirin, IL-12, INO-9112, polymer polyethyleneimine (PEI), Gepon, VGV-1, MOR-22, BMS-936559, RO-7011785, RO-6871765, AIC-649, and IR-103.

Toll-Like Receptor (TLR) Modulators

TLR modulators include modulators of TLR1, TLR2, TLR3, TLR4, TLR5, TLR6, TLR7, TLR8, TLR9, TLR10, TLR11, TLR12, and TLR13. Examples of TLR3 modulators include rintatolimod, poly-ICLC, RIBOXXON®, Apoxxim, RIBOXXIM®, IPH-33, MCT-465, MCT-475, GS-9688 and ND-1.1.

Examples of TLR7 modulators include GS-9620, GSK-2245035, imiquimod, resiquimod, DSR-6434, DSP-3025, IMO-4200, MCT-465, MEDI-9197, 3M-051, SB-9922, 3M-052, Limtop, TMX-30X, TMX-202, RG-7863, RG-7795, RG-7854, and the compounds disclosed in US20100143301 (Gilead Sciences), US20110098248 (Gilead Sciences), and US20090047249 (Gilead Sciences).

Examples of TLR8 modulators include motolimod, resiquimod, 3M-051, 3M-052, MCT-465, IMO-4200, VTX-763, VTX-1463, and the compounds disclosed in US20140045849 (Janssen), US20140073642 (Janssen), WO2014/056953 (Janssen), WO2014/076221 (Janssen), WO2014/128189 (Janssen), US20140350031 (Janssen), WO2014/023813 (Janssen), US20080234251 (Array Biopharma), US20080306050 (Array Biopharma), US20100029585 (Ventirx Pharma), US20110092485 (Ventirx Pharma), US20110118235 (Ventirx Pharma), US20120082658 (Ventirx Pharma), US20120219615 (Ventirx Pharma), US20140066432 (Ventirx Pharma), US20140088085 (Ventirx Pharma), US20140275167 (Novira Therapeutics), and US20130251673 (Novira Therapeutics).

Examples of TLR9 modulators include BB-001, BB-006, CYT-003, IMO-2055, IMO-2125, IMO-3100, IMO-8400, IR-103, IMO-9200, agatolimod, DIMS-9054, DV-1079, DV-1179, AZD-1419, leftolimod (MGN-1703), litenimod, and CYT-003-QbG10.

Interferon Alpha Receptor Ligands

Examples of interferon alpha receptor ligands include interferon alpha-2b (INTRON A®), pegylated interferon alpha-2a (PEGASYS®), PEGylated interferon alpha-1b, interferon alpha 1b (HAPGEN®), Veldona, Infradure, Roferon-A, YPEG-interferon alfa-2a (YPEG-rhIFNalpha-2a), P-1101, Algeron, Alfarona, Ingaron (interferon gamma), rSIFN-co (recombinant super compound interferon), Ypeginterferon alfa-2b (YPEG-rhIFNalpha-2b), MOR-22, peginterferon alfa-2b (PEG-INTRON®), Bioferon, Novaferon, Inmutag (Inferon), MULTIFERON®, interferon alfa-n1 (HUMOFERON®), interferon beta-1a (AVONEX®), Shaferon, interferon alfa-2b (Axxo), Alfaferone, interferon alfa-2b (BioGeneric Pharma), interferon-alpha 2 (CJ), Laferonum, VIPEG, BLAUFERON-A, BLAUFERON-B, Intermax Alpha, Realdiron, Lanstion, Pegaferon, PDferon-B PDferon-B, interferon alfa-2b (IFN, Laboratorios Bioprofarma), alfainterferona 2b, Kalferon, Pegnano, Feronsure, PegiHep, interferon alfa 2b (Zydus-Cadila), interferon alfa 2a, Optipeg A, Realfa 2B, Reliferon, interferon alfa-2b (Amega), interferon alfa-2b (Virchow), ropeginterferon alfa-2b, rHSA-IFN alpha-2a (recombinant human serum albumin interferon alpha 2a fusion protein), rHSA-IFN alpha 2b, recombinant human interferon alpha-(1b, 2a, 2b), peginterferon alfa-2b (Amega), peginterferon alfa-2a, Reaferon-EC, Proquiferon, Uniferon, Urifron, interferon alfa-2b (Changchun Institute of Biological Products), Anterferon, Shanferon, Layfferon, Shang Sheng Lei Tai, INTEFEN, SINOGEN, Fukangtai, Pegstat, rHSA-IFN alpha-2b, SFR-9216, and Interapo (Interapa).

Hyaluronidase Inhibitors

Examples of hyaluronidase inhibitors include astodrimer.

Hepatitis B Surface Antigen (HBsAg) Inhibitors

Examples of HBsAg inhibitors include HBF-0259, PBHBV-001, PBHBV-2-15, PBHBV-2-1, REP-9AC, REP-9C, REP-9, REP-2139, REP-2139-Ca, REP-2165, REP-2055, REP-2163, REP-2165, REP-2053, REP-2031 and REP-006, and REP-9AC'.

Examples of HBsAg secretion inhibitors include BM601.

Cytotoxic T-Lymphocyte-Associated Protein 4 (Ipi4) Inhibitors

Examples of Cytotoxic T-lymphocyte-associated protein 4 (ipi4) inhibitors include AGEN-2041, AGEN-1884, ipilumimab, belatacept, PSI-001, PRS-010, Probody mAbs, tremelimumab, and JHL-1155.

Cyclophilin Inhibitors

Examples of cyclophilin inhibitors include CPI-431-32, EDP-494, OCB-030, SCY-635, NVP-015, NVP-018, NVP-019, STG-175, and the compounds disclosed in U.S. Pat. No. 8,513,184 (Gilead Sciences), US20140030221 (Gilead Sciences), US20130344030 (Gilead Sciences), and US20130344029 (Gilead Sciences).

HBV Viral Entry Inhibitors

Examples of HBV viral entry inhibitors include Myrcludex B.

Antisense Oligonucleotide Targeting Viral mRNA

Examples of antisense oligonucleotide targeting viral mRNA include ISIS-HBVRx, IONIS-HBVRx, IONIS-GSK6-LRx, GSK-3389404, RG-6004.

Short Interfering RNAs (siRNA) and ddRNAi.

Examples of siRNA include TKM-HBV (TKM-HepB), ALN-HBV, SR-008, HepB-nRNA, and ARC-520, ARC-521, ARB-1740, ARB-1467.

Examples of DNA-directed RNA interference (ddRNAi) include BB-HB-331.

Endonuclease Modulators

Examples of endonuclease modulators include PGN-514.

Ribonucelotide Reductase Inhibitors

Examples of inhibitors of ribonucleotide reductase include Trimidox.

HBVE Antigen Inhibitors

Examples of HBV E antigen inhibitors include wogonin.

Covalently Closed Circular DNA (cccDNA) Inhibitors

Examples of cccDNA inhibitors include BSBI-25, and CHR-101.

Farnesoid X Receptor Agonist

Example of farnesoid x receptor agonist such as EYP-001.

HBV Antibodies

Examples of HBV antibodies targeting the surface antigens of the hepatitis B virus include GC-1102, XTL-17, XTL-19, KN-003, IV Hepabulin SN, and fully human monoclonal antibody therapy (hepatitis B virus infection, Humabs BioMed). Examples of HBV antibodies, including monoclonal antibodies and polyclonal antibodies, include Zutectra, Shang Sheng Gan Di, Uman Big (Hepatitis B Hyperimmune), Omri-Hep-B, Nabi-HB, Hepatect CP, Hepa-Gam B, igantibe, Niuliva, CT-P24, hepatitis B immunoglobulin (intravenous, pH4, HBV infection, Shanghai RAAS Blood Products), and Fovepta (BT-088). Fully human monoclonal antibodies such as HBC-34.

CCR2 Chemokine Antagonists

Examples of CCR2 chemokine antagonists include propagermanium.

Thymosin Agonists

Examples of thymosin agonists include Thymalfasin, recombinant thymosin alpha 1 (GeneScience).

Cytokines

Examples of cytokines include recombinant IL-7, CYT-107, interleukin-2 (IL-2, Immunex), recombinant human interleukin-2 (Shenzhen Neptunus), IL-15, IL-21, IL-24, and celmoleukin.

Nucleoprotein Modulators

Nucleoprotein modulators may be either HBV core or capsid protein inhibitors. Examples of nucleoprotein modulators include AB-423, AT-130, GLS4, NVR-1221, NVR-3778, BAY 41-4109, morphothiadine mesilate, JNJ-379, RG-7907, ABI-H0731, ABI-H2158 and DVR-23.

Examples of capsid inhibitors include the compounds disclosed in US20140275167 (Novira Therapeutics), US20130251673 (Novira Therapeutics), US20140343032 (Roche), WO2014037480 (Roche), US20130267517 (Roche), WO2014131847 (Janssen), WO2014033176 (Janssen), WO2014033170 (Janssen), WO2014033167 (Janssen), WO2015/059212 (Janssen), WO2015118057 (Janssen), WO2015011281 (Janssen), WO2014184365 (Janssen), WO2014184350 (Janssen), WO2014161888 (Janssen), WO2013096744 (Novira), US20150225355 (Novira), US20140178337 (Novira), US20150315159 (Novira), US20150197533 (Novira), US20150274652 (Novira), US20150259324, (Novira), US20150132258 (Novira), U.S. Pat. No. 9,181,288 (Novira), WO2014184350 (Janssen), WO2013144129 (Roche).

Retinoic Acid-inducible Gene 1 Stimulators

Examples of stimulators of retinoic acid-inducible gene 1 include SB-9200, SB-40, SB-44, ORI-7246, ORI-9350, ORI-7537, ORI-9020, ORI-9198, and ORI-7170, RGT-100.

NOD2 Stimulators

Examples of stimulators of NOD2 include SB-9200.

Phosphatidylinositol 3-Kinase (PI3K) Inhibitors

Examples of PI3K inhibitors include idelalisib, ACP-319, AZD-8186, AZD-8835, buparlisib, CDZ-173, CLR-457, pictilisib, neratinib, rigosertib, rigosertib sodium, EN-3342, TGR-1202, alpelisib, duvelisib, IPI-549, UCB-5857, taselisib, XL-765, gedatolisib, ME-401, VS-5584, copanlisib, CAI orotate, perifosine, RG-7666, GSK-2636771, DS-7423, panulisib, GSK-2269557, GSK-2126458, CUDC-907, PQR-309, INCB-40093, pilaralisib, BAY-1082439, puquitinib mesylate, SAR-245409, AMG-319, RP-6530, ZSTK-474, MLN-1117, SF-1126, RV-1729, sonolisib, LY-3023414, SAR-260301, TAK-117, HMPL-689, tenalisib, voxtalisib, and CLR-1401.

Indoleamine-2,3-Dioxygenase (IDO) Pathway Inhibitors

Examples of IDO inhibitors include epacadostat (INCB24360), resminostat (4SC-201), indoximod, F-001287, SN-35837, NLG-919, GDC-0919, GBV-1028, GBV-1012, NKTR-218, and the compounds disclosed in US20100015178 (Incyte), US2016137652 (Flexus Biosciences, Inc.), WO2014073738 (Flexus Biosciences, Inc.), and WO2015188085 (Flexus Biosciences, Inc.).

PD-1 Inhibitors

Examples of PD-1 inhibitors include nivolumab, pembrolizumab, pidilizumab, BGB-108, SHR-1210, PDR-001, PF-06801591, IBI-308, GB-226, STI-1110, and mDX-400.

PD-L1 Inhibitors

Examples of PD-L1 inhibitors include atezolizumab, avelumab, AMP-224, MEDI-0680, RG-7446, GX-P2, durvalumab, KY-1003, KD-033, MSB-0010718C, TSR-042, ALN-PDL, STI-A1014, CX-072, and BMS-936559.

In a particular embodiment, a compound disclosed herein, or a pharmaceutically acceptable salt thereof, is combined with compounds such as those disclosed in WO2018026971, US20180044329, US20180044305, US20180044304, US20180044303, US20180044350, US20180057455, US20180057486, US20180045142, US20180044963, WO2018044783, WO2018009505, WO20180044329, WO2017066227, WO2017087777, US20170145025, WO2017079669, WO2017070089, US2017107216, WO2017222976, US20170262253, WO2017205464, US20170320875, WO2017192961, WO2017112730, US20170174679, WO2017106634, WO2017202744, WO2017202275, WO2017202273, WO2017202274, WO2017202276, WO2017180769, WO2017118762, WO2016041511, WO2016039749, WO2016142835, WO2016142852, WO2016142886, WO2016142894, and WO2016142833.

Recombinant Thymosin Alpha-1

Examples of recombinant thymosin alpha-1 include NL-004 and PEGylated thymosin alpha-1.

Bruton's Tyrosine Kinase (BTK) Inhibitors

Examples of BTK inhibitors include ABBV-105, acalabrutinib (ACP-196), ARQ-531, BMS-986142, dasatinib, ibrutinib, GDC-0853, PRN-1008, SNS-062, ONO-4059, BGB-3111, ML-319, MSC-2364447, RDX-022, X-022, AC-058, RG-7845, spebrutinib, TAS-5315, TP-0158, TP-4207, HM-71224, KBP-7536, M-2951, TAK-020, AC-0025, and the compounds disclosed in US20140330015 (Ono Pharmaceutical), US20130079327 (Ono Pharmaceutical), and US20130217880 (Ono Pharmaceutical).

KDM Inhibitors

Examples of KDM5 inhibitors include the compounds disclosed in WO2016057924 (Genentech/Constellation Pharmaceuticals), US20140275092 (Genentech/Constellation Pharmaceuticals), US20140371195 (Epitherapeutics) and US20140371214 (Epitherapeutics), US20160102096 (Epitherapeutics), US20140194469 (Quanticel), US20140171432, US20140213591 (Quanticel), US20160039808 (Quanticel), US20140275084 (Quanticel), WO2014164708 (Quanticel).

Examples of KDM1 inhibitors include the compounds disclosed in U.S. Pat. No. 9,186,337B2 (Oryzon Genomics), and GSK-2879552, RG-6016, ORY-2001.

HBV Replication Inhibitors

Examples of hepatitis B virus replication inhibitors include isothiafludine, IQP-HBV, RM-5038, and Xingantie.

Arginase Inhibitors

Examples of Arginase inhibitors include CB-1158, C-201, and resminostat.

Gene Therapy and Cell Therapy

Gene Therapy and Cell Therapy including the genetic modification to silence a gene; genetic approaches to directly kill the infected cells; the infusion of immune cells designed to replace most of the patient's own immune system to enhance the immune response to infected cells, or activate the patient's own immune system to kill infected cells, or find and kill the infected cells; genetic approaches to modify cellular activity to further alter endogenous immune responsiveness against the infection.

Gene Editors

The genome editing system is selected from the group consisting of: a CRISPR/Cas9 system, a zinc finger nuclease system, a TALEN system, a homing endonucleases system, and a meganuclease system; e.g., cccDNA elimination via targeted cleavage, and altering one or more of the hepatitis B virus (HBV) viral genes. Altering (e.g., knocking out and/or knocking down) the PreC, C, X, PreSI, PreS2, S, P or SP gene refers to (1) reducing or eliminating PreC, C, X, PreSI, PreS2, S, P or SP gene expression, (2) interfering with Precore, Core, X protein, Long surface protein, middle surface protein, S protein (also known as HBs antigen and HBsAg), polymerase protein, and/or Hepatitis B spliced protein function (HBe, HBc, HBx, PreS1, PreS2, S, Pol, and/or HBSP or (3) reducing or eliminating the intracellular, serum and/or intraparenchymal levels of HBe, HBc, HBx, LHBs, MHBs, SHBs, Pol, and/or HBSP proteins. Knockdown of one or more of the PreC, C, X, PreSI, PreS2, S, P and/or SP gene(s) is performed by targeting the gene(s) within HBV cccDNA and/or integrated HBV DNA.

CAR-T Cell Therapy

A population of immune effector cells engineered to express a chimeric antigen receptor (CAR), wherein the CAR comprises an HBV antigen-binding domain. The immune effector cell is a T cell or an NK cell. In some embodiments, the T cell is a CD4+ T cell, a CD8+ T cell, or a combination thereof. Cells can be autologous or allogeneic.

TCR-T Cell Therapy

T cells expressing HBV-specific T cell receptors. TCR-T cells are engineered to target HBV derived peptides presented on the surface of virus-infected cells.

T-Cells expressing HBV surface antigen (HBsAg)-specific TCR.

TCR-T therapy directed to treatment of HBV, such as LTCR-H2-1

HBV Combination Therapy

In a particular embodiment, a compound disclosed herein, or a pharmaceutically acceptable salt thereof, is combined with one, two, three, or four additional therapeutic agent selected from the group consisting of adefovir (HEPSERA®), tenofovir disoproxil fumarate (VIREAD®), tenofovir alafenamide, tenofovir, tenofovir disoproxil, tenofovir alafenamide fumarate, tenofovir alafenamide hemifumarate, entecavir (BARACLUDE®), telbivudine (TYZEKA®), or lamivudine (EPIVIR-HBV®). In a particular embodiment, a compound disclosed herein, or a pharmaceutically acceptable salt thereof, is combined with a first additional therapeutic agent selected from the group consisting of adefovir (HEPSERA®), tenofovir disoproxil fumarate (VIREAD®), tenofovir alafenamide, tenofovir, tenofovir disoproxil, tenofovir alafenamide fumarate, tenofovir alafenamide hemifumarate, entecavir (BARACLUDE®), telbivudine (TYZEKA®), or lamivudine (EPIVIR-HBV®). In one embodiment, pharmaceutical compositions comprising a compound disclosed herein, or a pharmaceutically acceptable salt thereof, in combination with one or more (e.g., one, two, three, four, one or two, or one to three, or one to four) additional therapeutic agents and a pharmaceutically acceptable carrier, diluent, or excipient are provided.

HBV DNA Polymerase Inhibitor Combination Therapy

In a specific embodiment, a compound disclosed herein, or a pharmaceutically acceptable salt thereof, is combined with an HBV DNA polymerase inhibitor. In another specific embodiment, a compound disclosed herein, or a pharmaceutically acceptable salt thereof, is combined with an HBV DNA polymerase inhibitor and at least one additional therapeutic agent selected from the group consisting of: immunomodulators, TLR modulators, interferon alpha receptor ligands, hyaluronidase inhibitors, recombinant IL-7, HBsAg inhibitors, HBsAg secretion or assembly inhibitors, compounds targeting HBcAg, cyclophilin inhibitors, HBV vaccines, HBV viral entry inhibitors, NTCP inhibitors, antisense oligonucleotide targeting viral mRNA, siRNA, miRNA gene therapy agents, endonuclease modulators, inhibitors of ribonucleotide reductase, hepatitis B virus E antigen inhibitors, recombinant SRA proteins, src kinase inhibitors, HBx inhibitors, cccDNA inhibitors, sshRNAs, HBV antibodies including HBV antibodies targeting the surface antigens of the hepatitis B virus and bispecific antibodies and "antibody-like" therapeutic proteins (such as DARTs®, DUOBODIES®, BITES®, XmAbs®, TandAbs®, Fab derivatives, or TCR-like antibodies), CCR2 chemokine antagonists, thymosin agonists, cytokines, nucleoprotein modulators (HBV core or capsid protein modulators), stimulators of retinoic acid-inducible gene 1, stimulators of RIG-I like receptors, stimulators of NOD2, stimulators of NOD1, Arginase inhibitors, STING agonists, PI3K inhibitors, lymphotoxin beta receptor activators, natural killer cell receptor 2B4 inhibitors, Lymphocyte-activation gene 3 inhibitors, CD160 inhibitors, cytotoxic T-lymphocyte-associated protein 4 (ipi4) inhibitors, CD137 inhibitors, Killer cell lectin-like receptor subfamily G member 1 inhibitors, TIM-3 inhibitors, B- and T-lymphocyte attenuator inhibitors, CD305 inhibitors, PD-1 inhibitors, PD-L1 inhibitors, PEG-Interferon Lambda, recombinant thymosin alpha-1, BTK inhibitors, modulators of TIGIT, modulators of CD47, modulators of SIRPalpha, modulators of ICOS, modulators of CD27, modulators of CD70, modulators of OX40, epigenetic modifiers, modulators of NKG2D, modulators of Tim-4, modulators of B7-H4, modulators of B7-H3, modulators of NKG2A, modulators of GITR, modulators of CD160, modulators of HEVEM, modulators of CD161, modulators of Ax1, modulators of Mer, modulators of Tyro, gene modifiers or editors such as CRISPR (including CRISPR Cas9), zinc finger nucleases or synthetic nucleases (TALENs), IAPs inhibitors, SMAC mimetics, KDM5 inhibitors, IDO inhibitors, and hepatitis B virus replication inhibitors.

In another specific embodiment, a compound disclosed herein, or a pharmaceutically acceptable salt thereof, is combined with an HBV DNA polymerase inhibitor, one or two additional therapeutic agents selected from the group consisting of immunomodulators, TLR modulators, HBsAg inhibitors, HBsAg secretion or assembly inhibitors, HBV therapeutic vaccines, HBV antibodies including HBV antibodies targeting the surface antigens of the hepatitis B virus and bispecific antibodies and "antibody-like" therapeutic proteins (such as DARTs®, DUOBODIES®, BITES®, XmAbs®, TandAbs®, Fab derivatives, or TCR-like antibodies), cyclophilin inhibitors, stimulators of retinoic acid-inducible gene 1, stimulators of RIG-I like receptors, PD-1 inhibitors, PD-L1 inhibitors, Arginase inhibitors, PI3K inhibitors, IDO inhibitors, and stimulators of NOD2, and one or two additional therapeutic agents selected from the group consisting of HBV viral entry inhibitors, NTCP inhibitors, HBx inhibitors, cccDNA inhibitors, HBV antibodies targeting the surface antigens of the hepatitis B virus, siRNA, miRNA gene therapy agents, sshRNAs, KDM5 inhibitors, and nucleoprotein modulators (HBV core or capsid protein modulators).

In another specific embodiment, a compound disclosed herein, or a pharmaceutically acceptable salt thereof, is combined with an HBV DNA polymerase inhibitor and at least a second additional therapeutic agent selected from the group consisting of: immunomodulators, TLR modulators, HBsAg inhibitors, HBV therapeutic vaccines, HBV antibodies including HBV antibodies targeting the surface antigens of the hepatitis B virus and bispecific antibodies and "antibody-like" therapeutic proteins (such as DARTs®, DUOBODIES®, BITES®, XmAbs®, TandAbs®, Fab derivatives, or TCR-like antibodies), cyclophilin inhibitors, stimulators of retinoic acid-inducible gene 1, stimulators of RIG-I like receptors, PD-1 inhibitors, PD-L1 inhibitors, Arginase inhibitors, PI3K inhibitors, IDO inhibitors, and stimulators of NOD2.

In another specific embodiment, a compound disclosed herein, or a pharmaceutically acceptable salt thereof, is combined with an HBV DNA polymerase inhibitor and at least a second additional therapeutic agent selected from the group consisting of: HBV viral entry inhibitors, NTCP inhibitors, HBx inhibitors, cccDNA inhibitors, HBV antibodies targeting the surface antigens of the hepatitis B virus, siRNA, miRNA gene therapy agents, sshRNAs, KDM5 inhibitors, and nucleoprotein modulators (HBV core or capsid protein inhibitors).

HBV Drug Combination Therapy

In a particular embodiment, a compound disclosed herein, or a pharmaceutically acceptable salt thereof, is combined with a first additional therapeutic agent selected from the group consisting of adefovir (HEPSERA®), tenofovir disoproxil fumarate (VIREAD®), tenofovir alafenamide, tenofovir, tenofovir disoproxil, tenofovir alafenamide fumarate, tenofovir alafenamide hemifumarate, entecavir (BARACLUDE®), telbivudine (TYZEKA®), or lamivudine (EPIVIR-HBV®), and at least a second additional therapeutic agent selected from the group consisting of immunomodulators, TLR modulators, interferon alpha receptor ligands, hyaluronidase inhibitors, recombinant IL-7, HBsAg inhibitors, HBsAg secretion or assembly inhibitors, compounds targeting HBcAg, cyclophilin inhibitors, HBV vaccines, HBV viral entry inhibitors, NTCP inhibitors, antisense oligonucleotide targeting viral mRNA, siRNA, miRNA gene therapy agents, endonuclease modulators, inhibitors of ribonucleotide reductase, hepatitis B virus E antigen inhibitors, recombinant SRA proteins, src kinase inhibitors, HBx inhibitors, cccDNA inhibitors, sshRNAs, HBV antibodies including HBV antibodies targeting the surface antigens of the hepatitis B virus and bispecific antibodies and "antibody-like" therapeutic proteins (such as DARTs®, DUOBODIES®, BITES®, XmAbs®, TandAbs®, Fab derivatives, and TCR-like antibodies), CCR2 chemokine antagonists, thymosin agonists, cytokines, nucleoprotein modulators (HBV core or capsid protein modulators), stimulators of retinoic acid-inducible gene 1, stimulators of RIG-I like receptors, stimulators of NOD2, stimulators of NOD1, IDO inhibitors, recombinant thymosin alpha-1, Arginase inhibitors, STING agonists, PI3K inhibitors, lymphotoxin beta receptor activators, natural killer cell receptor 2B4 inhibitors, Lymphocyte-activation gene 3 inhibitors, CD160 inhibitors, ipi4 inhibitors, CD137 inhibitors, killer cell lectin-like receptor subfamily G member 1 inhibitors, TIM-3 inhibitors, B- and T-lymphocyte attenuator inhibitors, epigenetic modifiers, CD305 inhibitors, PD-1 inhibitors, PD-L1 inhibitors, PEG-Interferon Lambd, BTK inhibitors, modulators of TIGIT, modulators of CD47, modulators of SIRPalpha, modulators of ICOS, modulators of CD27, modulators of CD70, modulators of OX40, modulators of NKG2D, modulators of Tim-4, modulators of B7-H4, modulators of B7-H3, modulators of NKG2A, modulators of GITR, modulators of CD160, modulators of HEVEM, modulators of CD161, modulators of Ax1, modulators of Mer, modulators of Tyro, gene modifiers or editors such as CRISPR (including CRISPR Cas9), zinc finger nucleases or synthetic nucleases (TALENs), IAPs inhibitors, SMAC mimetics, KDM5 inhibitors, and hepatitis B virus replication inhibitors.

In a particular embodiment, a compound disclosed herein, or a pharmaceutically acceptable salt thereof, is combined with a first additional therapeutic agent selected from the group consisting of adefovir (HEPSERA®), tenofovir disoproxil fumarate (VIREAD®), tenofovir alafenamide, tenofovir, tenofovir disoproxil, tenofovir alafenamide fumarate, tenofovir alafenamide hemifumarate, entecavir (BARACLUDE®), telbivudine (TYZEKA®) or lamivudine (EPIVIR-HBV®) and at least a second additional therapeutic agent selected from the group consisting of peginterferon alfa-2b (PEG-INTRON®), MULTIFERON®, interferon alpha 1b (HAPGEN®), interferon alpha-2b (INTRON A®), pegylated interferon alpha-2a (PEGASYS®), interferon alfa-n1 (HUMOFERON®), ribavirin, interferon beta-la (AVONEX®), Bioferon, Ingaron, Inmutag (Inferon), Algeron, Roferon-A, Oligotide, Zutectra, Shaferon, interferon alfa-2b (AXXO), Alfaferone, interferon alfa-2b (Bio-Generic Pharma), Feron, interferon-alpha 2 (CJ), BEVAC, Laferonum, VIPEG, BLAUFERON-B, BLAUFERON-A, Intermax Alpha, Realdiron, Lanstion, Pegaferon, PDferon-B, interferon alfa-2b (IFN, Laboratorios Bioprofarma), alfainterferona 2b, Kalferon, Pegnano, Feronsure, PegiHep, interferon alfa 2b (Zydus-Cadila), Optipeg A, Realfa 2B, Reliferon, interferon alfa-2b (Amega), interferon alfa-2b (Virchow), peginterferon alfa-2b (Amega), Reaferon-EC, Proquiferon, Uniferon, Urifron, interferon alfa-2b (Changchun Institute of Biological Products), Anterferon, Shanferon, MOR-22, interleukin-2 (IL-2, Immunex), recombinant human interleukin-2 (Shenzhen Neptunus), Layfferon, Ka Shu Ning, Shang Sheng Lei Tai, INTEFEN, SINOGEN, Fukangtai, Alloferon, and celmoleukin.

In a particular embodiment, a compound disclosed herein, or a pharmaceutically acceptable salt thereof, is combined with a first additional therapeutic agent selected from the group consisting of adefovir (HEPSERA®), tenofovir disoproxil fumarate (VIREAD®), tenofovir alafenamide, tenofovir, tenofovir disoproxil, tenofovir alafenamide fumarate, tenofovir alafenamide hemifumarate, entecavir (BARACLUDE®), telbivudine (TYZEKA®), or lamivudine (EPIVIR-HBV®), and at least a second additional therapeutic agent selected from the group consisting of immunomodulators, TLR modulators, HBsAg inhibitors, HBsAg secretion or assembly inhibitors, HBV therapeutic vaccines, HBV antibodies including HBV antibodies targeting the surface antigens of the hepatitis B virus and bispecific antibodies and "antibody-like" therapeutic proteins (such as DARTs®, DUOBODIES®, BITES®, XmAbs®, TandAbs®, Fab derivatives, or TCR-like antibodies), cyclophilin inhibitors, stimulators of retinoic acid-inducible gene 1, stimulators of RIG-I like receptors, Arginase inhibitors, PI3K inhibitors, PD-1 inhibitors, PD-L1 inhibitors, IDO inhibitors, and stimulators of NOD2.

In a particular embodiment, a compound disclosed herein, or a pharmaceutically acceptable salt thereof, is combined with a first additional therapeutic agent selected from the group consisting of: adefovir (HEPSERA®), tenofovir disoproxil fumarate (VIREAD®), tenofovir alafenamide, tenofovir, tenofovir disoproxil, tenofovir alafenamide fumarate, tenofovir alafenamide hemifumarate, entecavir (BARACLUDE®), telbivudine (TYZEKA®), or lamivudine (EPIVIR-HBV®), and at least a second additional therapeutic agent selected from the group consisting of HBV viral entry inhibitors, NTCP inhibitors, HBx inhibitors, cccDNA inhibitors, HBV antibodies targeting the surface antigens of the hepatitis B virus, siRNA, miRNA gene therapy agents, sshRNAs, KDM5 inhibitors, and nucleoprotein modulators (HBV core or capsid protein modulators).

In a particular embodiment, a compound disclosed herein, or a pharmaceutically acceptable salt thereof, is combined with a first additional therapeutic agent selected from the group consisting of adefovir (HEPSERA®), tenofovir disoproxil fumarate (VIREAD®), tenofovir alafenamide, tenofovir, tenofovir disoproxil, tenofovir alafenamide fumarate, tenofovir alafenamide hemifumarate, entecavir (BARACLUDE®), telbivudine (TYZEKA®), or lamivudine (EPIVIR-HBV®); one, two, or three additional therapeutic agents selected from the group consisting of immunomodulators, TLR modulators, HBsAg inhibitors, HBsAg secretion or assembly inhibitors, HBV therapeutic vaccines, HBV antibodies including HBV antibodies targeting the surface antigens of the hepatitis B virus and bispecific antibodies and "antibody-like" therapeutic proteins (such as DARTs®, DUOBODIES®, BITES®, XmAbs®, TandAbs®, Fab derivatives, or TCR-like antibodies), cyclophilin inhibitors, stimulators of retinoic acid-inducible gene 1, stimulators of RIG-I like receptors, PD-1 inhibitors, PD-L1 inhibitors, Arginase inhibitors, PI3K inhibitors, IDO inhibitors, and stimulators of NOD2; and one or two additional therapeutic agents selected from the group consisting of HBV viral entry inhibitors, NTCP inhibitors, HBx inhibitors, cccDNA inhibitors, HBV antibodies targeting the surface antigens of the hepatitis B virus, siRNA, miRNA gene therapy agents, sshRNAs, KDM5 inhibitors, and nucleoprotein modulators (HBV core or capsid protein modulators).

In a particular embodiment, a compound disclosed herein, or a pharmaceutically acceptable salt thereof, is combined with a first additional therapeutic agent selected from the group consisting of adefovir (HEPSERA®), tenofovir disoproxil fumarate (VIREAD®), tenofovir alafenamide, tenofovir, tenofovir disoproxil, tenofovir alafenamide fumarate, tenofovir alafenamide hemifumarate, entecavir (BARACLUDE®), telbivudine (TYZEKA®), or lamivudine (EPIVIR-HBV®); one or two additional therapeutic agents selected from the group consisting of immunomodulators, TLR modulators, HBsAg inhibitors, HBsAg secretion or assembly inhibitors, HBV therapeutic vaccines, HBV antibodies including HBV antibodies targeting the surface antigens of the hepatitis B virus and bispecific antibodies and "antibody-like" therapeutic proteins (such as DARTs®, DUOBODIES®, BITES®, XmAbs®, TandAbs®, Fab derivatives, or TCR-like antibodies), cyclophilin inhibitors, stimulators of retinoic acid-inducible gene 1, stimulators of RIG-I like receptors, PD-1 inhibitors, PD-L1 inhibitors, Arginase inhibitors, PI3K inhibitors, IDO inhibitors, and stimulators of NOD2; and one or two additional therapeutic agents selected from the group consisting of HBV viral entry inhibitors, NTCP inhibitors, HBx inhibitors, cccDNA inhibitors, HBV antibodies targeting the surface antigens of the hepatitis B virus, siRNA, miRNA gene therapy agents, sshRNAs, KDM5 inhibitors, and nucleoprotein modulators (HBV core or capsid protein modulators).

In a particular embodiment, a compound disclosed herein, or a pharmaceutically acceptable salt thereof, is combined with a first additional therapeutic agent selected from the group consisting of adefovir (HEPSERA®), tenofovir disoproxil fumarate (VIREAD®), tenofovir alafenamide, tenofovir, tenofovir disoproxil, tenofovir alafenamide fumarate, tenofovir alafenamide hemifumarate, entecavir (BARACLUDE®), telbivudine (TYZEKA®), or lamivudine (EPIVIR-HBV®); and one, two, three, or four additional therapeutic agents selected from the group consisting of immunomodulators, TLR7 modulators, TLR8 modulators, HBsAg inhibitors, HBsAg secretion or assembly inhibitors, HBV therapeutic vaccines, HBV antibodies including HBV antibodies targeting the surface antigens of the hepatitis B virus and bispecific antibodies and "antibody-like" therapeutic proteins (such as DARTs®, DUOBODIES®, BITES®, XmAbs®, TandAbs®, Fab derivatives, or TCR-like antibodies), cyclophilin inhibitors, stimulators of retinoic acid-inducible gene 1, stimulators of RIG-I like receptors, PD-1 inhibitors, PD-L1 inhibitors, Arginase inhibitors, PI3K inhibitors, IDO inhibitors, stimulators of NOD2 HBV viral entry inhibitors, NTCP inhibitors, HBx inhibitors, cccDNA inhibitors, siRNA, miRNA gene therapy agents, sshRNAs, KDM5 inhibitors, and nucleoprotein modulators (HBV core or capsid protein modulators).

In a particular embodiment, a compound disclosed herein, or a pharmaceutically acceptable salt thereof, is combined with compounds such as those disclosed in U.S. Publication No. 2010/0143301 (Gilead Sciences), U.S. Publication No. 2011/0098248 (Gilead Sciences), U.S. Publication No. 2009/0047249 (Gilead Sciences), U.S. Pat. No. 8,722,054 (Gilead Sciences), U.S. Publication No. 2014/0045849 (Janssen), U.S. Publication No. 2014/0073642 (Janssen), WO2014/056953 (Janssen), WO2014/076221 (Janssen), WO2014/128189 (Janssen), U.S. Publication No. 2014/0350031 (Janssen), WO2014/023813 (Janssen), U.S. Publication No. 2008/0234251 (Array Biopharma), U.S. Publication No. 2008/0306050 (Array Biopharma), U.S. Publication No. 2010/0029585 (Ventirx Pharma), U.S. Publication No. 2011/0092485 (Ventirx Pharma), US2011/0118235 (Ventirx Pharma), U.S. Publication No. 2012/0082658 (Ventirx Pharma), U.S. Publication No. 2012/0219615 (Ventirx Pharma), U.S. Publication No. 2014/0066432 (Ventirx Pharma), U.S. Publication No. 2014/0088085 (Ventirx Pharma), U.S. Publication No. 2014/0275167 (Novira Therapeutics), U.S. Publication No. 2013/0251673 (Novira Therapeutics), U.S. Pat. No. 8,513,184 (Gilead Sciences), U.S. Publication No. 2014/0030221 (Gilead Sciences), U.S. Publication No. 2013/0344030 (Gilead Sciences), U.S. Publication No. 2013/0344029 (Gilead Sciences), US20140275167 (Novira Therapeutics), US20130251673 (Novira Therapeutics), U.S. Publication No. 2014/0343032 (Roche), WO2014037480 (Roche), U.S. Publication No. 2013/0267517 (Roche), WO2014131847 (Janssen), WO2014033176 (Janssen), WO2014033170 (Janssen), WO2014033167 (Janssen), WO2015/059212 (Janssen), WO2015118057 (Janssen), WO2015011281 (Janssen), WO2014184365 (Janssen), WO2014184350 (Janssen), WO2014161888 (Janssen), WO2013096744 (Novira), US20150225355 (Novira), US20140178337 (Novira), US20150315159 (Novira), US20150197533 (Novira), US20150274652 (Novira), US20150259324, (Novira), US20150132258 (Novira), U.S. Pat. No. 9,181,288 (Novira), WO2014184350 (Janssen), WO2013144129 (Roche), US20100015178 (Incyte), US2016137652 (Flexus Biosciences, Inc.), WO2014073738 (Flexus Biosciences, Inc.), WO2015188085 (Flexus Biosciences, Inc.), U.S. Publication No. 2014/0330015 (Ono Pharmaceutical), U.S. Publication No. 2013/0079327 (Ono Pharmaceutical), U.S. Publication No. 2013/0217880 (Ono pharmaceutical), WO2016057924 (Genentech/Constellation Pharmaceuticals), US20140275092 (Genentech/Constellation Pharmaceuticals), US20140371195 (Epitherapeutics) and US20140371214 (Epitherapeutics), US20160102096 (Epitherapeutics), US20140194469 (Quanticel), US20140171432, US20140213591 (Quanticel), US20160039808 (Quanticel), US20140275084 (Quanticel), WO2014164708 (Quanticel), U.S. Pat. No. 9,186,337B2 (Oryzon Genomics), and other drugs for treating hepatitis B virus (HBV), and combinations thereof.

In certain embodiments, a compound as disclosed herein (e.g., any compound of Formula I) may be combined with one or more (e.g., one, two, three, four, one or two, one to three, or one to four) additional therapeutic agents in any dosage amount of the compound of Formula (I) (e.g., from 10 mg to 1000 mg of compound).

In certain embodiments, a compound disclosed herein, or a pharmaceutically acceptable salt thereof, is combined with 5-30 mg tenofovir alafenamide fumarate, tenofovir alafenamide hemifumarate, or tenofovir alafenamide. In certain embodiments, a compound disclosed herein, or a pharmaceutically acceptable salt thereof, is combined with 5-10; 5-15; 5-20; 5-25; 25-30; 20-30; 15-30; or 10-30 mg tenofovir alafenamide fumarate, tenofovir alafenamide hemifumarate, or tenofovir alafenamide. In certain embodiments, a compound disclosed herein, or a pharmaceutically acceptable salt thereof, is combined with 10 mg tenofovir alafenamide fumarate, tenofovir alafenamide hemifumarate, or tenofovir alafenamide. In certain embodiments, a compound disclosed herein, or a pharmaceutically acceptable salt thereof, is combined with 25 mg tenofovir alafenamide fumarate, tenofovir alafenamide hemifumarate, or tenofovir alafenamide. A compound as disclosed herein (e.g., a compound of Formula I) may be combined with the agents provided herein in any dosage amount of the compound (e.g., from 50 mg to 500 mg of compound) the same as if each combination of dosages were specifically and individually listed.

In certain embodiments, a compound disclosed herein, or a pharmaceutically acceptable salt thereof, is combined with 100-400 mg tenofovir disoproxil fumarate, tenofovir disoproxil hemifumarate, or tenofovir disoproxil. In certain embodiments, a compound disclosed herein, or a pharmaceutically acceptable salt thereof, is combined with 100 mg to 150 mg; 100 mg to 200 mg; 100 mg to 250 mg; 100 mg to 300 mg; 100 mg to 350 mg; 150 mg to 200 mg; 150 mg to 250 mg; 150 mg to 300 mg; 150 mg to 350 mg; 150 mg to 400 mg; 200 mg to 250 mg; 200 mg to 300 mg; 200 mg to 350 mg; 200 mg to 400 mg; 250 mg to 350 mg; 250 mg to 400 mg; 350 mg to 400 or 300 mg to 400 mg tenofovir disoproxil fumarate, tenofovir disoproxil hemifumarate, or tenofovir disoproxil. In certain embodiments, a compound disclosed herein, or a pharmaceutically acceptable salt thereof, is combined with 300 mg tenofovir disoproxil fumarate, tenofovir disoproxil hemifumarate, or tenofovir disoproxil. In certain embodiments, a compound disclosed herein, or a pharmaceutically acceptable salt thereof, is combined with 250 mg tenofovir disoproxil fumarate, tenofovir disoproxil hemifumarate, or tenofovir disoproxil. In certain embodiments, a compound disclosed herein, or a pharmaceutically acceptable salt thereof, is combined with 150 mg tenofovir disoproxil fumarate, tenofovir disoproxil hemifumarate, or tenofovir disoproxil. A compound as disclosed herein (e.g., a compound of Formula I) may be combined with the agents provided herein in any dosage amount of the compound (e.g., from 50 mg to 500 mg of compound) the same as if each combination of dosages were specifically and individually listed.

In one embodiment, kits comprising a compound disclosed herein, or a pharmaceutically acceptable salt thereof, in combination with one or more (e.g., one, two, three, four, one or two, or one to three, or one to four) additional therapeutic agents are provided.

Any pharmaceutical composition provided in the present disclosure may be used in the kits, the same as if each and every composition were specifically and individually listed for use in a kit.

Synthesis

The compounds of the disclosure may be prepared using methods disclosed herein and routine modifications thereof which will be apparent given the disclosure herein and methods well known in the art. Conventional and well-known synthetic methods may be used in addition to the teachings herein.

The synthesis of typical compounds of formula (I), or a pharmaceutically acceptable salt thereof, e.g., compounds having structures described by one or more of formula (I), or other formulas or compounds disclosed herein, may be accomplished as described in the following examples.

General Syntheses

Typical embodiments of compounds in accordance with the present disclosure may be synthesized using the general reaction schemes and/or examples described below. It will be apparent given the description herein that the general schemes may be altered by substitution of the starting materials with other materials having similar structures to result in products that are correspondingly different. Descriptions of syntheses follow to provide numerous examples of how the starting materials may vary to provide corresponding products. Starting materials are typically obtained from commercial sources or synthesized using published methods for synthesizing compounds which are embodiments of the present disclosure, inspection of the structure of the compound to be synthesized will provide the identity of each substituent group. The identity of the final product will generally render apparent the identity of the necessary starting materials by a simple process of inspection, given the examples herein. Group labels (e.g., $R^1$, $R^a$, $R^b$) used in the reaction schemes herein are for illustrative purposes only and unless otherwise specified do not necessarily match by name or function the labels used elsewhere to describe compounds of formula (I) or aspects or fragments thereof.

Synthetic Reaction Parameters

The compounds of this disclosure can be prepared from readily available starting materials using, for example, the following general methods and procedures. It will be appreciated that where typical or preferred process conditions (i.e., reaction temperatures, times, mole ratios of reactants, solvents, pressures, etc.) are given; other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and G. M. Wuts (1999) *Protecting Groups in Organic Synthesis,* 3rd Edition, Wiley, New York, and references cited therein.

Furthermore, the compounds of this disclosure may contain one or more chiral centers. Accordingly, if desired, such compounds can be prepared or isolated as pure stereoisomers, i.e., as individual enantiomers or diastereomers or as stereoisomer-enriched mixtures. All such stereoisomers (and enriched mixtures) are included within the scope of this disclosure, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents, and the like.

The starting materials for the following reactions are generally known compounds or can be prepared by known procedures or obvious modifications thereof. For example, many of the starting materials are available from commercial suppliers such as Aldrich Chemical Co. (Milwaukee, Wis., USA). Others may be prepared by procedures or obvious modifications thereof, described in standard reference texts such as Fieser and Fieser's Reagents for Organic Synthesis, Volumes 1-15 (John Wiley, and Sons, 1991), Rodd's Chemistry of Carbon Compounds, Volumes 1-5, and Supplementals (Elsevier Science Publishers, 1989) organic Reactions, Volumes 1-40 (John Wiley, and Sons, 1991), March's Advanced Organic Chemistry, (John Wiley, and Sons, 5$^{th}$ Edition, 2001), and Larock's Comprehensive Organic Transformations (VCH Publishers Inc., 1989).

The terms "solvent," "inert organic solvent" or "inert solvent" refer to a solvent inert under the conditions of the reaction being described in conjunction therewith (including, for example, benzene, toluene, acetonitrile, tetrahydrofuran ("THF"), dimethylformamide ("DMF"), chloroform, methylene chloride (or dichloromethane), diethyl ether, methanol, pyridine and the like). Unless specified to the contrary, the solvents used in the reactions of the present disclosure are inert organic solvents, and the reactions are carried out under an inert gas, preferably nitrogen.

The term "q.s." means adding a quantity sufficient to achieve a stated function, e.g., to bring a solution to the desired volume (i.e., 100%).

Compounds as provided herein may be synthesized according to the general schemes provided below. In the Schemes below, it should be appreciated that each of the compounds shown therein may have protecting groups as required present at any step. Standard protecting groups are well within the pervue of one skilled in the art.

Scheme 1 shows exemplary synthetic routes for the synthesis of compounds of Formula (I). In Scheme 1, Q, $R^E$, $R^W$, $Z^1$, $Z^3$, n, m, are as defined herein, each $R^{50}$ is independently $C_{1-6}$ alkyl or two $R^{50}$ together with the atom to which they are attached form a ring, X is halo, and each FG is independently a functional group capable of forming a covalent bond with compound 105.

(e.g., using a palladium(0) catalyst) in a suitable solvent (e.g., DMF) under an inert atmosphere to provide compound 102. Compounds of Formula (I) are then provided by contacting compound 102 with appropriately substituted compound 106 under standard metal-catalyzed coupling conditions. Alternatively, compound 102 is contacted with compound 103 under standard metal-catalyzed coupling conditions to provide compound 104. Compound 104 is then reacted with compound 105 under conditions suitable to provide compounds of Formula (I). Exemplary conditions include, but are not limited to, reductive amination (FG is an aldehyde and compound 105 comprises a primary or secondary amine).

Symmetric compounds as provided herein, such as those of Formula (Id), may be synthesized according to Scheme 2 below. In Scheme 2, Q, $R^E$, $R^W$, $Z^1$, $Z^2$, n, m, are as defined herein, each $R^{50}$ is independently $C_{1-6}$ alkyl or two $R^{50}$ together with the atom to which they are attached form a

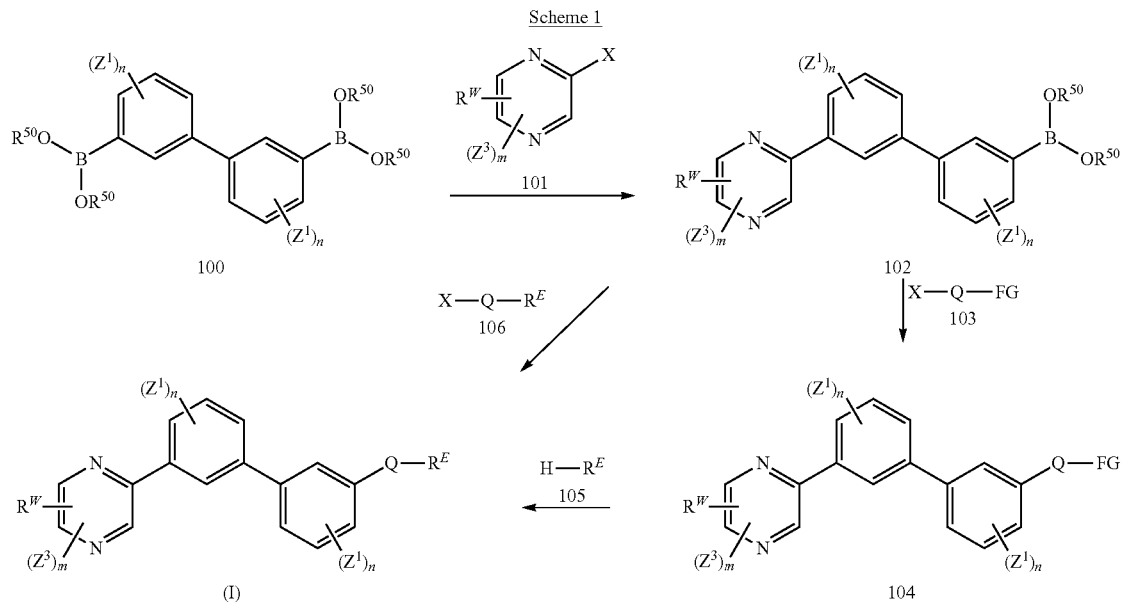

Scheme 1

In Scheme 1, compound 100 is coupled with compound 101 under standard metal-catalyzed coupling conditions ring, X is halo, and FG is a functional group capable of forming a covalent bond with compound 105.

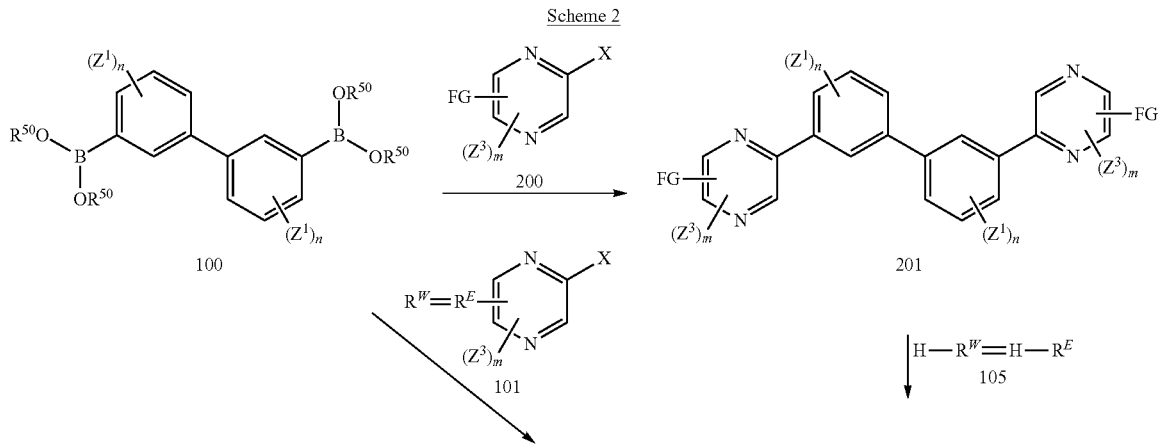

Scheme 2

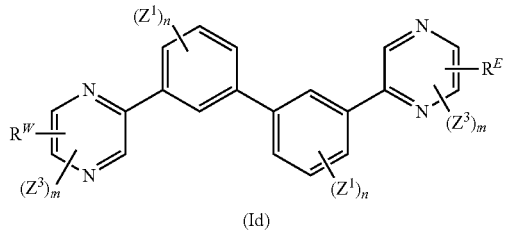

(Id)

In Scheme 2, symmetric compounds of Formula (Id) can be provided by coupling compound 100 with at least a two-fold excess of appropriately substituted compound 101 under standard metal-catalyzed coupling conditions (e.g., using a palladium(0) catalyst) in a suitable solvent (e.g., DMF) under an inert atmosphere. Alternatively, compound 100 is contacted with compound 200 under standard metal-catalyzed coupling conditions to provide compound 201. Compound 201 is then reacted with compound 105 under conditions suitable to provide compounds of Formula (Id). Exemplary conditions include, but are not limited to, reductive amination (FG is an aldehyde and compound 105 comprises a primary or secondary amine).

Suitably substituted compounds 100, 101, 103, 106 and 105 for use in the methods provided herein can be purchased from commercial sources or synthesized by known methods. Resolution of the isomers of Formula (I) can be performed as needed using standard chiral separation/resolution conditions (e.g., chromatography, crystallization, etc.).

EXAMPLES

The compounds were named using the IUPAC naming convention or using ChemBioDraw Ultra Version 14.0. Structures are drawn ChemBioDraw.

When production of starting materials is not particularly described, the compounds are known or may be prepared analogously to methods known in the art or as disclosed in the Examples. One of skill in the art will appreciate that synthetic methodologies described herein are only representative of methods for preparation of the compounds described herein, and that other known methods and variants of methods described herein may be used. The methods or features described in various Examples may be combined or adapted in various ways to provide additional ways of making the compounds described herein.

Exemplary Procedures for Select Intermediates:

Lactam Intermediates:

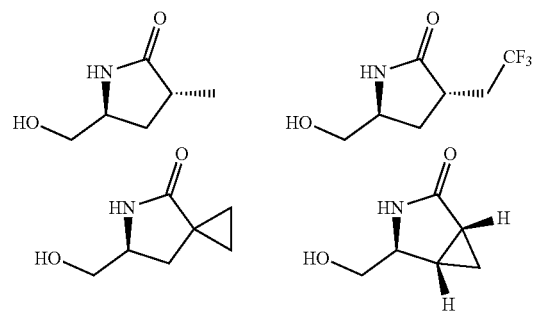

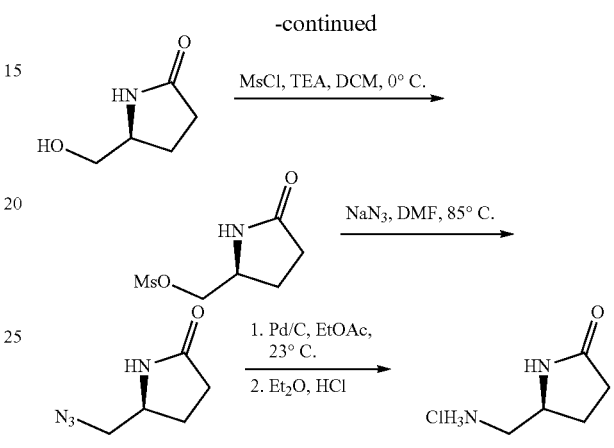

To the appropriate alcohol (above), as can be obtained as in PCT Int. Appl. WO 2015/150995, was added triethylamine (2.0 equiv.) and dichloromethane (0.1 M) at room temperature. The mixture was cooled to 0° C., and mesyl chloride (1.1 equiv.) was added dropwise. The mixture was stirred at 0° C. for 1 hour before being quenched with water. The organic layer was separated and washed once with brine, dried over magnesium sulfate, filtered, and concentrated. The residue was purified by silica gel chromatography. The mesylate was dissolved in dimethylformamide (0.5M) at room temperature, and sodium azide (5.0 equiv.) was added. The mixture was heated to 85° C. overnight. After cooling to room temperature, the mixture was diluted with ethyl acetate and water. The organic layer was then washed once with brine, dried over magnesium sulfate, filtered, and concentrated. The azide was used without further purification. To an oven-dried 40 mL vial was added the azide in ethyl acetate at room temperature. The vessel was purged with nitrogen, and Palladium on carbon was added (10 mol %). The vessel was then purged with hydrogen. After stirring for 4 hours, the contents were filtered through celite and concentrated. The crude amine was dissolved in ether and precipitated by the addition of 1.0 equiv. of HCl in dioxane. The solid HCl salt was isolated by filtration.

Pyrazine Intermediate:

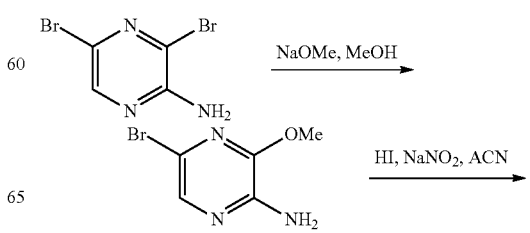

-continued

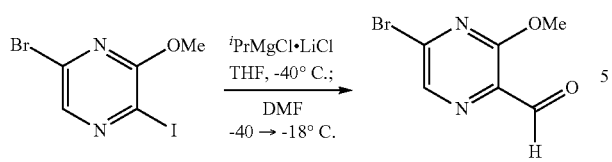

A 30 percent w/w solution of NaOMe in MeOH (168 mL, 896 mmol) was added to a stirring suspension of 3,5-dibromopyrazin-2-amine (200 g, 791 mmol) in dry MeOH (900 mL). The reaction mixture was heated to reflux and stirred for 3 h. The reaction mixture was allowed to cool to room temperature and concentrated to ⅓ volume. The resulted mixture was then partitioned between dichloromethane (DCM) and saturated aqueous NaHCO$_3$ solution. The layers were separated and the organic phase was washed with saturated aqueous NaHCO$_3$ solution. The combined aqueous portions were extracted with DCM. The combined organic portions were washed with brine, dried over Na$_2$SO$_4$, filtered and concentrated to give 5-bromo-3-methoxypyrazin-2-amine. $^1$H NMR: (400 MHz, CDCl$_3$) δ 7.64 (s, 1H), 4.79 (s, 2H), 4.00 (s, 3H).

A mixture of 5-bromo-3-methoxypyrazin-2-amine (20 g, 98 mmol), 55% aqueous HI (55%, 200 mL, 1462 mmol) and acetonitrile (200 mL) in water (300 mL) was stirred at 0° C. for 0.5 h. And a solution of sodium nitrite (120 g, 1740 mmol) in H$_2$O (200 mL) was added in a dropwise fashion. The reaction mixture warm to 23° C., and then stirred for 20 h at 50° C. After cooling, the solution was poured into 20% aqueous NaOH and extracted with ethyl acetate (2×200 mL). The combined organic layers were washed with saturated aqueous sodium metabisulfite (200 mL) and brine (200 mL), dried over Na$_2$SO$_4$, filtered and concentrated under vacuum to give the crude product. The crude product was purified by column chromatography on silica gel (CH$_2$Cl/hexanes=1:1) to give the desired product 5-bromo-2-iodo-3-methoxypyrazine. $^1$H NMR: (400 MHz, DMSO) δ 8.07 (s, 1H), 4.04 (s, 3H).

Isopropylmagnesium chloride lithium chloride complex solution (1.3 M in tetrahydrofuran, 59.22 mL, 75.6 mmol) was added via syringe over 5 min to a stirred solution of 5-bromo-2-iodo-3-methoxypyrazine (21 g, 66.69 mmol) in anhydrous tetrahydrofuran (147 mL) under an atmosphere of dry nitrogen at −40° C. After 25 min, anhydrous N,N-dimethylformamide (15.54 mL, 200.34 mmol) was added via syringe over 2 min, and the resulting mixture was allowed to warm to −18° C. over 25 min. Aqueous citric acid solution (5% w/v, 200 mL) was added slowly, and the resulting heterogeneous mixture was stirred vigorously and warmed to room temperature. After 10 min, ethyl acetate (450 mL) was added. The organic layer was washed with water (2×300 mL), was dried over anhydrous magnesium sulfate, was filtered, and was concentrated under reduced pressure. The residue was purified by flash column chromatography on silica gel (0 to 10% ethyl acetate in hexanes) to provide 5-bromo-3-methoxypyrazine-2-carbaldehyde. $^1$H NMR: (400 MHz, CDCl$_3$) δ 10.21 (s, 1H), 8.43 (s, 1H), 4.14 (s, 3H).

2,2'-(2,2'-dichloro-[1,1'-biphenyl]-3,3'-diyl)bis(4,4,5,5-tetramethyl-1,3,2-dioxaborolane)

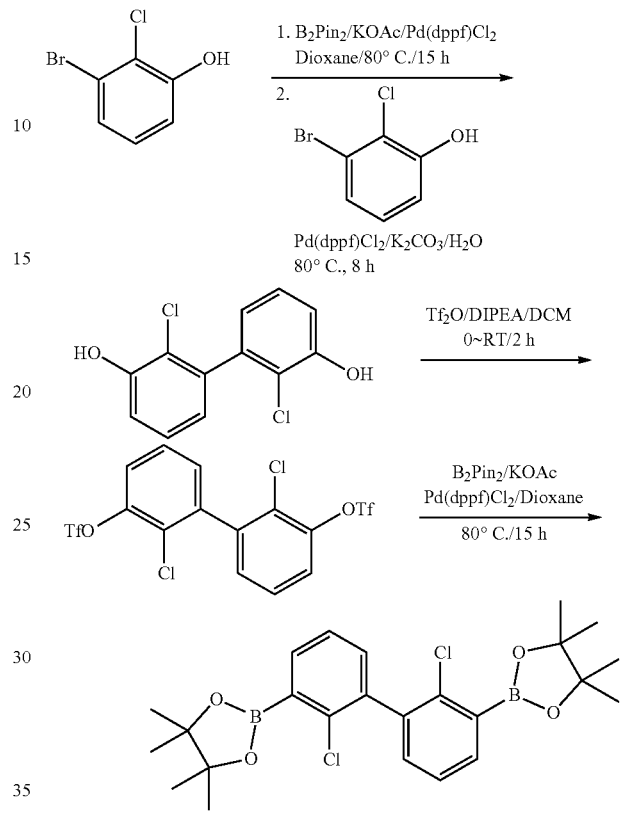

A mixture of 3-bromo-2-chlorophenol (73.5 g, 0.355 mol, 1.0 eq), B$_2$Pin$_2$ (98 g, 0.391 mol, 1.1 eq), KOAc (96.7 g, 0.987 mol, 2.78 eq) and Pd(dppf)Cl$_2$-DCM (25.97 g, 35.5 mmol, 0.1 eq) were suspended in dioxane (1.2 L) was stirred at 80° C. for 15 h under positive pressure of nitrogen. The resulting mixture was cooled to ambient temperature and filtered. The filter cake was washed with dioxane (500 mL). The filtrates were combined.

3-bromo-2-chlorophenol (73.5 g, 0.355 mol, 1.0 eq), K$_2$CO$_3$ (122 g, 0.888 mol, 2.5 eq) and Pd(dppf)Cl$_2$-DCM (8.8 g, 10.65 mmol, 0.03 eq) were added to the filtrate prepared above. The reaction was stirred at 80° C. for 8 h under positive pressure of nitrogen. The resulting mixture was cooled to ambient temperature and filtered. The filter cake was washed with dioxane (500 mL). The filtrate were combined and concentrated. The residue was dissolved with ethyl acetate (2 L). The solution was washed with water, brine, dried over sodium sulfate and concentrated. The crude was purified by silica gel chromatography (PE:EA=5:1) to give 2,2'-dichloro-[1,1'-biphenyl]-3,3'-diol.

To a solution of 2,2'-dichloro-[1,1'-biphenyl]-3,3'-diol (63.8 g, 0.251 mol, 1.0 eq) and DIPEA (121.5 g, 0.944 mol, 3.76 eq) in DCM (2 L) at 0° C. was added Tf$_2$O (166 g, 0.590 mol, 2.35 eq) dropwise slowly. Then the reaction was warmed to rt and stirred for 2 h. The pH of the reaction solution was greater than 7. Water (2 L) was added. The layers were separated, and the organic phase was washed with aqueous solution NaHCO$_3$, and brine, and dried over anhydrous sodium sulfate and concentrated. The crude was purified by silica gel chromatography, eluting with PE/DCM/EtOAc (1:1:0-1:1:0.2) to give 2,2'-dichloro-[1,1'-biphenyl]-3,3'-diyl bis(trifluoromethanesulfonate).

A mixture of 2,2'-dichloro-[1,1'-biphenyl]-3,3'-diyl bis(trifluoromethanesulfonate) (150 g, 0.289 mol, 1.0 eq), Bin$_2$Pin$_2$ (180 g, 0.722 mol, 2.5 eq) KOAc (113 g, 1.156 mol, 4.0 eq) and Pd(dppf)Cl$_2$-DCM (31.72 g, 0.0434 mol, 0.15 eq) in dioxane (1.5 L) was stirred at 80° C. for 15 h under positive pressure of nitrogen. The resulting mixture was cooled to ambient temperature. DCM (1.5 L) was added, and the mixture was stirred for 15 min at rt. The mixture was filtered and the filter cake was washed with DCM (500 mL). The filtrates were combined and concentrated. The crude was purified by silica gel chromatography (PE:EA, 10:1-5:1) to give 2,2'-(2,2'-dichloro-[1,1'-biphenyl]-3,3'-diyl)bis(4,4,5,5-tetramethyl-1,3,2-dioxaborolane). $^1$H NMR (400 MHz, DMSO-d6) δ 7.63 (d, J=6.7 Hz, 2H), 7.46-7.30 (m, 4H), 1.34 (s, 24H).

6-chloro-3-(4,5-dihydro-1H-imidazol-2-yl)-2-methoxypyridine

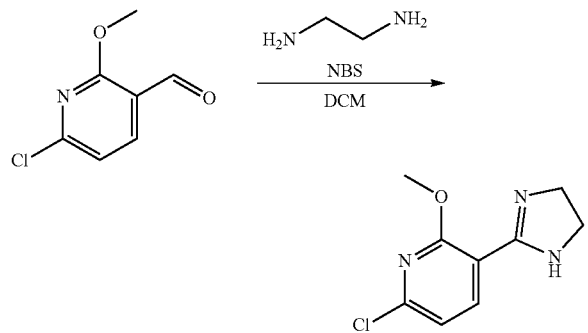

To a solution of aldehyde (3.5 g, 20.4 mmol) in 60 mL DCM at 0° C. was added ethylenediamine (1.50 mL, 22.44 mmol) dropwise. The solution was stirred at 0° C. for 30 minutes, then N-bromosuccinimide (3.99 g, 22.44 mmol) was added in one portion, and the reaction mixture was stirred for 16 hours with gradual warming to ambient temperature. Reaction was taken up in DCM and stirred vigorously with 1:1 sat. sodium thiosulfate and sat sodium carbonate for 15 min. The organic later was dried with MgSO$_4$, filtered and conc to provide 6-chloro-3-(4,5-dihydro-1H-imidazol-2-yl)-2-methoxypyridine.

General Reductive Amination Procedures:

Procedure A—Reductive Amination with DMF/TEA; NaBH(OAc)$_3$

Aldehyde (1 equiv) was suspended in DMF (0.025 M) and to this was added (3S)-4-Amino-3-hydroxybutanoic acid (6 equiv) followed by triethylamine (6 equiv) and the reaction stirred at room temperature for 90 minutes. To this was added sodium triacetoxyborohydride (6 equiv) and the reaction stirred an additional 4 hours. At this point TFA was added slowly dropwise to the reaction until the solution went clear. Reaction was diluted with 2 mL of water, filtered and purified by reverse phase HPLC (0.1% trifluoroacetic acid in acetonitrile/water) providing the final compound upon lyophilization as the bis-TFA salt.

Procedure B—Reductive Amination with DMF/Aq NaOH; NaBH(OAc)$_3$

A solution of aldehyde (1 equiv) in DMF (0.014 M) was added to a solution of the (S)-4-amino-3-hydroxybutanoic acid in 1N NaOH (10 equiv). After 2 h sodium triacetoxyborohydride (10 equiv) was added. After 30 min the reaction was complete and TFA was added. Solids were removed by filtration and rinsed with MeOH. Organic phase was removed under reduced pressure, and the crude subjected to purification by reverse phase HPLC (0.1% trifluoroacetic acid in acetonitrile/water) providing the final compound upon lyophilization as the bis-TFA salt.

Procedure C—Reductive Amination with DMF/AcOH; NaCNBH$_3$+NaBH(OAc)$_3$

To a stirred mixture of aldehyde (1 equiv) and (S)-3-aminobutanoic acid (15 equiv) in a 6:1 mixture of DMF/AcOH (0.02 M) at room temperature was added sequentially sodium cyanoborohydride (9 equiv) and sodium triacetoxyborohydride (9 equiv). After 15 min, trifluoroacetic acid was added until the solution went clear. The resulting mixture was purified by reverse phase HPLC (0.1% trifluoroacetic acid in acetonitrile/water) providing the final compound upon lyophilization as the bis-TFA salt.

Procedure D—Reductive Amination with DMSO/AcOH; NaBH(OAc)$_3$

To a stirred mixture of aldehyde (1 equiv) and (1R,2R)-2-aminocyclopentane-1-carboxylic acid (15 equiv) in 5:1 mixture of DMSO/AcOH (0.008 M) at room temperature was added sodium triacetoxyborohydride (9 equiv). After 1 h, TFA was added until the solution went clear. The resulting homogeneous mixture was purified by reverse phase HPLC (0.1% trifluoroacetic acid in acetonitrile/water) providing the final compound upon lyophilization as the bis-TFA salt.

Procedure E—Reductive Amination with MeOH/AcOH; 2-Methylpyridine Borane

Aldehyde A (1 equiv) was suspended in a 10:1 mixture of MeOH/AcOH (0.01M) and to this was added (3S)-4-amino-3-hydroxybutyric acid (3 equiv) at room temperature. Mixture was stirred at room temperature under argon for 1 hour. To this solution was added 2-methylpyridine borane (3 equiv) at room temperature and the reaction was stirred for an additional 2 hours. At this point, TFA was added dropwise to the reaction mixture until the solution went clear. Reaction was filtered and purified by reverse phase HPLC (0.1% trifluoroacetic acid in acetonitrile/water) providing the final compound upon lyophilization as the bis-TFA salt.

Procedure F—Reductive Amination with DMF/MeOH/AcOH; 2-Methylpyridine Borane

Aldehyde (1 equiv) was suspended in a 6:3:1 mixture of DMF/MeOH/AcOH (0.01 M) and to this was added (3S)-4-amino-3-hydroxybutyric acid (10 equiv) at room temperature. Mixture was stirred at room temperature under argon for 1 hour. To this solution was added 2-methylpyridine borane (10 equiv) at room temperature and the reaction was stirred for an additional 2 hours. At this point, TFA was added dropwise to the reaction mixture until the solution goes clear. Reaction was filtered and purified by reverse phase HPLC (0.1% trifluoroacetic acid in acetonitrile/water) providing the final compound upon lyophilization as the bis-TFA salt.

Procedure G—Reductive Amination with DCM/EtOH/KOH; Na(OAc)$_3$BH

To aldehyde in DCM (0.05M) was added a pre-sonicated 0.1M solution of KOH (10 equiv) and (3S)-4-amino-3-hydroxybutanoic acid (10 equiv) in EtOH. The reaction was stirred for 1 hour at rt before Na(OAc)$_3$BH (10 equiv) and AcOH (10 equiv) were added. The cloudy reaction was sonicated for 1 min, and stirred at rt for 2 h. The reaction was quenched with the addition of 1M HCl until the solution clears. The solution was concentrated in-vacuo, diluted with a mixture of MeCN/H$_2$O/DMF (1:1:1), and purified by purified by reverse phase HPLC (0.1% trifluoroacetic acid in acetonitrile/water) providing the final compound upon lyophilization as the bis-TFA salt.

Procedure H—Reductive Amination with DCM/DMF/DIPEA; Na(OAc)₃BH

The di aldehyde 6,6'-(((2,2'-dimethyl-[1,1'-biphenyl]-3,3'-diyl)bis(methylene))bis(oxy))bis(5-chloro-2-methoxynicotinaldehyde) (50 mg, 1 equiv) was taken in a vial and dissolved in DCM (1.5 mL). The (2S,4R)-4-hydroxypiperidine-2-carboxylic acid (125 mg, 10 equiv) was dissolved in mixture of DMF(3 mL), and DIPEA (0.15 mL, 10 equiv) in a another vial. These two solutions were mixed together and sonicated for 5 min, and allowed to stir for 1 h at room temperature. To well stirred mixture was added Na(OAc)₃BH at once and sonicated for 5 min to bring everything in to solution and allowed to stirred for overnight. The solution was concentrated under reduced pressure. The crude product was diluted with a mixture of MeCN/H₂O/(2:1, with 0.1% TFA), solids were removed by filtration and purified by reverse phase HPLC (0.1% trifluoroacetic acid in acetonitrile/water) providing the final compound as the bis-TFA salt.

A 40 mL reaction vial, fitted with a stir bar, was charged with aryl-boronic acid (16 mmol), aryl-bromide (16 mmol), Pd(dppf) (0.8 mmol) and potassium carbonate (32 mmol). DriSolv 1,4-Dioxane (27 mL) and distilled water (3 mL) were then added by syringe, and the mixture de-gassed by bubbling argon for 5 min while mixing. The reaction vial was then sealed with a septum cap and the reaction heated to 85° C. using a heating block, the reaction was monitored by LC/MS. Upon complete consumption of starting material, saturated NaCl in water was added and the reaction mixture was extracted three times with ethyl acetate. The organic layers were collected, volatiles removed and crude mixture purified by silica gel column chromatography. The desired product eluted at ~27% EtOAc/Hexanes.

A 100 mL round bottom flask fitted with a stir bar, was charged with Aryl-alcohol (10.37 mmol), N,N-diisopropylethylamine (41 mmol), dichloromethane (100 mL), placed under an atmosphere of argon and cooled to 0° C. with an ice water bath. While mixing triflic anhydride (26 mmol) was added by syringe dropwise and allowed to mix 1 h. The reaction was then quenched with a saturated solution of sodium bicarbonate and extracted three times with ethyl Procedure 1

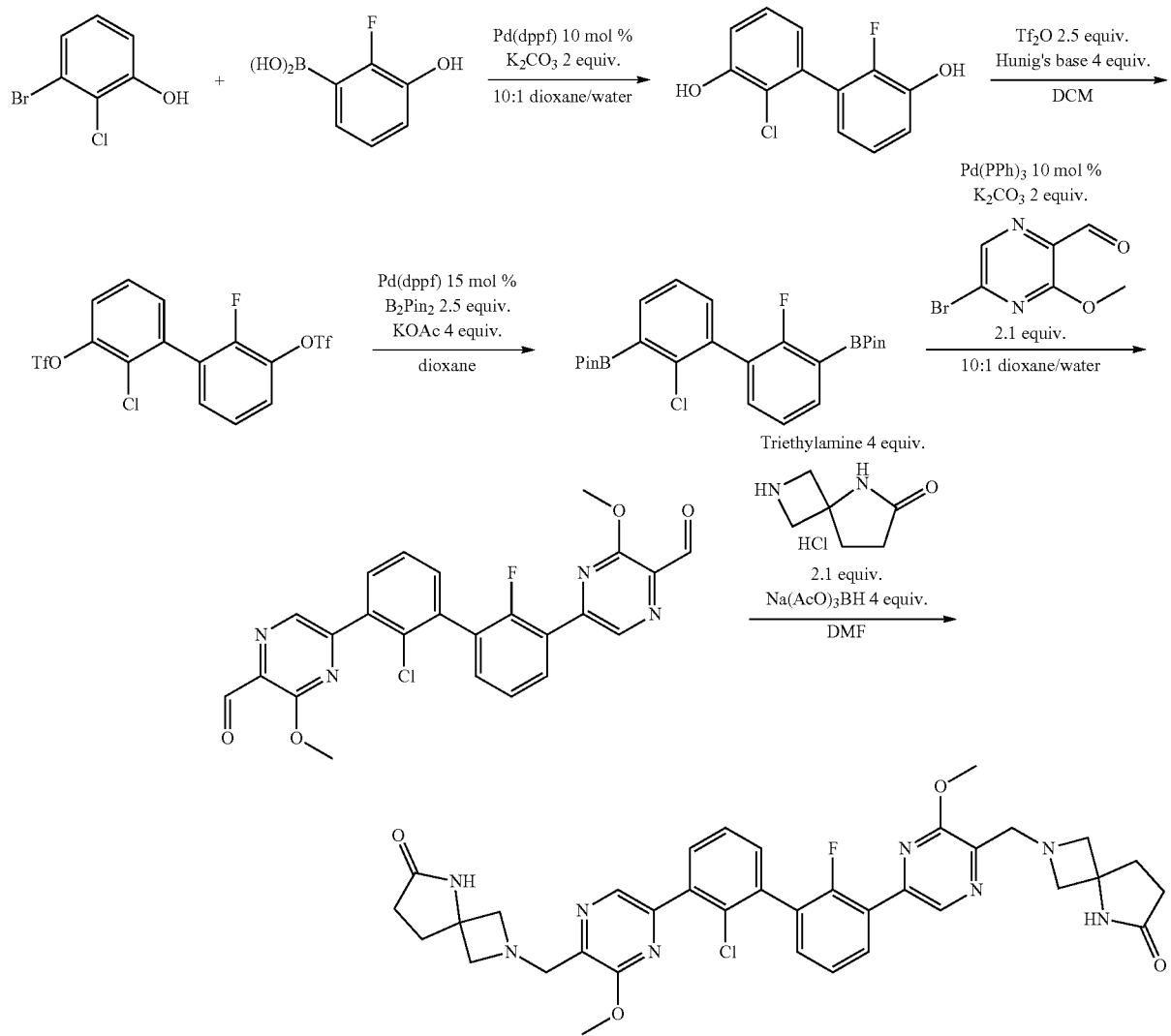

acetate. The organic layers were collected, volatiles removed and crude mixture purified by silica gel column chromatography. The desired product eluted at ~14% EtOAc/Hexanes.

A 40 mL screw cap vial, fitted with a stir bar, was charged with aryl-triflate (6.87 mmol), bis(pinacolato)diboron (17.17 mmol), potassium acetate (27.46 mmol) and Pd(dppf) (1.03 mmol). DriSolv 1,4-Dioxane (27 mL) was then added by syringe, and the mixture was de-gassed by bubbling argon through for 5 min while mixing. The vial was then sealed and the mixture heated to 85° C. for 5 h. The reaction was quenched with saturated NaCl in water and extracted three times with ethyl acetate. The organic layers were collected, volatiles removed and crude mixture purified by silica gel column chromatography.

A 40 mL reaction vial, fitted with a stir bar, was charged with aryl-bromide (0.97 mmol), aryl-Bpin (0.46 mmol), Pd(PPh$_3$)$_4$ (23 µmol) and potassium carbonate (1 mmol). DriSolv 1,4-Dioxane (3.6 mL) and distilled water (0.9 mL) were then added by syringe, the mixture was de-gassed by bubbling argon through for 5 min while mixing. The reaction vial was then sealed with a septum cap and the reaction heated to 85° C. using a heating block, the reaction was then monitored by LC/MS. Upon complete consumption of starting material, the reaction was quenched with saturated solution of NaCl in water and extracted three times with ethyl acetate. The organic layers we collected, volatiles removed and product isolated by crashing out of diethyl ether.

A 20 mL reaction vial, fitted with a stir bar, was charged with dialdehyde (0.14 mmol), amine salt (0.5 mmol), trimethylamine (0.57 mmol) and dimethylformamide (1.4 mL) and allotted to mix for 0.5 h. Sodium triacetoxy-borohydride (0.57 mmol) was then added and the reaction allowed to mix overnight. The next day the reaction was quenched with trifluoroacetic acid (0.65 mmol), filtered, diluted with a 1:4 solution DMF/water and purified by HPLC. $^1$H NMR (400 MHz, Methanol-d4) δ 8.70 (d, J=2.1 Hz, 1H), 8.52 (s, 1H), 8.21 (s, 1H), 7.74 (d, J=7.4 Hz, 1H), 7.68-7.44 (m, 4H), 4.82-4.03 (m, 16H), 2.58 (d, J=8.2 Hz, 4H), 2.46 (d, J=8.0 Hz, 4H). ES/MS m/z: 699.200 M+1

Procedure 2: (S)-5-((((5-(3'-(5-(((1-acetylazetidin-3-yl)amino)methyl)-6-methoxypyrazin-2-yl)-2,2'-dichloro-[1,1'-biphenyl]-3-yl)-3-methoxypyrazin-2-yl)methyl)amino)methyl)pyrrolidin-2-one

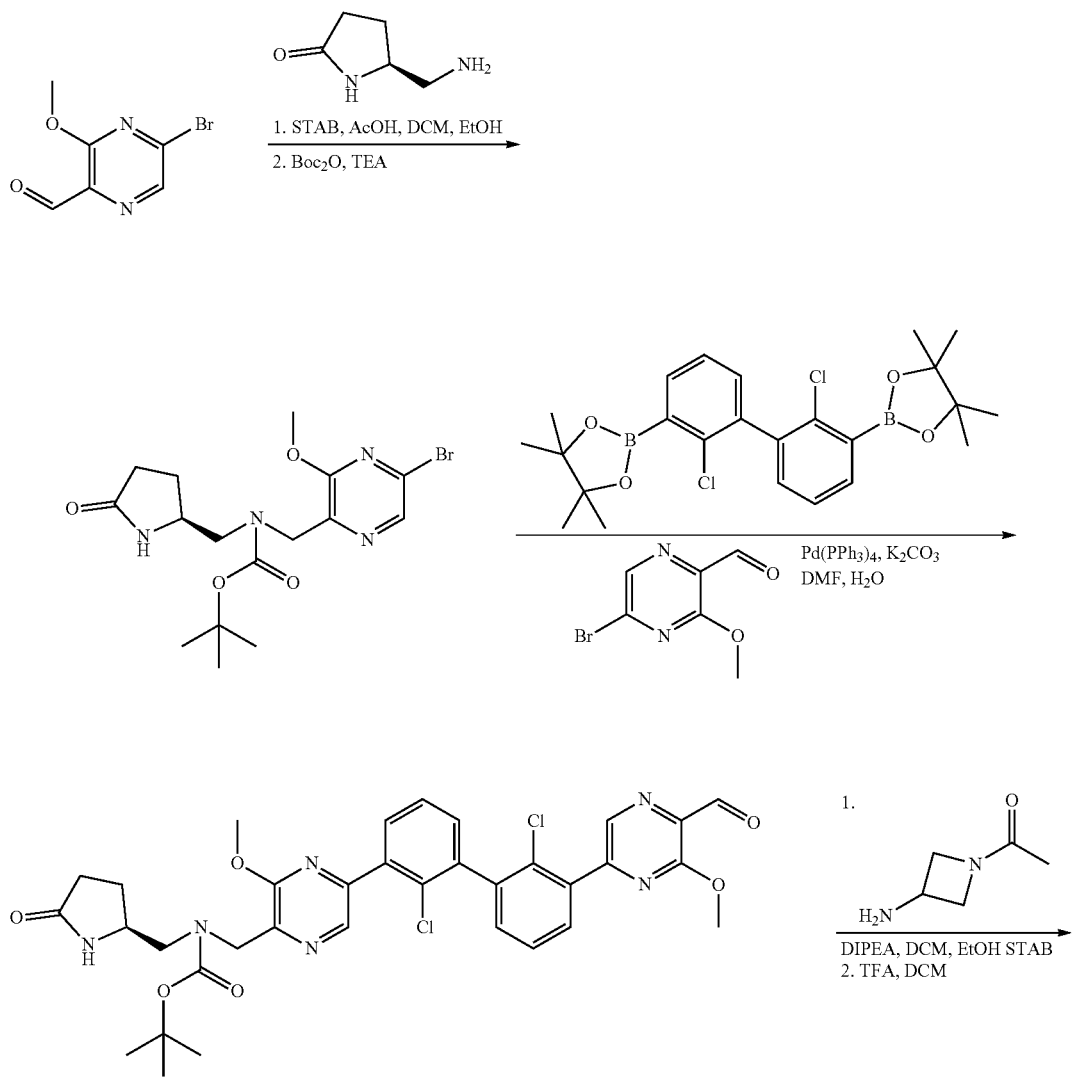

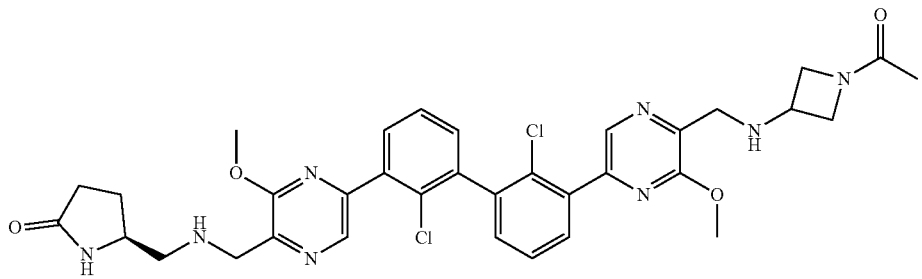

A solution of (S)-5-(aminomethyl)pyrrolidin-2-one (3.29 g, 2.8 mmol) and 5-bromo-3-methoxypyrazine-2-carbaldehyde (5.0 g, 2.3 mmol) in dimethylformamide (10 ml) was stirred for 90 minutes. Sodium triacetoxyborohydride (5.59 g, 3.1 mmol), acetic acid (1.78 ml, 3.1 mmol) and dimethylformamide (10 ml) were added. After 16 hours di-tert-butyl dicabonate (7.54 g, 3.5 mmol) and trimethylamine (8.42 ml, 6.0 mmol) were added. After 2 hours the reaction was partitioned with water (100 mL) and ethyl acetate (100 ml). The aqueous phase was extracted with ethyl acetate (2×75 mL). The combined organic phases were washed with brine (2×25 mL) and dried over sodium sulfate. The solvent was removed under reduced pressure. The residue was subjected to flash chromatography (0-20% methanol/dichloromethane). The fractions containing product were combined and the solvent was removed under reduced pressure providing tert-butyl (S)-((5-bromo-3-methoxypyrazin-2-yl)methyl)((5-oxopyrrolidin-2-yl)methyl)carbamate.

A mixture of 2,2'-(2,2'-dichloro-[1,1'-biphenyl]-3,3'-diyl)bis(4,4,5,5-tetramethyl-1,3,2-dioxaborolane) (2.29 g, 4.8 mmol), tert-butyl (S)-((5-bromo-3-methoxypyrazin-2-yl)methyl)((5-oxopyrrolidin-2-yl)methyl)carbamate (2.00 g, 4.8 mmol), 5-bromo-3-methoxypyrazine-2-carbaldehyde (1.05 g, 4.8 mmol), tetrakis(triphenylphosphine)palladium (0) (1.1 g, 0.96 mmol), potassium carbonate (2.00 g, 14.4 mmol) in dimethylformamide (40 ml) and water (6 ml) was degassed with argon of 10 minutes. The mixture was heated at 100° C. for 2 h. The mixture was portioned with water (50 ml) and ethyl acetate (200 ml). The organic phase was washed with 5% lithium chloride (2×50 ml) and brine (50 ml). The organic phase was dried over sodium sulfate and the solvent was removed under reduced pressure. The residue was subjected to flash chromatography (0-20% methanol/dichloromethane). The fractions containing product were combined and the solvent was removed under reduced pressure, providing tert-butyl (S)-((5-(2,2'-dichloro-3'-(5-formyl-6-methoxypyrazin-2-yl)-[1,1'-biphenyl]-3-yl)-3-methoxypyrazin-2-yl)methyl)((5-oxopyrrolidin-2-yl)methyl)carbamate.

A solution of tert-butyl (S)-((5-(2,2'-dichloro-3'-(5-formyl-6-methoxypyrazin-2-yl)-[1,1'-biphenyl]-3-yl)-3-methoxypyrazin-2-yl)methyl)((5-oxopyrrolidin-2-yl)methyl)carbamate (10 mg, 0.014 mmol), 1-(3-aminoazetidin-1-yl)ethan-1-one hydrochloride (6.6 mg, 0.058 mmol) and N,N-diisopropylethylamine (12.6 μL, 0.072 mmol) in dichloromethane (1 mL) and ethanol (1 mL) was stirred at room temperature for 10 minutes. Sodium tiracetoxyborohydride (30.6 mg, 0.144 mmol) and acetic acid (1 drop) were added. After 30 m the solvent was removed under reduced pressure. The residue was taken up in dichloromethane (2 mL) and trifluoroacetic acid (1 mL) were added. After 15 minutes the solvent was removed under reduced pressure. The residue was taken up in methanol (1 mL), water (0.75 mL). The solution was subjected to preparative HPLC (eluant 0.1% trifluoroacetic acid in water/ 0.1% trifluoroacetic acid in acetonitrile at a gradient of 20-100%). The clean fractions were combined and subjected to lyophilization, providing (S)-5-(((((5-(3'-(5-(((1-acetylazetidin-3-yl)amino)methyl)-6-methoxypyrazin-2-yl)-2,2'-dichloro-[1,1'-biphenyl]-3-yl)-3-methoxypyrazin-2-yl)methyl)amino)methyl)pyrrolidin-2-one.

Procedure 3: (5S,5'S)-5,5'-(((((2,2'-dichloro-[1,1'-biphenyl]-3,3'-diyl)bis(3-methoxypyrazine-5,2-diyl))bis(methylene))bis(azanediyl))bis(methylene))bis(pyrrolidin-2-one)

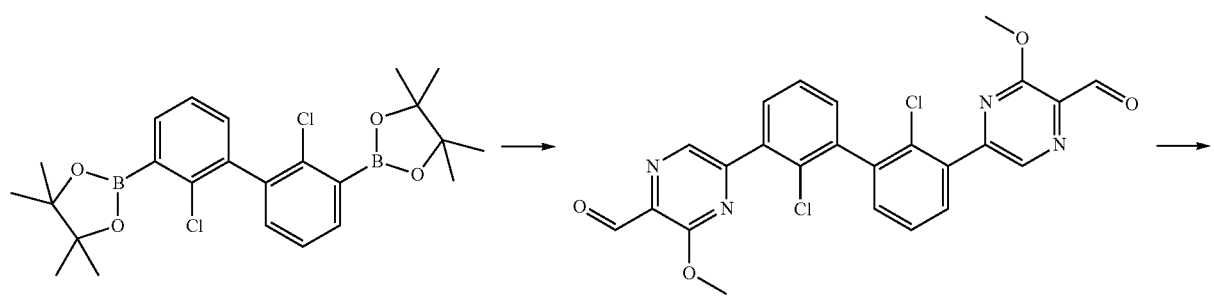

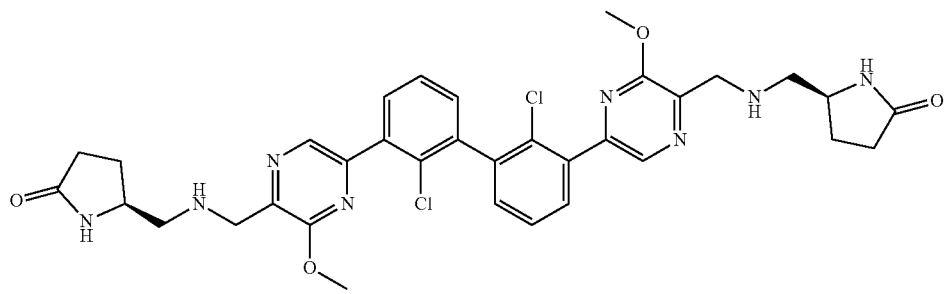

A vigorously stirred mixture of 2,2'-(2,2'-dichloro-[1,1'-biphenyl]-3,3'-diyl)bis(4,4,5,5-tetramethyl-1,3,2-dioxaborolane) (3.50 g, 7.37 mmol), 5-bromo-3-methoxypyrazine-2-carbaldehyde (3.52 g, 16.2 mmol), tetrakis(triphenylphosphine)palladium(0) (596 mg, 0.516 mmol), potassium carbonate (5.09 g, 36.8 mmol), water (5.0 mL), and 1,4-dioxane (24 mL) was heated to 100° C. After 40 min, the resulting mixture was cooled to room temperature. Ethyl acetate (125 mL) was added, and the organic layer was washed with a mixture of water and brine (1:1 v:v, 100 mL), was dried over anhydrous sodium sulfate, was filtered through celite, and was concentrated under reduced pressure. The residue was purified by flash column chromatography on silica gel (0 to 50% ethyl acetate in hexanes) to give 5,5'-(2,2'-dichloro-[1,1'-biphenyl]-3,3'-diyl)bis(3-methoxypyrazine-2-carbaldehyde) contaminated with pinacol. Dichloromethane (50 mL) was added, and the resulting mixture was stirred at room temperature. (S)-5-(Aminomethyl)pyrrolidin-2-one (2.52 g, 22.1 mmol) was added. After 15 min, acetic acid (1.05 mL, 18.4 mmol) was added via syringe. After 1 min, sodium triacetoxyborohydride (7.81 g, 36.9 mmol) was added. After 75 min, aqueous sodium hydroxide solution (2 M, 63 mL) was added, and the resulting biphasic mixture was stirred vigorously. After 10 min, saturated aqueous sodium carbonate solution (40 mL) was added. After 5 min, water (80 mL) and dichloromethane (40 mL) were added sequentially. The resulting biphasic mixture was agitated, and the layers were separated. The aqueous layer was extracted with dichloromethane (3×125 mL). The combined organic layers were dried over anhydrous sodium sulfate, were filtered through celite, and were concentrated under reduced pressure. The residue was purified by flash column chromatography on silica gel (0 to 20% methanol in dichloromethane) to give (5S,5'S)-5,5'-(((((2,2'-dichloro-[1,1'-biphenyl]-3,3'-diyl)bis(3-methoxypyrazine-5,2-diyl))bis(methylene))bis(azanediyl))bis(methylene))bis(pyrrolidin-2-one). Acetonitrile (15 mL) and methanol (15 mL) were added sequentially to dissolve the gel. Trifluoroacetic acid (1.0 mL) was added, and the resulting mixture was swirled vigorously. After 1 min, the resulting mixture was concentrated under reduced pressure. The residue was lyophilized from a mixture of acetonitrile and water (1:1 v:v, 30 mL) to give (5S,5'S)-5,5'-(((((2,2'-dichloro-[1,1'-biphenyl]-3,3'-diyl)bis(3-methoxypyrazine-5,2-diyl))bis(methylene))bis(azanediyl))bis(methylene))bis(pyrrolidin-2-one) bis(2,2,2-trifluoroacetate). A portion of this material (2.1 g) was dissolved in 10% acetonitrile in water (15 mL) and was further purified by reverse phase preparative HPLC (0.1% trifluoroacetic acid in acetonitrile/water) to give (5 S,5'S)-5,5'-(((((2,2'-dichloro-[1,1'-biphenyl]-3,3'-diyl)bis(3-methoxypyrazine-5,2-diyl))bis(methylene))bis(azanediyl))bis(methylene))bis(pyrrolidin-2-one) bis(2,2,2-trifluoroacetate). $^1$H NMR (400 MHz, Methanol-$d_4$) δ 8.53 (s, 2H), 7.72 (dd, J=7.6, 1.7 Hz, 2H), 7.58 (t, J=7.6 Hz, 2H), 7.48 (dd, J=7.6, 1.7 Hz, 2H), 4.58-4.47 (m, 4H), 4.18-4.07 (m, 2H), 4.12 (s, 6H), 3.42-3.27 (m, 4H), 2.54-2.25 (m, 6H), 2.08-1.83 (m, 2H); LRMS (ESI-TOF) Calc'd for $C_{34}H_{36}Cl_2N_8O_4$ [M+H]$^+$: 691.2; found 691.3.

Procedure 4: (1R,1'R,3R,3'R)-3,3'-(((((2,2'-dichloro-[1,1'-biphenyl]-3,3'-diyl)bis(3-(methylamino)pyrazine-5,2-diyl))bis(methylene))bis(azanediyl))bis(methylene))bis(cyclobutan-1-ol)

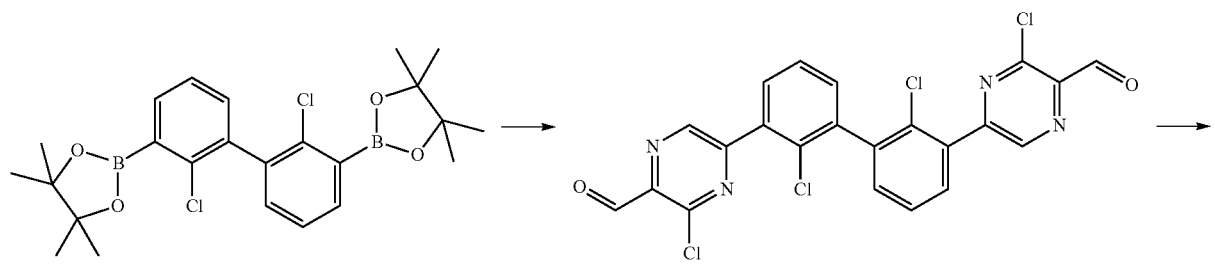

-continued

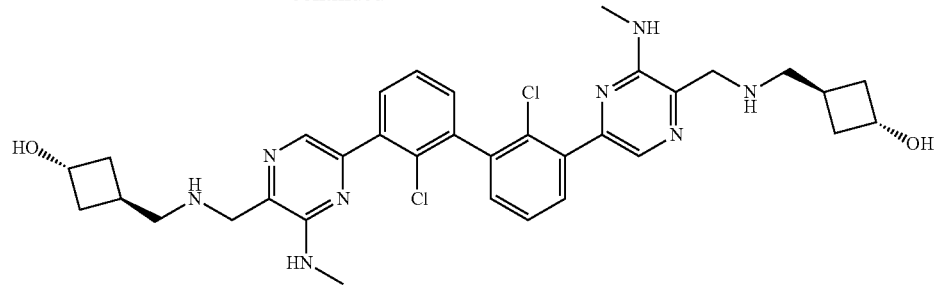

A vigorously stirred mixture of 2,2'-(2,2'-dichloro-[1,1'-biphenyl]-3,3'-diyl)bis(4,4,5,5-tetramethyl-1,3,2-dioxaborolane) (750 mg, 1.58 mmol), 3,5-dichloropyrazine-2-carbaldehyde (3.52 g, 16.2 mmol), [1,1'-bis(diphenylphosphino)ferrocene]dichloropalladium(II) (92 mg, 0.13 mmol), cesium carbonate (3.09 g, 9.47 mmol), water (1.8 mL), and 1,4-dioxane (11 mL) was heated to 100° C. After 60 min, the resulting mixture was cooled to room temperature, was filtered through celite, and was concentrated under reduced pressure. The residue was purified by flash column chromatography on silica gel (0 to 70% ethyl acetate in hexanes) to give 5,5'-(2,2'-dichloro-[1,1'-biphenyl]-3,3'-diyl)bis(3-chloropyrazine-2-carbaldehyde).

A stirred mixture of 5,5'-(2,2'-dichloro-[1,1'-biphenyl]-3,3'-diyl)bis(3-chloropyrazine-2-carbaldehyde) (55.0 mg, 0.019 mmol) and methylamine solution (2.0 M in tetrahydrofuran, 6.0 mL, 12 mmol) was heated to 70° C. After 60 min, acetic acid (0.5 mL) and water (2.0 mL) were sequentially added. After 30 min, the resulting mixture was cooled to room temperature. Ethyl acetate (15 ml) was added, and the organic layer was washed with water (2×15 mL), was dried over anhydrous sodium sulfate, was filtered, and was concentrated under reduced pressure. The residue was dissolved in dimethylsulfoxide (1.5 mL) and acetic acid (0.15 mL) and stirred at room temperature. (1r,3r)-3-(Aminomethyl)cyclobutan-1-ol hydrochloride (41.8 mg, 0.304 mmol), N,N-diisopropylethylamine (79.4 µL, 0.456 mmol), and sodium triacetoxyborohydride (64.4 mg, 0.304 mmol) were added sequentially, and the resulting mixture was heated to 57° C. After 60 min, the resulting mixture was cooled to room temperature and was purified by reverse phase preparative HPLC (0.1% trifluoroacetic acid in acetonitrile/water) to give (1r,1'r,3r,3'r)-3,3'-(((((2,2'-dichloro-[1,1'-biphenyl]-3,3'-diyl)bis(3-(methylamino)pyrazine-5,2-diyl))bis(azanediyl))bis(methylene))bis(cyclobutan-1-ol).

Procedure 5: 1,1'-(((2,2'-dichloro-[1,1'-biphenyl]-3,3'-diyl)bis(pyrazine-5,2-diyl))bis(methylene))bis(azetidin-3-ol)

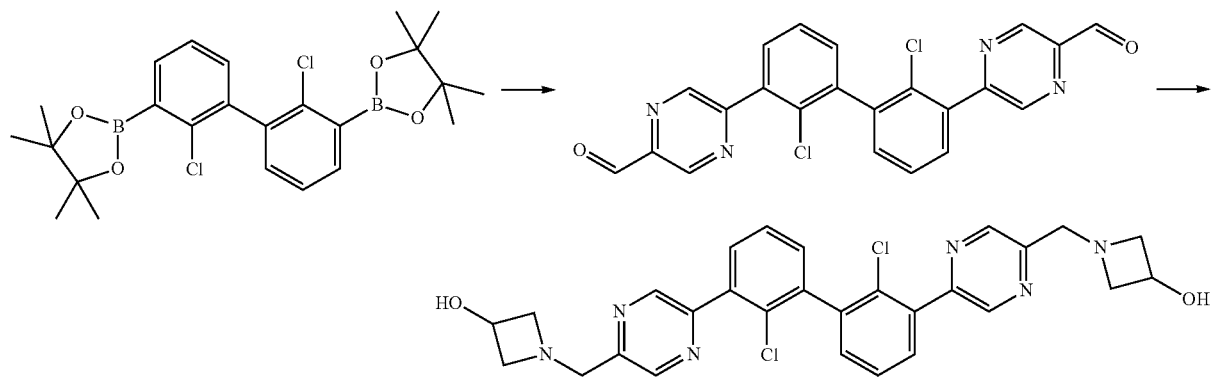

A vigorously stirred mixture of 2,2'-(2,2'-dichloro-[1,1'-biphenyl]-3,3'-diyl)bis(4,4,5,5-tetramethyl-1,3,2-dioxaborolane) (150 mg, 0.316 mmol), 5-chloropyrazine-2-carbaldehyde (135 mg, 0.947 mmol), tetrakis(triphenylphsophine)palladium(0) (26 mg, 0.022 mmol), potassium carbonate (218 mg, 1.58 mmol), water (5 mL), and 1,4-dioxane (24 mL) was heated to 100° C. After 60 min, the resulting mixture was cooled to room temperature, was filtered through celite, and was concentrated under reduced pressure. The residue was purified by flash column chromatography on silica gel (0 to 70% ethyl acetate in hexanes) to give 5,5'-(2,2'-dichloro-[1,1'-biphenyl]-3,3'-diyl)bis(pyrazine-2-carbaldehyde).

Sodium triacetoxyborohydride (82.8 mg, 0.391 mmol) was added to a stirred mixture of 5,5'-(2,2'-dichloro-[1,1'-biphenyl]-3,3'-diyl)bis(pyrazine-2-carbaldehyde) (17 mg, 0.039 mmol), 3-hydroxyazetidine hydrochloride (42.8 mg, 0.391 mmol), N,N-diisopropylethylamine (102 µL, 0.586 mmol), acetic acid (0.15 mL), and dimethylsulfoxide (1.5 mL) at 57° C. After 60 min, the resulting mixture was cooled to room temperature and was purified by reverse phase preparative HPLC (0.1% trifluoroacetic acid in acetonitrile/water) to give 1,1'-(((2,2'-dichloro-[1,1'-biphenyl]-3,3'-diyl)bis(pyrazine-5,2-diyl))bis(methylene))bis(azetidin-3-ol).

Procedure 6: 1,1'-(((2,2'-dichloro-[1,1'-biphenyl]-3,3'-diyl)bis(3-ethylpyrazine-5,2-diyl))bis(methylene))bis(azetidin-3-ol)

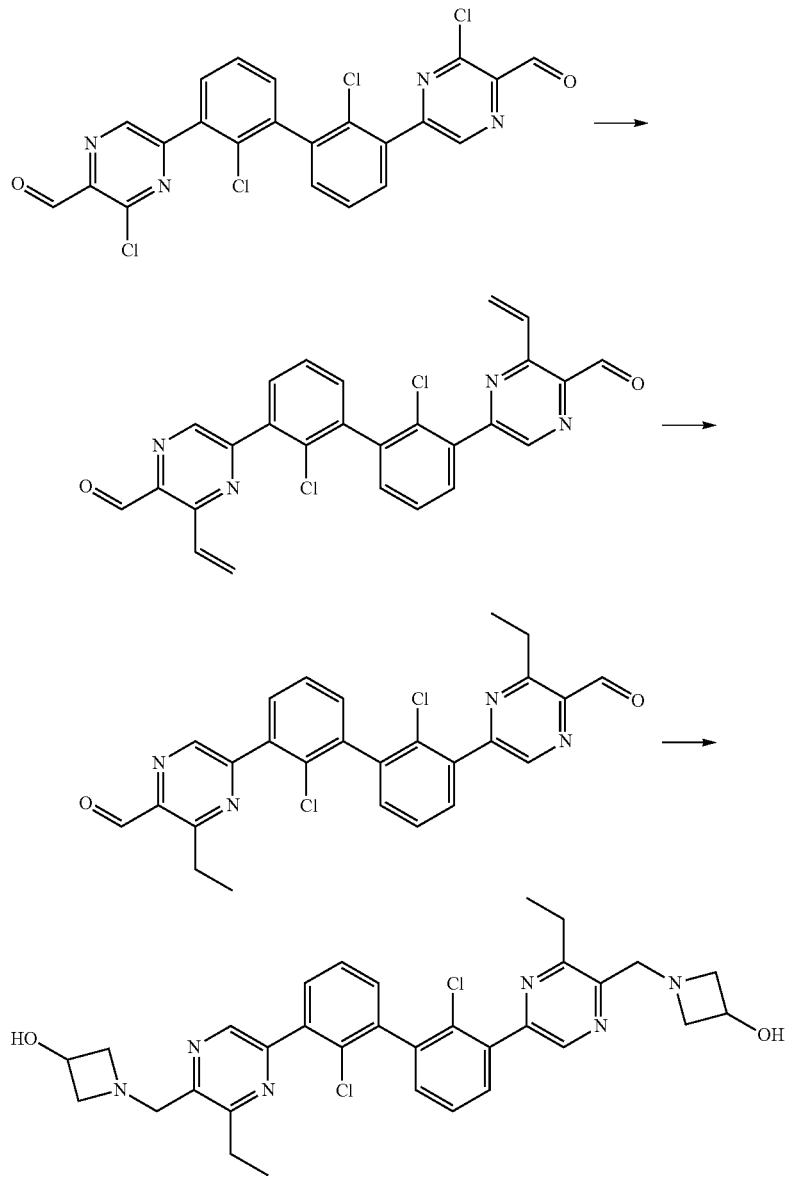

A stirred mixture of 5,5'-(2,2'-dichloro-[1,1'-biphenyl]-3,3'-diyl)bis(3-chloropyrazine-2-carbaldehyde) (84.2 mg, 0.167 mmol), tributyl(vinyl)stannane (390 µL, 1.336 mmol), and tetrakis(triphenylphsophine)palladium(0) (39 mg, 0.033 mmol) in toluene (2.0 mL) was heated to 110° C. After 37 min, the resulting mixture was cooled to room temperature and was purified by flash column chromatography on silica gel (0 to 35% ethyl acetate in hexanes) to give 5,5'-(2,2'-dichloro-[1,1'-biphenyl]-3,3'-diyl)bis(3-vinylpyrazine-2-carbaldehyde).

A mixture of 5,5'-(2,2'-dichloro-[1,1'-biphenyl]-3,3'-diyl)bis(3-vinylpyrazine-2-carbaldehyde) (53.8 mg, 0.110 mmol) and palladium on carbon (10% wt, 23.5 mg, 0.022 mmol) in ethanol (2.0 mL) and tetrahydrofuran (1.0 mL) was stirred under one atmosphere of hydrogen gas at room temperature. After 90 min, the reaction mixture was filtered through celite and was concentrated under reduced pressure to give 5,5'-(2,2'-dichloro-[1,1'-biphenyl]-3,3'-diyl)bis(3-ethylpyrazine-2-carbaldehyde).

Sodium triacetoxyborohydride (43.1 mg, 0.204 mmol) was added to a stirred mixture of 5,5'-(2,2'-dichloro-[1,1'-biphenyl]-3,3'-diyl)bis(3-ethylpyrazine-2-carbaldehyde) (10 mg, 0.020 mmol), 3-hydroxyazetidine hydrochloride (22.3 mg, 0.204 mmol), N,N-diisopropylethylamine (53.2 µL, 0.305 mmol), acetic acid (0.15 mL), and dimethylsulfoxide (1.5 mL) at 57° C. After 60 min, the resulting mixture was cooled to room temperature and was purified by reverse phase preparative HPLC (0.1% trifluoroacetic acid in acetonitrile/water) to give 1,1'-(((2,2'-dichloro-[1,1'-biphenyl]-3,3'-diyl)bis(3-ethylpyrazine-5,2-diyl))bis(methylene))bis(azetidin-3-ol).

Procedure 7: 5,5'-(2,2'-dichloro-[1,1'-biphenyl]-3,3'-diyl)bis(2-((3-methoxyazetidin-1-yl)methyl)-3-(methylthio)pyrazine)

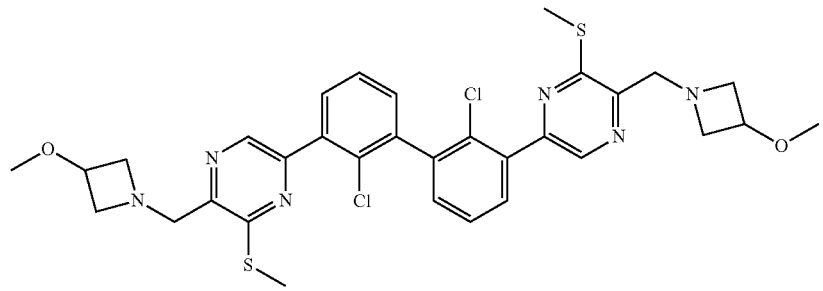

Sodium methanethiolate (72.3 mg, 1.03 mmol) was added to a stirred mixture of 5,5'-(2,2'-dichloro-[1,1'-biphenyl]-3,3'-diyl)bis(3-chloropyrazine-2-carbaldehyde) (104 mg, 0.206 mmol), in N,N-dimethylformamide (2.0 mL) at room temperature. After 20 min, diethyl ether (20 mL) and ethyl acetate (20 mL) were added. The organic layer was washed sequentially with aqueous sodium hydroxide solution (0.2 M, 30 mL) and water (30 mL), was dried over anhydrous magnesium sulfate, was filtered, and was concentrated under reduced pressure to give 5,5'-(2,2'-dichloro-[1,1'-biphenyl]-3,3'-diyl)bis(3-(methylthio)pyrazine-2-carbaldehyde).

5,5'-(2,2'-dichloro-[1,1'-biphenyl]-3,3'-diyl)bis(2-((3-methoxyazetidin-1-yl)methyl)-3-(methylthio)pyrazine) was synthesized in a manner similar to Procedure 6 using 5,5'-(2,2'-dichloro-[1,1'-biphenyl]-3,3'-diyl)bis(3-(methylthio)pyrazine-2-carbaldehyde) in place of 5,5'-(2,2'-dichloro-[1,1'-biphenyl]-3,3'-diyl)bis(3-ethylpyrazine-2-carbaldehyde) and using 3-methoxyazetidine hydrochloride in place of 3-hydroxyazetidine hydrochloride.

Procedure 8: 5,5'-(2,2'-dichloro-[1,1'-biphenyl]-3,3'-diyl)bis(2-((3-methoxyazetidin-1-yl)methyl)-3-methylpyrazine)

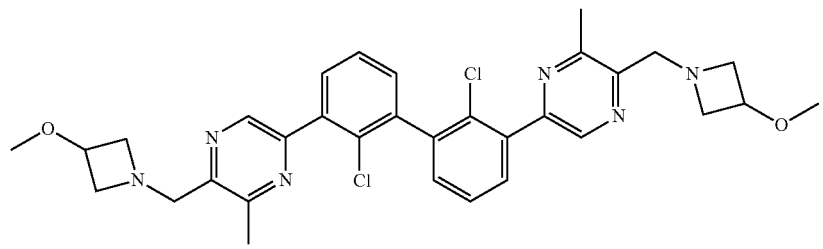

A vigorously stirred mixture of 5,5'-(2,2'-dichloro-[1,1'-biphenyl]-3,3'-diyl)bis(3-chloropyrazine-2-carbaldehyde) (60 mg, 0.12 mmol), tetramethyltin (165 µL, 1.19 mmol), and [1,1'-bis(diphenylphosphino)ferrocene]dichloropalladium(II) (8.7 mg, 0.012 mmol) in N,N-dimethylformamide (2.0 mL) was heated to 110° C. After 60 min, the resulting mixture was cooled to room temperature. An aliquot of the reaction mixture (0.4 mL) was removed via syringe and was added to a stirred mixture of 3-methoxyazetidine hydrochloride (26.7 mg, 0.216 mmol) and N,N-diisopropylethylamine (56.4 µL, 0.324 mmol) in N,N-dimethylformamide (1.5 mL) and acetic acid (0.15 mL) at 57° C. Sodium triacetoxyborohydride (45.7 mg, 0.217 mmol) was added. After 60 min, the resulting mixture was cooled to room temperature and was purified by reverse phase preparative HPLC (0.1% trifluoroacetic acid in acetonitrile/water) to give 5,5'-(2,2'-dichloro-[1,1'-biphenyl]-3,3'-diyl)bis(2-((3-methoxyazetidin-1-yl)methyl)-3-methylpyrazine).

Procedure 9: 1,1'-(((2,2'-dibromo-[1,1'-biphenyl]-3,3'-diyl)bis(3-methoxypyrazine-5,2-diyl))bis(methylene))bis(azetidin-3-ol)

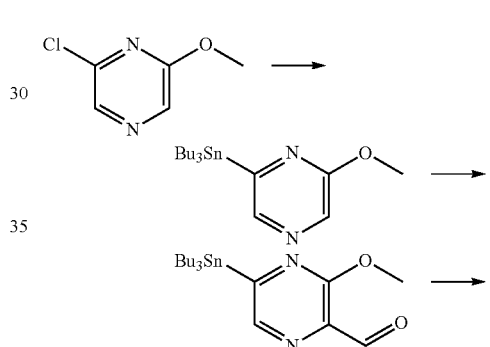

-continued

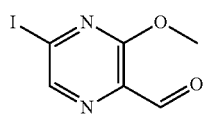

A stirred mixture of 2-chloro-6-methoxypyrazine (2.00 g, 13.8 mmol), hexabutylditin (8.74 mL, 17.3 mmol), and [1,1'-bis(diphenylphosphino)ferrocene]dichloropalladium (II) (304 mg, 0.415 mmol) in toluene (22 mL) was heated to 115° C. After 18 h, the resulting mixture was cooled to room temperature, was filtered through celite, and was concentrated under reduced pressure. The residue was purified by flash column chromatography on silica gel (0 to 10% ethyl acetate in hexanes) to give 2-methoxy-6-(tributylstannyl) pyrazine.

Lithium diisopropylamide solution (2.0 M in tetrahydrofuran/heptane/ethylbenzene, 2.4 mL, 4.8 mmol) was added over 2 min via syringe to a stirred solution of 2-methoxy-6-(tributylstannyl)pyrazine (872 mg, 2.19 mmol) in tetrahydrofuran (18 mL) at −78° C. After 100 min, N,N,-dimethylformamide (846 μL, 10.9 mmol) was added via syringe. After 45 min, saturated aqueous ammonium chloride solution (20 mL) and water (20 mL) were sequentially added, and the resulting biphasic mixture was warmed to room temperature with vigorous stirring. Diethyl ether (125 mL) was added, and the organic layer was washed sequentially with water (50 mL) and a mixture of water and saturated aqueous ammonium chloride solution (1:1 v:v, 100 mL), was dried over anhydrous magnesium sulfate, was filtered, and was concentrated under reduced pressure. The residue was purified by flash column chromatography on silica gel (0 to 10% ethyl acetate in hexanes) to give 3-methoxy-5-(tributylstannyl)pyrazine-2-carbaldehyde.

Iodine (79.1 mg, 0.312 mmol) was added to a stirred solution of give 3-methoxy-5-(tributylstannyl)pyrazine-2-carbaldehyde (133 mg, 0.312 mmol) in tetrahydrofuran (2 mL) at room temperature in the dark. After 15 h, sodium thiosulfate (20 mg) was added, and the resulting mixture was concentrated under reduced pressure. The residue was purified by flash column chromatography on silica gel (0 to 20% methanol in dichloromethane) to give 5-iodo-3-methoxypyrazine-2-carbaldehyde.

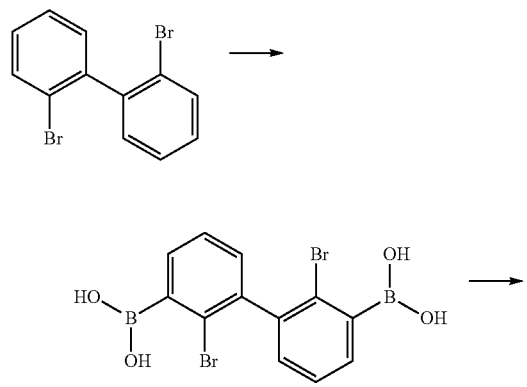

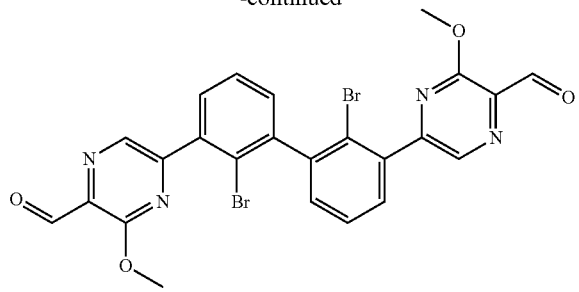

n-Butyl lithium solution (1.94 M in cyclohexane, 19.8 mL, 38.5 mmol) was added over 2 min via syringe to a stirred solution of 2,2,6,6-tetramethylpiperidine (6.49 mL, 38.5 mmol) in tetrahydrofuran (64 mL) at 0° C. After 10 min, the resulting mixture was cooled to −78° C. over 15 min. Triisopropyl borate (14.8 mL, 64.1 mmol) was added over 2 min via syringe. After 8 min, a solution of 2,2'-dibromo-1,1'-biphenyl (2.00 g, 6.41 mmol) in tetrahydrofuran (15 mL) at −78° C. was added over 5 min via cannula. After 3.5 h, triisopropyl borate (7.40 mL, 32.1 mmol) was added over 5 min via syringe, and the resulting mixture was allowed to warm to −45° C. over 15.5 h. Aqueous hydrogen chloride solution (1 M, 100 mL) was added, and the resulting biphasic mixture was warmed to rt. The aqueous layer was extracted with ethyl acetate (3×100 mL). The combined organic layers were extracted with aqueous sodium hydroxide solution (4×100 mL). Concentrated hydrochloric acid was added to the combined basic aqueous layers until the combined layers had a pH of 1, and the resulting combined aqueous layers were extracted with ethyl acetate (3×250 mL). The combined organic layers from this extraction were dried over anhydrous sodium sulfate, were filtered, and were concentrated under reduced pressure to give (2,2'-dibromo-[1,1'-biphenyl]-3,3'-diyl)diboronic acid.

A stirred mixture of (2,2'-dibromo-[1,1'-biphenyl]-3,3'-diyl)diboronic acid (40 mg, 0.100 mmol), 5-iodo-3-methoxypyrazine-2-carbaldehyde (52.9 mg, 0.200 mmol), tetrakis(triphenylphsophine)palladium(0) (12 mg, 0.010 mmol), and saturated aqueous sodium carbonate solution (400 μL) in 1,2-dimethoxyethane (2.0 mL) was heated to 100° C. After 2 h, the resulting mixture was cooled to room temperature. Ethyl acetate (30 mL) was added. The organic layer was washed with brine (20 mL), was dried over anhydrous sodium sulfate, was filtered, and was concentrated under reduced pressure. The residue was purified by flash column chromatography on silica gel (0 to 35% ethyl acetate in hexanes) to give 5,5'-(2,2'-dibromo-[1,1'-biphenyl]-3,3'-diyl)bis(3-methoxypyrazine-2-carbaldehyde).

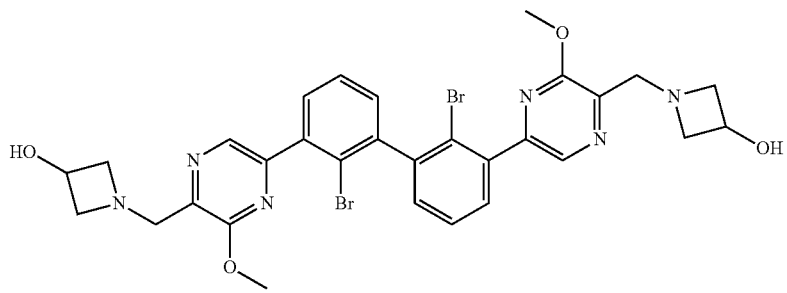 [SMILES: COc1nc(-c2cccc(-c3cccc(-c4cnc(CN5CC(O)C5)c(OC)n4)c3Br)c2Br)cnc1CN1CC(O)C1]

1,1'-(((2,2'-dibromo-[1,1'-biphenyl]-3,3'-diyl)bis(3-methoxypyrazine-5,2-diyl))bis(methylene))bis(azetidin-3-ol) was synthesized in a manner similar to Procedure 6 using 5,5'-(2,2'-dibromo-[1,1'-biphenyl]-3,3'-diyl)bis(3-methoxypyrazine-2-carbaldehyde) in place of 5,5'-(2,2'-dichloro-[1,1'-biphenyl]-3,3'-diyl)bis(3-ethylpyrazine-2-carbaldehyde).

Procedure 10: 2-((5-(2,2'-dichloro-3'-(5-(4,5-dihydro-1H-imidazol-2-yl)-6-methoxypyridin-2-yl)-[1,1'-biphenyl]-3-yl)-3-methoxypyrazin-2-yl)methyl)-2,6-diazaspiro[3.4]octan-7-one

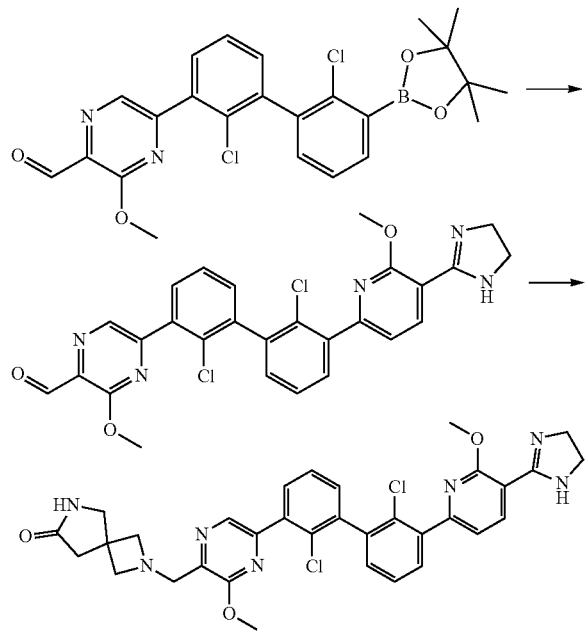

A vigorously stirred mixture of 5-(2,2'-dichloro-3'-(4,4,5,5-tetramethyl-1,3,2-dioxaborolan-2-yl)-[1,1'-biphenyl]-3-yl)-3-methoxypyrazine-2-carbaldehyde (35 mg, 0.072 mmol), 6-chloro-3-(4,5-dihydro-1H-imidazol-2-yl)-2-methoxypyridine (32 mg, 0.15 mmol), chloro(2-dicyclohexylphosphino-2',4',6'-triisopropyl-1,1'-biphenyl) [2-(2'-amino-1,1'-biphenyl)]palladium(II) (3 mg, 0.004 mmol), and saturated aqueous sodium carbonate solution (180 µL), in 1,4-dioxane (1.5 mL) was heated to 105° C. After 60 min, the resulting mixture was cooled to room temperature. Ethyl acetate (30 mL) was added, and the organic layer was washed with brine (20 mL), was dried over anhydrous sodium sulfate, was filtered, and was concentrated under reduced pressure to give 5-(2,2'-dichloro-3'-(5-(4,5-dihydro-1H-imidazol-2-yl)-6-methoxypyridin-2-yl)-[1,1'-biphenyl]-3-yl)-3-methoxypyrazine-2-carbaldehyde.

2-((5-(2,2'-dichloro-3'-(5-(4,5-dihydro-1H-imidazol-2-yl)-6-methoxypyridin-2-yl)-[1,1'-biphenyl]-3-yl)-3-methoxypyrazin-2-yl)methyl)-2,6-diazaspiro[3.4]octan-7-one was synthesized in a manner similar to Procedure 6 using 5-(2,2'-dichloro-3'-(5-(4,5-dihydro-1H-imidazol-2-yl)-6-methoxypyridin-2-yl)-[1,1'-biphenyl]-3-yl)-3-methoxypyrazine-2-carbaldehyde in place of 5,5'-(2,2'-dichloro-[1,1'-biphenyl]-3,3'-diyl)bis(3-ethylpyrazine-2-carbaldehyde) and using 2,6-diazaspiro[3.4]octan-7-one hydrochloride in place of 3-hydroxyazetidine hydrochloride.

Procedure 11: (5S,5'S)-5,5'-(((((2,2'-dichloro-5-fluoro-[1,1'-biphenyl]-3,3'-diyl)bis(3-methoxypyrazine-5,2-diyl))bis(methylene))bis(azanediyl))bis(methylene))bis(pyrrolidin-2-one)

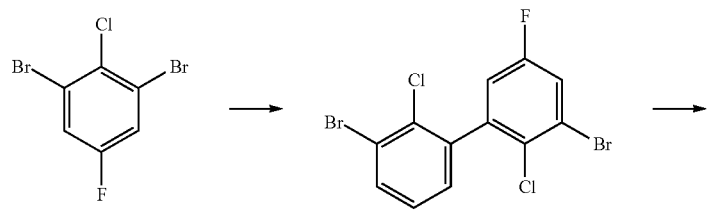

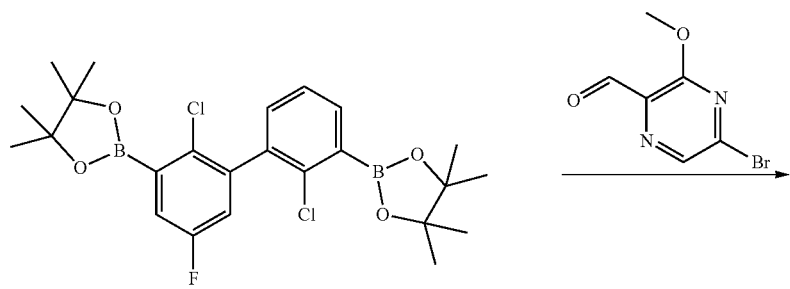

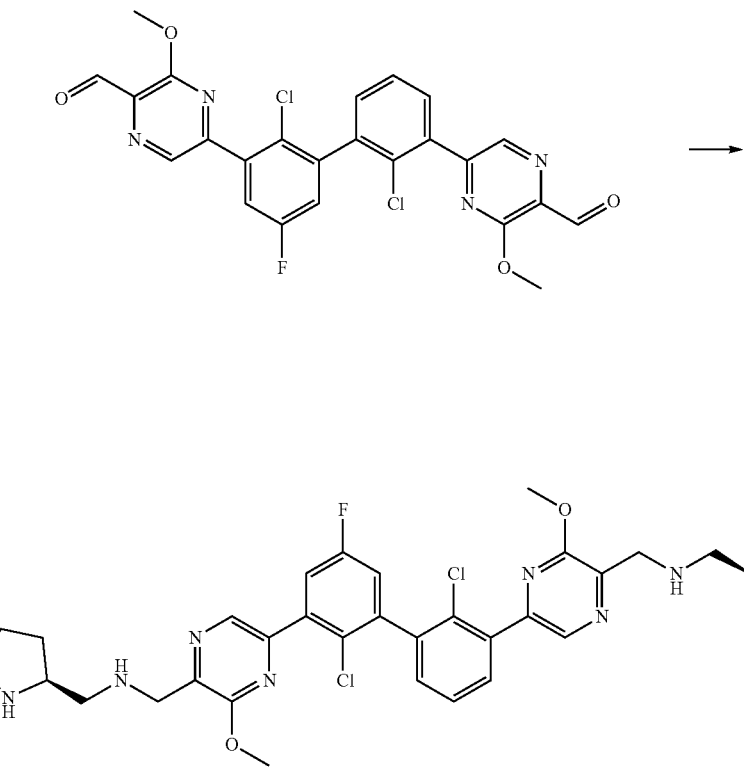

A stirred mixture of 1,3-dibromo-2-chloro-5-fluorobenzene (1.08 g, 3.75 mmol, (3-bromo-2-chlorophenyl)boronic acid (0.420 g, 1.79 mmol, aqueous sodium carbonate solution (2.0 M, 5.35 mL, 10.71 mmol), and tetrakis(triphenylphosphine)palladium(0) (103.15 mg, 0.089 mmol) in 1,4-dioxane (7 mL) was heated to 105° C. in a heating block. After 60 min, the resulting mixture was allowed to cool to room temperature. Ethyl acetate (30 mL) was added, and the organic layer was washed with brine (20 mL), was dried over anhydrous magnesium sulfate, was filtered, and was concentrated under reduced pressure. The residue was purified by flash column chromatography on silica gel (0 to 10% ethyl acetate in hexane) to give 3,3'-dibromo-2,2'-dichloro-5-fluoro-1,1'-biphenyl.

A stirred mixture of 3,3'-dibromo-2,2'-dichloro-5-fluoro-1,1'-biphenyl (0.443 g, 1.11 mmol), 4,4,4',4',5,5,5',5'-octamethyl-2,2'-bi(1,3,2-dioxaborolane) (0.705 g, 2.78 mmol), potassium acetate (0.545 g, 5.55 mmol), [1,1'-bis(diphenylphosphino)ferrocene]dichloropalladium(II) (0.041 g, 0.056 mmol) in dioxane (4 mL) was heated to 100° C. in a heating block. After 90 min, the resulting mixture was allowed to cool to room temperature and filtered through a pad of celite, was rinsed with EtOAc (10 mL), and was concentrated under reduced pressure. The residue was purified by flash column chromatography on silica gel (0 to 50% ethyl acetate in hexane) to give 2,2'-(2,2'-dichloro-5-fluoro-[1,1'-biphenyl]-3,3'-diyl)bis(4,4,5,5-tetramethyl-1,3,2-dioxaborolane).

A stirred mixture of 2,2'-(2,2'-dichloro-5-fluoro-[1,1'-biphenyl]-3,3'-diyl)bis(4,4,5,5-tetramethyl-1,3,2-dioxaborolane) (53 mg, 0.107 mmol), 5-bromo-3-methoxypyrazine-2-carbaldehyde (49 mg, 0.226 mmol), aqueous sodium carbonate solution (2.0 M, 323 µL, 0.645 mmol), and chloro(2-dicyclohexylphosphino-2',4',6'-triisopropyl-1,1'-biphenyl) [2-(2'-amino-1,1'-biphenyl)]palladium(II) (4 mg, 0.005 mmol) in 1,4-dioxane (0.5 mL) was heated to 105° C. in a heating block. After 60 min, the resulting mixture was allowed to cool to room temperature. Ethyl acetate (5 mL) was added, and the organic layer was washed with brine (2 mL), was dried over anhydrous magnesium sulfate, was filtered, and was concentrated under reduced pressure to give 5,5'-(2,2'-dichloro-5-fluoro-[1,1'-biphenyl]-3,3'-diyl)bis(3-methoxypyrazine-2-carbaldehyde).

N,N-diisopropylethylamine (76 µL, 0.430 mmol) was added via syringe to a stirred mixture of 5,5'-(2,2'-dichloro-5-fluoro-[1,1'-biphenyl]-3,3'-diyl)bis(3-methoxypyrazine-2-carbaldehyde). (15 mg, 0.029 mmol) and (S)-5-(aminomethyl)pyrrolidin-2-one hydrochloride (44 mg, 0.290 mmol) in dimethylsulfoxide (1 mL) at room temperature. After 10 min, sodium triacetoxyborohydride (62 mg, 0.290 mmol) was added as a solid, and the resulting mixture was heated to 60° C. in a heating block. After 30 min, the resulting mixture was allowed to cool to room temperature. The mixture was filtered and was purified by reverse phase preparative HPLC (0.1% trifluoroacetic acid in acetonitrile/water) to give (5 S,5'S)-5,5'-(((((2,2'-dichloro-5-fluoro-[1,1'-biphenyl]-3,3'-diyl)bis(3-methoxypyrazine-5,2-diyl))bis(methylene))bis(azanediyl))bis(methylene))bis(pyrrolidin-2-one).

Procedure 12: 2-((5-(2,2'-dichloro-3"-methoxy-4"-((7-oxo-2,6-diazaspiro[3.4]octan-2-yl)methyl)-[1,1': 3',1"-terphenyl]-3-yl)-3-methoxypyrazin-2-yl)methyl)-2,6-diazaspiro[3.4]octan-7-one

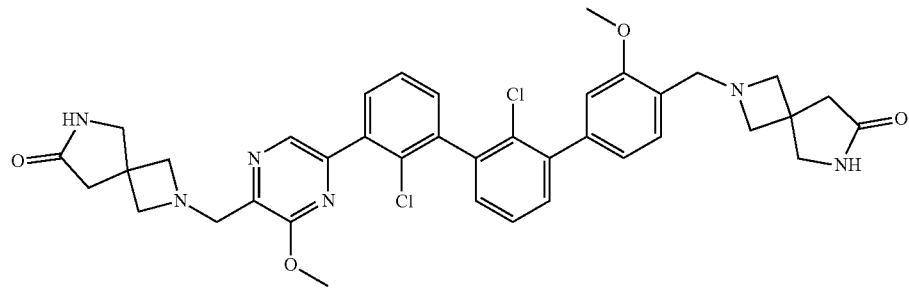 [SMILES: COc1cc(-c2cccc(-c3cccc(-c4cnc(CN5CC6(CNC(=O)C6)C5)c(OC)n4)c3Cl)c2Cl)ccc1CN1CC2(CNC(=O)C2)C1]

2-((5-(2,2'-dichloro-3"-methoxy-4"-((7-oxo-2,6-diazaspiro[3.4]octan-2-yl)methyl)-[1,1':3',1"-terphenyl]-3-yl)-3-methoxypyrazin-2-yl)methyl)-2,6-diazaspiro[3.4]octan-7-one was synthesized in a manner similar to 2-((5-(2,2'-dichloro-3'-(5-(4,5-dihydro-1H-imidazol-2-yl)-6-methoxypyridin-2-yl)-[1,1'-biphenyl]-3-yl)-3-methoxypyrazin-2-yl)methyl)-2,6-diazaspiro[3.4]octan-7-one (Procedure 10) using 4-bromo-2-methoxybenzaldehyde in place of 6-chloro-3-(4,5-dihydro-1H-imidazol-2-yl)-2-methoxypyridine.

Procedure 13: (S)-2',2"-dichloro-3"-(6-methoxy-5-(((((5-oxopyrrolidin-2-yl)methyl)amino)methyl)pyrazin-2-yl)-4-((6-oxo-2,5-diazaspiro[33.4]octan-2-yl)methyl)-[1,1':3',1"-terphenyl]-3-carbonitrile

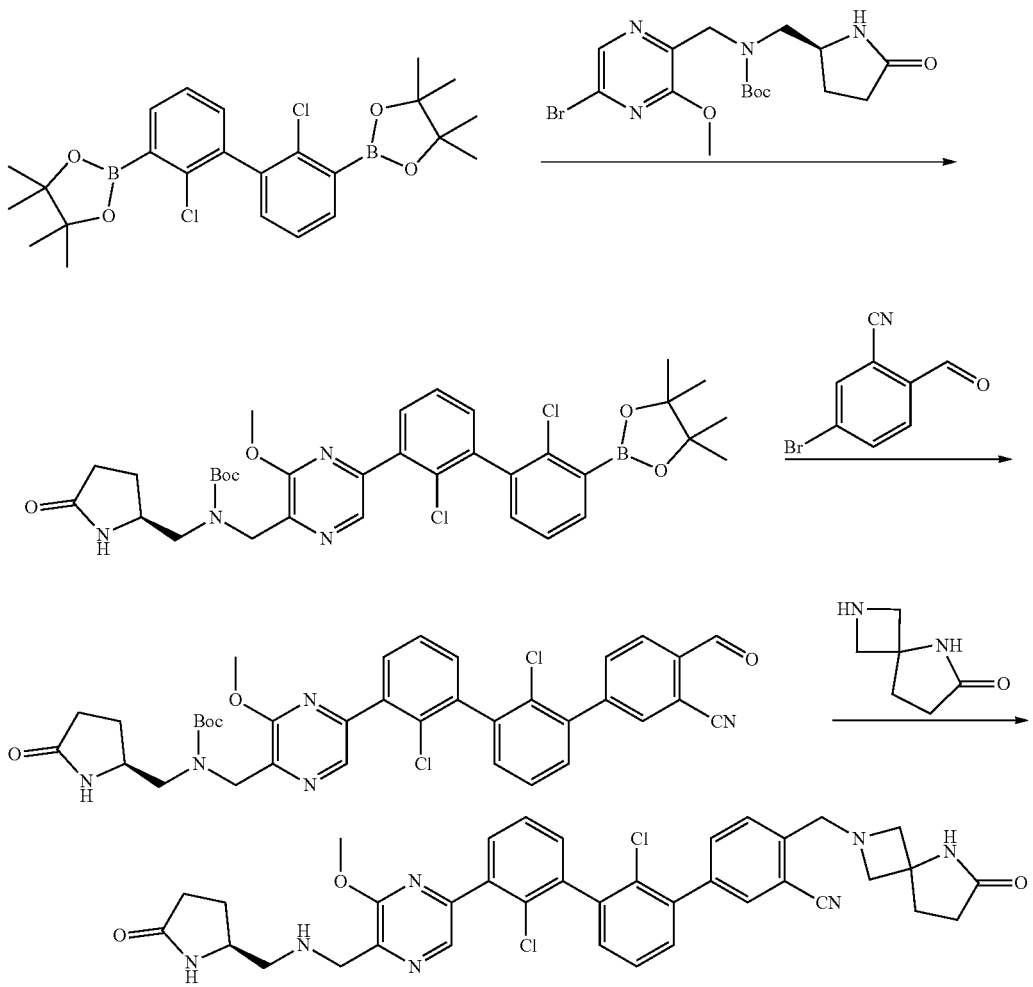

2,2'-(2,2'-dichloro-[1,1'-biphenyl]-3,3'-diyl)bis(4,4,5,5-tetramethyl-1,3,2-dioxaborolane) (302 mg, 0.64 mmol) and tert-butyl (S)-((5-bromo-3-methoxypyrazin-2-yl)methyl) ((5-oxopyrrolidin-2-yl)methyl)carbamate (220 mg, 0.53 mmol) were suspended in 1,4-dioxane (2 ml) and H₂O (0.3 mL), added potassium carbonate (95 mg, 0.69 mmol) and tetrakis(triphenylphosphine)palladium(0) (61 mg, 0.05 mmol). The mixture was heated at 85° C. After 90 min, LCMS showed almost complete conversion. The mixture was filtered through a short be of celite, washed with EtOAc. The filtrate was partitioned between EtOAc and brine. The organic layer was concentrated in vacuo. The residue was purified by silica gel chromatography using Hexanes/EtOAc as the eluent to afford tert-butyl (S)-((5-(2,2'-dichloro-3'-(4,4,5,5-tetramethyl-1,3,2-dioxaborolan-2-yl)-[1,1'-biphenyl]-3-yl)-3-methoxypyrazin-2-yl)methyl)((5-oxopyrrolidin-2-yl)methyl)carbamate.

tert-butyl (S)-((5-(2,2'-dichloro-3'-(4,4,5,5-tetramethyl-1,3,2-dioxaborolan-2-yl)-[1,1'-biphenyl]-3-yl)-3-methoxypyrazin-2-yl)methyl)((5-oxopyrrolidin-2-yl)methyl)carbamate (100 mg, 0.15 mmol) and 5-bromo-2-formylbenzonitrile (53 mg, 0.25 mmol) were suspended in 1,4-dioxane (5 mL) and H₂O (0.5 mL), added potassium carbonate (22.3 mg, 0.16 mmol) and tetrakis(triphenylphosphine)palladium(0) (34.3 mg, 0.03 mmol). The mixture was heated at 85° C. After 20 min, LCMS showed almost complete conversion. The mixture was filtered through a short be of celite, washed with EtOAc. The filtrate was partitioned between EtOAc and brine. The organic layer was concentrated in vacuo. The residue was purified by silica gel chromatography using Hexanes/EtOAc as the eluent to afford tert-butyl (S)-((5-(2,2'-dichloro-3"-cyano-4"-formyl-[1,1':3',1"-terphenyl]-3-yl)-3-methoxypyrazin-2-yl) methyl) ((5-oxopyrrolidin-2-yl) methyl) carbamate.

The title compound was synthesized according to general reductive amination procedure G.

Procedure 14: (S)-5-(((((5-(2,2'-dichloro-3'-(5-((3-(hydroxymethyl)-3-methylazetidin-1-yl) methyl)-6-methoxypyridin-2-yl)-[1,1'-biphenyl]-3-yl)-3-methoxypyrazin-2-yl)methyl)amino)methyl) pyrrolidin-2-one

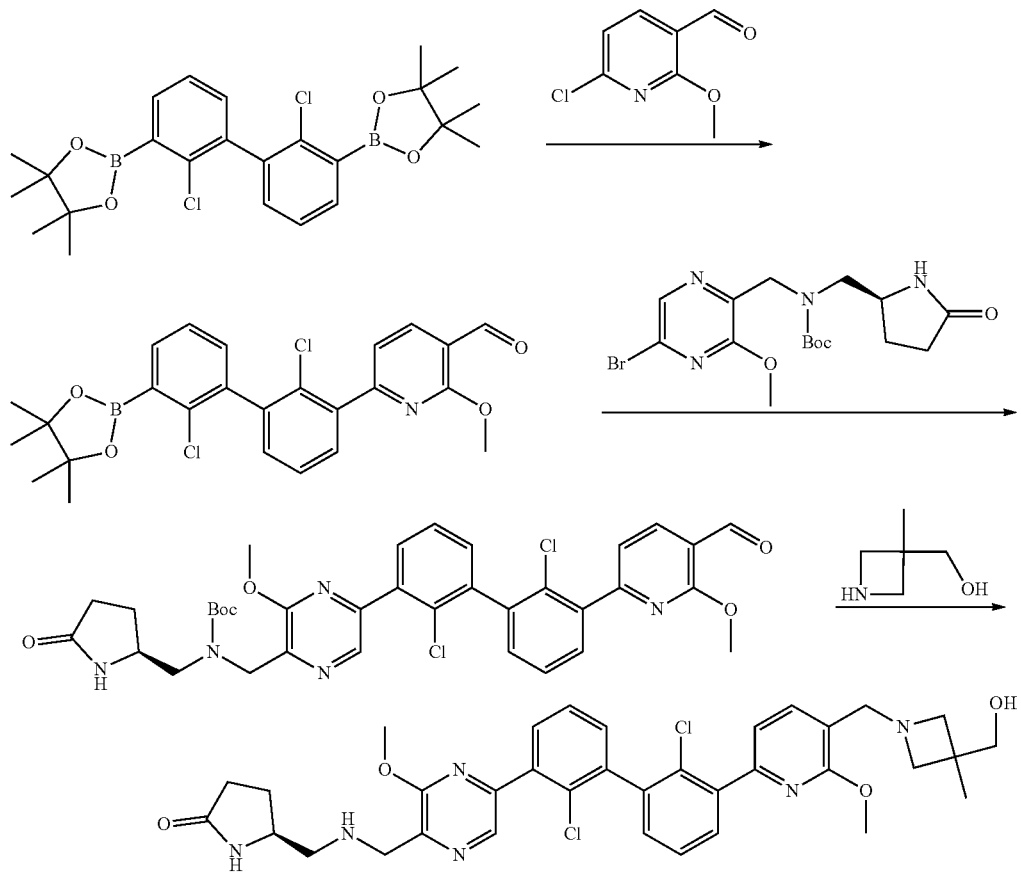

2,2'-(2,2'-dichloro-[1,1'-biphenyl]-3,3'-diyl)bis(4,4,5,5-tetramethyl-1,3,2-dioxaborolane) (3.32 g, 7.00 mmol) and 6-chloro-2-methoxynicotinaldehyde (1 g, 5.83 mmol) were suspended in 1,4-dioxane (18 mL) and H₂O (2.4 mL), added potassium carbonate (1.05 g, 7.58 mmol) and tetrakis(triphenylphosphine)palladium(0) (0.67 g, 0.58 mmol). The mixture was heated at 84° C. After 90 min, LCMS showed almost complete conversion. The mixture was filtered through a short be of celite, washed with EtOAc. The filtrate was partitioned between EtOAc and brine. The organic layer was concentrated in vacuo. The residue was purified by silica gel chromatography using Hexanes/EtOAc as the eluent to afford 6-(2,2'-dichloro-3'-(4,4,5,5-tetramethyl-1,3,2-dioxaborolan-2-yl)-[1,1'-biphenyl]-3-yl)-2-methoxynicotinaldehyde.

6-(2,2'-dichloro-3'-(4,4,5,5-tetramethyl-1,3,2-dioxaborolan-2-yl)-[1,1'-biphenyl]-3-yl)-2-methoxynicotinaldehyde (423 mg, 0.87 mmol) and tert-butyl (S)-((5-bromo-3-methoxypyrazin-2-yl)methyl)((5-oxopyrrolidin-2-yl)methyl)carbamate (330 mg, 0.79 mmol) were suspended in 1,4-dioxane (3 mL) and H₂O (0.6 mL), added potassium carbonate (132 mg, 0.95 mmol) and tetrakis(triphenylphosphine)palladium(0) (92 mg, 0.08 mmol). The mixture was heated at 84° C. After 90 min, LCMS showed almost complete conversion. The mixture was filtered through a short be of celite, washed with EtOAc. The filtrate was partitioned between EtOAc and brine. The organic layer was concentrated in vacuo. The residue was purified by silica gel chromatography using Hexanes/EtOAc as the eluent to afford tert-butyl (S)-((5-(2,2'-dichloro-3'-(5-formyl-6-methoxypyridin-2-yl)-[1,1'-biphenyl]-3-yl)-3-methoxypyrazin-2-yl)methyl)((5-oxopyrrolidin-2-yl)methyl)carbamate.

The title compound was synthesized according to general reductive amination procedure G followed by standard Boc deprotection with TFA.

Procedure 15: (S)-5-(((((5-(3'-(5-((R)-1-aminoethyl)-6-methoxypyrazin-2-yl)-2,2'-dichloro-[1,1'-biphenyl]-3-yl)-3-methoxypyrazin-2-yl)methyl)amino)methyl)pyrrolidin-2-one To an oven-dried 40 mL vial was added 5-bromo-3-methoxypyrazine-2-carbaldehyde, dichloromethane (0.5M), and (R)-2-methylpropane-2-sulfinamide (1.0 equiv.) at room temperature. To the vial was then added titanium tetraethoxide (2.0 equiv.). The mixture was stirred overnight before being diluted with sodium bicarbonate solution. The contents of the vial were filtered through celite, and the filtrate was washed once with water and once with brine. The organic layer was dried over magnesium sulfate, filtered, and concentrated. The residue was purified by silica gel chromatography using hexanes/ethyl acetate gradient to yield (R,E)-N-((5-bromo-3-methoxypyrazin-2-yl)methylene)-2-methylpropane-2-sulfinamide.

To an oven-dried 40 mL vial was added (R,E)-N-((5-bromo-3-methoxypyrazin-2-yl)methylene)-2-methylpropane-2-sulfinamide and dichloromethane (0.1M) at room temperature. The mixture was cooled to −78° C., and methyl magnesium iodide (1M in tetrahydrofuran, 1.6 equiv.) was added dropwise. The mixture was slowly warmed to room temperature and quenched with aqueous ammonium chloride solution, washed once with water, and washed once with brine. The organic layer was dried over magnesium sulfate, filtered, and concentrated. The residue was purified

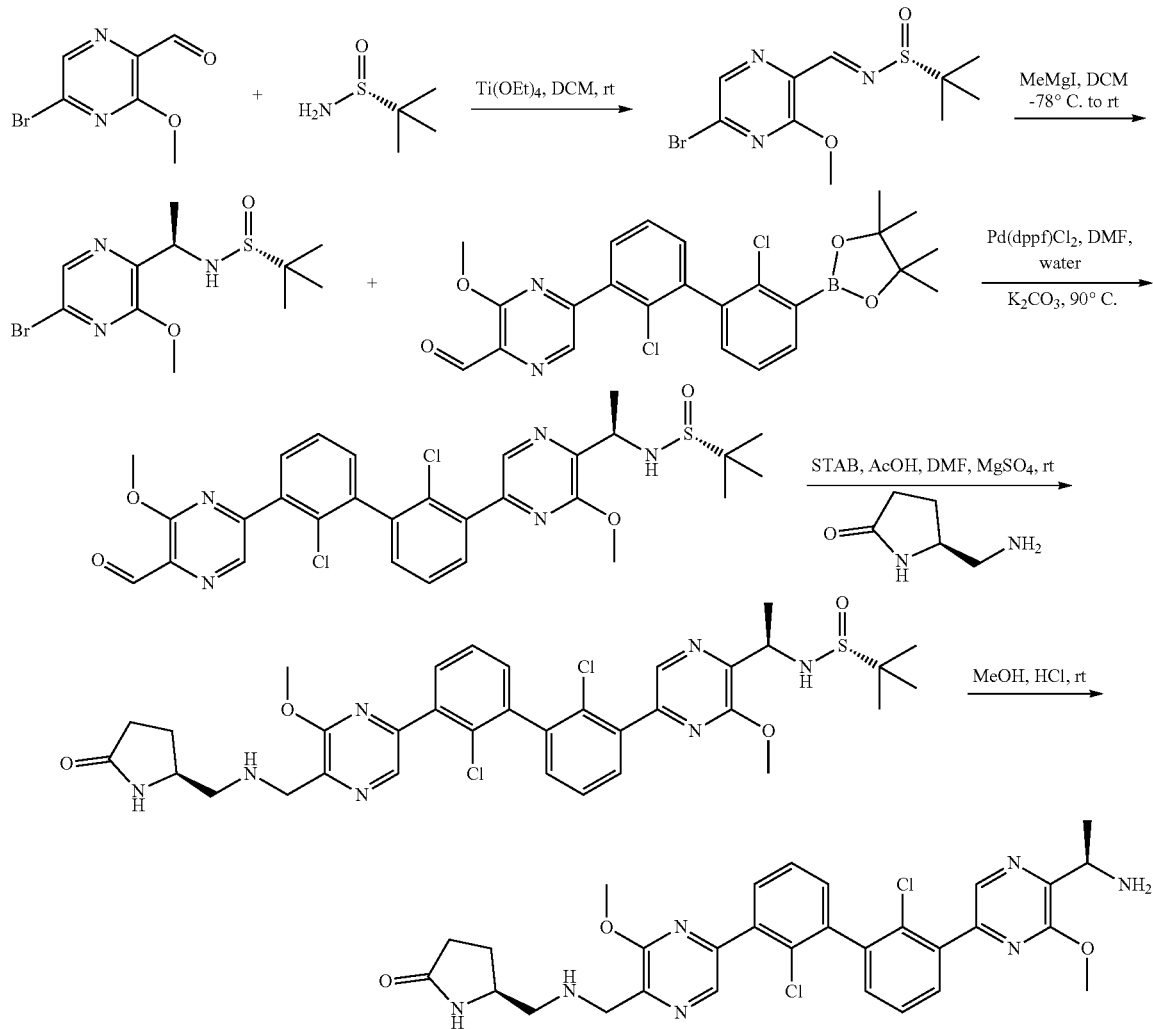

by silica gel chromatography using hexanes/ethyl acetate gradient to yield (R)—N—((R)-1-(5-bromo-3-methoxypyrazin-2-yl)ethyl)-2-methylpropane-2-sulfinamide and (R)—N—((S)-1-(5-bromo-3-methoxypyrazin-2-yl)ethyl)-2-methylpropane-2-sulfinamide.

To an oven-dried 40 mL vial was added (R)—N—((R)-1-(5-bromo-3-methoxypyrazin-2-yl)ethyl)-2-methylpropane-2-sulfinamide, 5-(2,2'-dichloro-3'-(4,4,5,5-tetramethyl-1,3,2-dioxaborolan-2-yl)-[1,1'-biphenyl]-3-yl)-3-methoxypyrazine-2-carbaldehyde (1.0 equiv.), potassium carbonate (2.0 equiv.), Pd(dppf)Cl$_2$ (10 mol %), dimethylformamide (0.2M), and water (10 vol %). The contents of the vial were sparged with nitrogen for 30 seconds then heated to 90° C. for 45 minutes. After cooling to room temperature, the mixture was diluted with ethyl acetate and filtered through celite. The filtrate was washed once with water and once with brine before being dried over magnesium sulfate, filtered, and concentrated. The residue was purified by silica gel chromatography with a methanol/dichloromethane gradient to yield (R)—N—((R)-1-(5-(2,2'-dichloro-3'-(5-formyl-6-methoxypyrazin-2-yl)-[1,1'-biphenyl]-3-yl)-3-methoxypyrazin-2-yl)ethyl)-2-methylpropane-2-sulfinamide.

(S)-5-(aminomethyl)pyrrolidin-2-one (3 equiv.) was reacted with (R)—N—((R)-1-(5-(2,2'-dichloro-3'-(5-formyl-6-methoxypyrazin-2-yl)-[1,1'-biphenyl]-3-yl)-3-methoxypyrazin-2-yl)ethyl)-2-methylpropane-2-sulfinamide following reductive amination procedure C to yield (R)—N—((R)-1-(5-(2,2'-dichloro-3'-(6-methoxy-5-(((((S)-5-oxopyrrolidin-2-yl)methyl)amino)methyl)pyrazin-2-yl)-[1,1'-biphenyl]-3-yl)-3-methoxypyrazin-2-yl)ethyl)-2-methylpropane-2-sulfinamide.

To an oven-dried 20 mL vial was added (R)—N—((R)-1-(5-(2,2'-dichloro-3'-(6-methoxy-5-(((((S)-5-oxopyrrolidin-2-yl)methyl)amino)methyl)pyrazin-2-yl)-[1,1'-biphenyl]-3-yl)-3-methoxypyrazin-2-yl)ethyl)-2-methylpropane-2-sulfinamide, methanol and 4M HCl in dioxane (2.0 equiv.). The mixture was stirred at room temperature for 30 minutes before being concentrated and purified by HPLC to yield (S)-5-((((5-(3'-(5-((R)-1-aminoethyl)-6-methoxypyrazin-2-yl)-2,2'-dichloro-[1,1'-biphenyl]-3-yl)-3-methoxypyrazin-2-yl)methyl)amino)methyl)pyrrolidin-2-one.

Procedure 16: (S)-5-((((5-(2,2'-dichloro-3'-(5-((2,5-dimethyl-1H-pyrrol-1-yl)methyl)-6-methoxypyrazin-2-yl)-[1,1'-biphenyl]-3-yl)-3-methoxypyrazin-2-yl)methyl)amino)methyl)pyrrolidin-2-one

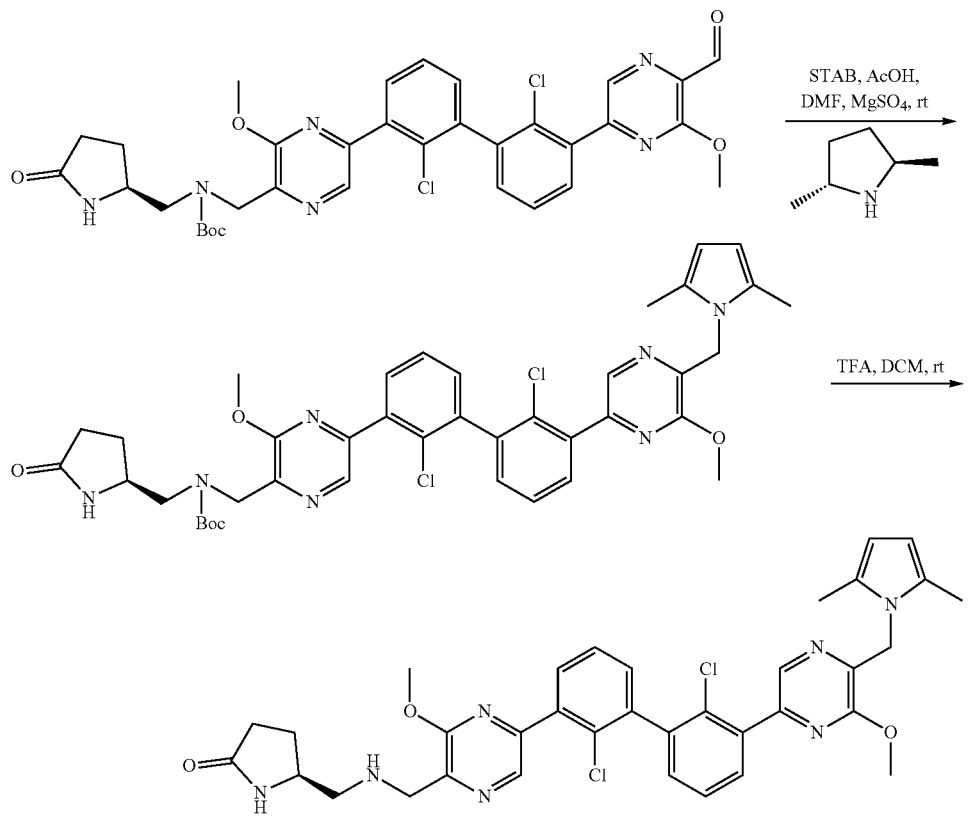

tert-butyl (S)-((5-(2,2'-dichloro-3'-(5-formyl-6-methoxypyrazin-2-yl)-[1,1'-biphenyl]-3-yl)-3-methoxypyrazin-2-yl)methyl)((5-oxopyrrolidin-2-yl)methyl)carbamate was reacted with (2R,5R)-2,5-dimethylpyrrolidine (3.0 equiv.) following reductive amination procedure C to obtain the undesired tert-butyl (S)-((5-(2,2'-dichloro-3'-(5-((2,5-dimethyl-1H-pyrrol-1-yl)methyl)-6-methoxypyrazin-2-yl)-[1,1'-biphenyl]-3-yl)-3-methoxypyrazin-2-yl)methyl)((5-oxopyrrolidin-2-yl)methyl)carbamate.

To an oven-dried 40 mL vial was added tert-butyl (S)-((5-(2,2'-dichloro-3'-(5-((2,5-dimethyl-1H-pyrroll-1-yl)methyl)-6-methoxypyrazin-2-yl)-[1,1'-biphenyl]-3-yl)-3-methoxypyrazin-2-yl)methyl)((5-oxopyrrolidin-2-yl)methyl)carbamate, dichloromethane (0.5M), and trifluoacetic acid (10 equiv.) at room temperature. The mixture was stirred for 30 minutes before being concentrated and purified by HPLC to furnish (S)-5-((((5-(2,2'-dichloro-3'-(5-((2,5-dimethyl-1H-pyrrol-1-yl)methyl)-6-methoxypyrazin-2-yl)-[1,1'-biphenyl]-3-yl)-3-methoxypyrazin-2-yl)methyl)amino)methyl)pyrrolidin-2-one.

Procedure 17: 2,2'-(((2-bromo-2'-chloro-[1,1'-biphenyl]-3,3'-diyl)bis(3-methoxypyrazine-5,2-diyl))bis(methylene))bis(2,6-diazaspiro[3.4]octan-7-one)

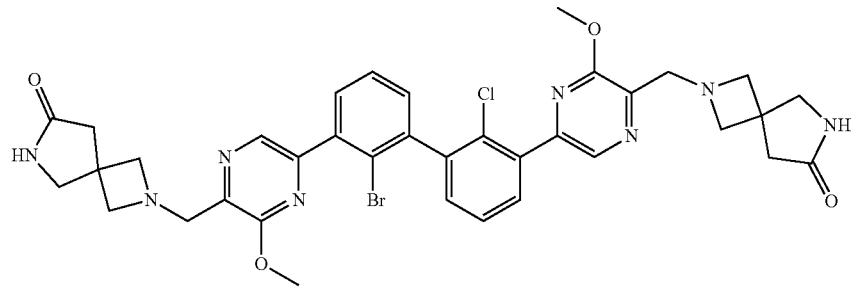 [SMILES: COc1nc(-c2cccc(-c3cccc(-c4cnc(CN5CC6(CNC(=O)C6)C5)c(OC)n4)c3Br)c2Cl)cnc1CN1CC2(CNC(=O)C2)C1]

2,2'-(((2-bromo-2'-chloro-[1,1'-biphenyl]-3,3'-diyl)bis(3-methoxypyrazine-5,2-diyl))bis(methylene))bis(2,6-diazaspiro[3.4]octan-7-one) was synthesized in a manner similar to Procedure 18 using (2-chlorophenyl)boronic acid in place of (2-fluorophenyl)boronic acid.

Procedure 18: 2,2'-(((2-bromo-2'-fluoro-[1,1'-biphenyl]-3,3'-diyl)bis(3-methoxypyrazine-5,2-diyl))bis(methylene))bis(2,6-diazaspiro[3.4]octan-7-one)

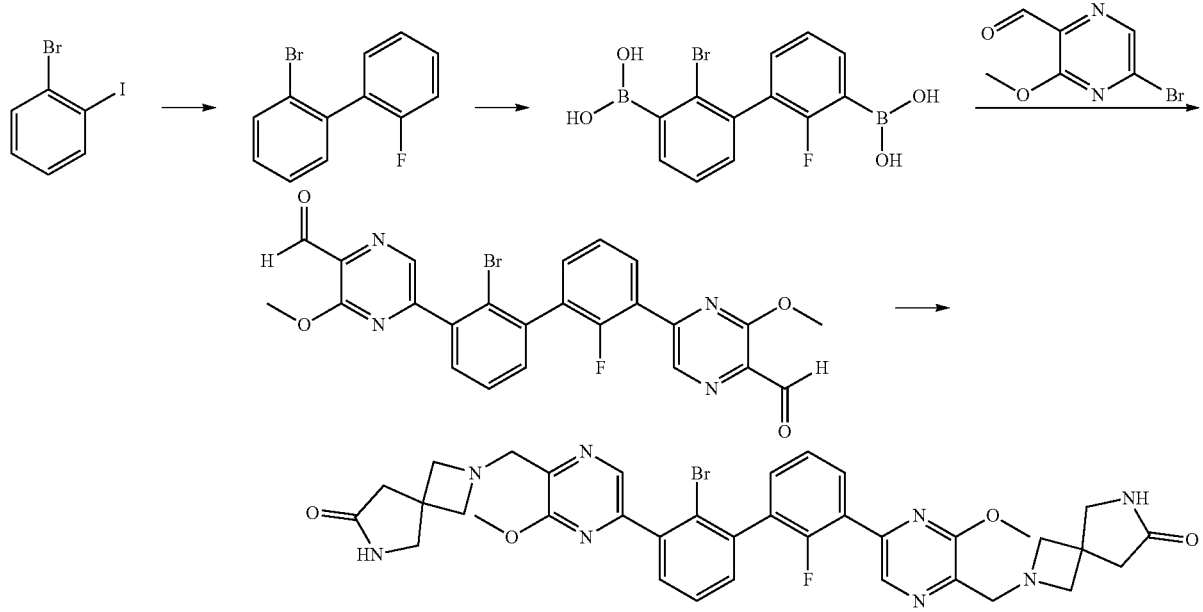

A stirred mixture of 1-bromo-2-iodobenzene (0.6 g, 4.29 mmol, (2-fluorophenyl)boronic acid (1.213 g, 4.29 mmol, potassium carbonate (1.48 g, 10.72 mmol), and tetrakis(triphenylphosphine)palladium(0) (0.149 g, 0.129 mmol) in dimethoxyethane (12.88 mL) and water (1.72 mL) was heated to 95° C. in a heating block. After 60 min, the resulting mixture was allowed to cool to room temperature. Ethyl acetate (50 mL) was added, and the organic layer was washed with brine (25 mL), was dried over anhydrous magnesium sulfate, was filtered, and was concentrated under reduced pressure. The residue was purified by flash column chromatography on silica gel (0 to 10% ethyl acetate in hexane) to give 2-bromo-2'-fluoro-1,1'-biphenyl.

N-Butyllithium solution (3.42 mL, 2.5 M in hexane, 8.56 mmol) was added via syringe to a stirred 2,2,6,6-tetramethylpiperidine (1.44 mL, 8.56 mmol) in anhydrous tetrahydrofuran (10.70 mL) at 0° C. The resulting mixture was stirred for 10 min and cooled to −78° C. Triisopropyl borate (3.29 mL, 14.27 mmol) was added and stirred for 8 min. 2-bromo-2'-fluoro-1,1'-biphenyl was added via syringe and the mixture was slowly warmed to room temperature overnight. 1M HCl (25 mL) was added, was extracted with ethyl acetate (3×25 mL), was extracted with 1M NaOH (25 mL), 0.5 N NaOH twice, was acidified with concentrated HCl to pH 1, was extracted with ethyl acetate (3×35 mL), was dried over anhydrous magnesium sulfate, was filtered, and was concentrated under reduced pressure to give (2-bromo-2'-fluoro-[1,1'-biphenyl]-3,3'-diyl)diboronic acid.

A stirred mixture of (2-bromo-2'-fluoro-[1,1'-biphenyl]-3,3'-diyl)diboronic acid (0.263 g, 0.776 mmol, 5-bromo-3-methoxypyrazine-2-carbaldehyde (0.506 g, 2.33 mmol, potassium carbonate (1.48 g, 10.72 mmol), aqueous sodium carbonate solution (2.0 M, 3.16 mL, 6.21 mmol) and chloro (2-dicyclohexylphosphino-2',4',6'-triisopropyl-1,1'-biphenyl) [2-(2'-amino-1,1'-biphenyl)]palladium(II) (0.031 g, 0.039 mmol) in dimethoxyethane (4 mL) was heated to 100° C. in a heating block. After 60 min, the resulting mixture was allowed to cool to room temperature. Ethyl acetate (40 mL) was added, and the organic layer was washed with brine (20 mL), was dried over anhydrous magnesium sulfate, was filtered, and was concentrated under reduced pressure. The residue was purified by flash column chromatography on silica gel (0 to 50% ethyl acetate in hexane) to give 5,5'-(2-bromo-2'-fluoro-[1,1'-biphenyl]-3,3'-diyl)bis(3-methoxypyrazine-2-carbaldehyde).

N,N-diisopropylethylamine (79 µL, 0.453 mmol) was added via syringe to a stirred mixture of 5,5'-(2-bromo-2'-fluoro-[1,1'-biphenyl]-3,3'-diyl)bis(3-methoxypyrazine-2-carbaldehyde). (15.8 mg, 0.030 mmol) and 2,6-diazaspiro[3.4]octan-7-one 4-methylbenzenesulfonate (90 mg, 0.302 mmol) in dimethylsulfoxide (1 mL) at room temperature. After 10 min, sodium triacetoxyborohydride (64 mg, 0.302 mmol) was added as a solid, and the resulting mixture was heated to 60° C. in a heating block. After 30 min, the resulting mixture was allowed to cool to room temperature. The mixture was filtered and was purified by reverse phase preparative HPLC (0.1% trifluoroacetic acid in acetonitrile/water) to give 2,2'-(((2-bromo-2'-fluoro-[1,1'-biphenyl]-3,3'-diyl)bis(3-methoxypyrazine-5,2-diyl))bis(methylene))bis(2,6-diazaspiro[3.4]octan-7-one).

Procedure 19: (5S,5'S)-5,5'-(((((2,2'-dichloro-5,5'-difluoro-[1,1'-biphenyl]-3,3'-diyl)bis(3-methoxypyrazine-5,2-diyl))bis(methylene))bis(azanediyl))bis(methylene))bis(pyrrolidin-2-one)

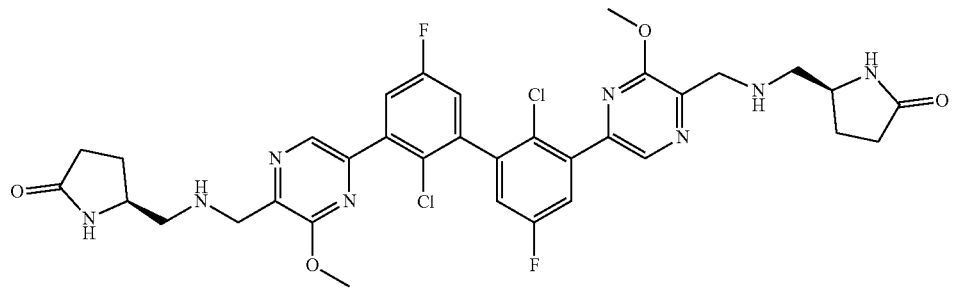 [SMILES: COc1nc(-c2cc(F)cc(-c3cc(F)cc(-c4cnc(CNC[C@@H]5CCC(=O)N5)c(OC)n4)c3Cl)c2Cl)cnc1CNC[C@@H]1CCC(=O)N1]

(5S,5'S)-5,5'-(((((2,2'-dichloro-5,5'-difluoro-[1,1'-biphenyl]-3,3'-diyl)bis(3-methoxypyrazine-5,2-diyl))bis(methylene))bis(azanediyl))bis(methylene))bis(pyrrolidin-2-one) was synthesized in a manner similar to Procedure 11 using 2-(3-bromo-2-chloro-5-fluorophenyl)-4,4,5,5-tetramethyl-1,3,2-dioxaborolane in place of (3-bromo-2-chlorophenyl)boronic acid.

Procedure 20: (5S,5'S)-5,5'-(((((2,2'-dichloro-[1,1'-biphenyl]-3,3'-diyl)bis(3-(methylamino)pyrazine-5,2-diyl))bis(methylene))bis(methylazanediyl))bis(methylene))bis(pyrrolidin-2-one)

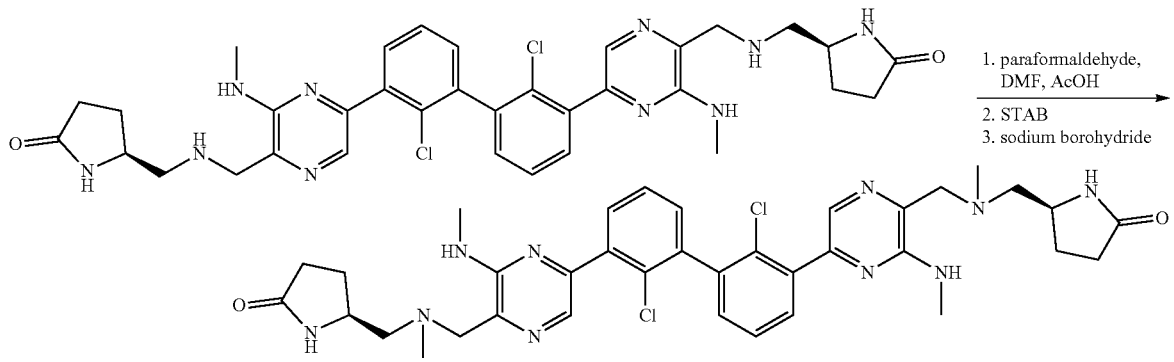

To an oven-dried 40 mL vial was added (5S,5'S)-5,5'-(((((2,2'-dichloro-[1,1'-biphenyl]-3,3'-diyl)bis(3-(methylamino)pyrazine-5,2-diyl))bis(methylene))bis(azanediyl))bis(methylene))bis(pyrrolidin-2-one), paraformaldehyde (10 equiv.), magnesium sulfate (2.0 equiv.), dimethylformamide (0.2 M), and acetic acid (10 equiv.) at room temperature. The mixture was stirred vigorously for 30 minutes before sodium triacetoxyborohydride (10 equiv.) was added. After 30 minutes, sodium borohydride (1.0 equiv.) was added, and the mixture was stirred for an additional 1 hour. The mixture was purified by HPLC to yield (5S,5'S)-5,5'-((((2,2'-dichloro-[1,1'-biphenyl]-3,3'-diyl)bis(3-(methylamino)pyrazine-5,2-diyl))bis(methylene))bis(methylazanediyl))bis(methylene))bis(pyrrolidin-2-one).

Procedure 21: ((5-(2,2'-dichloro-3'-(6-methoxy-5-(((((S)-5-oxopyrrolidin-2-yl)methyl)amino)methyl)pyrazin-2-yl)-[1,1'-biphenyl]-3-yl)-3-methoxypyrazin-2-yl)methyl)(((S)-5-oxopyrrolidin-2-yl)methyl)sulfamic acid romethane (3×15 mL), and the combined organic layers were dried over anhydrous sodium sulfate, were filtered, and were concentrated under reduced pressure. The residue was purified by flash column chromatography on silica gel (0 to 15% methanol in dichloromethane) to give tert-butyl ((5-(2,2'-dichloro-3'-(6-methoxy-5-(((((S)-5-oxopyrrolidin-2-yl)methyl)amino)methyl)pyrazin-2-yl)-[1,1'-biphenyl]-3-yl)-3-methoxypyrazin-2-yl)methyl)(((S)-5-oxopyrrolidin-2-yl)methyl)carbamate.

Chlorosulfonic acid (9.6 µL, 0.060 mmol) was added via syringe to a stirred mixture of tert-butyl ((5-(2,2'-dichloro-

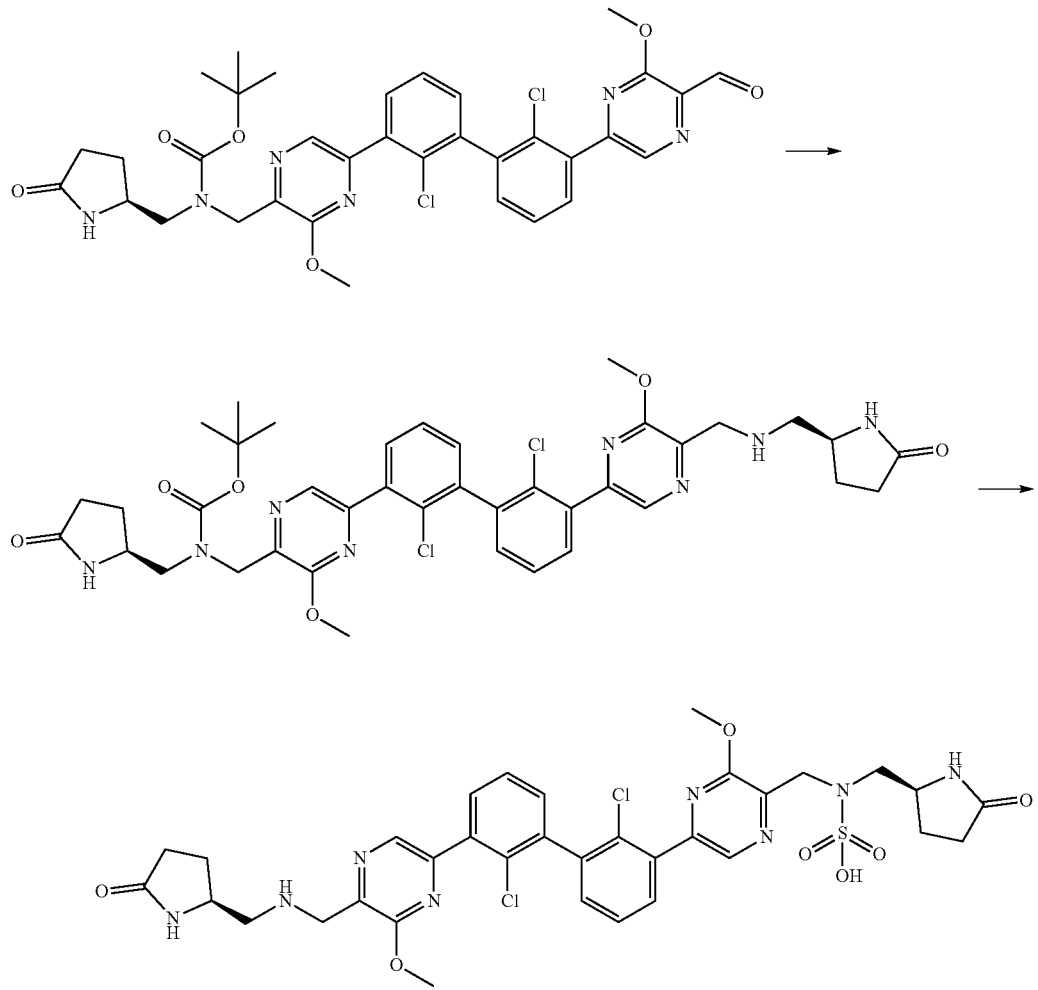

Sodium triacetoxyborohydride (122 mg, 0.577 mmol) was added to a stirred mixture of tert-butyl (S)-((5-(2,2'-dichloro-3'-(5-formyl-6-methoxypyrazin-2-yl)-[1,1'-biphenyl]-3-yl)-3-methoxypyrazin-2-yl)methyl)((5-oxopyrrolidin-2-yl)methyl)carbamate (200 mg, 0.288 mmol), (S)-5-(aminomethyl)pyrrolidin-2-one hydrochloride (87 mg, 0.58 mmol), N,N-diisopropylethylamine (200 µL, 1.2 mmol), and acetic acid (33 µL, 0.58 mmol) in dichloromethane (4.0 mL) at room temperature. After 75 min, aqueous sodium hydroxide solution (2 M, 1.5 mL) was added, and the resulting mixture was stirred vigorously. After 10 min, saturated aqueous sodium carbonate solution (3.0 mL), water (10 mL), and dichloromethane (15 mL) were added sequentially. The biphasic mixture was agitated, and the layers were separated. The aqueous layer was extracted with dichlo- 3'-(6-methoxy-5-(((((S)-5-oxopyrrolidin-2-yl)methyl)amino)methyl)pyrazin-2-yl)-[1,1'-biphenyl]-3-yl)-3-methoxypyrazin-2-yl)methyl)(((S)-5-oxopyrrolidin-2-yl)methyl)carbamate (43 mg, 0.055 mmol) and triethylamine (27 µL, 0.19 mmol) in dichloromethane (1.0 mL) at 0° C. After 5 min, the resulting mixture was warmed to room temperature. After 40 min, trifluoroacetic acid (1.0 mL) was added. After 30 min, the resulting mixture was concentrated under reduced pressure and was purified by reverse phase preparative HPLC (0.1% trifluoroacetic acid in acetonitrile/water) to give ((5-(2,2'-dichloro-3'-(6-methoxy-5-(((((S)-5-oxopyrrolidin-2-yl)methyl)amino)methyl)pyrazin-2-yl)-[1,1'-biphenyl]-3-yl)-3-methoxypyrazin-2-yl)methyl)(((S)-5-oxopyrrolidin-2-yl)methyl)sulfamic acid.

Procedure 22: 2,2'-((2,2'-dichloro-[1,1'-biphenyl]-3,3'-diyl)bis(3-methoxypyrazine-5,2-diyl))bis(5,5-difluoro-1,4,5,6-tetrahydropyrimidine)

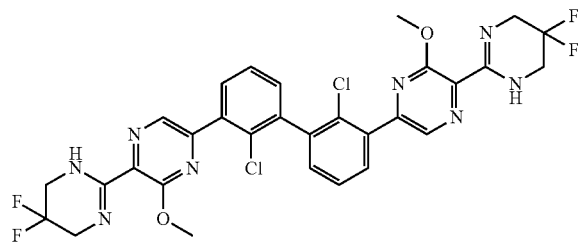 [SMILES: COc1nc(-c2cccc(-c3cccc(-c4cnc(C5=NCC(F)(F)CN5)c(OC)n4)c3Cl)c2Cl)cnc1C1=NCC(F)(F)CN1]

2,2-Difluoropropane-1,3-diamine dihydrochloride (22.2 mg, 0.121 mmol) was added to a vigorously stirred mixture of 5,5'-(2,2'-dichloro-[1,1'-biphenyl]-3,3'-diyl)bis(3-methoxypyrazine-2-carbaldehyde) (10 mg, 0.020 mmol) and potassium carbonate (33.5 mg, 0.242 mmol) in tetrahydrofuran (0.7 mL) and ethanol (1.3 mL) at room temperature, and the resulting mixture was heated to 80° C. After 20 min, the resulting mixture was cooled to room temperature over 5 min, and N-bromosuccinimide (28.8 mg, 0.162 mmol) was added. After 45 min, the resulting mixture was filtered and was purified by reverse phase preparative HPLC (0.1% trifluoroacetic acid in acetonitrile/water) to give 2,2'-((2,2'-dichloro-[1,1'-biphenyl]-3,3'-diyl)bis(3-methoxypyrazine-5,2-diyl))bis(5,5-difluoro-1,4,5,6-tetrahydropyrimidine).

Procedure 23: (S)-5-((((6-(2,2'-dichloro-3'-(6-methoxy-5-(((((S)-5-oxopyrrolidin-2-yl)methyl)amino)methyl)pyrazin-2-yl)-[1,1'-biphenyl]-3-yl)-2-methoxypyridin-3-yl)methyl)amino)methyl)pyrrolidin-2-one A vigorously stirred mixture of 6-(2,2'-dichloro-3'-(4,4,5,5-tetramethyl-1,3,2-dioxaborolan-2-yl)-[1,1'-biphenyl]-3-yl)-2-methoxynicotinaldehyde (1.00 g, 2.07 mmol), 5-bromo-3-methoxypyrazine-2-carbaldehyde (672 mg, 3.10 mmol), chloro(2-dicyclohexylphosphino-2',4',6'-triisopropyl-1,1'-biphenyl)[2-(2'-amino-1,1'-biphenyl)]palladium(II) (81.3 mg, 0.103 mmol), and saturated aqueous sodium carbonate solution (5.16 mL) in 1,4-dioxane (15 mL) was heated to 85° C. After 60 min, the resulting mixture was cooled to room temperature, and ethyl acetate (100 mL) was added. The organic layer was washed with brine (60 mL), was dried over anhydrous sodium sulfate, was filtered, and was concentrated under reduced pressure. The residue was purified by flash column chromatography on silica gel (0 to 50% ethyl acetate in hexanes) to give 5-(2,2'-dichloro-3'-(5-formyl-6-methoxypyridin-2-yl)-[1,1'-biphenyl]-3-yl)-3-methoxypyrazine-2-carbaldehyde.

Sodium triacetoxyborohydride (1.21 g, 5.71 mmol) was added to a vigorously stirred mixture of 5-(2,2'-dichloro-3'-(5-formyl-6-methoxypyridin-2-yl)-[1,1'-biphenyl]-3-yl)-3-methoxypyrazine-2-carbaldehyde (565 mg, 1.14 mmol), (S)-5-(aminomethyl)pyrrolidin-2-one (392 mg, 3.431 mmol), and acetic acid (65 µL, 1.1 mmol) in dichloromethane (25 mL) at room temperature. After 60 min, aqueous sodium hydroxide solution (2 M, 10 mL) was added, and the resulting biphasic mixture was stirred vigorously. After 2 min, saturated aqueous sodium carbonate solution (8 mL), water (50 mL), and brine (20 mL) were added sequentially. The aqueous layer was extracted with dichloromethane (2×100 mL), and the combined organic layers were dried over anhydrous sodium sulfate, were filtered through celite, and were concentrated under reduced pressure. The residue was purified by flash column chromatography on silica gel (0 to 20% methanol in dichloromethane) to give (S)-5-((((6-

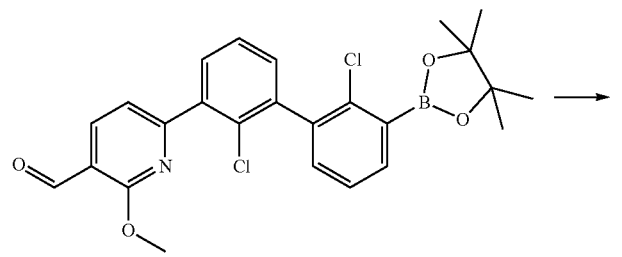

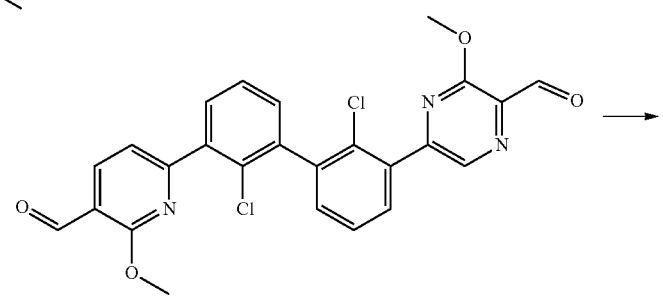

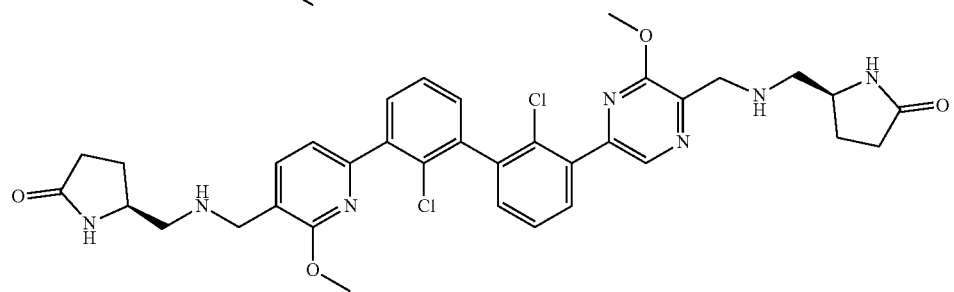

(2,2'-dichloro-3'-(6-methoxy-5-(((((S)-5-oxopyrrolidin-2-yl)methyl)amino)methyl)pyrazin-2-yl)-[1,1'-biphenyl]-3-yl)-2-methoxypyridin-3-yl)methyl)amino)methyl) pyrrolidin-2-one. Acetonitrile (15 mL) and methanol (15 mL) were added sequentially to dissolve the gel. Trifluoroacetic acid (0.4 mL) was added, and the resulting mixture was swirled vigorously. After 1 min, the resulting mixture was concentrated under reduced pressure. The residue was lyophilized from a mixture of acetonitrile and water (1:1 v:v, 30 mL) to give (S)-5-((((6-(2,2'-dichloro-3'-(6-methoxy-5-(((((S)-5-oxopyrrolidin-2-yl)methyl)amino)methyl)pyrazin-2-yl)-[1,1'-biphenyl]-3-yl)-2-methoxypyridin-3-yl)methyl) amino)methyl)pyrrolidin-2-one as its bis(2,2,2-trifluoroacetate) salt.

Procedure 24: 2-((5-(2,2'-dichloro-3'-(6-(methylamino)-5-((6-oxo-2,5-diazaspiro[3.4]octan-2-yl)methyl)pyrazin-2-yl)-[11,1'-biphenyl]-3-yl)-3-methoxypyrazin-2-yl)methyl)-2,5-diazaspiro[3.4]octan-6-one yl)-3-methoxypyrazine-2-carbaldehyde (526 mg, 1.08 mmol), 3,5-dichloropyrazine-2-carbaldehyde (288 mg, 1.63 mmol), [1,1'-bis(diphenylphosphino)ferrocene]dichloropalladium(II) (63 mg, 0.087 mmol), and cesium carbonate (1.06 g, 3.25 mmol), in 1,4-dioxane (11 mL) and water (1.8 mL) was heated to 100° C. After 60 min, the resulting mixture was cooled to room temperature, was filtered through celite, and was concentrated under reduced pressure. The residue was purified by flash column chromatography on silica gel (0 to 70% ethyl acetate in hexanes) to give 3-chloro-5-(2,2'-dichloro-3'-(5-formyl-6-methoxypyrazin-2-yl)-[1,1'-biphenyl]-3-yl)pyrazine-2-carbaldehyde.

A stirred mixture of 3-chloro-5-(2,2'-dichloro-3'-(5-formyl-6-methoxypyrazin-2-yl)-[1,1'-biphenyl]-3-yl)pyrazine-2-carbaldehyde (81.0 mg, 0.162 mmol) and methylamine solution (2.0 M in tetrahydrofuran, 3.0 mL, 6.0 mmol) was heated to 70° C. After 60 min, acetic acid (0.4 mL) and water (1.0 mL) were added sequentially, and the resulting biphasic mixture was stirred vigorously. After 15 min, the

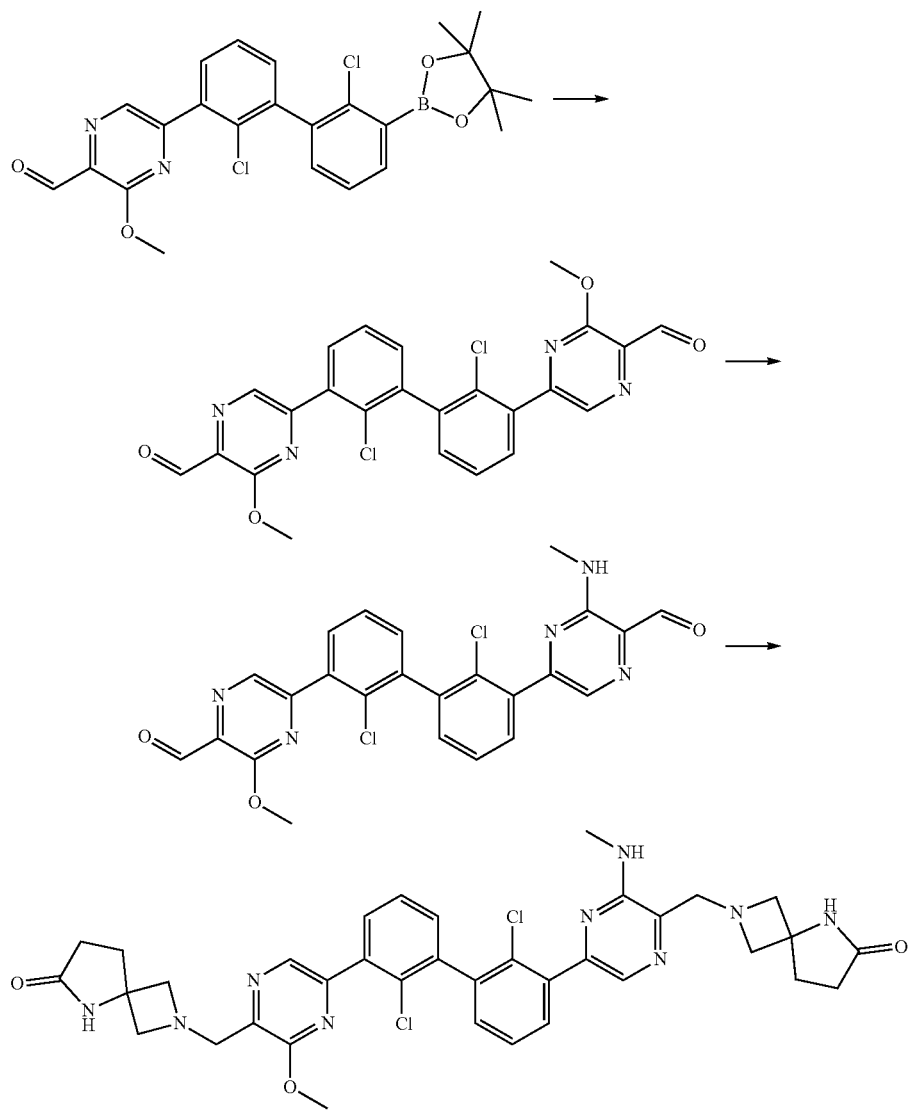

A vigorously stirred mixture of 5-(2,2'-dichloro-3'-(4,4,5,5-tetramethyl-1,3,2-dioxaborolan-2-yl)-[1,1'-biphenyl]-3- biphasic mixture was cooled to room temperature, and ethyl acetate (15 mL) was added. The organic layer was washed sequentially with water (15 mL) and a mixture of saturated aqueous sodium bicarbonate solution and brine (1:1 v:v, 15 mL), was dried over anhydrous sodium sulfate, was filtered, and was concentrated under reduced pressure to give 5-(2,2'-dichloro-3'-(5-formyl-6-(methylamino)pyrazin-2-yl)-[1,1'-biphenyl]-3-yl)-3-methoxypyrazine-2-carbaldehyde.

2-((5-(2,2'-Dichloro-3'-(6-(methylamino)-5-(((6-oxo-2,5-diazaspiro[3.4]octan-2-yl)methyl)pyrazin-2-yl)-[1,1'-biphenyl]-3-yl)-3-methoxypyrazin-2-yl)methyl)-2,5-diazaspiro[3.4]octan-6-one was synthesized in a manner similar to Procedure 6 using 5-(2,2'-dichloro-3'-(5-formyl-6-(methylamino)pyrazin-2-yl)-[1,1'-biphenyl]-3-yl)-3-methoxypyrazine-2-carbaldehyde in place of 5,5'-(2,2'-dichloro-[1,1'-biphenyl]-3,3'-diyl)bis(3-ethylpyrazine-2-carbaldehyde) and using 2,5-diazaspiro[3.4]octan-6-one hydrochloride in place of 3-hydroxyazetidine hydrochloride.

Procedure 26: 5-(2,2'-dichloro-3'-(6-methoxy-5-((3-methoxyazetidin-1-yl)methyl)pyridin-2-yl)-[1,1'-biphenyl]-3-yl)-3-methoxy-2-((3-methoxyazetidin-1-yl)methyl)pyrazine magnesium sulfate, was filtered, and was concentrated under reduced pressure. The residue was purified by flash column chromatography on silica gel (0 to 40% ethyl acetate in hexane) to give 5-(2,2'-dichloro-3'-(4,4,5,5-tetramethyl-1,3,2-dioxaborolan-2-yl)-[1,1'-biphenyl]-3-yl)-3-methoxypyrazine-2-carbaldehyde.

A stirred mixture of 5-(2,2'-dichloro-3'-(4,4,5,5-tetramethyl-1,3,2-dioxaborolan-2-yl)-[1,1'-biphenyl]-3-yl)-3-methoxypyrazine-2-carbaldehyde (50 mg, 0.103 mmol), 5-chloro-3-methoxypyridine-2-carbaldehyde (22.1 mg, 0.129 mmol), aqueous sodium carbonate solution (2.0 M, 206 µL, 0.412 mmol), and chloro(2-dicyclohexylphosphino-2',4',6'-triisopropyl-1,1'-biphenyl) [2-(2'-amino-1,1'-biphenyl)]palladium(II) (4.1 mg, 0.005 mmol) in 1,4-dioxane (0.5 mL) was heated to 105° C. in a heating block. After 60 min, the resulting mixture was allowed to cool to room temperature. Ethyl acetate (5 mL) was added, and the organic layer was washed with brine (2 mL), was dried over anhydrous magnesium sulfate, was filtered, and was concentrated under

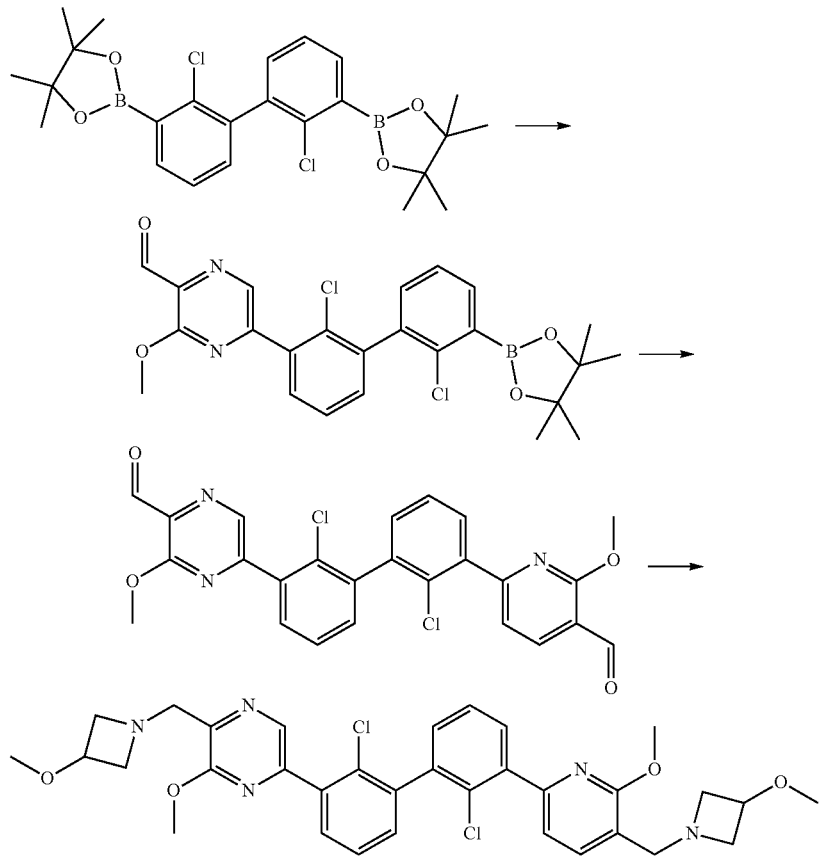

A stirred mixture of 2,2'-(2,2'-dichloro-[1,1'-biphenyl]-3,3'-diyl)bis(4,4,5,5-tetramethyl-1,3,2-dioxaborolane) (1.24 g, 2.54 mmol, 5-bromo-3-methoxypyrazine-2-carbaldehyde (0.500 g, 2.30 mmol, aqueous sodium carbonate solution (2.0 M, 4.61 mL, 9.22 mmol), and tetrakis(triphenylphosphine)palladium(0) (133 mg, 0.115 mmol) in 1,4-dioxane (6 mL) was heated to 105° C. in a heating block. After 60 min, the resulting mixture was allowed to cool to room temperature. Ethyl acetate (30 mL) was added, and the organic layer was washed with brine (20 mL), was dried over anhydrous reduced pressure to give 5-(2,2'-dichloro-3'-(5-formyl-6-methoxypyridin-2-yl)-[1,1'-biphenyl]-3-yl)-3-methoxypyrazine-2-carbaldehyde.

N,N-diisopropylethylamine (42 µL, 0.243 mmol) was added via syringe to a stirred mixture of 5-(2,2'-dichloro-3'-(5-formyl-6-methoxypyridin-2-yl)-[1,1'-biphenyl]-3-yl)-3-methoxypyrazine-2-carbaldehyde (8 mg, 0.016 mmol) and 3-methoxyazetidine hydrochloride (20 mg, 0.162 mmol) in dimethylsulfoxide (1 mL) at room temperature. After 10 min, sodium triacetoxyborohydride (34.3 mg, 0.162 mmol)

was added as a solid, and the resulting mixture was heated to 60° C. in a heating block. After 30 min, the resulting mixture was allowed to cool to room temperature. The mixture was filtered and was purified by reverse phase preparative hplc (0.1% trifluoroacetic acid in acetonitrile/water) to give 5-(2,2'-dichloro-3'-(6-methoxy-5-((3-methoxyazetidin-1-yl)methyl)pyridin-2-yl)-[1,1'-biphenyl]-3-yl)-3-methoxy-2-((3-methoxyazetidin-1-yl)methyl)pyrazine. 1H NMR (400 MHz, Methanol-d4) δ 8.53 (s, 1H), 7.92 (d, J=7.6 Hz, 2H), 7.72 (ddd, J=12.2, 7.7, 1.7 Hz, 2H), 7.60 (q, J=7.6 Hz, 3H), 7.53-7.43 (m, 2H), 7.41 (d, J=7.5 Hz, 2H), 4.76 (s, 2H), 4.52 (s, 2H), 4.15 (s, 3H), 4.12 (d, J=1.4 Hz, 5H), 3.41 (s, 3H), 3.40 (s, 4H).

The following compounds were prepared according to the procedures described herein (and indicated in Table 1 under Procedure) using the appropriate starting material(s) and appropriate protecting group chemistry as needed.

TABLE 1

| No. | Structure | ES/MS (m/z, M + H⁺) | Procedure |
|---|---|---|---|
| 1 | 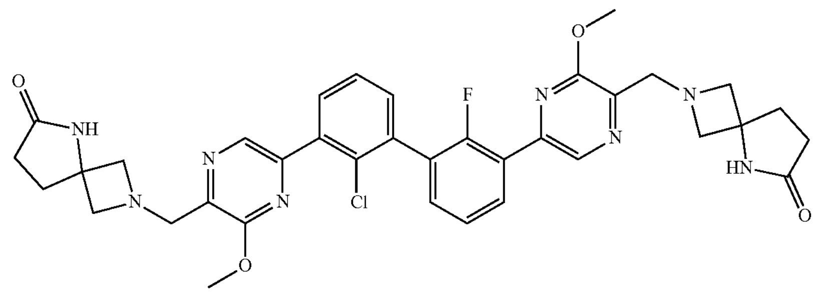 [SMILES: COc1nc(-c2cccc(-c3cccc(-c4cnc(CN5CC6(CCC(=O)N6)C5)c(OC)n4)c3Cl)c2F)cnc1CN1CC2(CCC(=O)N2)C1] | 699.2 | 1 |
| 2 | 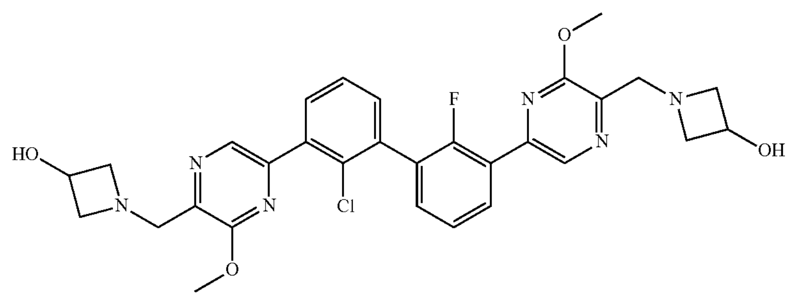 [SMILES: COc1nc(-c2cccc(-c3cccc(-c4cnc(CN5CC(O)C5)c(OC)n4)c3Cl)c2F)cnc1CN1CC(O)C1] | 593.2 | 1 |
| 3 | 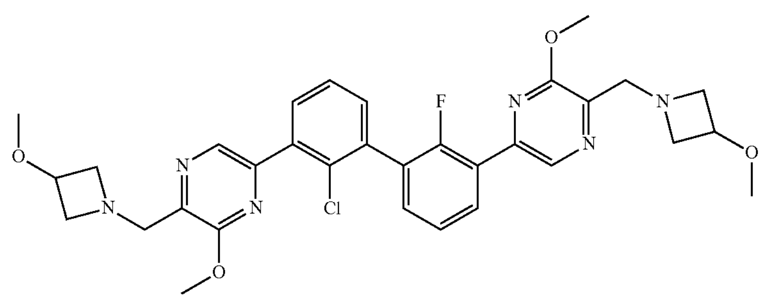 [SMILES: COc1nc(-c2cccc(-c3cccc(-c4cnc(CN5CC(OC)C5)c(OC)n4)c3Cl)c2F)cnc1CN1CC(OC)C1] | 621.2 | 1 |

TABLE 1-continued
| No. | Structure | ES/MS (m/z, M + H+) | Procedure |
|---|---|---|---|
| 4 | 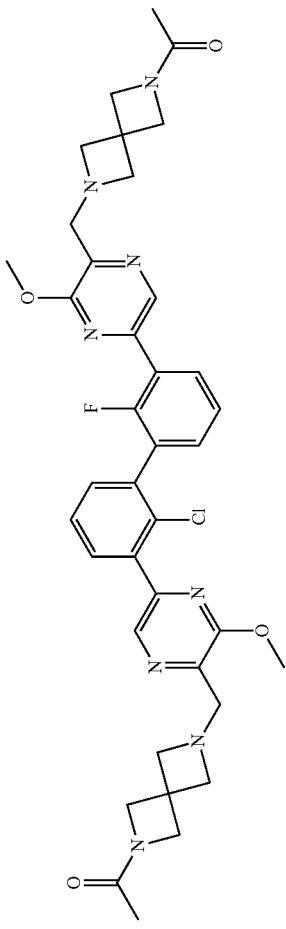 | 727.292 | 1 |
| 5 | 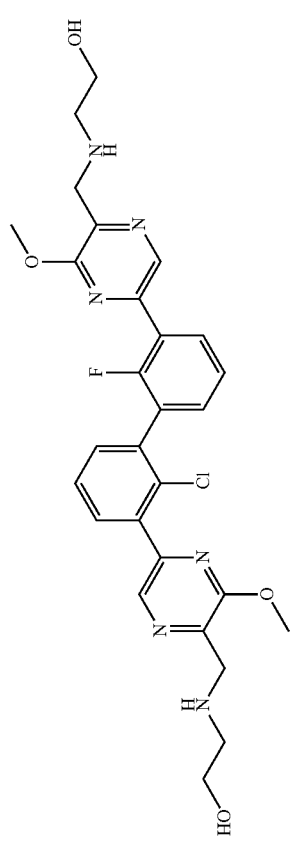 | 570.2 | 1 |
| 6 | 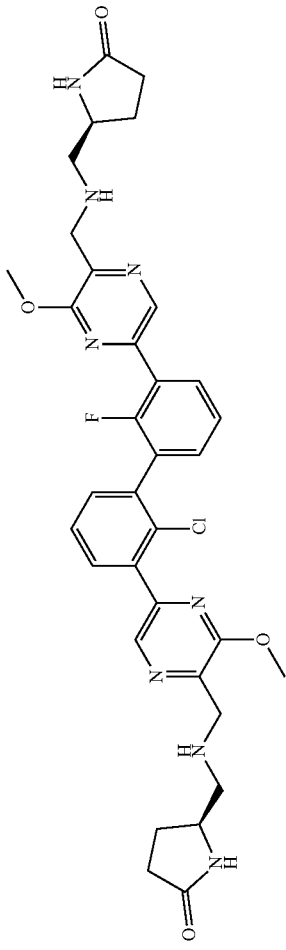 | 675.2 | 1 |

TABLE 1-continued

| No. | Structure | ES/MS (m/z, M + H⁺) | Procedure |
|---|---|---|---|
| 7 | 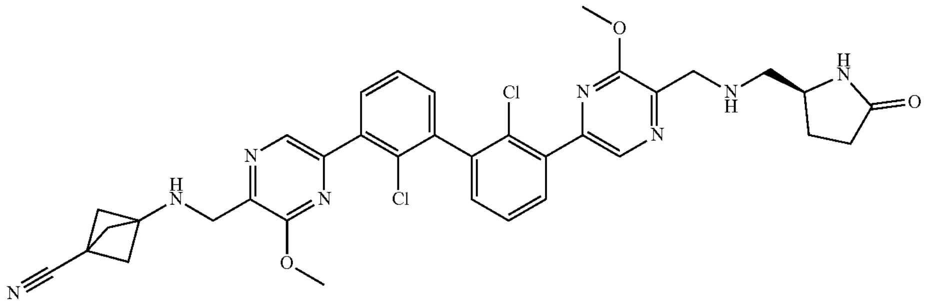 [SMILES: COc1nc(-c2cccc(-c3cccc(-c4cnc(CNC56CC(C#N)(C5)C6)c(OC)n4)c3Cl)c2Cl)cnc1CNC[C@@H]1CCC(=O)N1] | 685.11 | 2 |
| 8 | 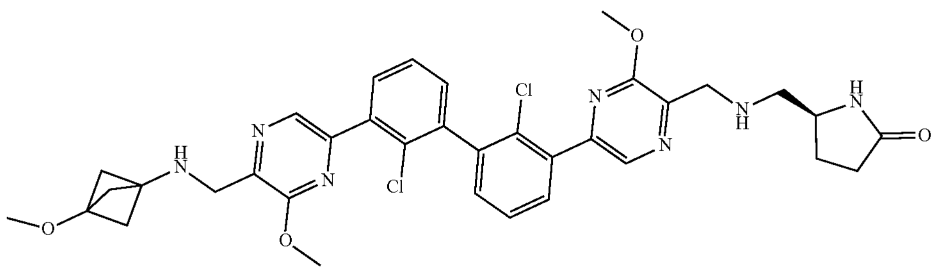 [SMILES: COc1nc(-c2cccc(-c3cccc(-c4cnc(CNC56CC(OC)(C5)C6)c(OC)n4)c3Cl)c2Cl)cnc1CNC[C@@H]1CCC(=O)N1] | 690.06 | 2 |
| 9 | 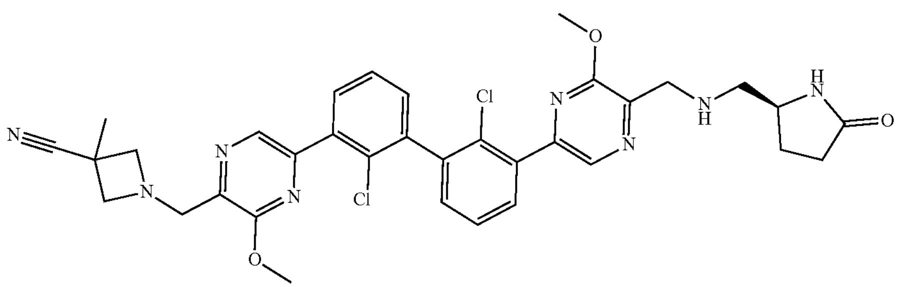 [SMILES: COc1nc(-c2cccc(-c3cccc(-c4cnc(CN5CC(C)(C#N)C5)c(OC)n4)c3Cl)c2Cl)cnc1CNC[C@@H]1CCC(=O)N1] | 673.19 | 2 |

TABLE 1-continued

| No. | Structure | ES/MS (m/z, M + H⁺) | Procedure |
|-----|-----------|---------------------|-----------|
| 10 | 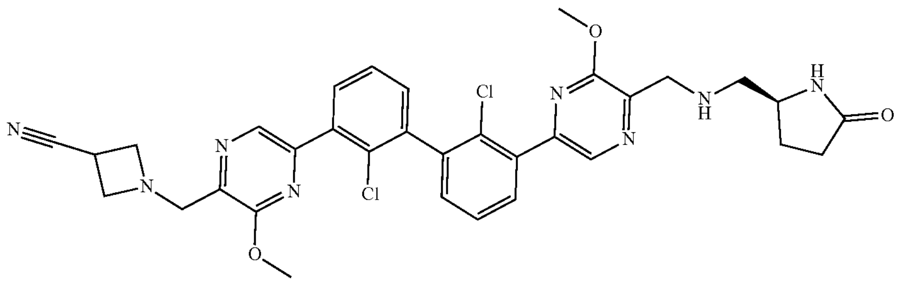 [SMILES: COc1nc(-c2cccc(-c3cccc(-c4cnc(CN5CC(C#N)C5)c(OC)n4)c3Cl)c2Cl)cnc1CNC[C@@H]1CCC(=O)N1] | 659.18 | 2 |
| 11 | 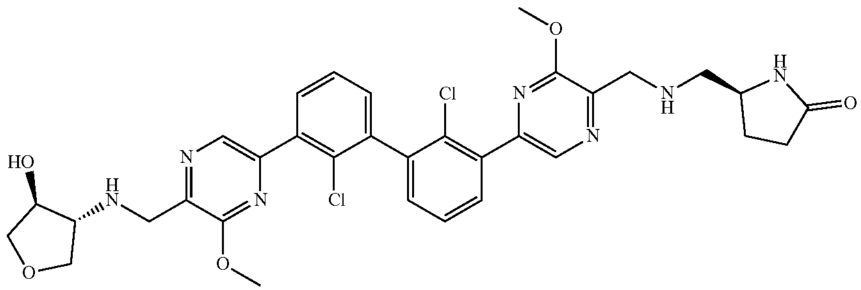 [SMILES: COc1nc(-c2cccc(-c3cccc(-c4cnc(CN[C@@H]5COC[C@H]5O)c(OC)n4)c3Cl)c2Cl)cnc1CNC[C@@H]1CCC(=O)N1] | 680.12 | 2 |
| 12 | 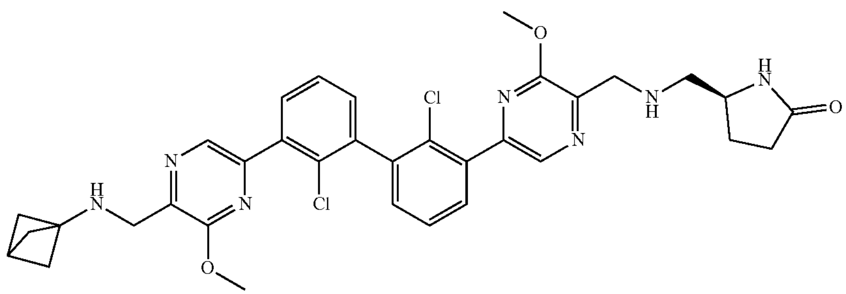 [SMILES: COc1nc(-c2cccc(-c3cccc(-c4cnc(CNC56CC(C5)C6)c(OC)n4)c3Cl)c2Cl)cnc1CNC[C@@H]1CCC(=O)N1] | 660.19 | 2 |

TABLE 1-continued

| No. | Structure | ES/MS (m/z, M + H⁺) | Procedure |
|---|---|---|---|
| 13 | 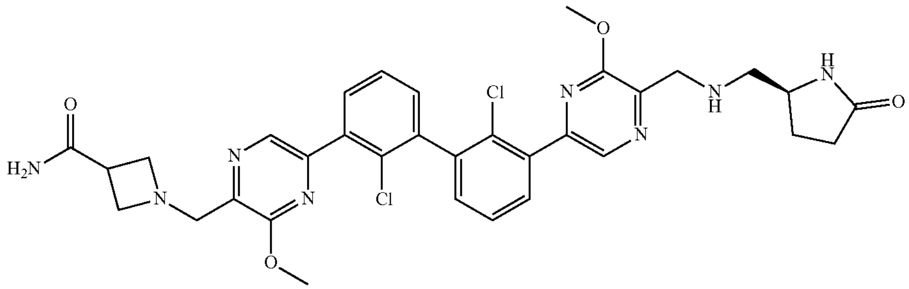 [SMILES: COc1nc(-c2cccc(-c3cccc(-c4cnc(CN5CC(C(N)=O)C5)c(OC)n4)c3Cl)c2Cl)cnc1CNC[C@@H]1CCC(=O)N1] | 676.14 | 2 |
| 14 | 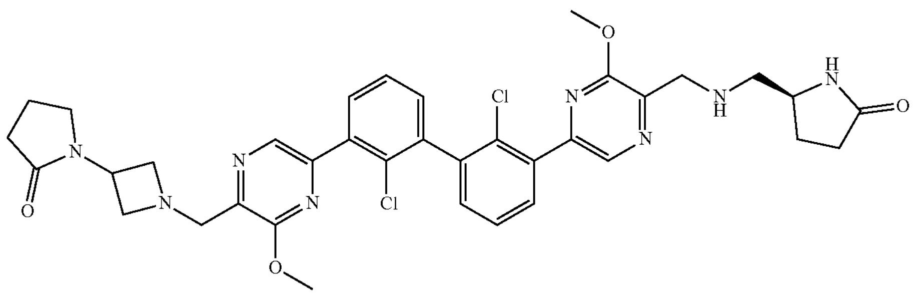 [SMILES: COc1nc(-c2cccc(-c3cccc(-c4cnc(CN5CC(N6CCCC6=O)C5)c(OC)n4)c3Cl)c2Cl)cnc1CNC[C@@H]1CCC(=O)N1] | 717.2 | 2 |
| 15 | 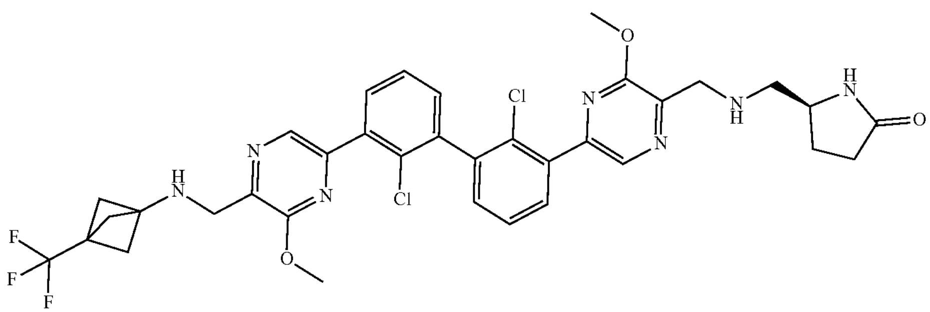 [SMILES: COc1nc(-c2cccc(-c3cccc(-c4cnc(CNC56CC(C(F)(F)F)(C5)C6)c(OC)n4)c3Cl)c2Cl)cnc1CNC[C@@H]1CCC(=O)N1] | 728.16 | 2 |

TABLE 1-continued

| No. | Structure | ES/MS (m/z, M + H⁺) | Procedure |
|---|---|---|---|
| 16 | 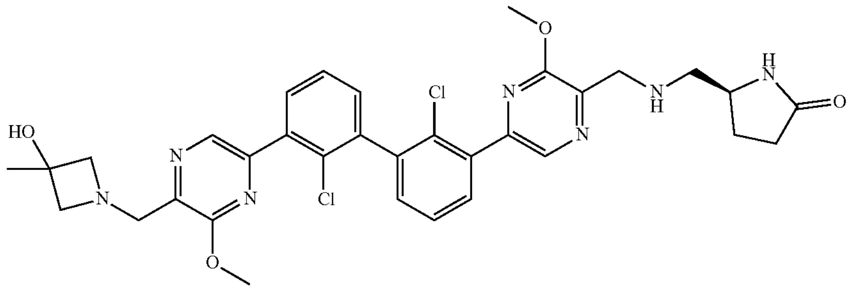 [SMILES: COc1nc(-c2cccc(-c3cccc(-c4cnc(CN5CC(C)(O)C5)c(OC)n4)c3Cl)c2Cl)cnc1CNC[C@@H]1CCC(=O)N1] | 664.16 | 2 |
| 17 | 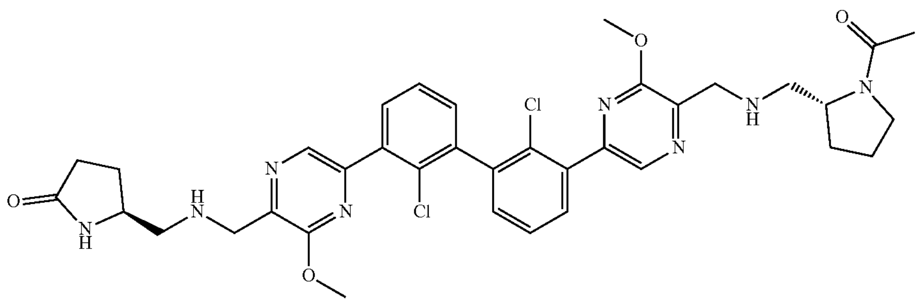 [SMILES: COc1nc(-c2cccc(-c3cccc(-c4cnc(CNC[C@H]5CCCN5C(C)=O)c(OC)n4)c3Cl)c2Cl)cnc1CNC[C@@H]1CCC(=O)N1] | 719.3 | 2 |
| 18 | 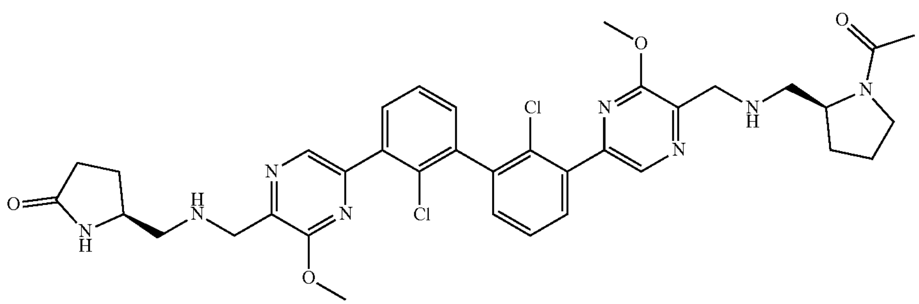 [SMILES: COc1nc(-c2cccc(-c3cccc(-c4cnc(CNC[C@@H]5CCCN5C(C)=O)c(OC)n4)c3Cl)c2Cl)cnc1CNC[C@@H]1CCC(=O)N1] | 719.3 | 2 |

TABLE 1-continued

| No. | Structure | ES/MS (m/z, M + H+) | Procedure |
|---|---|---|---|
| 19 | 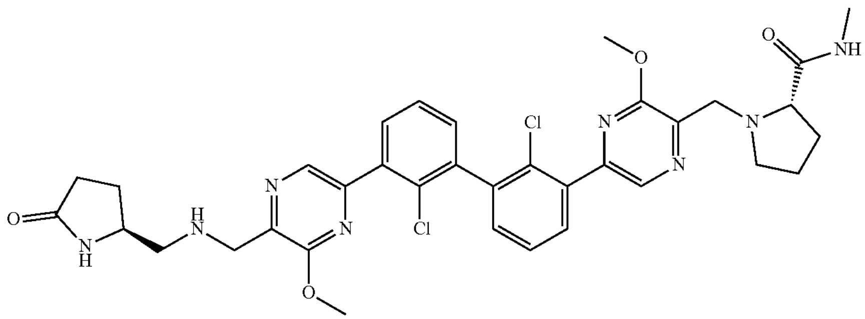 [SMILES: CNC(=O)[C@@H]1CCCN1Cc1ncc(-c2cccc(-c3cccc(-c4cnc(CNC[C@@H]5CCC(=O)N5)c(OC)n4)c3Cl)c2Cl)nc1OC] | 705.3 | 2 |
| 20 | 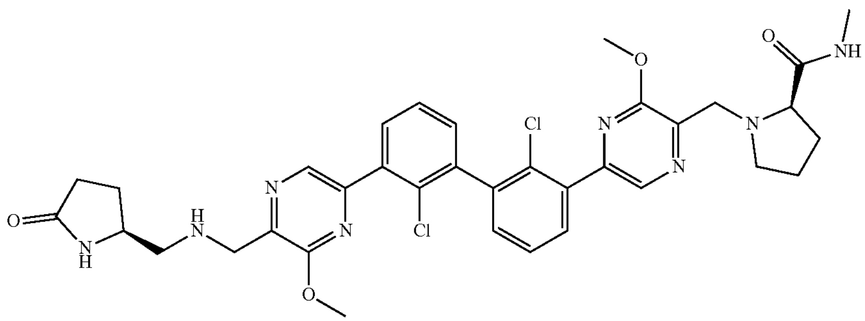 [SMILES: CNC(=O)[C@H]1CCCN1Cc1ncc(-c2cccc(-c3cccc(-c4cnc(CNC[C@@H]5CCC(=O)N5)c(OC)n4)c3Cl)c2Cl)nc1OC] | 705.1 | 2 |
| 21 | 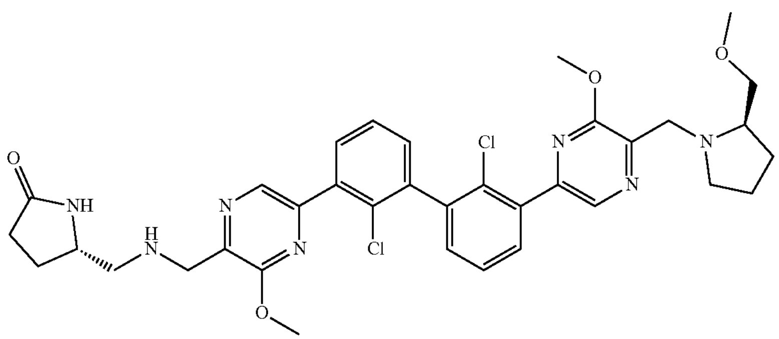 [SMILES: COC[C@H]1CCCN1Cc1ncc(-c2cccc(-c3cccc(-c4cnc(CNC[C@@H]5CCC(=O)N5)c(OC)n4)c3Cl)c2Cl)nc1OC] | 692.3 | 2 |

TABLE 1-continued

| No. | Structure | ES/MS (m/z, M + H⁺) | Procedure |
|---|---|---|---|
| 22 | 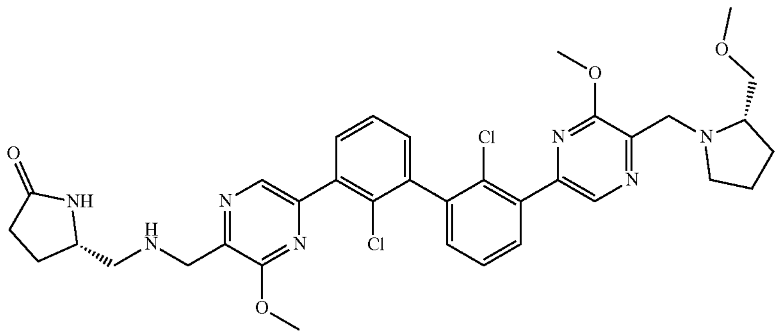 [SMILES: COC[C@@H]1CCCN1Cc1ncc(-c2cccc(-c3cccc(-c4cnc(CNC[C@@H]5CCC(=O)N5)c(OC)n4)c3Cl)c2Cl)nc1OC] | 692.3 | 2 |
| 23 | 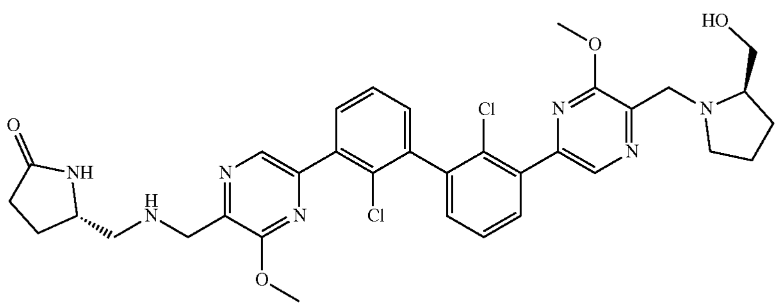 [SMILES: COc1nc(-c2cccc(-c3cccc(-c4cnc(CN5CCC[C@@H]5CO)c(OC)n4)c3Cl)c2Cl)cnc1CNC[C@@H]1CCC(=O)N1] | 678.2 | 2 |
| 24 | 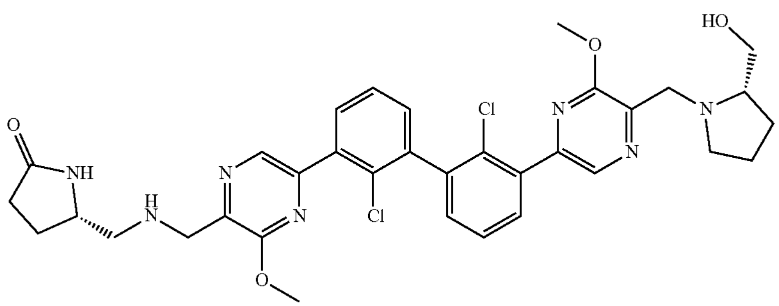 [SMILES: COc1nc(-c2cccc(-c3cccc(-c4cnc(CN5CCC[C@H]5CO)c(OC)n4)c3Cl)c2Cl)cnc1CNC[C@@H]1CCC(=O)N1] | 678.2 | 2 |

TABLE 1-continued

| No. | Structure | ES/MS (m/z, M + H+) | Procedure |
|---|---|---|---|
| 25 | 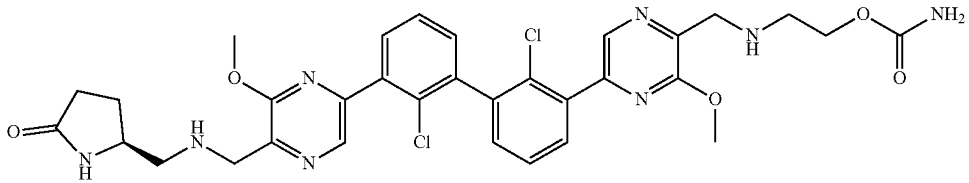 [SMILES: COc1nc(-c2cccc(-c3cccc(-c4cnc(CNC[C@@H]5CCC(=O)N5)c(OC)n4)c3Cl)c2Cl)cnc1CNCCOC(N)=O] | 681.2 | 2 |
| 26 | 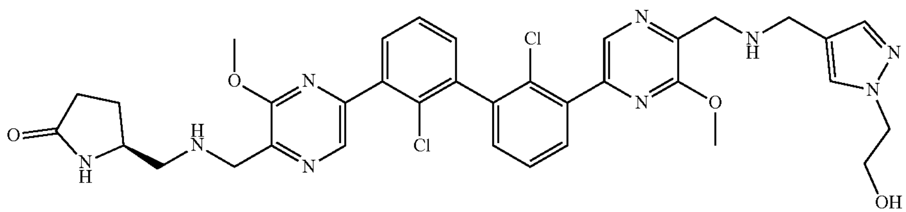 [SMILES: COc1nc(-c2cccc(-c3cccc(-c4cnc(CNC[C@@H]5CCC(=O)N5)c(OC)n4)c3Cl)c2Cl)cnc1CNCc1cnn(CCO)c1] | 718.2 | 2 |
| 27 | 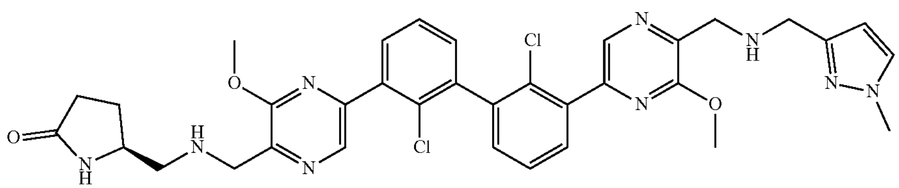 | 688.2 | 2 |
| 28 | 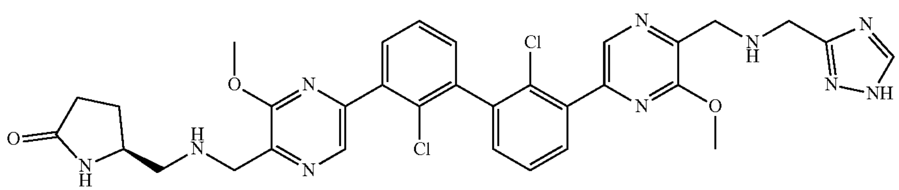 [SMILES: COc1nc(-c2cccc(-c3cccc(-c4cnc(CNC[C@@H]5CCC(=O)N5)c(OC)n4)c3Cl)c2Cl)cnc1CNCc1nc[nH]n1] | 675.1 | 2 |
| 29 | 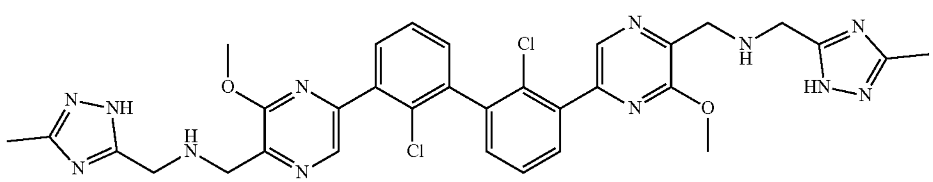 | 687.2 | 3 |

TABLE 1-continued

| No. | Structure | ES/MS (m/z, M + H⁺) | Procedure |
|---|---|---|---|
| 30 | 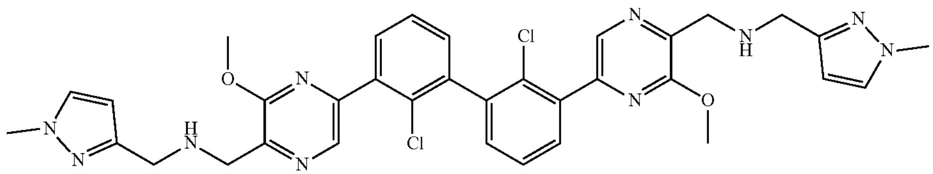 | 685.2 | 3 |
| 31 | 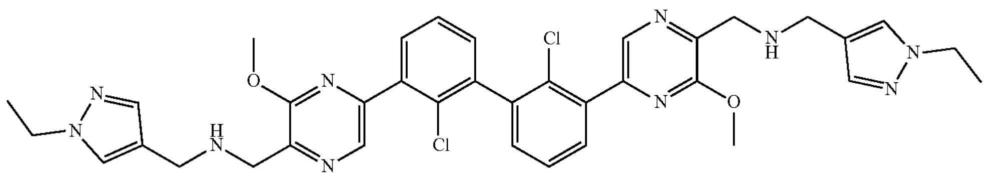 [SMILES: CCn1cc(CNCc2ncc(-c3cccc(-c4cccc(-c5cnc(CNCc6cnn(CC)c6)c(OC)n5)c4Cl)c3Cl)nc2OC)cn1] | 713.2 | 3 |
| 32 | 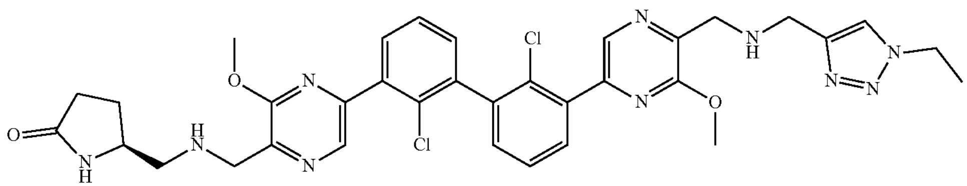 [SMILES: CCn1cc(CNCc2ncc(-c3cccc(-c4cccc(-c5cnc(CNC[C@@H]6CCC(=O)N6)c(OC)n5)c4Cl)c3Cl)nc2OC)nn1] | 703.2 | 2 |
| 33 | 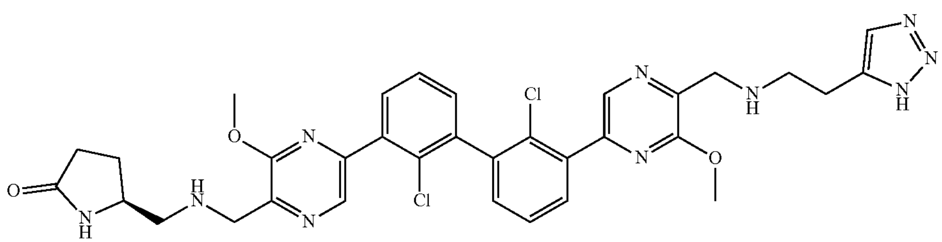 [SMILES: COc1nc(-c2cccc(-c3cccc(-c4cnc(CNC[C@@H]5CCC(=O)N5)c(OC)n4)c3Cl)c2Cl)cnc1CNCCc1cnn[nH]1] | 689.2 | 2 |
| 34 | 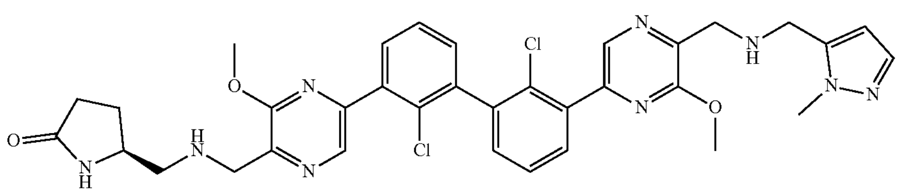 [SMILES: COc1nc(-c2cccc(-c3cccc(-c4cnc(CNC[C@@H]5CCC(=O)N5)c(OC)n4)c3Cl)c2Cl)cnc1CNCc1ccnn1C] | 688.2 | 2 |

TABLE 1-continued

| No. | Structure | ES/MS (m/z, M + H+) | Procedure |
|---|---|---|---|
| 35 | 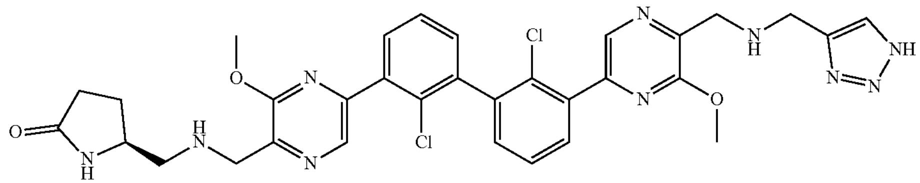 [SMILES: COc1nc(-c2cccc(-c3cccc(-c4cnc(CNC[C@@H]5CCC(=O)N5)c(OC)n4)c3Cl)c2Cl)cnc1CNCc1c[nH]nn1] | 675.2 | 2 |
| 36 | 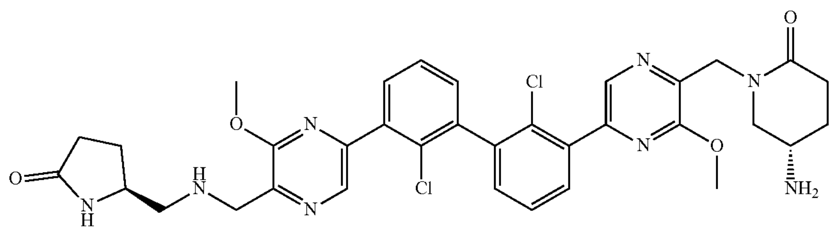 [SMILES: COc1nc(-c2cccc(-c3cccc(-c4cnc(CN5C[C@@H](N)CCC5=O)c(OC)n4)c3Cl)c2Cl)cnc1CNC[C@@H]1CCC(=O)N1] | 691.2 | 2 |
| 37 | 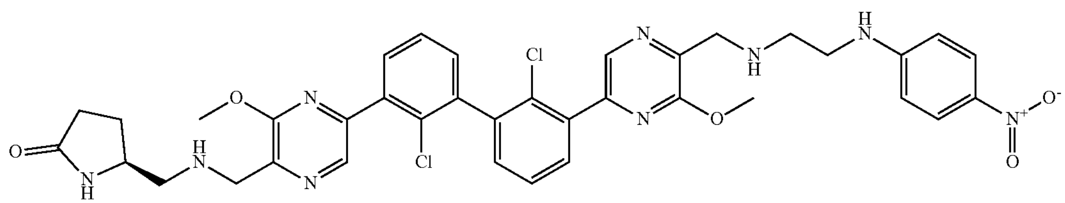 [SMILES: COc1nc(-c2cccc(-c3cccc(-c4cnc(CNC[C@@H]5CCC(=O)N5)c(OC)n4)c3Cl)c2Cl)cnc1CNCCNc1ccc([N+](=O)[O-])cc1] | 758.1 | 2 |
| 38 | 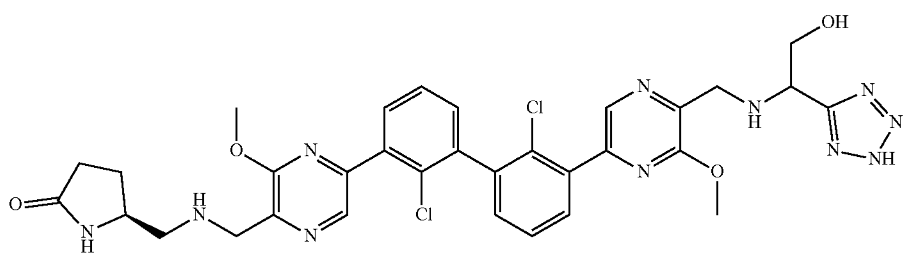 [SMILES: COc1nc(-c2cccc(-c3cccc(-c4cnc(CNC(CO)c5nn[nH]n5)c(OC)n4)c3Cl)c2Cl)cnc1CNC[C@@H]1CCC(=O)N1] | 706 | 2 |

TABLE 1-continued

| No. | Structure | ES/MS (m/z, M + H⁺) | Procedure |
|---|---|---|---|
| 39 | 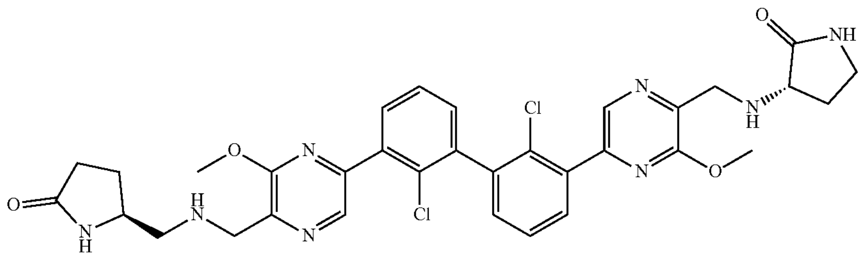 [SMILES: COc1nc(-c2cccc(-c3cccc(-c4cnc(CN[C@H]5CCNC5=O)c(OC)n4)c3Cl)c2Cl)cnc1CNC[C@@H]1CCC(=O)N1] | 677.2 | 2 |
| 40 | 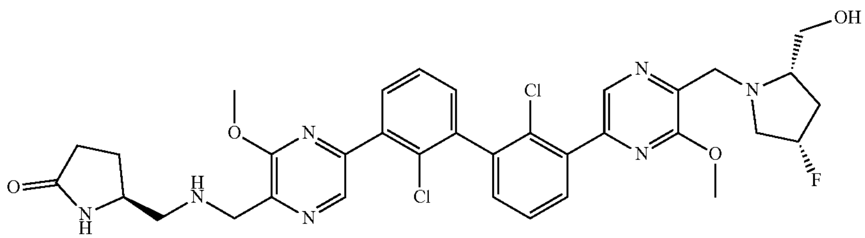 [SMILES: COc1nc(-c2cccc(-c3cccc(-c4cnc(CN5C[C@@H](F)C[C@H]5CO)c(OC)n4)c3Cl)c2Cl)cnc1CNC[C@@H]1CCC(=O)N1] | 696.1 | 2 |
| 41 | 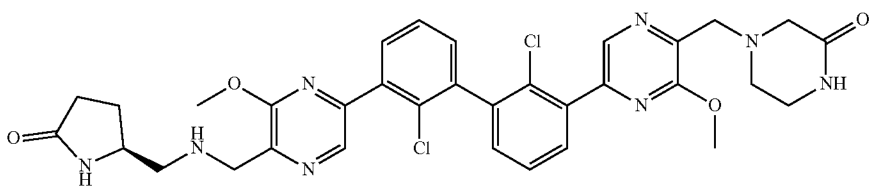 [SMILES: COc1nc(-c2cccc(-c3cccc(-c4cnc(CN5CCNC(=O)C5)c(OC)n4)c3Cl)c2Cl)cnc1CNC[C@@H]1CCC(=O)N1] | 677.1 | 2 |
| 42 | 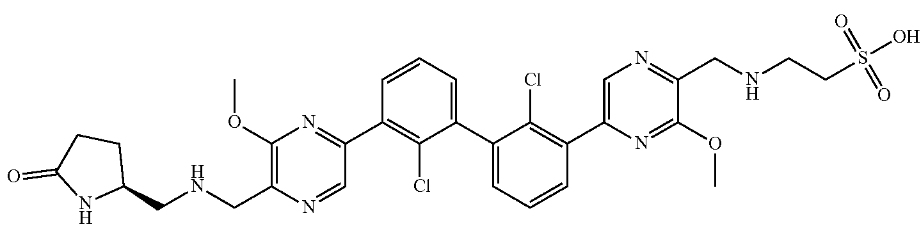 [SMILES: COc1nc(-c2cccc(-c3cccc(-c4cnc(CNC[C@@H]5CCC(=O)N5)c(OC)n4)c3Cl)c2Cl)cnc1CNCCS(=O)(=O)O] | 702.2 | 2 |

TABLE 1-continued

| No. | Structure | ES/MS (m/z, M + H⁺) | Procedure |
|---|---|---|---|
| 43 | 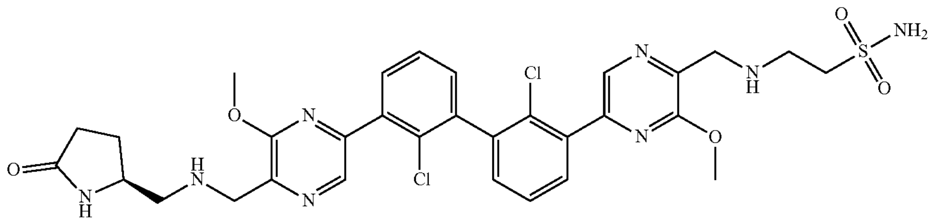 [SMILES: COc1nc(-c2cccc(-c3cccc(-c4cnc(CNC[C@@H]5CCC(=O)N5)c(OC)n4)c3Cl)c2Cl)cnc1CNCCS(N)(=O)=O] | 701.3 | 2 |
| 44 | 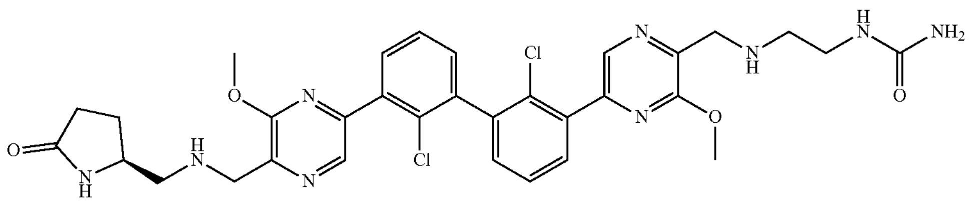 [SMILES: COc1nc(-c2cccc(-c3cccc(-c4cnc(CNC[C@@H]5CCC(=O)N5)c(OC)n4)c3Cl)c2Cl)cnc1CNCCNC(N)=O] | 680.1 | 2 |
| 45 | 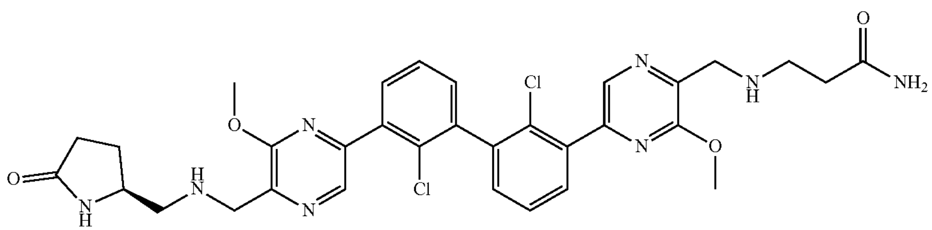 [SMILES: COc1nc(-c2cccc(-c3cccc(-c4cnc(CNC[C@@H]5CCC(=O)N5)c(OC)n4)c3Cl)c2Cl)cnc1CNCCC(N)=O] | 665.1 | 2 |
| 46 | 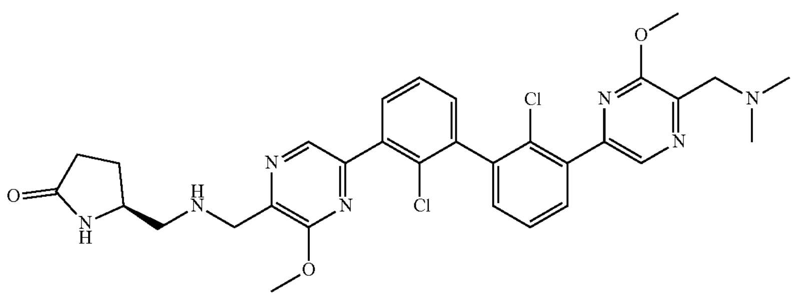 [SMILES: COc1nc(-c2cccc(-c3cccc(-c4cnc(CN(C)C)c(OC)n4)c3Cl)c2Cl)cnc1CNC[C@@H]1CCC(=O)N1] | 622.1 | 2 |

TABLE 1-continued
| No. | Structure | ES/MS (m/z, M + H+) | Procedure |
|---|---|---|---|
| 47 | 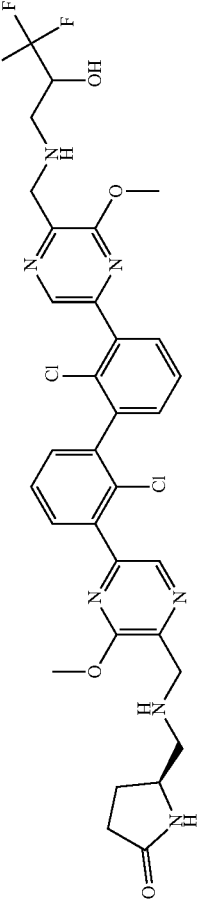 | 706.1 | 2 |
| 48 | 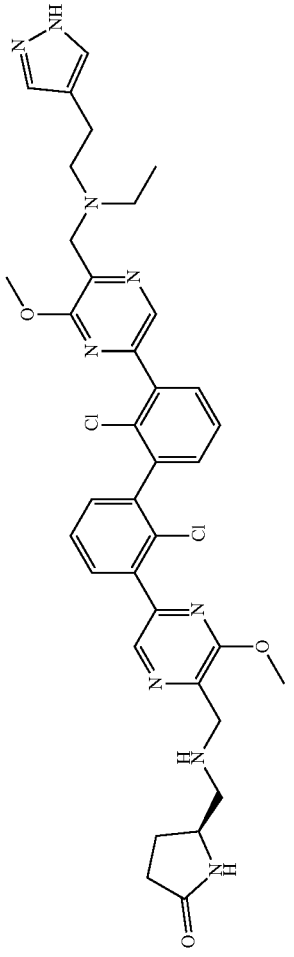 | 716.1 | 2 |
| 49 | 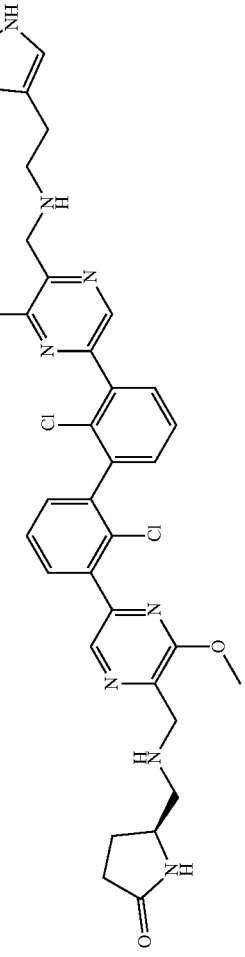 | 688.1 | 2 |

TABLE 1-continued

| No. | Structure | ES/MS (m/z, M + H⁺) | Procedure |
|---|---|---|---|
| 50 | 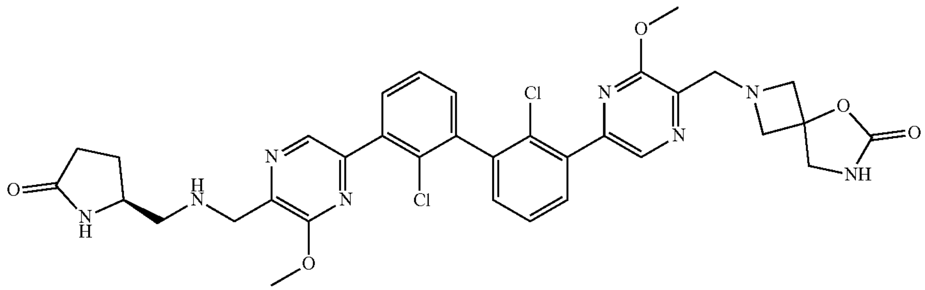 [SMILES: COc1nc(-c2cccc(-c3cccc(-c4cnc(CN5CC6(CNC(=O)O6)C5)c(OC)n4)c3Cl)c2Cl)cnc1CNC[C@@H]1CCC(=O)N1] | 705.1 | 2 |
| 51 | 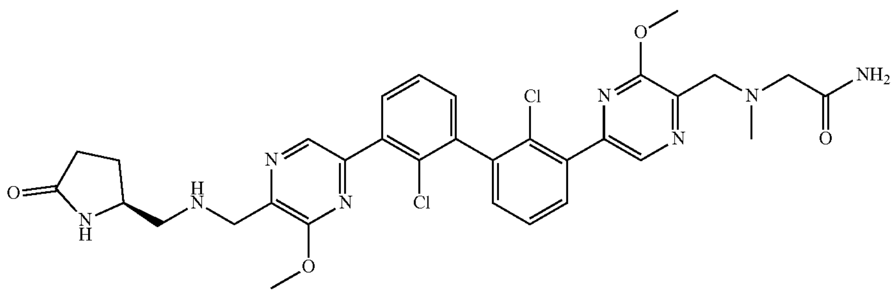 [SMILES: COc1nc(-c2cccc(-c3cccc(-c4cnc(CN(C)CC(N)=O)c(OC)n4)c3Cl)c2Cl)cnc1CNC[C@@H]1CCC(=O)N1] | 665.1 | 2 |
| 52 | 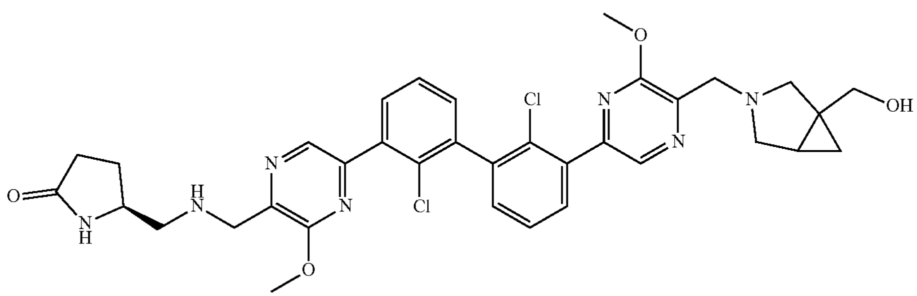 [SMILES: COc1nc(-c2cccc(-c3cccc(-c4cnc(CN5CC6CC6(CO)C5)c(OC)n4)c3Cl)c2Cl)cnc1CNC[C@@H]1CCC(=O)N1] | 690.2 | 2 |

TABLE 1-continued

| No. | Structure | ES/MS (m/z, M + H⁺) | Procedure |
|---|---|---|---|
| 53 | 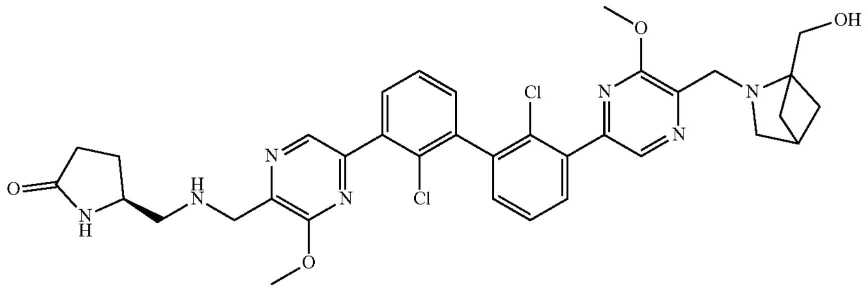 [SMILES: COc1nc(-c2cccc(-c3cccc(-c4cnc(CN5CC6CC5(CO)C6)c(OC)n4)c3Cl)c2Cl)cnc1CNC[C@@H]1CCC(=O)N1] | 690.2 | 2 |
| 54 | 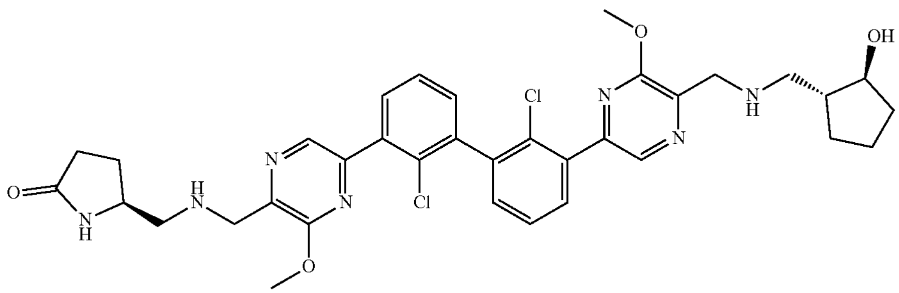 [SMILES: COc1nc(-c2cccc(-c3cccc(-c4cnc(CNC[C@H]5CCC[C@@H]5O)c(OC)n4)c3Cl)c2Cl)cnc1CNC[C@@H]1CCC(=O)N1] | 692.2 | 2 |
| 55 | 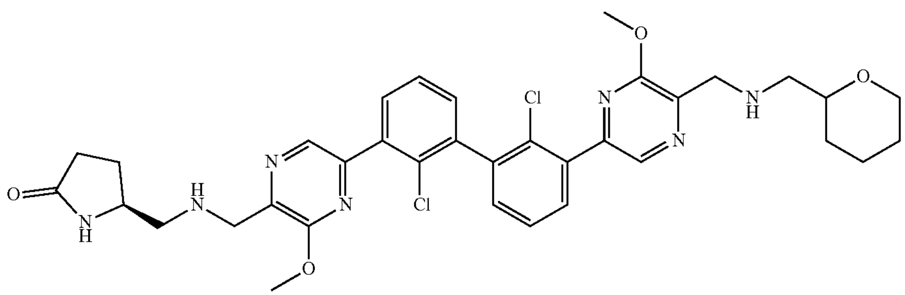 [SMILES: COc1nc(-c2cccc(-c3cccc(-c4cnc(CNC[C@@H]5CCC(=O)N5)c(OC)n4)c3Cl)c2Cl)cnc1CNCC1CCCCO1] | 692.2 | 2 |

TABLE 1-continued

| No. | Structure | ES/MS (m/z, M + H+) | Procedure |
|---|---|---|---|
| 56 | 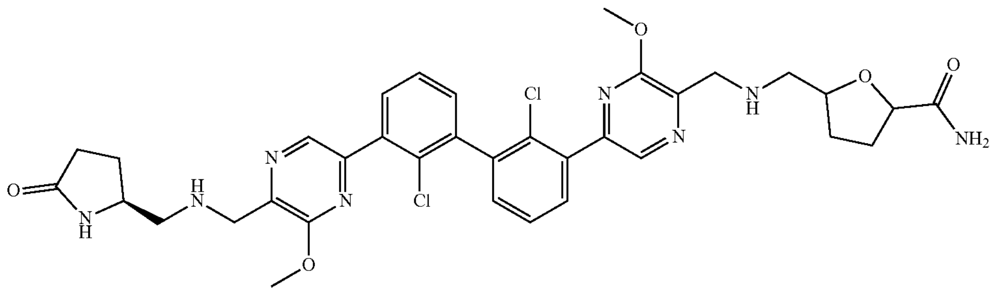 [SMILES: COc1nc(-c2cccc(-c3cccc(-c4cnc(CNC[C@@H]5CCC(=O)N5)c(OC)n4)c3Cl)c2Cl)cnc1CNCC1CCC(C(N)=O)O1] | 721.2 | 2 |
| 57 | 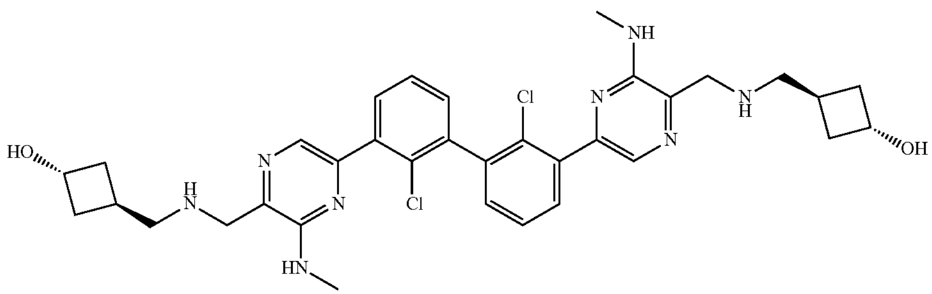 [SMILES: CNc1nc(-c2cccc(-c3cccc(-c4cnc(CNC[C@H]5C[C@H](O)C5)c(NC)n4)c3Cl)c2Cl)cnc1CNC[C@H]1C[C@H](O)C1] | 663.2 | 4 |
| 58 | 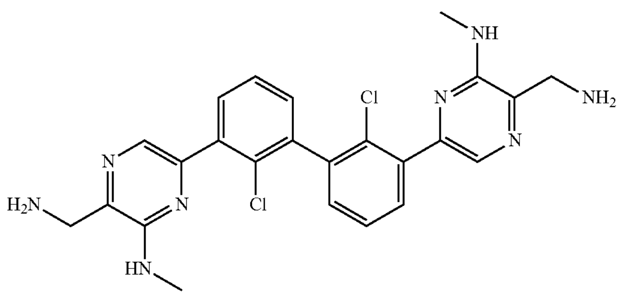 [SMILES: CNc1nc(-c2cccc(-c3cccc(-c4cnc(CN)c(NC)n4)c3Cl)c2Cl)cnc1CN] | 495.2 | 4 |

TABLE 1-continued

| No. | Structure | ES/MS (m/z, M + H⁺) | Procedure |
|-----|-----------|---------------------|-----------|
| 59  | 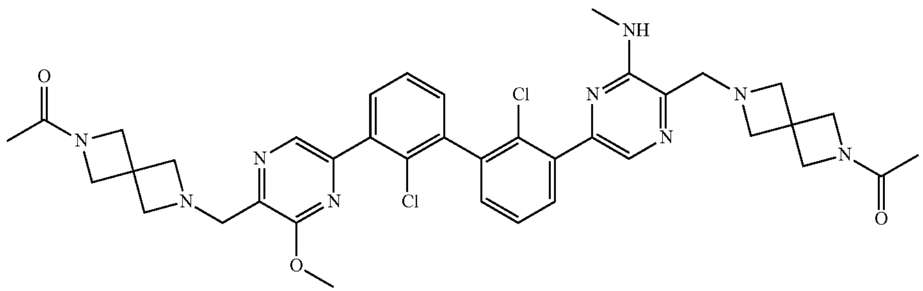 [SMILES: CNc1nc(-c2cccc(-c3cccc(-c4cnc(CN5CC6(C5)CN(C(C)=O)C6)c(OC)n4)c3Cl)c2Cl)cnc1CN1CC2(C1)CN(C(C)=O)C2]          | 742.2               | 24        |
| 60  | 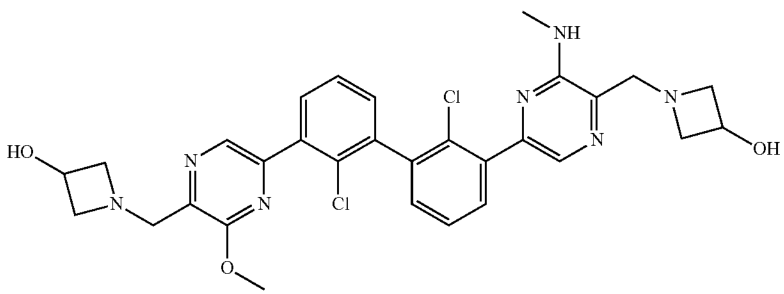 [SMILES: CNc1nc(-c2cccc(-c3cccc(-c4cnc(CN5CC(O)C5)c(OC)n4)c3Cl)c2Cl)cnc1CN1CC(O)C1]          | 608.2               | 24        |
| 61  | 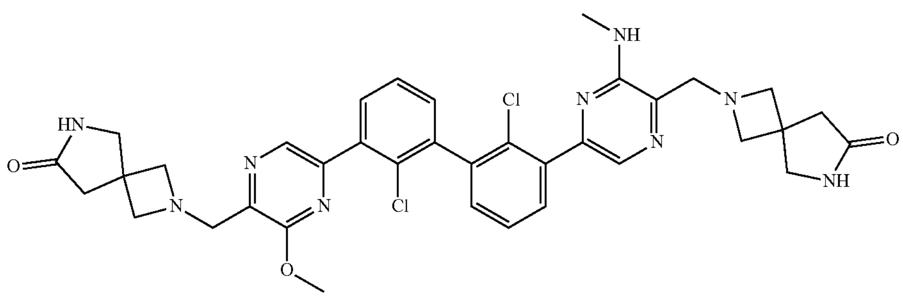 [SMILES: CNc1nc(-c2cccc(-c3cccc(-c4cnc(CN5CC6(CNC(=O)C6)C5)c(OC)n4)c3Cl)c2Cl)cnc1CN1CC2(CNC(=O)C2)C1]          | 714.2               | 24        |

TABLE 1-continued

| No. | Structure | ES/MS (m/z, M + H⁺) | Procedure |
|---|---|---|---|
| 62 | 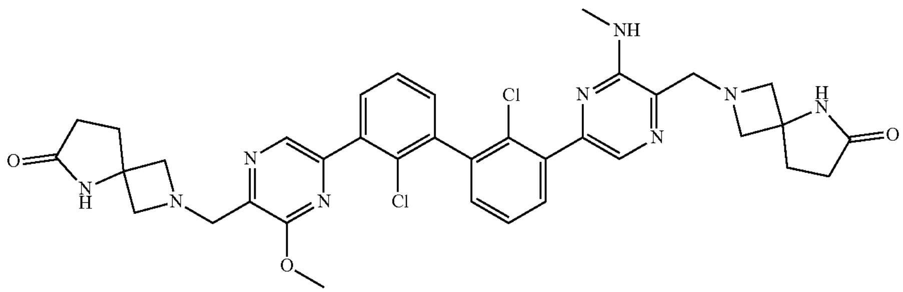 [SMILES: CNc1nc(-c2cccc(-c3cccc(-c4cnc(CN5CC6(CCC(=O)N6)C5)c(OC)n4)c3Cl)c2Cl)cnc1CN1CC2(CCC(=O)N2)C1] | 714.2 | 24 |
| 63 | 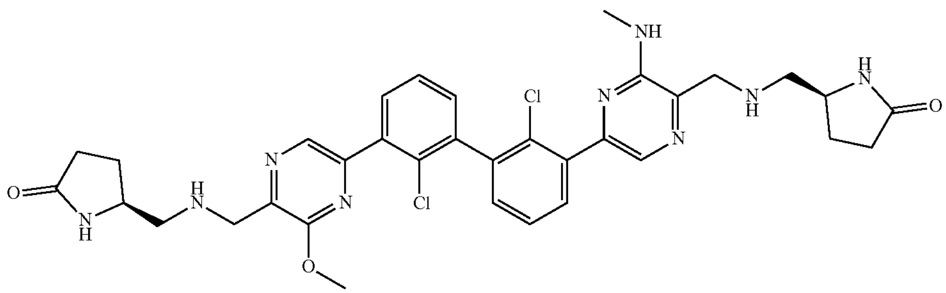 [SMILES: CNc1nc(-c2cccc(-c3cccc(-c4cnc(CNC[C@@H]5CCC(=O)N5)c(OC)n4)c3Cl)c2Cl)cnc1CNC[C@@H]1CCC(=O)N1] | 690.1 | 24 |
| 64 | 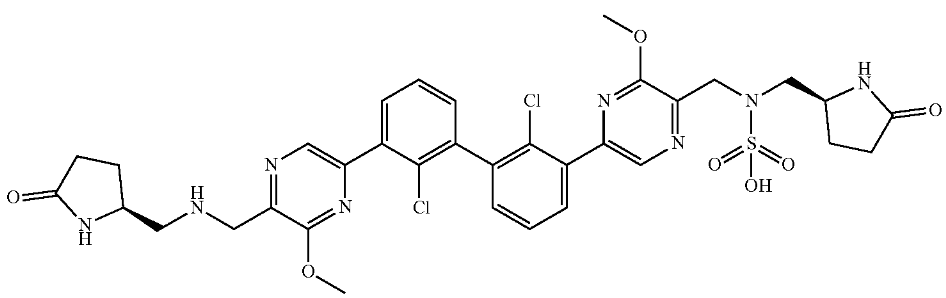 [SMILES: COc1nc(-c2cccc(-c3cccc(-c4cnc(CN(C[C@@H]5CCC(=O)N5)S(=O)(=O)O)c(OC)n4)c3Cl)c2Cl)cnc1CNC[C@@H]1CCC(=O)N1] | 793.3 (M + Na)+ | 21 |

TABLE 1-continued

| No. | Structure | ES/MS (m/z, M + H+) | Procedure |
|---|---|---|---|
| 65 | 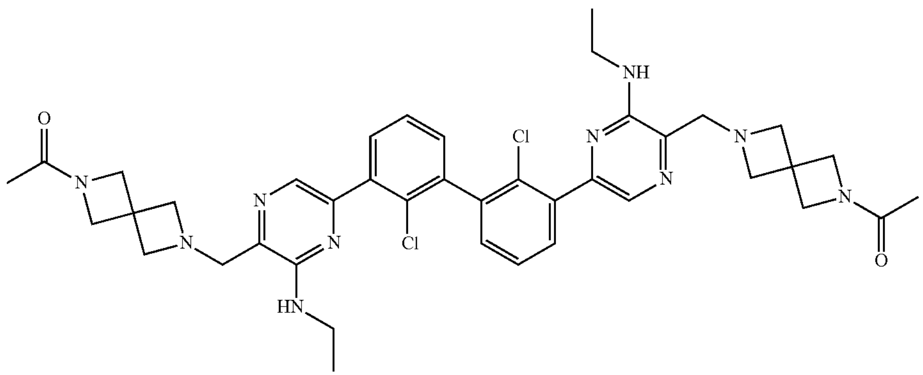 [SMILES: CCNc1nc(-c2cccc(-c3cccc(-c4cnc(CN5CC6(C5)CN(C(C)=O)C6)c(NCC)n4)c3Cl)c2Cl)cnc1CN1CC2(C1)CN(C(C)=O)C2] | 769.2 | 4 |
| 66 | 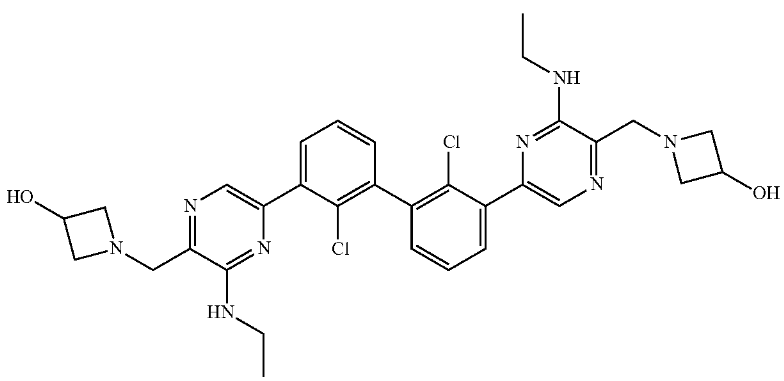 [SMILES: CCNc1nc(-c2cccc(-c3cccc(-c4cnc(CN5CC(O)C5)c(NCC)n4)c3Cl)c2Cl)cnc1CN1CC(O)C1] | 635.2 | 4 |

TABLE 1-continued
| No. | Structure | ES/MS (m/z, M + H+) | Procedure |
|---|---|---|---|
| 67 | 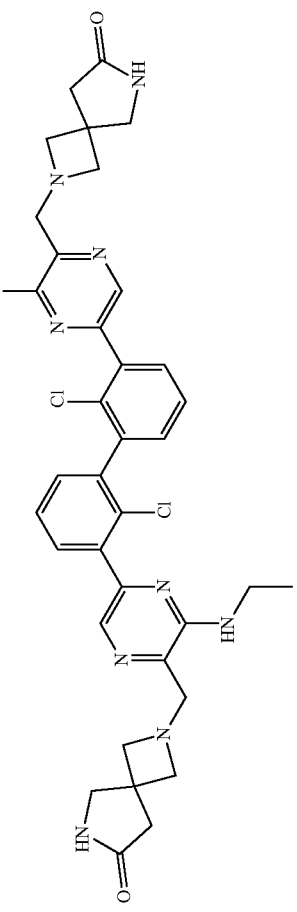 | 741.3 | 4 |
| 68 | 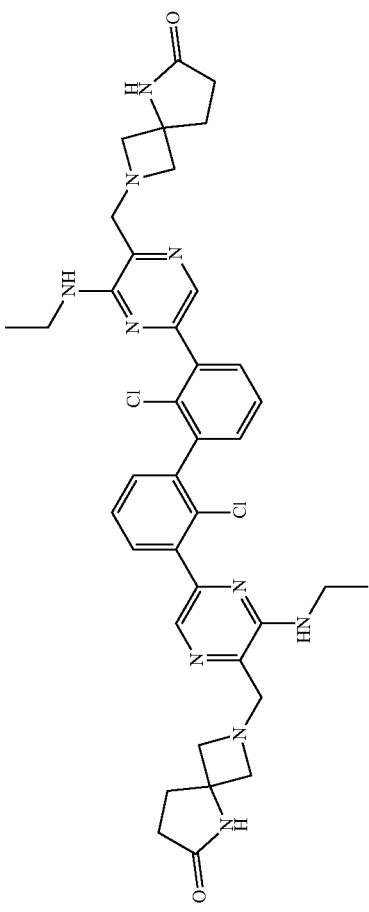 | 371.2 (M + 2H) 2+ | 4 |

TABLE 1-continued

| No. | Structure | ES/MS (m/z, M + H⁺) | Procedure |
|---|---|---|---|
| 69 | 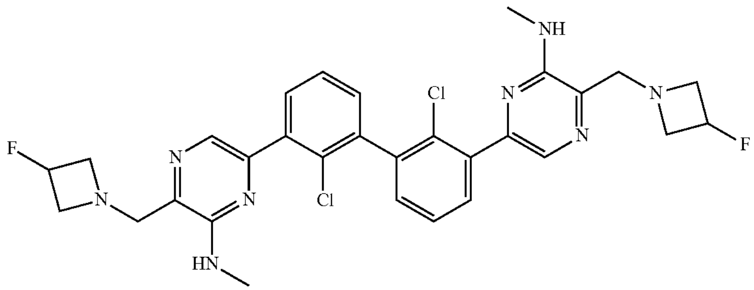 [SMILES: CNc1nc(-c2cccc(-c3cccc(-c4cnc(CN5CC(F)C5)c(NC)n4)c3Cl)c2Cl)cnc1CN1CC(F)C1] | 611.2 | 4 |
| 70 | 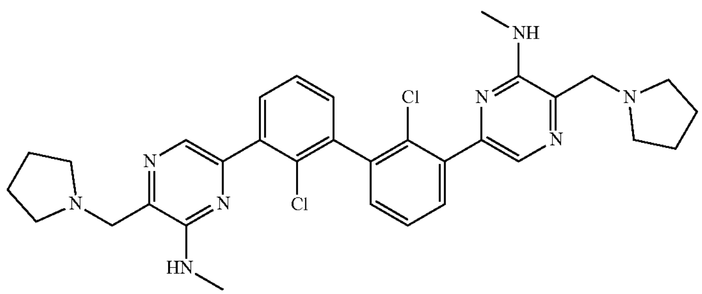 [SMILES: CNc1nc(-c2cccc(-c3cccc(-c4cnc(CN5CCCC5)c(NC)n4)c3Cl)c2Cl)cnc1CN1CCCC1] | 603.2 | 4 |
| 71 | 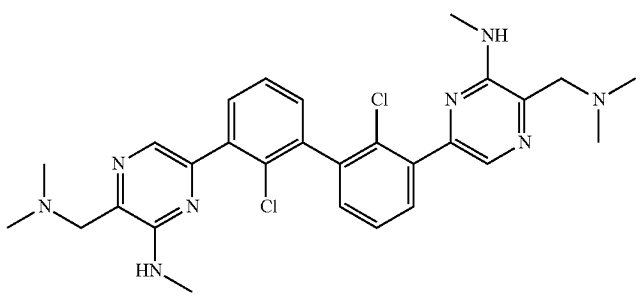 | 551.2 | 4 |

TABLE 1-continued

| No. | Structure | ES/MS (m/z, M + H+) | Procedure |
|---|---|---|---|
| 72 | 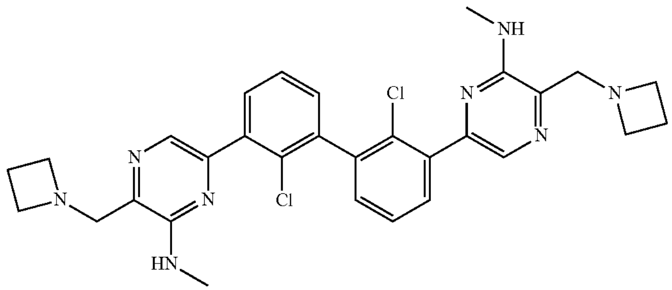 [SMILES: CNc1nc(-c2cccc(-c3cccc(-c4cnc(CN5CCC5)c(NC)n4)c3Cl)c2Cl)cnc1CN1CCC1] | 288.1 (M + 2H) 2+ | 4 |
| 73 | 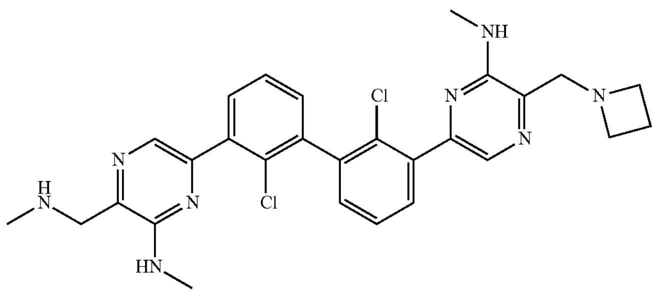 [SMILES: CNCc1ncc(-c2cccc(-c3cccc(-c4cnc(CN5CCC5)c(NC)n4)c3Cl)c2Cl)nc1NC] | 549.2 | 4 |
| 74 | 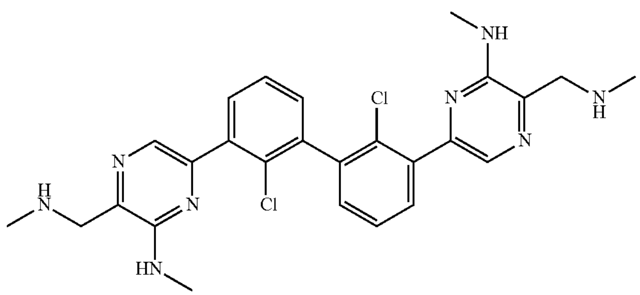 | 523.2 | 4 |

TABLE 1-continued

| No. | Structure | ES/MS (m/z, M + H⁺) | Procedure |
|---|---|---|---|
| 75 | 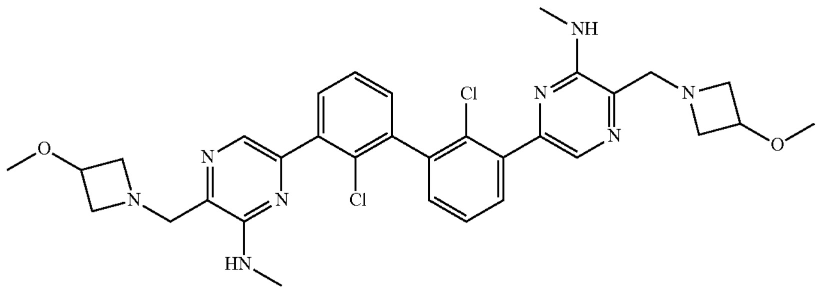 | 635.3 | 4 |
| 76 | 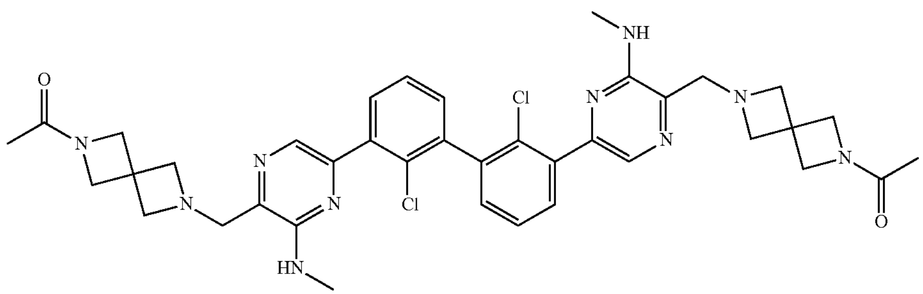 [SMILES: CNc1nc(-c2cccc(-c3cccc(-c4cnc(CN5CC6(C5)CN(C(C)=O)C6)c(NC)n4)c3Cl)c2Cl)cnc1CN1CC2(C1)CN(C(C)=O)C2] | 741.3 | 4 |
| 77 | 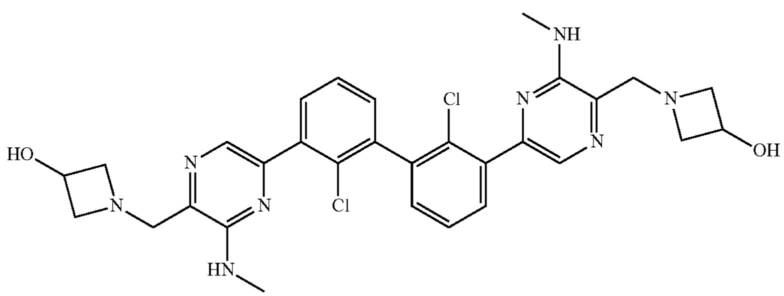 [SMILES: CNc1nc(-c2cccc(-c3cccc(-c4cnc(CN5CC(O)C5)c(NC)n4)c3Cl)c2Cl)cnc1CN1CC(O)C1] | 607.2 | 4 |

TABLE 1-continued
| No. | Structure | ES/MS (m/z, M + H+) | Procedure |
|---|---|---|---|
| 78 | 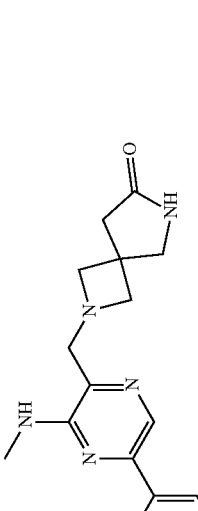 | 713.3 | 4 |
| 79 | 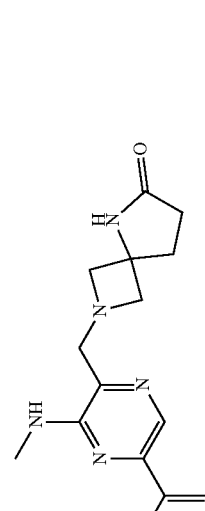 | 713.3 | 4 |
| 80 | 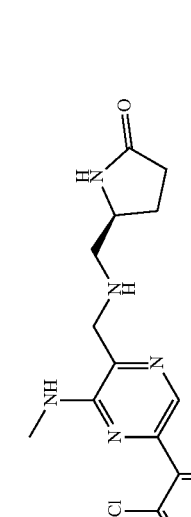 | 689.2 | 4 |

TABLE 1-continued

| No. | Structure | ES/MS (m/z, M + H+) | Procedure |
|---|---|---|---|
| 81 | 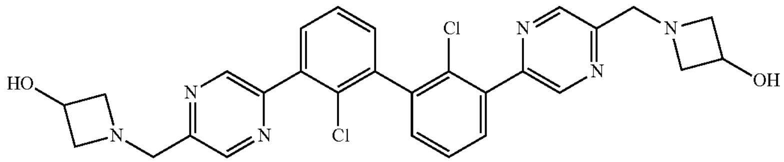 [SMILES: OC1CN(Cc2cnc(-c3cccc(-c4cccc(-c5cnc(CN6CC(O)C6)cn5)c4Cl)c3Cl)cn2)C1] | 549.1 | 5 |
| 82 | 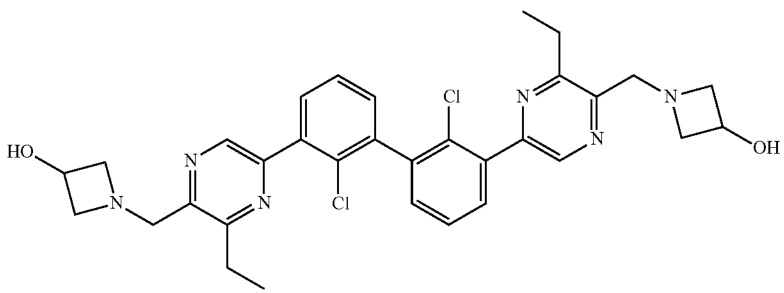 [SMILES: CCc1nc(-c2cccc(-c3cccc(-c4cnc(CN5CC(O)C5)c(CC)n4)c3Cl)c2Cl)cnc1CN1CC(O)C1] | 605.2 | 6 |
| 83 | 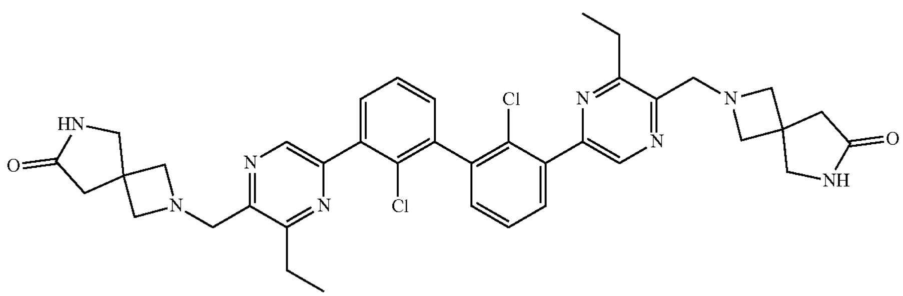 | 711.3 | 6 |

TABLE 1-continued

| No. | Structure | ES/MS (m/z, M + H⁺) | Procedure |
|---|---|---|---|
| 84 | 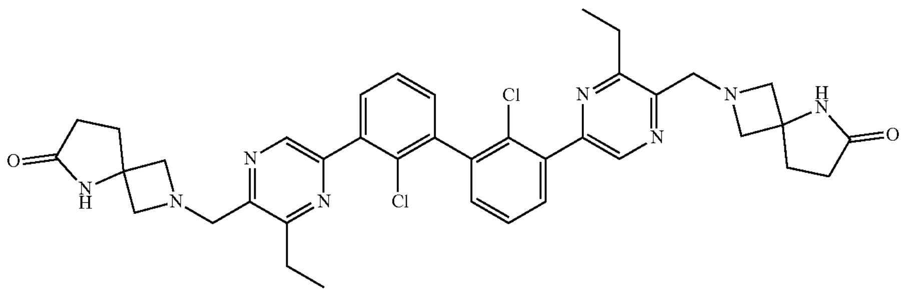 [SMILES: CCc1nc(-c2cccc(-c3cccc(-c4cnc(CN5CC6(CCC(=O)N6)C5)c(CC)n4)c3Cl)c2Cl)cnc1CN1CC2(CCC(=O)N2)C1] | 711.3 | 6 |
| 85 | 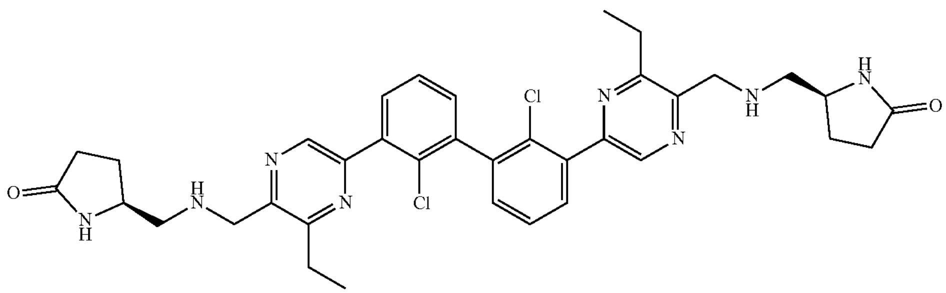 [SMILES: CCc1nc(-c2cccc(-c3cccc(-c4cnc(CNC[C@@H]5CCC(=O)N5)c(CC)n4)c3Cl)c2Cl)cnc1CNC[C@@H]1CCC(=O)N1] | 687.3 | 6 |
| 86 | 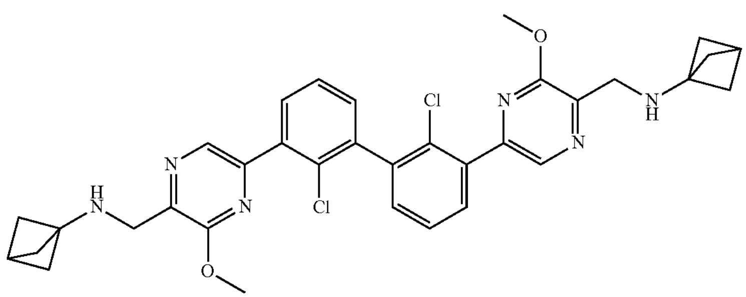 [SMILES: COc1nc(-c2cccc(-c3cccc(-c4cnc(CNC56CC(C5)C6)c(OC)n4)c3Cl)c2Cl)cnc1CNC12CC(C1)C2] | 629.2 | 3 |

TABLE 1-continued
| No. | Structure | ES/MS (m/z, M + H⁺) | Procedure |
|---|---|---|---|
| 87 | 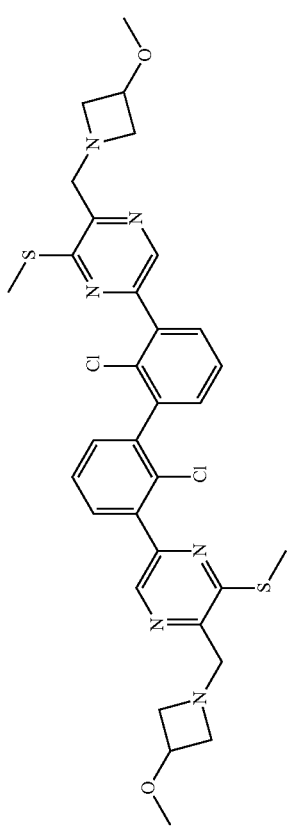 | 669.2 | 7 |
| 88 | 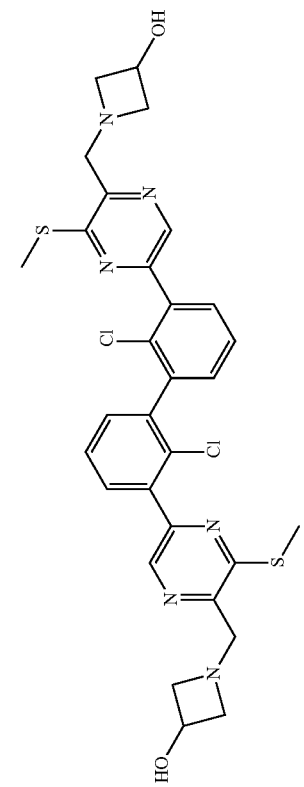 | 641.1 | 7 |
| 89 | 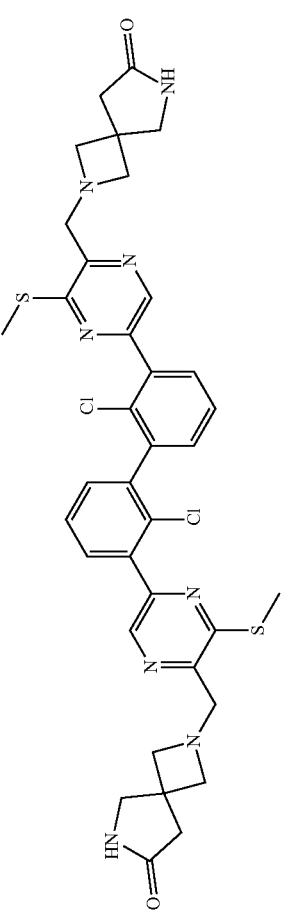 | 747.2 | 7 |

TABLE 1-continued
| No. | Structure | ES/MS (m/z, M + H⁺) | Procedure |
|---|---|---|---|
| 90 | 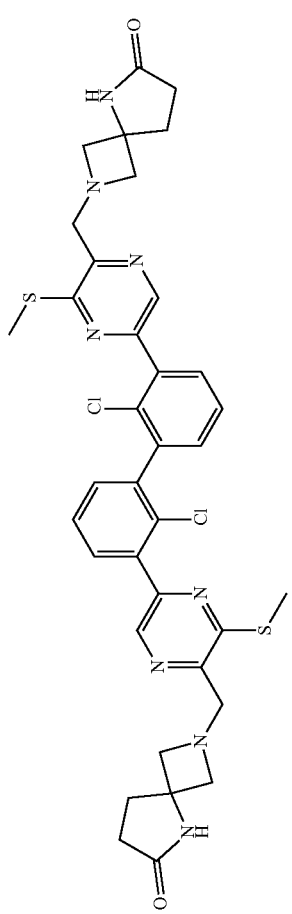 | 747.2 | 7 |
| 91 | 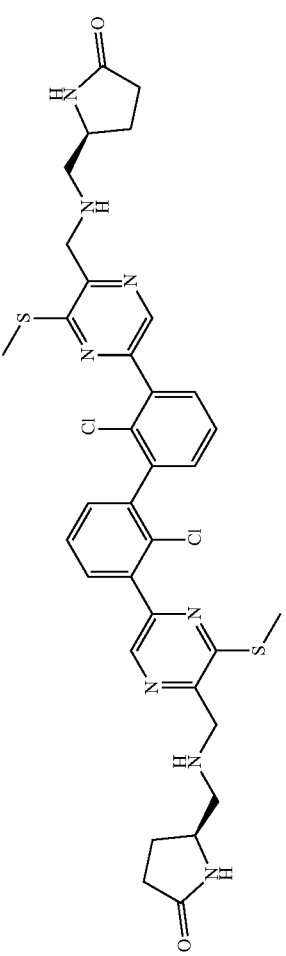 | 723.2 | 7 |
| 92 | 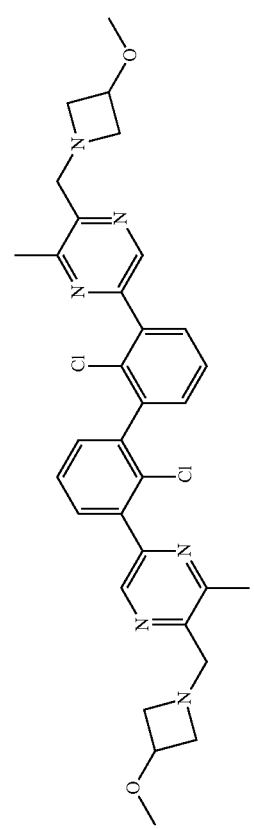 | 605.2 | 8 |

TABLE 1-continued

| No. | Structure | ES/MS (m/z, M + H+) | Procedure |
|-----|-----------|---------------------|-----------|
| 93  | 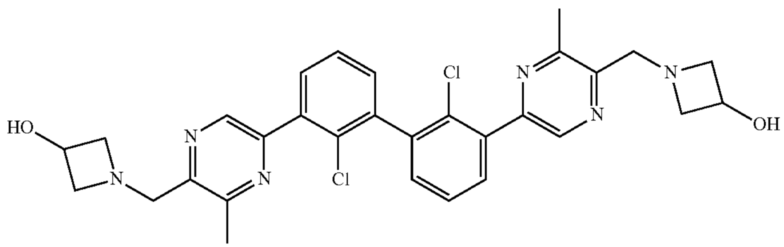 [SMILES: Cc1nc(-c2cccc(-c3cccc(-c4cnc(CN5CC(O)C5)c(C)n4)c3Cl)c2Cl)cnc1CN1CC(O)C1]          | 577.2               | 8         |
| 94  | 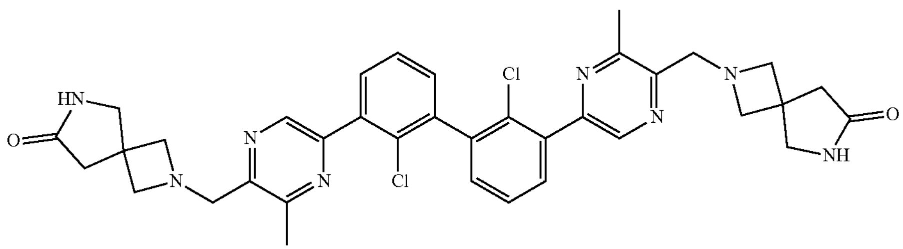 [SMILES: Cc1nc(-c2cccc(-c3cccc(-c4cnc(CN5CC6(CNC(=O)C6)C5)c(C)n4)c3Cl)c2Cl)cnc1CN1CC2(CNC(=O)C2)C1]          | 683.2               | 8         |
| 95  | 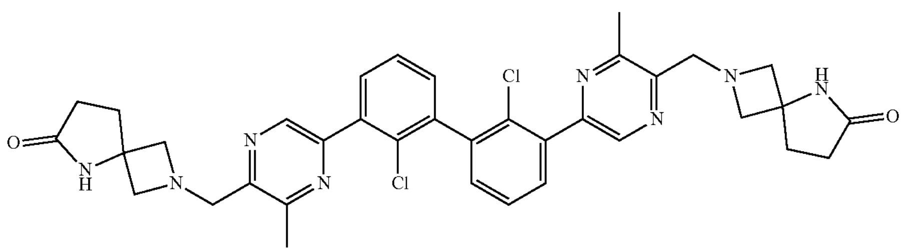 [SMILES: Cc1nc(-c2cccc(-c3cccc(-c4cnc(CN5CC6(CCC(=O)N6)C5)c(C)n4)c3Cl)c2Cl)cnc1CN1CC2(CCC(=O)N2)C1]          | 683.2               | 8         |
| 96  | 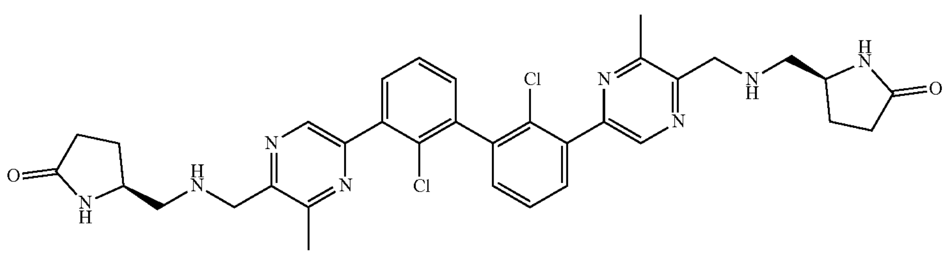 [SMILES: Cc1nc(-c2cccc(-c3cccc(-c4cnc(CNC[C@@H]5CCC(=O)N5)c(C)n4)c3Cl)c2Cl)cnc1CNC[C@@H]1CCC(=O)N1]          | 659.3               | 8         |

TABLE 1-continued

| No. | Structure | ES/MS (m/z, M + H+) | Procedure |
|---|---|---|---|
| 97 | 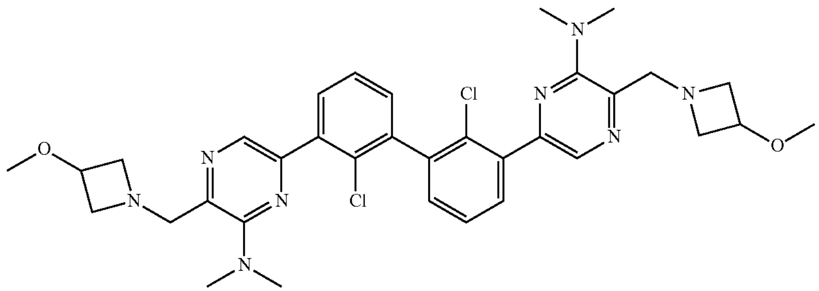 | 663.3 | 4 |
| 98 | 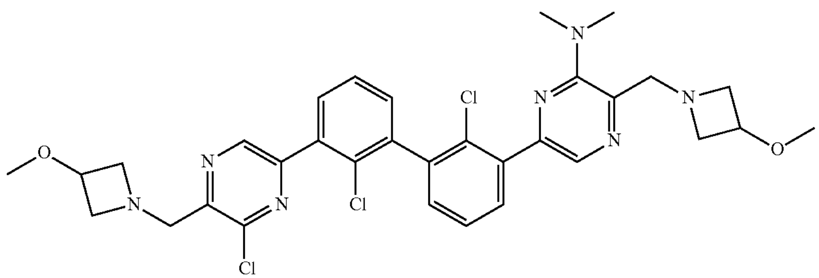 | 654.3 | 4 (byproduct) |
| 99 | 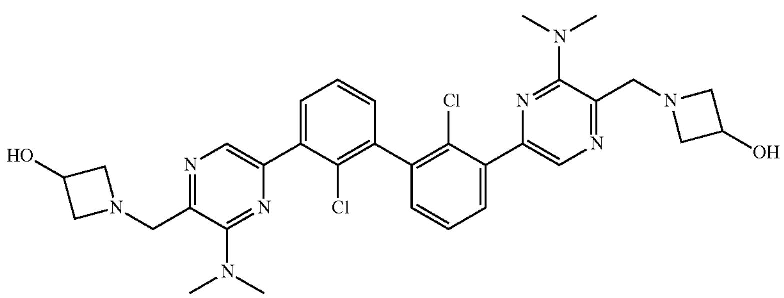 [SMILES: CN(C)c1nc(-c2cccc(-c3cccc(-c4cnc(CN5CC(O)C5)c(N(C)C)n4)c3Cl)c2Cl)cnc1CN1CC(O)C1] | 635.2 | 4 |

TABLE 1-continued

| No. | Structure | ES/MS (m/z, M + H⁺) | Procedure |
|---|---|---|---|
| 100 | 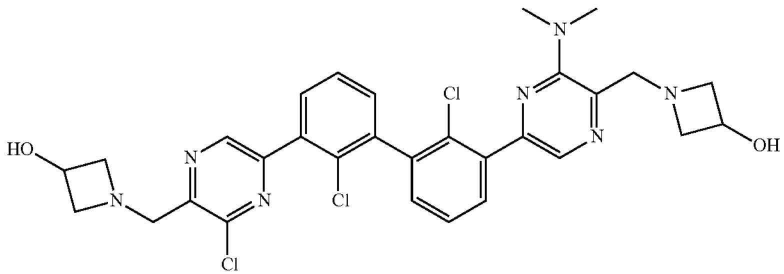 [SMILES: CN(C)c1nc(-c2cccc(-c3cccc(-c4cnc(CN5CC(O)C5)c(Cl)n4)c3Cl)c2Cl)cnc1CN1CC(O)C1] | 626.1 | 4 (byproduct) |
| 101 | 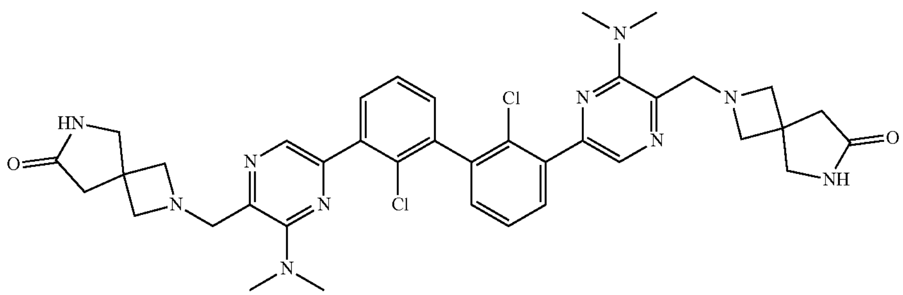 [SMILES: CN(C)c1nc(-c2cccc(-c3cccc(-c4cnc(CN5CC6(CNC(=O)C6)C5)c(N(C)C)n4)c3Cl)c2Cl)cnc1CN1CC2(CNC(=O)C2)C1] | 741.3 | 4 |
| 102 | 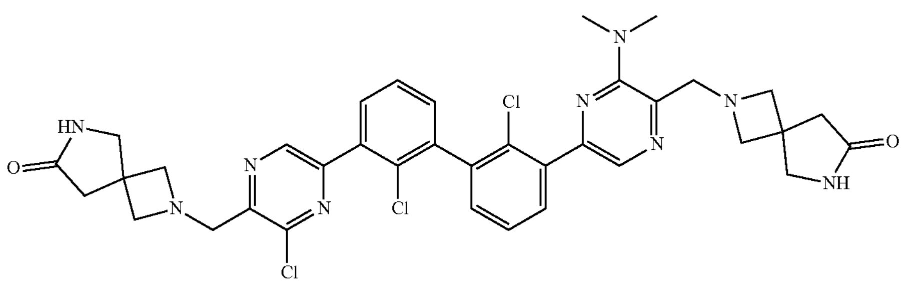 [SMILES: CN(C)c1nc(-c2cccc(-c3cccc(-c4cnc(CN5CC6(CNC(=O)C6)C5)c(Cl)n4)c3Cl)c2Cl)cnc1CN1CC2(CNC(=O)C2)C1] | 732.3 | 4 (byproduct) |

TABLE 1-continued

| No. | Structure | ES/MS (m/z, M + H⁺) | Procedure |
|---|---|---|---|
| 103 | 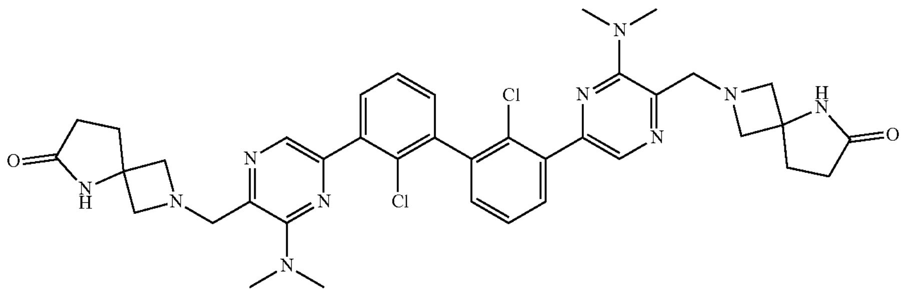 [SMILES: CN(C)c1nc(-c2cccc(-c3cccc(-c4cnc(CN5CC6(CCC(=O)N6)C5)c(N(C)C)n4)c3Cl)c2Cl)cnc1CN1CC2(CCC(=O)N2)C1] | 741.2 | 4 |
| 104 | 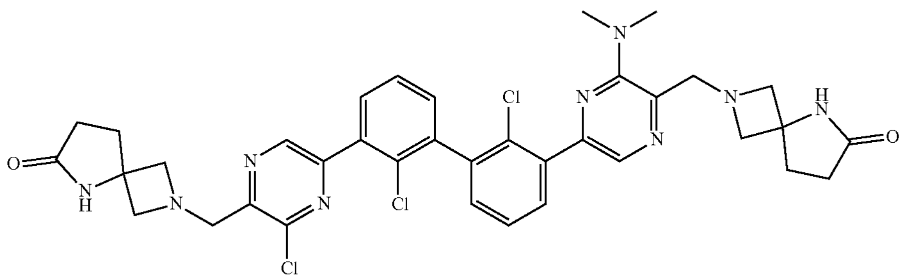 [SMILES: CN(C)c1nc(-c2cccc(-c3cccc(-c4cnc(CN5CC6(CCC(=O)N6)C5)c(Cl)n4)c3Cl)c2Cl)cnc1CN1CC2(CCC(=O)N2)C1] | 732.3 | 4 (byproduct) |
| 105 | 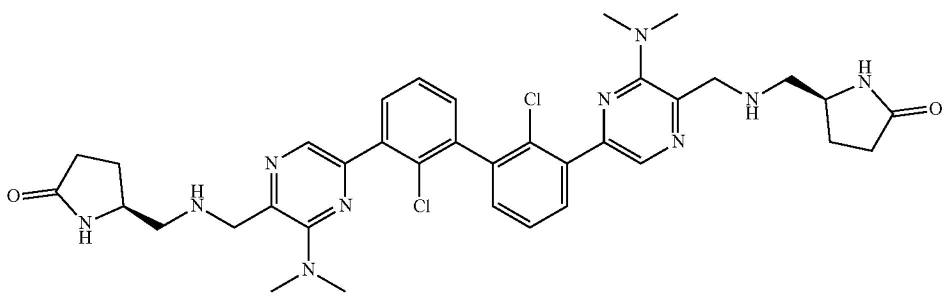 [SMILES: CN(C)c1nc(-c2cccc(-c3cccc(-c4cnc(CNC[C@@H]5CCC(=O)N5)c(N(C)C)n4)c3Cl)c2Cl)cnc1CNC[C@@H]1CCC(=O)N1] | 717.2 | 4 |

TABLE 1-continued
| No. | Structure | ES/MS (m/z, M + H+) | Procedure |
|---|---|---|---|
| 106 | 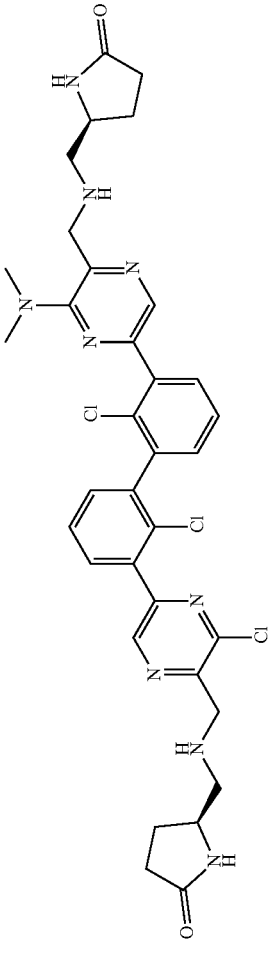 | 708.3 | 4 (byproduct) |
| 107 | 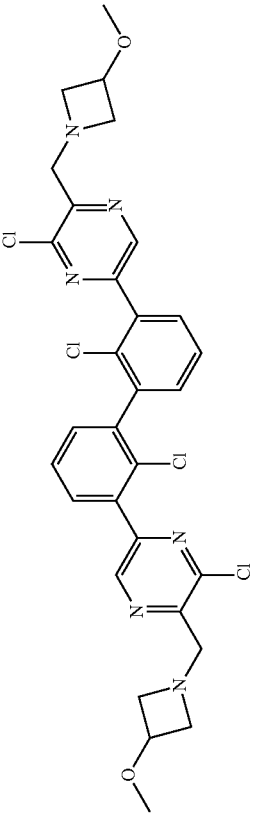 | 645.1 | 4 |
| 108 | 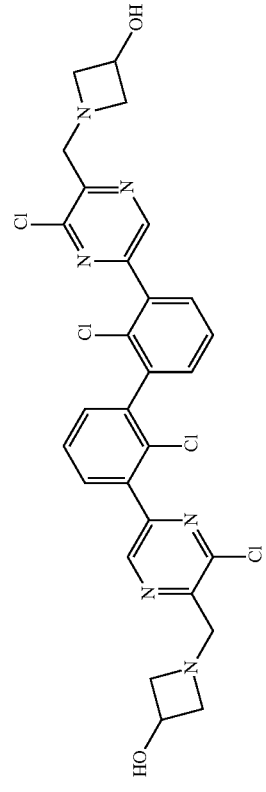 | 617.1 | 4 |

TABLE 1-continued

| No. | Structure | ES/MS (m/z, M + H+) | Procedure |
|---|---|---|---|
| 109 | 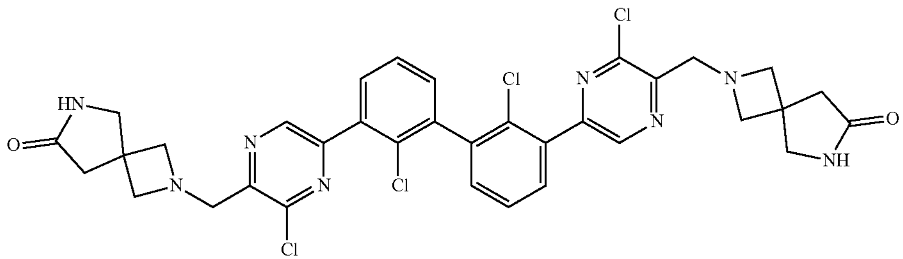 [SMILES: O=C1CC2(CN1)CN(Cc1ncc(-c3cccc(-c4cccc(-c5cnc(CN6CC7(CNC(=O)C7)C6)c(Cl)n5)c4Cl)c3Cl)nc1Cl)C2] | 723.2 | 4 |
| 110 | 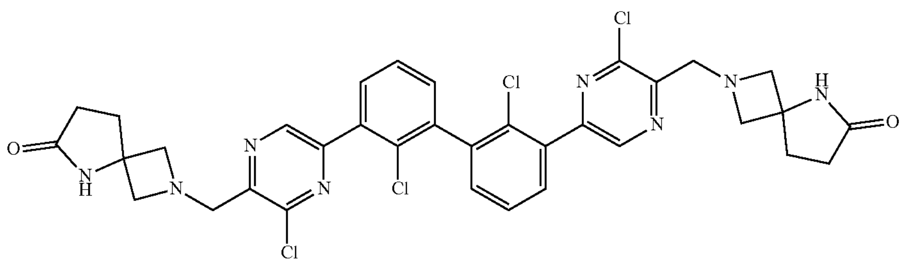 [SMILES: O=C1CCC2(CN(Cc3ncc(-c4cccc(-c5cccc(-c6cnc(CN7CC8(CCC(=O)N8)C7)c(Cl)n6)c5Cl)c4Cl)nc3Cl)C2)N1] | 723.2 | 4 |
| 111 | 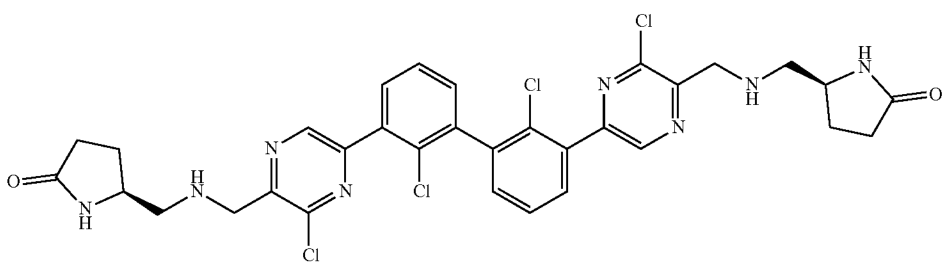 [SMILES: O=C1CC[C@@H](CNCc2ncc(-c3cccc(-c4cccc(-c5cnc(CNC[C@@H]6CCC(=O)N6)c(Cl)n5)c4Cl)c3Cl)nc2Cl)N1] | 699.1 | 4 |

TABLE 1-continued
| No. | Structure | ES/MS (m/z, M + H+) | Procedure |
|---|---|---|---|
| 112 | 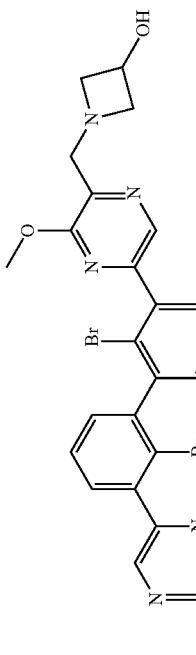 | 697.2 | 9 |
| 113 | 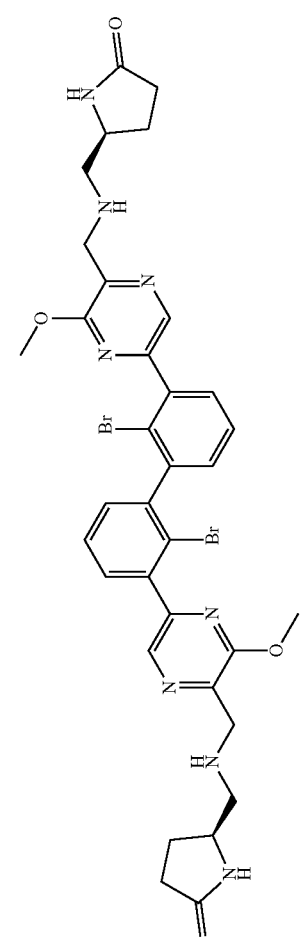 | 779.2 | 9 |
| 114 | 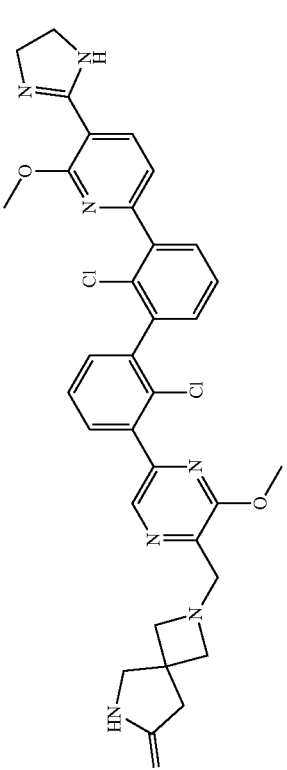 | 644.2 | 10 |

TABLE 1-continued

| No. | Structure | ES/MS (m/z, M + H+) | Procedure |
|---|---|---|---|
| 115 | 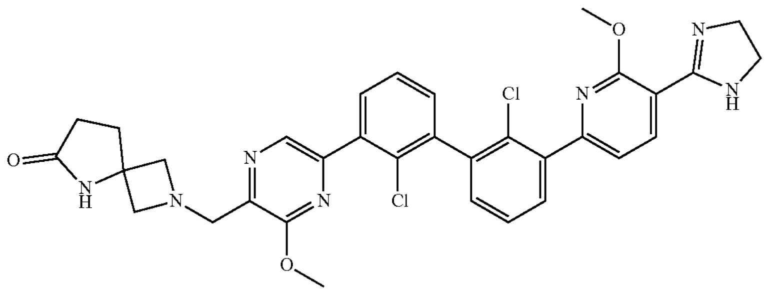 [SMILES: COc1nc(-c2cccc(-c3cccc(-c4cnc(CN5CC6(CCC(=O)N6)C5)c(OC)n4)c3Cl)c2Cl)ccc1C1=NCCN1] | 644.2 | 10 |
| 116 | 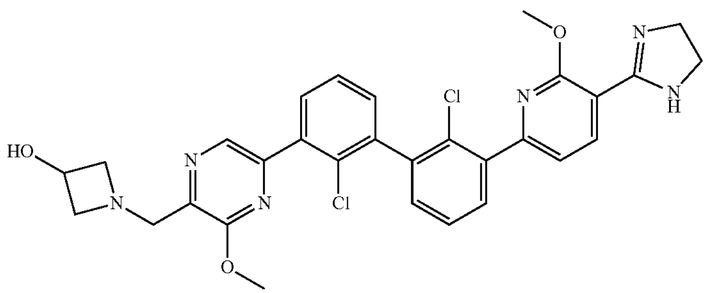 [SMILES: COc1nc(-c2cccc(-c3cccc(-c4cnc(CN5CC(O)C5)c(OC)n4)c3Cl)c2Cl)ccc1C1=NCCN1] | 591.2 | 10 |
| 117 | 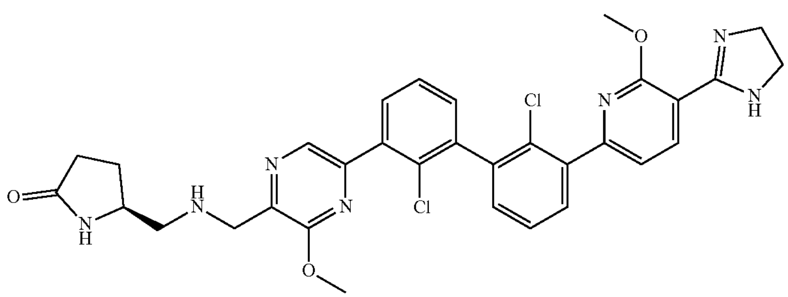 [SMILES: COc1nc(-c2cccc(-c3cccc(-c4cnc(CNC[C@@H]5CCC(=O)N5)c(OC)n4)c3Cl)c2Cl)ccc1C1=NCCN1] | 632.2 | 10 |

TABLE 1-continued

| No. | Structure | ES/MS (m/z, M + H+) | Procedure |
|---|---|---|---|
| 118 | 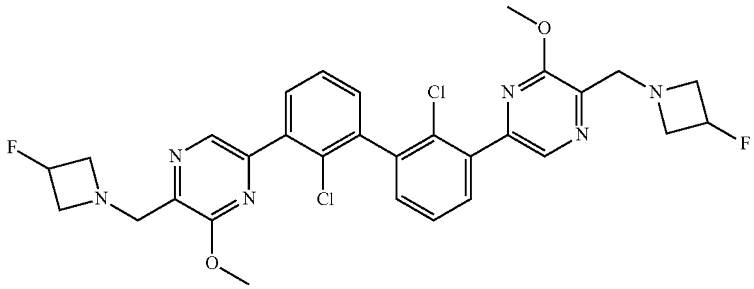 [SMILES: COc1nc(-c2cccc(-c3cccc(-c4cnc(CN5CC(F)C5)c(OC)n4)c3Cl)c2Cl)cnc1CN1CC(F)C1] | 613.2 | 3 |
| 119 | 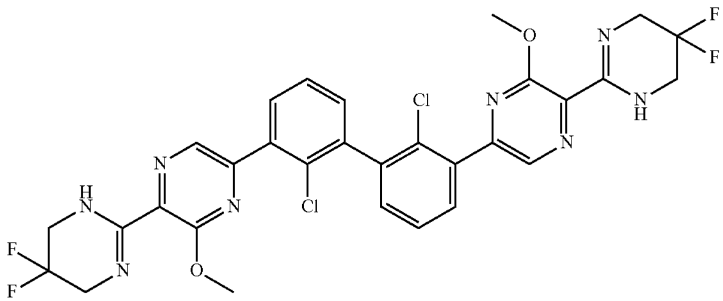 [SMILES: COc1nc(-c2cccc(-c3cccc(-c4cnc(C5=NCC(F)(F)CN5)c(OC)n4)c3Cl)c2Cl)cnc1C1=NCC(F)(F)CN1] | 675.3 | 22 |
| 120 | 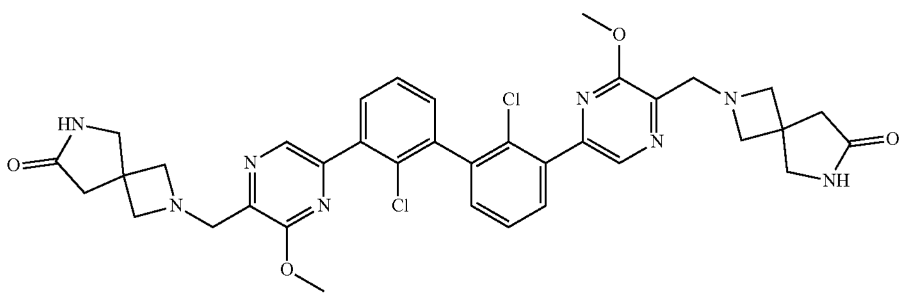 | 715.3 | 3 |

TABLE 1-continued

| No. | Structure | ES/MS (m/z, M + H⁺) | Procedure |
|-----|-----------|---------------------|-----------|
| 121 | 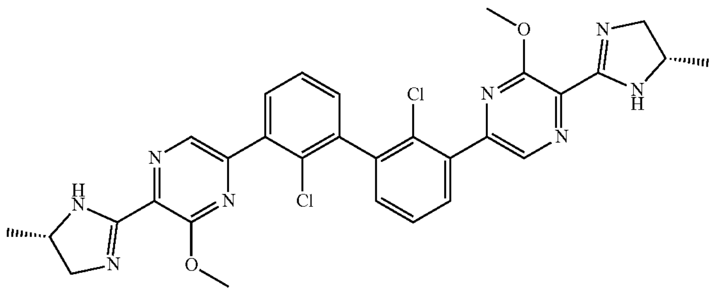 | 603.3 | 22 |
| 122 | 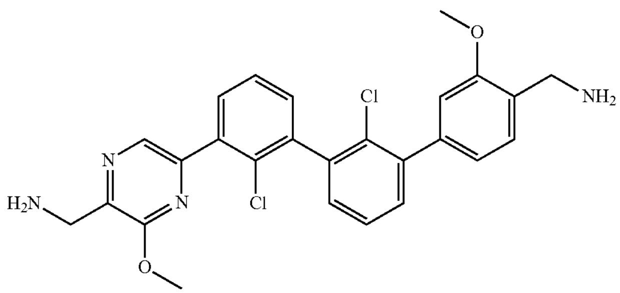 [SMILES: COc1cc(-c2cccc(-c3cccc(-c4cnc(CN)c(OC)n4)c3Cl)c2Cl)ccc1CN] | 495.2 | 12 |
| 123 | 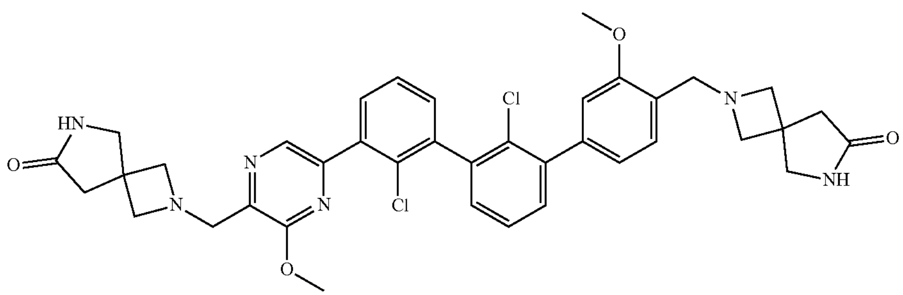 [SMILES: COc1cc(-c2cccc(-c3cccc(-c4cnc(CN5CC6(CNC(=O)C6)C5)c(OC)n4)c3Cl)c2Cl)ccc1CN1CC2(CNC(=O)C2)C1] | 713.2 | 12 |

TABLE 1-continued
| No. | Structure | ES/MS (m/z, M + H+) | Procedure |
|---|---|---|---|
| 124 | 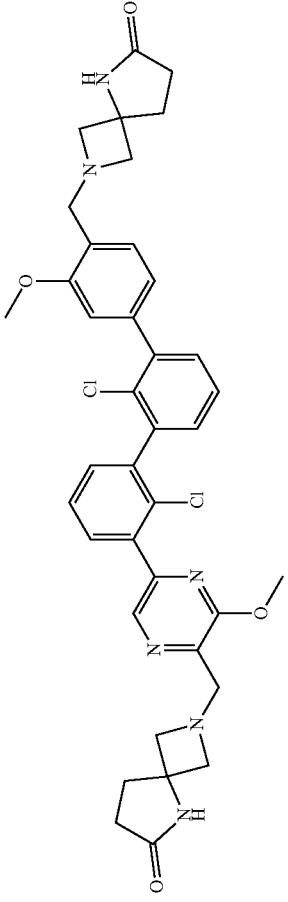 | 713.2 | 12 |
| 125 | 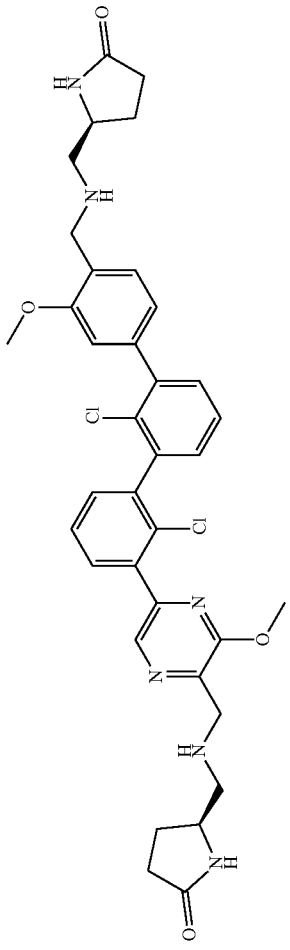 | 689.3 | 12 |
| 126 | 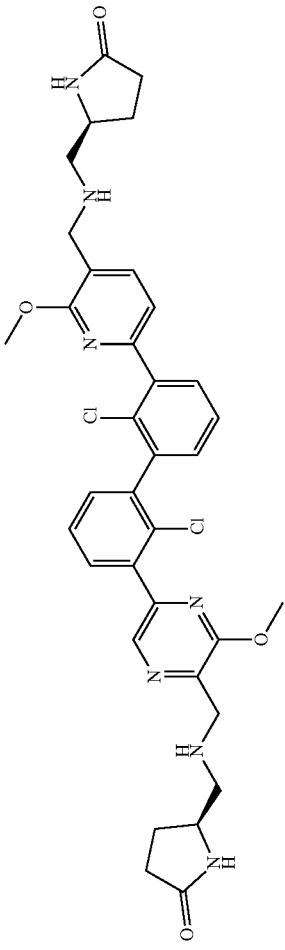 | 690.2 | 23 |

TABLE 1-continued

| No. | Structure | ES/MS (m/z, M + H+) | Procedure |
|---|---|---|---|
| 127 | 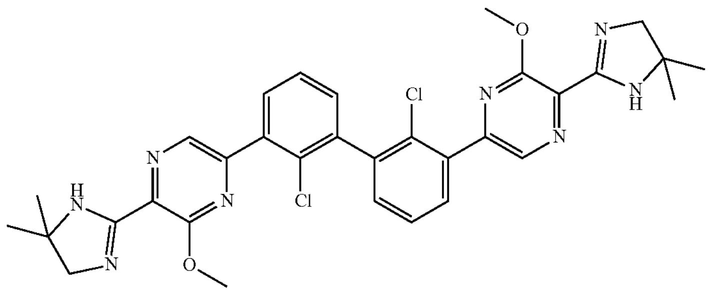 | 631.4 | 22 |
| 128 | 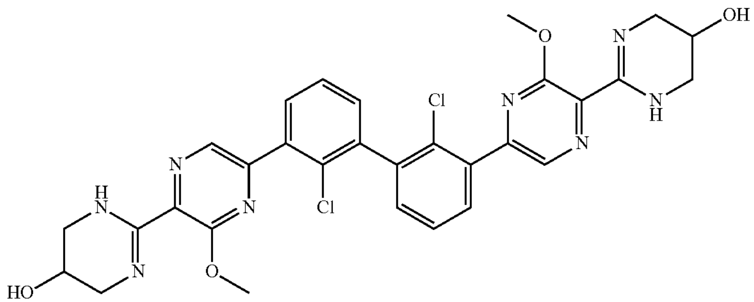 [SMILES: COc1nc(-c2cccc(-c3cccc(-c4cnc(C5=NCC(O)CN5)c(OC)n4)c3Cl)c2Cl)cnc1C1=NCC(O)CN1] | 635.2 | 22 |
| 129 | 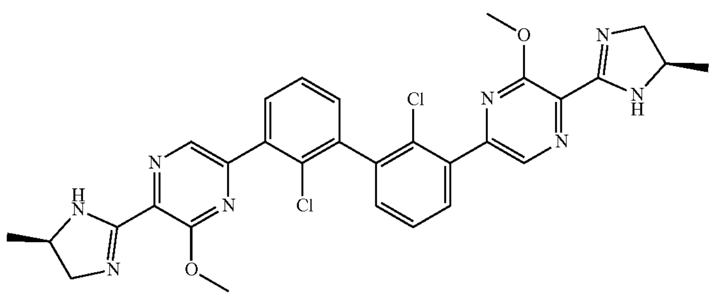 | 603.3 | 22 |

TABLE 1-continued
| No. | Structure | ES/MS (m/z, M + H⁺) | Procedure |
|---|---|---|---|
| 130 | 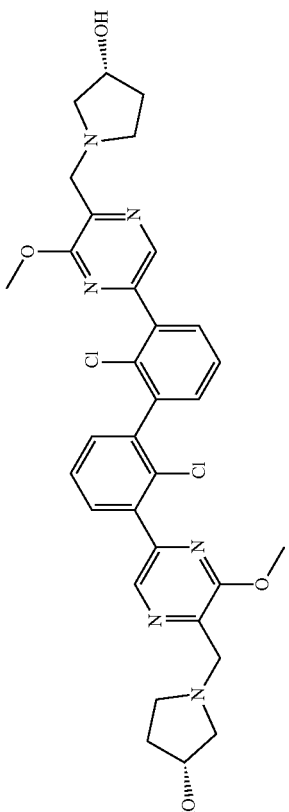 | 637.3 | 3 |
| 131 | 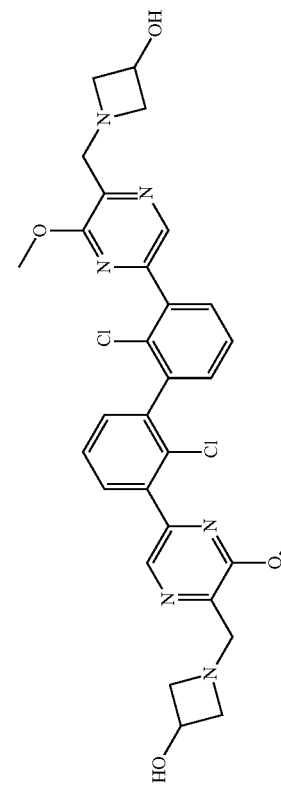 | 609.2 | 3 |
| 132 | 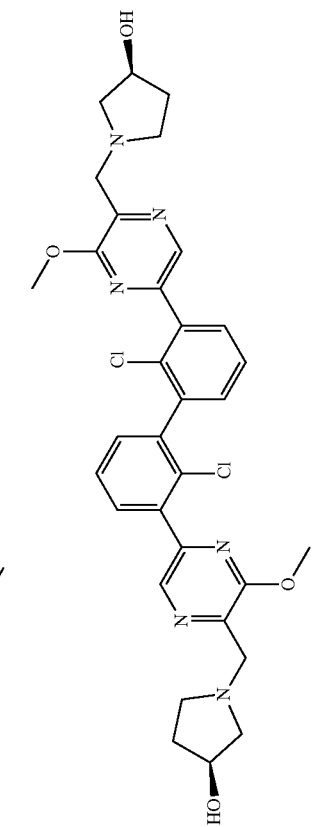 | 637.4 | 3 |

TABLE 1-continued
| No. | Structure | ES/MS (m/z, M + H+) | Procedure |
|---|---|---|---|
| 133 | 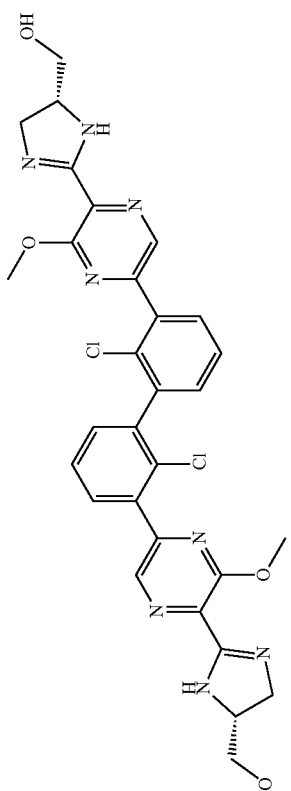 | 635.1 | 22 |
| 134 | 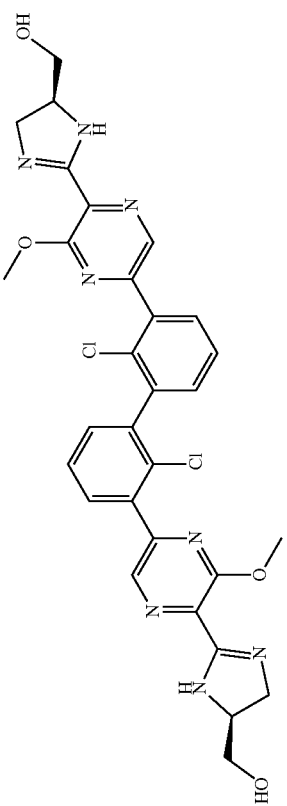 | 635.1 | 22 |
| 135 | 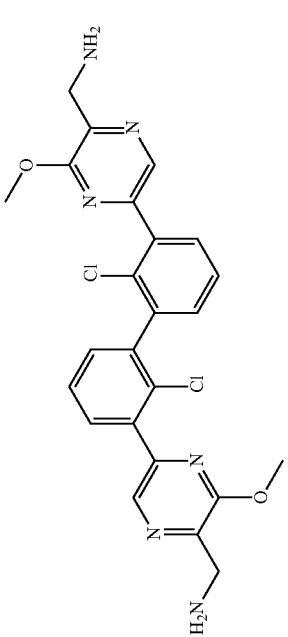 | 497.3 | 3 |

TABLE 1-continued

| No. | Structure | ES/MS (m/z, M + H⁺) | Procedure |
|---|---|---|---|
| 136 | 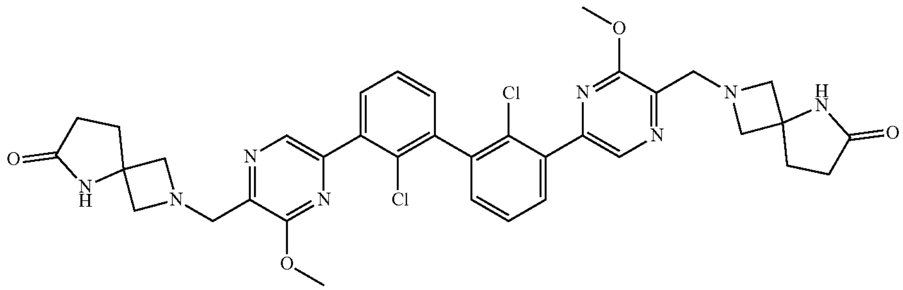 | 715.2 | 3 |
| 137 | 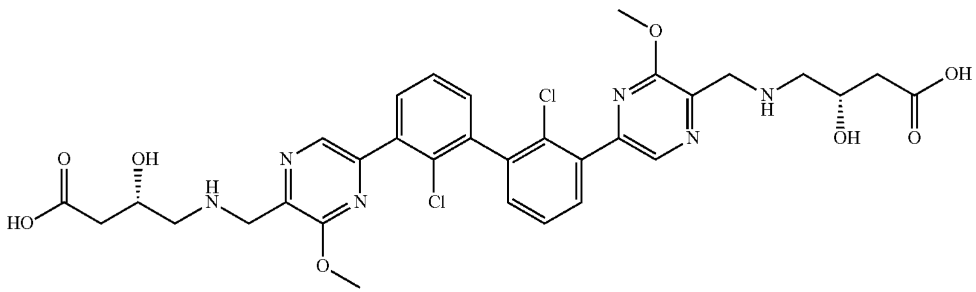 [SMILES: COc1nc(-c2cccc(-c3cccc(-c4cnc(CNC[C@@H](O)CC(=O)O)c(OC)n4)c3Cl)c2Cl)cnc1CNC[C@@H](O)CC(=O)O] | 701.2 | 3 |
| 138 | 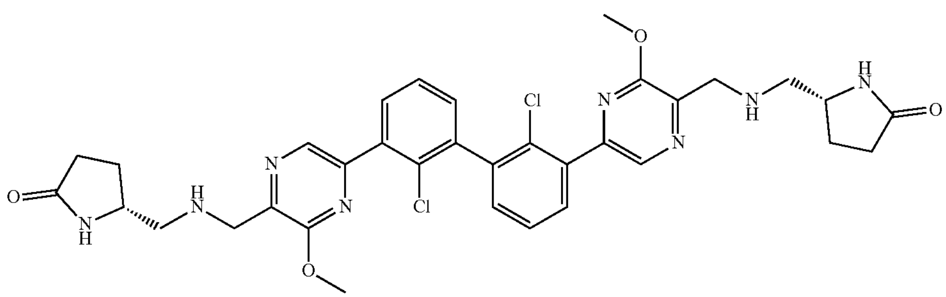 [SMILES: COc1nc(-c2cccc(-c3cccc(-c4cnc(CNC[C@H]5CCC(=O)N5)c(OC)n4)c3Cl)c2Cl)cnc1CNC[C@H]1CCC(=O)N1] | 691.2 | 3 |

TABLE 1-continued

| No. | Structure | ES/MS (m/z, M + H⁺) | Procedure |
|-----|-----------|---------------------|-----------|
| 139 | 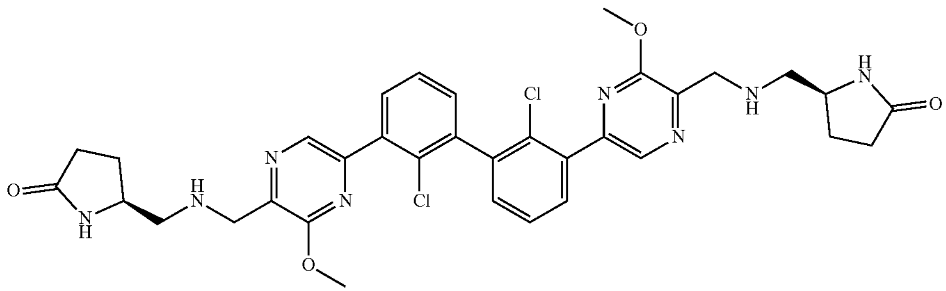 [SMILES: COc1nc(-c2cccc(-c3cccc(-c4cnc(CNC[C@@H]5CCC(=O)N5)c(OC)n4)c3Cl)c2Cl)cnc1CNC[C@@H]1CCC(=O)N1] | 691.3 | 3 |
| 140 | 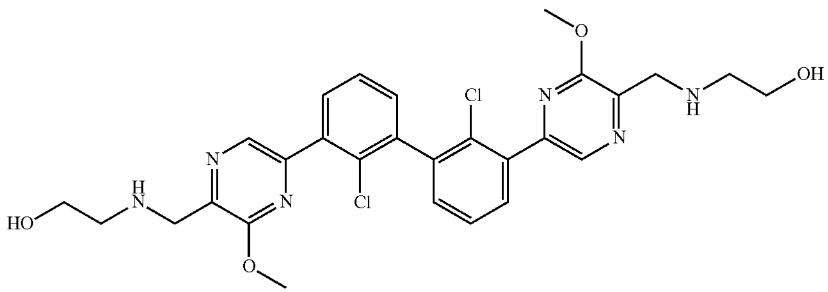 [SMILES: COc1nc(-c2cccc(-c3cccc(-c4cnc(CNCCO)c(OC)n4)c3Cl)c2Cl)cnc1CNCCO] | 585.2 | 3 |
| 141 | 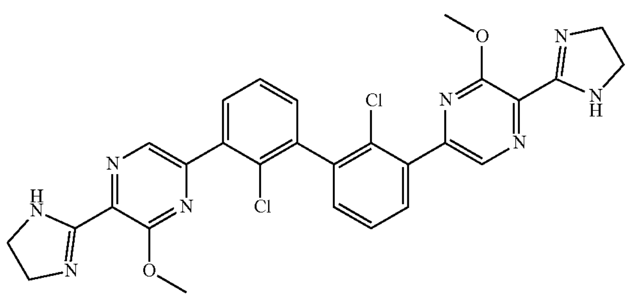 [SMILES: COc1nc(-c2cccc(-c3cccc(-c4cnc(C5=NCCN5)c(OC)n4)c3Cl)c2Cl)cnc1C1=NCCN1] | 575.2 | 22 |

TABLE 1-continued
| No. | Structure | ES/MS (m/z, M + H+) | Procedure |
|---|---|---|---|
| 142 | 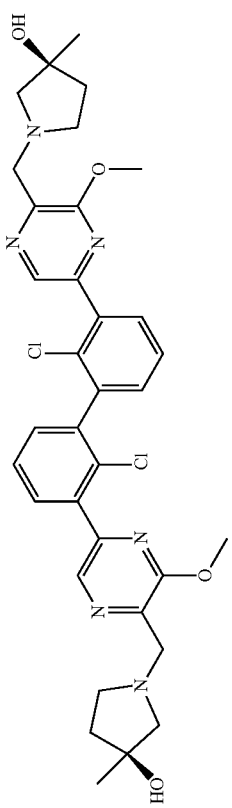 | 665.174 | 3 |
| 143 | 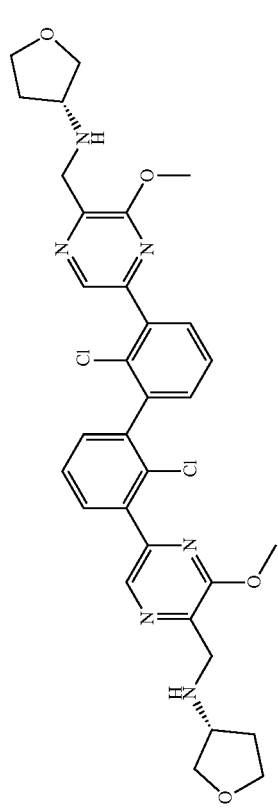 | 637.064 | 3 |
| 144 | 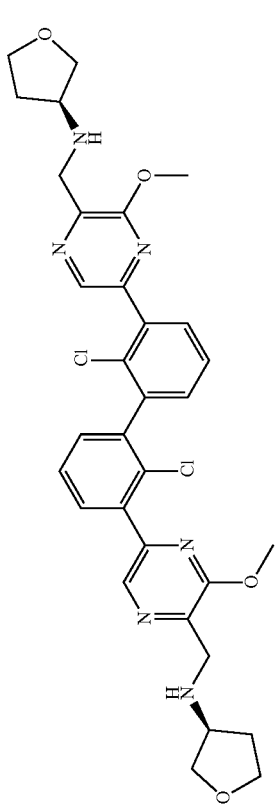 | 637.054 | 3 |

TABLE 1-continued

| No. | Structure | ES/MS (m/z, M + H⁺) | Procedure |
|---|---|---|---|
| 145 | 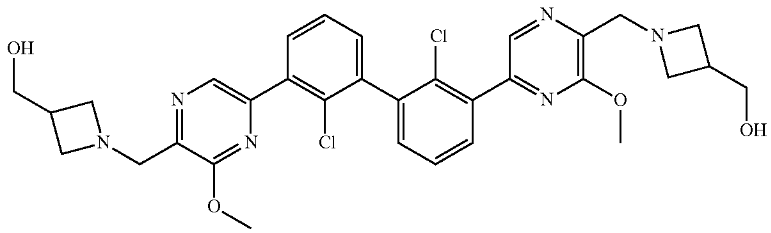 [SMILES: COc1nc(-c2cccc(-c3cccc(-c4cnc(CN5CC(CO)C5)c(OC)n4)c3Cl)c2Cl)cnc1CN1CC(CO)C1] | 637.141 | 3 |
| 146 | 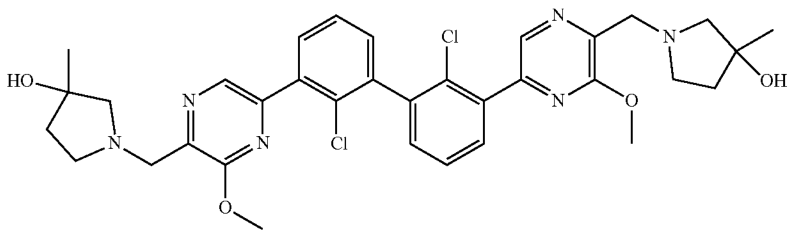 [SMILES: COc1nc(-c2cccc(-c3cccc(-c4cnc(CN5CCC(C)(O)C5)c(OC)n4)c3Cl)c2Cl)cnc1CN1CCC(C)(O)C1] | 665.107 | 3 |
| 147 | 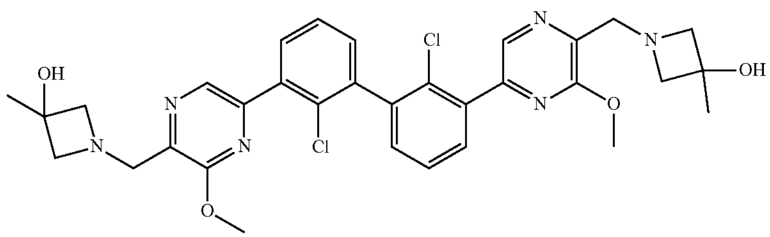 [SMILES: COc1nc(-c2cccc(-c3cccc(-c4cnc(CN5CC(C)(O)C5)c(OC)n4)c3Cl)c2Cl)cnc1CN1CC(C)(O)C1] | 637.089 | 3 |
| 148 | 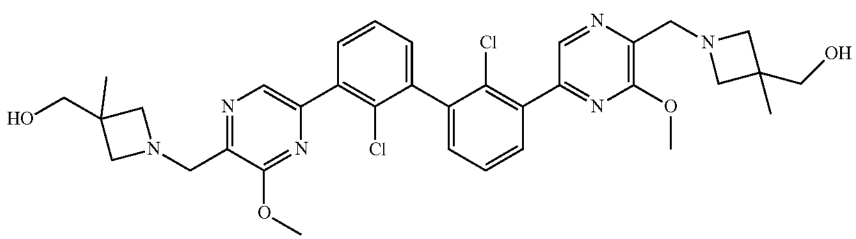 [SMILES: COc1nc(-c2cccc(-c3cccc(-c4cnc(CN5CC(C)(CO)C5)c(OC)n4)c3Cl)c2Cl)cnc1CN1CC(C)(CO)C1] | 665.169 | 3 |

TABLE 1-continued

| No. | Structure | ES/MS (m/z, M + H+) | Procedure |
|---|---|---|---|
| 149 | 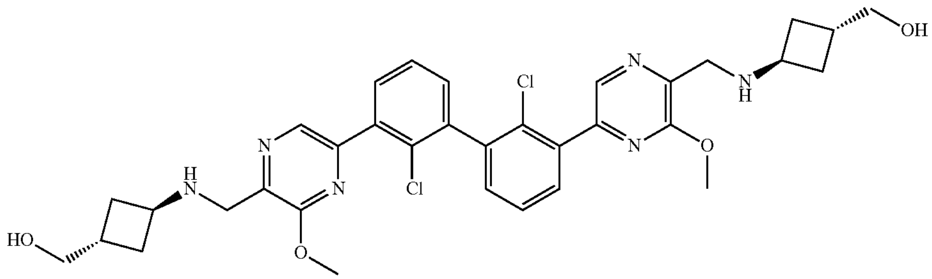 [SMILES: COc1nc(-c2cccc(-c3cccc(-c4cnc(CN[C@H]5C[C@H](CO)C5)c(OC)n4)c3Cl)c2Cl)cnc1CN[C@H]1C[C@H](CO)C1] | 665.105 | 3 |
| 150 | 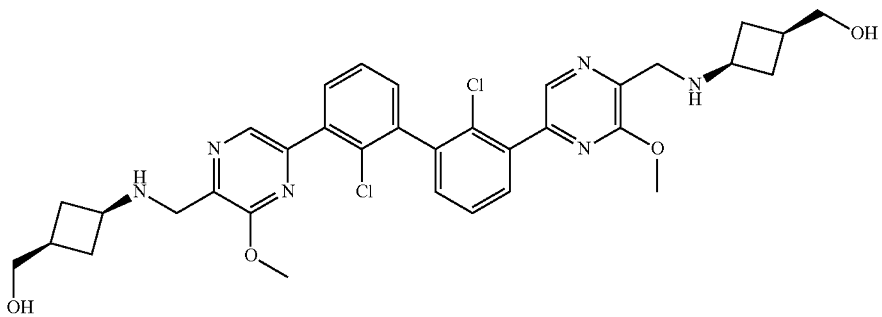 [SMILES: COc1nc(-c2cccc(-c3cccc(-c4cnc(CN[C@H]5C[C@@H](CO)C5)c(OC)n4)c3Cl)c2Cl)cnc1CN[C@H]1C[C@@H](CO)C1] | 665.13 | 3 |
| 151 | 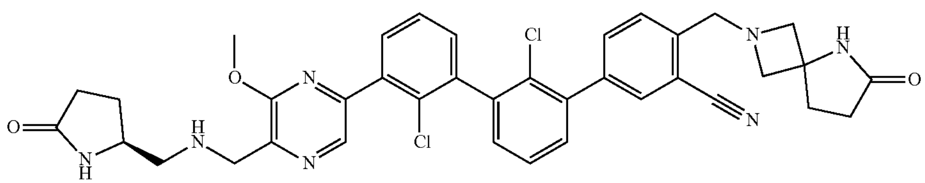 [SMILES: COc1nc(-c2cccc(-c3cccc(-c4ccc(CN5CC6(CCC(=O)N6)C5)c(C#N)c4)c3Cl)c2Cl)cnc1CNC[C@@H]1CCC(=O)N1] | 696.151 | 13 |
| 152 | 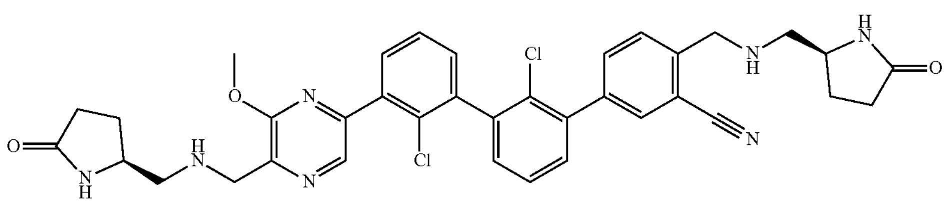 [SMILES: COc1nc(-c2cccc(-c3cccc(-c4ccc(CNC[C@@H]5CCC(=O)N5)c(C#N)c4)c3Cl)c2Cl)cnc1CNC[C@@H]1CCC(=O)N1] | 684.135 | 13 |

TABLE 1-continued

| No. | Structure | ES/MS (m/z, M + H⁺) | Procedure |
|---|---|---|---|
| 153 | 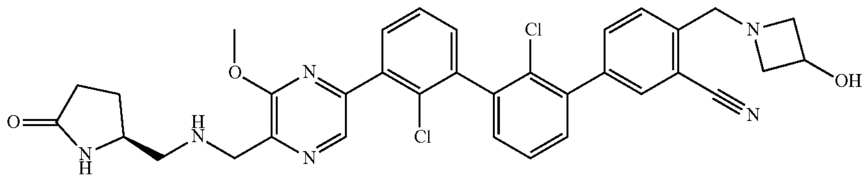 [SMILES: COc1nc(-c2cccc(-c3cccc(-c4ccc(CN5CC(O)C5)c(C#N)c4)c3Cl)c2Cl)cnc1CNC[C@@H]1CCC(=O)N1] | 643.123 | 13 |
| 154 | 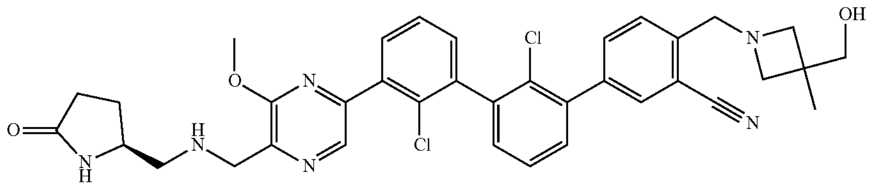 [SMILES: COc1nc(-c2cccc(-c3cccc(-c4ccc(CN5CC(C)(CO)C5)c(C#N)c4)c3Cl)c2Cl)cnc1CNC[C@@H]1CCC(=O)N1] | 671.204 | 13 |
| 155 | 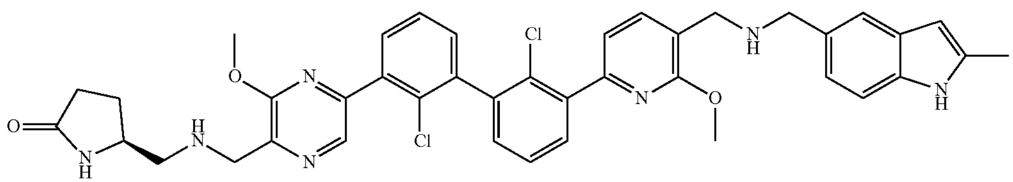 [SMILES: COc1nc(-c2cccc(-c3cccc(-c4cnc(CNC[C@@H]5CCC(=O)N5)c(OC)n4)c3Cl)c2Cl)ccc1CNCc1ccc2[nH]c(C)cc2c1] | 735.972 | 14 |
| 156 | 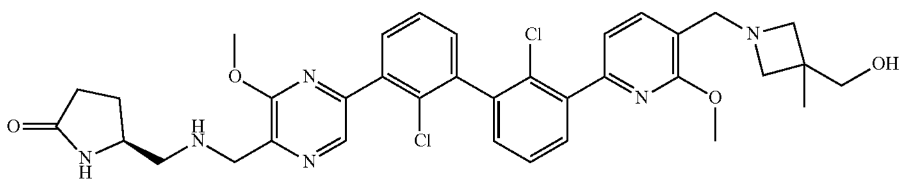 [SMILES: COc1nc(-c2cccc(-c3cccc(-c4cnc(CNC[C@@H]5CCC(=O)N5)c(OC)n4)c3Cl)c2Cl)ccc1CN1CC(C)(CO)C1] | 677.123 | 14 |
| 157 | 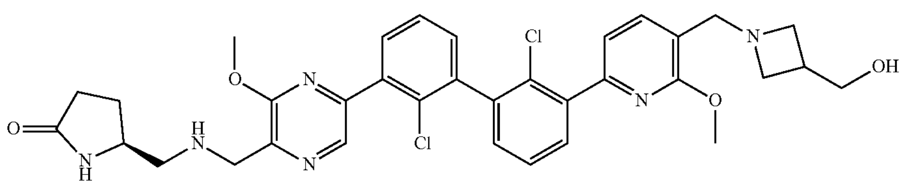 [SMILES: COc1nc(-c2cccc(-c3cccc(-c4cnc(CNC[C@@H]5CCC(=O)N5)c(OC)n4)c3Cl)c2Cl)ccc1CN1CC(CO)C1] | 663.07 | 14 |

TABLE 1-continued

| No. | Structure | ES/MS (m/z, M + H+) | Procedure |
|---|---|---|---|
| 158 | 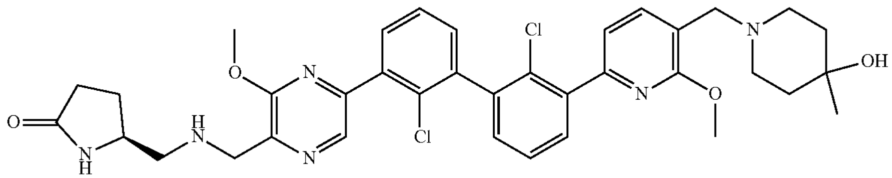 [SMILES: COc1nc(-c2cccc(-c3cccc(-c4cnc(CNC[C@@H]5CCC(=O)N5)c(OC)n4)c3Cl)c2Cl)ccc1CN1CCC(C)(O)CC1] | 691.202 | 14 |
| 159 | 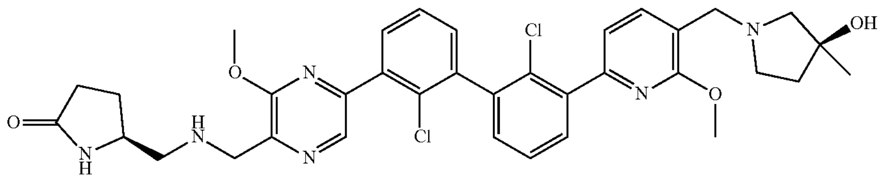 [SMILES: COc1nc(-c2cccc(-c3cccc(-c4cnc(CNC[C@@H]5CCC(=O)N5)c(OC)n4)c3Cl)c2Cl)ccc1CN1CC[C@](C)(O)C1] | 677.068 | 14 |
| 160 | 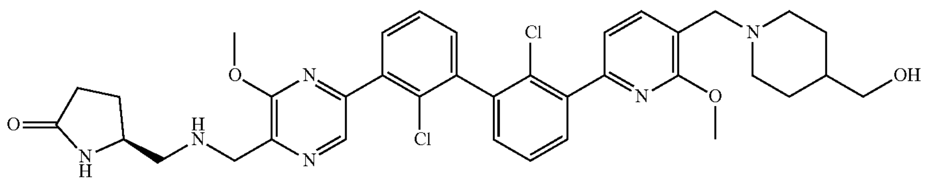 [SMILES: COc1nc(-c2cccc(-c3cccc(-c4cnc(CNC[C@@H]5CCC(=O)N5)c(OC)n4)c3Cl)c2Cl)ccc1CN1CCC(CO)CC1] | 691.19 | 14 |
| 161 | 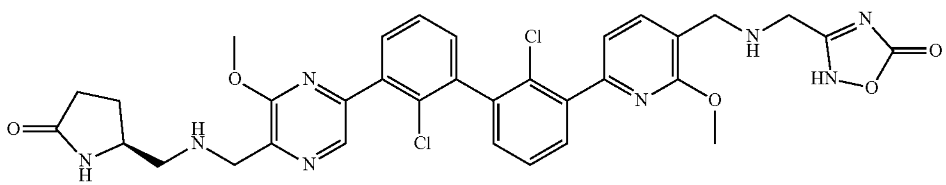 [SMILES: COc1nc(-c2cccc(-c3cccc(-c4cnc(CNC[C@@H]5CCC(=O)N5)c(OC)n4)c3Cl)c2Cl)ccc1CNCc1nc(=O)o[nH]1] | 691.062 | 14 |
| 162 | 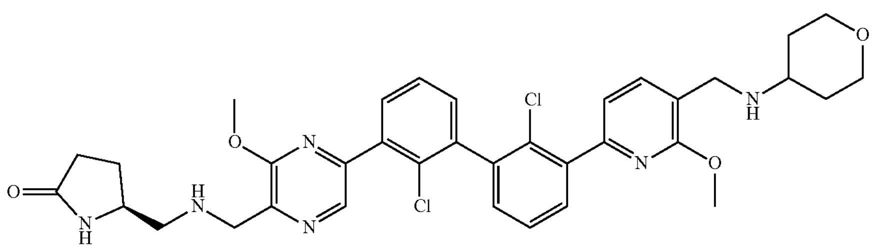 [SMILES: COc1nc(-c2cccc(-c3cccc(-c4cnc(CNC[C@@H]5CCC(=O)N5)c(OC)n4)c3Cl)c2Cl)ccc1CNC1CCOCC1] | 677.015 | 14 |

TABLE 1-continued

| No. | Structure | ES/MS (m/z, M + H+) | Procedure |
|---|---|---|---|
| 163 | 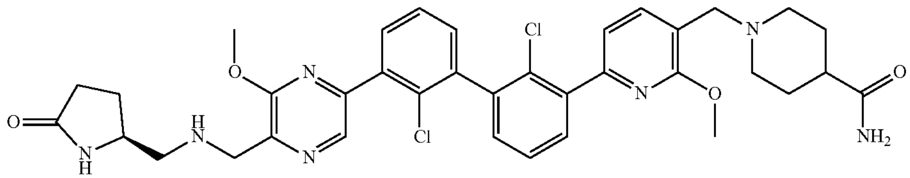 [SMILES: COc1nc(-c2cccc(-c3cccc(-c4cnc(CNC[C@@H]5CCC(=O)N5)c(OC)n4)c3Cl)c2Cl)ccc1CN1CCC(C(N)=O)CC1] | 704.118 | 14 |
| 164 | 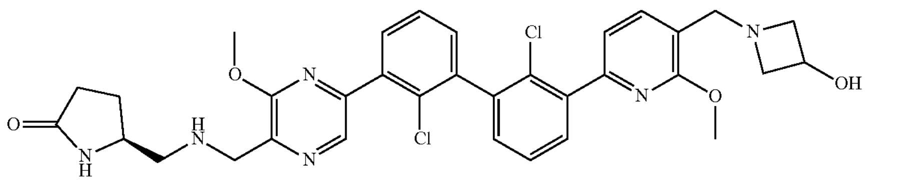 [SMILES: COc1nc(-c2cccc(-c3cccc(-c4cnc(CNC[C@@H]5CCC(=O)N5)c(OC)n4)c3Cl)c2Cl)ccc1CN1CC(O)C1] | 649.083 | 14 |
| 165 | 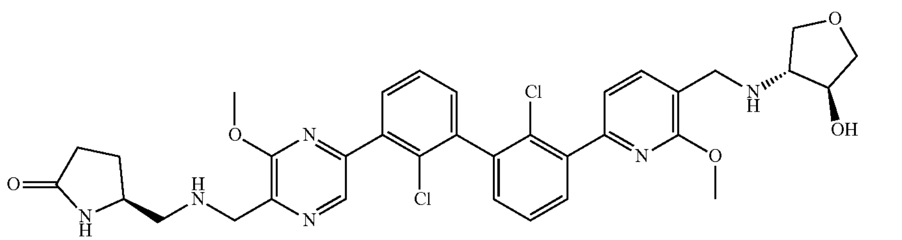 [SMILES: COc1nc(-c2cccc(-c3cccc(-c4cnc(CNC[C@@H]5CCC(=O)N5)c(OC)n4)c3Cl)c2Cl)ccc1CN[C@@H]1COC[C@H]1O] | 679.094 | 14 |
| 166 | 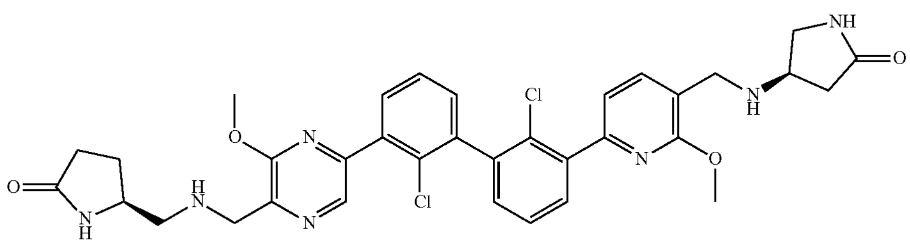 [SMILES: COc1nc(-c2cccc(-c3cccc(-c4cnc(CNC[C@@H]5CCC(=O)N5)c(OC)n4)c3Cl)c2Cl)ccc1CN[C@H]1CNC(=O)C1] | 676.149 | 14 |

TABLE 1-continued

| No. | Structure | ES/MS (m/z, M + H⁺) | Procedure |
|---|---|---|---|
| 167 | 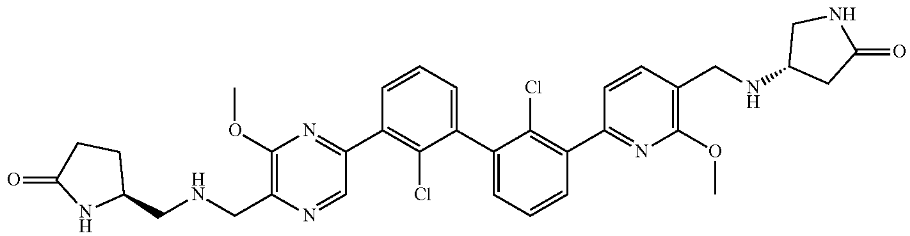 [SMILES: COc1nc(-c2cccc(-c3cccc(-c4cnc(CNC[C@@H]5CCC(=O)N5)c(OC)n4)c3Cl)c2Cl)ccc1CN[C@@H]1CNC(=O)C1] | 676.008 | 14 |
| 168 | 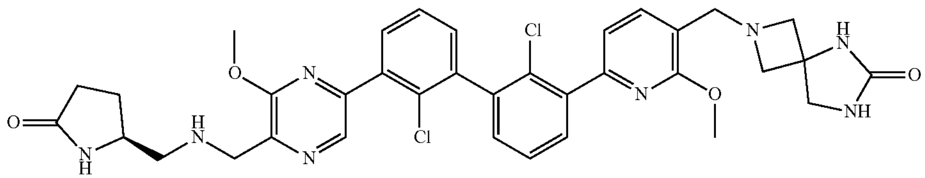 [SMILES: COc1nc(-c2cccc(-c3cccc(-c4cnc(CNC[C@@H]5CCC(=O)N5)c(OC)n4)c3Cl)c2Cl)ccc1CN1CC2(CNC(=O)N2)C1] | 703.141 | 14 |
| 169 | 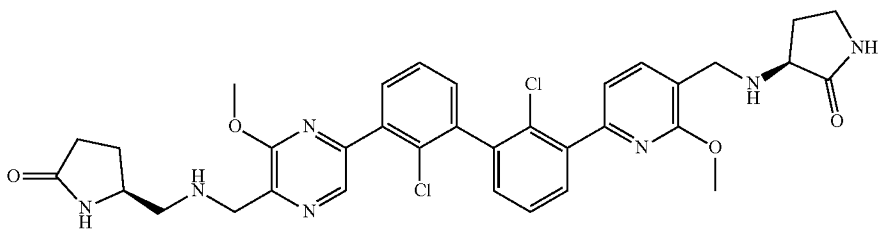 [SMILES: COc1nc(-c2cccc(-c3cccc(-c4cnc(CNC[C@@H]5CCC(=O)N5)c(OC)n4)c3Cl)c2Cl)ccc1CN[C@H]1CCNC1=O] | 675.991 | 14 |
| 170 | 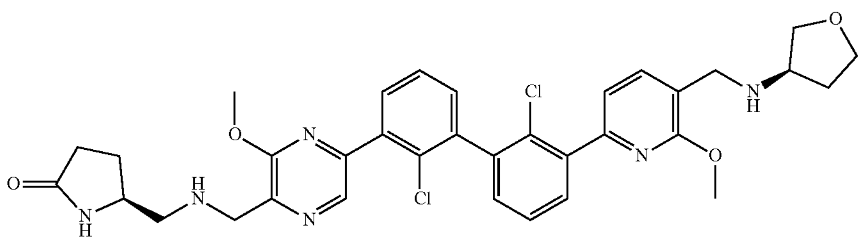 [SMILES: COc1nc(-c2cccc(-c3cccc(-c4cnc(CNC[C@@H]5CCC(=O)N5)c(OC)n4)c3Cl)c2Cl)ccc1CN[C@@H]1CCOC1] | 663.107 | 14 |

TABLE 1-continued

| No. | Structure | ES/MS (m/z, M + H⁺) | Procedure |
|---|---|---|---|
| 171 | 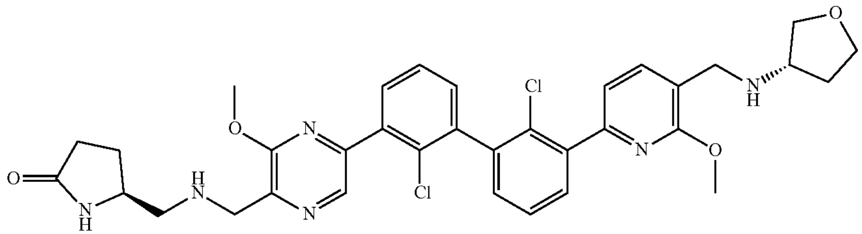 [SMILES: COc1nc(-c2cccc(-c3cccc(-c4cnc(CNC[C@@H]5CCC(=O)N5)c(OC)n4)c3Cl)c2Cl)ccc1CN[C@H]1CCOC1] | 663 | 14 |
| 172 | 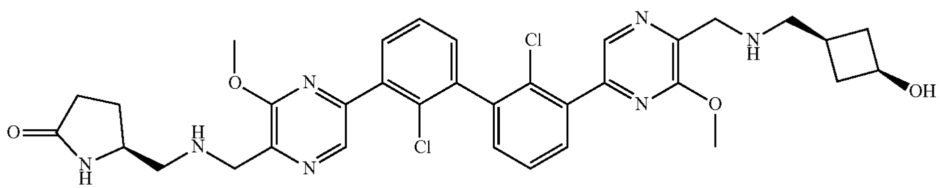 [SMILES: COc1nc(-c2cccc(-c3cccc(-c4cnc(CNC[C@H]5C[C@@H](O)C5)c(OC)n4)c3Cl)c2Cl)cnc1CNC[C@@H]1CCC(=O)N1] | 678.078 | 2 |
| 173 | 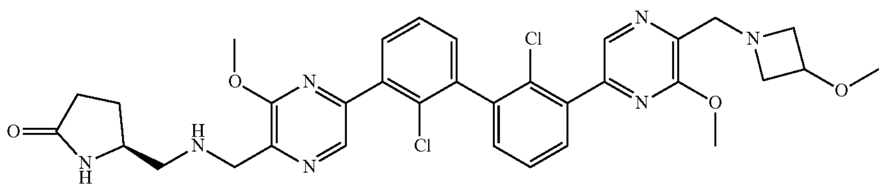 [SMILES: COc1nc(-c2cccc(-c3cccc(-c4cnc(CN5CC(OC)C5)c(OC)n4)c3Cl)c2Cl)cnc1CNC[C@@H]1CCC(=O)N1] | 664.044 | 2 |
| 174 | 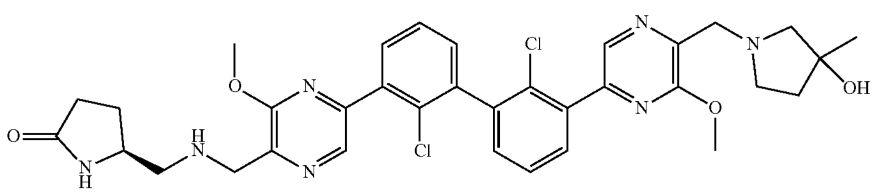 [SMILES: COc1nc(-c2cccc(-c3cccc(-c4cnc(CN5CCC(C)(O)C5)c(OC)n4)c3Cl)c2Cl)cnc1CNC[C@@H]1CCC(=O)N1] | 678.077 | 2 |
| 175 | 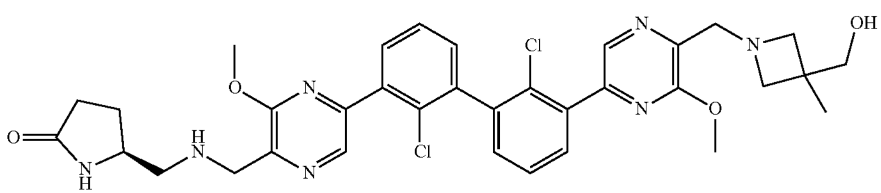 [SMILES: COc1nc(-c2cccc(-c3cccc(-c4cnc(CN5CC(C)(CO)C5)c(OC)n4)c3Cl)c2Cl)cnc1CNC[C@@H]1CCC(=O)N1] | 678.143 | 2 |

TABLE 1-continued
| No. | Structure | ES/MS (m/z, M + H+) | Procedure |
|---|---|---|---|
| 176 | 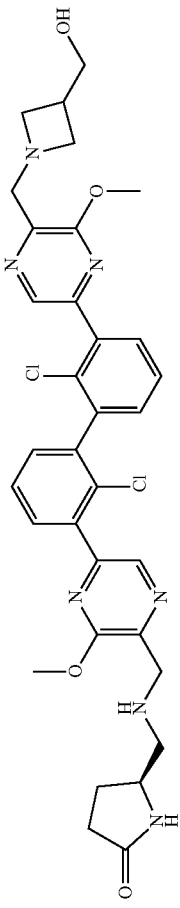 | 664.136 | 2 |
| 177 | 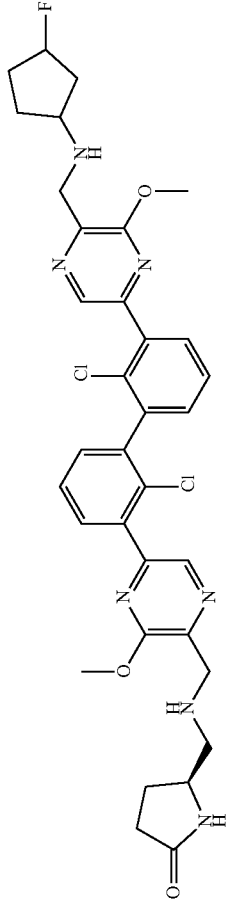 | 680.043 | 2 |
| 178 | 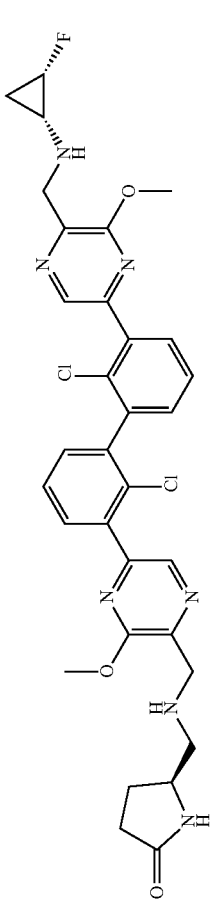 | 651.916 | 2 |
| 179 | 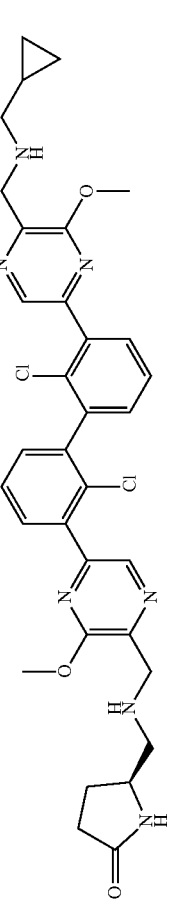 | 648.076 | 2 |

TABLE 1-continued

| No. | Structure | ES/MS (m/z, M + H+) | Procedure |
|---|---|---|---|
| 180 | 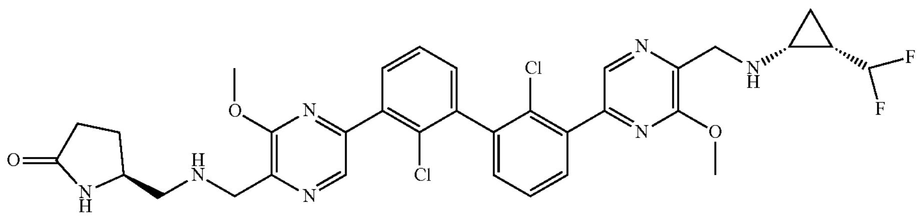 [SMILES: COc1nc(-c2cccc(-c3cccc(-c4cnc(CN[C@@H]5C[C@@H]5C(F)F)c(OC)n4)c3Cl)c2Cl)cnc1CNC[C@@H]1CCC(=O)N1] | 683.908 | 2 |
| 181 | 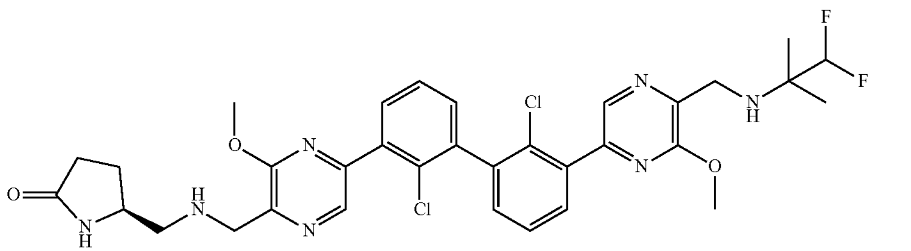 [SMILES: COc1nc(-c2cccc(-c3cccc(-c4cnc(CNC(C)(C)C(F)F)c(OC)n4)c3Cl)c2Cl)cnc1CNC[C@@H]1CCC(=O)N1] | 685.985 | 2 |
| 182 | 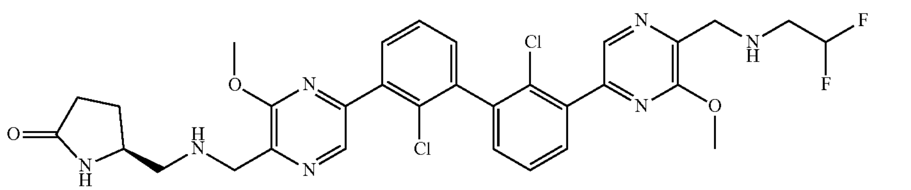 [SMILES: COc1nc(-c2cccc(-c3cccc(-c4cnc(CNC[C@@H]5CCC(=O)N5)c(OC)n4)c3Cl)c2Cl)cnc1CNCC(F)F] | 700.069 | 2 |
| 183 | 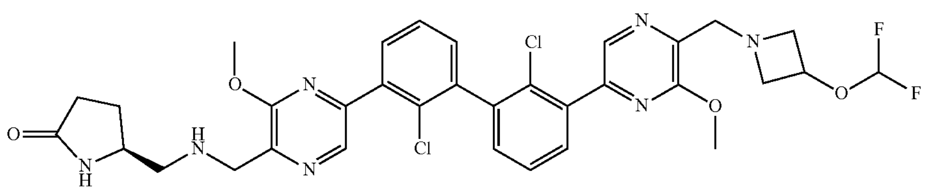 [SMILES: COc1nc(-c2cccc(-c3cccc(-c4cnc(CN5CC(OC(F)F)C5)c(OC)n4)c3Cl)c2Cl)cnc1CNC[C@@H]1CCC(=O)N1] | 657.987 | 2 |

TABLE 1-continued

| No. | Structure | ES/MS (m/z, M + H⁺) | Procedure |
|---|---|---|---|
| 184 | 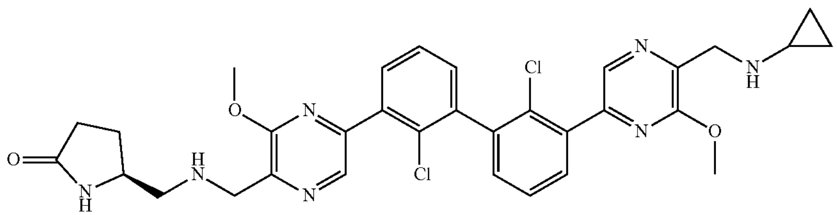 [SMILES: COc1nc(-c2cccc(-c3cccc(-c4cnc(CNC5CC5)c(OC)n4)c3Cl)c2Cl)cnc1CNC[C@@H]1CCC(=O)N1] | 633.983 | 2 |
| 185 | 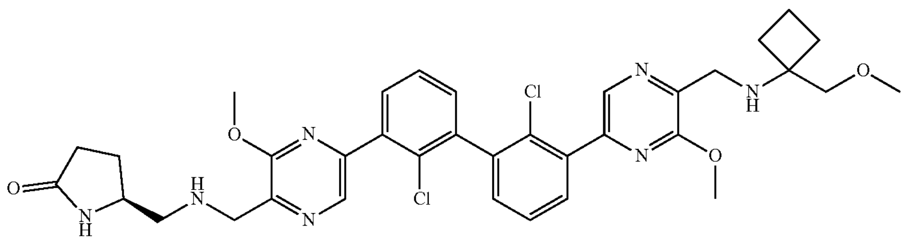 [SMILES: COCC1(NCc2ncc(-c3cccc(-c4cccc(-c5cnc(CNC[C@@H]6CCC(=O)N6)c(OC)n5)c4Cl)c3Cl)nc2OC)CCC1] | 692.17 | 2 |
| 186 | 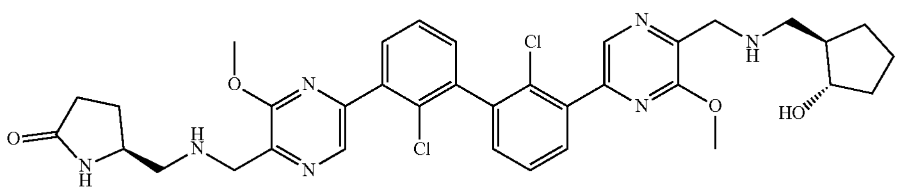 [SMILES: COc1nc(-c2cccc(-c3cccc(-c4cnc(CNC[C@H]5CCC[C@@H]5O)c(OC)n4)c3Cl)c2Cl)cnc1CNC[C@@H]1CCC(=O)N1] | 692.18 | 2 |
| 187 | 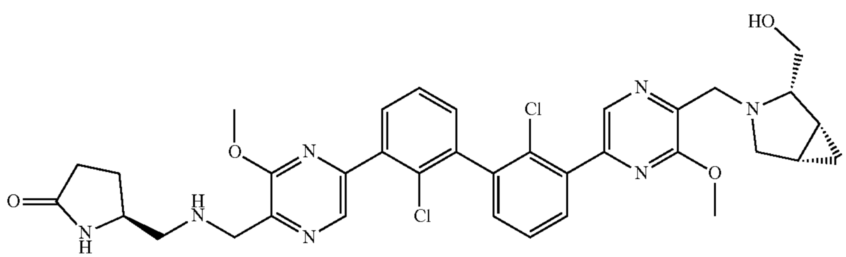 [SMILES: COc1nc(-c2cccc(-c3cccc(-c4cnc(CN5C[C@H]6C[C@H]6[C@H]5CO)c(OC)n4)c3Cl)c2Cl)cnc1CNC[C@@H]1CCC(=O)N1] | 690.19 | 2 |

TABLE 1-continued
| No. | Structure | ES/MS (m/z, M + H+) | Procedure |
|---|---|---|---|
| 188 | 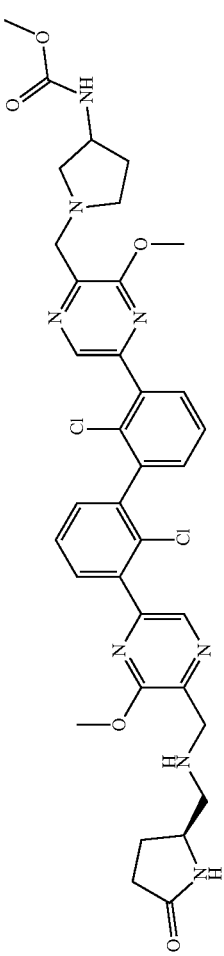 | 721.19 | 2 |
| 189 | 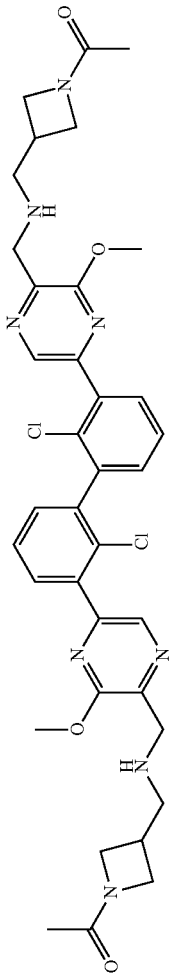 | 719.26 | 3 |
| 190 | 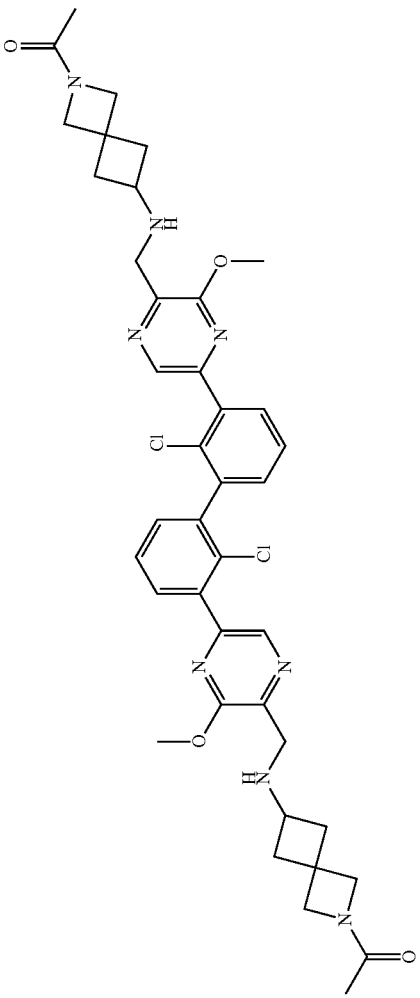 | 771.27 | 3 |

TABLE 1-continued

| No. | Structure | ES/MS (m/z, M + H⁺) | Procedure |
|---|---|---|---|
| 191 | 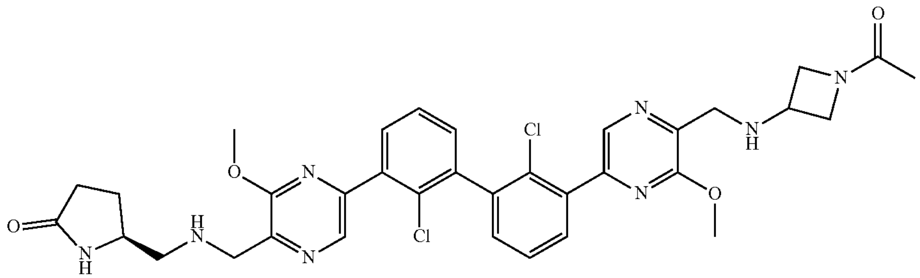 [SMILES: COc1nc(-c2cccc(-c3cccc(-c4cnc(CNC5CN(C(C)=O)C5)c(OC)n4)c3Cl)c2Cl)cnc1CNC[C@@H]1CCC(=O)N1] | 691.35 | 2 |
| 192 | 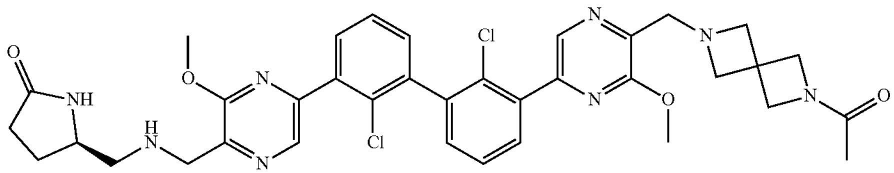 [SMILES: COc1nc(-c2cccc(-c3cccc(-c4cnc(CN5CC6(C5)CN(C(C)=O)C6)c(OC)n4)c3Cl)c2Cl)cnc1CNC[C@H]1CCC(=O)N1] | 717.3 | 2 |
| 193 | 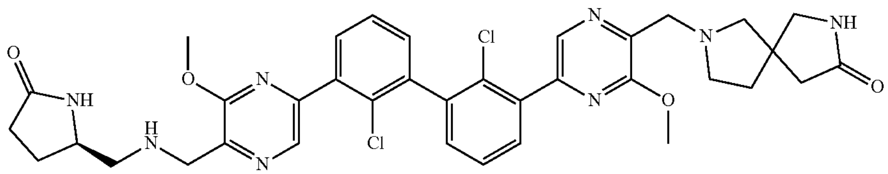 [SMILES: COc1nc(-c2cccc(-c3cccc(-c4cnc(CN5CCC6(CNC(=O)C6)C5)c(OC)n4)c3Cl)c2Cl)cnc1CNC[C@H]1CCC(=O)N1] | 717.2 | 2 |
| 194 | 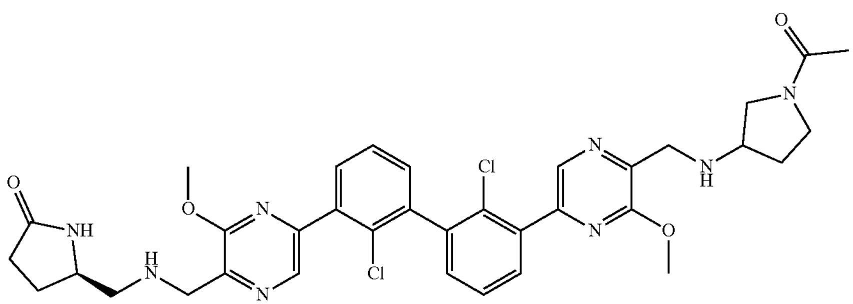 [SMILES: COc1nc(-c2cccc(-c3cccc(-c4cnc(CNC5CCN(C(C)=O)C5)c(OC)n4)c3Cl)c2Cl)cnc1CNC[C@H]1CCC(=O)N1] | 705.16 | 2 |

TABLE 1-continued

| No. | Structure | ES/MS (m/z, M + H⁺) | Procedure |
|---|---|---|---|
| 195 | 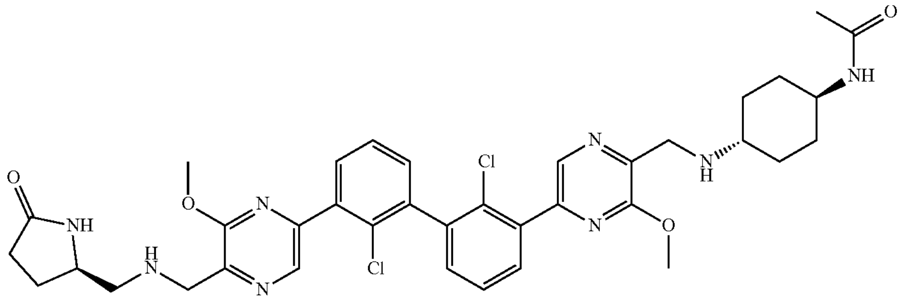 [SMILES: COc1nc(-c2cccc(-c3cccc(-c4cnc(CN[C@H]5CC[C@H](NC(C)=O)CC5)c(OC)n4)c3Cl)c2Cl)cnc1CNC[C@H]1CCC(=O)N1] | 733.48 | 2 |
| 196 | 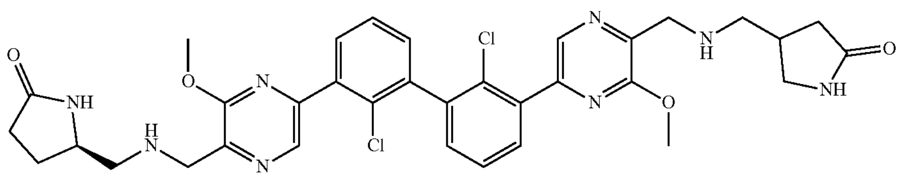 [SMILES: COc1nc(-c2cccc(-c3cccc(-c4cnc(CNC[C@H]5CCC(=O)N5)c(OC)n4)c3Cl)c2Cl)cnc1CNCC1CNC(=O)C1] | 691.13 | 2 |
| 197 | 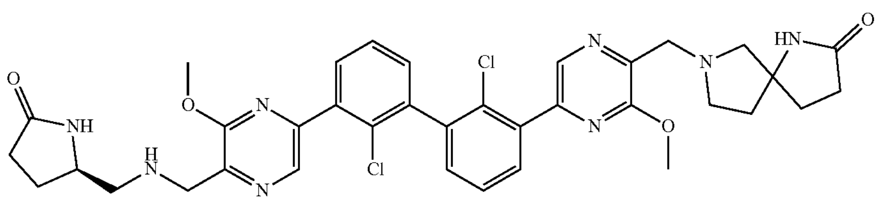 [SMILES: COc1nc(-c2cccc(-c3cccc(-c4cnc(CN5CCC6(CCC(=O)N6)C5)c(OC)n4)c3Cl)c2Cl)cnc1CNC[C@H]1CCC(=O)N1] | 717.3 | 2 |
| 198 | 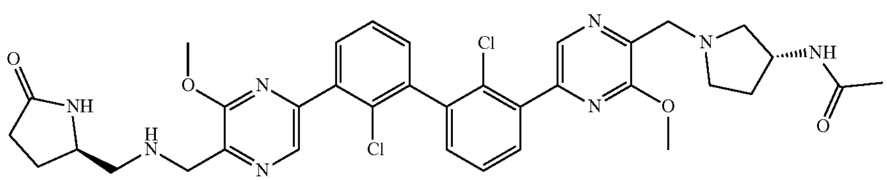 [SMILES: COc1nc(-c2cccc(-c3cccc(-c4cnc(CN5CC[C@@H](NC(C)=O)C5)c(OC)n4)c3Cl)c2Cl)cnc1CNC[C@H]1CCC(=O)N1] | 705.2 | 2 |

TABLE 1-continued
| No. | Structure | ES/MS (m/z, M + H⁺) | Procedure |
|---|---|---|---|
| 199 | 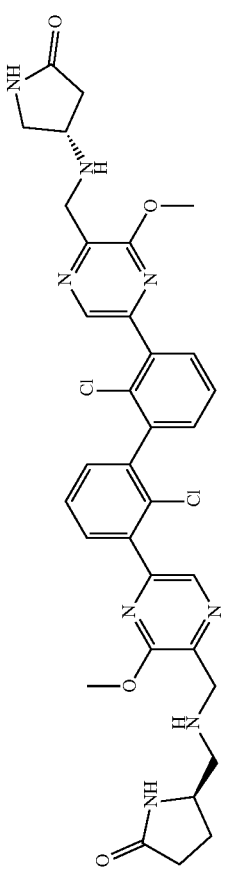 | 677.08 | 2 |
| 200 | 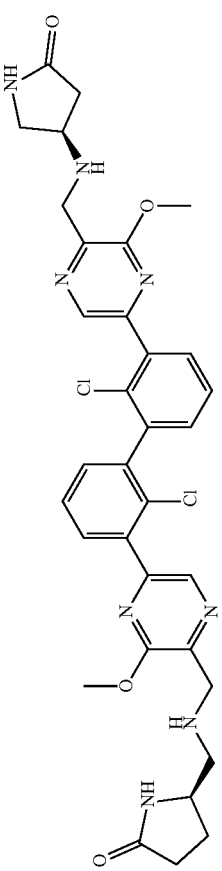 | 677.1 | 2 |
| 201 | 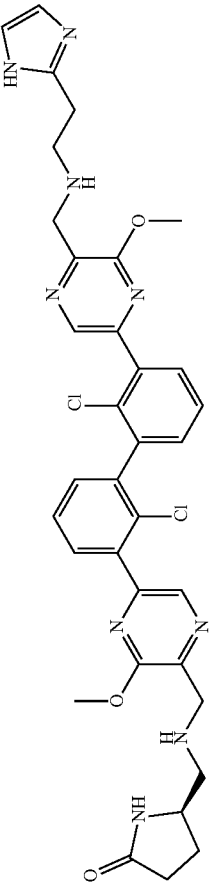 | 688.32 | 2 |
| 202 | 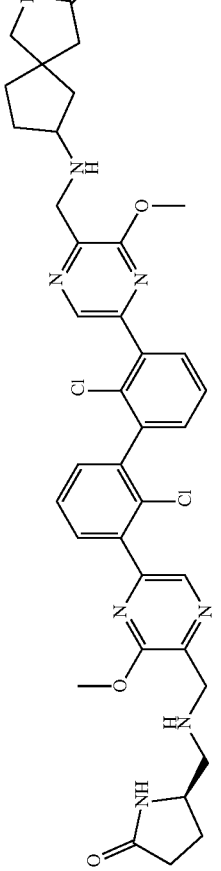 | 731.33 | 2 |

TABLE 1-continued

| No. | Structure | ES/MS (m/z, M + H+) | Procedure |
|---|---|---|---|
| 203 | 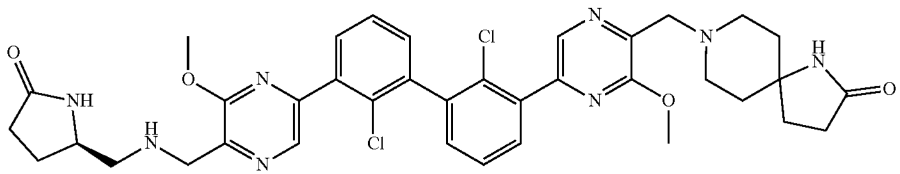 [SMILES: COc1nc(-c2cccc(-c3cccc(-c4cnc(CN5CCC6(CCC(=O)N6)CC5)c(OC)n4)c3Cl)c2Cl)cnc1CNC[C@H]1CCC(=O)N1] | 731.21 | 2 |
| 204 | 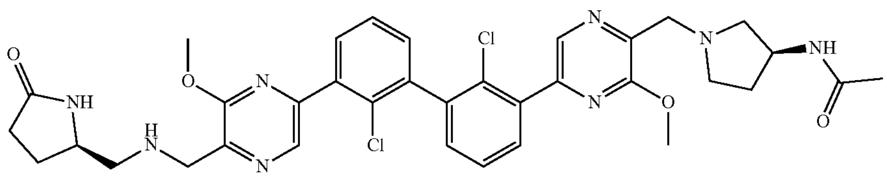 [SMILES: COc1nc(-c2cccc(-c3cccc(-c4cnc(CN5CC[C@H](NC(C)=O)C5)c(OC)n4)c3Cl)c2Cl)cnc1CNC[C@H]1CCC(=O)N1] | 705.28 | 2 |
| 205 | 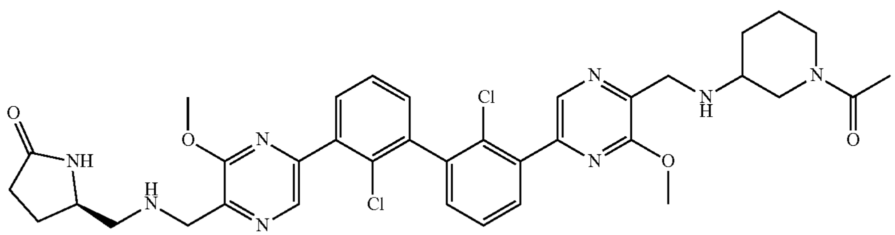 [SMILES: COc1nc(-c2cccc(-c3cccc(-c4cnc(CNC5CCCN(C(C)=O)C5)c(OC)n4)c3Cl)c2Cl)cnc1CNC[C@H]1CCC(=O)N1] | 719.25 | 2 |
| 206 | 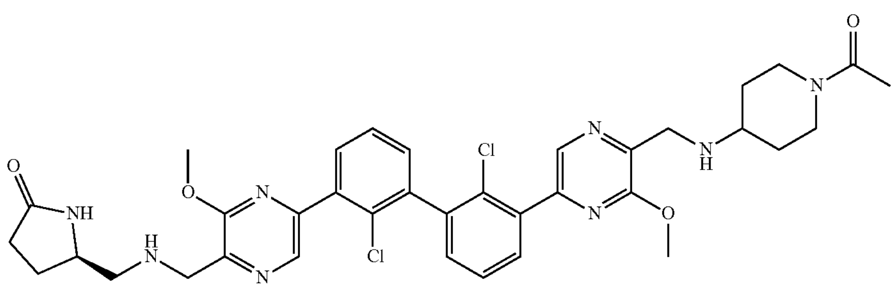 [SMILES: COc1nc(-c2cccc(-c3cccc(-c4cnc(CNC5CCN(C(C)=O)CC5)c(OC)n4)c3Cl)c2Cl)cnc1CNC[C@H]1CCC(=O)N1] | 719.34 | 2 |

TABLE 1-continued

| No. | Structure | ES/MS (m/z, M + H⁺) | Procedure |
|-----|-----------|---------------------|-----------|
| 207 | 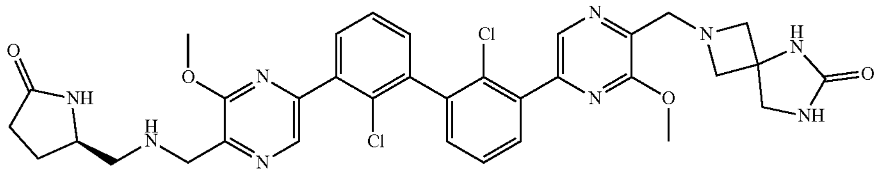 [SMILES: COc1nc(-c2cccc(-c3cccc(-c4cnc(CN5CC6(CNC(=O)N6)C5)c(OC)n4)c3Cl)c2Cl)cnc1CNC[C@H]1CCC(=O)N1] | 704.22 | 2 |
| 208 | 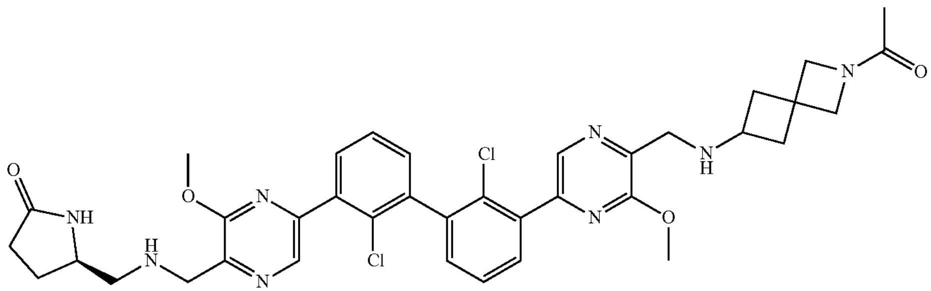 [SMILES: COc1nc(-c2cccc(-c3cccc(-c4cnc(CNC5CC6(C5)CN(C(C)=O)C6)c(OC)n4)c3Cl)c2Cl)cnc1CNC[C@H]1CCC(=O)N1] | 731.25 | 2 |
| 209 | 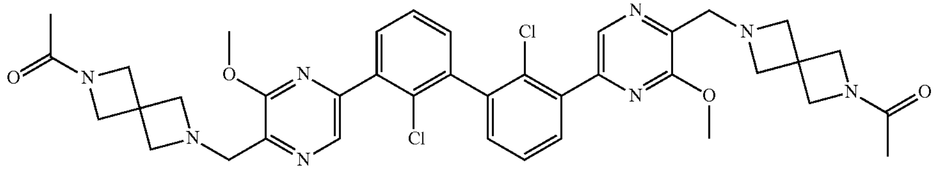 [SMILES: COc1nc(-c2cccc(-c3cccc(-c4cnc(CN5CC6(C5)CN(C(C)=O)C6)c(OC)n4)c3Cl)c2Cl)cnc1CN1CC2(C1)CN(C(C)=O)C2] | 743.16 | 3 |
| 210 | 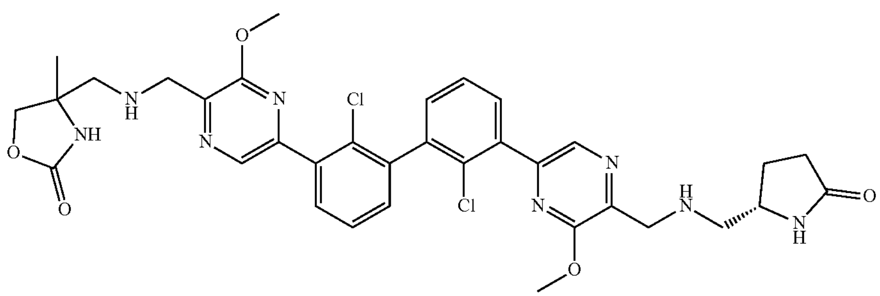 [SMILES: COc1nc(-c2cccc(-c3cccc(-c4cnc(CNCC5(C)COC(=O)N5)c(OC)n4)c3Cl)c2Cl)cnc1CNC[C@@H]1CCC(=O)N1] | 707.23 | 2 |

TABLE 1-continued
| No. | Structure | ES/MS (m/z, M + H+) | Procedure |
|---|---|---|---|
| 211 | 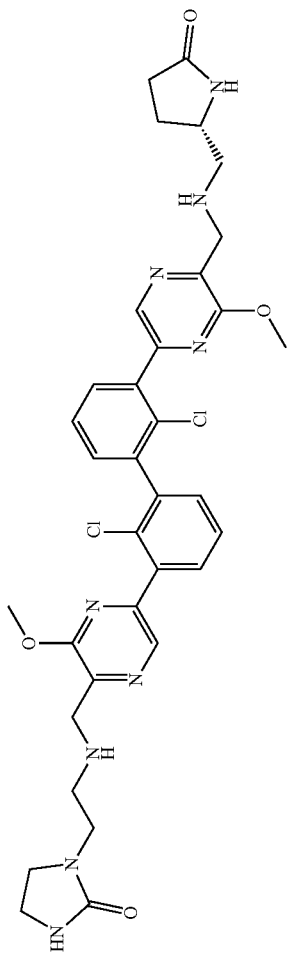 | 706.24 | 2 |
| 212 | 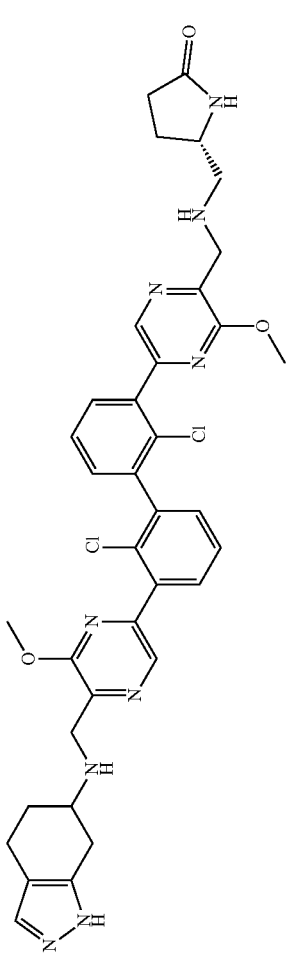 | 714.25 | 2 |
| 213 | 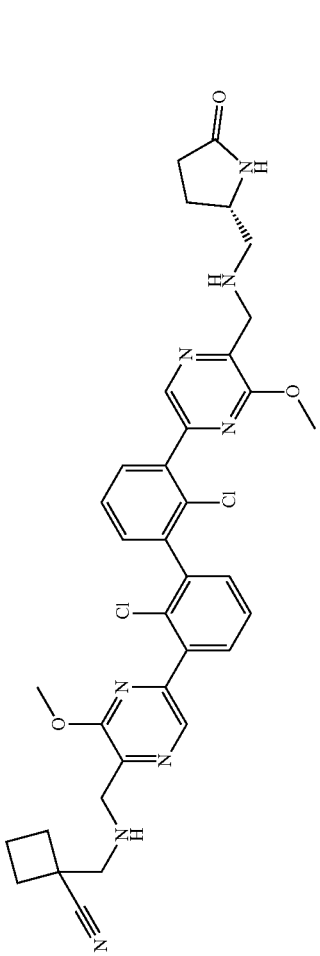 | 687.24 | 2 |

TABLE 1-continued

| No. | Structure | ES/MS (m/z, M + H⁺) | Procedure |
|---|---|---|---|
| 214 | 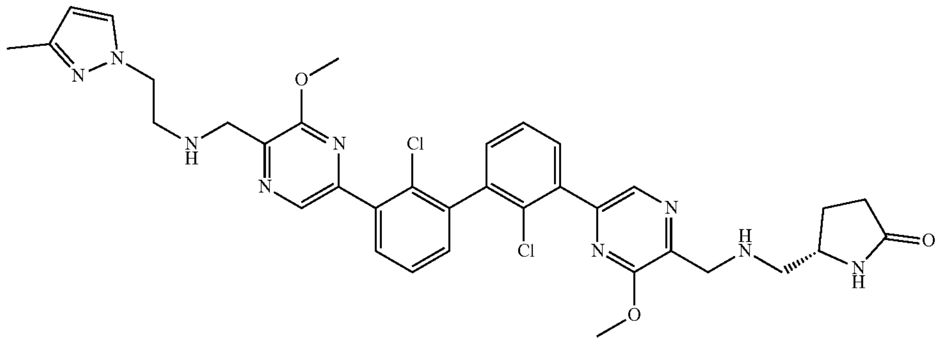 [SMILES: COc1nc(-c2cccc(-c3cccc(-c4cnc(CNC[C@@H]5CCC(=O)N5)c(OC)n4)c3Cl)c2Cl)cnc1CNCCn1ccc(C)n1] | 702.25 | 2 |
| 215 | 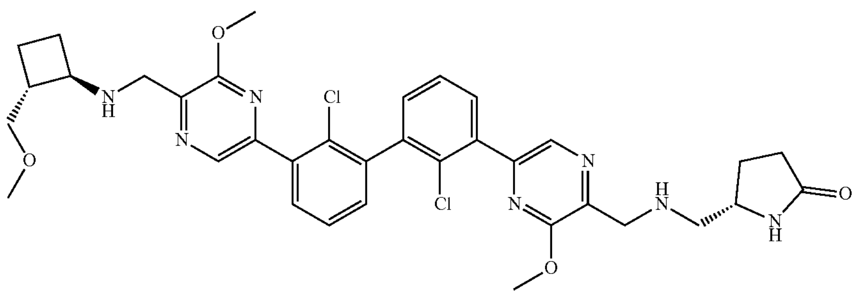 [SMILES: COC[C@@H]1CC[C@H]1NCc1ncc(-c2cccc(-c3cccc(-c4cnc(CNC[C@@H]5CCC(=O)N5)c(OC)n4)c3Cl)c2Cl)nc1OC] | 692.25 | 2 |
| 216 | 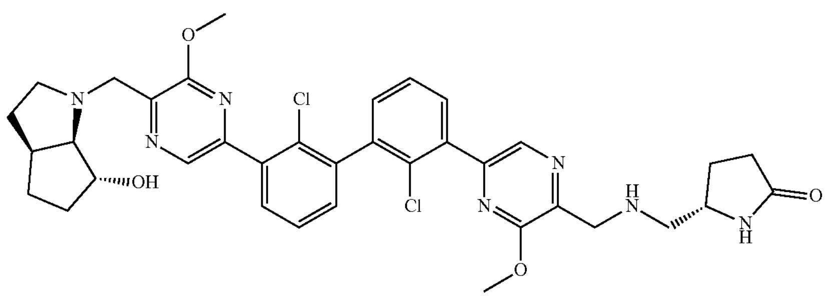 [SMILES: COc1nc(-c2cccc(-c3cccc(-c4cnc(CN5CC[C@@H]6CC[C@@H](O)[C@@H]65)c(OC)n4)c3Cl)c2Cl)cnc1CNC[C@@H]1CCC(=O)N1] | 704.25 | 2 |

TABLE 1-continued

| No. | Structure | ES/MS (m/z, M + H⁺) | Procedure |
|-----|-----------|---------------------|-----------|
| 217 | 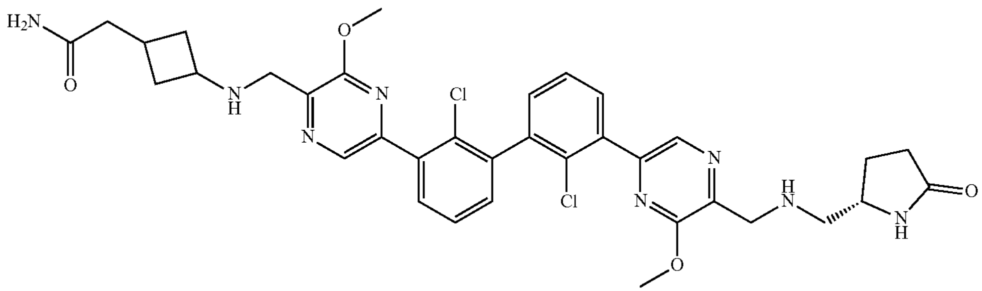 [SMILES: COc1nc(-c2cccc(-c3cccc(-c4cnc(CNC5CC(CC(N)=O)C5)c(OC)n4)c3Cl)c2Cl)cnc1CNC[C@@H]1CCC(=O)N1]          | 705.25              | 2         |
| 218 | 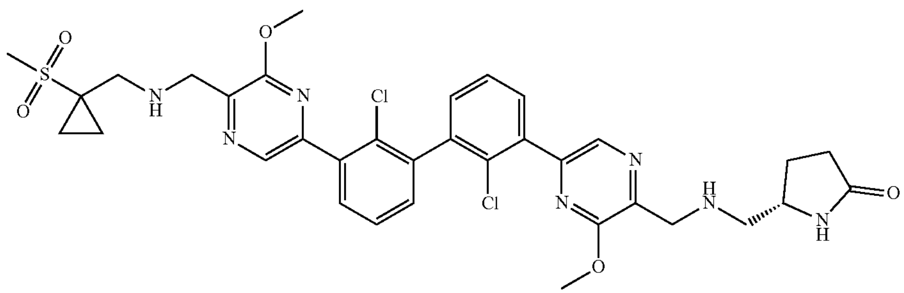 [SMILES: COc1nc(-c2cccc(-c3cccc(-c4cnc(CNCC5(S(C)(=O)=O)CC5)c(OC)n4)c3Cl)c2Cl)cnc1CNC[C@@H]1CCC(=O)N1]          | 726.2               | 2         |
| 219 | 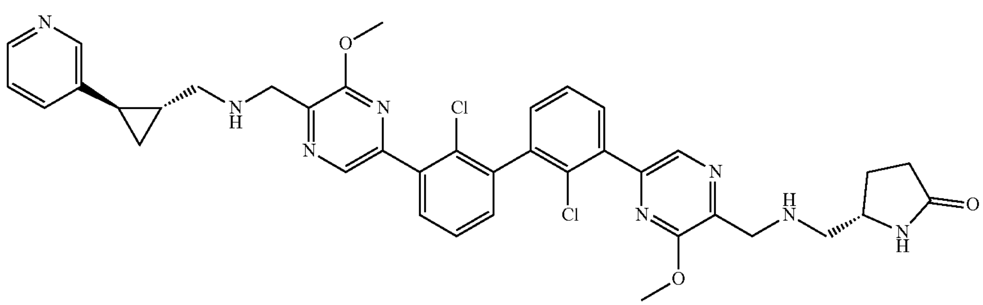 [SMILES: COc1nc(-c2cccc(-c3cccc(-c4cnc(CNC[C@@H]5C[C@H]5c5cccnc5)c(OC)n4)c3Cl)c2Cl)cnc1CNC[C@@H]1CCC(=O)N1]          | 725.25              | 2         |

TABLE 1-continued

| No. | Structure | ES/MS (m/z, M + H+) | Procedure |
|---|---|---|---|
| 220 | 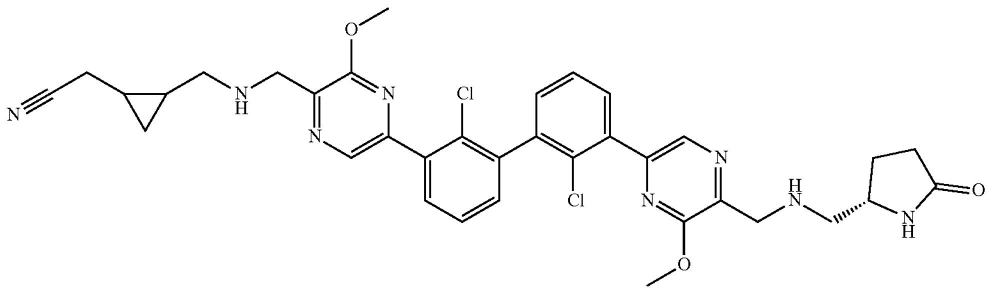 [SMILES: COc1nc(-c2cccc(-c3cccc(-c4cnc(CNC[C@@H]5CCC(=O)N5)c(OC)n4)c3Cl)c2Cl)cnc1CNCC1CC1CC#N] | 687.24 | 2 |
| 221 | 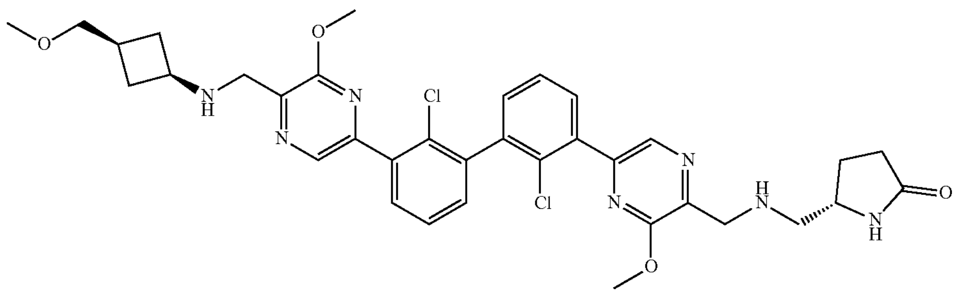 [SMILES: COC[C@H]1C[C@@H](NCc2ncc(-c3cccc(-c4cccc(-c5cnc(CNC[C@@H]6CCC(=O)N6)c(OC)n5)c4Cl)c3Cl)nc2OC)C1] | 692.25 | 2 |
| 222 | 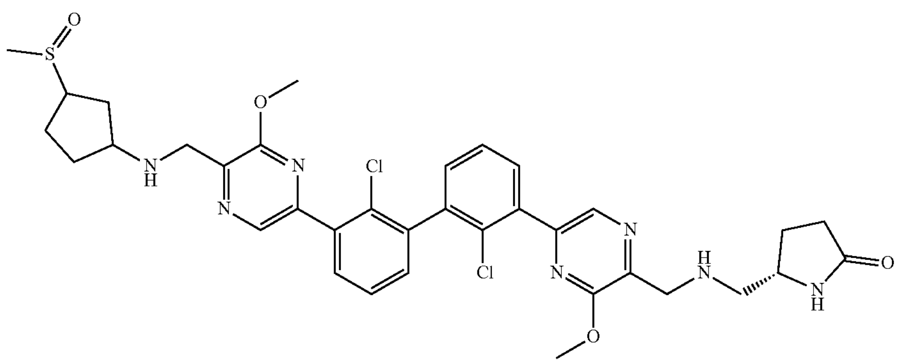 [SMILES: COc1nc(-c2cccc(-c3cccc(-c4cnc(CNC5CCC(S(C)=O)C5)c(OC)n4)c3Cl)c2Cl)cnc1CNC[C@@H]1CCC(=O)N1] | 724.22 | 2 |

TABLE 1-continued

| No. | Structure | ES/MS (m/z, M + H⁺) | Procedure |
|---|---|---|---|
| 223 | 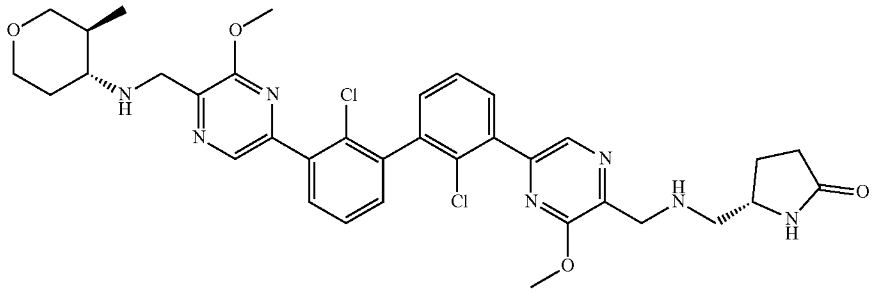 [SMILES: COc1nc(-c2cccc(-c3cccc(-c4cnc(CN[C@@H]5CCOC[C@H]5C)c(OC)n4)c3Cl)c2Cl)cnc1CNC[C@@H]1CCC(=O)N1] | 692.25 | 2 |
| 224 | 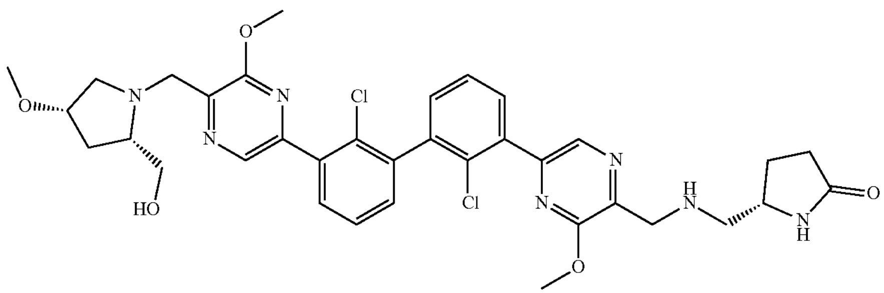 [SMILES: COc1nc(-c2cccc(-c3cccc(-c4cnc(CN5C[C@@H](OC)C[C@H]5CO)c(OC)n4)c3Cl)c2Cl)cnc1CNC[C@@H]1CCC(=O)N1] | 708.25 | 2 |
| 225 | 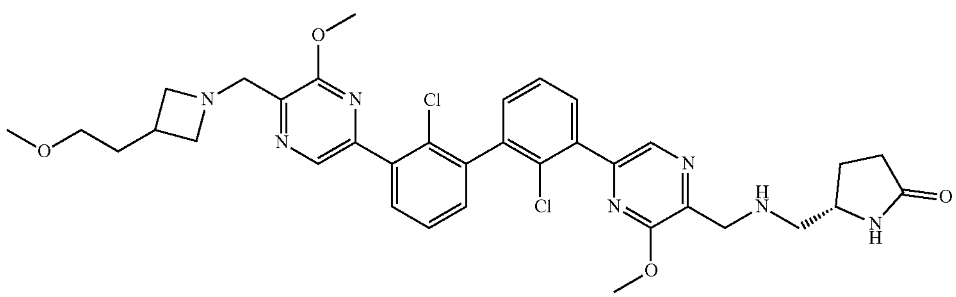 [SMILES: COCCC1CN(Cc2ncc(-c3cccc(-c4cccc(-c5cnc(CNC[C@@H]6CCC(=O)N6)c(OC)n5)c4Cl)c3Cl)nc2OC)C1] | 692.25 | 2 |

TABLE 1-continued

| No. | Structure | ES/MS (m/z, M + H⁺) | Procedure |
|---|---|---|---|
| 226 | 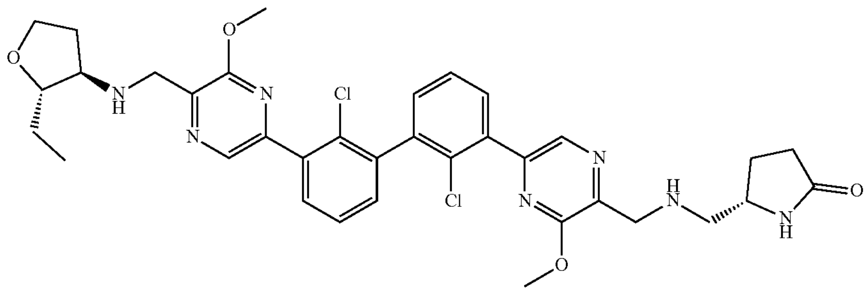 [SMILES: CC[C@@H]1OCC[C@H]1NCc1ncc(-c2cccc(-c3cccc(-c4cnc(CNC[C@@H]5CCC(=O)N5)c(OC)n4)c3Cl)c2Cl)nc1OC] | 692.25 | 2 |
| 227 | 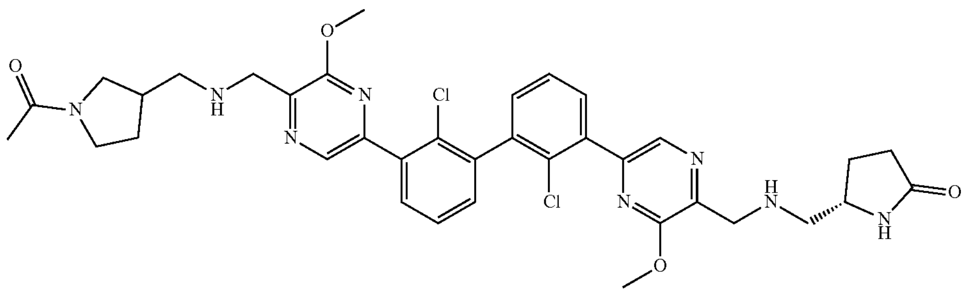 [SMILES: COc1nc(-c2cccc(-c3cccc(-c4cnc(CNC[C@@H]5CCC(=O)N5)c(OC)n4)c3Cl)c2Cl)cnc1CNCC1CCN(C(C)=O)C1] | 719.26 | 2 |
| 228 | 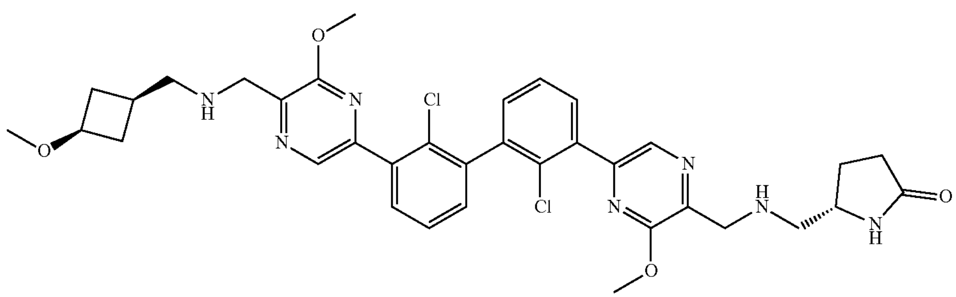 [SMILES: COc1nc(-c2cccc(-c3cccc(-c4cnc(CNC[C@H]5C[C@@H](OC)C5)c(OC)n4)c3Cl)c2Cl)cnc1CNC[C@@H]1CCC(=O)N1] | 692.25 | 2 |

TABLE 1-continued

| No. | Structure | ES/MS (m/z, M + H⁺) | Procedure |
|---|---|---|---|
| 229 | 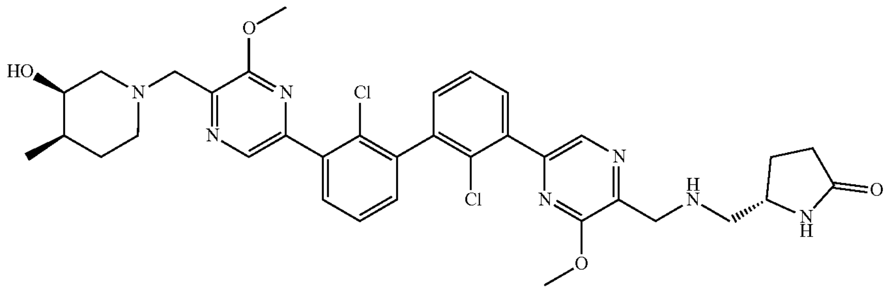 [SMILES: COc1nc(-c2cccc(-c3cccc(-c4cnc(CN5CC[C@@H](C)[C@@H](O)C5)c(OC)n4)c3Cl)c2Cl)cnc1CNC[C@@H]1CCC(=O)N1] | 692.25 | 2 |
| 230 | 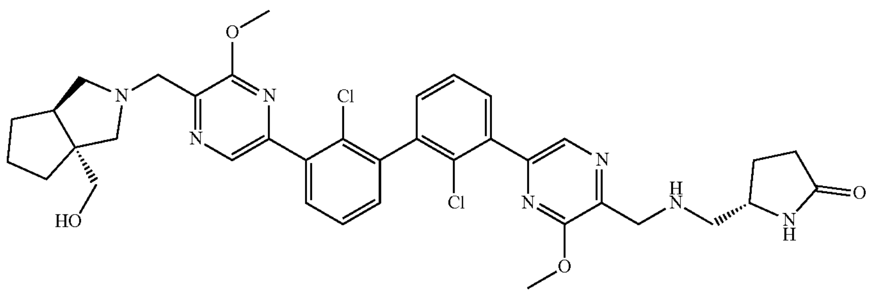 [SMILES: COc1nc(-c2cccc(-c3cccc(-c4cnc(CN5C[C@@H]6CCC[C@]6(CO)C5)c(OC)n4)c3Cl)c2Cl)cnc1CNC[C@@H]1CCC(=O)N1] | 718.27 | 2 |
| 231 | 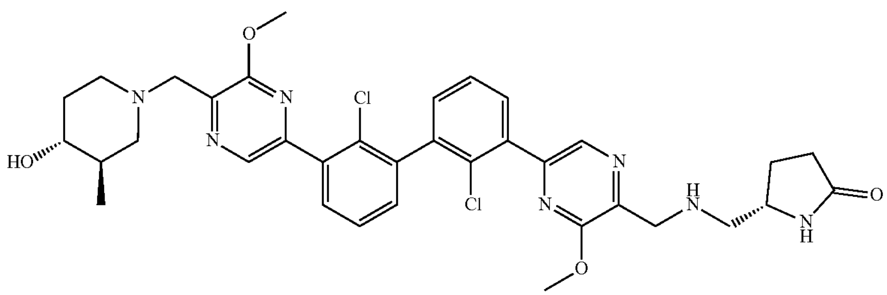 [SMILES: COc1nc(-c2cccc(-c3cccc(-c4cnc(CN5CC[C@@H](O)[C@H](C)C5)c(OC)n4)c3Cl)c2Cl)cnc1CNC[C@@H]1CCC(=O)N1] | 692.25 | 2 |

TABLE 1-continued

| No. | Structure | ES/MS (m/z, M + H+) | Procedure |
|---|---|---|---|
| 232 | 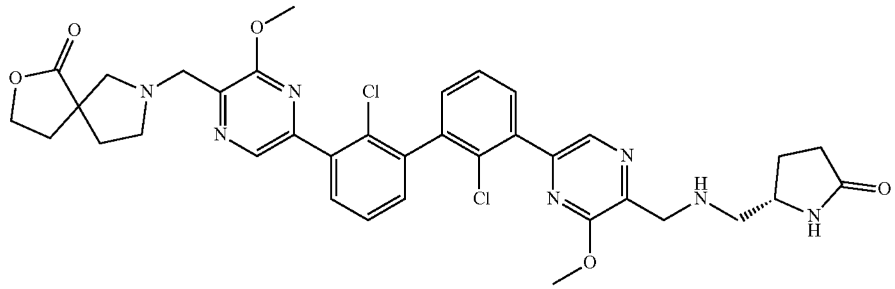 [SMILES: COc1nc(-c2cccc(-c3cccc(-c4cnc(CN5CCC6(CCOC6=O)C5)c(OC)n4)c3Cl)c2Cl)cnc1CNC[C@@H]1CCC(=O)N1] | 718.23 | 2 |
| 233 | 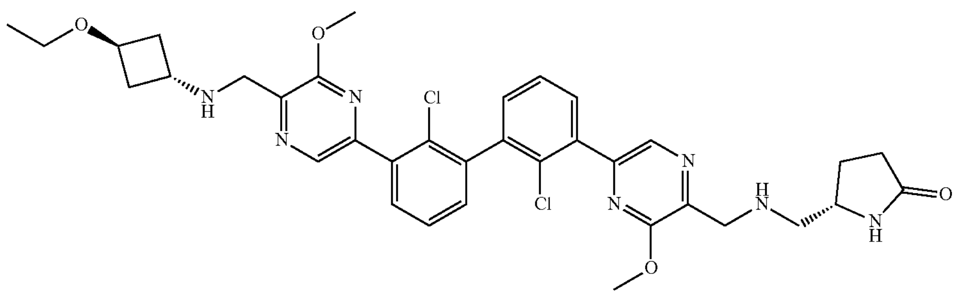 [SMILES: CCO[C@H]1C[C@H](NCc2ncc(-c3cccc(-c4cccc(-c5cnc(CNC[C@@H]6CCC(=O)N6)c(OC)n5)c4Cl)c3Cl)nc2OC)C1] | 692.25 | 2 |
| 234 | 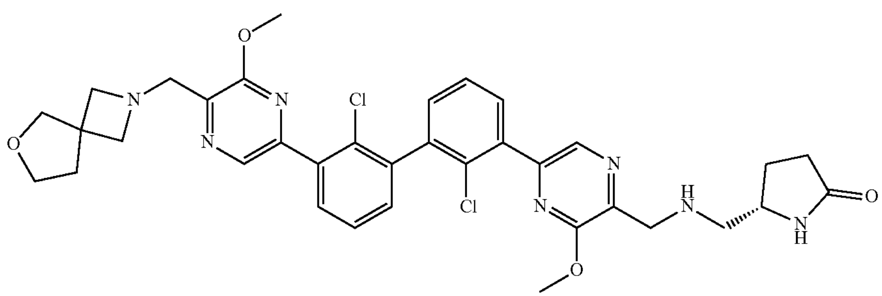 [SMILES: COc1nc(-c2cccc(-c3cccc(-c4cnc(CN5CC6(CCOC6)C5)c(OC)n4)c3Cl)c2Cl)cnc1CNC[C@@H]1CCC(=O)N1] | 690.24 | 2 |

TABLE 1-continued
| No. | Structure | ES/MS (m/z, M + H+) | Procedure |
|---|---|---|---|
| 235 | 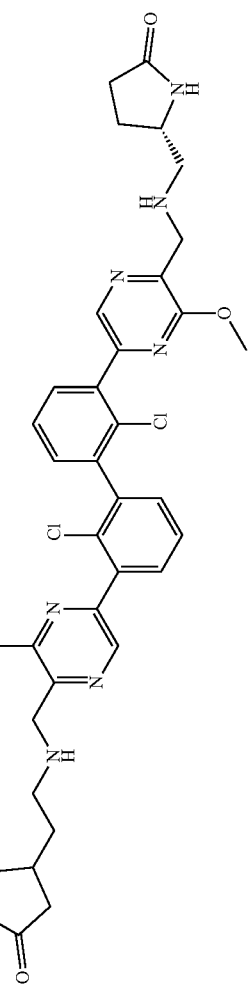 | 705.25 | 2 |
| 236 | 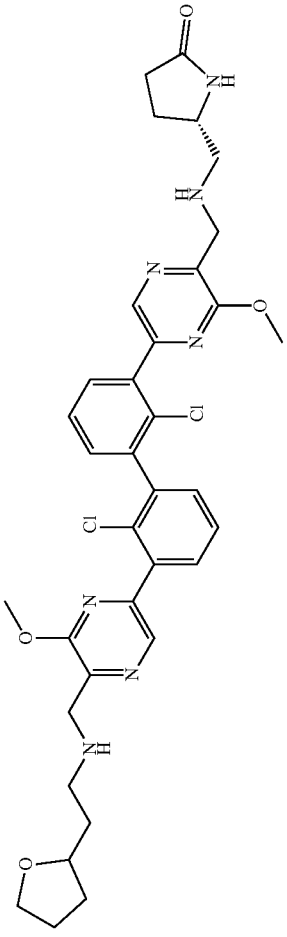 | 692.25 | 2 |
| 237 | 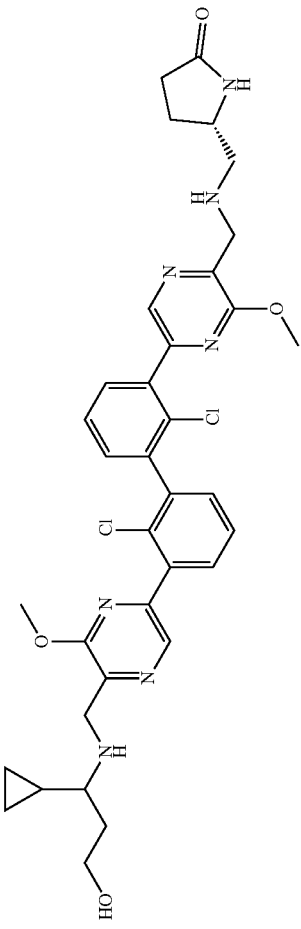 | 692.25 | 2 |

TABLE 1-continued

| No. | Structure | ES/MS (m/z, M + H⁺) | Procedure |
|---|---|---|---|
| 238 | 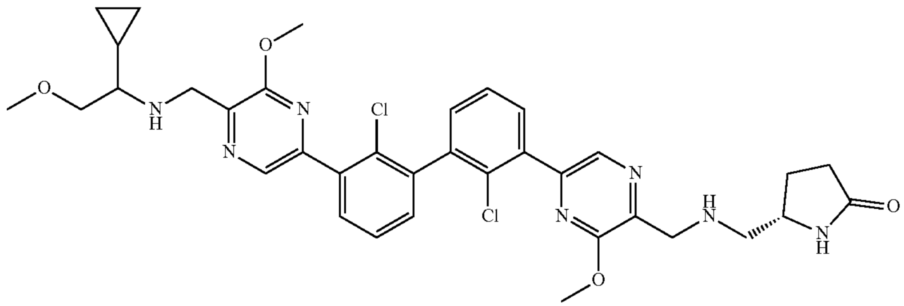 [SMILES: COCC(NCc1ncc(-c2cccc(-c3cccc(-c4cnc(CNC[C@@H]5CCC(=O)N5)c(OC)n4)c3Cl)c2Cl)nc1OC)C1CC1] | 692.25 | 2 |
| 239 | 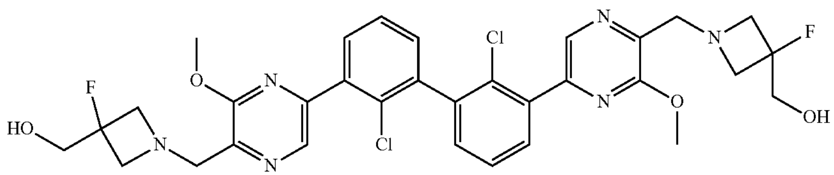 [SMILES: COc1nc(-c2cccc(-c3cccc(-c4cnc(CN5CC(F)(CO)C5)c(OC)n4)c3Cl)c2Cl)cnc1CN1CC(F)(CO)C1] | 673.09 | 3 |
| 240 | 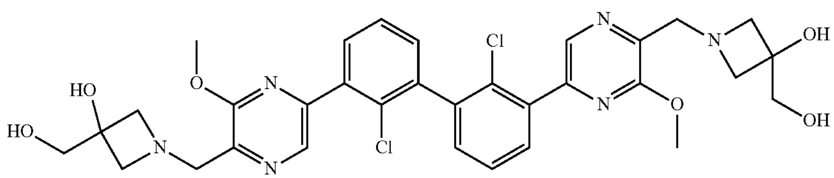 [SMILES: COc1nc(-c2cccc(-c3cccc(-c4cnc(CN5CC(O)(CO)C5)c(OC)n4)c3Cl)c2Cl)cnc1CN1CC(O)(CO)C1] | 669.17 | 3 |
| 241 | 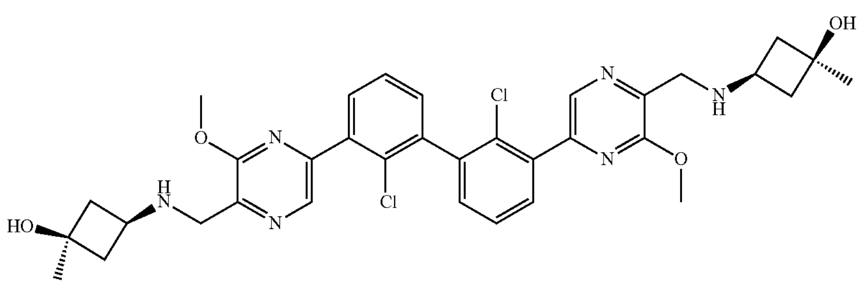 [SMILES: COc1nc(-c2cccc(-c3cccc(-c4cnc(CN[C@H]5C[C@@](C)(O)C5)c(OC)n4)c3Cl)c2Cl)cnc1CN[C@H]1C[C@@](C)(O)C1] | 665.14 | 3 |

TABLE 1-continued

| No. | Structure | ES/MS (m/z, M + H+) | Procedure |
|---|---|---|---|
| 242 | 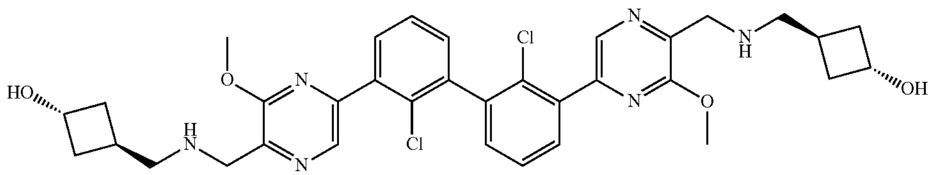 [SMILES: COc1nc(-c2cccc(-c3cccc(-c4cnc(CNC[C@H]5C[C@H](O)C5)c(OC)n4)c3Cl)c2Cl)cnc1CNC[C@H]1C[C@H](O)C1] | 665.2 | 3 |
| 243 | 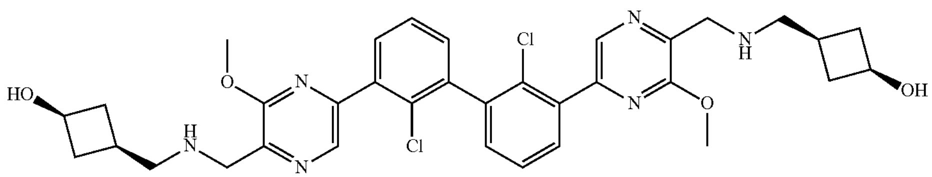 [SMILES: COc1nc(-c2cccc(-c3cccc(-c4cnc(CNC[C@H]5C[C@@H](O)C5)c(OC)n4)c3Cl)c2Cl)cnc1CNC[C@H]1C[C@@H](O)C1] | 665.16 | 3 |
| 244 | 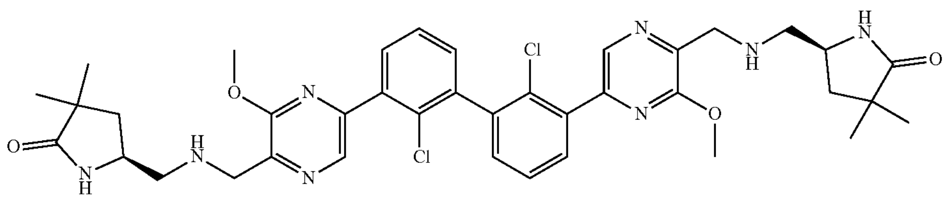 [SMILES: COc1nc(-c2cccc(-c3cccc(-c4cnc(CNC[C@@H]5CC(C)(C)C(=O)N5)c(OC)n4)c3Cl)c2Cl)cnc1CNC[C@@H]1CC(C)(C)C(=O)N1] | 747.21 | 3 |
| 245 | 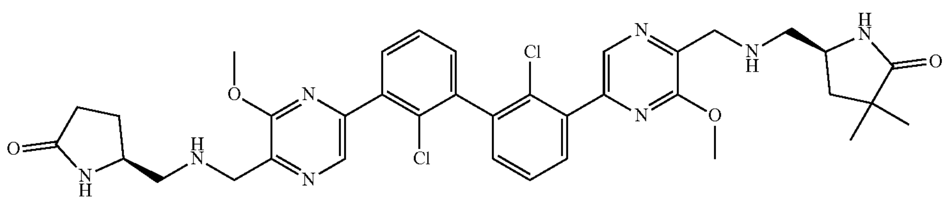 [SMILES: COc1nc(-c2cccc(-c3cccc(-c4cnc(CNC[C@@H]5CC(C)(C)C(=O)N5)c(OC)n4)c3Cl)c2Cl)cnc1CNC[C@@H]1CCC(=O)N1] | 719.16 | 2 |
| 246 | 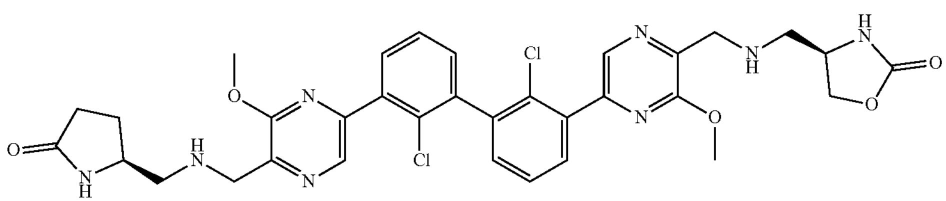 [SMILES: COc1nc(-c2cccc(-c3cccc(-c4cnc(CNC[C@@H]5COC(=O)N5)c(OC)n4)c3Cl)c2Cl)cnc1CNC[C@@H]1CCC(=O)N1] | 693.15 | 2 |

TABLE 1-continued

| No. | Structure | ES/MS (m/z, M + H+) | Procedure |
|---|---|---|---|
| 247 | 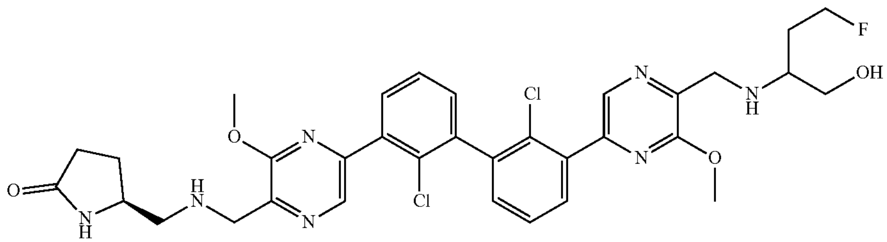 [SMILES: COc1nc(-c2cccc(-c3cccc(-c4cnc(CNC(CO)CCF)c(OC)n4)c3Cl)c2Cl)cnc1CNC[C@@H]1CCC(=O)N1] | 684.15 | 2 |
| 248 | 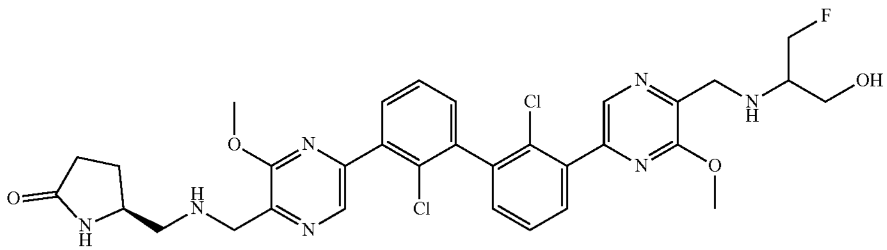 [SMILES: COc1nc(-c2cccc(-c3cccc(-c4cnc(CNC(CO)CF)c(OC)n4)c3Cl)c2Cl)cnc1CNC[C@@H]1CCC(=O)N1] | 670.16 | 2 |
| 249 | 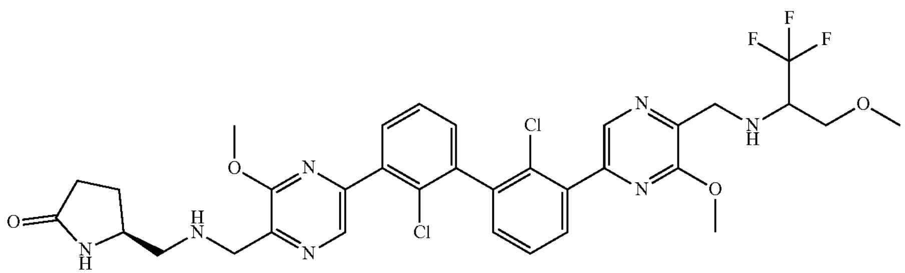 [SMILES: COCC(NCc1ncc(-c2cccc(-c3cccc(-c4cnc(CNC[C@@H]5CCC(=O)N5)c(OC)n4)c3Cl)c2Cl)nc1OC)C(F)(F)F] | 719.99 | 2 |
| 250 | 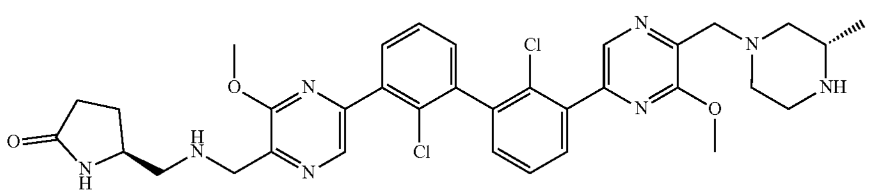 [SMILES: COc1nc(-c2cccc(-c3cccc(-c4cnc(CN5CCN[C@@H](C)C5)c(OC)n4)c3Cl)c2Cl)cnc1CNC[C@@H]1CCC(=O)N1] | 677.27 | 2 |

TABLE 1-continued

| No. | Structure | ES/MS (m/z, M + H⁺) | Procedure |
|---|---|---|---|
| 251 | 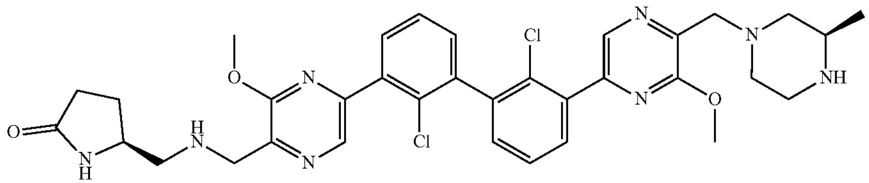 [SMILES: COc1nc(-c2cccc(-c3cccc(-c4cnc(CN5CCN[C@H](C)C5)c(OC)n4)c3Cl)c2Cl)cnc1CNC[C@@H]1CCC(=O)N1] | 677.27 | 2 |
| 252 | 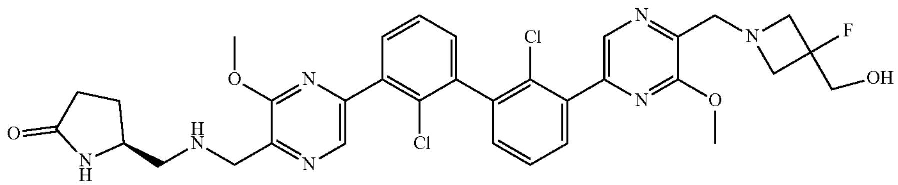 [SMILES: COc1nc(-c2cccc(-c3cccc(-c4cnc(CN5CC(F)(CO)C5)c(OC)n4)c3Cl)c2Cl)cnc1CNC[C@@H]1CCC(=O)N1] | 682.28 | 2 |
| 253 | 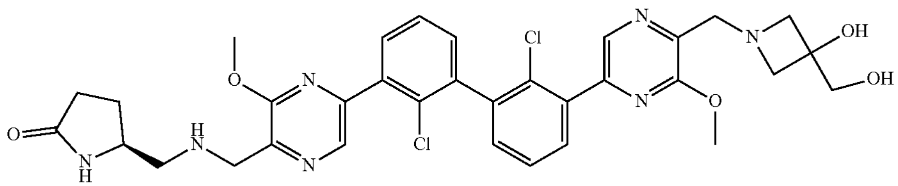 [SMILES: COc1nc(-c2cccc(-c3cccc(-c4cnc(CN5CC(O)(CO)C5)c(OC)n4)c3Cl)c2Cl)cnc1CNC[C@@H]1CCC(=O)N1] | 680.2 | 2 |
| 254 | 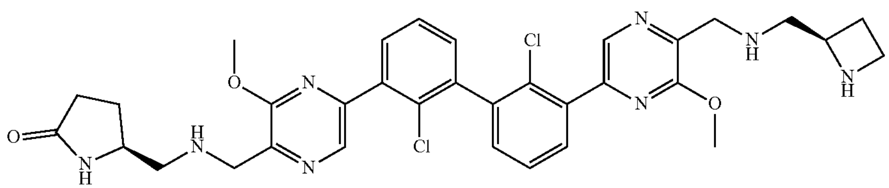 [SMILES: COc1nc(-c2cccc(-c3cccc(-c4cnc(CNC[C@@H]5CCC(=O)N5)c(OC)n4)c3Cl)c2Cl)cnc1CNC[C@H]1CCN1] | 663.28 | 2 |
| 255 | 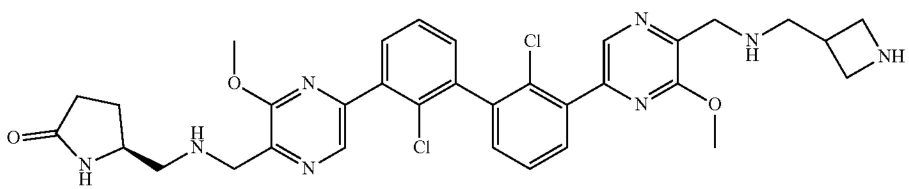 [SMILES: COc1nc(-c2cccc(-c3cccc(-c4cnc(CNC[C@@H]5CCC(=O)N5)c(OC)n4)c3Cl)c2Cl)cnc1CNCC1CNC1] | 663.32 | 2 |

TABLE 1-continued

| No. | Structure | ES/MS (m/z, M + H⁺) | Procedure |
|---|---|---|---|
| 256 | 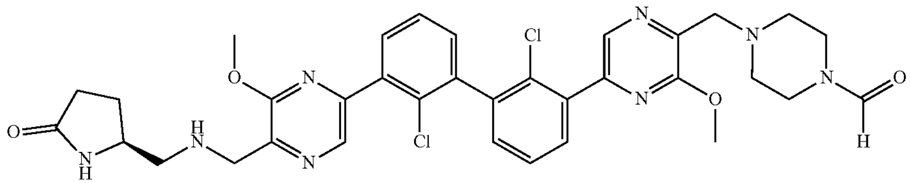 [SMILES: COc1nc(-c2cccc(-c3cccc(-c4cnc(CN5CCN(C=O)CC5)c(OC)n4)c3Cl)c2Cl)cnc1CNC[C@@H]1CCC(=O)N1] | 691.16 | 2 |
| 257 | 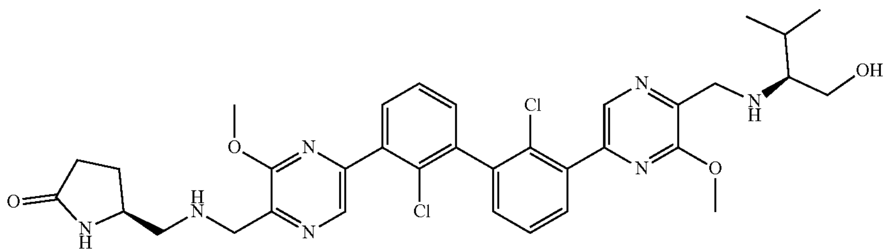 [SMILES: COc1nc(-c2cccc(-c3cccc(-c4cnc(CN[C@H](CO)C(C)C)c(OC)n4)c3Cl)c2Cl)cnc1CNC[C@@H]1CCC(=O)N1] | 680.12 | 2 |
| 258 | 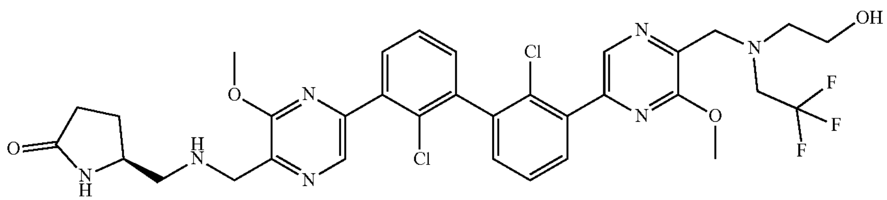 [SMILES: COc1nc(-c2cccc(-c3cccc(-c4cnc(CN(CCO)CC(F)(F)F)c(OC)n4)c3Cl)c2Cl)cnc1CNC[C@@H]1CCC(=O)N1] | 720.01 | 2 |
| 259 | 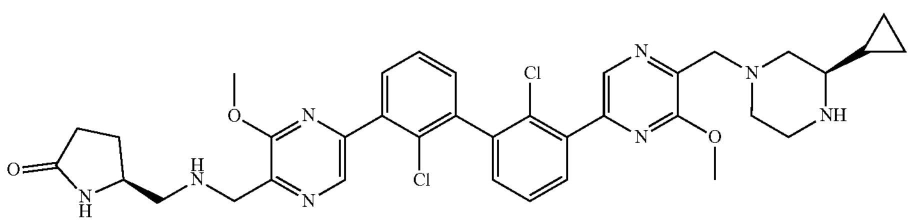 [SMILES: COc1nc(-c2cccc(-c3cccc(-c4cnc(CN5CCN[C@H](C6CC6)C5)c(OC)n4)c3Cl)c2Cl)cnc1CNC[C@@H]1CCC(=O)N1] | 703.18 | 2 |

TABLE 1-continued

| No. | Structure | ES/MS (m/z, M + H+) | Procedure |
|-----|-----------|---------------------|-----------|
| 260 | 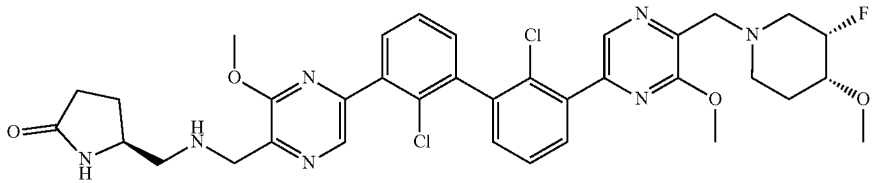 [SMILES: COc1nc(-c2cccc(-c3cccc(-c4cnc(CN5CC[C@@H](OC)[C@@H](F)C5)c(OC)n4)c3Cl)c2Cl)cnc1CNC[C@@H]1CCC(=O)N1] | 710.05 | 2 |
| 261 | 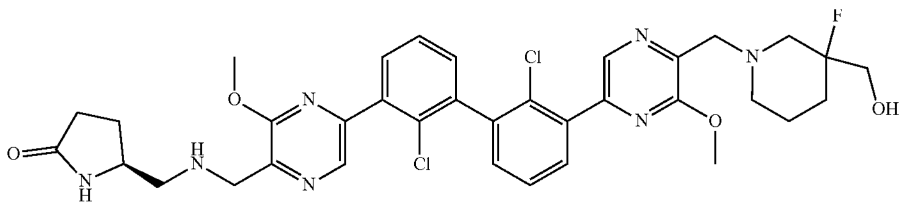 [SMILES: COc1nc(-c2cccc(-c3cccc(-c4cnc(CN5CCCC(F)(CO)C5)c(OC)n4)c3Cl)c2Cl)cnc1CNC[C@@H]1CCC(=O)N1] | 710.11 | 2 |
| 262 | 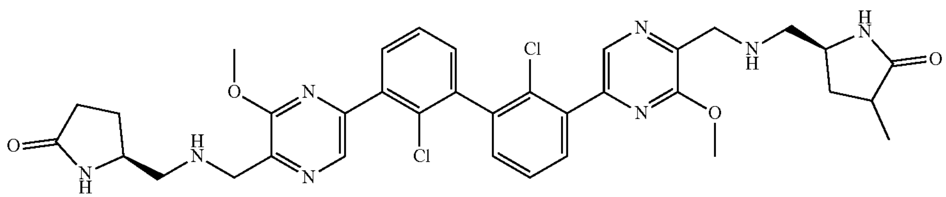 [SMILES: COc1nc(-c2cccc(-c3cccc(-c4cnc(CNC[C@@H]5CC(C)C(=O)N5)c(OC)n4)c3Cl)c2Cl)cnc1CNC[C@@H]1CCC(=O)N1] | 705.09 | 2 |
| 263 | 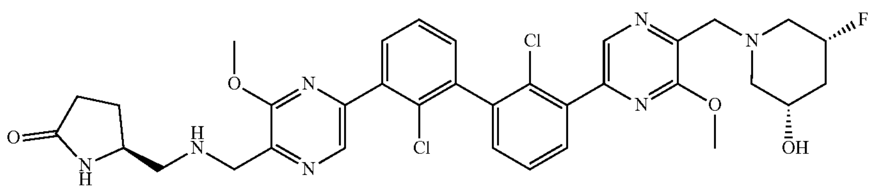 [SMILES: COc1nc(-c2cccc(-c3cccc(-c4cnc(CN5C[C@@H](O)C[C@@H](F)C5)c(OC)n4)c3Cl)c2Cl)cnc1CNC[C@@H]1CCC(=O)N1] | 696.1 | 2 |
| 264 | 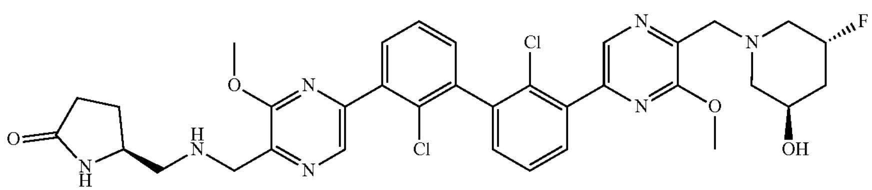 [SMILES: COc1nc(-c2cccc(-c3cccc(-c4cnc(CN5C[C@H](O)C[C@@H](F)C5)c(OC)n4)c3Cl)c2Cl)cnc1CNC[C@@H]1CCC(=O)N1] | 696.07 | 2 |

TABLE 1-continued

| No. | Structure | ES/MS (m/z, M + H+) | Procedure |
|---|---|---|---|
| 265 | 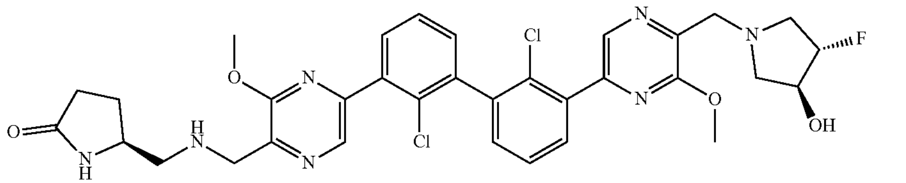 [SMILES: COc1nc(-c2cccc(-c3cccc(-c4cnc(CN5C[C@H](O)[C@@H](F)C5)c(OC)n4)c3Cl)c2Cl)cnc1CNC[C@@H]1CCC(=O)N1] | 682.09 | 2 |
| 266 | 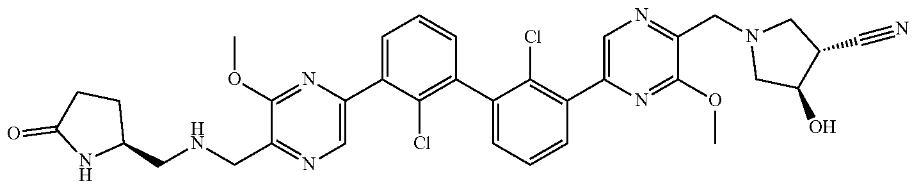 [SMILES: COc1nc(-c2cccc(-c3cccc(-c4cnc(CN5C[C@H](O)[C@@H](C#N)C5)c(OC)n4)c3Cl)c2Cl)cnc1CNC[C@@H]1CCC(=O)N1] | 689.05 | 2 |
| 267 | 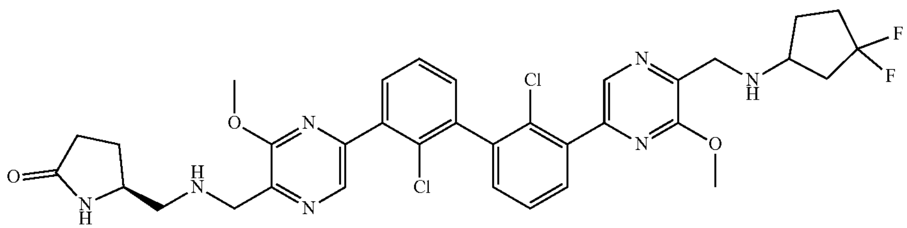 [SMILES: COc1nc(-c2cccc(-c3cccc(-c4cnc(CNC5CCC(F)(F)C5)c(OC)n4)c3Cl)c2Cl)cnc1CNC[C@@H]1CCC(=O)N1] | 698.08 | 2 |
| 268 | 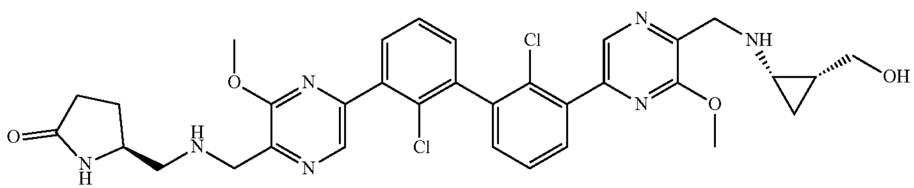 [SMILES: COc1nc(-c2cccc(-c3cccc(-c4cnc(CN[C@H]5C[C@H]5CO)c(OC)n4)c3Cl)c2Cl)cnc1CNC[C@@H]1CCC(=O)N1] | 663.95 | 2 |
| 269 | 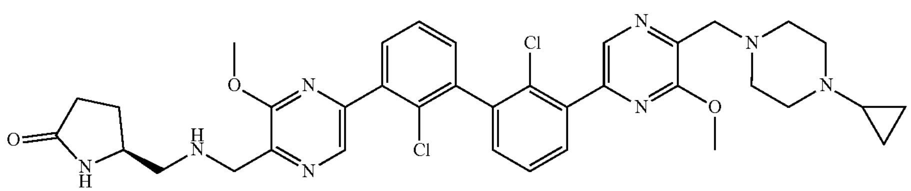 [SMILES: COc1nc(-c2cccc(-c3cccc(-c4cnc(CN5CCN(C6CC6)CC5)c(OC)n4)c3Cl)c2Cl)cnc1CNC[C@@H]1CCC(=O)N1] | 703.2 | 2 |

TABLE 1-continued

| No. | Structure | ES/MS (m/z, M + H+) | Procedure |
|---|---|---|---|
| 270 | 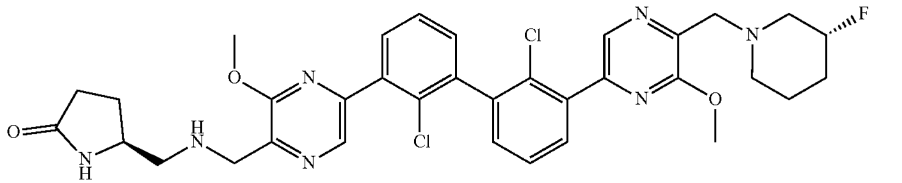 [SMILES: COc1nc(-c2cccc(-c3cccc(-c4cnc(CN5CCC[C@@H](F)C5)c(OC)n4)c3Cl)c2Cl)cnc1CNC[C@@H]1CCC(=O)N1] | 680.12 | 2 |
| 271 | 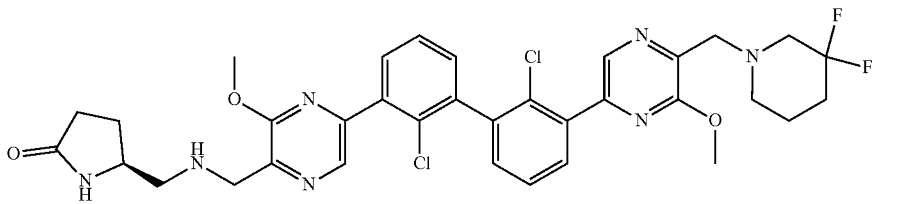 [SMILES: COc1nc(-c2cccc(-c3cccc(-c4cnc(CN5CCCC(F)(F)C5)c(OC)n4)c3Cl)c2Cl)cnc1CNC[C@@H]1CCC(=O)N1] | 698.05 | 2 |
| 272 | 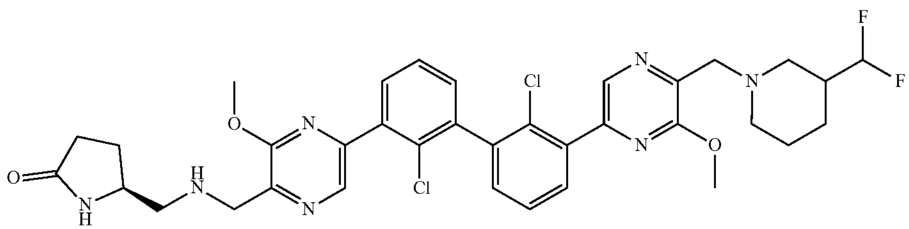 [SMILES: COc1nc(-c2cccc(-c3cccc(-c4cnc(CN5CCCC(C(F)F)C5)c(OC)n4)c3Cl)c2Cl)cnc1CNC[C@@H]1CCC(=O)N1] | 712.1 | 2 |
| 273 | 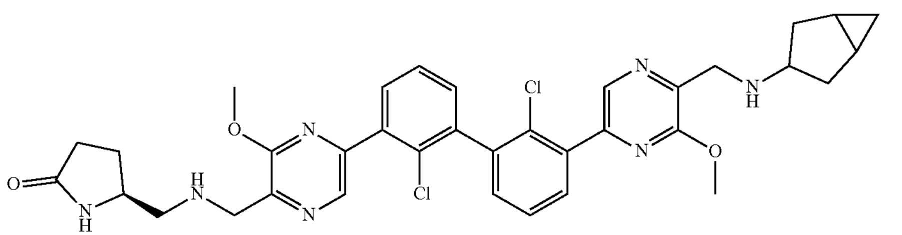 [SMILES: COc1nc(-c2cccc(-c3cccc(-c4cnc(CNC5CC6CC6C5)c(OC)n4)c3Cl)c2Cl)cnc1CNC[C@@H]1CCC(=O)N1] | 674.13 | 2 |

TABLE 1-continued

| No. | Structure | ES/MS (m/z, M + H+) | Procedure |
|---|---|---|---|
| 274 | 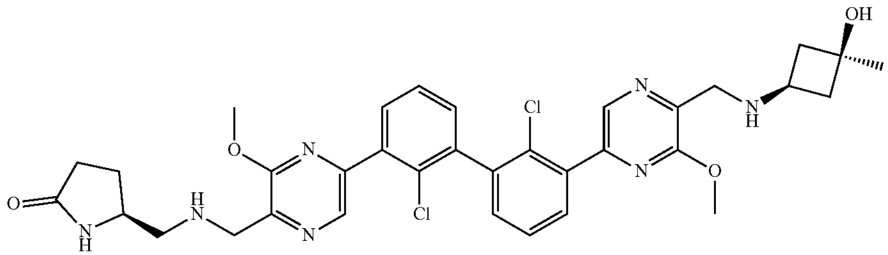 [SMILES: COc1nc(-c2cccc(-c3cccc(-c4cnc(CN[C@H]5C[C@@](C)(O)C5)c(OC)n4)c3Cl)c2Cl)cnc1CNC[C@@H]1CCC(=O)N1] | 678.1 | 2 |
| 275 | 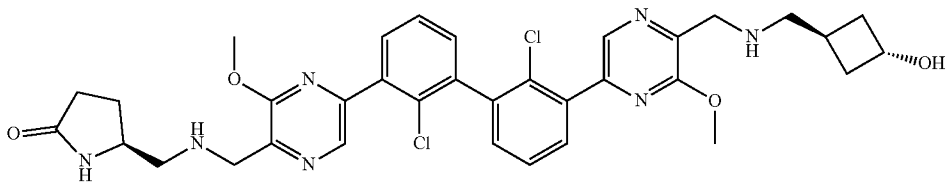 [SMILES: COc1nc(-c2cccc(-c3cccc(-c4cnc(CNC[C@H]5C[C@H](O)C5)c(OC)n4)c3Cl)c2Cl)cnc1CNC[C@@H]1CCC(=O)N1] | 678.12 | 2 |
| 276 | 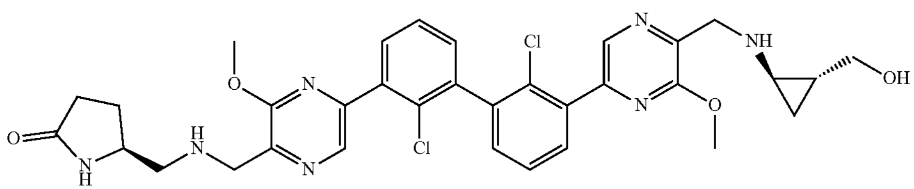 [SMILES: COc1nc(-c2cccc(-c3cccc(-c4cnc(CN[C@@H]5C[C@H]5CO)c(OC)n4)c3Cl)c2Cl)cnc1CNC[C@@H]1CCC(=O)N1] | 663.81 | 2 |
| 277 | 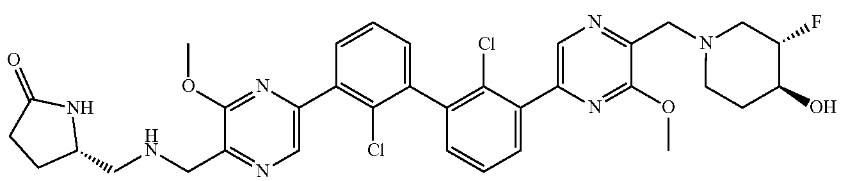 [SMILES: COc1nc(-c2cccc(-c3cccc(-c4cnc(CN5CC[C@H](O)[C@@H](F)C5)c(OC)n4)c3Cl)c2Cl)cnc1CNC[C@@H]1CCC(=O)N1] | 696.25 | 2 |
| 278 | 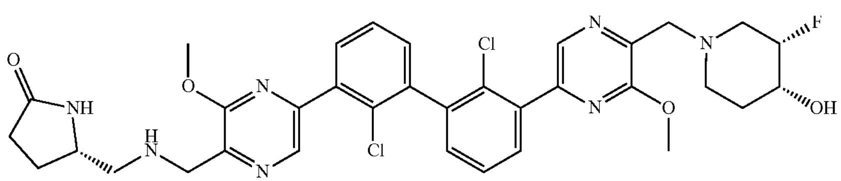 [SMILES: COc1nc(-c2cccc(-c3cccc(-c4cnc(CN5CC[C@@H](O)[C@@H](F)C5)c(OC)n4)c3Cl)c2Cl)cnc1CNC[C@@H]1CCC(=O)N1] | 696.17 | 2 |

TABLE 1-continued

| No. | Structure | ES/MS (m/z, M + H+) | Procedure |
|---|---|---|---|
| 279 | 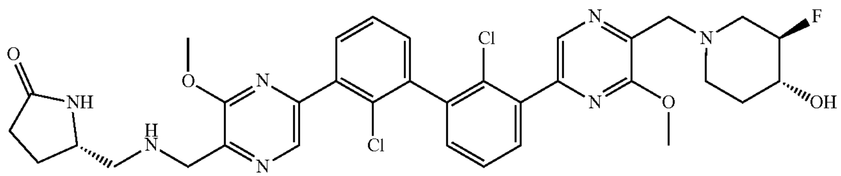 [SMILES: COc1nc(-c2cccc(-c3cccc(-c4cnc(CN5CC[C@@H](O)[C@H](F)C5)c(OC)n4)c3Cl)c2Cl)cnc1CNC[C@@H]1CCC(=O)N1] | 696.13 | 2 |
| 280 | 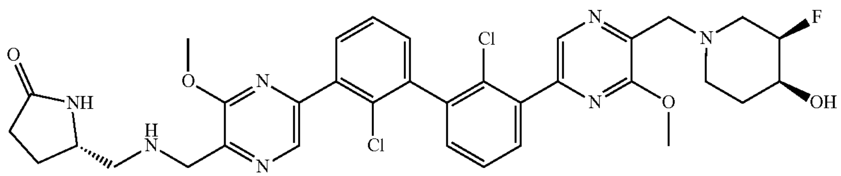 [SMILES: COc1nc(-c2cccc(-c3cccc(-c4cnc(CN5CC[C@H](O)[C@H](F)C5)c(OC)n4)c3Cl)c2Cl)cnc1CNC[C@@H]1CCC(=O)N1] | 696.04 | 2 |
| 281 | 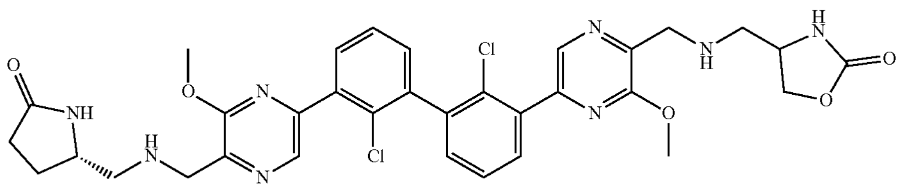 [SMILES: COc1nc(-c2cccc(-c3cccc(-c4cnc(CNC[C@@H]5CCC(=O)N5)c(OC)n4)c3Cl)c2Cl)cnc1CNCC1COC(=O)N1] | 693.14 | 2 |
| 282 | 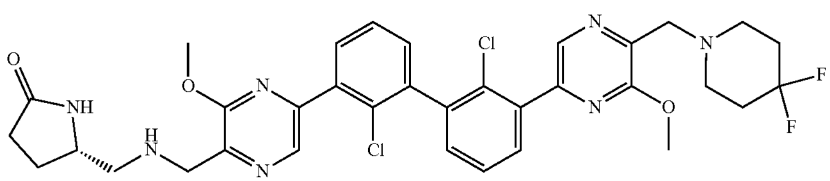 [SMILES: COc1nc(-c2cccc(-c3cccc(-c4cnc(CN5CCC(F)(F)CC5)c(OC)n4)c3Cl)c2Cl)cnc1CNC[C@@H]1CCC(=O)N1] | 698.15 | 2 |
| 283 | 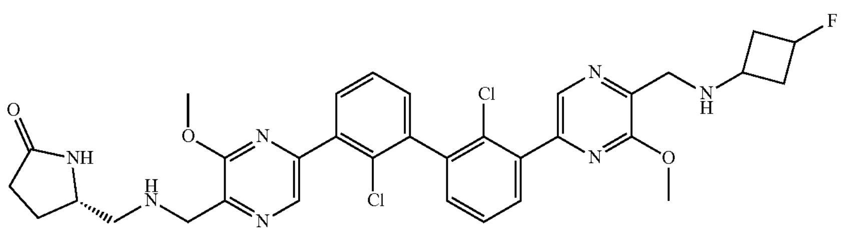 [SMILES: COc1nc(-c2cccc(-c3cccc(-c4cnc(CNC5CC(F)C5)c(OC)n4)c3Cl)c2Cl)cnc1CNC[C@@H]1CCC(=O)N1] | 666.06 | 2 |

TABLE 1-continued
| No. | Structure | ES/MS (m/z, M + H+) | Procedure |
|---|---|---|---|
| 284 | 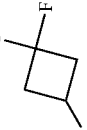 | 684.05 | 2 |
| 285 | 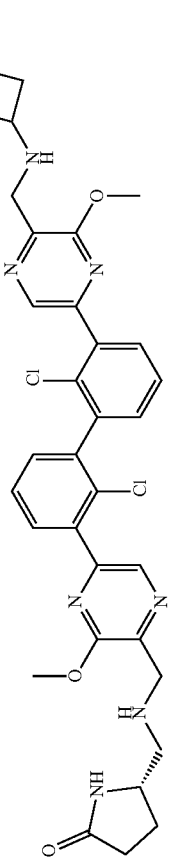 | 719.2 | 2 |
| 286 | 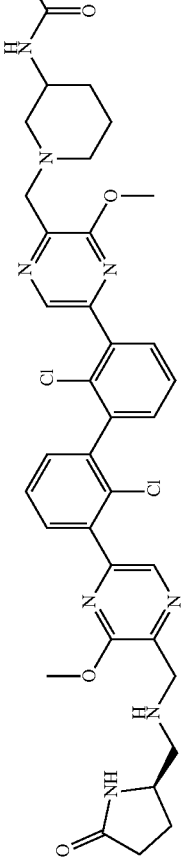 | 742.2 | 2 |
| 287 | 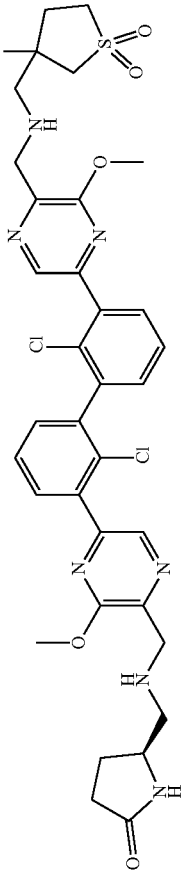 | 703.16 | 2 |

TABLE 1-continued

| No. | Structure | ES/MS (m/z, M + H⁺) | Procedure |
|---|---|---|---|
| 288 | 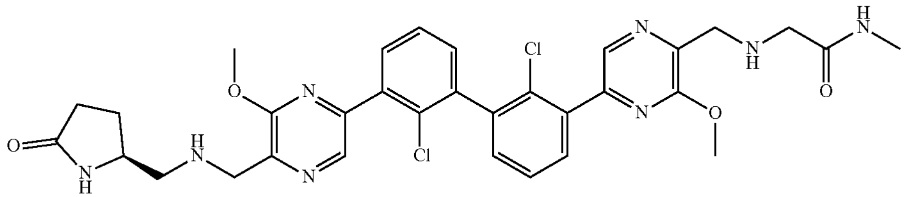 [SMILES: CNC(=O)CNCc1ncc(-c2cccc(-c3cccc(-c4cnc(CNC[C@@H]5CCC(=O)N5)c(OC)n4)c3Cl)c2Cl)nc1OC] | 665.12 | 2 |
| 289 | 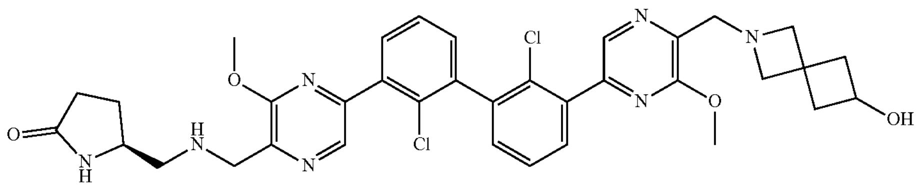 [SMILES: COc1nc(-c2cccc(-c3cccc(-c4cnc(CN5CC6(CC(O)C6)C5)c(OC)n4)c3Cl)c2Cl)cnc1CNC[C@@H]1CCC(=O)N1] | 690.17 | 2 |
| 290 | 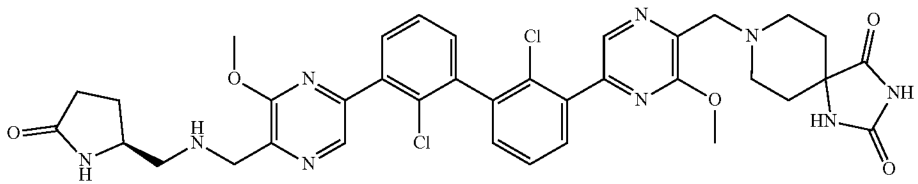 [SMILES: COc1nc(-c2cccc(-c3cccc(-c4cnc(CN5CCC6(CC5)NC(=O)NC6=O)c(OC)n4)c3Cl)c2Cl)cnc1CNC[C@@H]1CCC(=O)N1] | 746.09 | 2 |
| 291 | 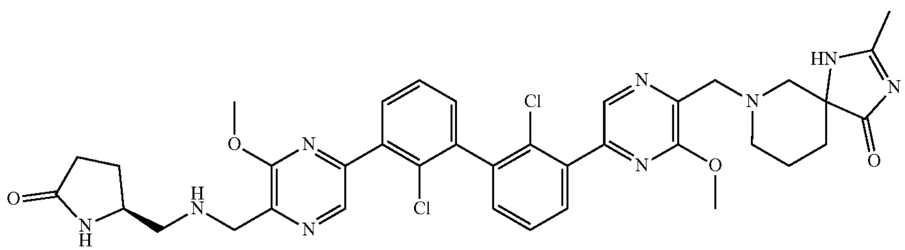 [SMILES: COc1nc(-c2cccc(-c3cccc(-c4cnc(CN5CCCC6(C5)NC(C)=NC6=O)c(OC)n4)c3Cl)c2Cl)cnc1CNC[C@@H]1CCC(=O)N1] | 744.15 | 2 |

TABLE 1-continued
| No. | Structure | ES/MS (m/z, M + H+) | Procedure |
|---|---|---|---|
| 292 | 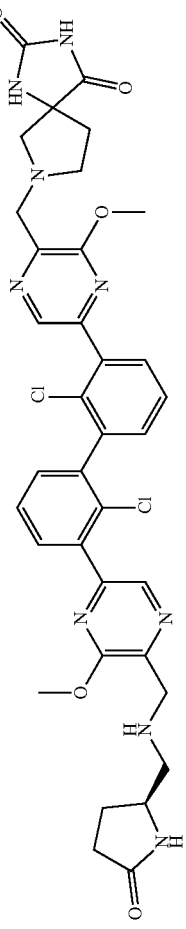 | 732.13 | 2 |
| 293 | 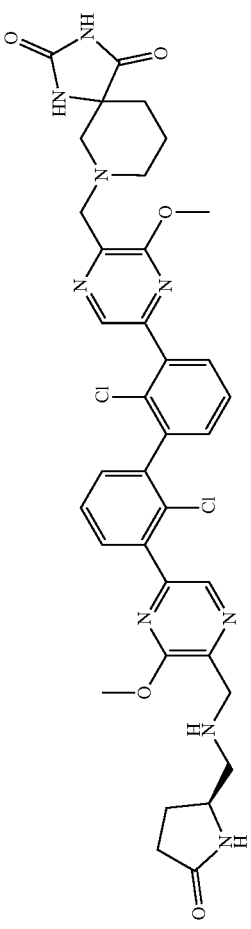 | 746.06 | 2 |
| 294 | 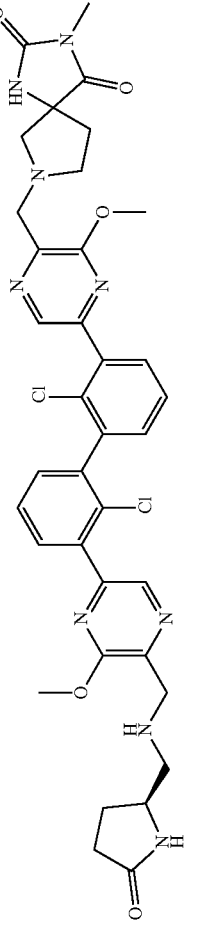 | 746.05 | 2 |
| 295 | 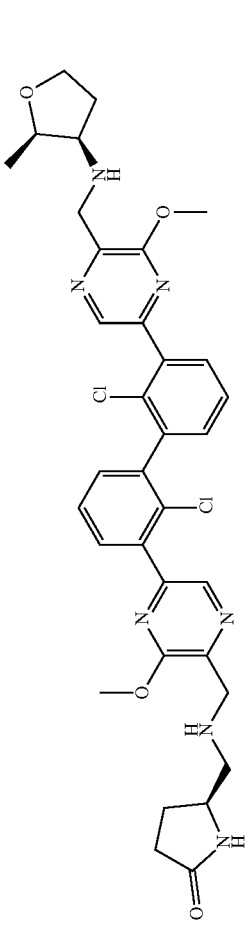 | 678.22 | 2 |

TABLE 1-continued

| No. | Structure | ES/MS (m/z, M + H+) | Procedure |
|---|---|---|---|
| 296 | 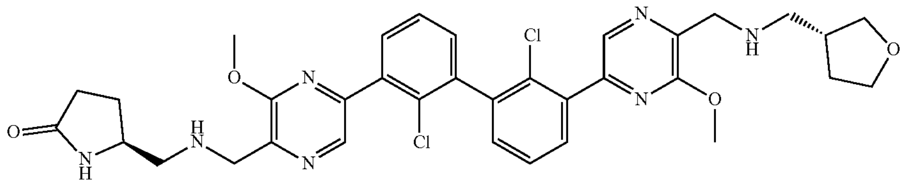 [SMILES: COc1nc(-c2cccc(-c3cccc(-c4cnc(CNC[C@@H]5CCC(=O)N5)c(OC)n4)c3Cl)c2Cl)cnc1CNC[C@H]1CCOC1] | 678.05 | 2 |
| 297 | 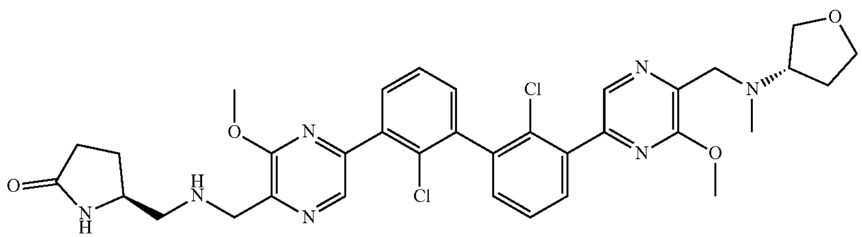 [SMILES: COc1nc(-c2cccc(-c3cccc(-c4cnc(CN(C)[C@H]5CCOC5)c(OC)n4)c3Cl)c2Cl)cnc1CNC[C@@H]1CCC(=O)N1] | 678.07 | 2 |
| 298 | 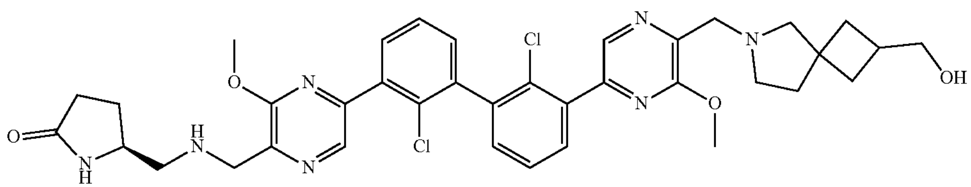 [SMILES: COc1nc(-c2cccc(-c3cccc(-c4cnc(CN5CCC6(CC(CO)C6)C5)c(OC)n4)c3Cl)c2Cl)cnc1CNC[C@@H]1CCC(=O)N1] | 718.19 | 2 |
| 299 | 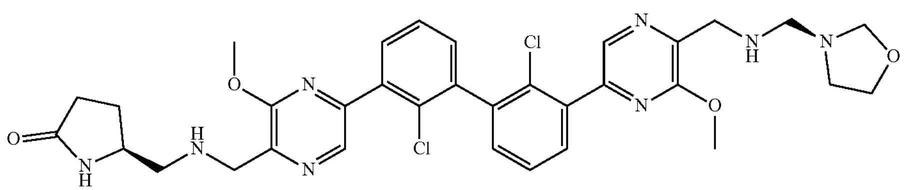 | 678.23 | 2 |
| 300 | 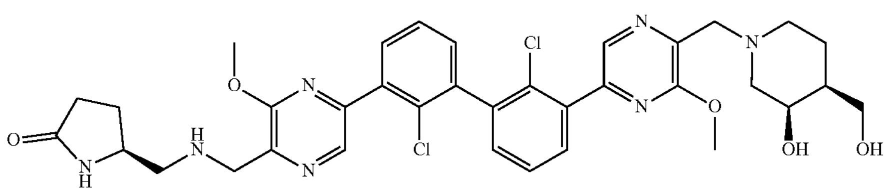 [SMILES: COc1nc(-c2cccc(-c3cccc(-c4cnc(CN5CC[C@@H](CO)[C@@H](O)C5)c(OC)n4)c3Cl)c2Cl)cnc1CNC[C@@H]1CCC(=O)N1] | 708.2 | 2 |

TABLE 1-continued

| No. | Structure | ES/MS (m/z, M + H+) | Procedure |
|---|---|---|---|
| 301 | 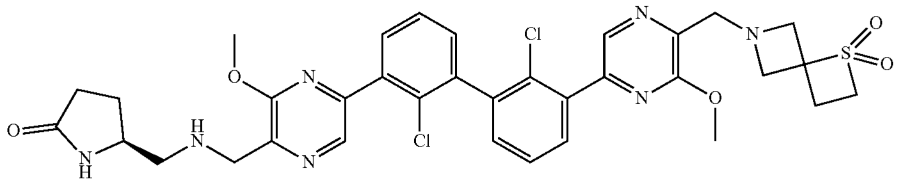 [SMILES: COc1nc(-c2cccc(-c3cccc(-c4cnc(CN5CC6(CCS6(=O)=O)C5)c(OC)n4)c3Cl)c2Cl)cnc1CNC[C@@H]1CCC(=O)N1] | 724.11 | 2 |
| 302 | 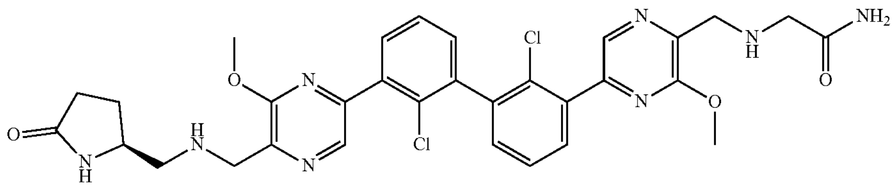 [SMILES: COc1nc(-c2cccc(-c3cccc(-c4cnc(CNC[C@@H]5CCC(=O)N5)c(OC)n4)c3Cl)c2Cl)cnc1CNCC(N)=O] | 651.04 | 2 |
| 303 | 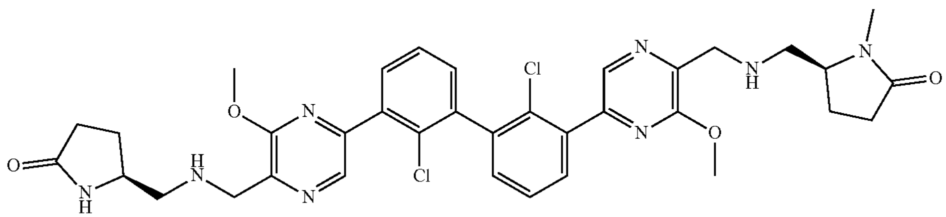 [SMILES: COc1nc(-c2cccc(-c3cccc(-c4cnc(CNC[C@@H]5CCC(=O)N5C)c(OC)n4)c3Cl)c2Cl)cnc1CNC[C@@H]1CCC(=O)N1] | 705.15 | 2 |
| 304 | 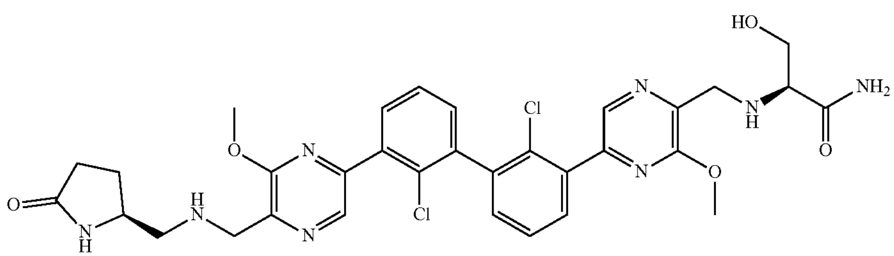 [SMILES: COc1nc(-c2cccc(-c3cccc(-c4cnc(CN[C@@H](CO)C(N)=O)c(OC)n4)c3Cl)c2Cl)cnc1CNC[C@@H]1CCC(=O)N1] | 681.1 | 2 |

TABLE 1-continued

| No. | Structure | ES/MS (m/z, M + H+) | Procedure |
|---|---|---|---|
| 305 | 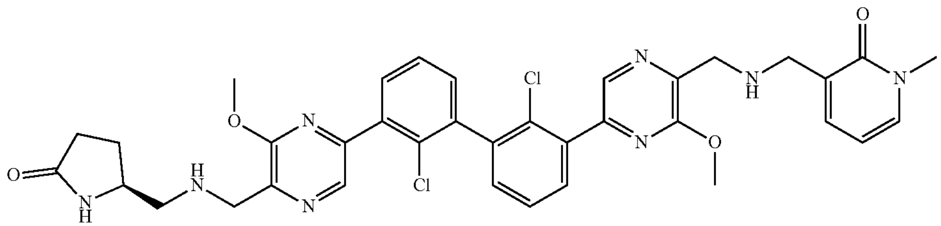 [SMILES: COc1nc(-c2cccc(-c3cccc(-c4cnc(CNC[C@@H]5CCC(=O)N5)c(OC)n4)c3Cl)c2Cl)cnc1CNCc1cccn(C)c1=O] | 715.08 | 2 |
| 306 | 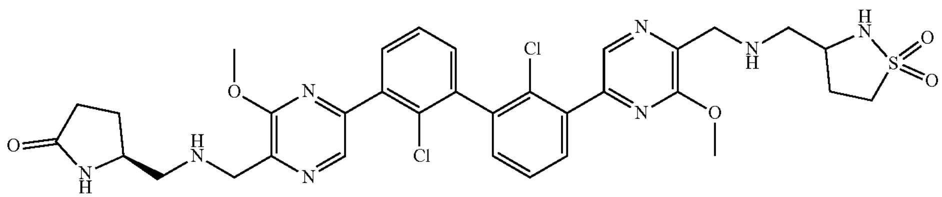 [SMILES: COc1nc(-c2cccc(-c3cccc(-c4cnc(CNC[C@@H]5CCC(=O)N5)c(OC)n4)c3Cl)c2Cl)cnc1CNCC1CCS(=O)(=O)N1] | 727.03 | 2 |
| 307 | 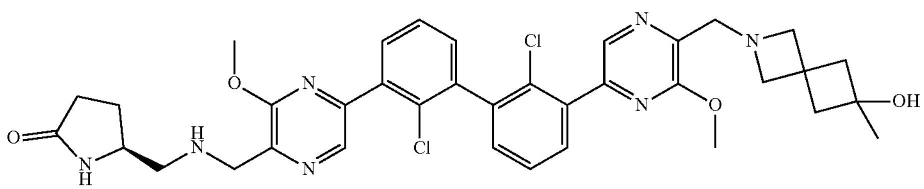 [SMILES: COc1nc(-c2cccc(-c3cccc(-c4cnc(CN5CC6(C5)CC(C)(O)C6)c(OC)n4)c3Cl)c2Cl)cnc1CNC[C@@H]1CCC(=O)N1] | 704.65 | 2 |
| 308 | 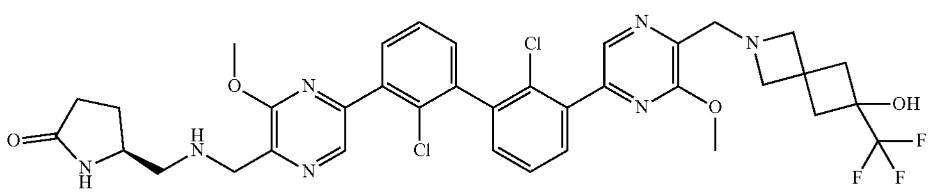 [SMILES: COc1nc(-c2cccc(-c3cccc(-c4cnc(CN5CC6(C5)CC(O)(C(F)(F)F)C6)c(OC)n4)c3Cl)c2Cl)cnc1CNC[C@@H]1CCC(=O)N1] | 758.14 | 2 |

TABLE 1-continued

| No. | Structure | ES/MS (m/z, M + H⁺) | Procedure |
|-----|-----------|---------------------|-----------|
| 309 | 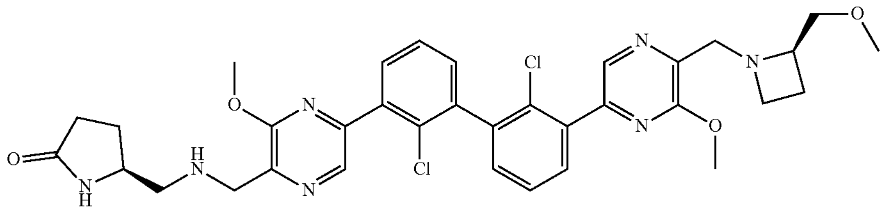 [SMILES: COC[C@H]1CCN1Cc1ncc(-c2cccc(-c3cccc(-c4cnc(CNC[C@@H]5CCC(=O)N5)c(OC)n4)c3Cl)c2Cl)nc1OC] | 678.17 | 2 |
| 310 | 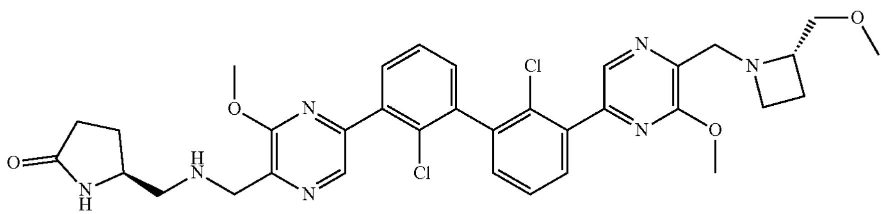 [SMILES: COC[C@@H]1CCN1Cc1ncc(-c2cccc(-c3cccc(-c4cnc(CNC[C@@H]5CCC(=O)N5)c(OC)n4)c3Cl)c2Cl)nc1OC] | 678.17 | 2 |
| 311 | 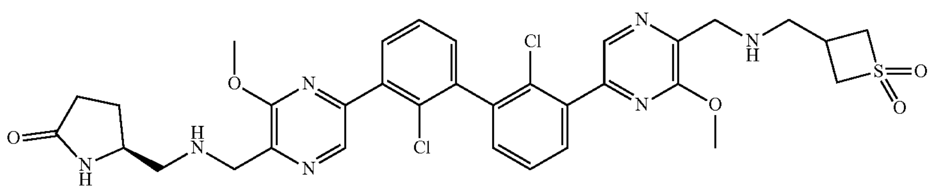 [SMILES: COc1nc(-c2cccc(-c3cccc(-c4cnc(CNC[C@@H]5CCC(=O)N5)c(OC)n4)c3Cl)c2Cl)cnc1CNCC1CS(=O)(=O)C1] | 712.08 | 2 |
| 312 | 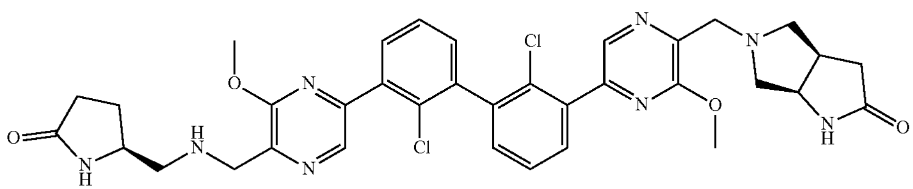 [SMILES: COc1nc(-c2cccc(-c3cccc(-c4cnc(CN5C[C@H]6CC(=O)N[C@H]6C5)c(OC)n4)c3Cl)c2Cl)cnc1CNC[C@@H]1CCC(=O)N1] | 703.14 | 2 |
| 313 | 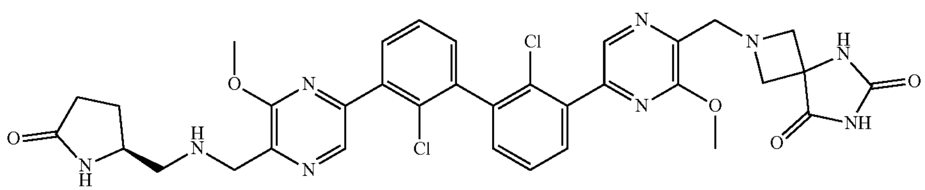 [SMILES: COc1nc(-c2cccc(-c3cccc(-c4cnc(CN5CC6(C5)NC(=O)NC6=O)c(OC)n4)c3Cl)c2Cl)cnc1CNC[C@@H]1CCC(=O)N1] | 708.08 | 2 |

TABLE 1-continued
| No. | Structure | ES/MS (m/z, M + H⁺) | Procedure |
|-----|-----------|---------------------|-----------|
| 314 | 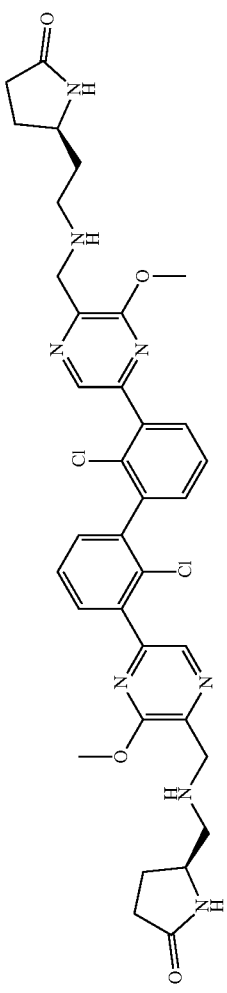 | 705.15 | 2 |
| 315 | 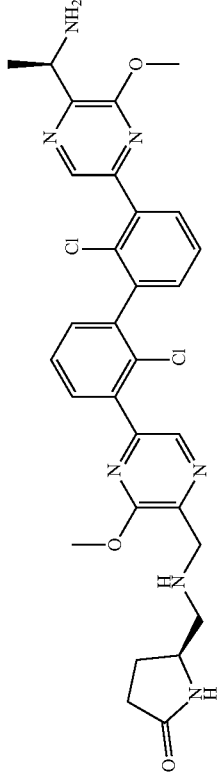 | 608.2 | 15 |
| 316 | 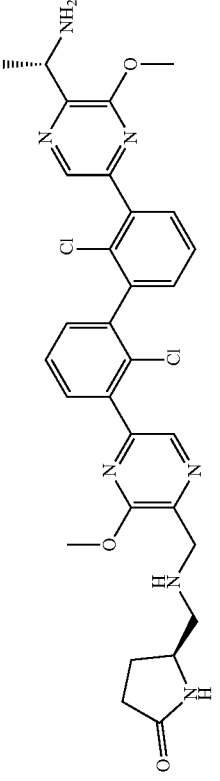 | 608.2 | 15 |
| 317 | 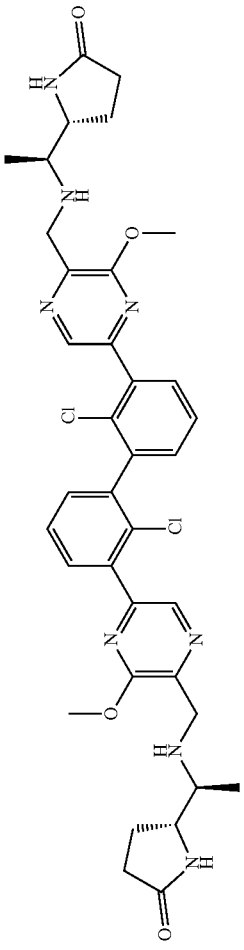 | 719.7 | 3 |

TABLE 1-continued

| No. | Structure | ES/MS (m/z, M + H⁺) | Procedure |
|-----|-----------|---------------------|-----------|
| 318 | 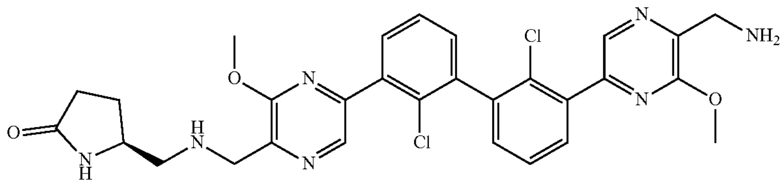 [SMILES: COc1nc(-c2cccc(-c3cccc(-c4cnc(CNC[C@@H]5CCC(=O)N5)c(OC)n4)c3Cl)c2Cl)cnc1CN] | 594.2 | 2 |
| 319 | 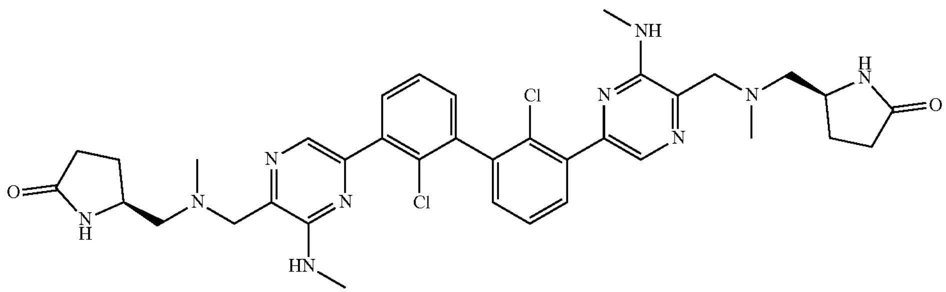 [SMILES: CNc1nc(-c2cccc(-c3cccc(-c4cnc(CN(C)C[C@@H]5CCC(=O)N5)c(NC)n4)c3Cl)c2Cl)cnc1CN(C)C[C@@H]1CCC(=O)N1] | 717.3 | 20 |
| 320 | 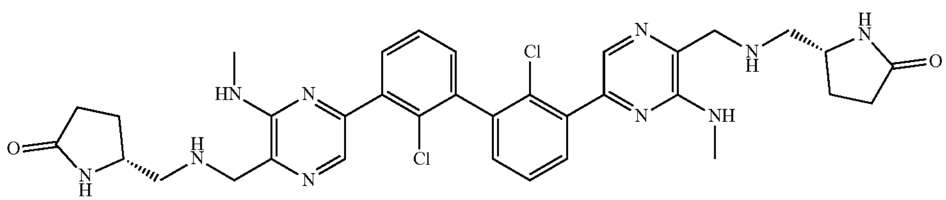 [SMILES: CNc1nc(-c2cccc(-c3cccc(-c4cnc(CNC[C@H]5CCC(=O)N5)c(NC)n4)c3Cl)c2Cl)cnc1CNC[C@H]1CCC(=O)N1] | 689.3 | 4 |
| 321 | 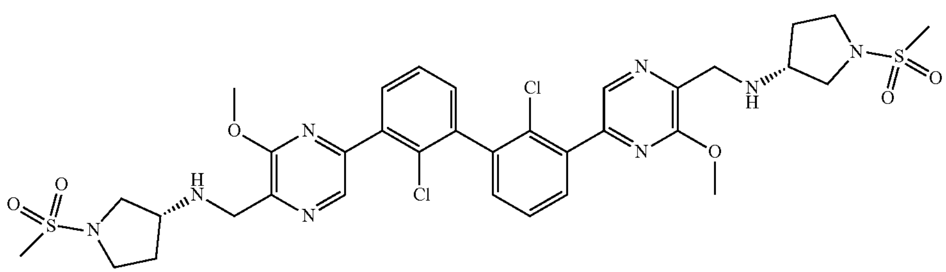 [SMILES: COc1nc(-c2cccc(-c3cccc(-c4cnc(CN[C@@H]5CCN(S(C)(=O)=O)C5)c(OC)n4)c3Cl)c2Cl)cnc1CN[C@@H]1CCN(S(C)(=O)=O)C1] | 791.2 | 3 |

TABLE 1-continued

| No. | Structure | ES/MS (m/z, M + H⁺) | Procedure |
|---|---|---|---|
| 322 | 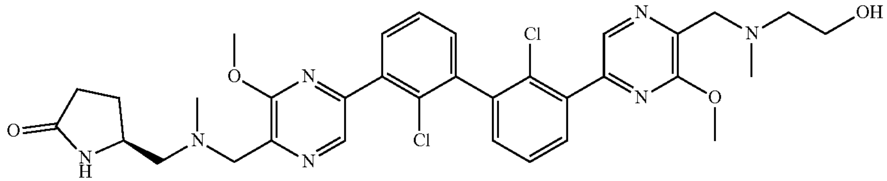 [SMILES: COc1nc(-c2cccc(-c3cccc(-c4cnc(CN(C)C[C@@H]5CCC(=O)N5)c(OC)n4)c3Cl)c2Cl)cnc1CN(C)CCO] | 666.2 | 2 |
| 323 | 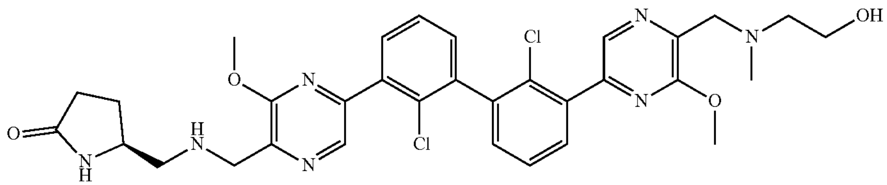 [SMILES: COc1nc(-c2cccc(-c3cccc(-c4cnc(CN(C)CCO)c(OC)n4)c3Cl)c2Cl)cnc1CNC[C@@H]1CCC(=O)N1] | 652.2 | 2 |
| 324 | 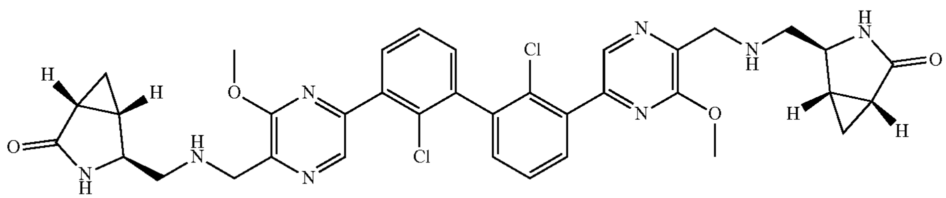 [SMILES: COc1nc(-c2cccc(-c3cccc(-c4cnc(CNC[C@H]5NC(=O)[C@@H]6C[C@H]56)c(OC)n4)c3Cl)c2Cl)cnc1CNC[C@H]1NC(=O)[C@@H]2C[C@H]12] | 715.2 | 3 |
| 325 | 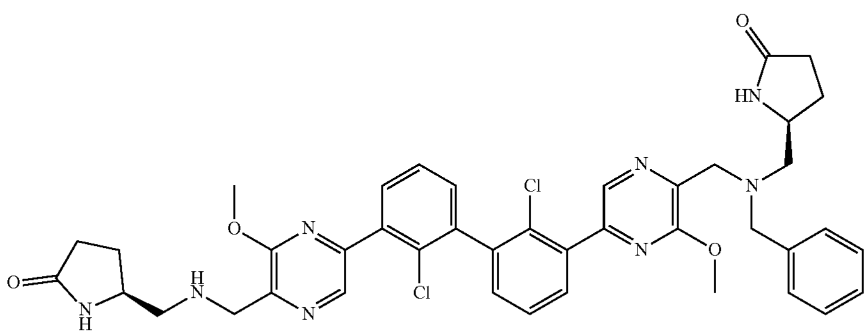 [SMILES: COc1nc(-c2cccc(-c3cccc(-c4cnc(CN(Cc5ccccc5)C[C@@H]5CCC(=O)N5)c(OC)n4)c3Cl)c2Cl)cnc1CNC[C@@H]1CCC(=O)N1] | 781.3 | 2 |

TABLE 1-continued

| No. | Structure | ES/MS (m/z, M + H⁺) | Procedure |
|---|---|---|---|
| 326 | 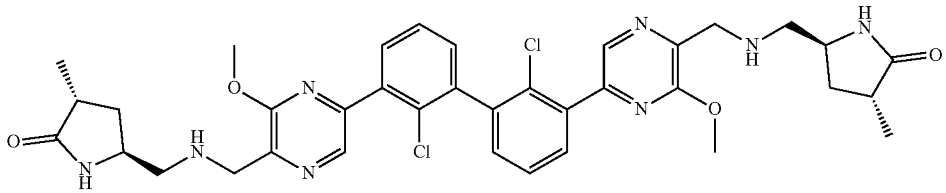 [SMILES: COc1nc(-c2cccc(-c3cccc(-c4cnc(CNC[C@@H]5C[C@@H](C)C(=O)N5)c(OC)n4)c3Cl)c2Cl)cnc1CNC[C@@H]1C[C@@H](C)C(=O)N1] | 719.3 | 3 |
| 327 | 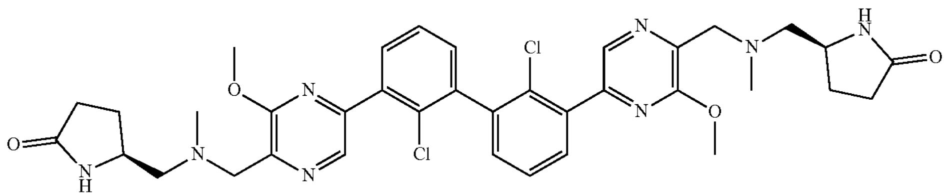 [SMILES: COc1nc(-c2cccc(-c3cccc(-c4cnc(CN(C)C[C@@H]5CCC(=O)N5)c(OC)n4)c3Cl)c2Cl)cnc1CN(C)C[C@@H]1CCC(=O)N1] | 719.3 | 3 |
| 328 | 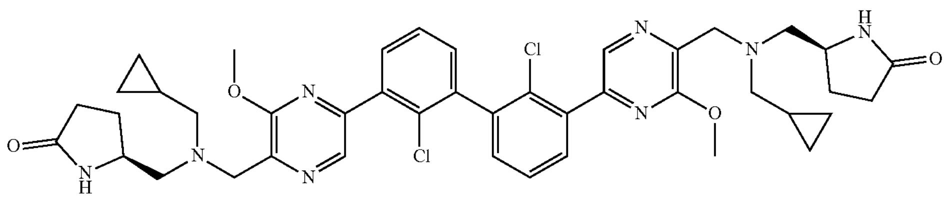 [SMILES: COc1nc(-c2cccc(-c3cccc(-c4cnc(CN(CC5CC5)C[C@@H]5CCC(=O)N5)c(OC)n4)c3Cl)c2Cl)cnc1CN(CC1CC1)C[C@@H]1CCC(=O)N1] | 799.3 | 3 |
| 329 | 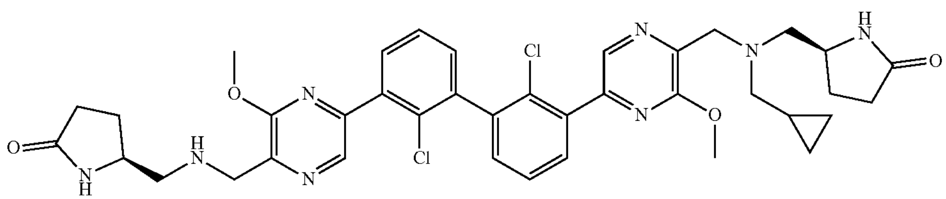 [SMILES: COc1nc(-c2cccc(-c3cccc(-c4cnc(CN(CC5CC5)C[C@@H]5CCC(=O)N5)c(OC)n4)c3Cl)c2Cl)cnc1CNC[C@@H]1CCC(=O)N1] | 744.3 | 2 |

TABLE 1-continued

| No. | Structure | ES/MS (m/z, M + H+) | Procedure |
|---|---|---|---|
| 330 | 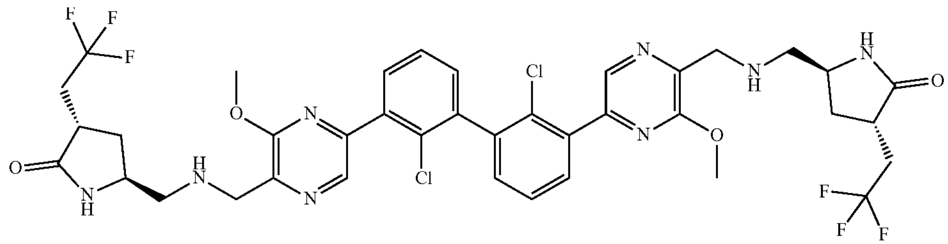 [SMILES: COc1nc(-c2cccc(-c3cccc(-c4cnc(CNC[C@@H]5C[C@@H](CC(F)(F)F)C(=O)N5)c(OC)n4)c3Cl)c2Cl)cnc1CNC[C@@H]1C[C@@H](CC(F)(F)F)C(=O)N1] | 855.2 | 3 |
| 331 | 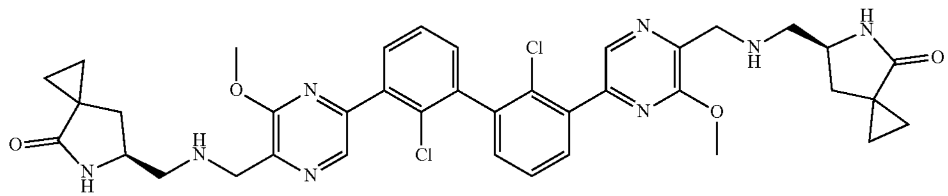 [SMILES: COc1nc(-c2cccc(-c3cccc(-c4cnc(CNC[C@@H]5CC6(CC6)C(=O)N5)c(OC)n4)c3Cl)c2Cl)cnc1CNC[C@@H]1CC2(CC2)C(=O)N1] | 743.3 | 3 |
| 332 | 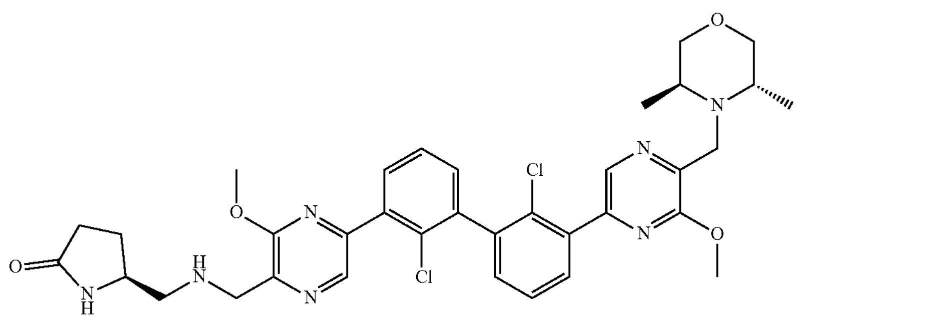 [SMILES: COc1nc(-c2cccc(-c3cccc(-c4cnc(CN5[C@@H](C)COC[C@@H]5C)c(OC)n4)c3Cl)c2Cl)cnc1CNC[C@@H]1CCC(=O)N1] | 692.2 | 2 |
| 333 | 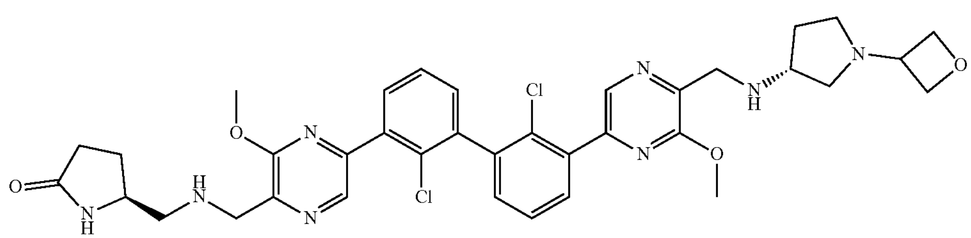 [SMILES: COc1nc(-c2cccc(-c3cccc(-c4cnc(CN[C@@H]5CCN(C6COC6)C5)c(OC)n4)c3Cl)c2Cl)cnc1CNC[C@@H]1CCC(=O)N1] | 719.3 | 2 |

TABLE 1-continued

| No. | Structure | ES/MS (m/z, M + H⁺) | Procedure |
|---|---|---|---|
| 334 | 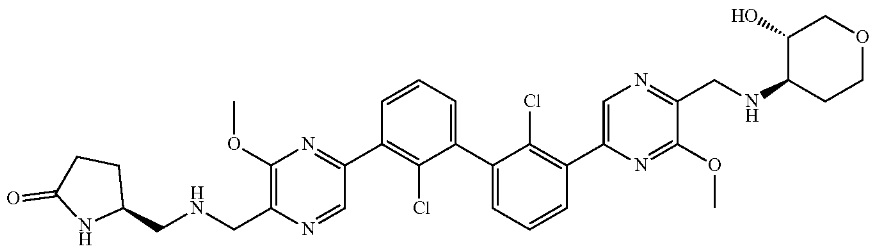 [SMILES: COc1nc(-c2cccc(-c3cccc(-c4cnc(CN[C@@H]5CCOC[C@H]5O)c(OC)n4)c3Cl)c2Cl)cnc1CNC[C@@H]1CCC(=O)N1] | 694.2 | 2 |
| 335 | 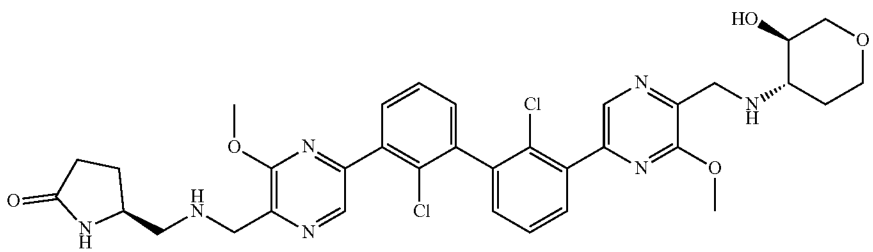 [SMILES: COc1nc(-c2cccc(-c3cccc(-c4cnc(CN[C@H]5CCOC[C@@H]5O)c(OC)n4)c3Cl)c2Cl)cnc1CNC[C@@H]1CCC(=O)N1] | 694.2 | 2 |
| 336 | 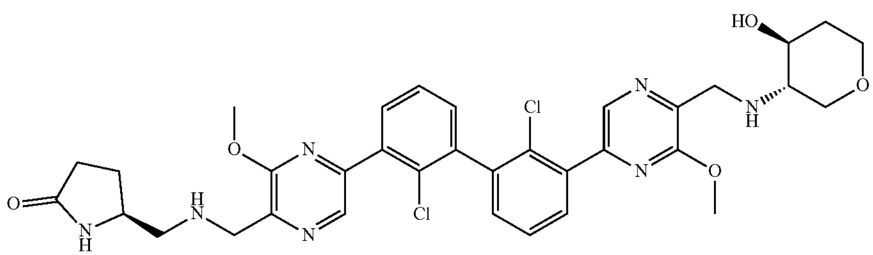 [SMILES: COc1nc(-c2cccc(-c3cccc(-c4cnc(CN[C@H]5COCC[C@@H]5O)c(OC)n4)c3Cl)c2Cl)cnc1CNC[C@@H]1CCC(=O)N1] | 694.2 | 2 |
| 337 | 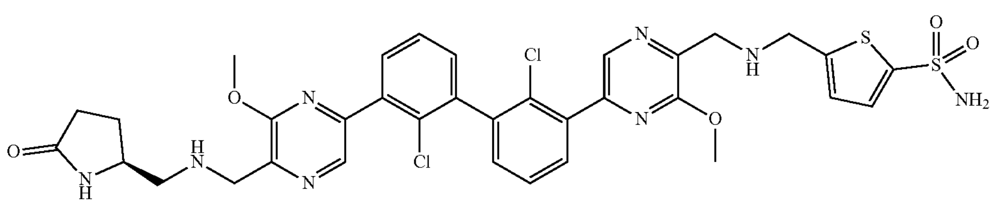 [SMILES: COc1nc(-c2cccc(-c3cccc(-c4cnc(CNC[C@@H]5CCC(=O)N5)c(OC)n4)c3Cl)c2Cl)cnc1CNCc1ccc(S(N)(=O)=O)s1] | 769.2 | 2 |

TABLE 1-continued

| No. | Structure | ES/MS (m/z, M + H⁺) | Procedure |
|---|---|---|---|
| 338 | 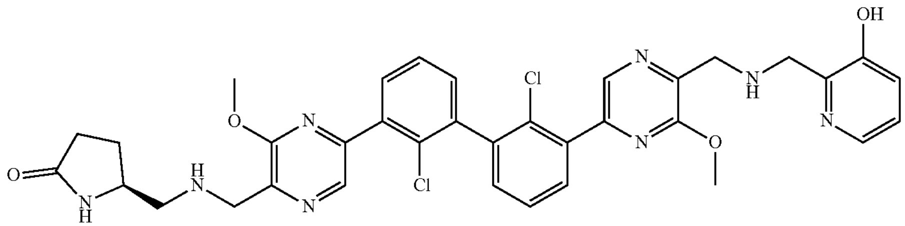 [SMILES: COc1nc(-c2cccc(-c3cccc(-c4cnc(CNC[C@@H]5CCC(=O)N5)c(OC)n4)c3Cl)c2Cl)cnc1CNCc1ncccc1O] | 701.2 | 2 |
| 339 | 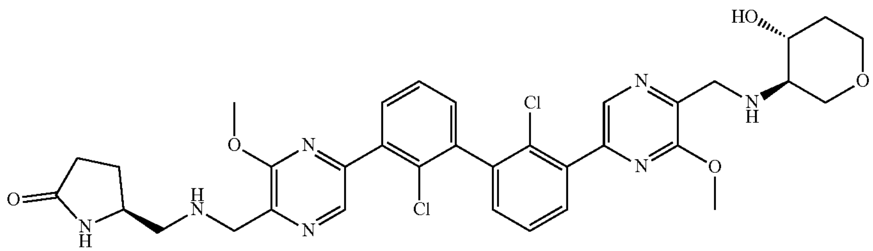 [SMILES: COc1nc(-c2cccc(-c3cccc(-c4cnc(CN[C@@H]5COCC[C@H]5O)c(OC)n4)c3Cl)c2Cl)cnc1CNC[C@@H]1CCC(=O)N1] | 694.2 | 2 |
| 340 | 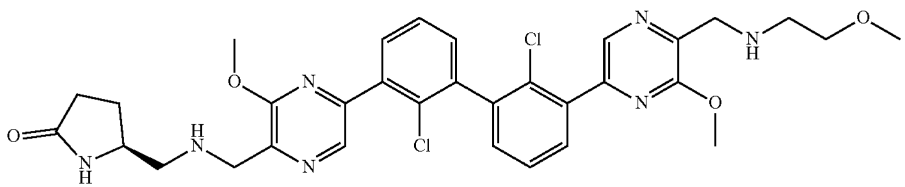 [SMILES: COCCNCc1ncc(-c2cccc(-c3cccc(-c4cnc(CNC[C@@H]5CCC(=O)N5)c(OC)n4)c3Cl)c2Cl)nc1OC] | 652.2 | 2 |
| 341 | 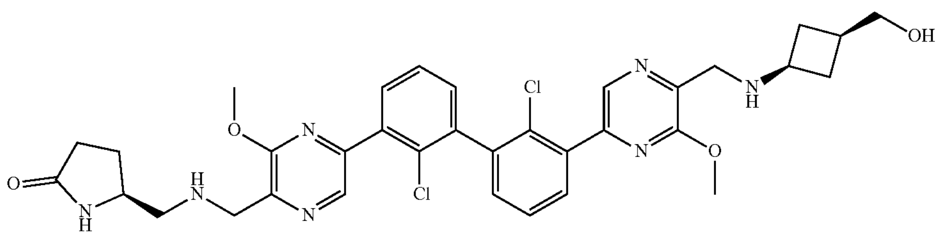 [SMILES: COc1nc(-c2cccc(-c3cccc(-c4cnc(CN[C@H]5C[C@@H](CO)C5)c(OC)n4)c3Cl)c2Cl)cnc1CNC[C@@H]1CCC(=O)N1] | 678.2 | 2 |

TABLE 1-continued

| No. | Structure | ES/MS (m/z, M + H+) | Procedure |
|---|---|---|---|
| 342 | 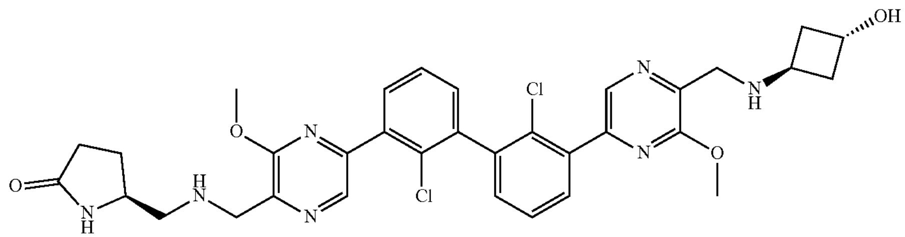 [SMILES: COc1nc(-c2cccc(-c3cccc(-c4cnc(CN[C@H]5C[C@H](O)C5)c(OC)n4)c3Cl)c2Cl)cnc1CNC[C@@H]1CCC(=O)N1] | 664.2 | 2 |
| 343 | 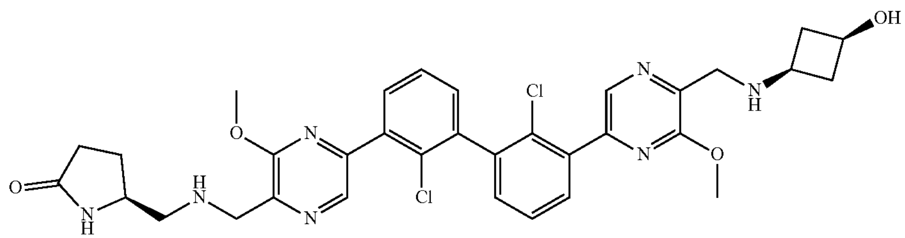 [SMILES: COc1nc(-c2cccc(-c3cccc(-c4cnc(CN[C@H]5C[C@@H](O)C5)c(OC)n4)c3Cl)c2Cl)cnc1CNC[C@@H]1CCC(=O)N1] | 664.2 | 2 |
| 344 | 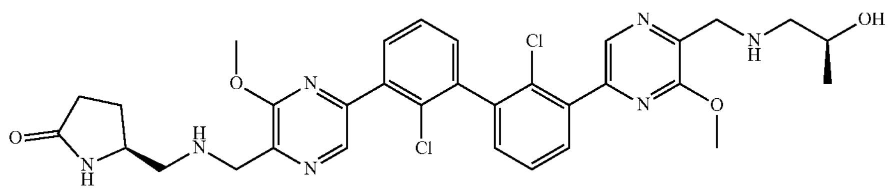 [SMILES: COc1nc(-c2cccc(-c3cccc(-c4cnc(CNC[C@H](C)O)c(OC)n4)c3Cl)c2Cl)cnc1CNC[C@@H]1CCC(=O)N1] | 652.2 | 2 |
| 345 | 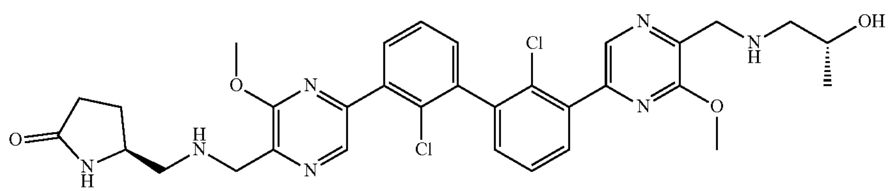 [SMILES: COc1nc(-c2cccc(-c3cccc(-c4cnc(CNC[C@@H](C)O)c(OC)n4)c3Cl)c2Cl)cnc1CNC[C@@H]1CCC(=O)N1] | 652.2 | 2 |

TABLE 1-continued

| No. | Structure | ES/MS (m/z, M + H⁺) | Procedure |
|---|---|---|---|
| 346 | 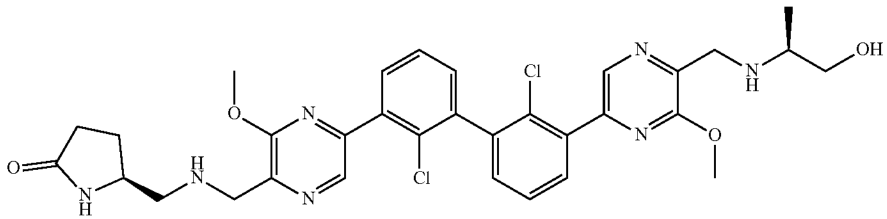 [SMILES: COc1nc(-c2cccc(-c3cccc(-c4cnc(CN[C@@H](C)CO)c(OC)n4)c3Cl)c2Cl)cnc1CNC[C@@H]1CCC(=O)N1] | 652.2 | 2 |
| 347 | 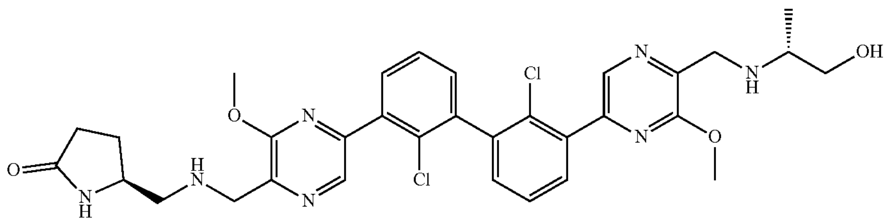 [SMILES: COc1nc(-c2cccc(-c3cccc(-c4cnc(CN[C@H](C)CO)c(OC)n4)c3Cl)c2Cl)cnc1CNC[C@@H]1CCC(=O)N1] | 652.2 | 2 |
| 348 | 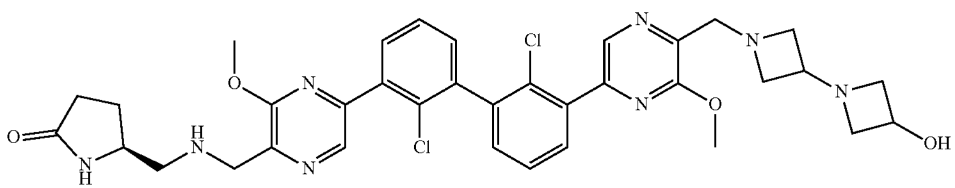 [SMILES: COc1nc(-c2cccc(-c3cccc(-c4cnc(CN5CC(N6CC(O)C6)C5)c(OC)n4)c3Cl)c2Cl)cnc1CNC[C@@H]1CCC(=O)N1] | 705.2 | 2 |
| 349 | 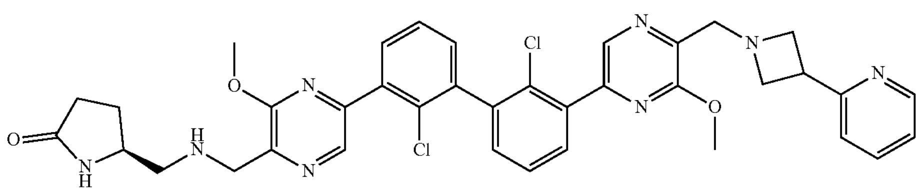 [SMILES: COc1nc(-c2cccc(-c3cccc(-c4cnc(CN5CC(c6ccccn6)C5)c(OC)n4)c3Cl)c2Cl)cnc1CNC[C@@H]1CCC(=O)N1] | 711.2 | 2 |

TABLE 1-continued

| No. | Structure | ES/MS (m/z, M + H⁺) | Procedure |
|---|---|---|---|
| 350 | 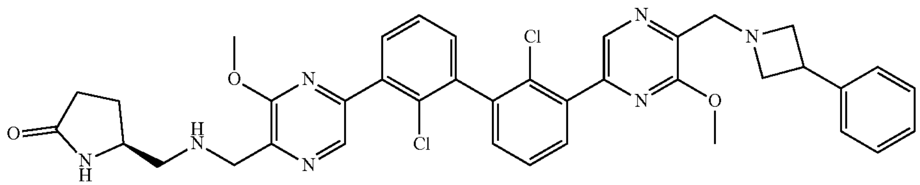 [SMILES: COc1nc(-c2cccc(-c3cccc(-c4cnc(CN5CC(c6ccccc6)C5)c(OC)n4)c3Cl)c2Cl)cnc1CNC[C@@H]1CCC(=O)N1] | 710.2 | 2 |
| 351 | 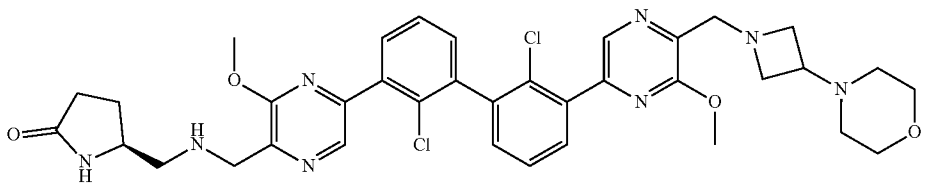 [SMILES: COc1nc(-c2cccc(-c3cccc(-c4cnc(CN5CC(N6CCOCC6)C5)c(OC)n4)c3Cl)c2Cl)cnc1CNC[C@@H]1CCC(=O)N1] | 719.3 | 2 |
| 352 | 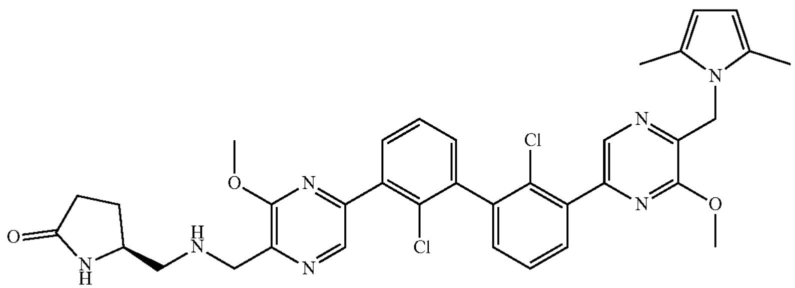 [SMILES: COc1nc(-c2cccc(-c3cccc(-c4cnc(Cn5c(C)ccc5C)c(OC)n4)c3Cl)c2Cl)cnc1CNC[C@@H]1CCC(=O)N1] | 672.2 | 16 |
| 353 | 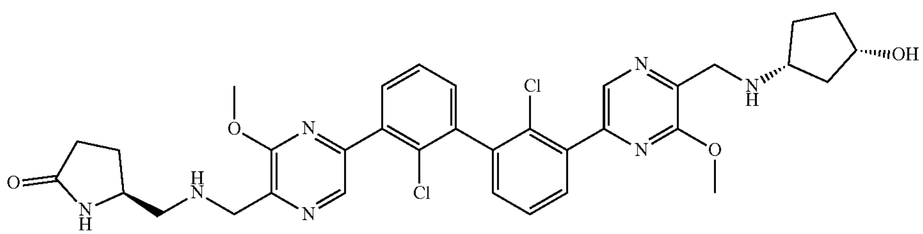 [SMILES: COc1nc(-c2cccc(-c3cccc(-c4cnc(CN[C@@H]5CC[C@H](O)C5)c(OC)n4)c3Cl)c2Cl)cnc1CNC[C@@H]1CCC(=O)N1] | 678.2 | 2 |

TABLE 1-continued

| No. | Structure | ES/MS (m/z, M + H+) | Procedure |
|---|---|---|---|
| 354 | 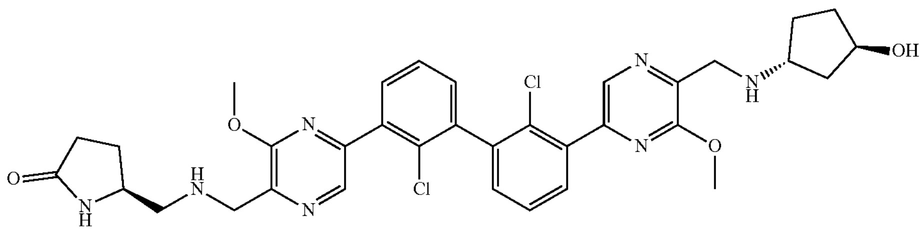 [SMILES: COc1nc(-c2cccc(-c3cccc(-c4cnc(CN[C@@H]5CC[C@@H](O)C5)c(OC)n4)c3Cl)c2Cl)cnc1CNC[C@@H]1CCC(=O)N1] | 678.2 | 2 |
| 355 | 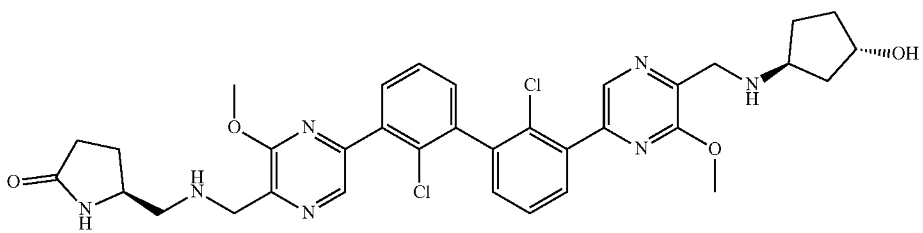 [SMILES: COc1nc(-c2cccc(-c3cccc(-c4cnc(CN[C@H]5CC[C@H](O)C5)c(OC)n4)c3Cl)c2Cl)cnc1CNC[C@@H]1CCC(=O)N1] | 678.2 | 2 |
| 356 | 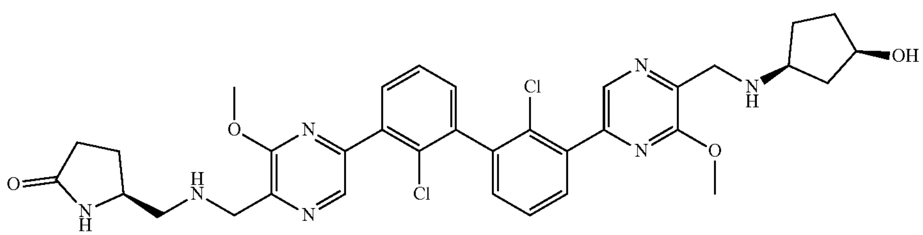 [SMILES: COc1nc(-c2cccc(-c3cccc(-c4cnc(CN[C@H]5CC[C@@H](O)C5)c(OC)n4)c3Cl)c2Cl)cnc1CNC[C@@H]1CCC(=O)N1] | 678.2 | 2 |
| 357 | 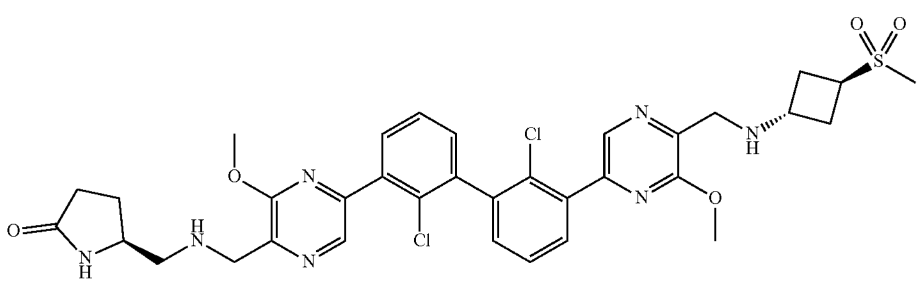 [SMILES: COc1nc(-c2cccc(-c3cccc(-c4cnc(CN[C@H]5C[C@H](S(C)(=O)=O)C5)c(OC)n4)c3Cl)c2Cl)cnc1CNC[C@@H]1CCC(=O)N1] | 726.2 | 2 |

TABLE 1-continued

| No. | Structure | ES/MS (m/z, M + H⁺) | Procedure |
|-----|-----------|---------------------|-----------|
| 358 | 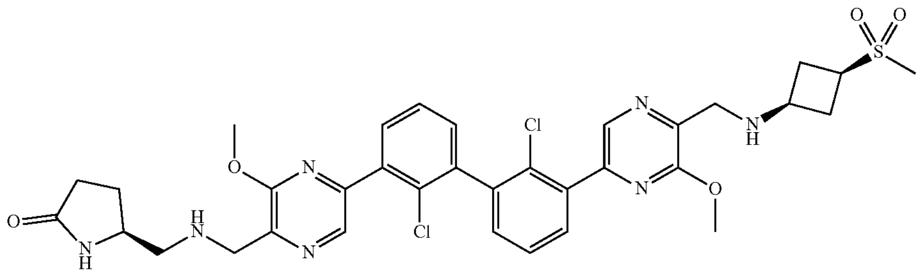 [SMILES: COc1nc(-c2cccc(-c3cccc(-c4cnc(CN[C@H]5C[C@@H](S(C)(=O)=O)C5)c(OC)n4)c3Cl)c2Cl)cnc1CNC[C@@H]1CCC(=O)N1] | 726.2 | 2 |
| 359 | 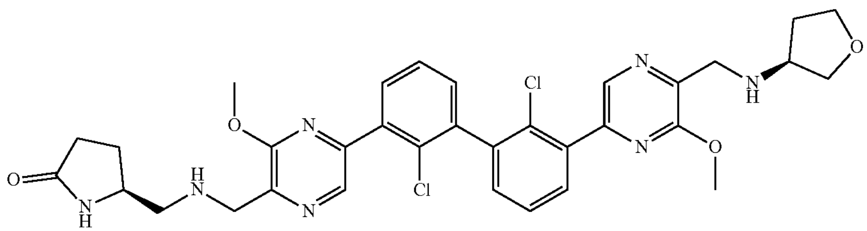 [SMILES: COc1nc(-c2cccc(-c3cccc(-c4cnc(CN[C@H]5CCOC5)c(OC)n4)c3Cl)c2Cl)cnc1CNC[C@@H]1CCC(=O)N1] | 664.2 | 2 |
| 360 | 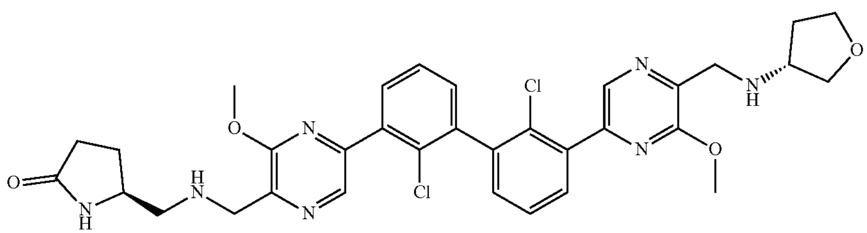 [SMILES: COc1nc(-c2cccc(-c3cccc(-c4cnc(CN[C@@H]5CCOC5)c(OC)n4)c3Cl)c2Cl)cnc1CNC[C@@H]1CCC(=O)N1] | 664.2 | 2 |
| 361 | 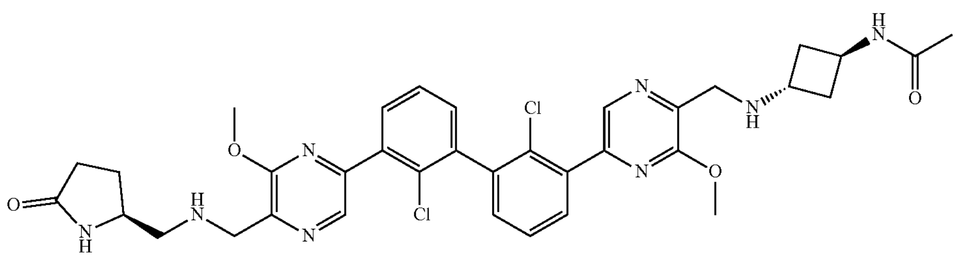 [SMILES: COc1nc(-c2cccc(-c3cccc(-c4cnc(CN[C@H]5C[C@H](NC(C)=O)C5)c(OC)n4)c3Cl)c2Cl)cnc1CNC[C@@H]1CCC(=O)N1] | 705.2 | 2 |

TABLE 1-continued

| No. | Structure | ES/MS (m/z, M + H⁺) | Procedure |
|---|---|---|---|
| 362 | 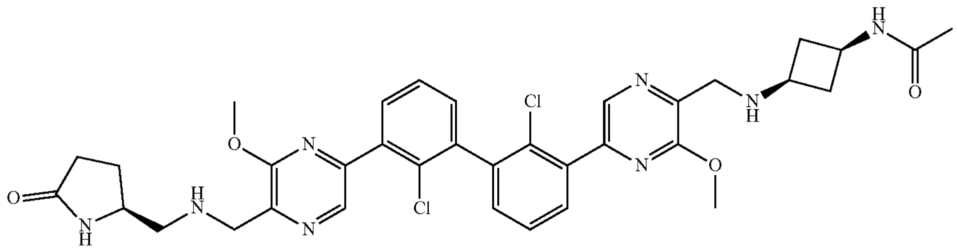 [SMILES: COc1nc(-c2cccc(-c3cccc(-c4cnc(CN[C@H]5C[C@@H](NC(C)=O)C5)c(OC)n4)c3Cl)c2Cl)cnc1CNC[C@@H]1CCC(=O)N1] | 705.2 | 2 |
| 363 | 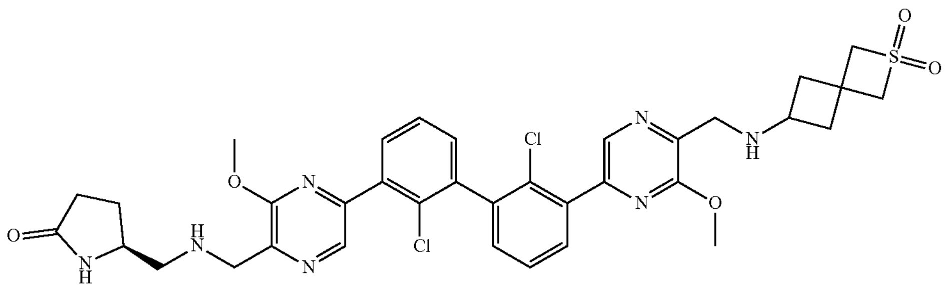 [SMILES: COc1nc(-c2cccc(-c3cccc(-c4cnc(CNC5CC6(C5)CS(=O)(=O)C6)c(OC)n4)c3Cl)c2Cl)cnc1CNC[C@@H]1CCC(=O)N1] | 738.2 | 2 |
| 364 | 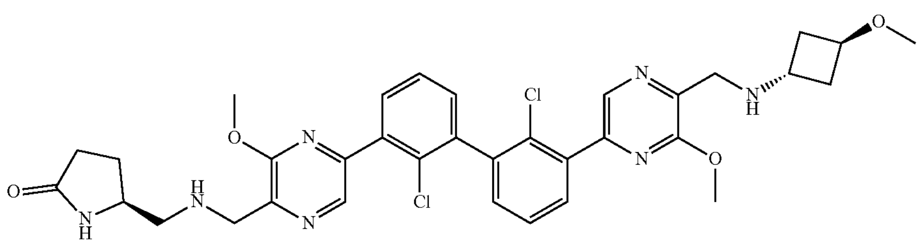 [SMILES: COc1nc(-c2cccc(-c3cccc(-c4cnc(CN[C@H]5C[C@H](OC)C5)c(OC)n4)c3Cl)c2Cl)cnc1CNC[C@@H]1CCC(=O)N1] | 678.2 | 2 |
| 365 | 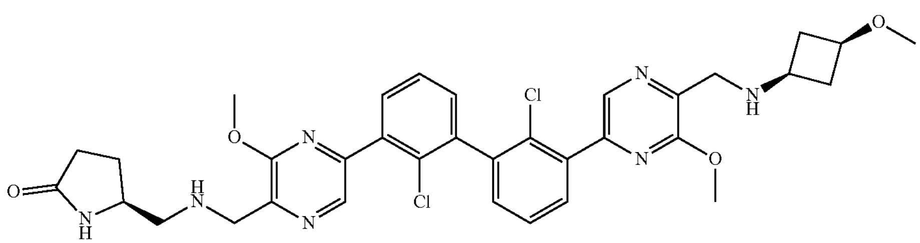 [SMILES: COc1nc(-c2cccc(-c3cccc(-c4cnc(CN[C@H]5C[C@@H](OC)C5)c(OC)n4)c3Cl)c2Cl)cnc1CNC[C@@H]1CCC(=O)N1] | 678.2 | 2 |

TABLE 1-continued

| No. | Structure | ES/MS (m/z, M + H⁺) | Procedure |
|---|---|---|---|
| 366 | 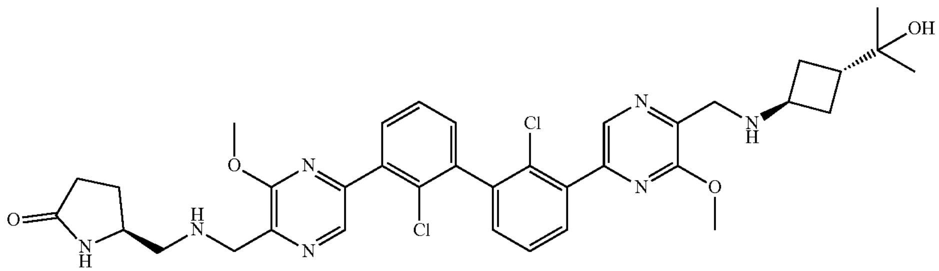 [SMILES: COc1nc(-c2cccc(-c3cccc(-c4cnc(CN[C@H]5C[C@H](C(C)(C)O)C5)c(OC)n4)c3Cl)c2Cl)cnc1CNC[C@@H]1CCC(=O)N1] | 706.3 | 2 |
| 367 | 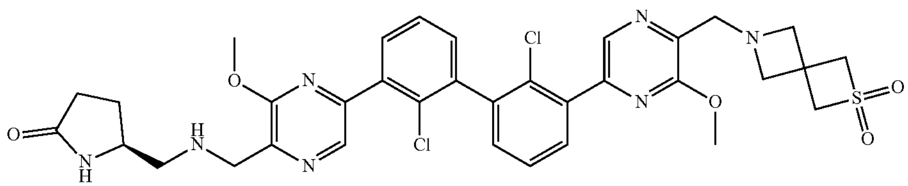 [SMILES: COc1nc(-c2cccc(-c3cccc(-c4cnc(CN5CC6(C5)CS(=O)(=O)C6)c(OC)n4)c3Cl)c2Cl)cnc1CNC[C@@H]1CCC(=O)N1] | 724.2 | 2 |
| 368 | 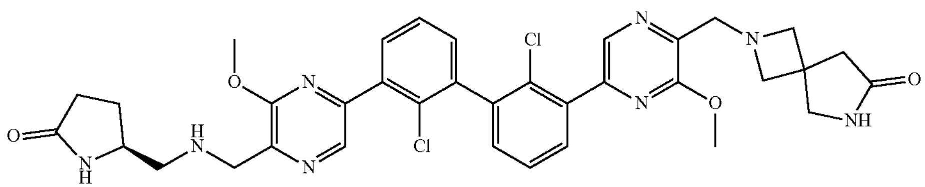 [SMILES: COc1nc(-c2cccc(-c3cccc(-c4cnc(CN5CC6(CNC(=O)C6)C5)c(OC)n4)c3Cl)c2Cl)cnc1CNC[C@@H]1CCC(=O)N1] | 703.2 | 2 |
| 369 | 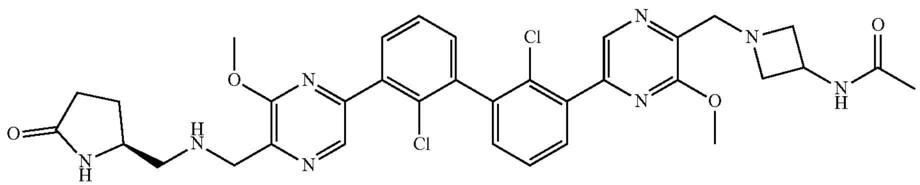 [SMILES: COc1nc(-c2cccc(-c3cccc(-c4cnc(CN5CC(NC(C)=O)C5)c(OC)n4)c3Cl)c2Cl)cnc1CNC[C@@H]1CCC(=O)N1] | 691.2 | 2 |

TABLE 1-continued

| No. | Structure | ES/MS (m/z, M + H+) | Procedure |
|---|---|---|---|
| 370 | 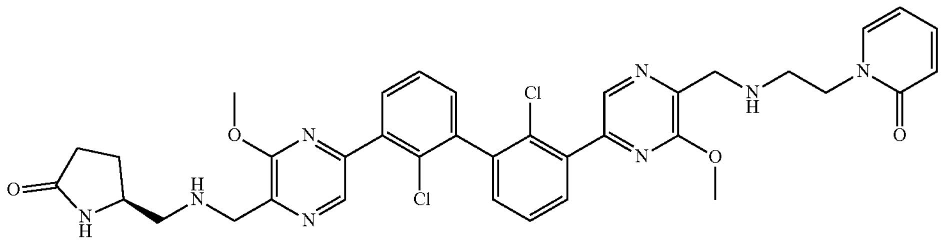 [SMILES: COc1nc(-c2cccc(-c3cccc(-c4cnc(CNC[C@@H]5CCC(=O)N5)c(OC)n4)c3Cl)c2Cl)cnc1CNCCn1ccccc1=O] | 715.2 | 2 |
| 371 | 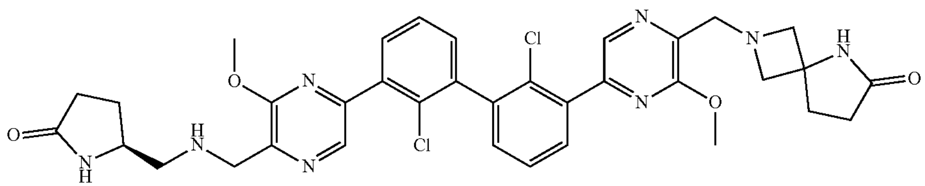 [SMILES: COc1nc(-c2cccc(-c3cccc(-c4cnc(CN5CC6(CCC(=O)N6)C5)c(OC)n4)c3Cl)c2Cl)cnc1CNC[C@@H]1CCC(=O)N1] | 703.2 | 2 |
| 372 | 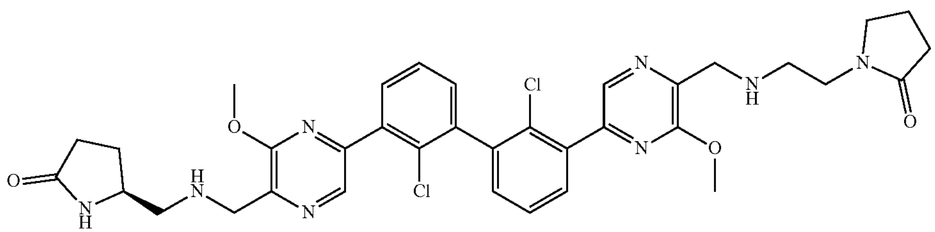 [SMILES: COc1nc(-c2cccc(-c3cccc(-c4cnc(CNC[C@@H]5CCC(=O)N5)c(OC)n4)c3Cl)c2Cl)cnc1CNCCN1CCCC1=O] | 705.2 | 2 |
| 373 | 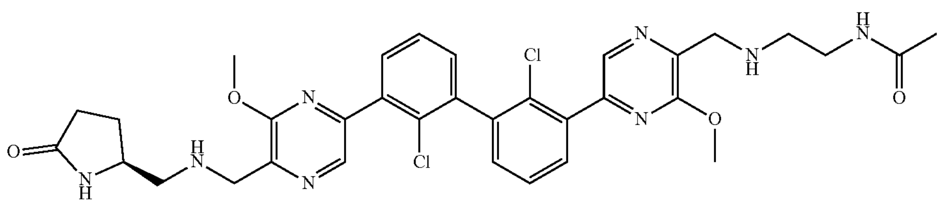 [SMILES: COc1nc(-c2cccc(-c3cccc(-c4cnc(CNC[C@@H]5CCC(=O)N5)c(OC)n4)c3Cl)c2Cl)cnc1CNCCNC(C)=O] | 679.2 | 2 |

TABLE 1-continued

| No. | Structure | ES/MS (m/z, M + H⁺) | Procedure |
|---|---|---|---|
| 374 | 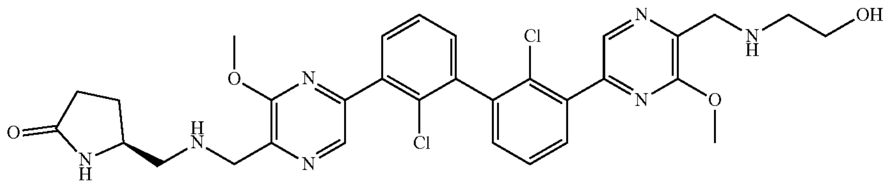 [SMILES: COc1nc(-c2cccc(-c3cccc(-c4cnc(CNC[C@@H]5CCC(=O)N5)c(OC)n4)c3Cl)c2Cl)cnc1CNCCO] | 638.2 | 2 |
| 375 | 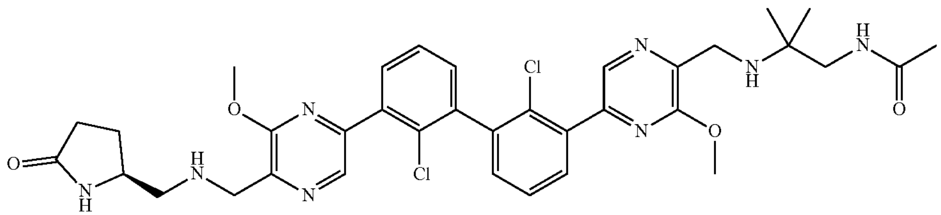 [SMILES: COc1nc(-c2cccc(-c3cccc(-c4cnc(CNC(C)(C)CNC(C)=O)c(OC)n4)c3Cl)c2Cl)cnc1CNC[C@@H]1CCC(=O)N1] | 707.3 | 2 |
| 376 | 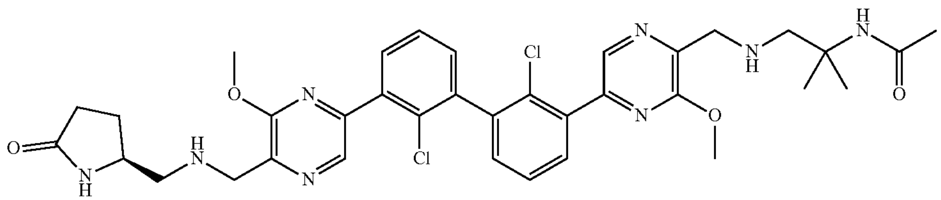 [SMILES: COc1nc(-c2cccc(-c3cccc(-c4cnc(CNCC(C)(C)NC(C)=O)c(OC)n4)c3Cl)c2Cl)cnc1CNC[C@@H]1CCC(=O)N1] | 707.3 | 2 |
| 377 | 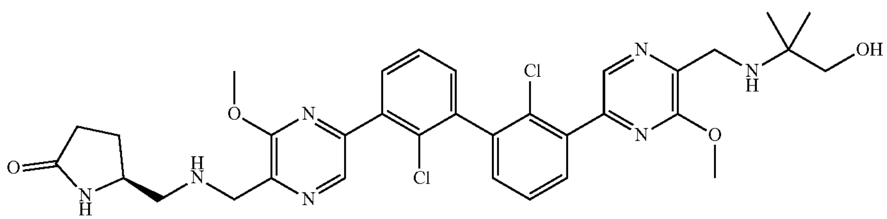 [SMILES: COc1nc(-c2cccc(-c3cccc(-c4cnc(CNC(C)(C)CO)c(OC)n4)c3Cl)c2Cl)cnc1CNC[C@@H]1CCC(=O)N1] | 666.2 | 2 |
| 378 | 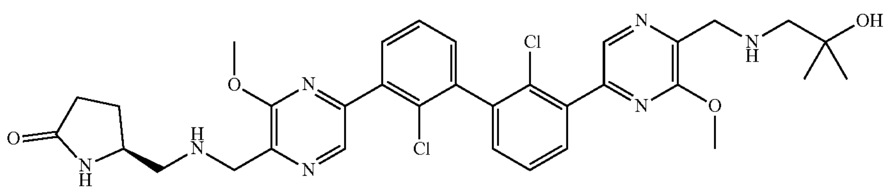 [SMILES: COc1nc(-c2cccc(-c3cccc(-c4cnc(CNCC(C)(C)O)c(OC)n4)c3Cl)c2Cl)cnc1CNC[C@@H]1CCC(=O)N1] | 666.2 | 2 |

TABLE 1-continued

| No. | Structure | ES/MS (m/z, M + H⁺) | Procedure |
|---|---|---|---|
| 379 | 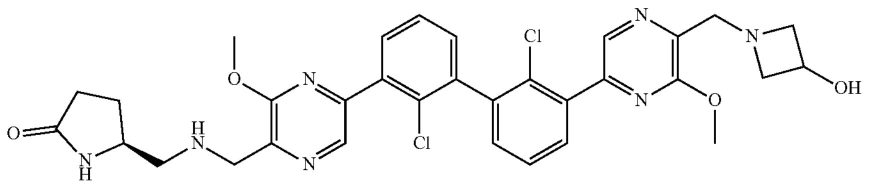 [SMILES: COc1nc(-c2cccc(-c3cccc(-c4cnc(CN5CC(O)C5)c(OC)n4)c3Cl)c2Cl)cnc1CNC[C@@H]1CCC(=O)N1] | 650.2 | 2 |
| 380 | 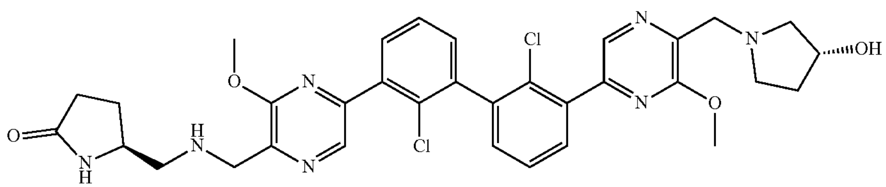 [SMILES: COc1nc(-c2cccc(-c3cccc(-c4cnc(CN5CC[C@@H](O)C5)c(OC)n4)c3Cl)c2Cl)cnc1CNC[C@@H]1CCC(=O)N1] | 664.2 | 2 |
| 381 | 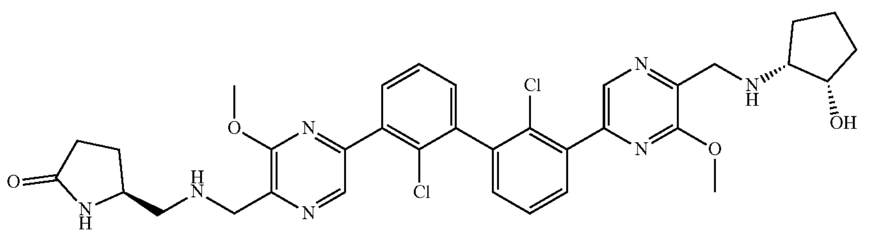 [SMILES: COc1nc(-c2cccc(-c3cccc(-c4cnc(CN[C@@H]5CCC[C@@H]5O)c(OC)n4)c3Cl)c2Cl)cnc1CNC[C@@H]1CCC(=O)N1] | 678.2 | 2 |
| 382 | 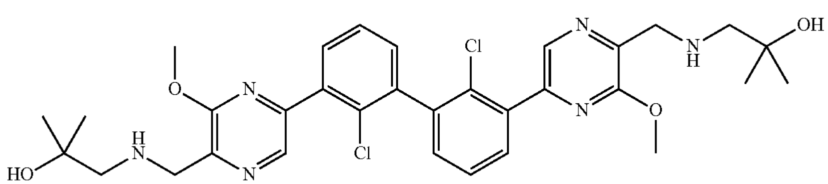 [SMILES: COc1nc(-c2cccc(-c3cccc(-c4cnc(CNCC(C)(C)O)c(OC)n4)c3Cl)c2Cl)cnc1CNCC(C)(C)O] | 641.2 | 3 |

TABLE 1-continued
| No. | Structure | ES/MS (m/z, M + H+) | Procedure |
|---|---|---|---|
| 383 | 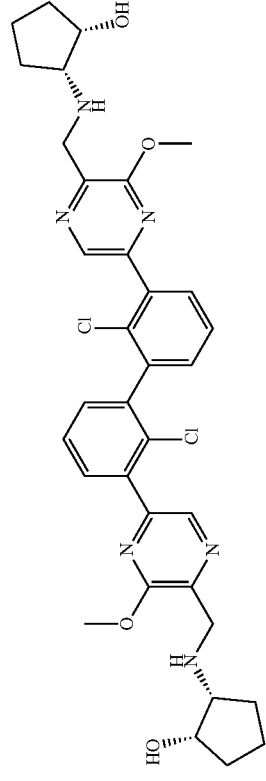 | 665.2 | 3 |
| 384 | 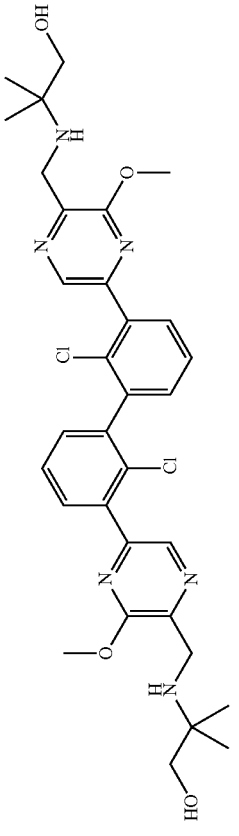 | 641.2 | 3 |
| 385 | 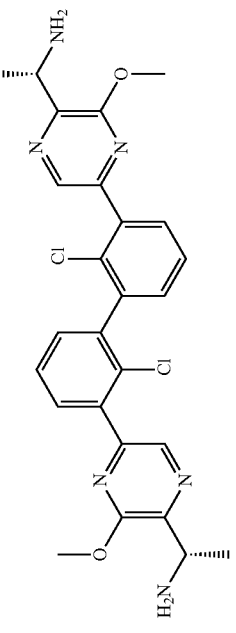 | 525.2 | 15 |
| 386 | 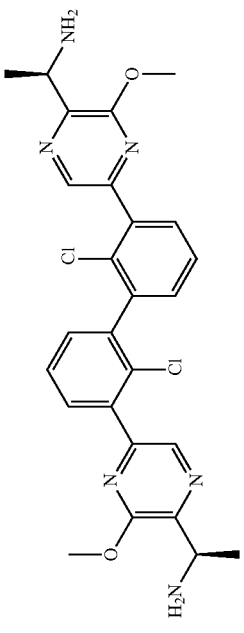 | 525.2 | 15 |

TABLE 1-continued

| No. | Structure | ES/MS (m/z, M + H+) | Procedure |
|---|---|---|---|
| 387 | 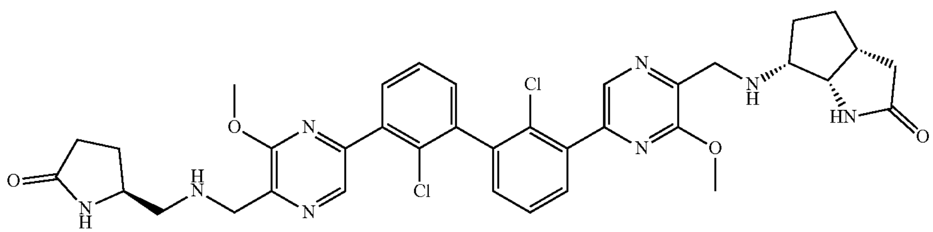 [SMILES: COc1nc(-c2cccc(-c3cccc(-c4cnc(CN[C@@H]5CC[C@@H]6CC(=O)N[C@@H]65)c(OC)n4)c3Cl)c2Cl)cnc1CNC[C@@H]1CCC(=O)N1] | 717.299 | 2 |
| 388 | 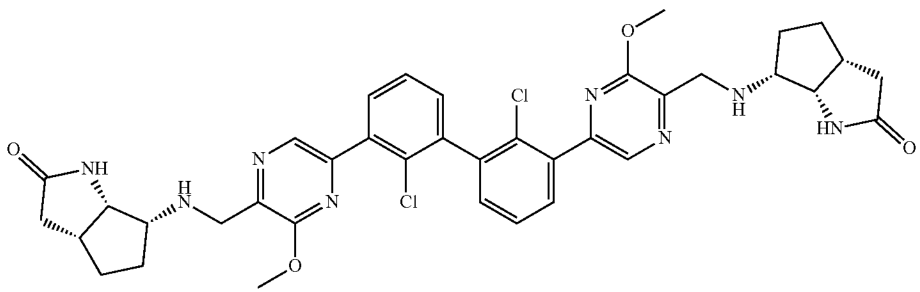 [SMILES: COc1nc(-c2cccc(-c3cccc(-c4cnc(CN[C@@H]5CC[C@@H]6CC(=O)N[C@@H]65)c(OC)n4)c3Cl)c2Cl)cnc1CN[C@@H]1CC[C@@H]2CC(=O)N[C@@H]21] | 765.483 (m/z M + Na+) | 3 |
| 389 | 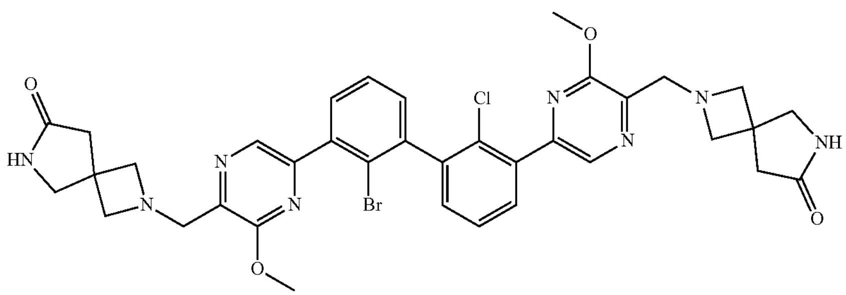 [SMILES: COc1nc(-c2cccc(-c3cccc(-c4cnc(CN5CC6(CNC(=O)C6)C5)c(OC)n4)c3Br)c2Cl)cnc1CN1CC2(CNC(=O)C2)C1] | 761.156 | 17 |

TABLE 1-continued

| No. | Structure | ES/MS (m/z, M + H+) | Procedure |
|---|---|---|---|
| 390 | 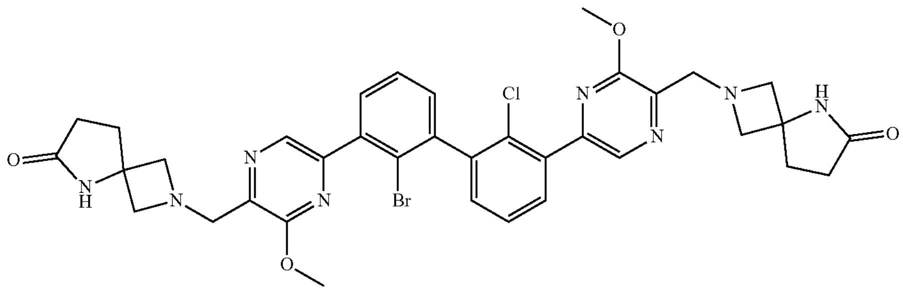 | 761.161 | 17 |
| 391 | 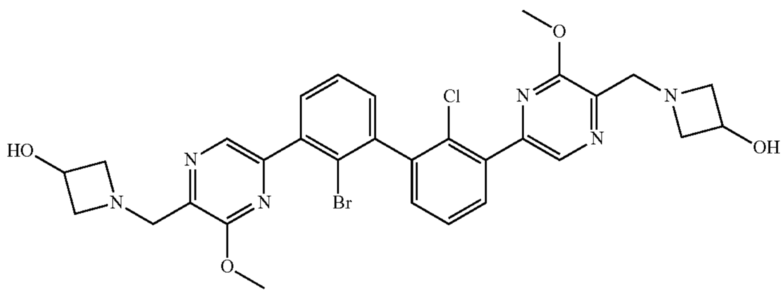 | 653.12 | 17 |
| 392 | 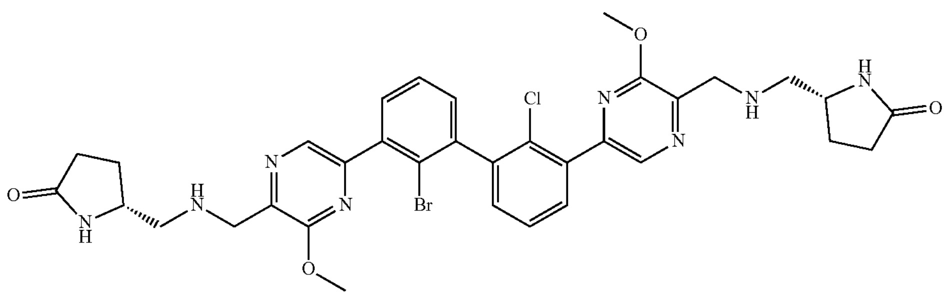 [SMILES: COc1nc(-c2cccc(-c3cccc(-c4cnc(CNC[C@H]5CCC(=O)N5)c(OC)n4)c3Br)c2Cl)cnc1CNC[C@H]1CCC(=O)N1] | 736.104 | 17 |

TABLE 1-continued

| No. | Structure | ES/MS (m/z, M + H+) | Procedure |
|---|---|---|---|
| 393 | 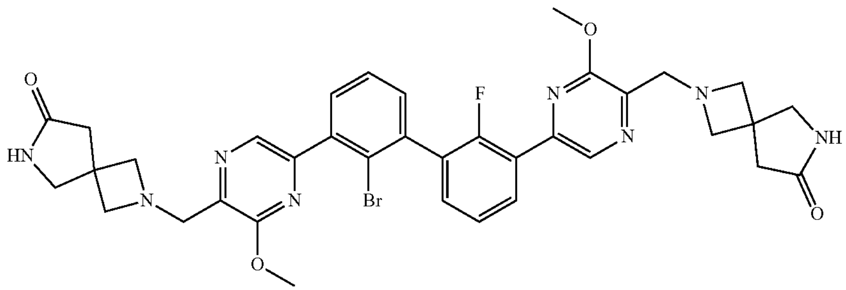 [SMILES: COc1nc(-c2cccc(-c3cccc(-c4cnc(CN5CC6(CNC(=O)C6)C5)c(OC)n4)c3Br)c2F)cnc1CN1CC2(CNC(=O)C2)C1] | 743.096 | 18 |
| 394 | 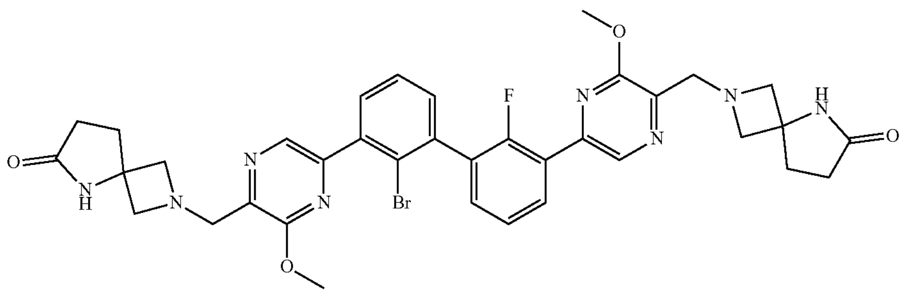 [SMILES: COc1nc(-c2cccc(-c3cccc(-c4cnc(CN5CC6(CCC(=O)N6)C5)c(OC)n4)c3Br)c2F)cnc1CN1CC2(CCC(=O)N2)C1] | 743.268 | 18 |
| 395 | 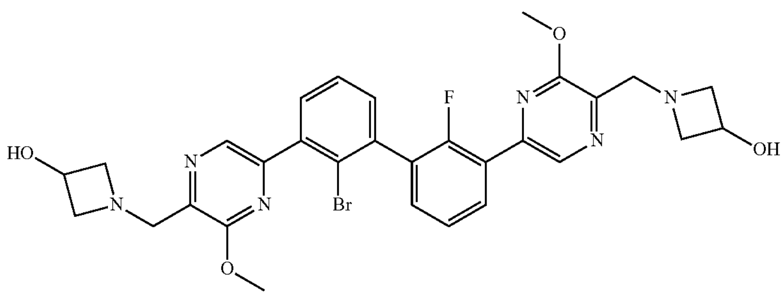 [SMILES: COc1nc(-c2cccc(-c3cccc(-c4cnc(CN5CC(O)C5)c(OC)n4)c3Br)c2F)cnc1CN1CC(O)C1] | 637.69 | 18 |

TABLE 1-continued

| No. | Structure | ES/MS (m/z, M + H+) | Procedure |
|---|---|---|---|
| 396 | 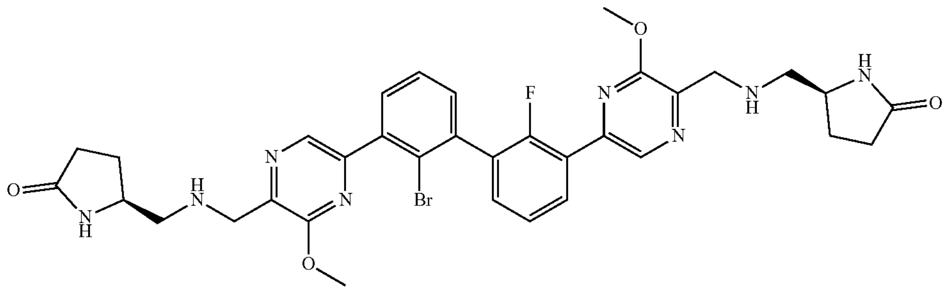 [SMILES: COc1nc(-c2cccc(-c3cccc(-c4cnc(CNC[C@@H]5CCC(=O)N5)c(OC)n4)c3Br)c2F)cnc1CNC[C@@H]1CCC(=O)N1] | 717.045 | 18 |
| 397 | 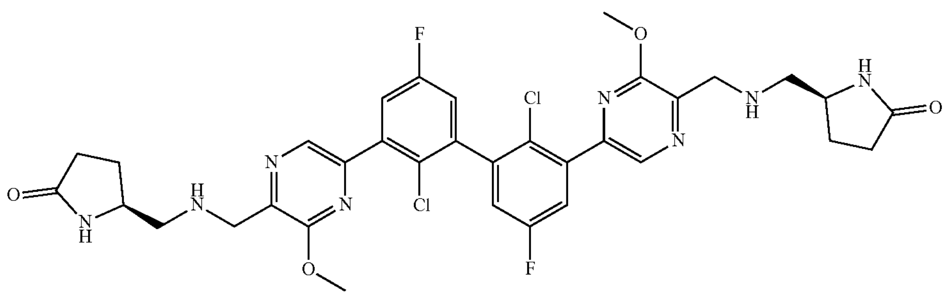 [SMILES: COc1nc(-c2cc(F)cc(-c3cc(F)cc(-c4cnc(CNC[C@@H]5CCC(=O)N5)c(OC)n4)c3Cl)c2Cl)cnc1CNC[C@@H]1CCC(=O)N1] | 727.327 | 19 |
| 398 | 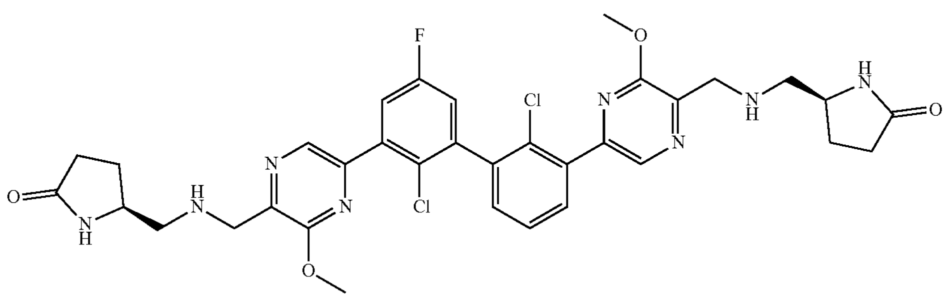 [SMILES: COc1nc(-c2cccc(-c3cc(F)cc(-c4cnc(CNC[C@@H]5CCC(=O)N5)c(OC)n4)c3Cl)c2Cl)cnc1CNC[C@@H]1CCC(=O)N1] | 709.596 | 11 |

TABLE 1-continued
| No. | Structure | ES/MS (m/z, M + H+) | Procedure |
|---|---|---|---|
| 399 | 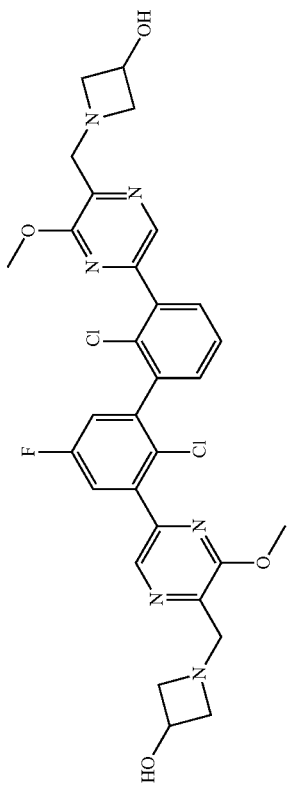 | 627.114 | 11 |
| 400 | 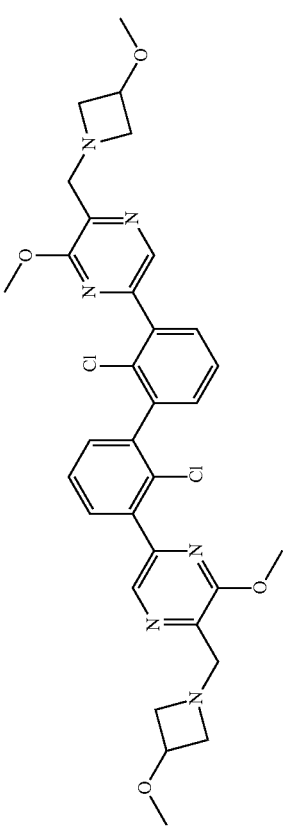 | 637.4 | 3 |
| 401 | 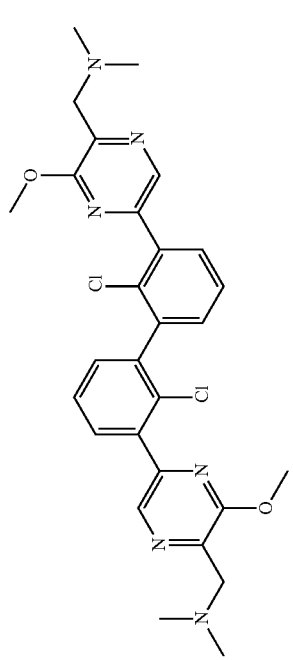 | 553.308 | 3 |

TABLE 1-continued

| No. | Structure | ES/MS (m/z, M + H⁺) | Procedure |
|-----|-----------|---------------------|-----------|
| 402 | 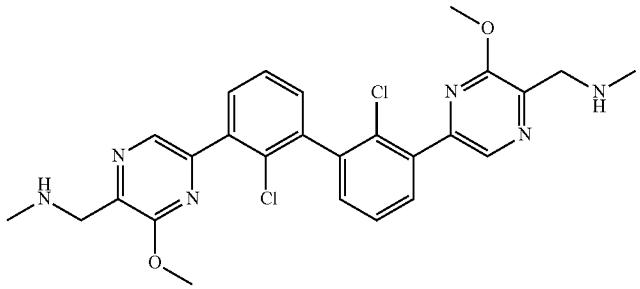 | 525.282 | 3 |
| 403 | 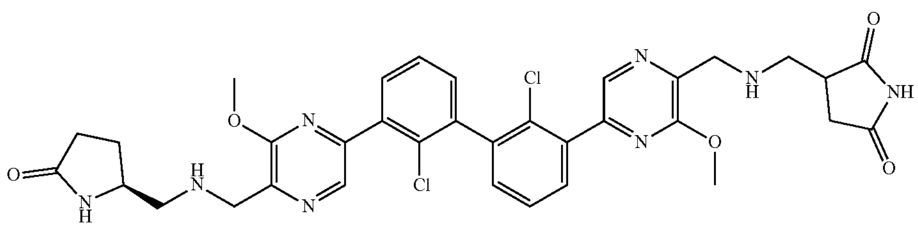 [SMILES: COc1nc(-c2cccc(-c3cccc(-c4cnc(CNC[C@@H]5CCC(=O)N5)c(OC)n4)c3Cl)c2Cl)cnc1CNCC1CC(=O)NC1=O] | 705.2 | 2 |
| 404 | 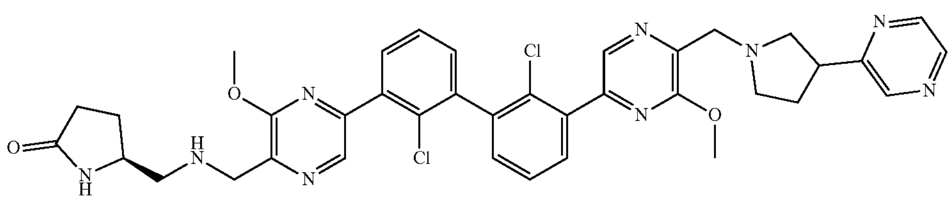 [SMILES: COc1nc(-c2cccc(-c3cccc(-c4cnc(CN5CCC(c6cnccn6)C5)c(OC)n4)c3Cl)c2Cl)cnc1CNC[C@@H]1CCC(=O)N1] | 726.2 | 2 |
| 405 | 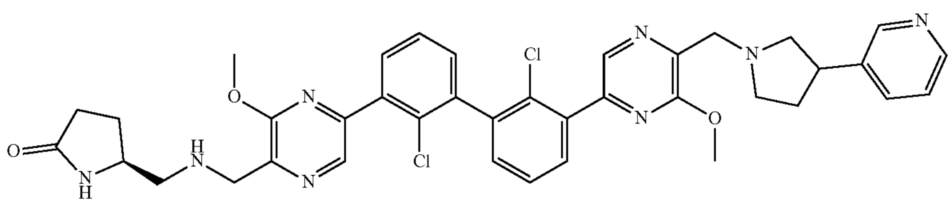 [SMILES: COc1nc(-c2cccc(-c3cccc(-c4cnc(CN5CCC(c6cccnc6)C5)c(OC)n4)c3Cl)c2Cl)cnc1CNC[C@@H]1CCC(=O)N1] | 725.2 | 2 |

TABLE 1-continued

| No. | Structure | ES/MS (m/z, M + H+) | Procedure |
|---|---|---|---|
| 406 | 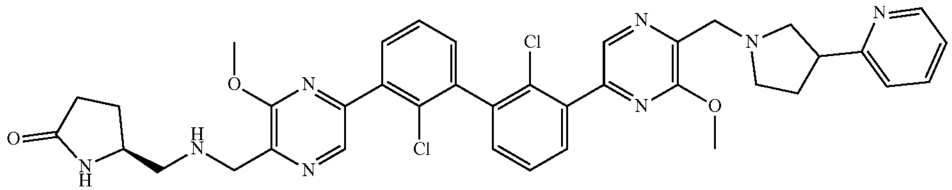 [SMILES: COc1nc(-c2cccc(-c3cccc(-c4cnc(CN5CCC(c6ccccn6)C5)c(OC)n4)c3Cl)c2Cl)cnc1CNC[C@@H]1CCC(=O)N1] | 725.2 | 2 |
| 407 | 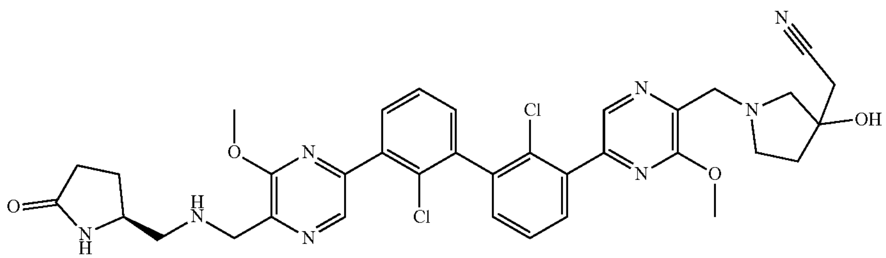 [SMILES: COc1nc(-c2cccc(-c3cccc(-c4cnc(CN5CCC(O)(CC#N)C5)c(OC)n4)c3Cl)c2Cl)cnc1CNC[C@@H]1CCC(=O)N1] | 703.2 | 2 |
| 408 | 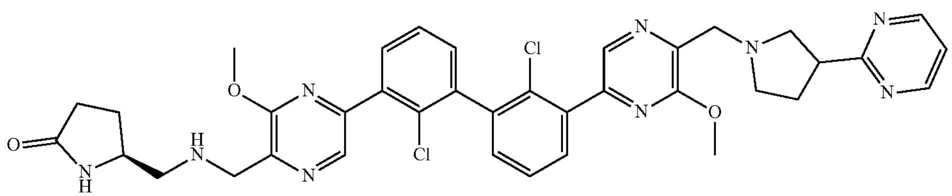 [SMILES: COc1nc(-c2cccc(-c3cccc(-c4cnc(CN5CCC(c6ncccn6)C5)c(OC)n4)c3Cl)c2Cl)cnc1CNC[C@@H]1CCC(=O)N1] | 726.3 | 2 |
| 409 | 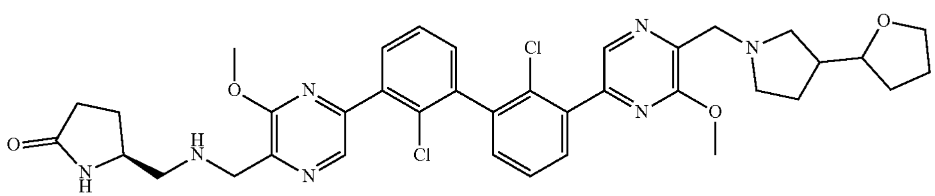 [SMILES: COc1nc(-c2cccc(-c3cccc(-c4cnc(CN5CCC(C6CCCO6)C5)c(OC)n4)c3Cl)c2Cl)cnc1CNC[C@@H]1CCC(=O)N1] | 718.3 | 2 |

TABLE 1-continued

| No. | Structure | ES/MS (m/z, M + H+) | Procedure |
|---|---|---|---|
| 410 | 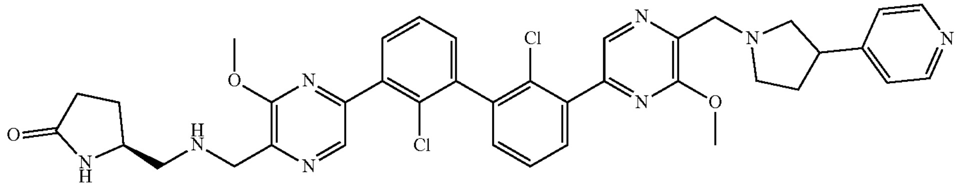 [SMILES: COc1nc(-c2cccc(-c3cccc(-c4cnc(CN5CCC(c6ccncc6)C5)c(OC)n4)c3Cl)c2Cl)cnc1CNC[C@@H]1CCC(=O)N1] | 725.2 | 2 |
| 411 | 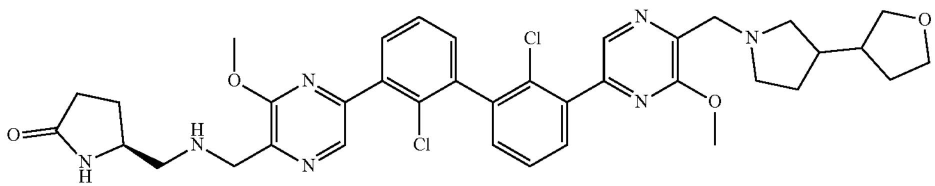 [SMILES: COc1nc(-c2cccc(-c3cccc(-c4cnc(CN5CCC(C6CCOC6)C5)c(OC)n4)c3Cl)c2Cl)cnc1CNC[C@@H]1CCC(=O)N1] | 718.4 | 2 |
| 412 | 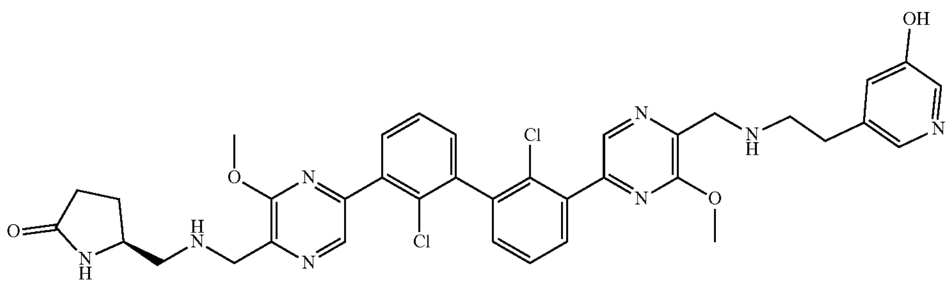 [SMILES: COc1nc(-c2cccc(-c3cccc(-c4cnc(CNC[C@@H]5CCC(=O)N5)c(OC)n4)c3Cl)c2Cl)cnc1CNCCc1cncc(O)c1] | 715.2 | 2 |
| 413 | 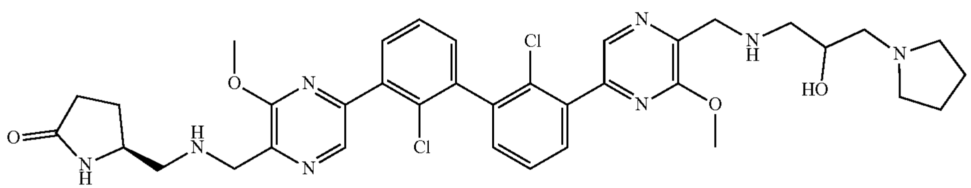 [SMILES: COc1nc(-c2cccc(-c3cccc(-c4cnc(CNC[C@@H]5CCC(=O)N5)c(OC)n4)c3Cl)c2Cl)cnc1CNCC(O)CN1CCCC1] | 721.3 | 2 |

TABLE 1-continued

| No. | Structure | ES/MS (m/z, M + H⁺) | Procedure |
|---|---|---|---|
| 414 | 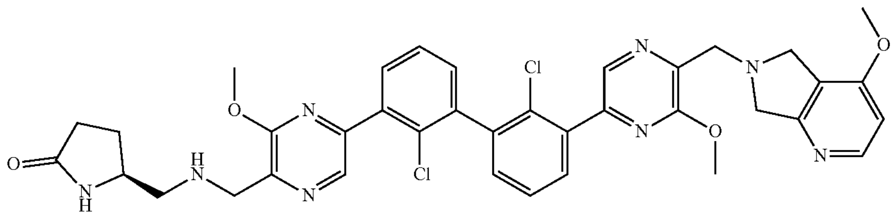 [SMILES: COc1ccnc2c1CN(Cc1ncc(-c3cccc(-c4cccc(-c5cnc(CNC[C@@H]6CCC(=O)N6)c(OC)n5)c4Cl)c3Cl)nc1OC)C2] | 727.1 | 2 |
| 415 | 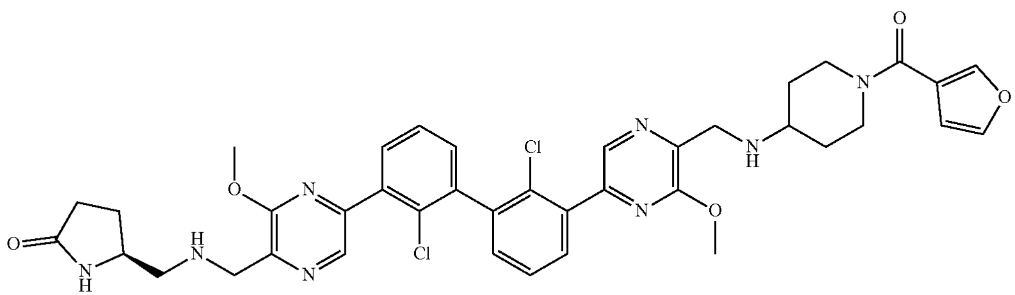 [SMILES: COc1nc(-c2cccc(-c3cccc(-c4cnc(CNC5CCN(C(=O)c6ccoc6)CC5)c(OC)n4)c3Cl)c2Cl)cnc1CNC[C@@H]1CCC(=O)N1] | 771.3 | 2 |
| 416 | 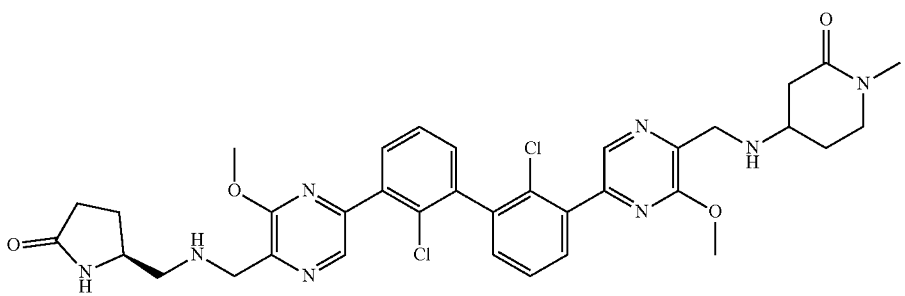 [SMILES: COc1nc(-c2cccc(-c3cccc(-c4cnc(CNC5CCN(C)C(=O)C5)c(OC)n4)c3Cl)c2Cl)cnc1CNC[C@@H]1CCC(=O)N1] | 705 | 2 |

TABLE 1-continued

| No. | Structure | ES/MS (m/z, M + H+) | Procedure |
|---|---|---|---|
| 417 | 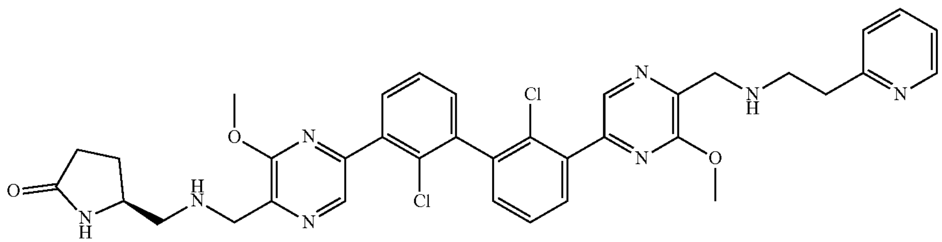 [SMILES: COc1nc(-c2cccc(-c3cccc(-c4cnc(CNC[C@@H]5CCC(=O)N5)c(OC)n4)c3Cl)c2Cl)cnc1CNCCc1ccccn1] | 699.1 | 2 |
| 418 | 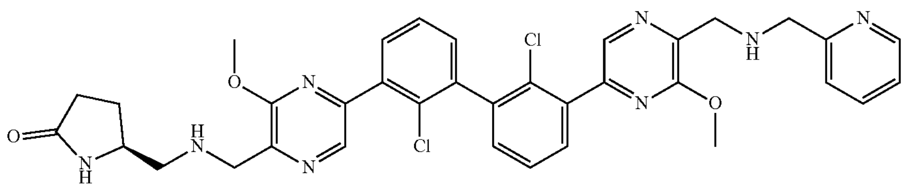 [SMILES: COc1nc(-c2cccc(-c3cccc(-c4cnc(CNC[C@@H]5CCC(=O)N5)c(OC)n4)c3Cl)c2Cl)cnc1CNCc1ccccn1] | 685.1 | 2 |
| 419 | 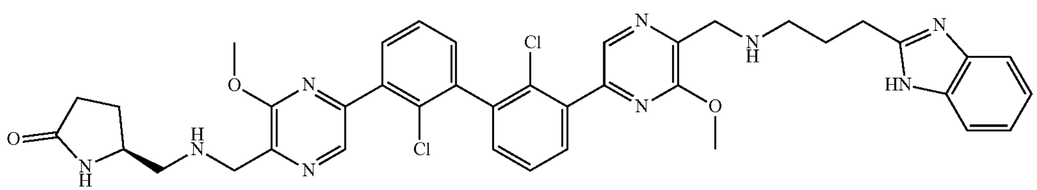 [SMILES: COc1nc(-c2cccc(-c3cccc(-c4cnc(CNC[C@@H]5CCC(=O)N5)c(OC)n4)c3Cl)c2Cl)cnc1CNCCCc1nc2ccccc2[nH]1] | 752.2 | 2 |
| 420 | 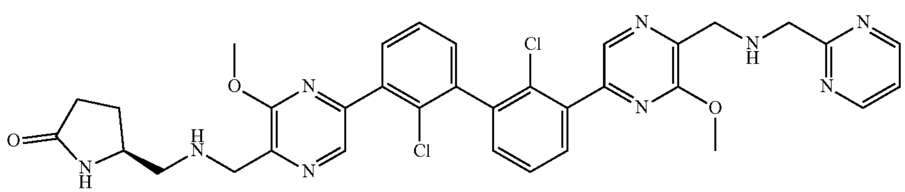 [SMILES: COc1nc(-c2cccc(-c3cccc(-c4cnc(CNC[C@@H]5CCC(=O)N5)c(OC)n4)c3Cl)c2Cl)cnc1CNCc1ncccn1] | 686.1 | 2 |

TABLE 1-continued

| No. | Structure | ES/MS (m/z, M + H+) | Procedure |
|---|---|---|---|
| 421 | 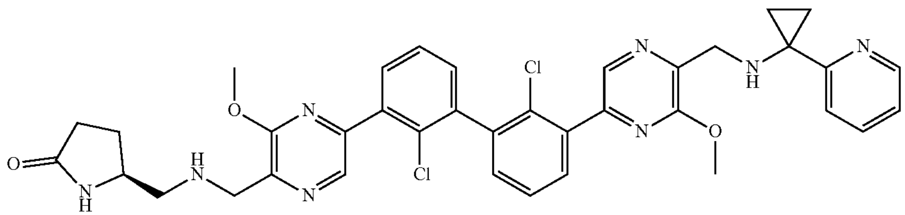 [SMILES: COc1nc(-c2cccc(-c3cccc(-c4cnc(CNC5(c6ccccn6)CC5)c(OC)n4)c3Cl)c2Cl)cnc1CNC[C@@H]1CCC(=O)N1] | 711.2 | 2 |
| 422 | 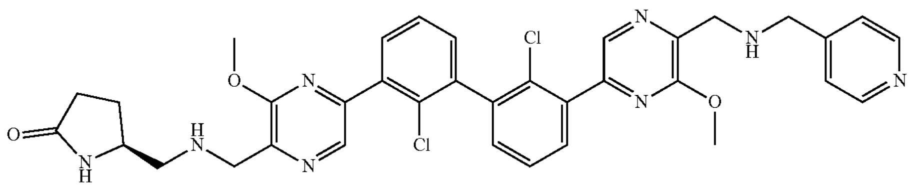 [SMILES: COc1nc(-c2cccc(-c3cccc(-c4cnc(CNC[C@@H]5CCC(=O)N5)c(OC)n4)c3Cl)c2Cl)cnc1CNCc1ccncc1] | 685.1 | 2 |
| 423 | 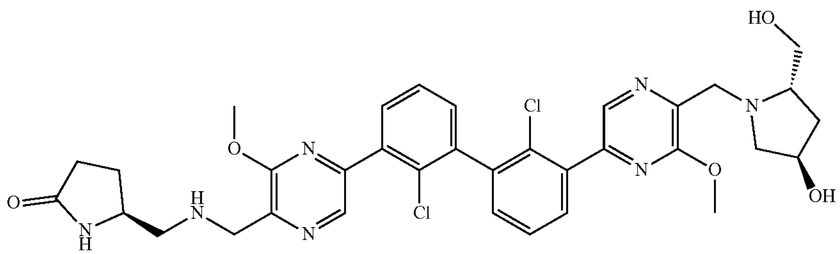 [SMILES: COc1nc(-c2cccc(-c3cccc(-c4cnc(CN5C[C@H](O)C[C@H]5CO)c(OC)n4)c3Cl)c2Cl)cnc1CNC[C@@H]1CCC(=O)N1] | 694.2 | 2 |
| 424 | 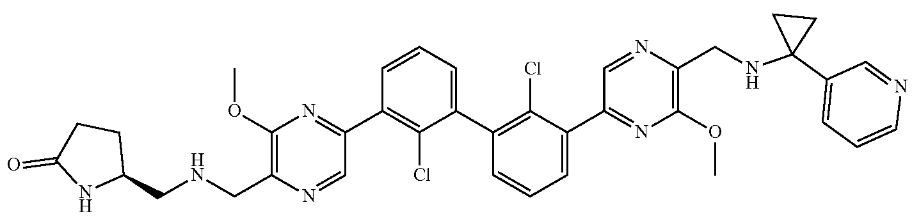 [SMILES: COc1nc(-c2cccc(-c3cccc(-c4cnc(CNC5(c6cccnc6)CC5)c(OC)n4)c3Cl)c2Cl)cnc1CNC[C@@H]1CCC(=O)N1] | 711.2 | 2 |

TABLE 1-continued

| No. | Structure | ES/MS (m/z, M + H⁺) | Procedure |
|---|---|---|---|
| 425 | 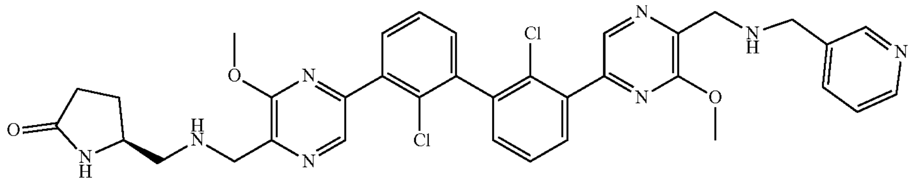 [SMILES: COc1nc(-c2cccc(-c3cccc(-c4cnc(CNC[C@@H]5CCC(=O)N5)c(OC)n4)c3Cl)c2Cl)cnc1CNCc1cccnc1] | 685.1 | 2 |
| 426 | 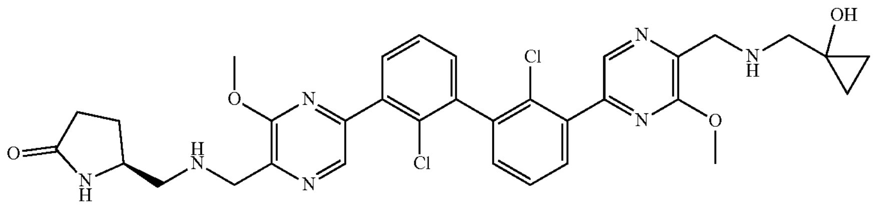 [SMILES: COc1nc(-c2cccc(-c3cccc(-c4cnc(CNCC5(O)CC5)c(OC)n4)c3Cl)c2Cl)cnc1CNC[C@@H]1CCC(=O)N1] | 664.1 | 2 |
| 427 | 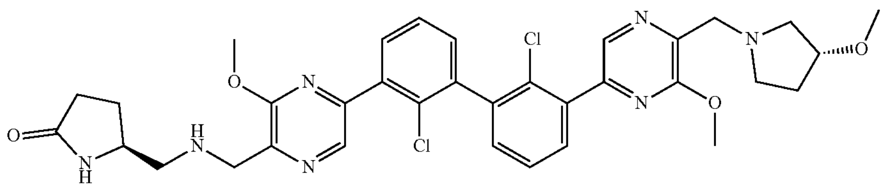 [SMILES: COc1nc(-c2cccc(-c3cccc(-c4cnc(CN5CC[C@@H](OC)C5)c(OC)n4)c3Cl)c2Cl)cnc1CNC[C@@H]1CCC(=O)N1] | 678.2 | 2 |
| 428 | 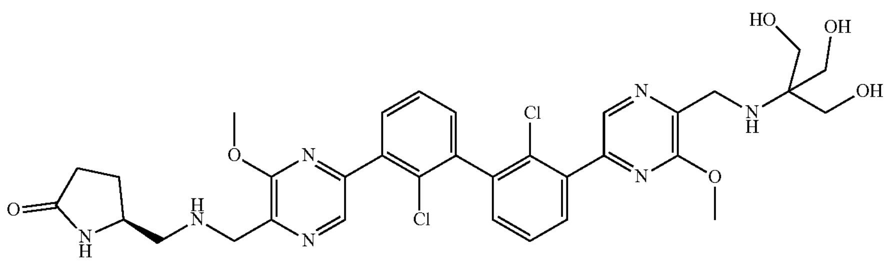 [SMILES: COc1nc(-c2cccc(-c3cccc(-c4cnc(CNC(CO)(CO)CO)c(OC)n4)c3Cl)c2Cl)cnc1CNC[C@@H]1CCC(=O)N1] | 698.2 | 2 |

TABLE 1-continued

| No. | Structure | ES/MS (m/z, M + H+) | Procedure |
|---|---|---|---|
| 429 | 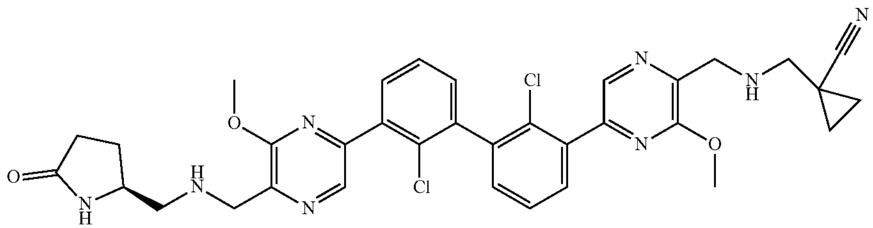 [SMILES: COc1nc(-c2cccc(-c3cccc(-c4cnc(CNCC5(C#N)CC5)c(OC)n4)c3Cl)c2Cl)cnc1CNC[C@@H]1CCC(=O)N1] | 673 | 2 |
| 430 | 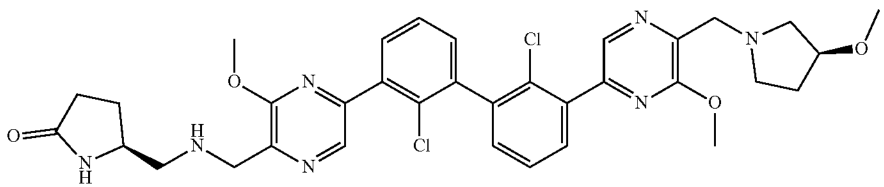 [SMILES: COc1nc(-c2cccc(-c3cccc(-c4cnc(CN5CC[C@H](OC)C5)c(OC)n4)c3Cl)c2Cl)cnc1CNC[C@@H]1CCC(=O)N1] | 678.2 | 2 |
| 431 | 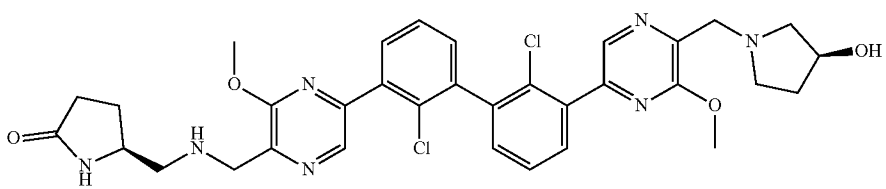 [SMILES: COc1nc(-c2cccc(-c3cccc(-c4cnc(CN5CC[C@H](O)C5)c(OC)n4)c3Cl)c2Cl)cnc1CNC[C@@H]1CCC(=O)N1] | 664.2 | 2 |
| 432 | 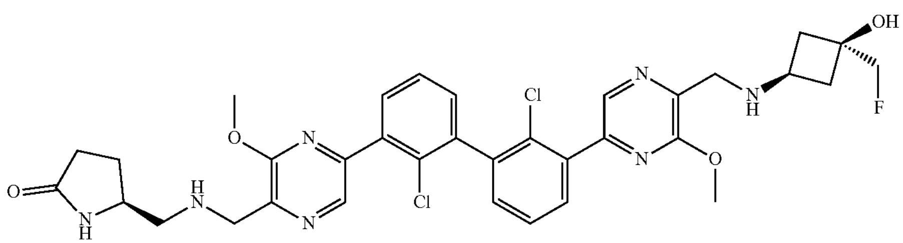 [SMILES: COc1nc(-c2cccc(-c3cccc(-c4cnc(CN[C@H]5C[C@](O)(CF)C5)c(OC)n4)c3Cl)c2Cl)cnc1CNC[C@@H]1CCC(=O)N1] | 696.0 | 2 |

TABLE 1-continued
| No. | Structure | ES/MS (m/z, M + H+) | Procedure |
|---|---|---|---|
| 433 | 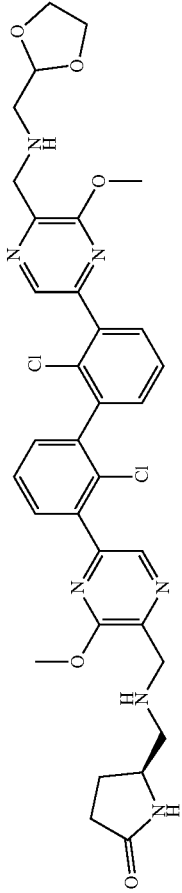 | 680.1 | 2 |
| 434 | 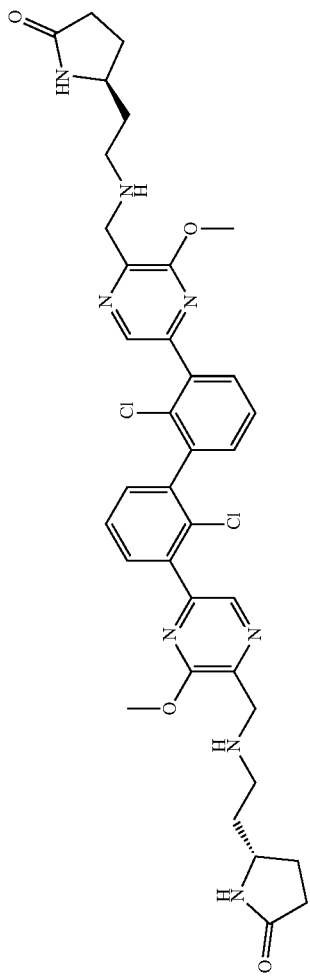 | 719.20 | 3 |
| 435 | 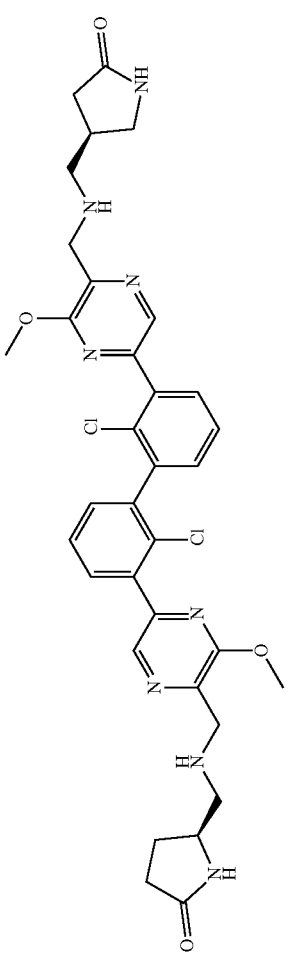 | 691.2 | 2 |

TABLE 1-continued

| No. | Structure | ES/MS (m/z, M + H⁺) | Procedure |
|---|---|---|---|
| 436 | 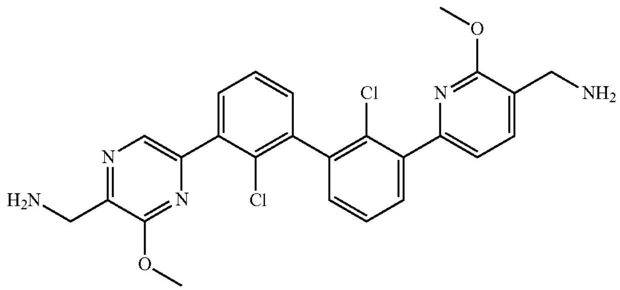 [SMILES: COc1nc(-c2cccc(-c3cccc(-c4cnc(CN)c(OC)n4)c3Cl)c2Cl)ccc1CN] | 496.3 | 26 |
| 437 | 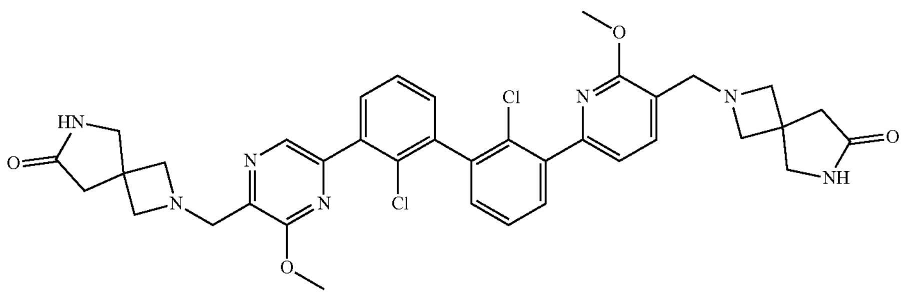 [SMILES: COc1nc(-c2cccc(-c3cccc(-c4cnc(CN5CC6(CNC(=O)C6)C5)c(OC)n4)c3Cl)c2Cl)ccc1CN1CC2(CNC(=O)C2)C1] | 714.3 | 26 |
| 438 | 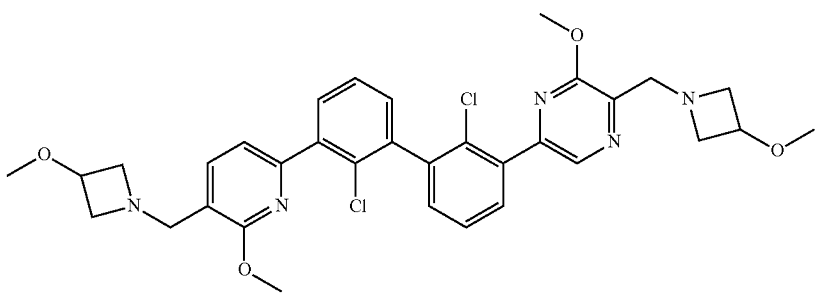 | 636.226 | 26 |

TABLE 1-continued

| No. | Structure | ES/MS (m/z, M + H⁺) | Procedure |
|---|---|---|---|
| 439 | 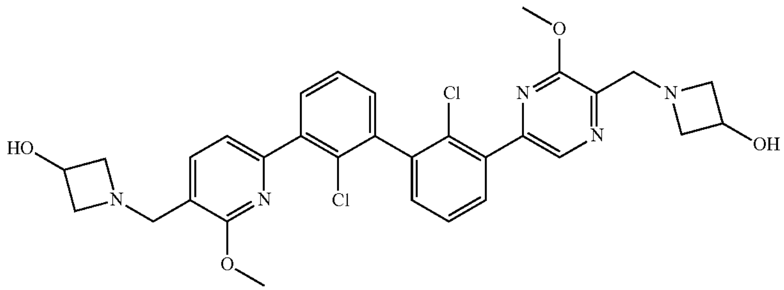 [SMILES: COc1nc(-c2cccc(-c3cccc(-c4cnc(CN5CC(O)C5)c(OC)n4)c3Cl)c2Cl)ccc1CN1CC(O)C1] | 608.242 | 26 |
| 440 | 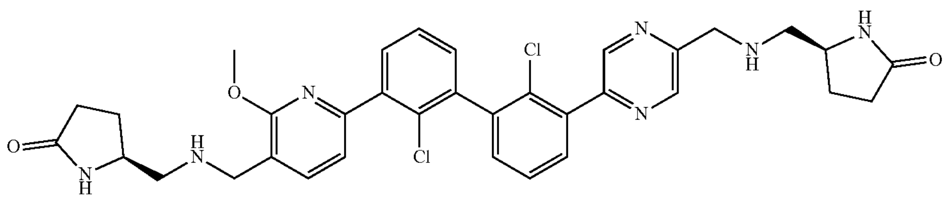 [SMILES: COc1nc(-c2cccc(-c3cccc(-c4cnc(CNC[C@@H]5CCC(=O)N5)cn4)c3Cl)c2Cl)ccc1CNC[C@@H]1CCC(=O)N1] | 660.1 | 26 |
| 441 | 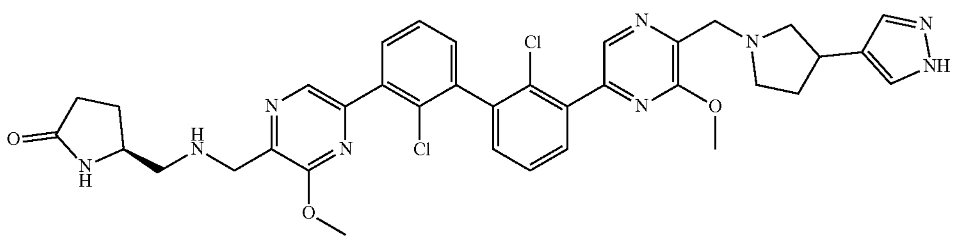 [SMILES: COc1nc(-c2cccc(-c3cccc(-c4cnc(CN5CCC(c6cn[nH]c6)C5)c(OC)n4)c3Cl)c2Cl)cnc1CNC[C@@H]1CCC(=O)N1] | 714.3 | 2 |
| 442 | 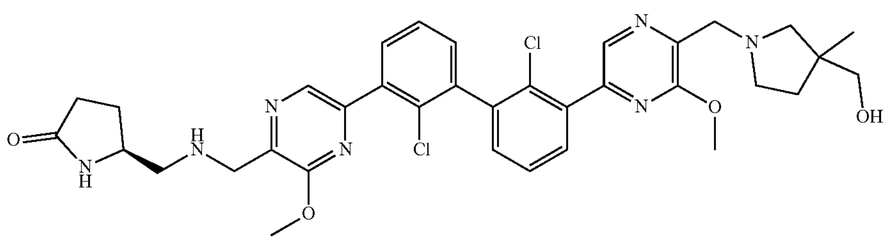 [SMILES: COc1nc(-c2cccc(-c3cccc(-c4cnc(CN5CCC(C)(CO)C5)c(OC)n4)c3Cl)c2Cl)cnc1CNC[C@@H]1CCC(=O)N1] | 692.2 | 2 |

TABLE 1-continued
| No. | Structure | ES/MS (m/z, M + H+) | Procedure |
|---|---|---|---|
| 443 | 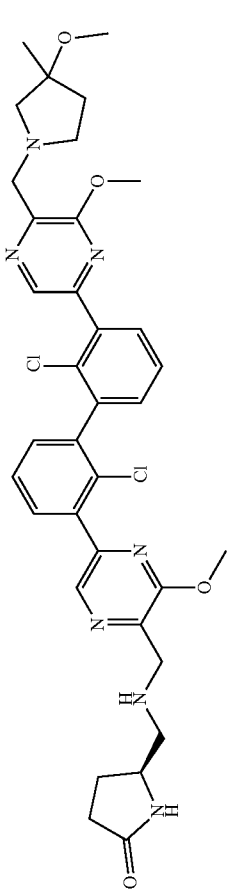 | 692.198 | 2 |
| 444 | 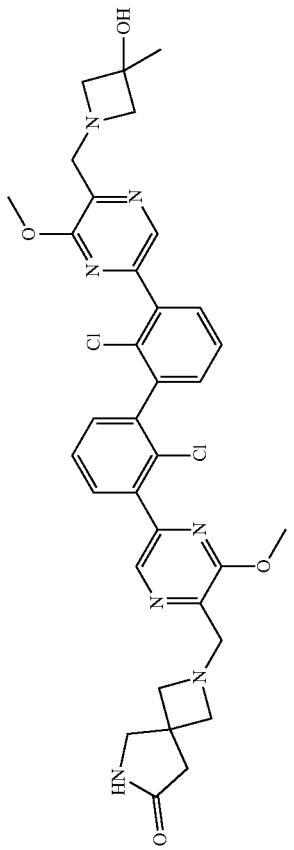 | 676.16 | 2 |
| 445 | 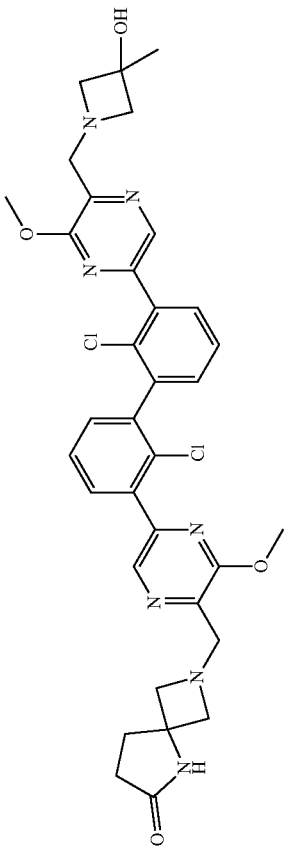 | 676.14 | 2 |

TABLE 1-continued

| No. | Structure | ES/MS (m/z, M + H+) | Procedure |
|---|---|---|---|
| 446 | 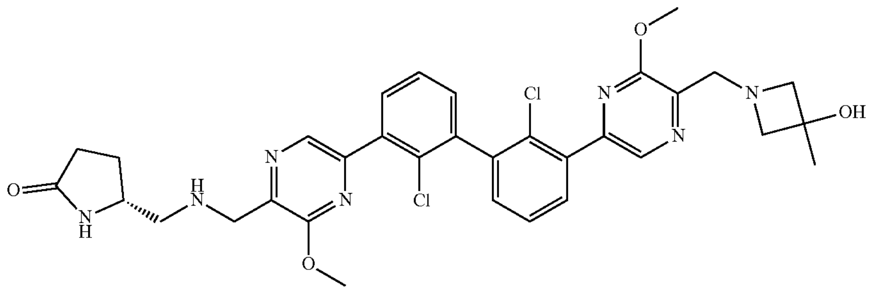 [SMILES: COc1nc(-c2cccc(-c3cccc(-c4cnc(CN5CC(C)(O)C5)c(OC)n4)c3Cl)c2Cl)cnc1CNC[C@H]1CCC(=O)N1] | 664.16 | 2 |
| 447 | 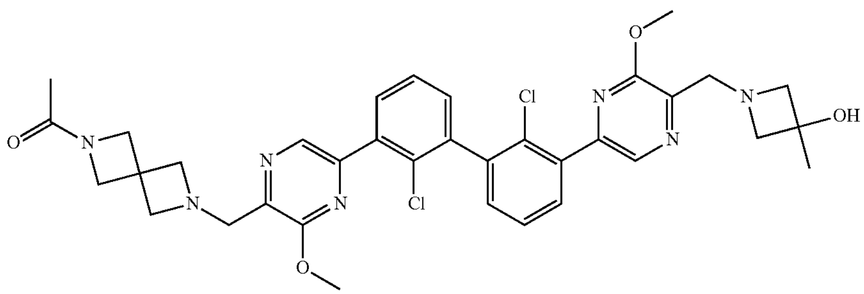 [SMILES: COc1nc(-c2cccc(-c3cccc(-c4cnc(CN5CC6(C5)CN(C(C)=O)C6)c(OC)n4)c3Cl)c2Cl)cnc1CN1CC(C)(O)C1] | 690.09 | 2 |
| 448 | 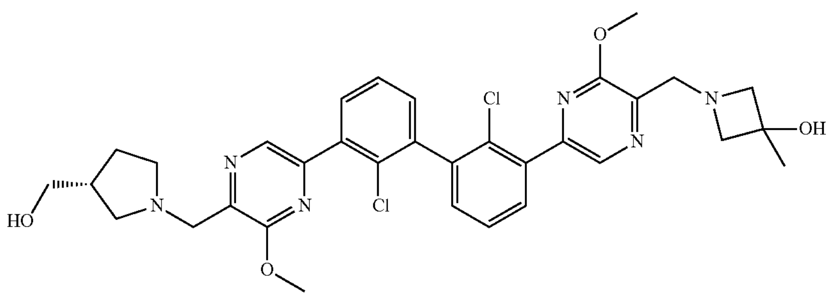 [SMILES: COc1nc(-c2cccc(-c3cccc(-c4cnc(CN5CC(C)(O)C5)c(OC)n4)c3Cl)c2Cl)cnc1CN1CC[C@@H](CO)C1] | 651.13 | 2 |

TABLE 1-continued

| No. | Structure | ES/MS (m/z, M + H⁺) | Procedure |
|-----|-----------|---------------------|-----------|
| 449 | 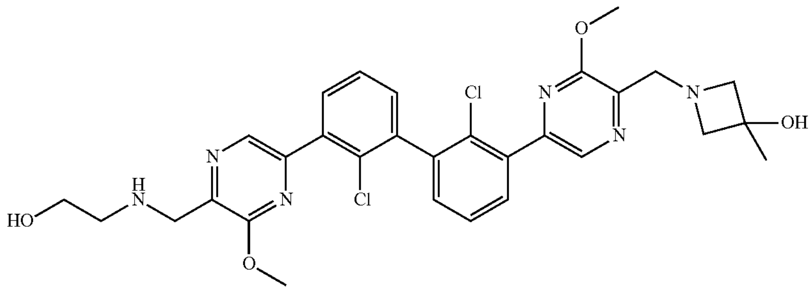 [SMILES: COc1nc(-c2cccc(-c3cccc(-c4cnc(CN5CC(C)(O)C5)c(OC)n4)c3Cl)c2Cl)cnc1CNCCO] | 611.16 | 2 |
| 450 | 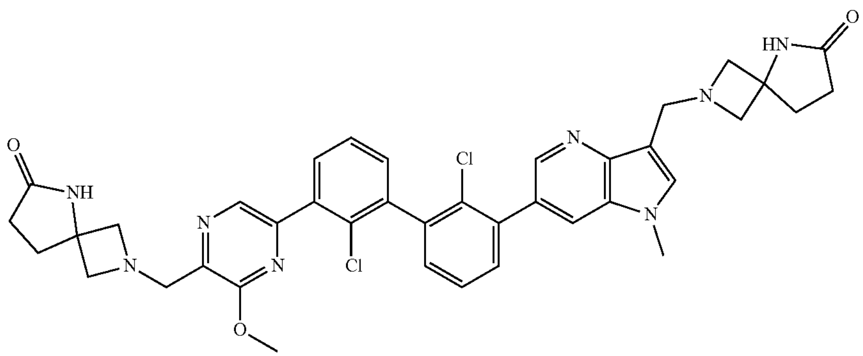 [SMILES: COc1nc(-c2cccc(-c3cccc(-c4cnc5c(CN6CC7(CCC(=O)N7)C6)cn(C)c5c4)c3Cl)c2Cl)cnc1CN1CC2(CCC(=O)N2)C1] | 737.2 | 12 |
| 451 | 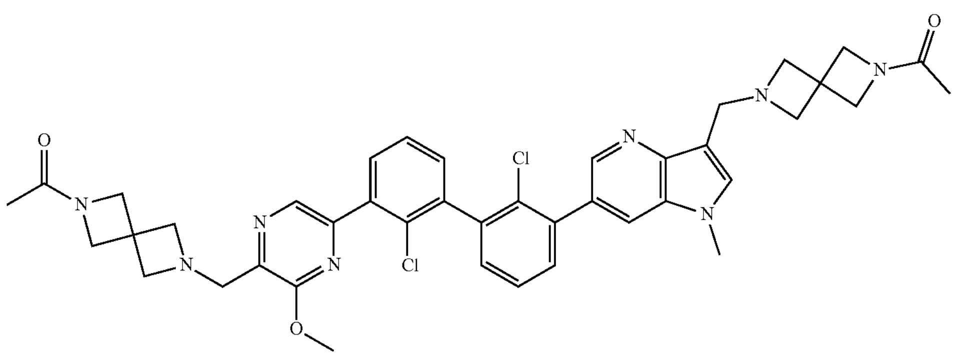 [SMILES: COc1nc(-c2cccc(-c3cccc(-c4cnc5c(CN6CC7(C6)CN(C(C)=O)C7)cn(C)c5c4)c3Cl)c2Cl)cnc1CN1CC2(C1)CN(C(C)=O)C2] | 765.2 | 12 |

TABLE 1-continued

| No. | Structure | ES/MS (m/z, M + H⁺) | Procedure |
|---|---|---|---|
| 452 | 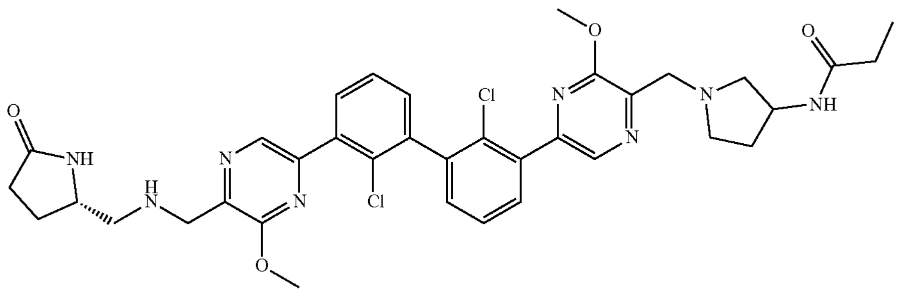 [SMILES: CCC(=O)NC1CCN(Cc2ncc(-c3cccc(-c4cccc(-c5cnc(CNC[C@@H]6CCC(=O)N6)c(OC)n5)c4Cl)c3Cl)nc2OC)C1] | 719.2 | 2 |
| 453 | 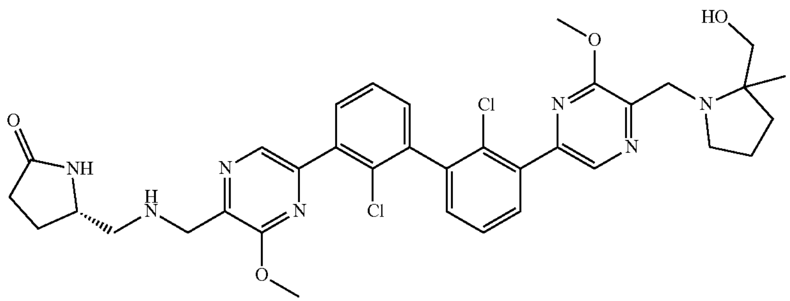 [SMILES: COc1nc(-c2cccc(-c3cccc(-c4cnc(CN5CCCC5(C)CO)c(OC)n4)c3Cl)c2Cl)cnc1CNC[C@@H]1CCC(=O)N1] | 692.2 | 2 |
| 454 | 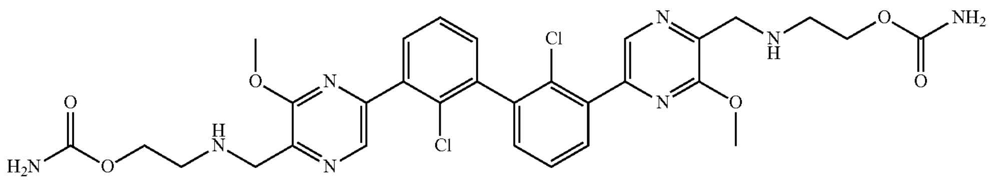 [SMILES: COc1nc(-c2cccc(-c3cccc(-c4cnc(CNCCOC(N)=O)c(OC)n4)c3Cl)c2Cl)cnc1CNCCOC(N)=O] | 671.2 | 3 |
| 455 | 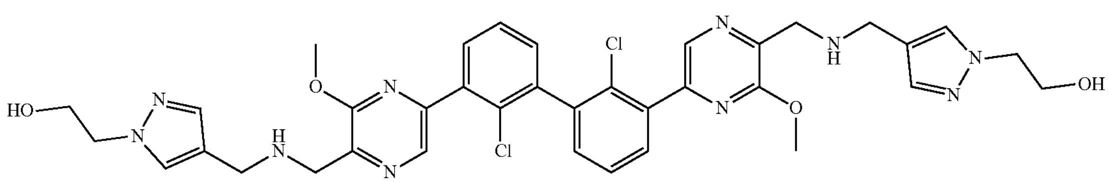 [SMILES: COc1nc(-c2cccc(-c3cccc(-c4cnc(CNCc5cnn(CCO)c5)c(OC)n4)c3Cl)c2Cl)cnc1CNCc1cnn(CCO)c1] | 745.2 | 3 |

TABLE 1-continued

| No. | Structure | ES/MS (m/z, M + H⁺) | Procedure |
|---|---|---|---|
| 456 | 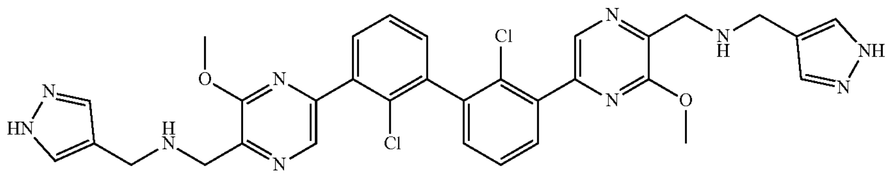 [SMILES: COc1nc(-c2cccc(-c3cccc(-c4cnc(CNCc5cn[nH]c5)c(OC)n4)c3Cl)c2Cl)cnc1CNCc1cn[nH]c1] | 657.2 | 3 |
| 457 | 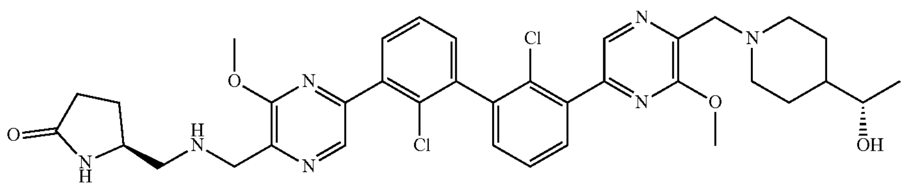 [SMILES: COc1nc(-c2cccc(-c3cccc(-c4cnc(CN5CCC([C@H](C)O)CC5)c(OC)n4)c3Cl)c2Cl)cnc1CNC[C@@H]1CCC(=O)N1] | 706.2 | 2 |
| 458 | 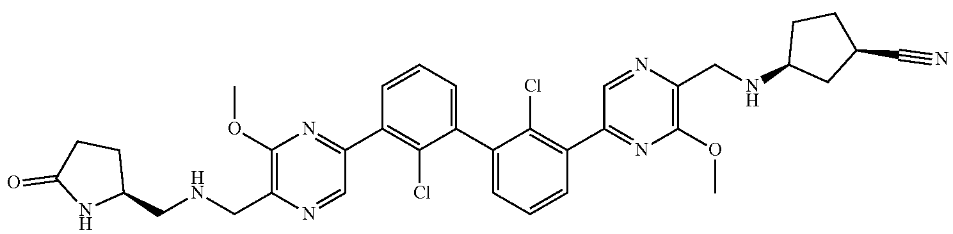 [SMILES: COc1nc(-c2cccc(-c3cccc(-c4cnc(CN[C@H]5CC[C@@H](C#N)C5)c(OC)n4)c3Cl)c2Cl)cnc1CNC[C@@H]1CCC(=O)N1] | 687.2 | 2 |
| 459 | 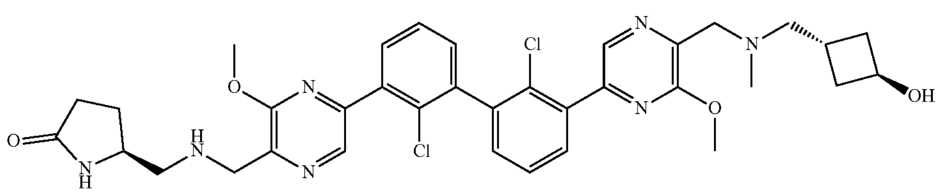 [SMILES: COc1nc(-c2cccc(-c3cccc(-c4cnc(CN(C)C[C@H]5C[C@H](O)C5)c(OC)n4)c3Cl)c2Cl)cnc1CNC[C@@H]1CCC(=O)N1] | 692.2 | 2 |

TABLE 1-continued
| No. | Structure | ES/MS (m/z, M + H+) | Procedure |
|---|---|---|---|
| 460 | 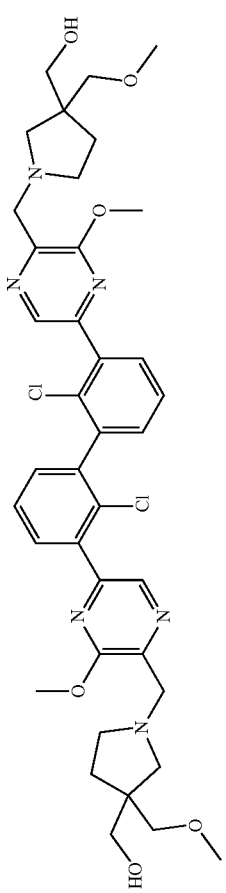 | 753.2 | 3 |
| 461 | 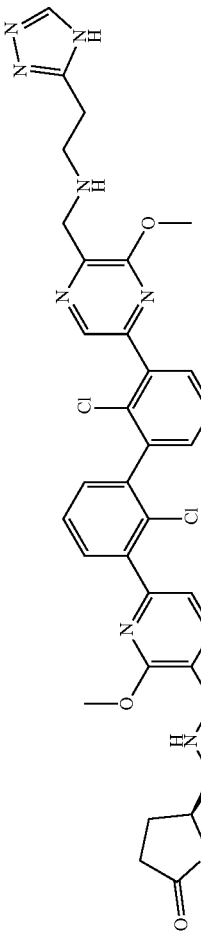 | 689.1 | 2 |
| 462 | 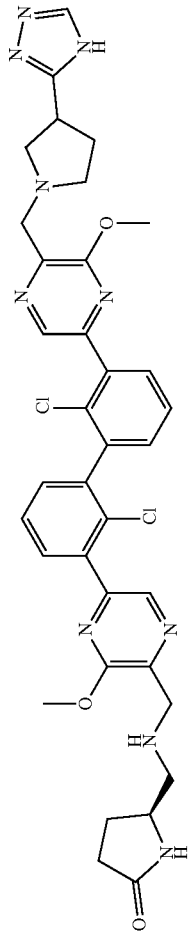 | 715.1 | 2 |
| 463 | 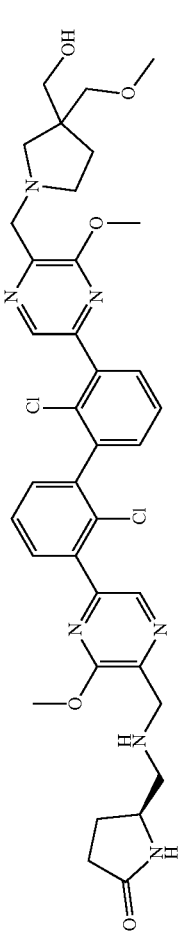 | 722.1 | 2 |

TABLE 1-continued

| No. | Structure | ES/MS (m/z, M + H+) | Procedure |
|---|---|---|---|
| 464 | (structure) | 691.1 | 2 |
| 465 | (structure) | 691.1 | 2 |
| 466 | (structure) | 749.2 | 3 |

TABLE 1-continued

| No. | Structure | ES/MS (m/z, M + H⁺) | Procedure |
|-----|-----------|---------------------|-----------|
| 467 | 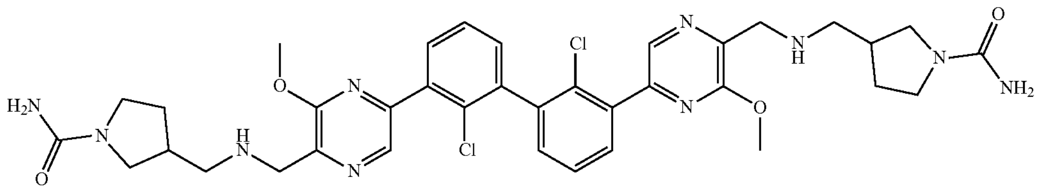 [SMILES: COc1nc(-c2cccc(-c3cccc(-c4cnc(CNCC5CCN(C(N)=O)C5)c(OC)n4)c3Cl)c2Cl)cnc1CNCC1CCN(C(N)=O)C1] | 749.1 | 3 |
| 468 | 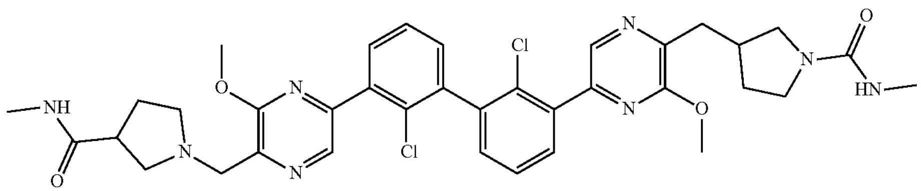 | 719.2 | 3 |
| 469 | 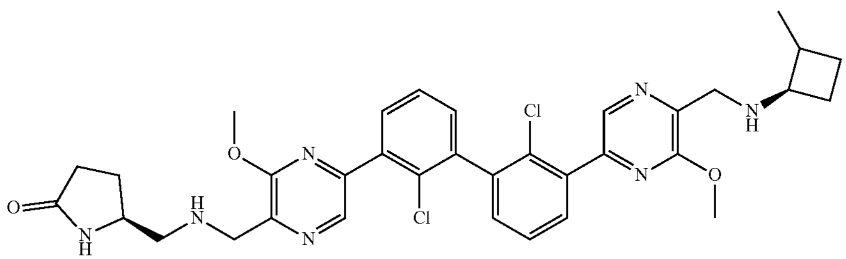 [SMILES: COc1nc(-c2cccc(-c3cccc(-c4cnc(CN[C@@H]5CCC5C)c(OC)n4)c3Cl)c2Cl)cnc1CNC[C@@H]1CCC(=O)N1] | 662.2 | 2 |
| 470 | 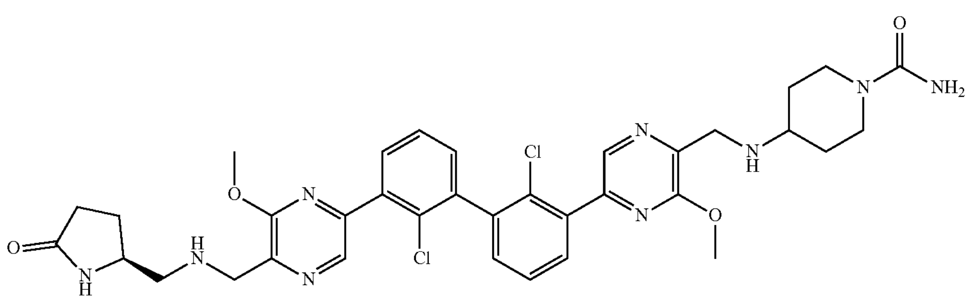 [SMILES: COc1nc(-c2cccc(-c3cccc(-c4cnc(CNC5CCN(C(N)=O)CC5)c(OC)n4)c3Cl)c2Cl)cnc1CNC[C@@H]1CCC(=O)N1] | 720.1 | 2 |

TABLE 1-continued

| No. | Structure | ES/MS (m/z, M + H+) | Procedure |
|---|---|---|---|
| 471 | 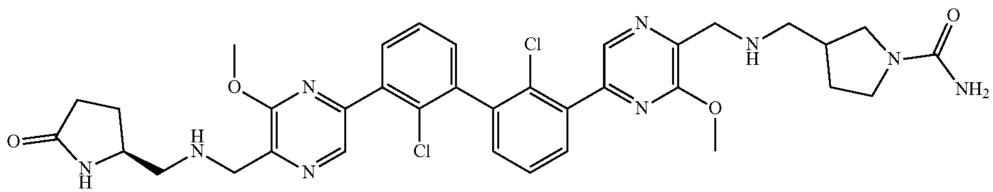 [SMILES: COc1nc(-c2cccc(-c3cccc(-c4cnc(CNC[C@@H]5CCC(=O)N5)c(OC)n4)c3Cl)c2Cl)cnc1CNCC1CCN(C(N)=O)C1] | 720.1 | 2 |
| 472 | 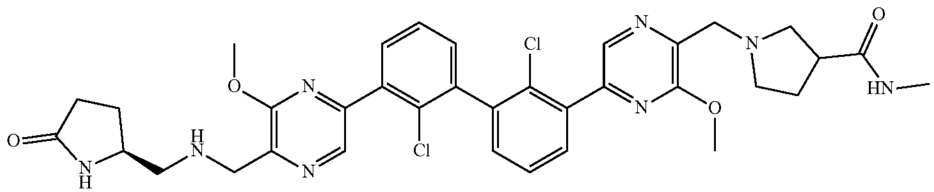 [SMILES: CNC(=O)C1CCN(Cc2ncc(-c3cccc(-c4cccc(-c5cnc(CNC[C@@H]6CCC(=O)N6)c(OC)n5)c4Cl)c3Cl)nc2OC)C1] | 705.2 | 2 |
| 473 | 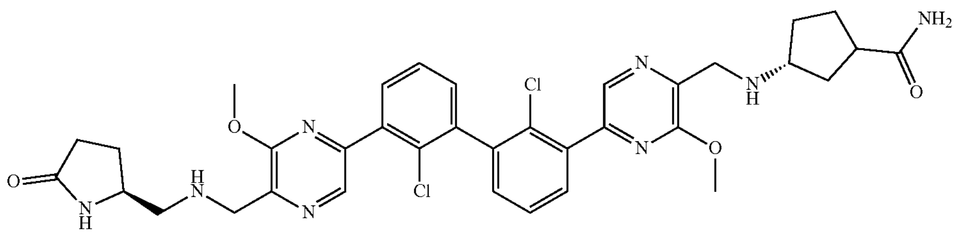 [SMILES: COc1nc(-c2cccc(-c3cccc(-c4cnc(CN[C@@H]5CCC(C(N)=O)C5)c(OC)n4)c3Cl)c2Cl)cnc1CNC[C@@H]1CCC(=O)N1] | 705.1 | 2 |
| 474 | 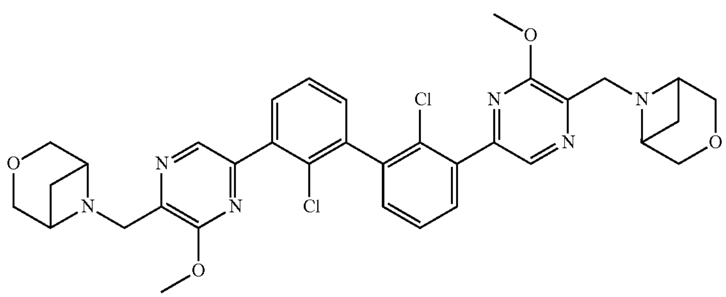 [SMILES: COc1nc(-c2cccc(-c3cccc(-c4cnc(CN5C6COCC5C6)c(OC)n4)c3Cl)c2Cl)cnc1CN1C2COCC1C2] | 661.2 | 3 |

TABLE 1-continued

| No. | Structure | ES/MS (m/z, M + H⁺) | Procedure |
|---|---|---|---|
| 475 | 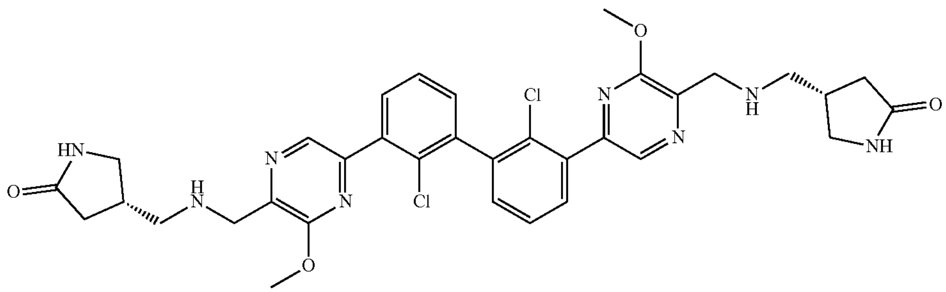 [SMILES: COc1nc(-c2cccc(-c3cccc(-c4cnc(CNC[C@H]5CNC(=O)C5)c(OC)n4)c3Cl)c2Cl)cnc1CNC[C@H]1CNC(=O)C1] | 691.2 | 3 |
| 476 | 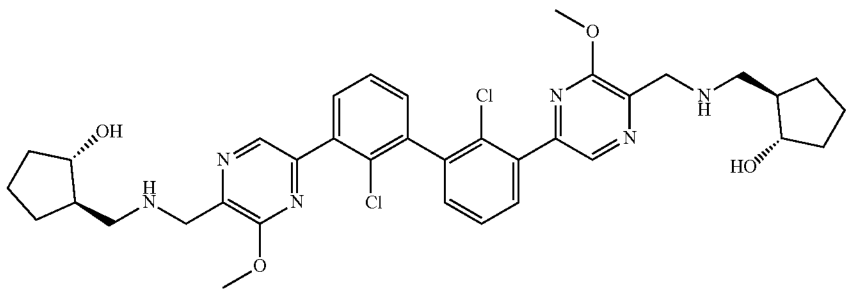 [SMILES: COc1nc(-c2cccc(-c3cccc(-c4cnc(CNC[C@H]5CCC[C@@H]5O)c(OC)n4)c3Cl)c2Cl)cnc1CNC[C@H]1CCC[C@@H]1O] | 693.2 | 3 |
| 477 | 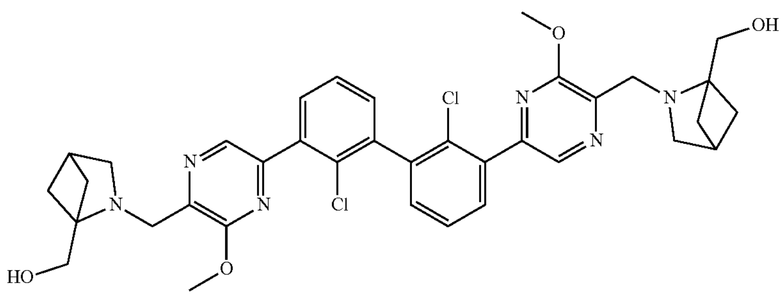 [SMILES: COc1nc(-c2cccc(-c3cccc(-c4cnc(CN5CC6CC5(CO)C6)c(OC)n4)c3Cl)c2Cl)cnc1CN1CC2CC1(CO)C2] | 689.2 | 3 |

TABLE 1-continued

| No. | Structure | ES/MS (m/z, M + H+) | Procedure |
|---|---|---|---|
| 478 | 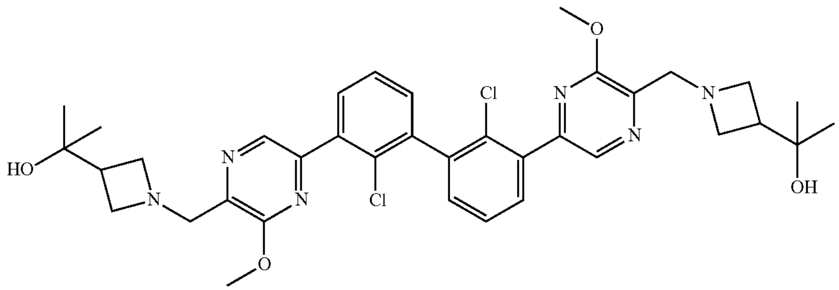 [SMILES: COc1nc(-c2cccc(-c3cccc(-c4cnc(CN5CC(C(C)(C)O)C5)c(OC)n4)c3Cl)c2Cl)cnc1CN1CC(C(C)(C)O)C1] | 693.2 | 3 |
| 479 | 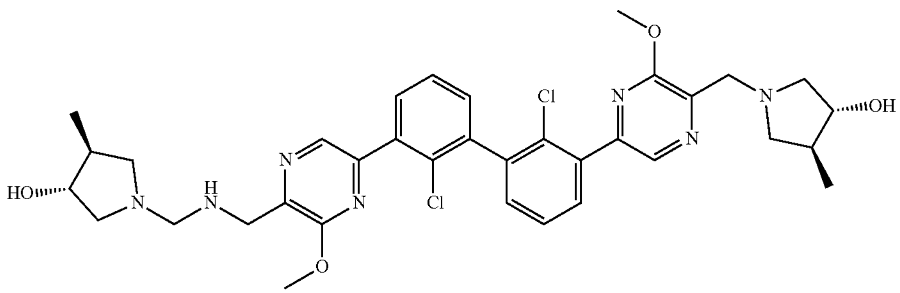 [SMILES: COc1nc(-c2cccc(-c3cccc(-c4cnc(CN5C[C@H](C)[C@@H](O)C5)c(OC)n4)c3Cl)c2Cl)cnc1CNCN1C[C@H](C)[C@@H](O)C1] | 665.2 | 3 |
| 480 | 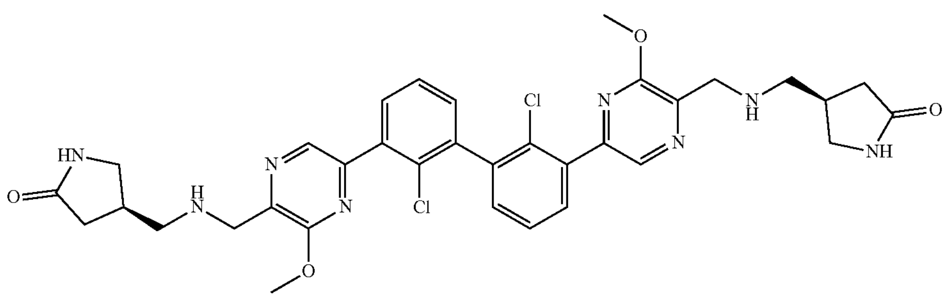 [SMILES: COc1nc(-c2cccc(-c3cccc(-c4cnc(CNC[C@@H]5CNC(=O)C5)c(OC)n4)c3Cl)c2Cl)cnc1CNC[C@@H]1CNC(=O)C1] | 691.2 | 3 |

TABLE 1-continued

| No. | Structure | ES/MS (m/z, M + H+) | Procedure |
|---|---|---|---|
| 481 | 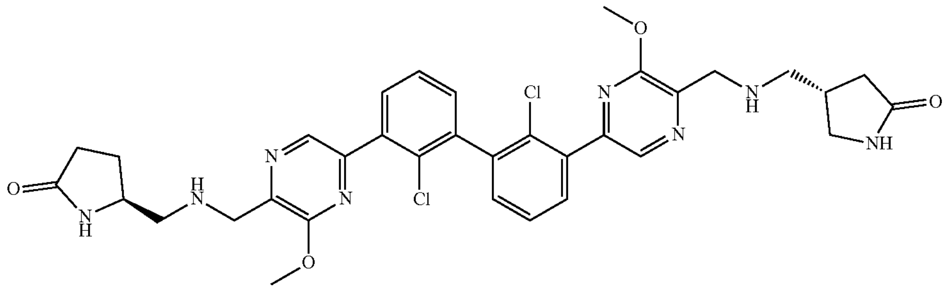 [SMILES: COc1nc(-c2cccc(-c3cccc(-c4cnc(CNC[C@@H]5CCC(=O)N5)c(OC)n4)c3Cl)c2Cl)cnc1CNC[C@H]1CNC(=O)C1] | 691.2 | 2 |
| 482 | 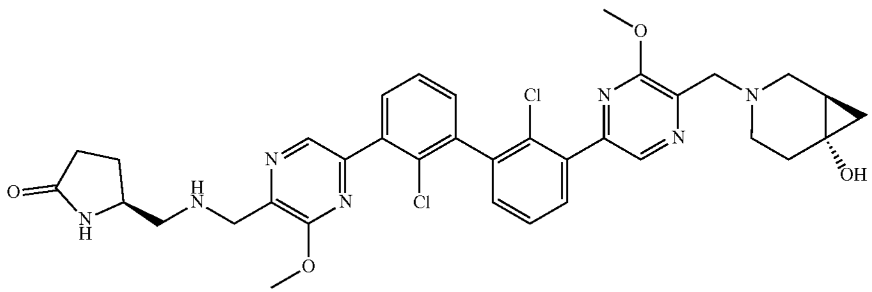 [SMILES: COc1nc(-c2cccc(-c3cccc(-c4cnc(CN5CC[C@]6(O)C[C@@H]6C5)c(OC)n4)c3Cl)c2Cl)cnc1CNC[C@@H]1CCC(=O)N1] | 690.2 | 2 |
| 483 | 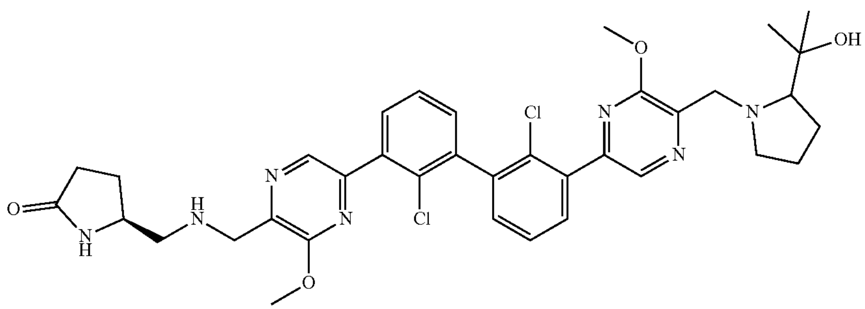 [SMILES: COc1nc(-c2cccc(-c3cccc(-c4cnc(CN5CCCC5C(C)(C)O)c(OC)n4)c3Cl)c2Cl)cnc1CNC[C@@H]1CCC(=O)N1] | 706.2 | 2 |

TABLE 1-continued

| No. | Structure | ES/MS (m/z, M + H⁺) | Procedure |
|---|---|---|---|
| 484 | 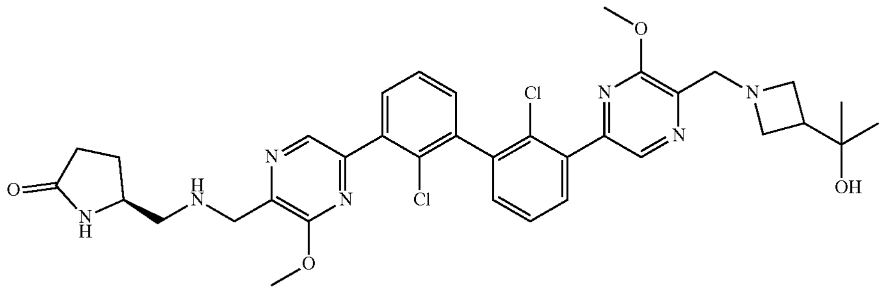 [SMILES: COc1nc(-c2cccc(-c3cccc(-c4cnc(CN5CC(C(C)(C)O)C5)c(OC)n4)c3Cl)c2Cl)cnc1CNC[C@@H]1CCC(=O)N1] | 692.2 | 2 |
| 485 | 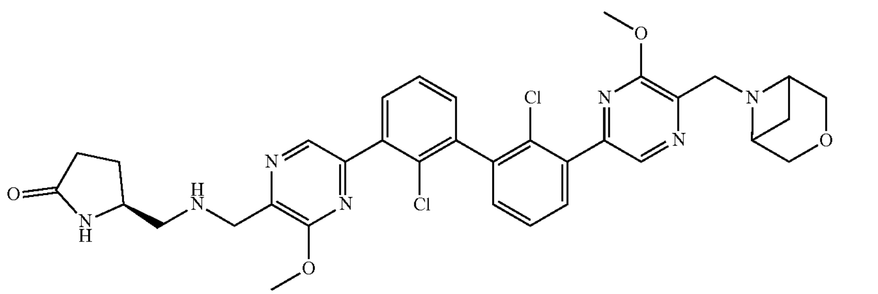 [SMILES: COc1nc(-c2cccc(-c3cccc(-c4cnc(CN5C6COCC5C6)c(OC)n4)c3Cl)c2Cl)cnc1CNC[C@@H]1CCC(=O)N1] | 676.2 | 2 |
| 486 | 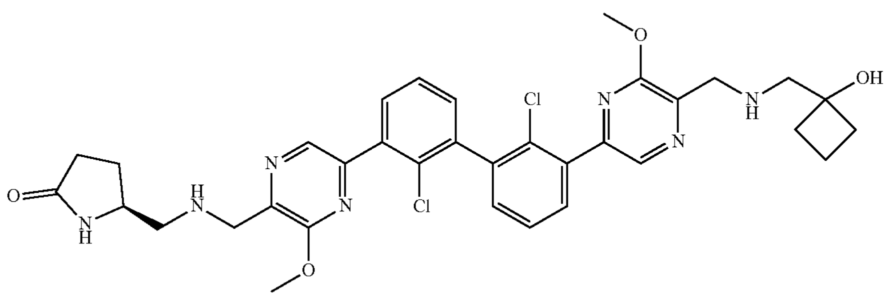 [SMILES: COc1nc(-c2cccc(-c3cccc(-c4cnc(CNCC5(O)CCC5)c(OC)n4)c3Cl)c2Cl)cnc1CNC[C@@H]1CCC(=O)N1] | 678.2 | 2 |

TABLE 1-continued

| No. | Structure | ES/MS (m/z, M + H+) | Procedure |
|---|---|---|---|
| 487 | 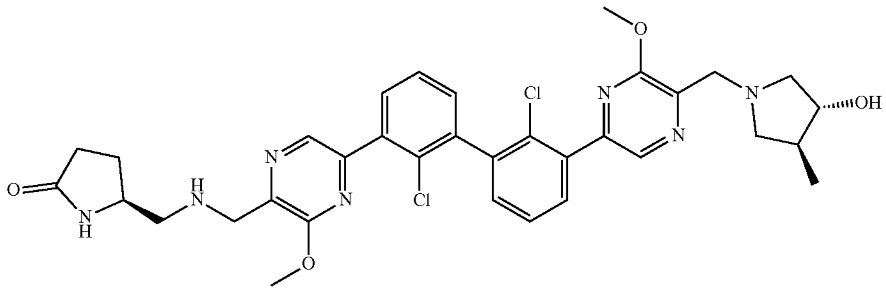 [SMILES: COc1nc(-c2cccc(-c3cccc(-c4cnc(CN5C[C@H](C)[C@@H](O)C5)c(OC)n4)c3Cl)c2Cl)cnc1CNC[C@@H]1CCC(=O)N1] | 678.2 | 2 |
| 488 | 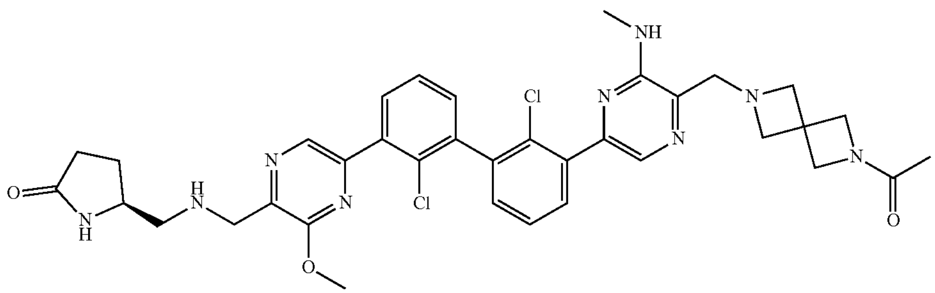 [SMILES: CNc1nc(-c2cccc(-c3cccc(-c4cnc(CNC[C@@H]5CCC(=O)N5)c(OC)n4)c3Cl)c2Cl)cnc1CN1CC2(C1)CN(C(C)=O)C2] | 716.3 | 13 |
| 489 | 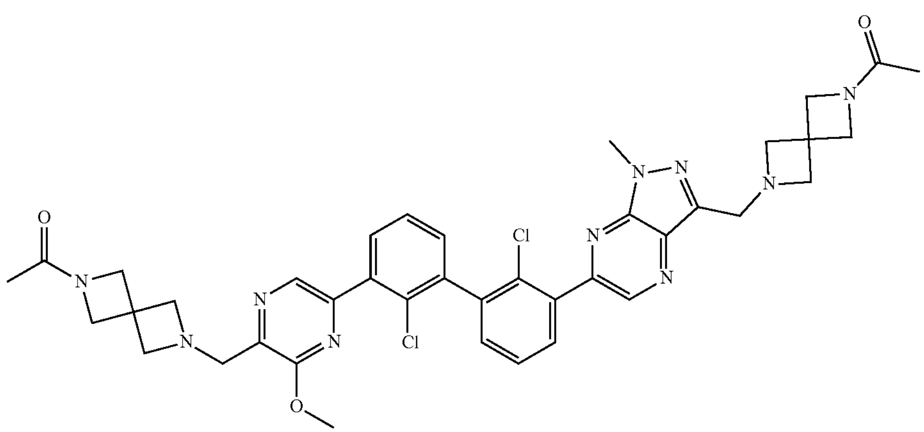 [SMILES: COc1nc(-c2cccc(-c3cccc(-c4cnc5c(CN6CC7(C6)CN(C(C)=O)C7)nn(C)c5n4)c3Cl)c2Cl)cnc1CN1CC2(C1)CN(C(C)=O)C2] | 767.2 | 12 |

TABLE 1-continued
| No. | Structure | ES/MS (m/z, M + H+) | Procedure |
|---|---|---|---|
| 490 | 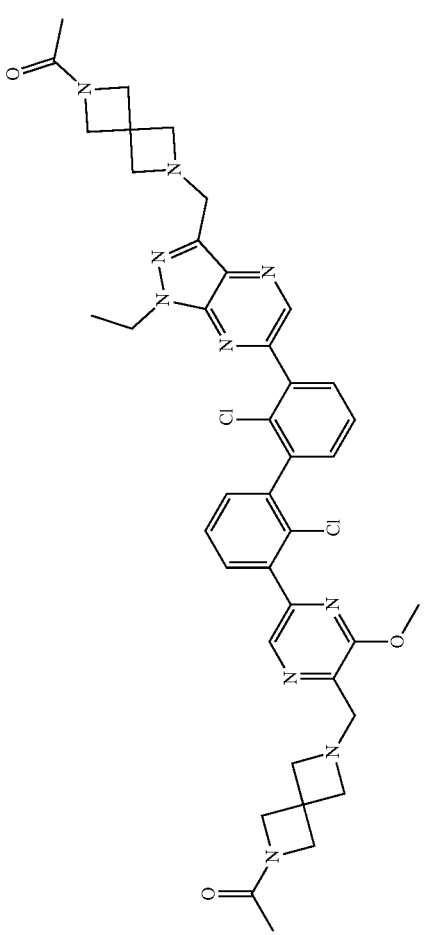 | 781.2 | 12 |
| 491 | 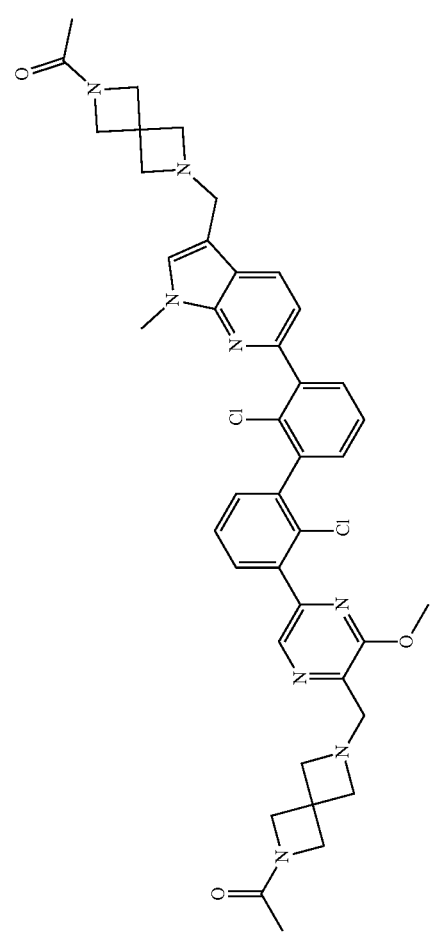 | 765.2 | 12 |

TABLE 1-continued
| No. | Structure | ES/MS (m/z, M + H+) | Procedure |
|---|---|---|---|
| 492 | 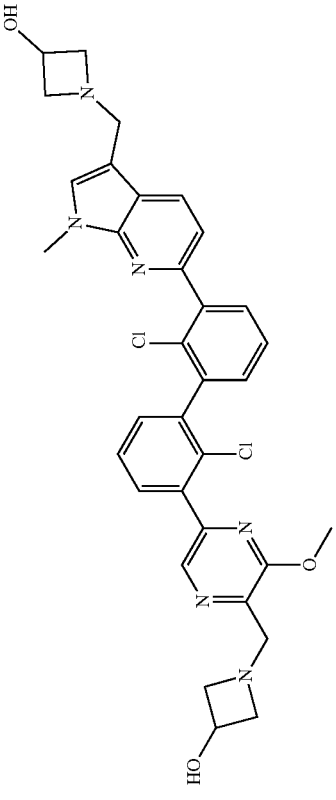 | 631.2 | 12 |
| 493 | 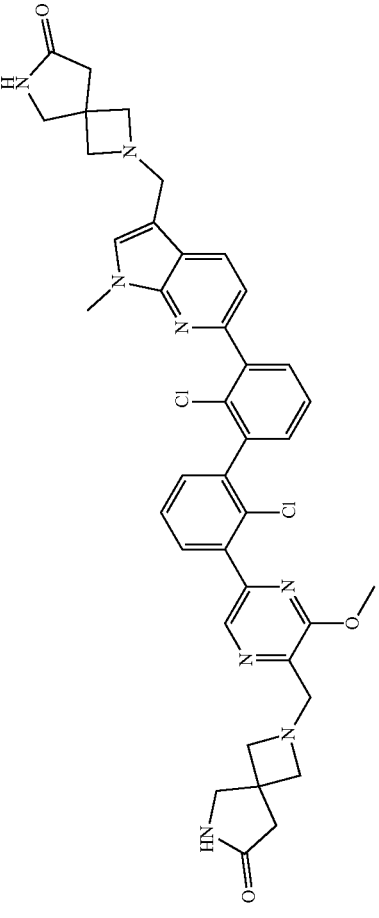 | 737.2 | 12 |

TABLE 1-continued

| No. | Structure | ES/MS (m/z, M + H⁺) | Procedure |
|---|---|---|---|
| 494 | 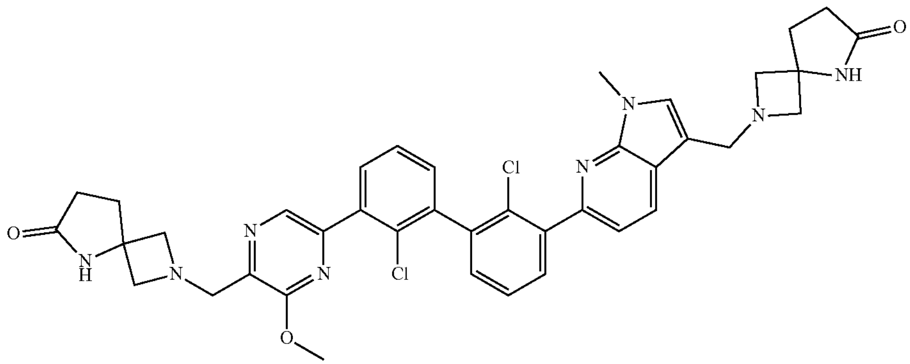 [SMILES: COc1nc(-c2cccc(-c3cccc(-c4ccc5c(CN6CC7(CCC(=O)N7)C6)cn(C)c5n4)c3Cl)c2Cl)cnc1CN1CC2(CCC(=O)N2)C1] | 737.2 | 12 |
| 495 | 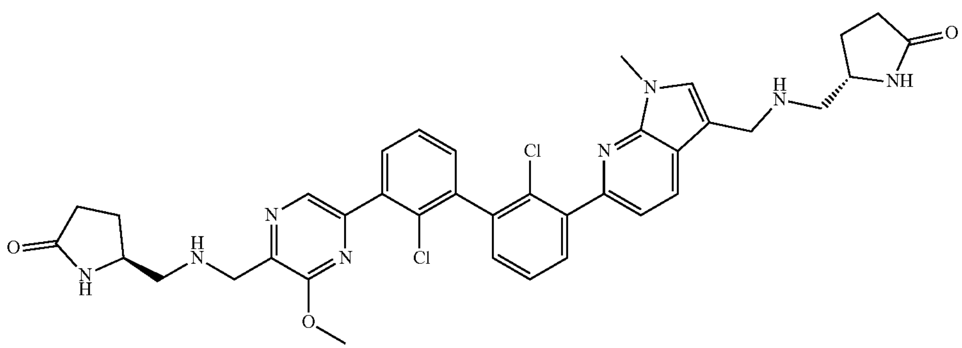 [SMILES: COc1nc(-c2cccc(-c3cccc(-c4ccc5c(CNC[C@@H]6CCC(=O)N6)cn(C)c5n4)c3Cl)c2Cl)cnc1CNC[C@@H]1CCC(=O)N1] | 713.2 | 12 |

TABLE 1-continued
| No. | Structure | ES/MS (m/z, M + H+) | Procedure |
|---|---|---|---|
| 496 | 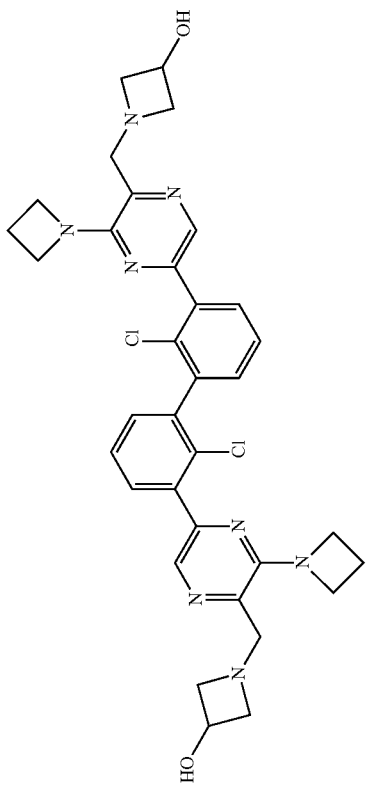 | 659.2 | 4 |
| 497 | 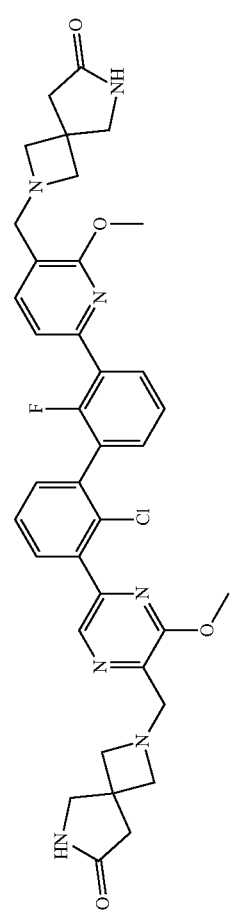 | 698.139 | 26 |
| 498 | 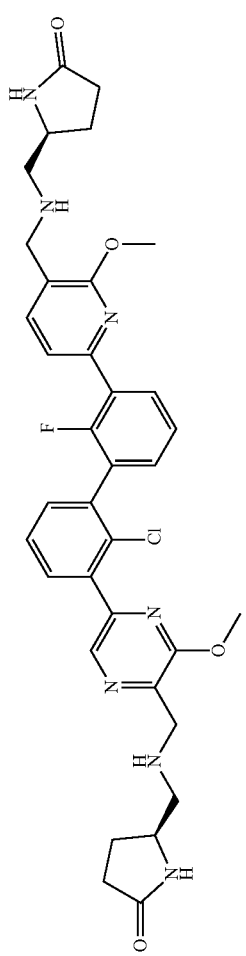 | 674.085 | 26 |

TABLE 1-continued

| No. | Structure | ES/MS (m/z, M + H+) | Procedure |
|---|---|---|---|
| 499 | 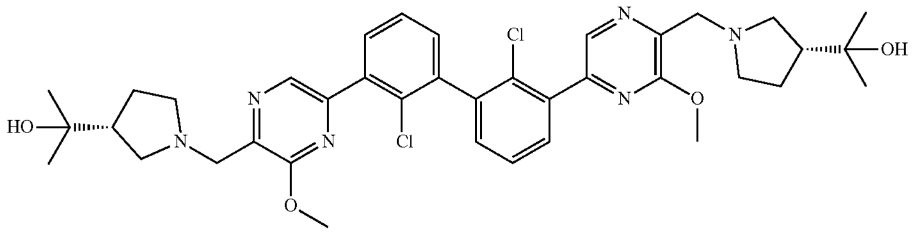 [SMILES: COc1nc(-c2cccc(-c3cccc(-c4cnc(CN5CC[C@@H](C(C)(C)O)C5)c(OC)n4)c3Cl)c2Cl)cnc1CN1CC[C@@H](C(C)(C)O)C1] | 721.151 | 3 |
| 500 | 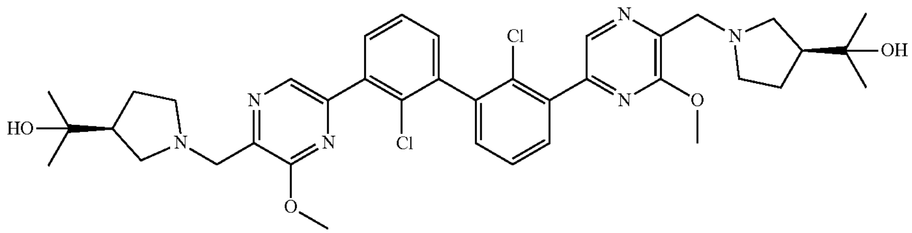 [SMILES: COc1nc(-c2cccc(-c3cccc(-c4cnc(CN5CC[C@H](C(C)(C)O)C5)c(OC)n4)c3Cl)c2Cl)cnc1CN1CC[C@H](C(C)(C)O)C1] | 721.142 | 3 |
| 501 | 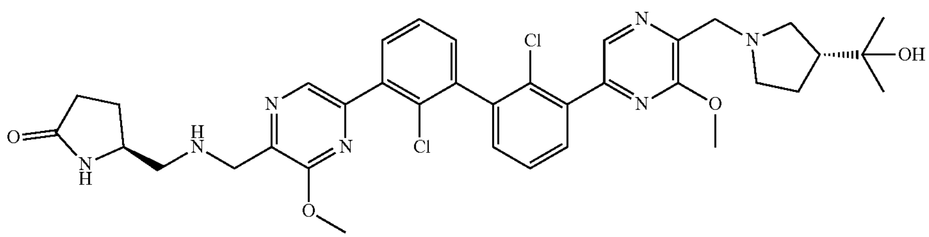 [SMILES: COc1nc(-c2cccc(-c3cccc(-c4cnc(CN5CC[C@@H](C(C)(C)O)C5)c(OC)n4)c3Cl)c2Cl)cnc1CNC[C@@H]1CCC(=O)N1] | 706.114 | 2 |
| 502 | 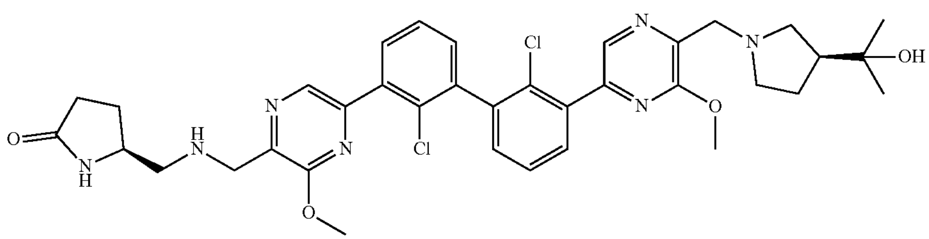 [SMILES: COc1nc(-c2cccc(-c3cccc(-c4cnc(CN5CC[C@H](C(C)(C)O)C5)c(OC)n4)c3Cl)c2Cl)cnc1CNC[C@@H]1CCC(=O)N1] | 706.132 | 2 |

TABLE 1-continued

| No. | Structure | ES/MS (m/z, M + H+) | Procedure |
|---|---|---|---|
| 508 | 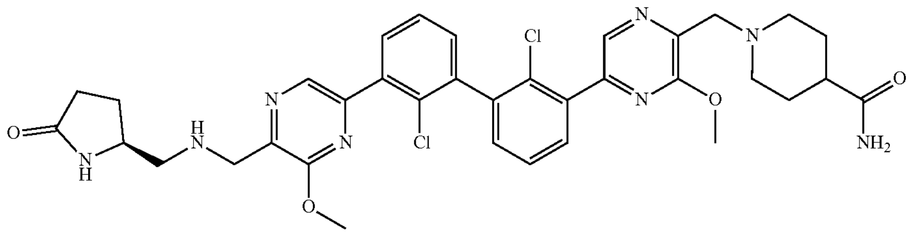 [SMILES: COc1nc(-c2cccc(-c3cccc(-c4cnc(CN5CCC(C(N)=O)CC5)c(OC)n4)c3Cl)c2Cl)cnc1CNC[C@@H]1CCC(=O)N1] | 705.16 | 2 |
| 509 | 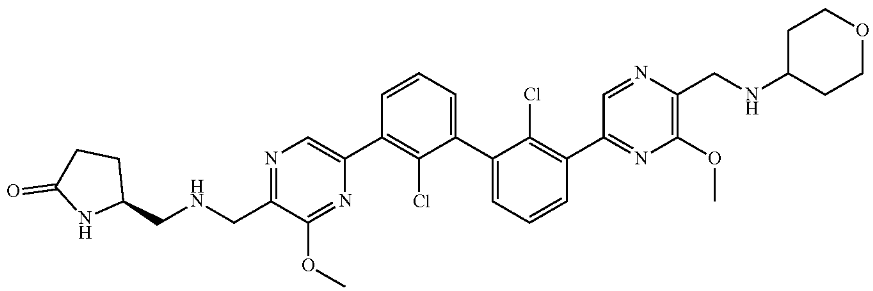 [SMILES: COc1nc(-c2cccc(-c3cccc(-c4cnc(CNC5CCOCC5)c(OC)n4)c3Cl)c2Cl)cnc1CNC[C@@H]1CCC(=O)N1] | 678.133 | 2 |
| 510 | 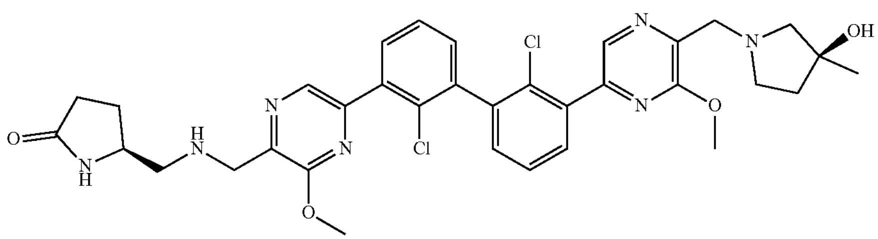 [SMILES: COc1nc(-c2cccc(-c3cccc(-c4cnc(CN5CC[C@](C)(O)C5)c(OC)n4)c3Cl)c2Cl)cnc1CNC[C@@H]1CCC(=O)N1] | 678.119 | 2 |

TABLE 1-continued

| No. | Structure | ES/MS (m/z, M + H+) | Procedure |
|---|---|---|---|
| 511 | 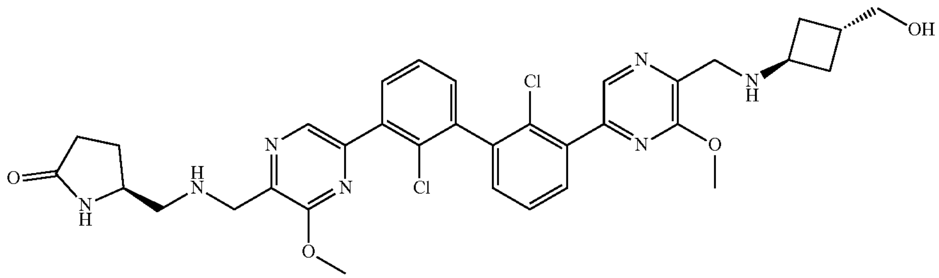 [SMILES: COc1nc(-c2cccc(-c3cccc(-c4cnc(CN[C@H]5C[C@H](CO)C5)c(OC)n4)c3Cl)c2Cl)cnc1CNC[C@@H]1CCC(=O)N1] | 678.164 | 2 |
| 512 | 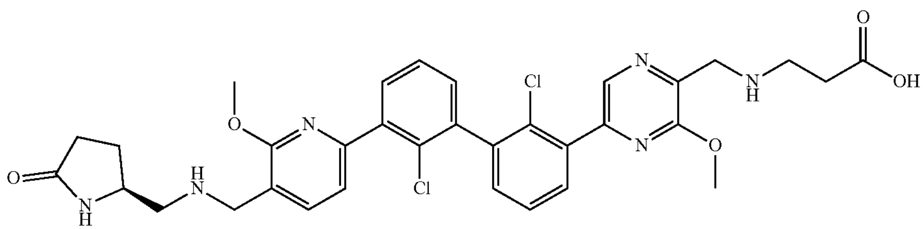 [SMILES: COc1nc(-c2cccc(-c3cccc(-c4cnc(CNCCC(=O)O)c(OC)n4)c3Cl)c2Cl)ccc1CNC[C@@H]1CCC(=O)N1] | 665.2 | 2 |
| 513 | 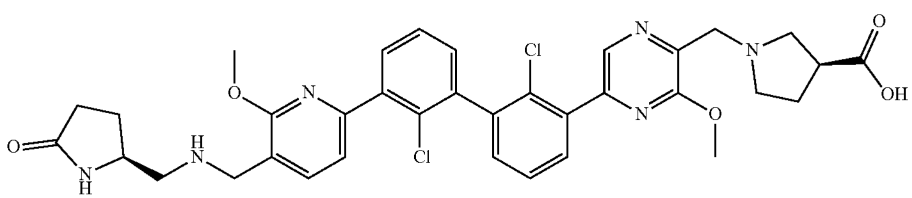 [SMILES: COc1nc(-c2cccc(-c3cccc(-c4cnc(CN5CC[C@H](C(=O)O)C5)c(OC)n4)c3Cl)c2Cl)ccc1CNC[C@@H]1CCC(=O)N1] | 691.2 | 2 |
| 514 | 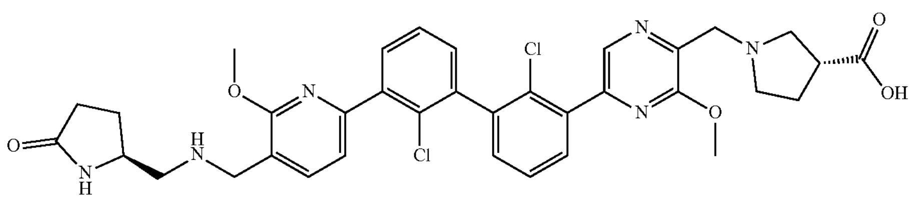 [SMILES: COc1nc(-c2cccc(-c3cccc(-c4cnc(CN5CC[C@@H](C(=O)O)C5)c(OC)n4)c3Cl)c2Cl)ccc1CNC[C@@H]1CCC(=O)N1] | 691.14 | 2 |

TABLE 1-continued
| No. | Structure | ES/MS (m/z, M + H+) | Procedure |
|---|---|---|---|
| 515 | 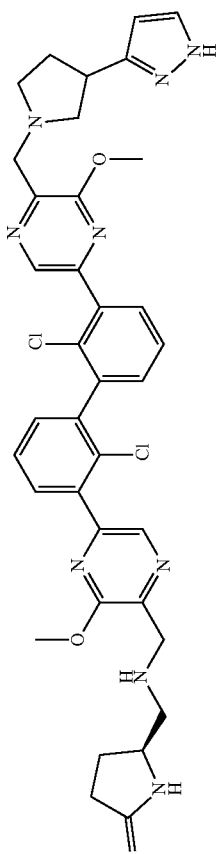 | 714.23 | 2 |
| 516 | 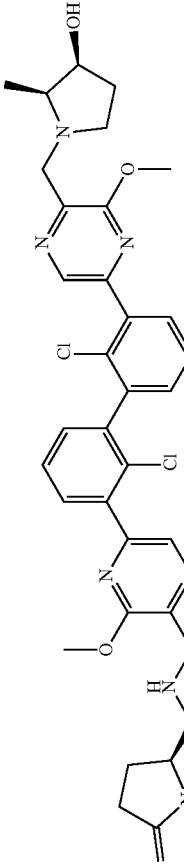 | 678.22 | 2 |
| 517 | 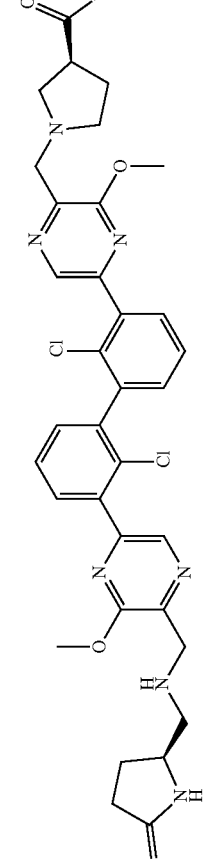 | 691.25 | 2 |
| 518 | 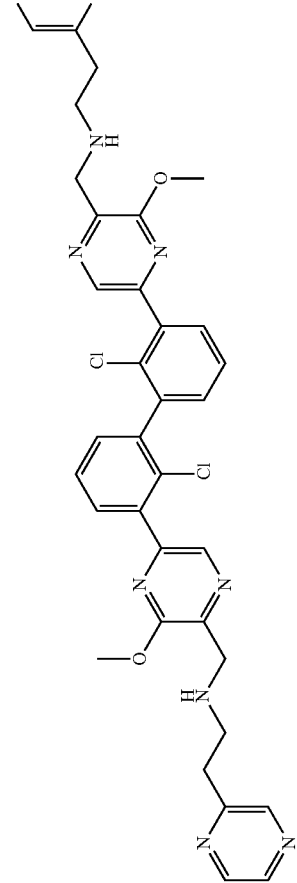 | 709.15 | 3 |

TABLE 1-continued

| No. | Structure | ES/MS (m/z, M + H⁺) | Procedure |
|---|---|---|---|
| 519 | 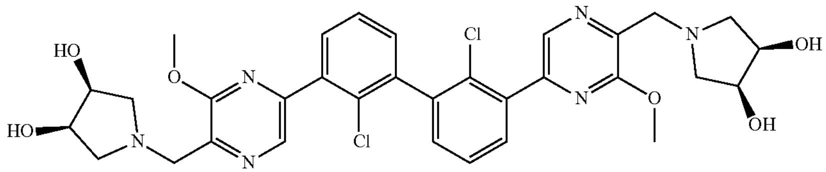 [SMILES: COc1nc(-c2cccc(-c3cccc(-c4cnc(CN5C[C@@H](O)[C@@H](O)C5)c(OC)n4)c3Cl)c2Cl)cnc1CN1C[C@@H](O)[C@@H](O)C1] | 669.23 | 3 |
| 520 | 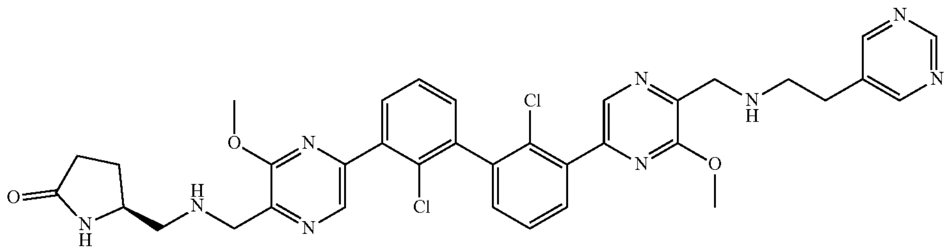 [SMILES: COc1nc(-c2cccc(-c3cccc(-c4cnc(CNC[C@@H]5CCC(=O)N5)c(OC)n4)c3Cl)c2Cl)cnc1CNCCc1cncnc1] | 700.16 | 2 |
| 521 | 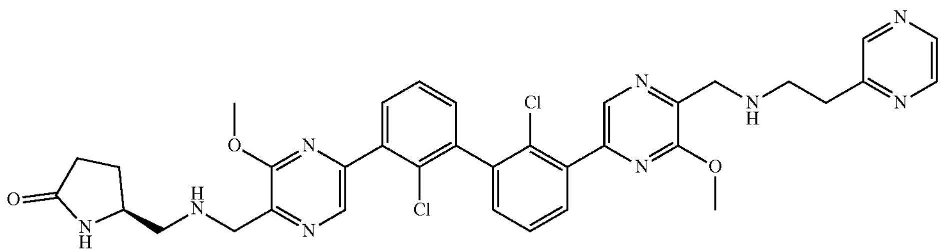 [SMILES: COc1nc(-c2cccc(-c3cccc(-c4cnc(CNC[C@@H]5CCC(=O)N5)c(OC)n4)c3Cl)c2Cl)cnc1CNCCc1cnccn1] | 700.25 | 2 |
| 522 | 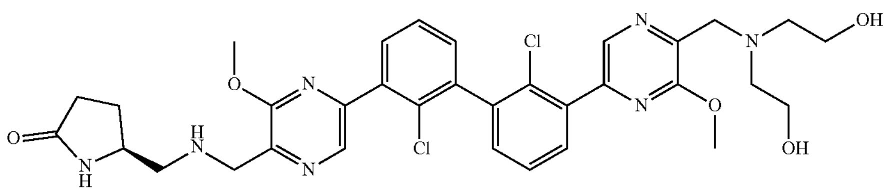 [SMILES: COc1nc(-c2cccc(-c3cccc(-c4cnc(CN(CCO)CCO)c(OC)n4)c3Cl)c2Cl)cnc1CNC[C@@H]1CCC(=O)N1] | 682.1 | 2 |

TABLE 1-continued

| No. | Structure | ES/MS (m/z, M + H⁺) | Procedure |
|---|---|---|---|
| 523 | 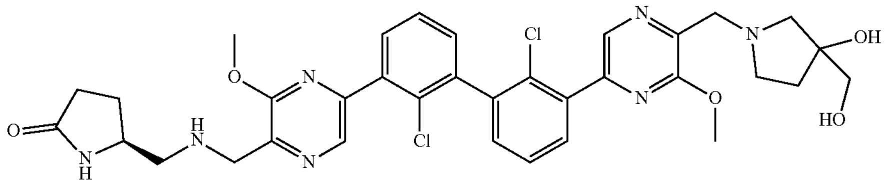 [SMILES: COc1nc(-c2cccc(-c3cccc(-c4cnc(CN5CCC(O)(CO)C5)c(OC)n4)c3Cl)c2Cl)cnc1CNC[C@@H]1CCC(=O)N1] | 694.18 | 2 |
| 524 | 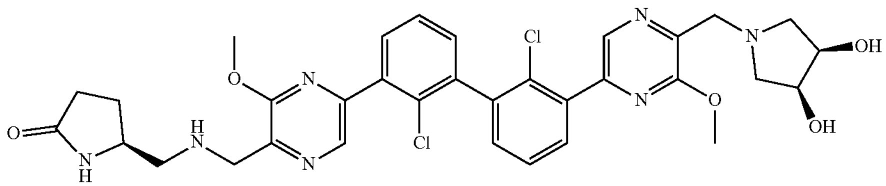 [SMILES: COc1nc(-c2cccc(-c3cccc(-c4cnc(CN5C[C@@H](O)[C@@H](O)C5)c(OC)n4)c3Cl)c2Cl)cnc1CNC[C@@H]1CCC(=O)N1] | 680.14 | 2 |
| 525 | 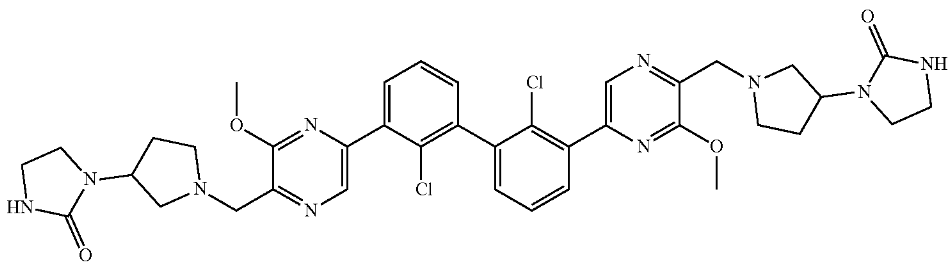 [SMILES: COc1nc(-c2cccc(-c3cccc(-c4cnc(CN5CCC(N6CCNC6=O)C5)c(OC)n4)c3Cl)c2Cl)cnc1CN1CCC(N2CCNC2=O)C1] | 773.26 | 3 |
| 526 | 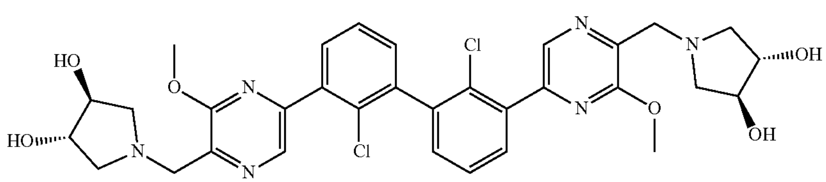 [SMILES: COc1nc(-c2cccc(-c3cccc(-c4cnc(CN5C[C@H](O)[C@@H](O)C5)c(OC)n4)c3Cl)c2Cl)cnc1CN1C[C@H](O)[C@@H](O)C1] | 669.21 | 3 |
| 527 | 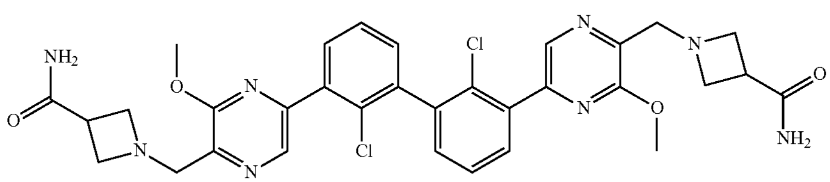 [SMILES: COc1nc(-c2cccc(-c3cccc(-c4cnc(CN5CC(C(N)=O)C5)c(OC)n4)c3Cl)c2Cl)cnc1CN1CC(C(N)=O)C1] | 663.63 | 3 |

TABLE 1-continued

| No. | Structure | ES/MS (m/z, M + H+) | Procedure |
|---|---|---|---|
| 528 | 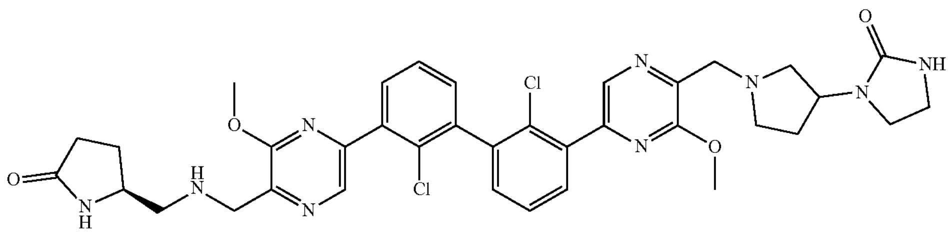 [SMILES: COc1nc(-c2cccc(-c3cccc(-c4cnc(CN5CCC(N6CCNC6=O)C5)c(OC)n4)c3Cl)c2Cl)cnc1CNC[C@@H]1CCC(=O)N1] | 732.22 | 2 |
| 529 | 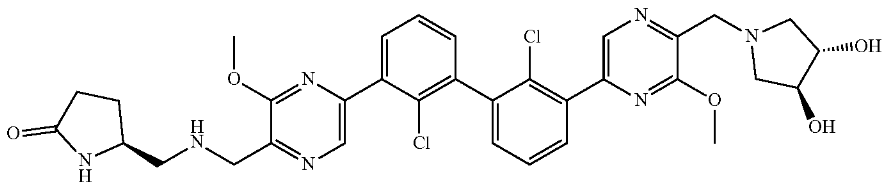 [SMILES: COc1nc(-c2cccc(-c3cccc(-c4cnc(CN5C[C@H](O)[C@@H](O)C5)c(OC)n4)c3Cl)c2Cl)cnc1CNC[C@@H]1CCC(=O)N1] | 680.48 | 2 |
| 530 | 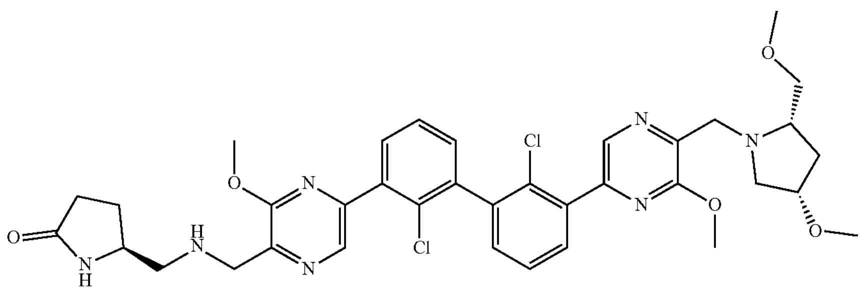 [SMILES: COC[C@@H]1C[C@H](OC)CN1Cc1ncc(-c2cccc(-c3cccc(-c4cnc(CNC[C@@H]5CCC(=O)N5)c(OC)n4)c3Cl)c2Cl)nc1OC] | 722.38 | 2 |
| 531 | 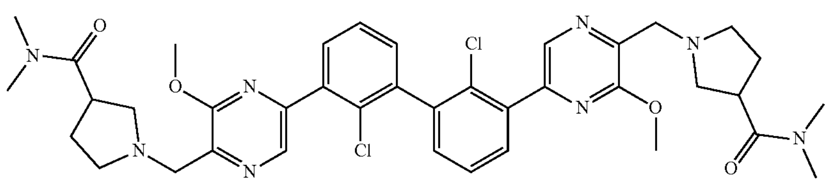 | 747.32 | 3 |

TABLE 1-continued

| No. | Structure | ES/MS (m/z, M + H+) | Procedure |
|---|---|---|---|
| 532 | 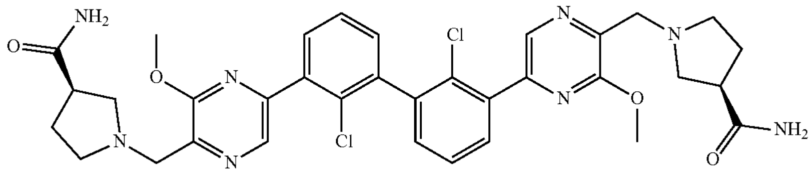 [SMILES: COc1nc(-c2cccc(-c3cccc(-c4cnc(CN5CC[C@@H](C(N)=O)C5)c(OC)n4)c3Cl)c2Cl)cnc1CN1CC[C@@H](C(N)=O)C1] | 691.15 | 3 |
| 533 | 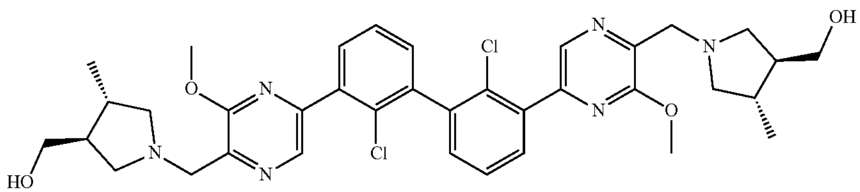 [SMILES: COc1nc(-c2cccc(-c3cccc(-c4cnc(CN5C[C@@H](CO)[C@H](C)C5)c(OC)n4)c3Cl)c2Cl)cnc1CN1C[C@@H](CO)[C@H](C)C1] | 693.18 | 3 |
| 534 | 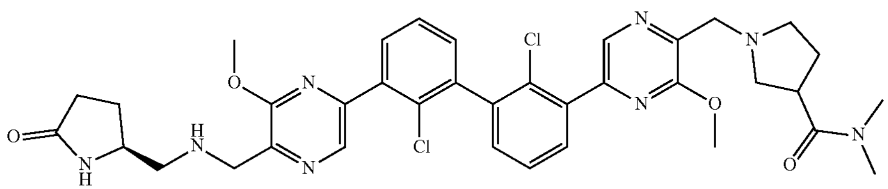 [SMILES: COc1nc(-c2cccc(-c3cccc(-c4cnc(CN5CCC(C(=O)N(C)C)C5)c(OC)n4)c3Cl)c2Cl)cnc1CNC[C@@H]1CCC(=O)N1] | 719.45 | 2 |
| 535 | 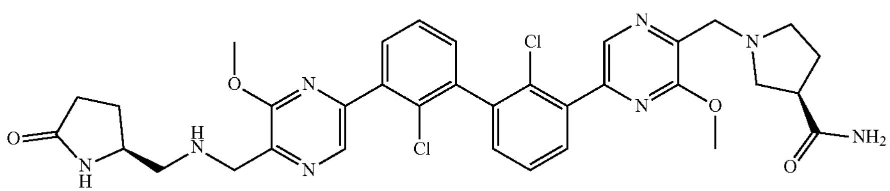 [SMILES: COc1nc(-c2cccc(-c3cccc(-c4cnc(CN5CC[C@@H](C(N)=O)C5)c(OC)n4)c3Cl)c2Cl)cnc1CNC[C@@H]1CCC(=O)N1] | 691.21 | 2 |

TABLE 1-continued

| No. | Structure | ES/MS (m/z, M + H⁺) | Procedure |
|-----|-----------|---------------------|-----------|
| 536 | 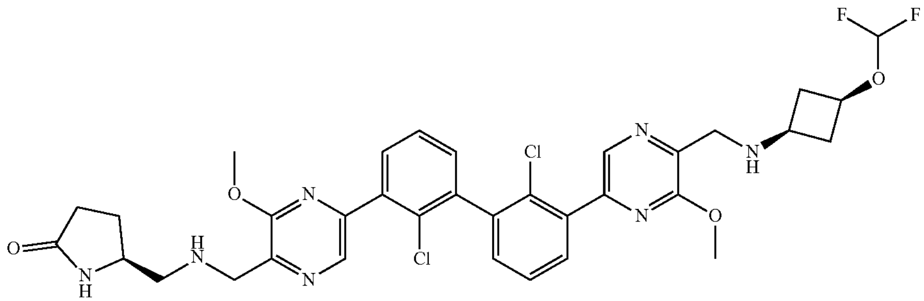 [SMILES: COc1nc(-c2cccc(-c3cccc(-c4cnc(CN[C@H]5C[C@@H](OC(F)F)C5)c(OC)n4)c3Cl)c2Cl)cnc1CNC[C@@H]1CCC(=O)N1] | 714.07 | 2 |
| 537 | 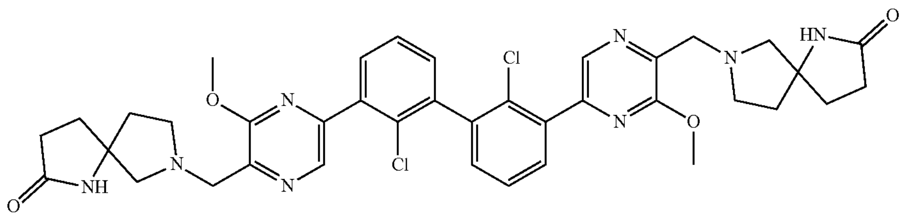 [SMILES: COc1nc(-c2cccc(-c3cccc(-c4cnc(CN5CCC6(CCC(=O)N6)C5)c(OC)n4)c3Cl)c2Cl)cnc1CN1CCC2(CCC(=O)N2)C1] | 743.2 | 3 |
| 538 | 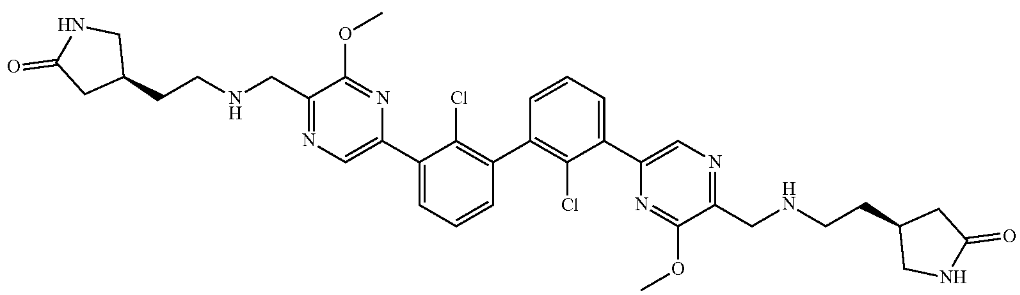 [SMILES: COc1nc(-c2cccc(-c3cccc(-c4cnc(CNCC[C@@H]5CNC(=O)C5)c(OC)n4)c3Cl)c2Cl)cnc1CNCC[C@@H]1CNC(=O)C1] | 720.31 | 3 |

TABLE 1-continued

| No. | Structure | ES/MS (m/z, M + H+) | Procedure |
|---|---|---|---|
| 539 | 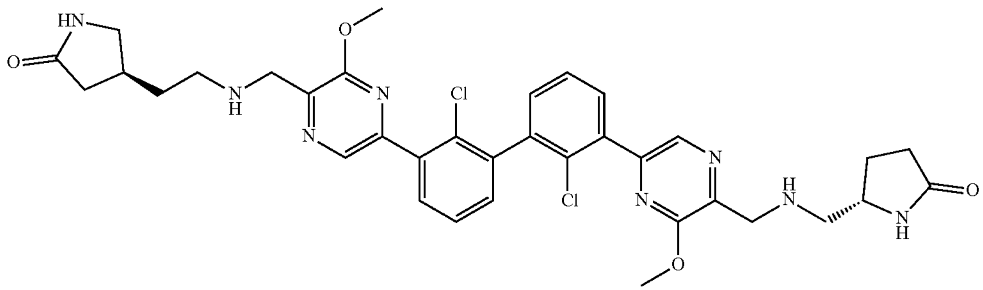 [SMILES: COc1nc(-c2cccc(-c3cccc(-c4cnc(CNC[C@@H]5CCC(=O)N5)c(OC)n4)c3Cl)c2Cl)cnc1CNCC[C@@H]1CNC(=O)C1] | 705.22 | 2 |
| 540 | 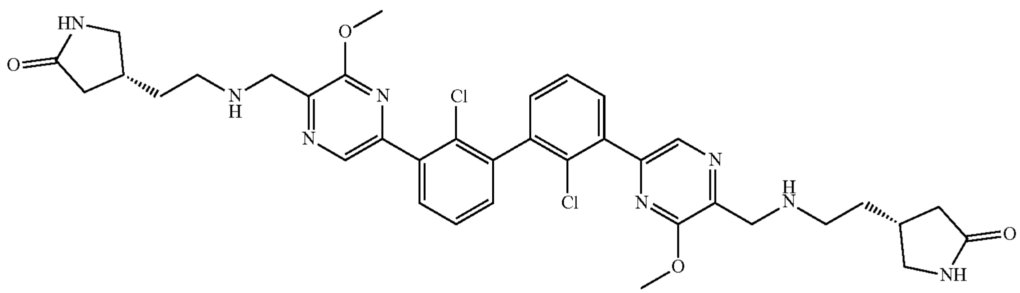 [SMILES: COc1nc(-c2cccc(-c3cccc(-c4cnc(CNCC[C@H]5CNC(=O)C5)c(OC)n4)c3Cl)c2Cl)cnc1CNCC[C@H]1CNC(=O)C1] | 720.19 | 3 |
| 541 | 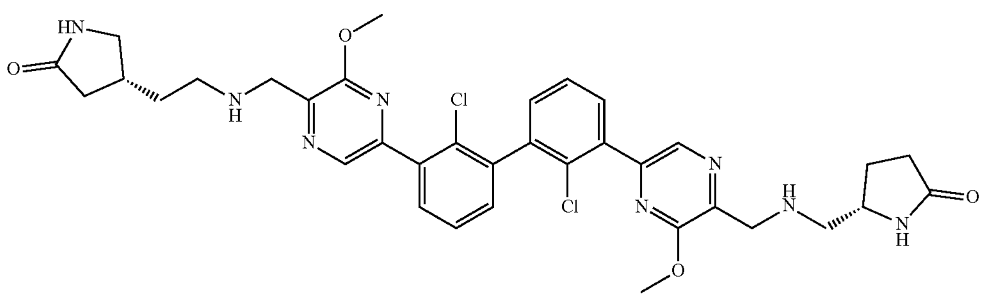 [SMILES: COc1nc(-c2cccc(-c3cccc(-c4cnc(CNC[C@@H]5CCC(=O)N5)c(OC)n4)c3Cl)c2Cl)cnc1CNCC[C@H]1CNC(=O)C1] | 705.2 | 2 |

TABLE 1-continued

| No. | Structure | ES/MS (m/z, M + H⁺) | Procedure |
|---|---|---|---|
| 542 | 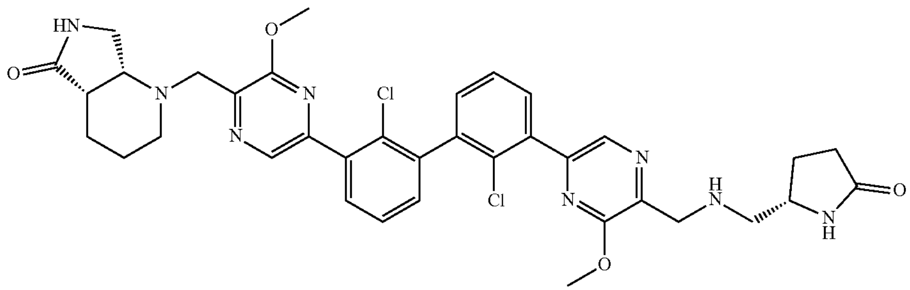 [SMILES: COc1nc(-c2cccc(-c3cccc(-c4cnc(CN5CCC[C@@H]6C(=O)NC[C@@H]65)c(OC)n4)c3Cl)c2Cl)cnc1CNC[C@@H]1CCC(=O)N1] | 717.19 | 2 |
| 543 | 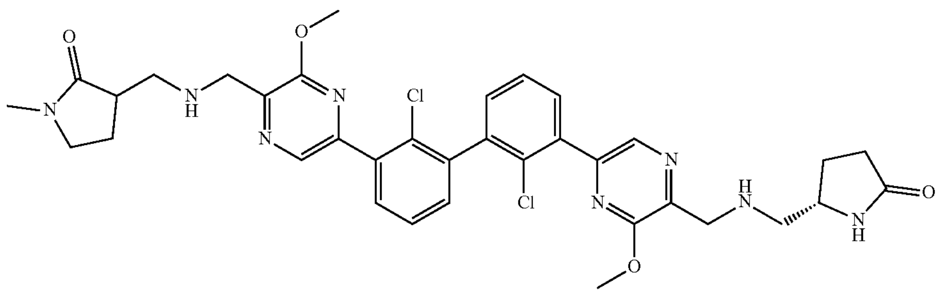 [SMILES: COc1nc(-c2cccc(-c3cccc(-c4cnc(CNC[C@@H]5CCC(=O)N5)c(OC)n4)c3Cl)c2Cl)cnc1CNCC1CCN(C)C1=O] | 705.3 | 2 |
| 544 | 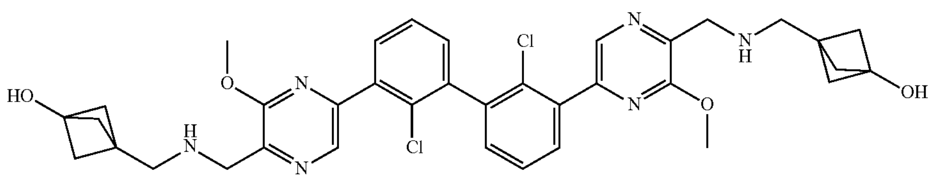 [SMILES: COc1nc(-c2cccc(-c3cccc(-c4cnc(CNCC56CC(O)(C5)C6)c(OC)n4)c3Cl)c2Cl)cnc1CNCC12CC(O)(C1)C2] | 689.13 | 3 |
| 545 | 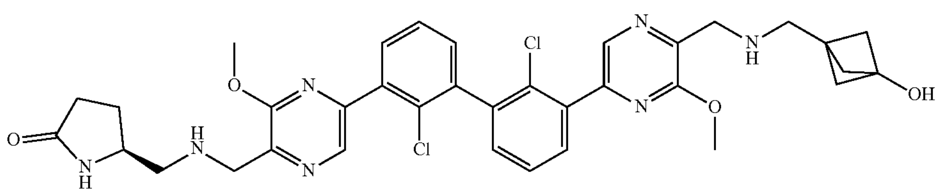 [SMILES: COc1nc(-c2cccc(-c3cccc(-c4cnc(CNCC56CC(O)(C5)C6)c(OC)n4)c3Cl)c2Cl)cnc1CNC[C@@H]1CCC(=O)N1] | 690.1 | 2 |

TABLE 1-continued

| No. | Structure | ES/MS (m/z, M + H⁺) | Procedure |
|---|---|---|---|
| 546 | 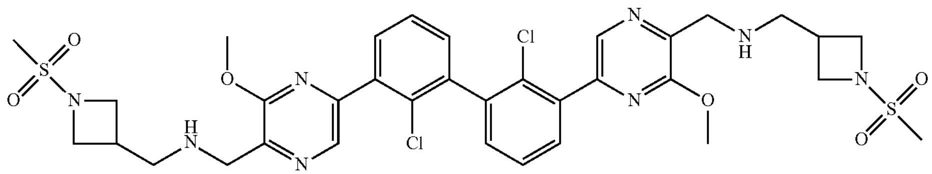 [SMILES: COc1nc(-c2cccc(-c3cccc(-c4cnc(CNCC5CN(S(C)(=O)=O)C5)c(OC)n4)c3Cl)c2Cl)cnc1CNCC1CN(S(C)(=O)=O)C1] | 791.12 | 3 |
| 547 | 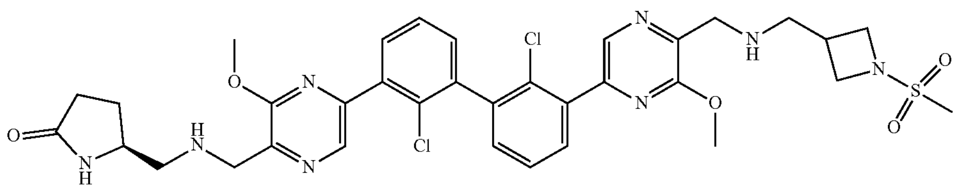 [SMILES: COc1nc(-c2cccc(-c3cccc(-c4cnc(CNC[C@@H]5CCC(=O)N5)c(OC)n4)c3Cl)c2Cl)cnc1CNCC1CN(S(C)(=O)=O)C1] | 741.17 | 2 |
| 548 | 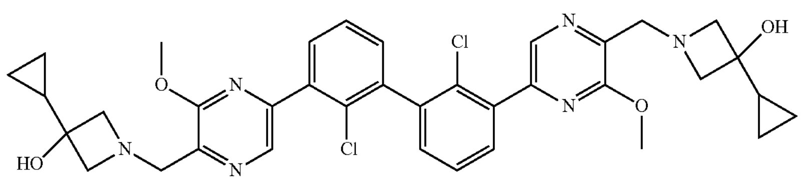 [SMILES: COc1nc(-c2cccc(-c3cccc(-c4cnc(CN5CC(O)(C6CC6)C5)c(OC)n4)c3Cl)c2Cl)cnc1CN1CC(O)(C2CC2)C1] | 689.17 | 3 |
| 549 | 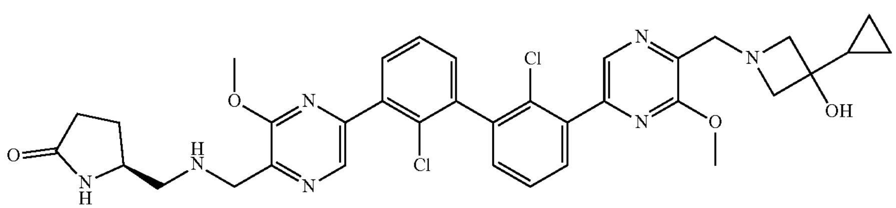 [SMILES: COc1nc(-c2cccc(-c3cccc(-c4cnc(CN5CC(O)(C6CC6)C5)c(OC)n4)c3Cl)c2Cl)cnc1CNC[C@@H]1CCC(=O)N1] | 690.19 | 2 |
| 550 | 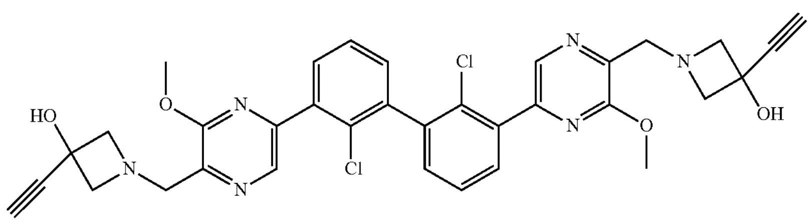 [SMILES: C#CC1(O)CN(Cc2ncc(-c3cccc(-c4cccc(-c5cnc(CN6CC(O)(C#C)C6)c(OC)n5)c4Cl)c3Cl)nc2OC)C1] | 659.14 | 3 |

TABLE 1-continued

| No. | Structure | ES/MS (m/z, M + H⁺) | Procedure |
|-----|-----------|---------------------|-----------|
| 551 | 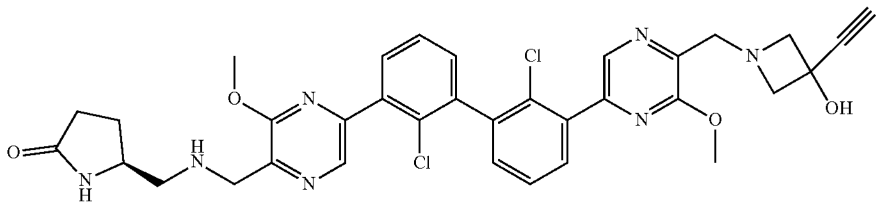 [SMILES: C#CC1(O)CN(Cc2ncc(-c3cccc(-c4cccc(-c5cnc(CNC[C@@H]6CCC(=O)N6)c(OC)n5)c4Cl)c3Cl)nc2OC)C1] | 674.14 | 2 |
| 552 | 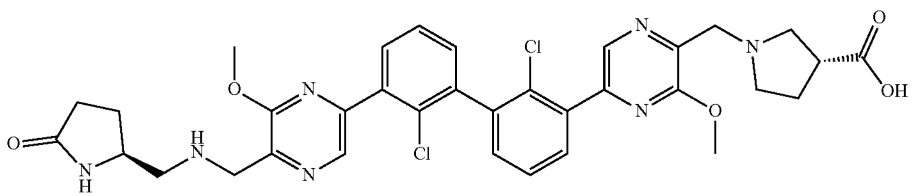 [SMILES: COc1nc(-c2cccc(-c3cccc(-c4cnc(CN5CC[C@@H](C(=O)O)C5)c(OC)n4)c3Cl)c2Cl)cnc1CNC[C@@H]1CCC(=O)N1] | 692.21 | 2 |
| 553 | 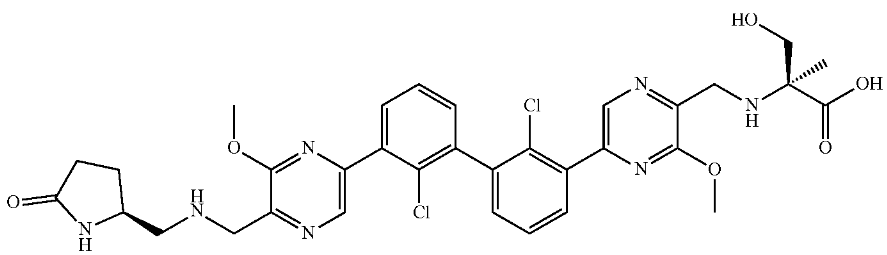 [SMILES: COc1nc(-c2cccc(-c3cccc(-c4cnc(CN[C@@](C)(CO)C(=O)O)c(OC)n4)c3Cl)c2Cl)cnc1CNC[C@@H]1CCC(=O)N1] | 696.07 | 2 |
| 554 | 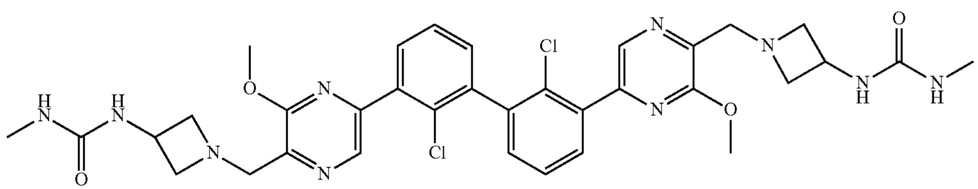 | 721.14 | 3 |

TABLE 1-continued

| No. | Structure | ES/MS (m/z, M + H+) | Procedure |
|---|---|---|---|
| 555 | 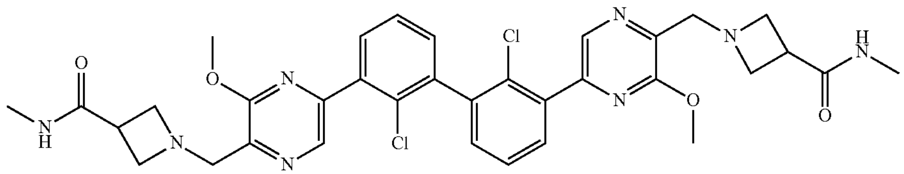 | 691.18 | 3 |
| 556 | 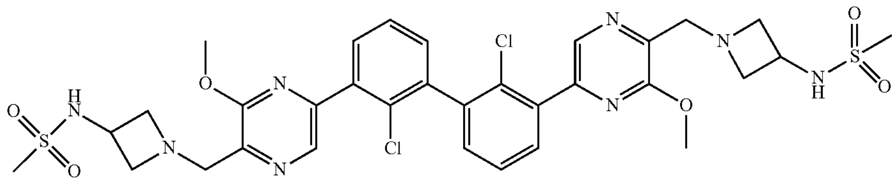 | 763.11 | 3 |
| 557 | 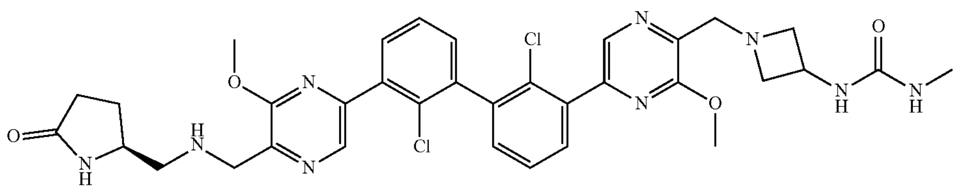 [SMILES: CNC(=O)NC1CN(Cc2ncc(-c3cccc(-c4cccc(-c5cnc(CNC[C@@H]6CCC(=O)N6)c(OC)n5)c4Cl)c3Cl)nc2OC)C1] | 706.19 | 2 |
| 558 | 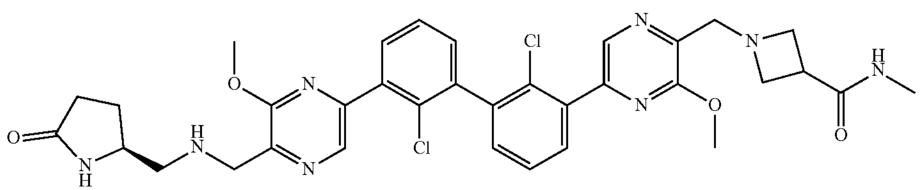 [SMILES: CNC(=O)C1CN(Cc2ncc(-c3cccc(-c4cccc(-c5cnc(CNC[C@@H]6CCC(=O)N6)c(OC)n5)c4Cl)c3Cl)nc2OC)C1] | 691.19 | 2 |
| 559 | 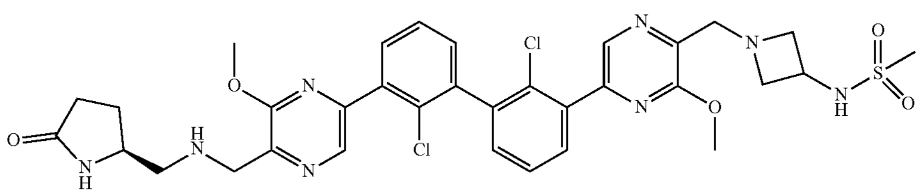 [SMILES: COc1nc(-c2cccc(-c3cccc(-c4cnc(CN5CC(NS(C)(=O)=O)C5)c(OC)n4)c3Cl)c2Cl)cnc1CNC[C@@H]1CCC(=O)N1] | 727.13 | 2 |

TABLE 1-continued
| No. | Structure | ES/MS (m/z, M + H+) | Procedure |
|---|---|---|---|
| 560 | 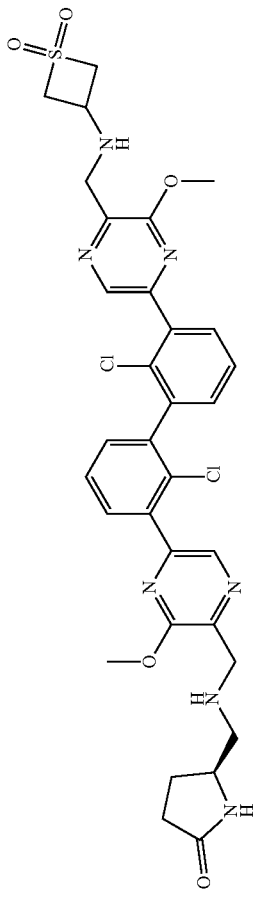 | 698.11 | 2 |
| 561 | 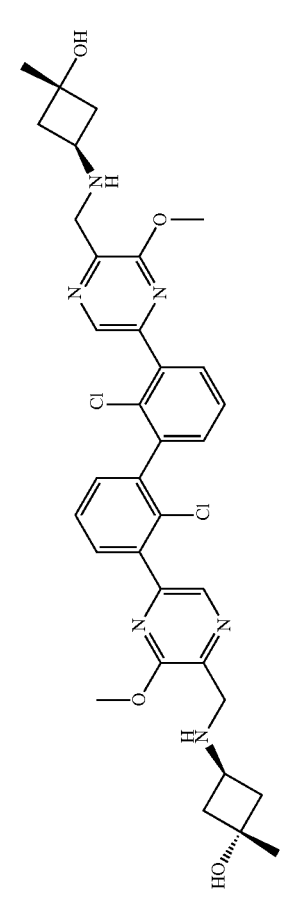 | 665.12 | 3 |
| 562 | 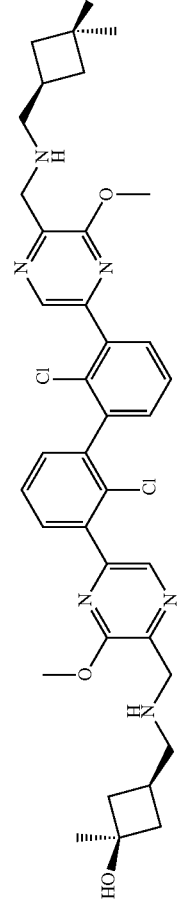 | 693.14 | 3 |
| 563 | 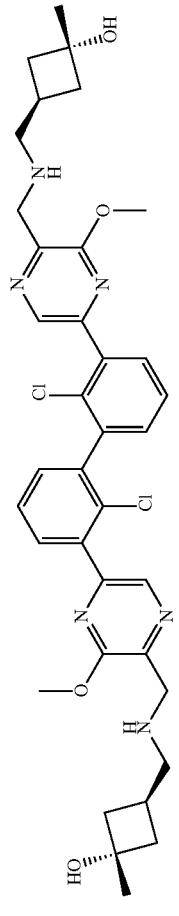 | 693.13 | 3 |

TABLE 1-continued

| No. | Structure | ES/MS (m/z, M + H+) | Procedure |
|---|---|---|---|
| 564 | 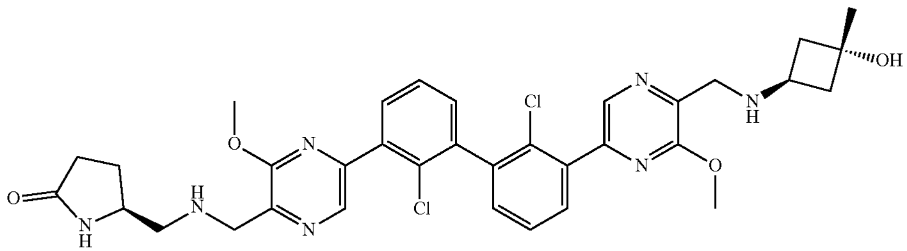 [SMILES: COc1nc(-c2cccc(-c3cccc(-c4cnc(CN[C@H]5C[C@](C)(O)C5)c(OC)n4)c3Cl)c2Cl)cnc1CNC[C@@H]1CCC(=O)N1] | 678.12 | 2 |
| 565 | 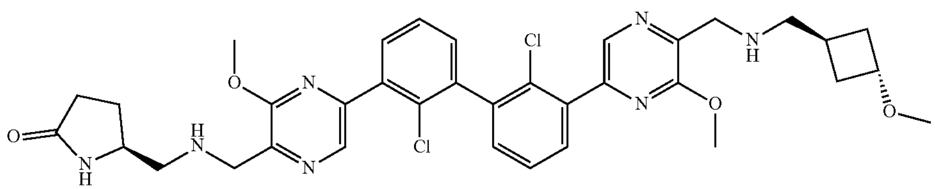 [SMILES: COc1nc(-c2cccc(-c3cccc(-c4cnc(CNC[C@H]5C[C@H](OC)C5)c(OC)n4)c3Cl)c2Cl)cnc1CNC[C@@H]1CCC(=O)N1] | 692.12 | 2 |
| 566 | 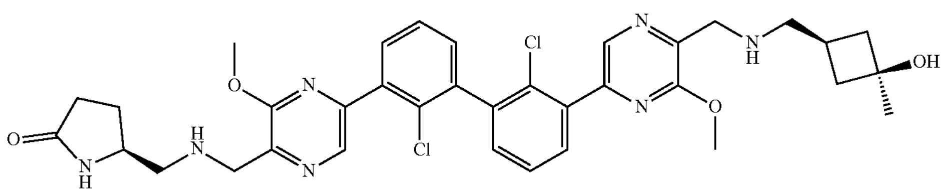 [SMILES: COc1nc(-c2cccc(-c3cccc(-c4cnc(CNC[C@H]5C[C@@](C)(O)C5)c(OC)n4)c3Cl)c2Cl)cnc1CNC[C@@H]1CCC(=O)N1] | 692.12 | 2 |
| 567 | 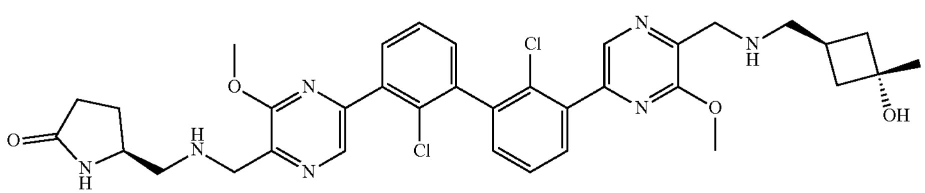 [SMILES: COc1nc(-c2cccc(-c3cccc(-c4cnc(CNC[C@H]5C[C@](C)(O)C5)c(OC)n4)c3Cl)c2Cl)cnc1CNC[C@@H]1CCC(=O)N1] | 692.13 | 2 |

TABLE 1-continued

| No. | Structure | ES/MS (m/z, M + H+) | Procedure |
|---|---|---|---|
| 568 | 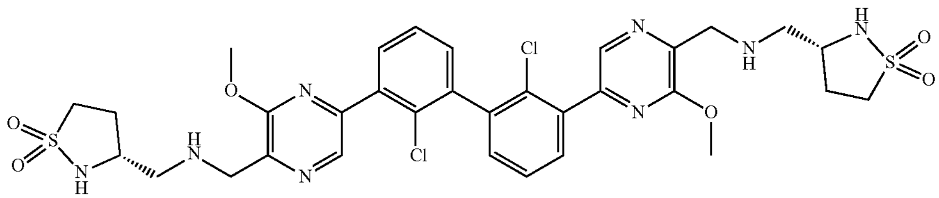 [SMILES: COc1nc(-c2cccc(-c3cccc(-c4cnc(CNC[C@H]5CCS(=O)(=O)N5)c(OC)n4)c3Cl)c2Cl)cnc1CNC[C@H]1CCS(=O)(=O)N1] | 763.03 | 3 |
| 569 | 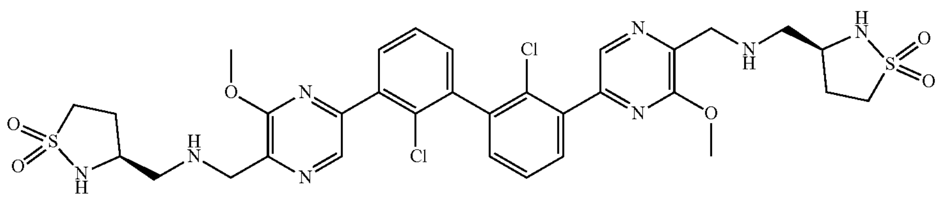 [SMILES: COc1nc(-c2cccc(-c3cccc(-c4cnc(CNC[C@@H]5CCS(=O)(=O)N5)c(OC)n4)c3Cl)c2Cl)cnc1CNC[C@@H]1CCS(=O)(=O)N1] | 763.03 | 3 |
| 570 | 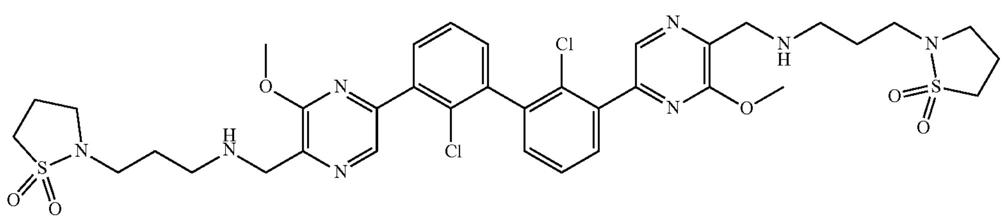 [SMILES: COc1nc(-c2cccc(-c3cccc(-c4cnc(CNCCCN5CCCS5(=O)=O)c(OC)n4)c3Cl)c2Cl)cnc1CNCCCN1CCCS1(=O)=O] | 819.11 | 3 |
| 571 | 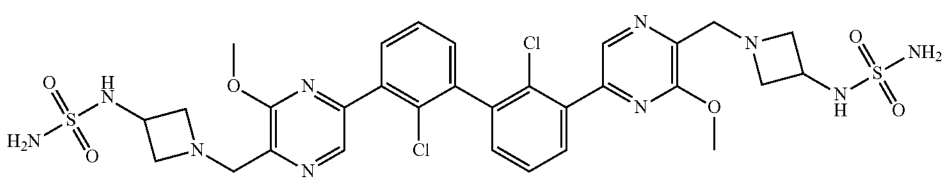 [SMILES: COc1nc(-c2cccc(-c3cccc(-c4cnc(CN5CC(NS(N)(=O)=O)C5)c(OC)n4)c3Cl)c2Cl)cnc1CN1CC(NS(N)(=O)=O)C1] | 764.92 | 3 |

TABLE 1-continued

| No. | Structure | ES/MS (m/z, M + H+) | Procedure |
|---|---|---|---|
| 572 | 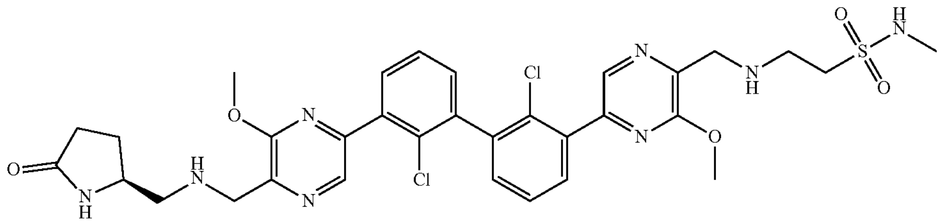 [SMILES: CNS(=O)(=O)CCNCc1ncc(-c2cccc(-c3cccc(-c4cnc(CNC[C@@H]5CCC(=O)N5)c(OC)n4)c3Cl)c2Cl)nc1OC] | 715.01 | 2 |
| 573 | 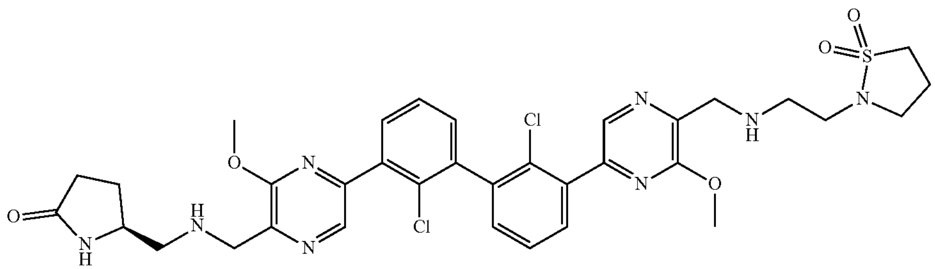 [SMILES: COc1nc(-c2cccc(-c3cccc(-c4cnc(CNC[C@@H]5CCC(=O)N5)c(OC)n4)c3Cl)c2Cl)cnc1CNCCN1CCCS1(=O)=O] | 741.14 | 2 |
| 574 | 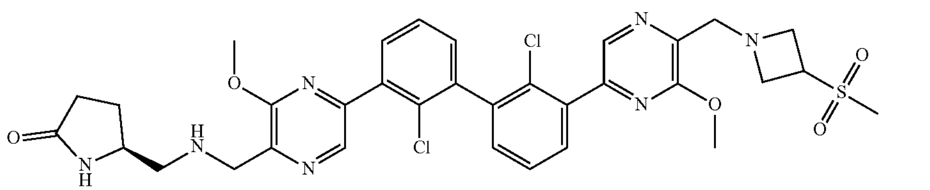 [SMILES: COc1nc(-c2cccc(-c3cccc(-c4cnc(CN5CC(S(C)(=O)=O)C5)c(OC)n4)c3Cl)c2Cl)cnc1CNC[C@@H]1CCC(=O)N1] | 712.12 | 2 |
| 575 | 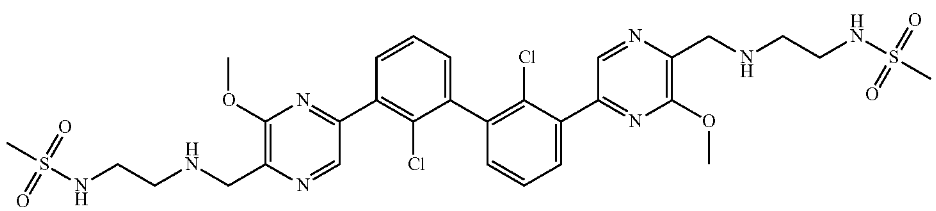 | 739.06 | 3 |

TABLE 1-continued

| No. | Structure | ES/MS (m/z, M + H⁺) | Procedure |
|---|---|---|---|
| 576 | 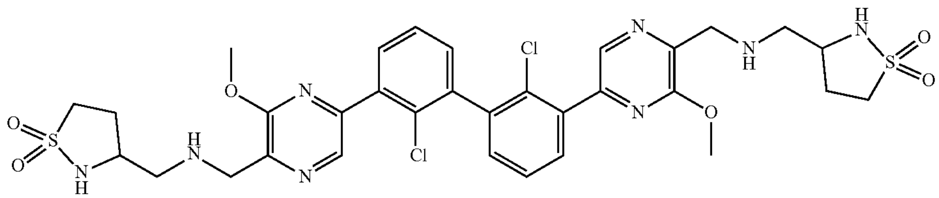 [SMILES: COc1nc(-c2cccc(-c3cccc(-c4cnc(CNCC5CCS(=O)(=O)N5)c(OC)n4)c3Cl)c2Cl)cnc1CNCC1CCS(=O)(=O)N1] | 763.1 | 3 |
| 577 | 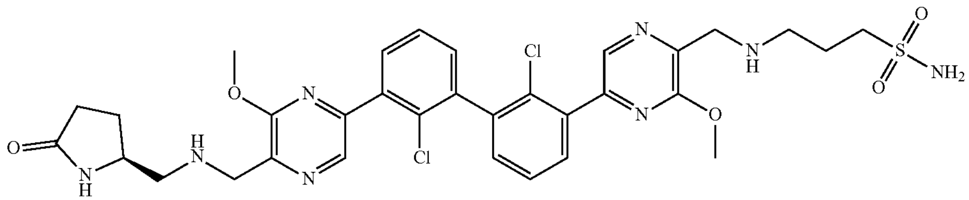 [SMILES: COc1nc(-c2cccc(-c3cccc(-c4cnc(CNC[C@@H]5CCC(=O)N5)c(OC)n4)c3Cl)c2Cl)cnc1CNCCCS(N)(=O)=O] | 715.06 | 2 |
| 578 | 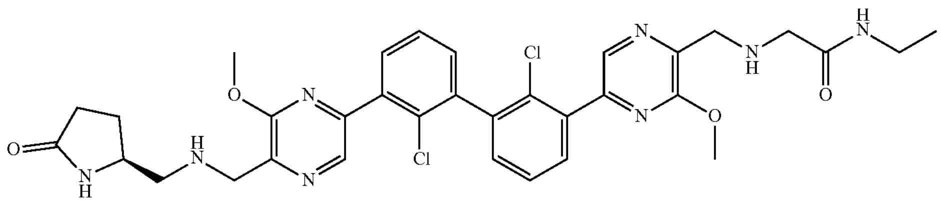 [SMILES: CCNC(=O)CNCc1ncc(-c2cccc(-c3cccc(-c4cnc(CNC[C@@H]5CCC(=O)N5)c(OC)n4)c3Cl)c2Cl)nc1OC] | 679.12 | 2 |
| 579 | 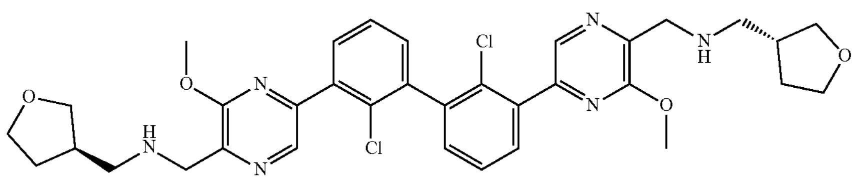 [SMILES: COc1nc(-c2cccc(-c3cccc(-c4cnc(CNC[C@H]5CCOC5)c(OC)n4)c3Cl)c2Cl)cnc1CNC[C@H]1CCOC1] | 665.13 | 3 |
| 580 | 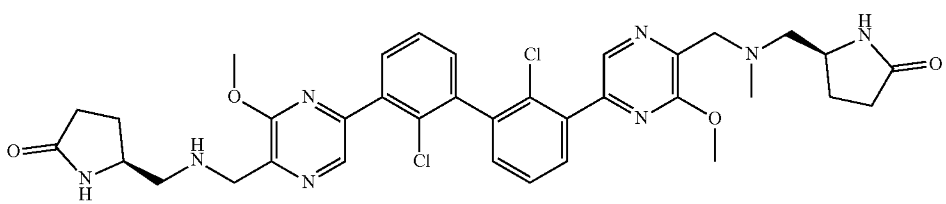 [SMILES: COc1nc(-c2cccc(-c3cccc(-c4cnc(CN(C)C[C@@H]5CCC(=O)N5)c(OC)n4)c3Cl)c2Cl)cnc1CNC[C@@H]1CCC(=O)N1] | 705.18 | 2 |

TABLE 1-continued

| No. | Structure | ES/MS (m/z, M + H+) | Procedure |
|---|---|---|---|
| 581 | 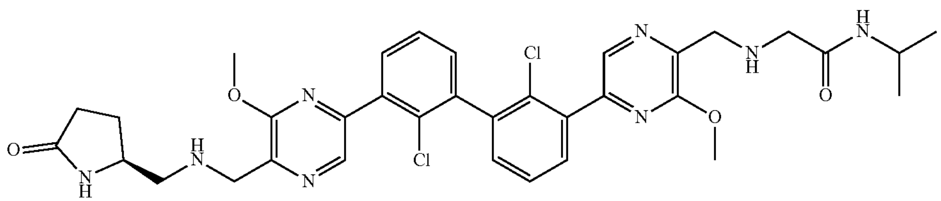 [SMILES: COc1nc(-c2cccc(-c3cccc(-c4cnc(CNC[C@@H]5CCC(=O)N5)c(OC)n4)c3Cl)c2Cl)cnc1CNCC(=O)NC(C)C] | 693.1 | 2 |
| 582 | 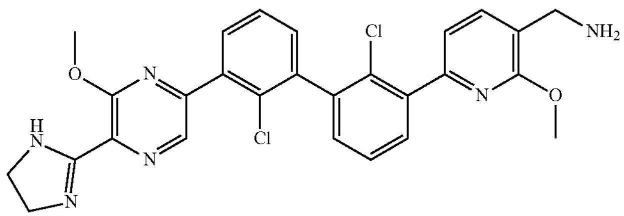 [SMILES: COc1nc(-c2cccc(-c3cccc(-c4cnc(C5=NCCN5)c(OC)n4)c3Cl)c2Cl)ccc1CN] | 535.1 | 10 |
| 583 | 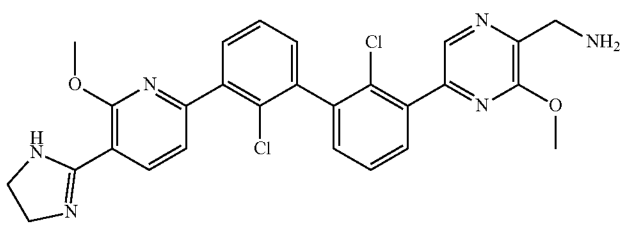 [SMILES: COc1nc(-c2cccc(-c3cccc(-c4cnc(CN)c(OC)n4)c3Cl)c2Cl)ccc1C1=NCCN1] | 535.1 | 10 |
| 584 | 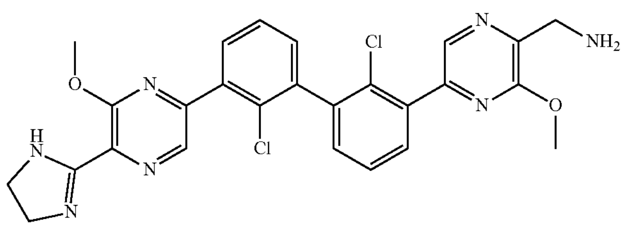 [SMILES: COc1nc(-c2cccc(-c3cccc(-c4cnc(C5=NCCN5)c(OC)n4)c3Cl)c2Cl)cnc1CN] | 536.1 | 10 |

TABLE 1-continued

| No. | Structure | ES/MS (m/z, M + H+) | Procedure |
|---|---|---|---|
| 585 | 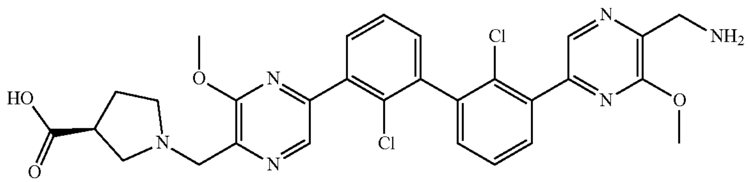 [SMILES: COc1nc(-c2cccc(-c3cccc(-c4cnc(CN5CC[C@H](C(=O)O)C5)c(OC)n4)c3Cl)c2Cl)cnc1CN] | 594.9 | 2 |
| 586 | 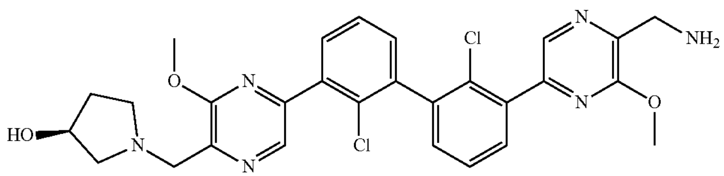 [SMILES: COc1nc(-c2cccc(-c3cccc(-c4cnc(CN5CC[C@H](O)C5)c(OC)n4)c3Cl)c2Cl)cnc1CN] | 567.2 | 2 |
| 587 | 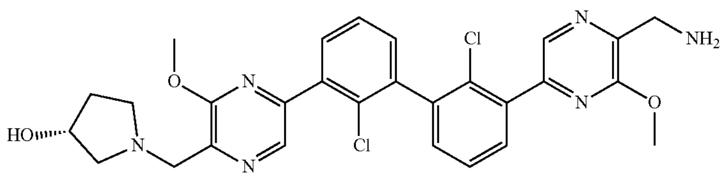 [SMILES: COc1nc(-c2cccc(-c3cccc(-c4cnc(CN5CC[C@@H](O)C5)c(OC)n4)c3Cl)c2Cl)cnc1CN] | 567.2 | 2 |
| 588 | 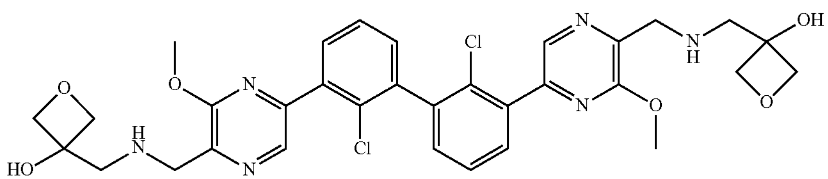 [SMILES: COc1nc(-c2cccc(-c3cccc(-c4cnc(CNCC5(O)COC5)c(OC)n4)c3Cl)c2Cl)cnc1CNCC1(O)COC1] | 670.1 | 3 |
| 589 | 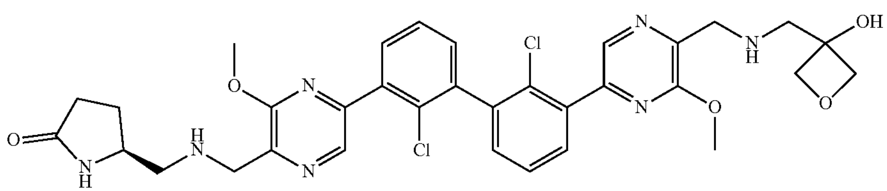 [SMILES: COc1nc(-c2cccc(-c3cccc(-c4cnc(CNCC5(O)COC5)c(OC)n4)c3Cl)c2Cl)cnc1CNC[C@@H]1CCC(=O)N1] | 680.9 | 2 |

TABLE 1-continued

| No. | Structure | ES/MS (m/z, M + H⁺) | Procedure |
|---|---|---|---|
| 590 | 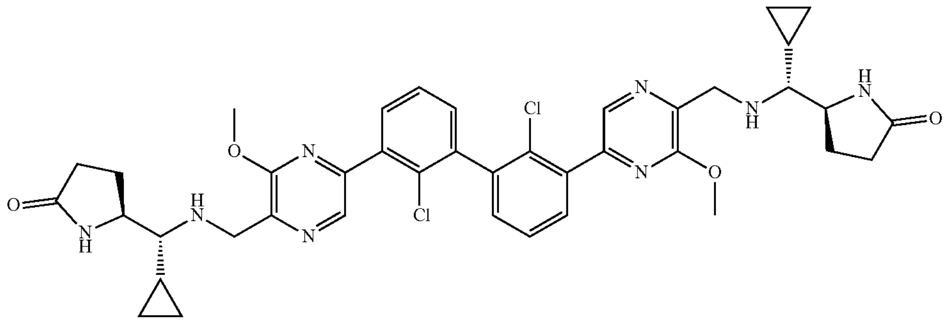 [SMILES: COc1nc(-c2cccc(-c3cccc(-c4cnc(CN[C@H](C5CC5)[C@@H]5CCC(=O)N5)c(OC)n4)c3Cl)c2Cl)cnc1CN[C@H](C1CC1)[C@@H]1CCC(=O)N1] | 772.3 | 3 |
| 591 | 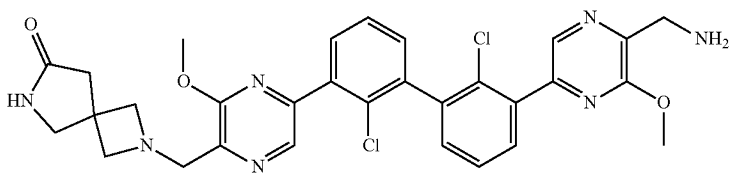 [SMILES: COc1nc(-c2cccc(-c3cccc(-c4cnc(CN5CC6(CNC(=O)C6)C5)c(OC)n4)c3Cl)c2Cl)cnc1CN] | 607.1 | 2 |
| 592 | 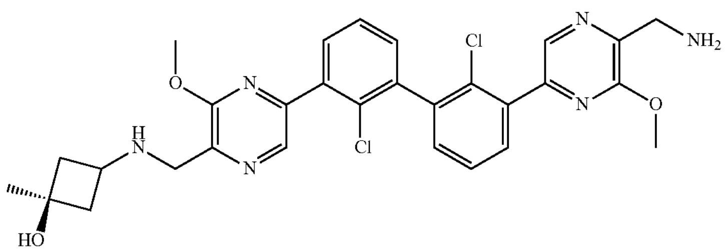 | 581.2 | 2 |
| 593 | 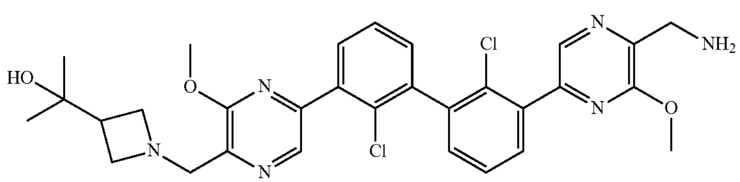 [SMILES: COc1nc(-c2cccc(-c3cccc(-c4cnc(CN5CC(C(C)(C)O)C5)c(OC)n4)c3Cl)c2Cl)cnc1CN] | 596.2 | 2 |

TABLE 1-continued

| No. | Structure | ES/MS (m/z, M + H+) | Procedure |
|---|---|---|---|
| 594 | 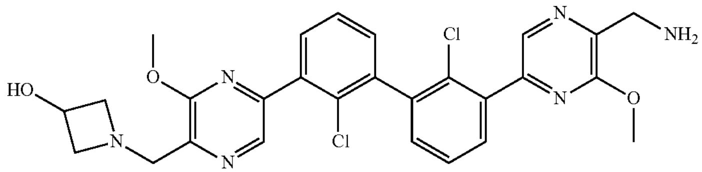 [SMILES: COc1nc(-c2cccc(-c3cccc(-c4cnc(CN5CC(O)C5)c(OC)n4)c3Cl)c2Cl)cnc1CN] | 553 | 2 |
| 595 | 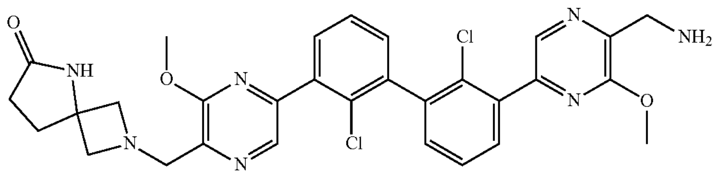 [SMILES: COc1nc(-c2cccc(-c3cccc(-c4cnc(CN5CC6(CCC(=O)N6)C5)c(OC)n4)c3Cl)c2Cl)cnc1CN] | 607 | 2 |
| 596 | 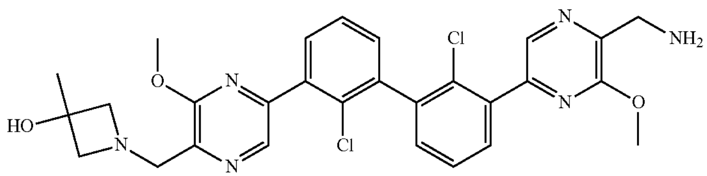 [SMILES: COc1nc(-c2cccc(-c3cccc(-c4cnc(CN5CC(C)(O)C5)c(OC)n4)c3Cl)c2Cl)cnc1CN] | 567 | 2 |
| 597 | 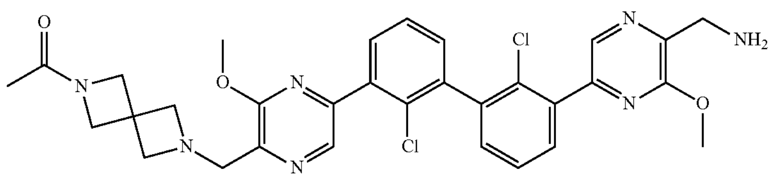 [SMILES: COc1nc(-c2cccc(-c3cccc(-c4cnc(CN5CC6(C5)CN(C(C)=O)C6)c(OC)n4)c3Cl)c2Cl)cnc1CN] | 620.2 | 2 |
| 598 | 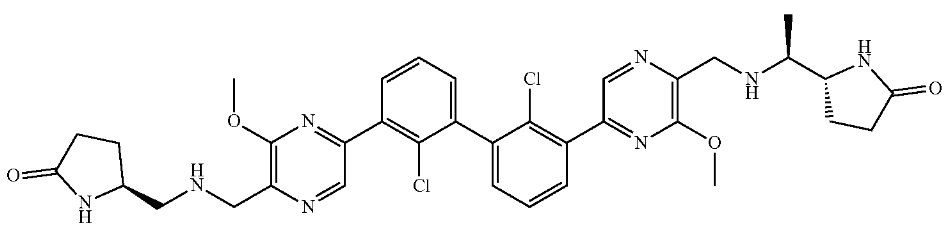 [SMILES: COc1nc(-c2cccc(-c3cccc(-c4cnc(CN[C@@H](C)[C@H]5CCC(=O)N5)c(OC)n4)c3Cl)c2Cl)cnc1CNC[C@@H]1CCC(=O)N1] | 706 | 2 |

TABLE 1-continued

| No. | Structure | ES/MS (m/z, M + H⁺) | Procedure |
|---|---|---|---|
| 599 | 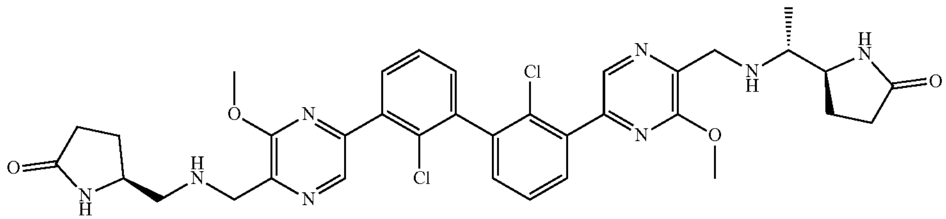 [SMILES: COc1nc(-c2cccc(-c3cccc(-c4cnc(CN[C@H](C)[C@@H]5CCC(=O)N5)c(OC)n4)c3Cl)c2Cl)cnc1CNC[C@@H]1CCC(=O)N1] | 706 | 2 |
| 600 | 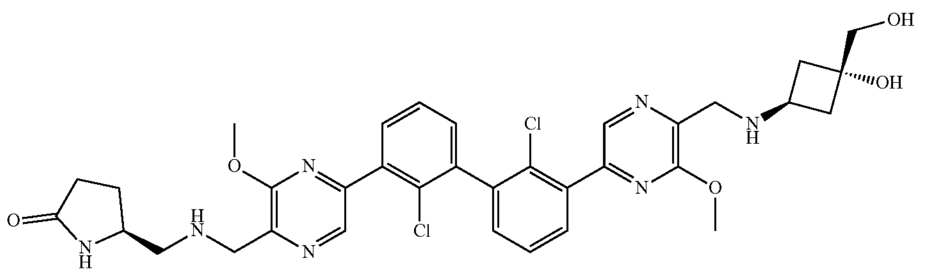 [SMILES: COc1nc(-c2cccc(-c3cccc(-c4cnc(CN[C@H]5C[C@@](O)(CO)C5)c(OC)n4)c3Cl)c2Cl)cnc1CNC[C@@H]1CCC(=O)N1] | 695.1 | 2 |
| 601 | 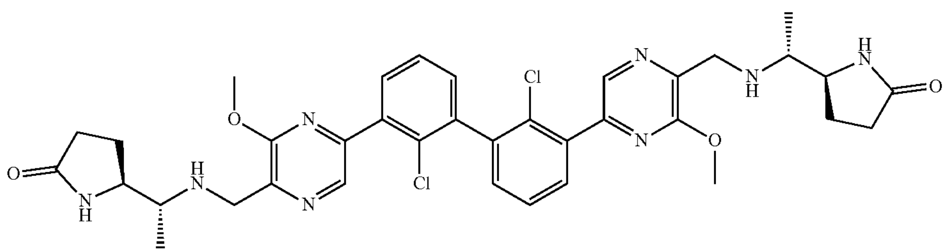 [SMILES: COc1nc(-c2cccc(-c3cccc(-c4cnc(CN[C@H](C)[C@@H]5CCC(=O)N5)c(OC)n4)c3Cl)c2Cl)cnc1CN[C@H](C)[C@@H]1CCC(=O)N1] | 719.2 | 3 |
| 602 | 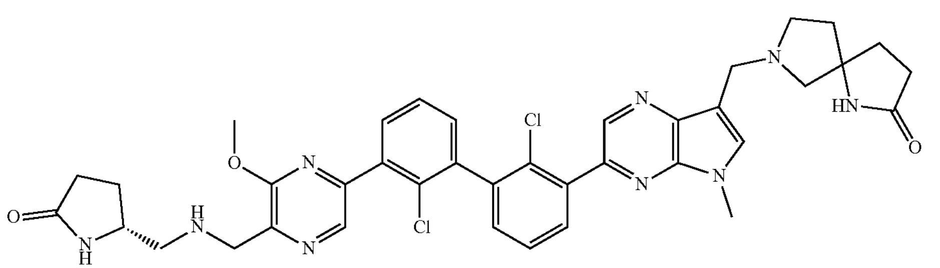 [SMILES: COc1nc(-c2cccc(-c3cccc(-c4cnc5c(CN6CCC7(CCC(=O)N7)C6)cn(C)c5n4)c3Cl)c2Cl)cnc1CNC[C@H]1CCC(=O)N1] | 740.216 | 13 |

TABLE 1-continued

| No. | Structure | ES/MS (m/z, M + H+) | Procedure |
|---|---|---|---|
| 603 | 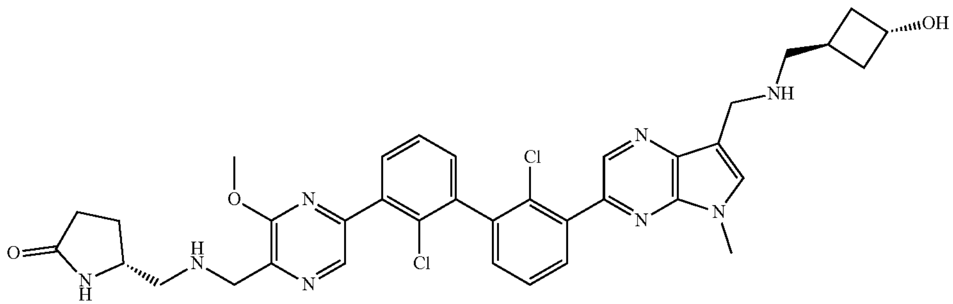 [SMILES: COc1nc(-c2cccc(-c3cccc(-c4cnc5c(CNC[C@H]6C[C@H](O)C6)cn(C)c5n4)c3Cl)c2Cl)cnc1CNC[C@H]1CCC(=O)N1] | 701.2 | 13 |
| 604 | 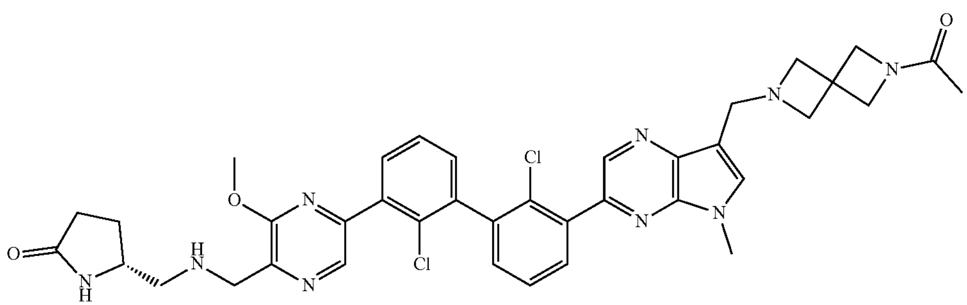 [SMILES: COc1nc(-c2cccc(-c3cccc(-c4cnc5c(CN6CC7(C6)CN(C(C)=O)C7)cn(C)c5n4)c3Cl)c2Cl)cnc1CNC[C@H]1CCC(=O)N1] | 740.201 | 13 |
| 605 | 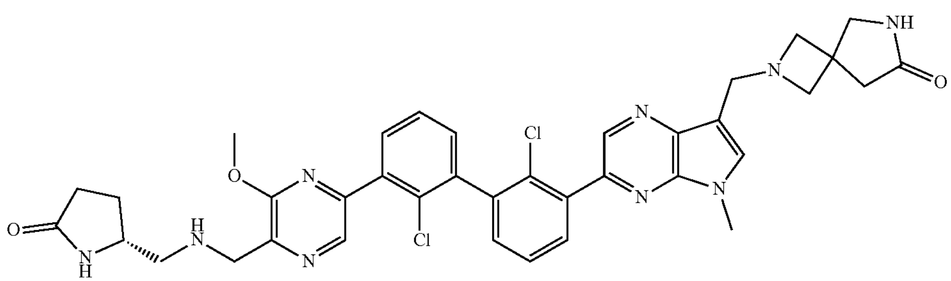 [SMILES: COc1nc(-c2cccc(-c3cccc(-c4cnc5c(CN6CC7(CNC(=O)C7)C6)cn(C)c5n4)c3Cl)c2Cl)cnc1CNC[C@H]1CCC(=O)N1] | 726.2 | 13 |

TABLE 1-continued
| No. | Structure | ES/MS (m/z, M + H+) | Procedure |
|---|---|---|---|
| 606 | 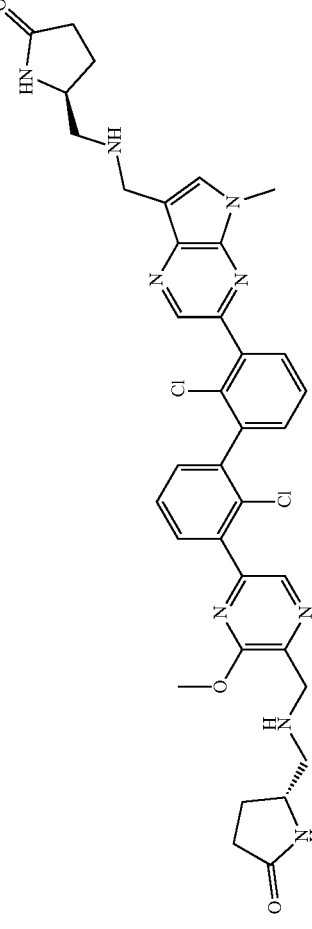 | 714.2 | 13 |
| 607 | 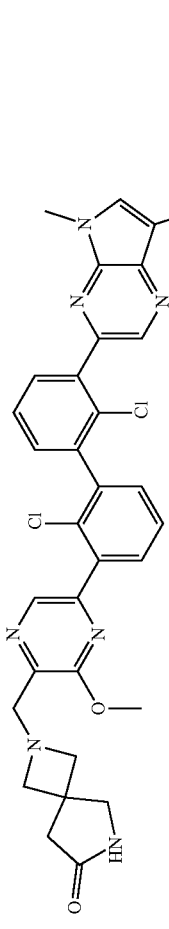 | 738.198 | 12 |
| 608 | 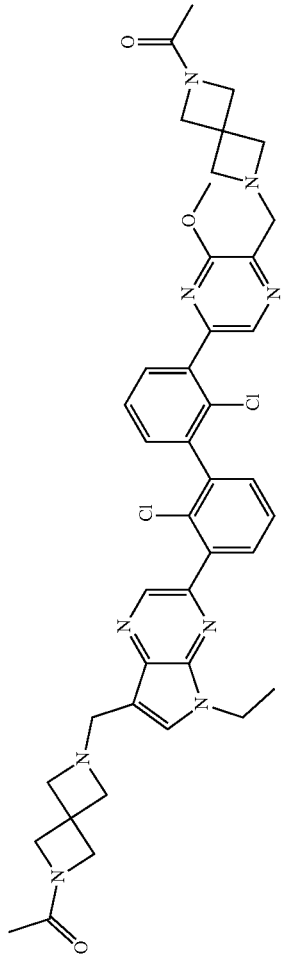 | 780.2 | 12 |

TABLE 1-continued

| No. | Structure | ES/MS (m/z, M + H+) | Procedure |
|---|---|---|---|
| 609 | 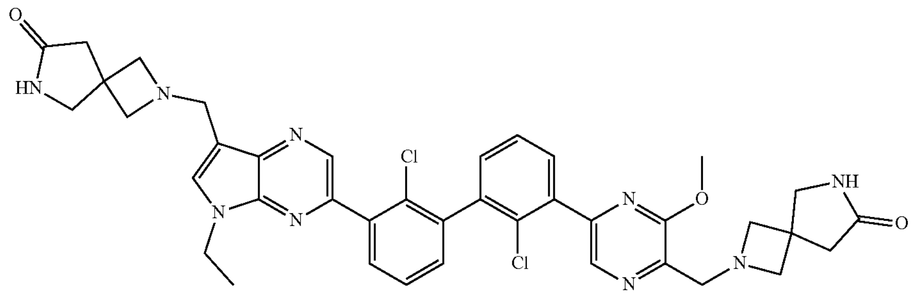 [SMILES: CCn1cc(CN2CC3(CNC(=O)C3)C2)c2ncc(-c3cccc(-c4cccc(-c5cnc(CN6CC7(CNC(=O)C7)C6)c(OC)n5)c4Cl)c3Cl)nc21] | 752.198 | 12 |
| 610 | 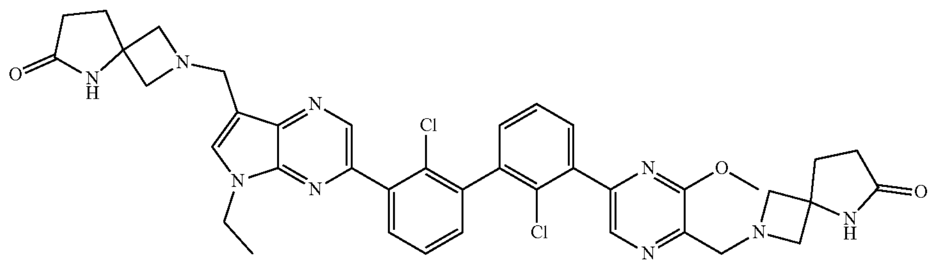 [SMILES: CCn1cc(CN2CC3(CCC(=O)N3)C2)c2ncc(-c3cccc(-c4cccc(-c5cnc(CN6CC7(CCC(=O)N7)C6)c(OC)n5)c4Cl)c3Cl)nc21] | 752.2 | 12 |
| 611 | 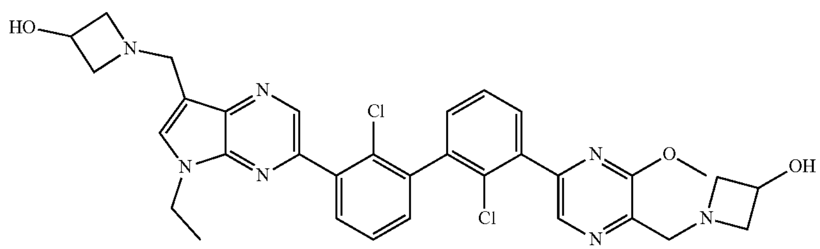 [SMILES: CCn1cc(CN2CC(O)C2)c2ncc(-c3cccc(-c4cccc(-c5cnc(CN6CC(O)C6)c(OC)n5)c4Cl)c3Cl)nc21] | 646.12 | 12 |

TABLE 1-continued

| No. | Structure | ES/MS (m/z, M + H+) | Procedure |
|-----|-----------|---------------------|-----------|
| 612 | 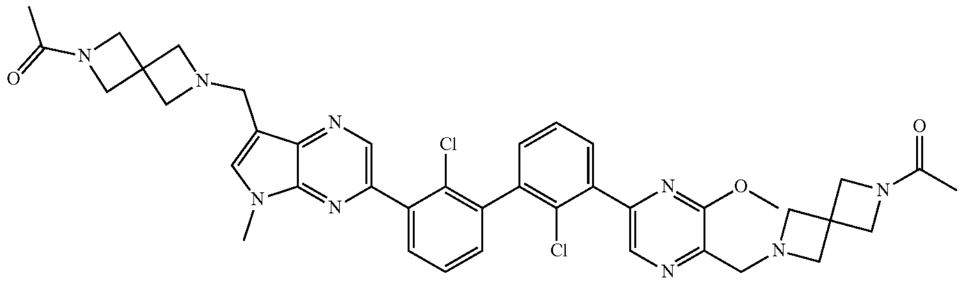 [SMILES: COc1nc(-c2cccc(-c3cccc(-c4cnc5c(CN6CC7(C6)CN(C(C)=O)C7)cn(C)c5n4)c3Cl)c2Cl)cnc1CN1CC2(C1)CN(C(C)=O)C2] | 766.2 | 12 |
| 613 | 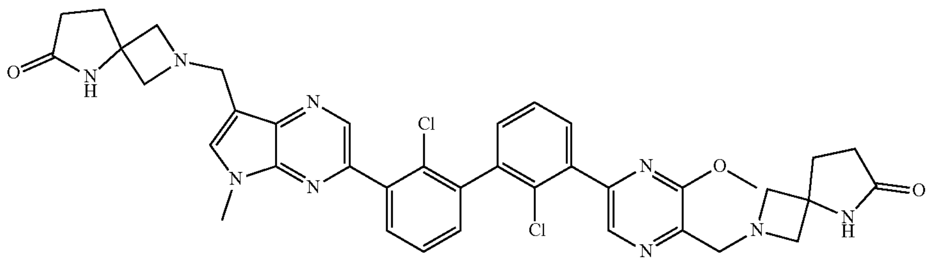 [SMILES: COc1nc(-c2cccc(-c3cccc(-c4cnc5c(CN6CC7(CCC(=O)N7)C6)cn(C)c5n4)c3Cl)c2Cl)cnc1CN1CC2(CCC(=O)N2)C1] | 738.14 | 12 |
| 614 | 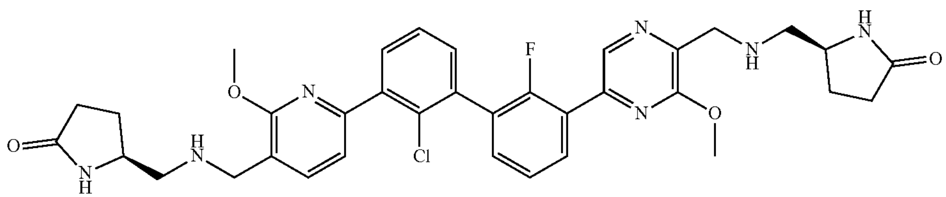 [SMILES: COc1nc(-c2cccc(-c3cccc(-c4cnc(CNC[C@@H]5CCC(=O)N5)c(OC)n4)c3F)c2Cl)ccc1CNC[C@@H]1CCC(=O)N1] | 674.1 | 26 |
| 615 | 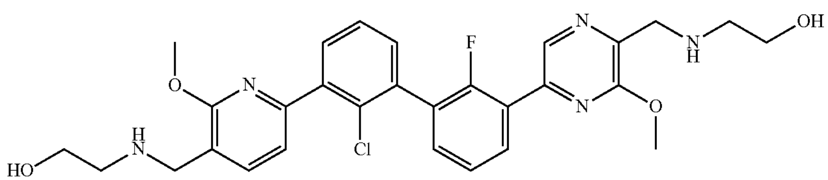 [SMILES: COc1nc(-c2cccc(-c3cccc(-c4cnc(CNCCO)c(OC)n4)c3F)c2Cl)ccc1CNCCO] | 568.0 | 26 |

TABLE 1-continued

| No. | Structure | ES/MS (m/z, M + H+) | Procedure |
|---|---|---|---|
| 616 | 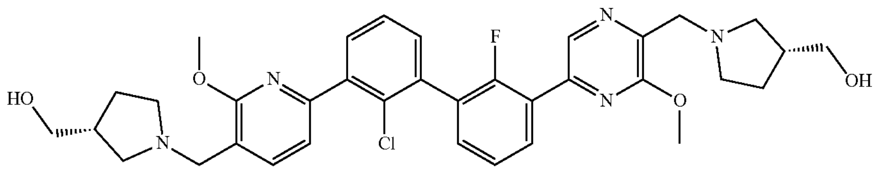 [SMILES: COc1nc(-c2cccc(-c3cccc(-c4cnc(CN5CC[C@@H](CO)C5)c(OC)n4)c3F)c2Cl)ccc1CN1CC[C@@H](CO)C1] | 648.2 | 26 |
| 617 | 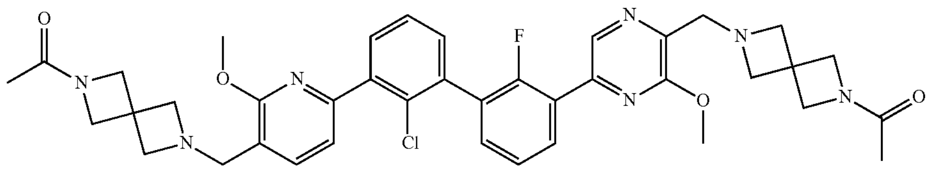 [SMILES: COc1nc(-c2cccc(-c3cccc(-c4cnc(CN5CC6(C5)CN(C(C)=O)C6)c(OC)n4)c3F)c2Cl)ccc1CN1CC2(C1)CN(C(C)=O)C2] | 726.2 | 26 |
| 618 | 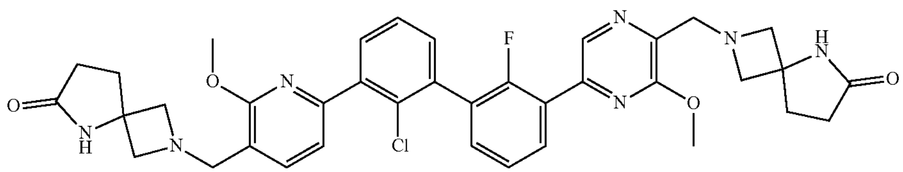 [SMILES: COc1nc(-c2cccc(-c3cccc(-c4cnc(CN5CC6(CCC(=O)N6)C5)c(OC)n4)c3F)c2Cl)ccc1CN1CC2(CCC(=O)N2)C1] | 698.1 | 26 |
| 619 | 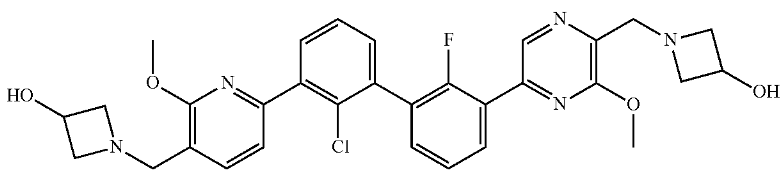 [SMILES: COc1nc(-c2cccc(-c3cccc(-c4cnc(CN5CC(O)C5)c(OC)n4)c3F)c2Cl)ccc1CN1CC(O)C1] | 592.0 | 26 |
| 620 | 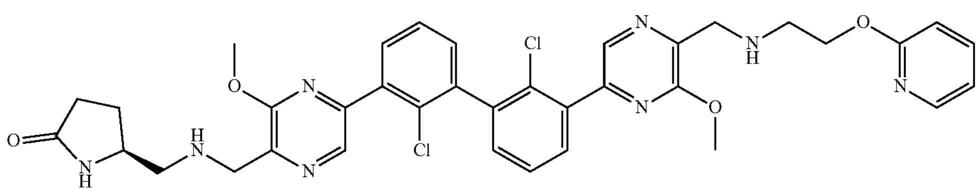 [SMILES: COc1nc(-c2cccc(-c3cccc(-c4cnc(CNC[C@@H]5CCC(=O)N5)c(OC)n4)c3Cl)c2Cl)cnc1CNCCOc1ccccn1] | 715.0 | 2 |

TABLE 1-continued

| No. | Structure | ES/MS (m/z, M + H⁺) | Procedure |
|-----|-----------|---------------------|-----------|
| 621 | 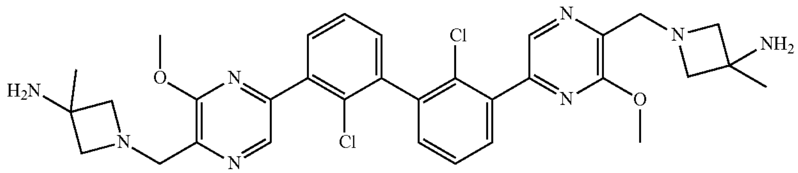 [SMILES: COc1nc(-c2cccc(-c3cccc(-c4cnc(CN5CC(C)(N)C5)c(OC)n4)c3Cl)c2Cl)cnc1CN1CC(C)(N)C1] | 635.1 | 3 |
| 622 | 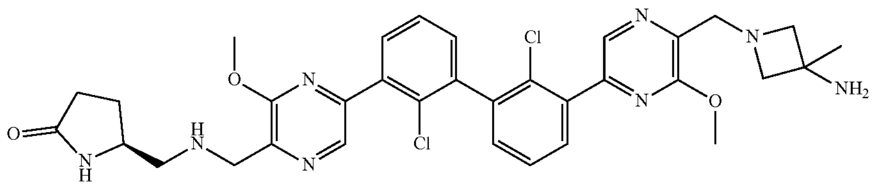 [SMILES: COc1nc(-c2cccc(-c3cccc(-c4cnc(CN5CC(C)(N)C5)c(OC)n4)c3Cl)c2Cl)cnc1CNC[C@@H]1CCC(=O)N1] | 663.2 | 2 |
| 623 | 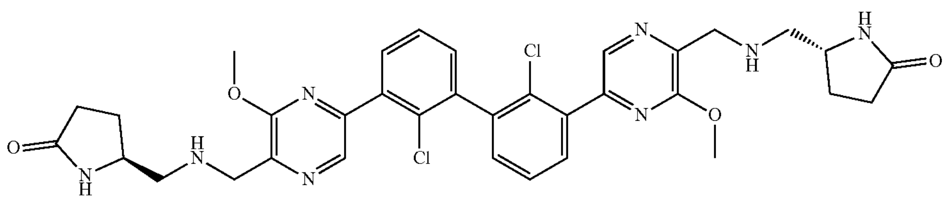 [SMILES: COc1nc(-c2cccc(-c3cccc(-c4cnc(CNC[C@@H]5CCC(=O)N5)c(OC)n4)c3Cl)c2Cl)cnc1CNC[C@H]1CCC(=O)N1] | 691.1 | 2 |
| 624 | 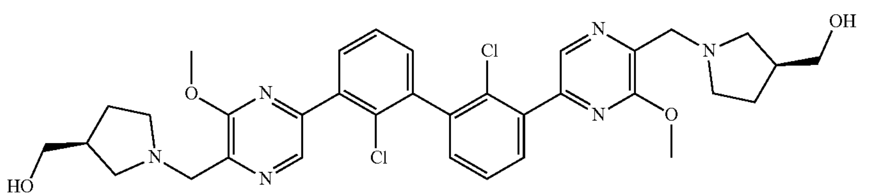 [SMILES: COc1nc(-c2cccc(-c3cccc(-c4cnc(CN5CC[C@H](CO)C5)c(OC)n4)c3Cl)c2Cl)cnc1CN1CC[C@H](CO)C1] | 665.2 | 3 |
| 625 | 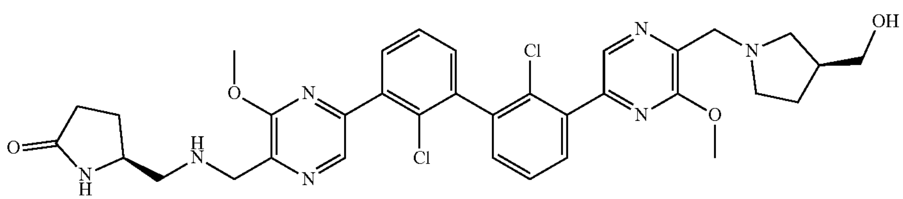 [SMILES: COc1nc(-c2cccc(-c3cccc(-c4cnc(CN5CC[C@H](CO)C5)c(OC)n4)c3Cl)c2Cl)cnc1CNC[C@@H]1CCC(=O)N1] | 678.2 | 2 |

TABLE 1-continued

| No. | Structure | ES/MS (m/z, M + H+) | Procedure |
|---|---|---|---|
| 626 | 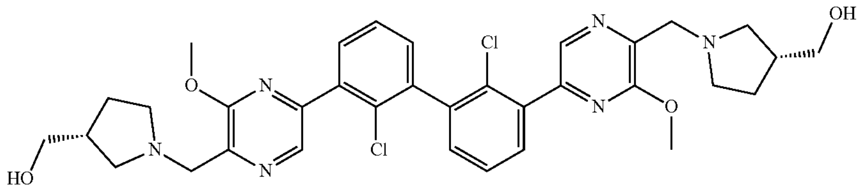 [SMILES: COc1nc(-c2cccc(-c3cccc(-c4cnc(CN5CC[C@@H](CO)C5)c(OC)n4)c3Cl)c2Cl)cnc1CN1CC[C@@H](CO)C1] | 665.3 | 3 |
| 627 | 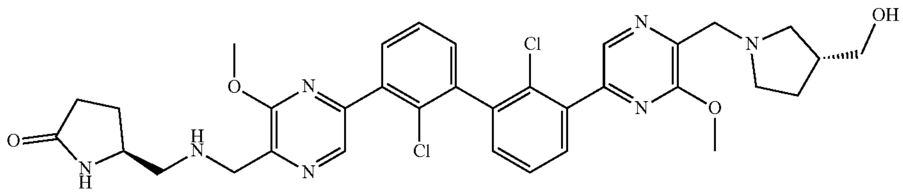 [SMILES: COc1nc(-c2cccc(-c3cccc(-c4cnc(CN5CC[C@@H](CO)C5)c(OC)n4)c3Cl)c2Cl)cnc1CNC[C@@H]1CCC(=O)N1] | 678.2 | 2 |
| 628 | 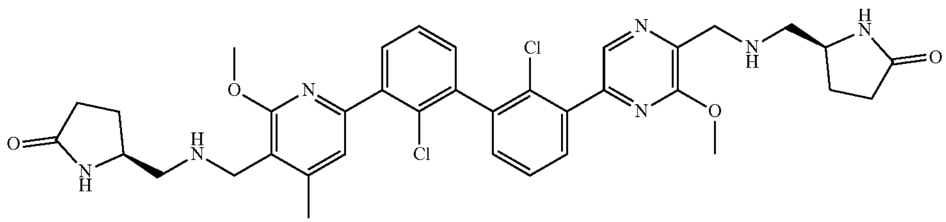 [SMILES: COc1nc(-c2cccc(-c3cccc(-c4cc(C)c(CNC[C@@H]5CCC(=O)N5)c(OC)n4)c3Cl)c2Cl)cnc1CNC[C@@H]1CCC(=O)N1] | 704.1 | 13 |
| 629 | 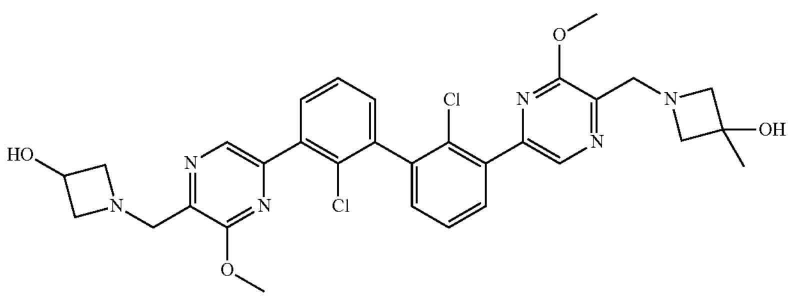 [SMILES: COc1nc(-c2cccc(-c3cccc(-c4cnc(CN5CC(C)(O)C5)c(OC)n4)c3Cl)c2Cl)cnc1CN1CC(O)C1] | 623.11 | 2 |

TABLE 1-continued

| No. | Structure | ES/MS (m/z, M + H+) | Procedure |
|---|---|---|---|
| 630 | 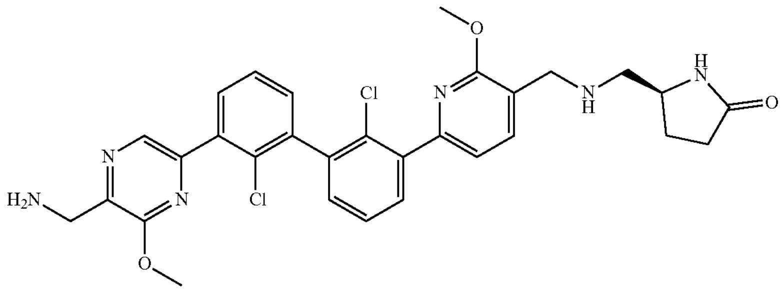 [SMILES: COc1nc(-c2cccc(-c3cccc(-c4cnc(CN)c(OC)n4)c3Cl)c2Cl)ccc1CNC[C@@H]1CCC(=O)N1] | 593.2 | 14 |
| 631 | 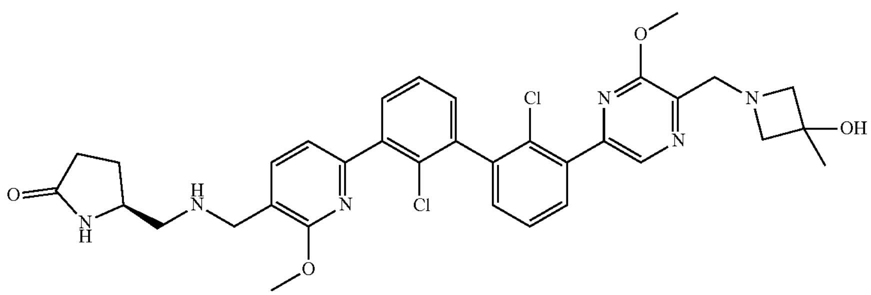 [SMILES: COc1nc(-c2cccc(-c3cccc(-c4cnc(CN5CC(C)(O)C5)c(OC)n4)c3Cl)c2Cl)ccc1CNC[C@@H]1CCC(=O)N1] | 663.1 | 14 |
| 632 | 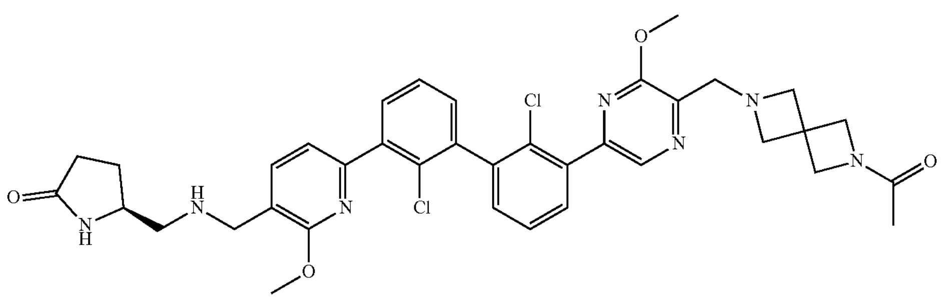 [SMILES: COc1nc(-c2cccc(-c3cccc(-c4cnc(CN5CC6(C5)CN(C(C)=O)C6)c(OC)n4)c3Cl)c2Cl)ccc1CNC[C@@H]1CCC(=O)N1] | 716.1 | 14 |

TABLE 1-continued

| No. | Structure | ES/MS (m/z, M + H+) | Procedure |
|---|---|---|---|
| 633 | 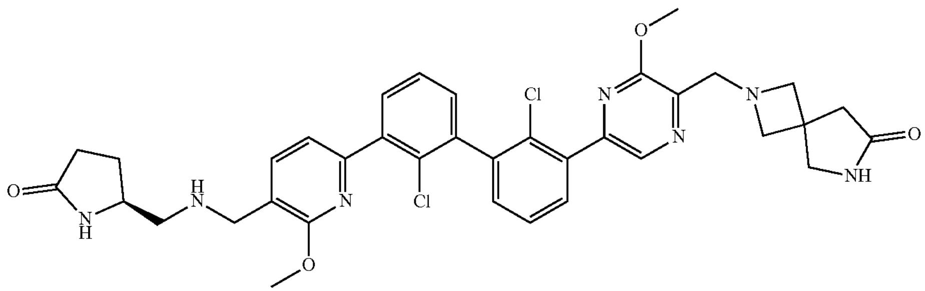 [SMILES: COc1nc(-c2cccc(-c3cccc(-c4cnc(CN5CC6(CNC(=O)C6)C5)c(OC)n4)c3Cl)c2Cl)ccc1CNC[C@@H]1CCC(=O)N1] | 702.1 | 14 |
| 634 | 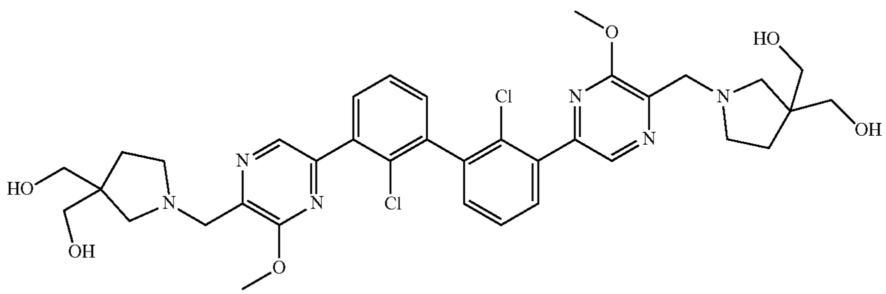 [SMILES: COc1nc(-c2cccc(-c3cccc(-c4cnc(CN5CCC(CO)(CO)C5)c(OC)n4)c3Cl)c2Cl)cnc1CN1CCC(CO)(CO)C1] | 725.2 | 3 |
| 635 | 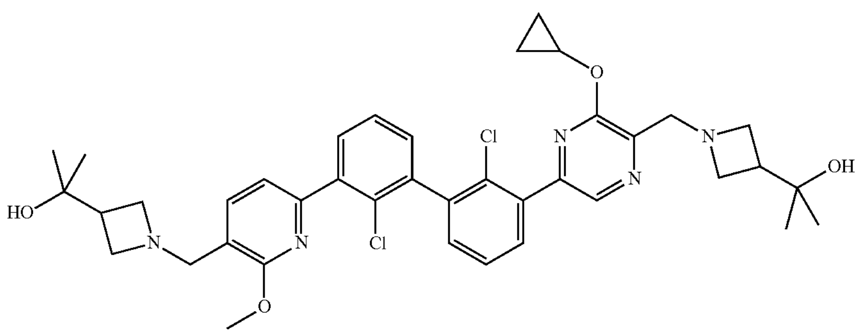 [SMILES: COc1nc(-c2cccc(-c3cccc(-c4cnc(CN5CC(C(C)(C)O)C5)c(OC5CC5)n4)c3Cl)c2Cl)ccc1CN1CC(C(C)(C)O)C1] | 718.2 | 26 |

TABLE 1-continued

| No. | Structure | ES/MS (m/z, M + H+) | Procedure |
|---|---|---|---|
| 636 | 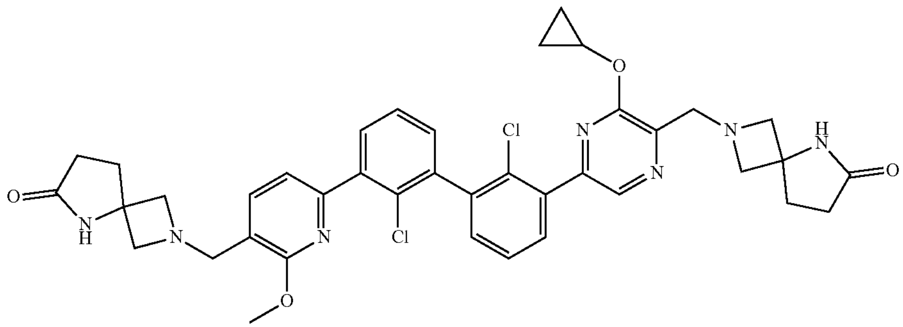 [SMILES: COc1nc(-c2cccc(-c3cccc(-c4cnc(CN5CC6(CCC(=O)N6)C5)c(OC5CC5)n4)c3Cl)c2Cl)ccc1CN1CC2(CCC(=O)N2)C1] | 740.2 | 26 |
| 637 | 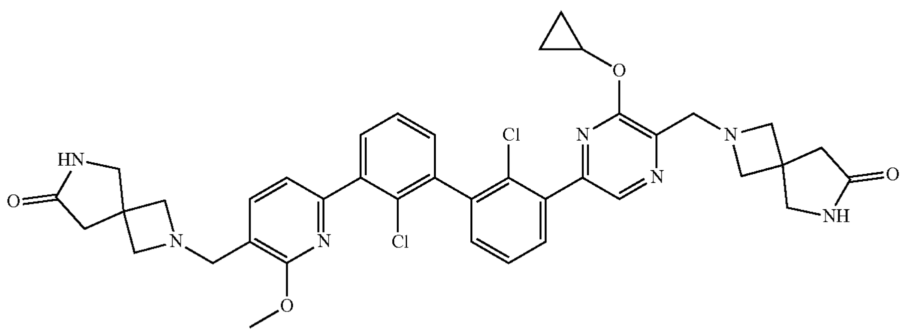 [SMILES: COc1nc(-c2cccc(-c3cccc(-c4cnc(CN5CC6(CNC(=O)C6)C5)c(OC5CC5)n4)c3Cl)c2Cl)ccc1CN1CC2(CNC(=O)C2)C1] | 740.2 | 26 |
| 638 | 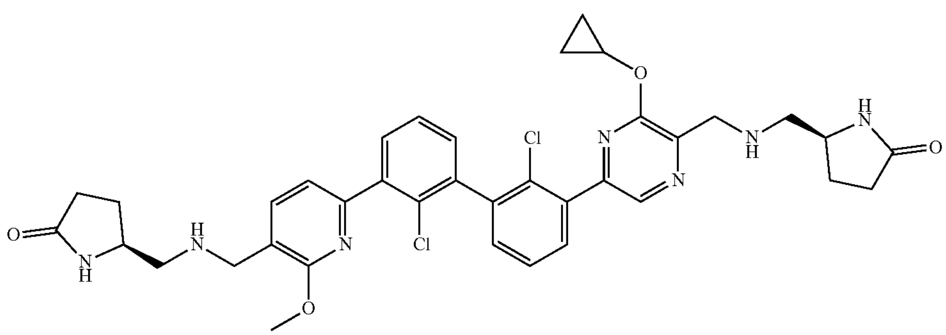 [SMILES: COc1nc(-c2cccc(-c3cccc(-c4cnc(CNC[C@@H]5CCC(=O)N5)c(OC5CC5)n4)c3Cl)c2Cl)ccc1CNC[C@@H]1CCC(=O)N1] | 716.3 | 26 |

TABLE 1-continued

| No. | Structure | ES/MS (m/z, M + H+) | Procedure |
|---|---|---|---|
| 639 | 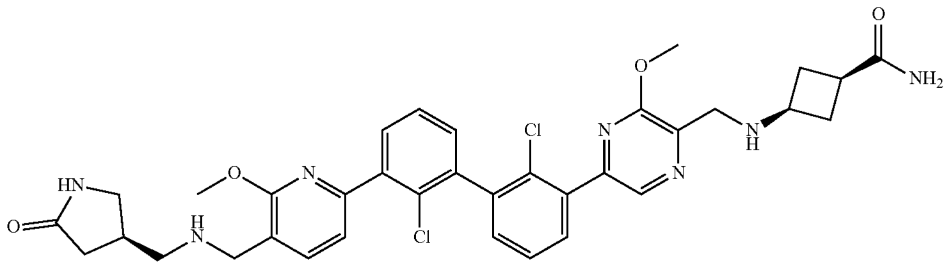 [SMILES: COc1nc(-c2cccc(-c3cccc(-c4cnc(CN[C@H]5C[C@@H](C(N)=O)C5)c(OC)n4)c3Cl)c2Cl)ccc1CNC[C@@H]1CNC(=O)C1] | 690.2 | 14 |
| 640 | 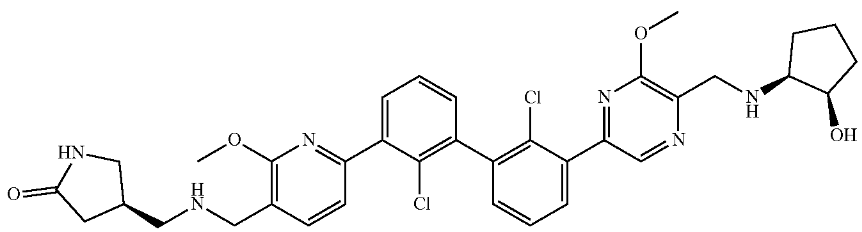 [SMILES: COc1nc(-c2cccc(-c3cccc(-c4cnc(CN[C@H]5CCC[C@H]5O)c(OC)n4)c3Cl)c2Cl)ccc1CNC[C@@H]1CNC(=O)C1] | 677.2 | 14 |
| 641 | 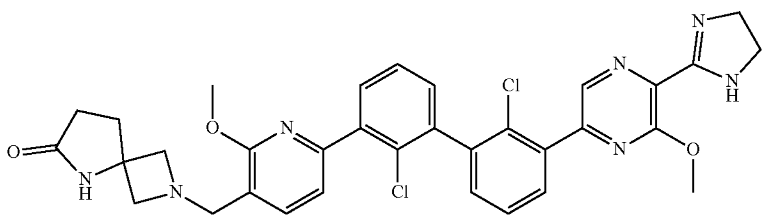 [SMILES: COc1nc(-c2cccc(-c3cccc(-c4cnc(C5=NCCN5)c(OC)n4)c3Cl)c2Cl)ccc1CN1CC2(CCC(=O)N2)C1] | 644.168 | 10 |
| 642 | 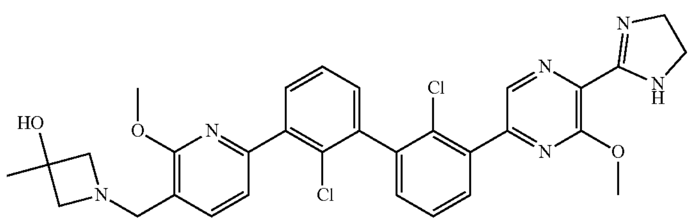 [SMILES: COc1nc(-c2cccc(-c3cccc(-c4cnc(C5=NCCN5)c(OC)n4)c3Cl)c2Cl)ccc1CN1CC(C)(O)C1] | 605.182 | 10 |

TABLE 1-continued

| No. | Structure | ES/MS (m/z, M + H+) | Procedure |
|---|---|---|---|
| 643 | 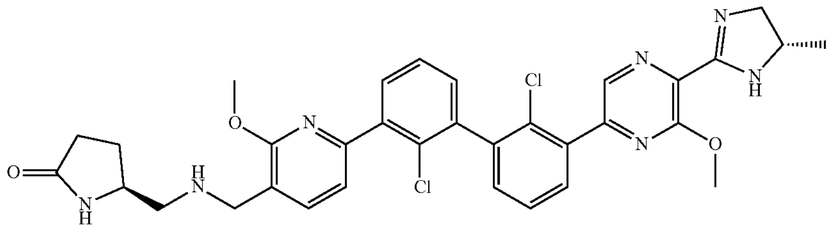 [SMILES: COc1nc(-c2cccc(-c3cccc(-c4cnc(C5=NC[C@H](C)N5)c(OC)n4)c3Cl)c2Cl)ccc1CNC[C@@H]1CCC(=O)N1] | 646.196 | 10 |
| 644 | 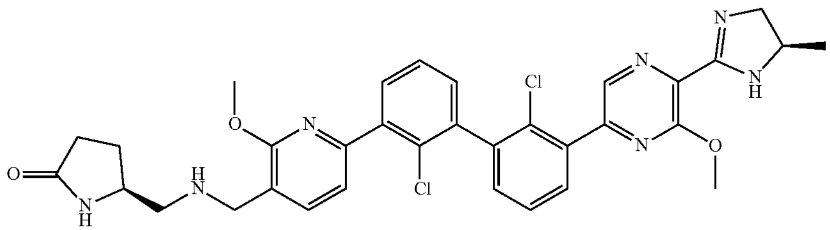 [SMILES: COc1nc(-c2cccc(-c3cccc(-c4cnc(C5=NC[C@@H](C)N5)c(OC)n4)c3Cl)c2Cl)ccc1CNC[C@@H]1CCC(=O)N1] | 646.211 | 10 |
| 645 | 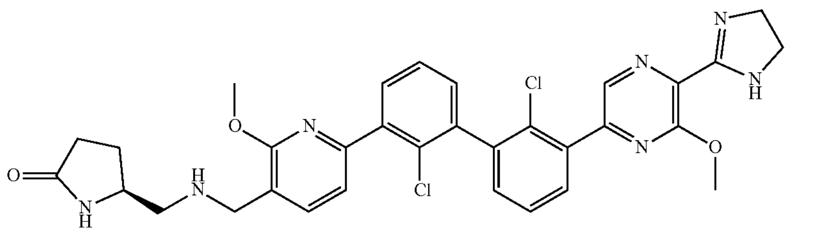 [SMILES: COc1nc(-c2cccc(-c3cccc(-c4cnc(C5=NCCN5)c(OC)n4)c3Cl)c2Cl)ccc1CNC[C@@H]1CCC(=O)N1] | 632.19 | 10 |
| 646 | 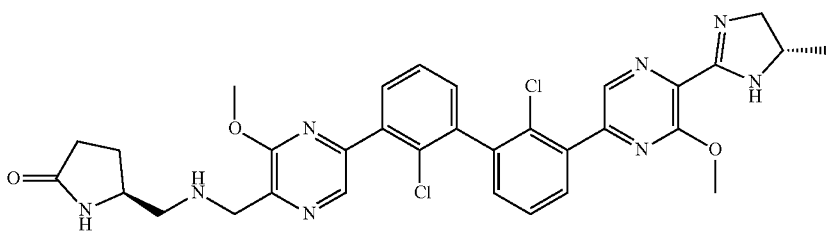 [SMILES: COc1nc(-c2cccc(-c3cccc(-c4cnc(C5=NC[C@H](C)N5)c(OC)n4)c3Cl)c2Cl)cnc1CNC[C@@H]1CCC(=O)N1] | 647.195 | 10 |

TABLE 1-continued

| No. | Structure | ES/MS (m/z, M + H+) | Procedure |
|-----|-----------|---------------------|-----------|
| 647 | 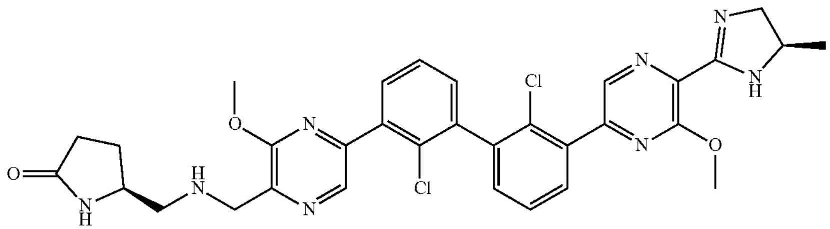 | 647.209 | 10 |
| 648 | 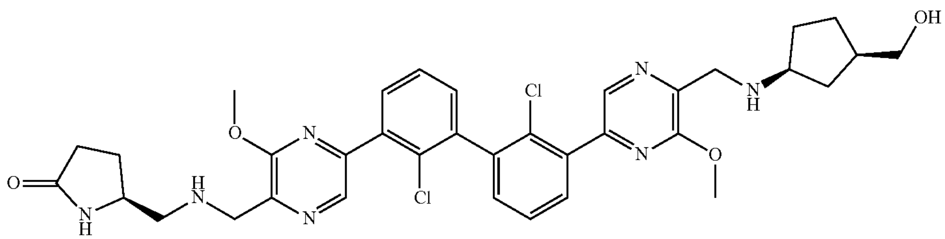 [SMILES: COc1nc(-c2cccc(-c3cccc(-c4cnc(CN[C@H]5CC[C@@H](CO)C5)c(OC)n4)c3Cl)c2Cl)cnc1CNC[C@@H]1CCC(=O)N1] | 692.175 | 2 |
| 649 | 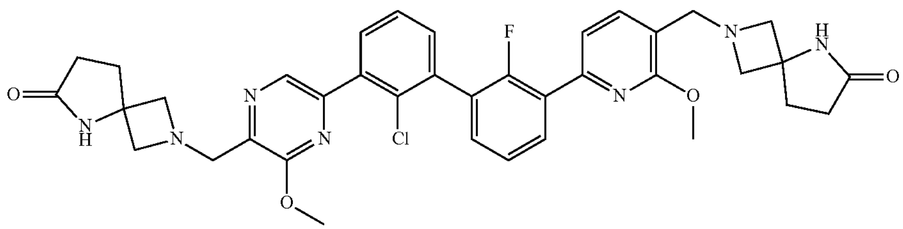 [SMILES: COc1nc(-c2cccc(-c3cccc(-c4cnc(CN5CC6(CCC(=O)N6)C5)c(OC)n4)c3Cl)c2F)ccc1CN1CC2(CCC(=O)N2)C1] | 698.096 | 26 |
| 650 | 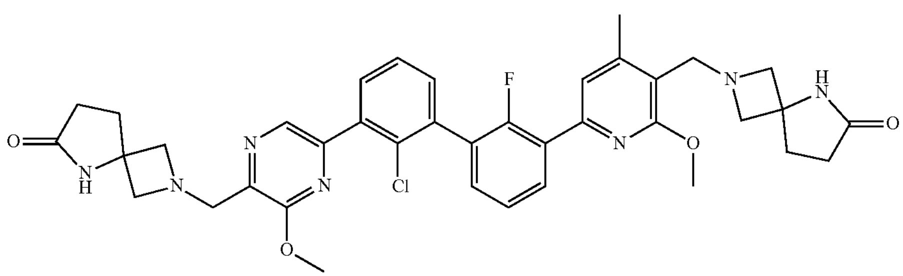 [SMILES: COc1nc(-c2cccc(-c3cccc(-c4cc(C)c(CN5CC6(CCC(=O)N6)C5)c(OC)n4)c3F)c2Cl)cnc1CN1CC2(CCC(=O)N2)C1] | 712.055 | 26 |

TABLE 1-continued

| No. | Structure | ES/MS (m/z, M + H+) | Procedure |
|---|---|---|---|
| 651 | 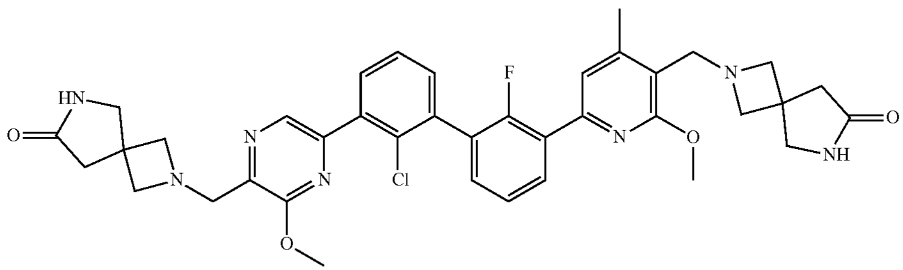 [SMILES: COc1nc(-c2cccc(-c3cccc(-c4cc(C)c(CN5CC6(CNC(=O)C6)C5)c(OC)n4)c3F)c2Cl)cnc1CN1CC2(CNC(=O)C2)C1] | 712.082 | 26 |
| 652 | 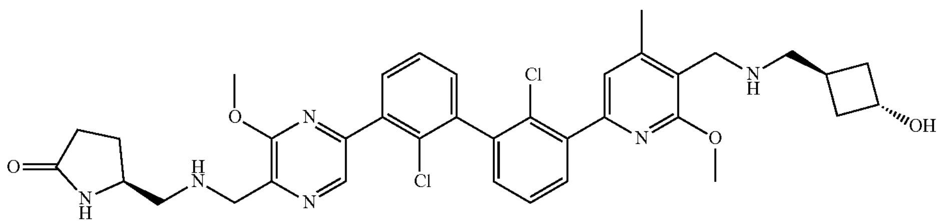 [SMILES: COc1nc(-c2cccc(-c3cccc(-c4cc(C)c(CNC[C@H]5C[C@H](O)C5)c(OC)n4)c3Cl)c2Cl)cnc1CNC[C@@H]1CCC(=O)N1] | 691.07 | 13 |
| 653 | 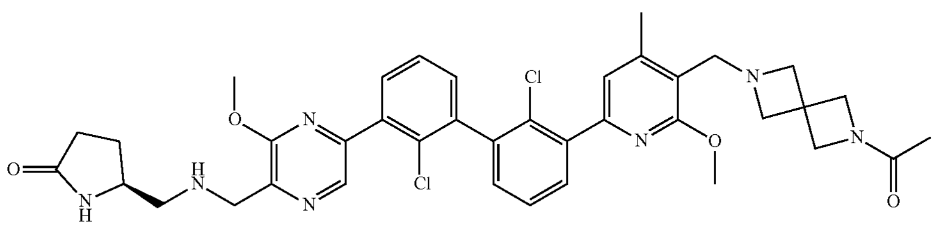 [SMILES: COc1nc(-c2cccc(-c3cccc(-c4cc(C)c(CN5CC6(C5)CN(C(C)=O)C6)c(OC)n4)c3Cl)c2Cl)cnc1CNC[C@@H]1CCC(=O)N1] | 730.12 | 13 |
| 654 | 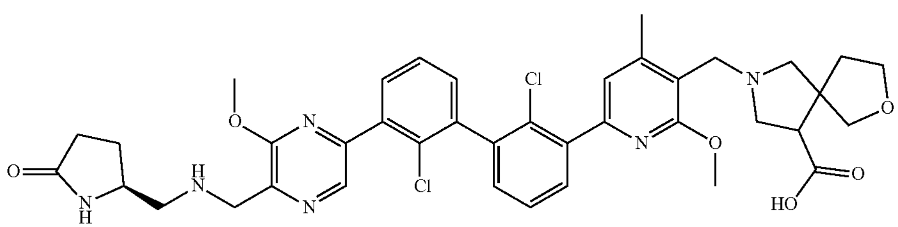 [SMILES: COc1nc(-c2cccc(-c3cccc(-c4cc(C)c(CN5CC(C(=O)O)C6(CCOC6)C5)c(OC)n4)c3Cl)c2Cl)cnc1CNC[C@@H]1CCC(=O)N1] | 760.96 | 13 |

TABLE 1-continued

| No. | Structure | ES/MS (m/z, M + H⁺) | Procedure |
|---|---|---|---|
| 655 | 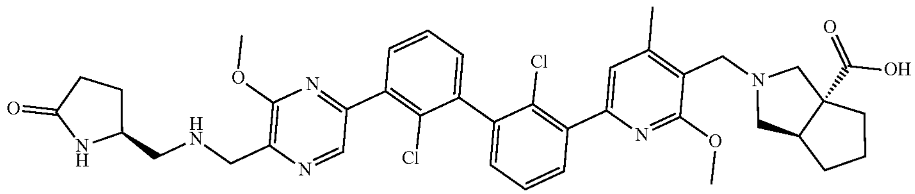 [SMILES: COc1nc(-c2cccc(-c3cccc(-c4cc(C)c(CN5C[C@@H]6CCC[C@]6(C(=O)O)C5)c(OC)n4)c3Cl)c2Cl)cnc1CNC[C@@H]1CCC(=O)N1] | 745.1 | 13 |
| 656 | 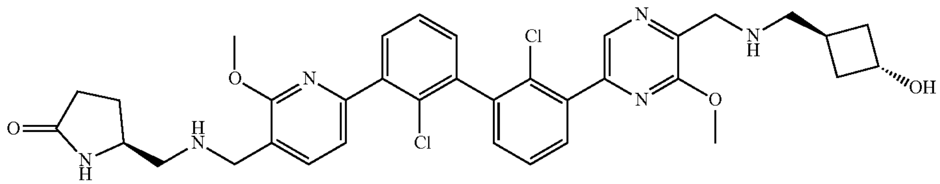 [SMILES: COc1nc(-c2cccc(-c3cccc(-c4cnc(CNC[C@H]5C[C@H](O)C5)c(OC)n4)c3Cl)c2Cl)ccc1CNC[C@@H]1CCC(=O)N1] | 677.33 | 14 |
| 657 | 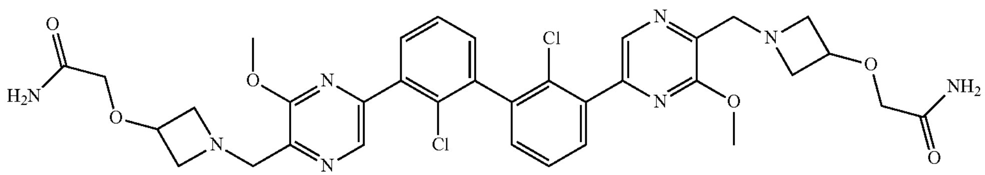 [SMILES: COc1nc(-c2cccc(-c3cccc(-c4cnc(CN5CC(OCC(N)=O)C5)c(OC)n4)c3Cl)c2Cl)cnc1CN1CC(OCC(N)=O)C1] | 723.1 | 3 |
| 658 | 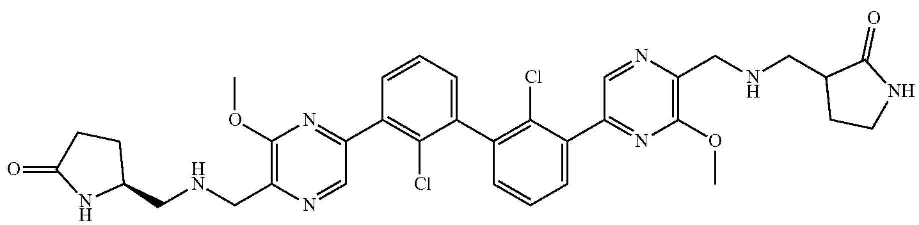 [SMILES: COc1nc(-c2cccc(-c3cccc(-c4cnc(CNC[C@@H]5CCC(=O)N5)c(OC)n4)c3Cl)c2Cl)cnc1CNCC1CCNC1=O] | 691.14 | 2 |
| 659 | 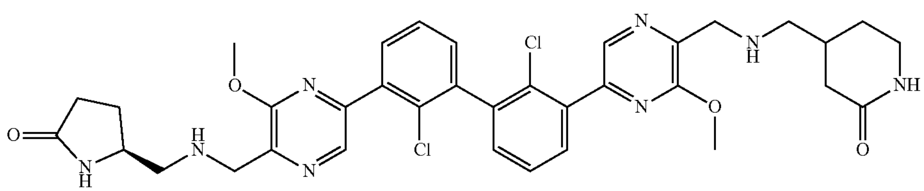 [SMILES: COc1nc(-c2cccc(-c3cccc(-c4cnc(CNC[C@@H]5CCC(=O)N5)c(OC)n4)c3Cl)c2Cl)cnc1CNCC1CCNC(=O)C1] | 705.17 | 2 |

TABLE 1-continued

| No. | Structure | ES/MS (m/z, M + H⁺) | Procedure |
|---|---|---|---|
| 660 | 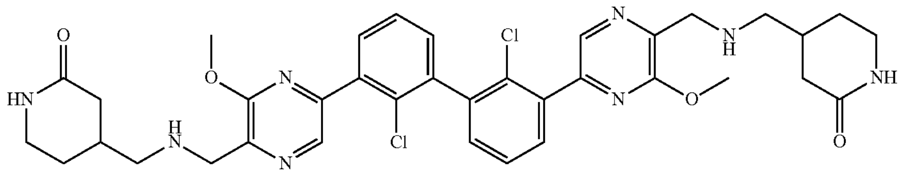 [SMILES: COc1nc(-c2cccc(-c3cccc(-c4cnc(CNCC5CCNC(=O)C5)c(OC)n4)c3Cl)c2Cl)cnc1CNCC1CCNC(=O)C1] | 719.8 | 3 |
| 661 | 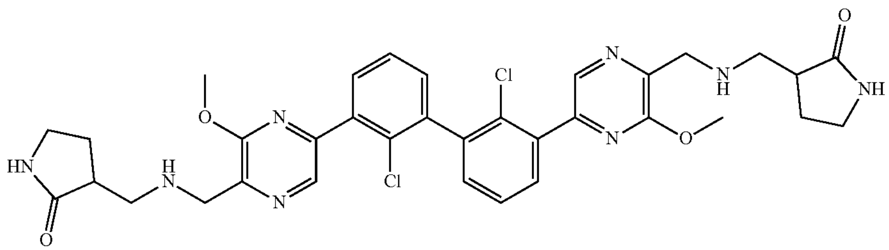 [SMILES: COc1nc(-c2cccc(-c3cccc(-c4cnc(CNCC5CCNC5=O)c(OC)n4)c3Cl)c2Cl)cnc1CNCC1CCNC1=O] | 691.16 | 3 |
| 662 | 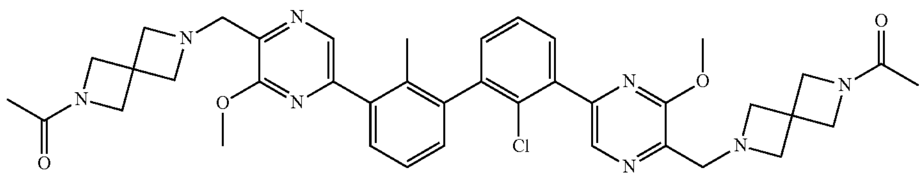 [SMILES: COc1nc(-c2cccc(-c3cccc(-c4cnc(CN5CC6(C5)CN(C(C)=O)C6)c(OC)n4)c3Cl)c2C)cnc1CN1CC2(C1)CN(C(C)=O)C2] | 723.389 | 1 |
| 663 | 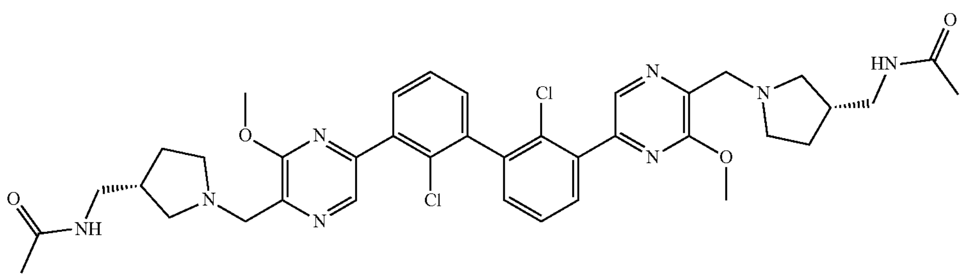 [SMILES: COc1nc(-c2cccc(-c3cccc(-c4cnc(CN5CC[C@@H](CNC(C)=O)C5)c(OC)n4)c3Cl)c2Cl)cnc1CN1CC[C@@H](CNC(C)=O)C1] | 747.2 | 3 |

NMR data for select compounds is shown below in Table 2.

TABLE 2

| No. | NMR |
|---|---|
| 1 | $^1$H NMR (400 MHz, Methanol-d$_4$) δ 8.70 (d, J = 2.1 Hz, 1H), 8.52 (s, 1H), 8.21 (s, 1H), 7.74 (d, J = 7.4 Hz, 1H), 7.68-7.44 (m, 4H), 4.82-4.03 (m, 16H), 2.58 (d, J = 8.2 Hz, 4H), 2.46 (d, J = 8.0 Hz, 4H). |
| 2 | $^1$H NMR (400 MHz, Methanol-d$_4$) δ 8.67 (d, J = 2.3 Hz, 1H), 8.49 (s, 1H), 8.19 (td, J = 7.2, 2.7 Hz, 1H), 7.71 (dd, J = 7.3, 2.2 Hz, 1H), 7.65-7.42 (m, 4H), 4.72 (s, 9H), 4.34 (d, J = 34.3 Hz, 1H), 4.14 (d, J = 21.4 Hz, 9H). |
| 3 | $^1$H NMR (400 MHz, Methanol-d$_4$) δ 8.67 (s, 1H), 8.49 (s, 1H), 8.19 (s, 1H), 7.71 (d, J = 7.1 Hz, 1H), 7.65-7.41 (m, 4H), 4.72 (s, 6H), 4.39 (s, 6H), 4.14 (d, J = 21.3 Hz, 8H), 3.37 (s, 6H). |
| 4 | $^1$H NMR (400 MHz, Methanol-d$_4$) δ 8.66 (s, 1H), 8.49 (s, 1H), 8.20 (d, J = 7.2 Hz, 1H), 7.71 (d, J = 8.0 Hz, 1H), 7.66-7.43 (m, 4H), 4.79-4.02 (m, 24H), 1.86 (s, 6H). |
| 5 | $^1$H NMR (400 MHz, Methanol-d4) δ 8.77-8.66 (m, 1H), 8.53 (s, 1H), 8.26-8.14 (m, 1H), 7.80-7.67 (m, 1H), 7.66-7.43 (m, 4H), 4.49 (d, J = 6.5 Hz, 4H), 4.18 (s, 3H), 4.13 (s, 3H), 3.95-3.83 (m, 4H). |
| 6 | $^1$H NMR (400 MHz, Methanol-d4) δ 8.80-8.66 (m, 1H), 8.62-8.51 (m, 1H), 8.31-8.11 (m, 1H), 7.83-7.40 (m, 5H), 4.66-4.43 (m, 4H), 4.23-4.05 (m, 7H), 3.05 (d, J = 6.2 Hz, 2H), 2.52-2.32 (m, 5H), 1.97 (d, J = 8.9 Hz, 2H). |
| 7 | $^1$H NMR (400 MHz, DMSO-d6) δ 9.25 (s, 1H), 9.15 (s, 1H), 8.57 (d, J = 0.8 Hz, 1H), 8.50 (s, 1H), 7.75 (dt, J = 7.6, 1.6 Hz, 2H), 7.63 (dq, J = 7.6, 4.0 Hz, 3H), 7.55 (ddd, J = 7.5, 5.7, 1.8 Hz, 2H), 4.46 (s, 2H), 4.22 (d, J = 7.0 Hz, 2H), 4.01 (d, J = 7.8 Hz, 6H), 3.93 (m, 1H), 3.20 (s, 2H), 2.48-2.42 (m, 5H), 2.25-2.09 (m, 3H), 1.81 (m, 1H), 1.78 (s, 1H). |
| 8 | $^1$H NMR (400 MHz, DMSO-d6) δ 9.23 (s, 1H), 8.56 (d, J = 7.4 Hz, 2H), 7.76 (dt, J = 7.7, 2.0 Hz, 2H), 7.68-7.59 (m, 3H), 7.56 (dd, J = 7.9, 1.8 Hz, 2H), 4.46 (s, 2H), 4.33 (s, 2H), 4.02 (s, 6H), 3.94 (t, J = 6.9 Hz, 1H), 3.22 (s, 3H), 3.17 (s, 1H), 2.25-2.13 (m, 2H), 2.14 (s, 6H), 1.80 (dd, J = 11.9, 6.3 Hz, 1H). |
| 9 | $^1$H NMR (400 MHz, DMSO-d6) δ 9.26 (s, 1H), 9.14 (s, 1H), 8.57 (s, 1H), 8.48 (s, 1H), 7.74 (ddd, J = 8.6, 7.6, 1.8 Hz, 2H), 7.68-7.58 (m, 3H), 7.55 (ddd, J = 7.6, 5.1, 1.8 Hz, 2H), 4.68 (s, 2H), 4.55 (s, 2H), 4.46 (s, 2H), 4.01 (d, J = 9.2 Hz, 6H), 3.94 (s, 1H), 3.19 (s, 2H), 2.24-2.09 (m, 3H), 1.85-1.74 (m, 1H), 1.69 (s, 3H). |
| 10 | $^1$H NMR (400 MHz, DMSO-d6) δ 9.24 (s, 1H), 9.12 (s, 1H), 8.57 (s, 1H), 8.48 (s, 1H), 7.74 (ddd, J = 9.2, 7.6, 1.8 Hz, 2H), 7.68-7.51 (m, 6H), 4.65 (s, 2H), 4.46 (s, 2H), 4.40 (s, 2H), 4.02 (s, 2H), 3.99 (s, 3H), 3.94 (s, 2H), 3.20 (s, 2H), 2.25-2.09 (m, 4H), 1.78 (s, 1H). |
| 11 | $^1$H NMR (400 MHz, DMSO-d6) δ 9.54 (s, 2H), 9.21 (s, 2H), 8.57 (d, J = 2.4 Hz, 2H), 7.75 (dd, J = 7.7, 1.8 Hz, 2H), 7.68-7.59 (m, 3H), 7.56 (dd, J = 7.6, 1.8 Hz, 2H), 5.62 (s, 1H), 4.47 (s, 5H), 4.09-3.95 (m, 6H), 3.96-3.83 (m, 2H), 3.70 (s, 1H), 3.50 (dd, J = 9.4, 3.8 Hz, 1H), 3.19 (s, 2H), 2.24-2.09 (m, 3H), 1.78 (s, 1H). |
| 12 | $^1$H NMR (400 MHz, DMSO-d6) δ 9.90 (s, 2H), 9.21 (s, 2H), 8.56 (d, J = 7.1 Hz, 2H), 7.76 (dt, J = 7.6, 1.9 Hz, 2H), 7.68-7.59 (m, 3H), 7.56 (dd, J = 7.6, 1.8 Hz, 2H), 4.46 (s, 2H), 4.32 (s, 2H), 4.02 (s, 6H), 3.94 (s, 1H), 3.19 (s, 2H), 2.67 (s, 1H), 2.26-2.09 (m, 3H), 2.03 (s, 3H), 1.85-1.75 (m, 1H). |
| 13 | $^1$H NMR (400 MHz, DMSO-d6) δ 9.25 (s, 2H), 9.14 (s, 1H), 8.55 (d, J = 16.1 Hz, 2H), 7.79-7.52 (m, 9H), 4.46 (s, 3H), 4.32 (s, 1H), 4.01 (m, 6H), 3.43 (s, 1H), 3.25 (d, J = 6.7 Hz, 2H), 2.52 (s, 1H), 2.25-2.19 (m, 2H), 2.23-2.09 (m, 3H), 1.80 (dd, J = 11.8, 6.3 Hz, 1H). |
| 14 | $^1$H NMR (400 MHz, DMSO-d6) δ 10.48 (s, 1H), 9.23 (s, 1H), 9.13 (s, 1H), 8.57 (s, 1H), 8.50 (s, 1H), 7.74 (td, J = 7.4, 1.8 Hz, 2H), 7.68-7.56 (m, 3H), 7.56 (ddd, J = 7.6, 3.0, 1.8 Hz, 2H), 5.04 (s, 1H), 4.88 (d, J = 8.4 Hz, 1H), 4.78 (d, J = 14.9 Hz, 2H), 4.59 (s, 1H), 4.44 (d, J = 18.7 Hz, 5H), 4.35 (s, 1H), 4.02 (s, 2H), 3.94 (s, 1H), 3.92 (d, J = 6.7 Hz, 1H), 3.52 (t, J = 7.1 Hz, 1H), 3.29-3.10 (m, 2H) 2.29-2.09 (m, 5H), 1.94 (dd, J = 14.1, 7.1 Hz, 2H), 1.80 (dd, J = 12.1, 6.5 Hz, 1H). |
| 15 | $^1$H NMR (400 MHz, DMSO-d6) δ 9.22 (s, 1H), 9.11 (s, 1H), 8.57 (s, 1H), 8.50 (s, 1H), 7.75 (dd, J = 7.6, 1.8 Hz, 2H), 7.68-7.51 (m, 6H), 4.46 (s, 2H), 4.22 (s, 2H), 4.02 (s, 3), 3.99 (s, 3H), 3.94 (t, J = 5.7 Hz, 1H), 3.20 (s, 2H), 2.25-2.09 (m, 8H), 1.80 (dd, J = 11.7, 6.4 Hz, 1H). |
| 16 | $^1$H NMR (400 MHz, DMSO-d6) δ 10.50 (s, 1H), 9.23 (s, 1H), 9.12 (s, 1H), 8.57 (s, 1H), 8.51 (d, J = 1.7 Hz, 1H), 7.74 (td, J = 7.4, 1.8 Hz, 2H), 7.68-7.52 (m, 5H), 6.07 (s, 1H), 4.75-4.67 (m, 2H), 4.46 (s, 2H), 4.12 (dd, J = 25.4, 6.6 Hz, 2H), 4.02 (d, J = 4.9 Hz, 6H), 3.94 (t, J = 6.2 Hz, 1H), 3.20 (s, 2H), 2.25-2.09 (m, 3H), 1.80 (dd, J = 11.8, 6.5 Hz, 1H), 1.44 (d, J = 18.5 Hz, 3H). |
| 17 | $^1$H NMR (400 MHz, Methanol-d$_4$) δ 8.54 (s, 1H), 8.52 (s, 1H), 7.72 (ddd, J = 7.7, 1.8, 0.9 Hz, 2H), 7.58 (td, J = 7.6, 1.3 Hz, 2H), 7.49 (ddd, J = 7.6, 2.5, 1.8 Hz, 2H), 4.53 (d, J = 4.0 Hz, 2H), 4.51-4.38 (m, 3H), 4.12 (d, J = 3.1 Hz, 7H), 3.69-3.56 (m, 2H), 3.41-3.33 (m, 4H), 2.50-2.35 (m, 3H), 2.22 (dt, J = 12.9, 7.8 Hz, 1H), 2.14 (s, 3H), 2.10-1.92 (m, 3H), 1.88-1.77 (m, 1H). |
| 21 | $^1$H NMR (400 MHz, Methanol-d4) δ 8.56 (s, 1H), 8.55 (s, 1H), 7.73 (ddd, J = 7.7, 3.3, 1.7 Hz, 2H), 7.63-7.56 (m, 2H), 7.50 (dd, J = 7.8, 1.8 Hz, 2H), 4.90 (s, 1H), 4.61-4.48 (m, 3H), 4.16-4.07 (m, 7H), 4.04-3.93 (m, 1H), 3.88-3.76 (m, 2H), 3.67 (dd, J = 11.1, 7.2 Hz, 1H), 3.37 (d, J = 12.9 Hz, 5H), 2.51-2.28 (m, 5H), 2.25-2.15 (m, 1H), 2.09 (dd, J = 14.4, 7.3 Hz, 1H), 2.02-1.86 (m, 3H). |
| 23 | $^1$H NMR (400 MHz, Methanol-d4) δ 8.56 (s, 1H), 8.54 (s, 1H), 7.73 (ddd, J = 7.7, 4.3, 1.7 Hz, 2H), 7.59 (t, J = 7.7 Hz, 2H), 7.49 (dd, J = 7.7, 1.7 Hz, 2H), 4.94 (d, J = 15.4 Hz, 1H), 4.62-4.55 (m, 1H), 4.54 (d, J = 3.9 Hz, 2H), 4.13 (d, J = 0.8 Hz, 7H), 3.99 (dd, J = 11.7, 3.3 Hz, 1H), 3.92-3.77 (m, 3H), 3.44-3.33 (m, 3H), 2.51-2.37 (m, 3H), 2.36-1.89 (m, 7H). |

TABLE 2-continued

| No. | NMR |
|---|---|
| 24 | ¹H NMR (400 MHz, Methanol-d4) δ 8.56 (s, 1H), 8.54 (s, 1H), 7.73 (ddd, J = 7.7, 4.4, 1.7 Hz, 2H), 7.59 (t, J = 7.6 Hz, 2H), 7.49 (dd, J = 7.6, 1.7 Hz, 2H), 4.94 (d, J = 15.4 Hz, 1H), 4.62-4.55 (m, 1H), 4.53 (d, J = 3.9 Hz, 2H), 4.13 (s, 7H), 3.99 (dd, J = 11.7, 3.2 Hz, 1H), 3.91-3.77 (m, 3H), 3.44-3.33 (m, 4H), 2.51-2.36 (m, 3H), 2.36-1.89 (m, 6H). |
| 28 | ¹H (MeOH-d4, 400 MHz, d): 8.58 (s, 1H); 8.56 (s, 1H); 8.55 (s, 1H); 7.74 (dd, 2H); 7.61 (td, 2H); 7.50 (dt, 2H); 4.61 (d, 2H); 4.56 (dd, 2H); 4.14 (s, 3H); 4.13 (s, 3H); 3.37 (m, 2H); 2.50-2.38 (m, 3H); 2.02 (d, 2H); 2.00 (m, 2H). |
| 30 | ¹H (MeOH-d4, 400 MHz, d): 8.54 (s, 2H); 7.74 (dd, 2H); 7.68 (d, 2H); 7.61 (t, 2H); 7.50 (dd, 2H); 6.46 (d, 2H); 4.49 (s, 4H); 4.41 (s, 4H); 4.13 (s, 6H); 3.94 (s, 6H). |
| 32 | ¹H (MeOH-d4, 400 MHz, d): 8.58 (s, 1H); 8.56 (s, 1H); 8.17 (s, 1H); 7.75 (dd, 2H); 7.62 (td, 2H); 7.48 (dt, 2H); 4.60-4.45 (m, 8H); 4.14 (s, 3H); 4.13 (s, 3H); 4.20-4.08 (m, 1H); 3.38 (m, 2H); 2.60-2.40 (m, 3H); 2.00-1.85 (m, 1H); 1.55 (t, 3H). |
| 33 | ¹H (MeOH-d4, 400 MHz, d): 8.57 (s, 1H); 8.55 (s, 1H); 7.79 (s, 1H); 7.75 (dd, 2H); 7.62 (td, 2H); 7.48 (dt, 2H); 4.60 (broad s, 4H); 4.15 (broad s, 6H); 4.17-4.12 (m, 2H); 3.60 (t, 2H); 3.38 (t, 2H); 3.28 (t, 2H); 2.50-2.38 (m, 3H); 2.05-1.95 (m, 2H). |
| 35 | ¹H (MeOH-d4, 400 MHz, d): 8.52 (s, 1H); 8.51 (s, 1H); 7.98 (s, 1H); 7.72 (dd, 2H); 7.57 (td, 2H); 7.48 (dt, 2H); 4.58 (s, 2H); 4.52 (broad s, 4H); 4.11 (s, 3H); 4.10 (s, 3H); 4.17-4.12 (m, 2H); 3.38 (m, 2H); 2.50-2.38 (m, 3H); 2.05-1.95 (m, 2H). |
| 43 | ¹H NMR (400 MHz, Methanol-d4) δ 8.52 (d, J = 3.1 Hz, 2H), 7.71 (dd, J = 7.7, 1.7 Hz, 2H), 7.57 (t, J = 7.6 Hz, 2H), 7.47 (dd, J = 7.6, 1.7 Hz, 2H), 4.63-4.43 (m, 4H), 4.11 (s, 7H), 3.71 (td, J = 6.8, 1.1 Hz, 2H), 3.61 (td, J = 6.7, 1.1 Hz, 2H), 3.36 (h, J = 5.4 Hz, 2H), 2.53-2.26 (m, 3H), 2.05-1.89 (m, 1H). |
| 44 | ¹H NMR (400 MHz, DMSO-d6) δ 9.20 (d, J = 46.7 Hz, 4H), 8.55 (d, J = 13.3 Hz, 2H), 7.75 (dt, J = 7.6, 1.6 Hz, 2H), 7.69-7.59 (m, 3H), 7.56 (dt, J = 7.6, 2.2 Hz, 2H), 6.36 (t, J = 5.7 Hz, 1H), 5.81 (s, 2H), 4.43 (dd, J = 14.8, 8.9 Hz, 5H), 4.02 (d, J = 4.5 Hz, 7H), 3.93 (d, J = 6.9 Hz, 1H), 3.33 (q, J = 5.7 Hz, 2H), 3.27-3.02 (m, 5H), 2.27-2.09 (m, 3H), 1.79 (tt, J = 11.1, 5.5 Hz, 1H). |
| 45 | ¹H NMR (400 MHz, DMSO-d6) δ 9.19 (d, J = 49.3 Hz, 5H), 8.56 (d, J = 8.4 Hz, 2H), 7.75 (dd, J = 7.6, 1.7 Hz, 2H), 7.69-7.50 (m, 7H), 7.12 (s, 1H), 4.62-4.34 (m, 5H), 4.02 (d, J = 3.7 Hz, 7H), 3.93 (d, J = 6.3 Hz, 1H), 3.34-3.08 (m, 6H), 2.58 (t, J = 7.0 Hz, 3H), 2.28-2.06 (m, 3H), 1.90-1.67 (m, 1H). |
| 46 | ¹H NMR (400 MHz, Methanol-d4) δ 8.54 (d, J = 11.8 Hz, 2H), 7.72 (ddd, J = 7.7, 5.9, 1.7 Hz, 2H), 7.58 (td, J = 7.7, 1.0 Hz, 2H), 7.48 (dt, J = 7.6, 1.5 Hz, 2H), 4.59 (s, 2H), 4.52 (d, J = 3.8 Hz, 2H), 4.12 (s, 7H), 3.36 (h, J = 5.5 Hz, 2H), 3.05 (s, 6H), 2.52-2.29 (m, 3H), 2.04-1.90 (m, 1H). |
| 47 | ¹H NMR (400 MHz, Methanol-d4) δ 8.52 (d, J = 2.3 Hz, 2H), 7.75-7.67 (m, 2H), 7.57 (t, J = 7.7 Hz, 2H), 7.48 (dd, J = 7.6, 1.7 Hz, 2H), 4.63-4.45 (m, 6H), 4.11 (d, J = 1.0 Hz, 7H), 3.64-3.32 (m, 5H), 2.53-2.23 (m, 3H), 2.06-1.88 (m, 1H). |
| 49 | ¹H NMR (400 MHz, Methanol-d4) δ 8.52 (s, 1H), 8.51 (s, 1H), 7.74-7.67 (m, 4H), 7.57 (td, J = 7.7, 0.7 Hz, 2H), 7.47 (dd, J = 7.6, 1.7 Hz, 2H), 4.52 (d, J = 3.8 Hz, 2H), 4.48 (s, 2H), 4.11 (d, J = 3.8 Hz, 7H), 3.50-3.39 (m, 2H), 3.39-3.32 (m, 2H), 3.05 (t, J = 7.8 Hz, 2H), 2.52-2.30 (m, 3H), 2.05-1.88 (m, 1H). |
| 50 | ¹H NMR (400 MHz, Methanol-d4) δ 8.52 (s, 1H), 8.48 (s, 1H), 7.70 (ddd, J = 7.7, 4.2, 1.7 Hz, 2H), 7.57 (td, J = 7.7, 1.5 Hz, 2H), 7.47 (dd, J = 7.6, 1.8 Hz, 2H), 4.80 (s, 2H), 4.70 (s, 4H), 4.52 (d, J = 3.8 Hz, 2H), 4.11 (d, J = 2.3 Hz, 7H), 3.90 (s, 2H), 3.42-3.33 (m, 2H), 3.05 (s, 1H), 2.52-2.30 (m, 3H), 2.07-1.86 (m, 1H). |
| 72 | ¹H NMR (400 MHz, Methanol-d4) δ 8.01 (s, 2H), 7.63 (dd, J = 7.7, 1.7 Hz, 2H), 7.51 (t, J = 7.7 Hz, 2H), 7.41 (dd, J = 7.6, 1.7 Hz, 2H), 4.52-4.42 (m, 4H), 4.45 (s, 4H), 4.18 (q, J = 10.0, 9.5 Hz, 4H), 3.02 (s, 6H), 2.76-2.63 (m, 2H), 2.63-2.48 (m, 2H). |
| 73 | ¹H NMR (400 MHz, Methanol-d4) δ 8.05 (s, 1H), 8.01 (s, 1H), 7.68-7.59 (m, 2H), 7.56-7.47 (m, 2H), 7.45-7.38 (m, 2H), 4.53-4.42 (m, 2H), 4.46 (s, 2H), 4.23-4.13 (m, 2H), 4.21 (s, 2H), 3.02 (s, 3H), 3.02 (s, 3H), 2.88 (s, 3H), 2.75-2.62 (m, 1H), 2.60-2.50 (m, 1H). |
| 74 | ¹H NMR (400 MHz, Methanol-d4) δ 8.05 (s, 2H), 7.64 (dd, J = 7.7, 1.7 Hz, 2H), 7.52 (t, J = 7.6 Hz, 2H), 7.42 (dd, J = 7.6, 1.7 Hz, 2H), 4.21 (s, 4H), 3.02 (s, 6H), 2.88 (s, 6H). |
| 76 | ¹H NMR (400 MHz, Methanol-d4) δ 8.01 (s, 2H), 7.62 (dd, J = 7.6, 1.8 Hz, 2H), 7.51 (t, J = 7.6 Hz, 2H), 7.41 (dd, J = 7.6, 1.7 Hz, 2H), 4.77-4.07 (m, 20H), 3.01 (s, 6H), 1.86 (s, 6H). |
| 77 | ¹H NMR (400 MHz, Methanol-d4) δ 8.02 (s, 2H), 7.63 (dd, J = 7.7, 1.7 Hz, 2H), 7.51 (t, J = 7.6 Hz, 2H), 7.41 (dd, J = 7.6, 1.7 Hz, 2H), 4.81-3.88 (m, 14H), 3.01 (s, 6H). |
| 78 | ¹H NMR (400 MHz, Methanol-d4) δ 8.02 (s, 2H), 7.62 (dd, J = 7.6, 1.8 Hz, 2H), 7.51 (t, J = 7.6 Hz, 2H), 7.41 (dd, J = 7.6, 1.8 Hz, 2H), 4.73-4.13 (m, 12H), 3.91-3.59 (m, 4H), 3.02 (s, 6H), 2.90-2.67 (m, 4H). |
| 79 | ¹H NMR (400 MHz, Methanol-d4) δ 8.02 (s, 2H), 7.64-7.60 (m, 2H), 7.52 (t, J = 7.6 Hz, 2H), 7.41 (dd, J = 7.6, 1.7 Hz, 2H), 4.94-4.06 (m, 12H), 3.02 (s, 6H), 2.57 (t, J = 7.9 Hz, 4H), 2.42 (t, J = 7.9 Hz, 4H). |
| 82 | ¹H NMR (400 MHz, Methanol-d4) δ 8.75 (s, 2H), 7.67 (dd, J = 7.6, 1.7 Hz, 2H), 7.58 (t, J = 7.6 Hz, 2H), 7.49 (dd, J = 7.6, 1.7 Hz, 2H), 4.97-3.83 (m, 14), 2.92 (q, J = 7.5 Hz, 4H), 1.38 (t, J = 7.5 Hz, 6H). |
| 83 | ¹H NMR (400 MHz, Methanol-d4) δ 8.76 (s, 2H), 7.71-7.66 (m, 2H), 7.58 (t, J = 7.7 Hz, 2H), 7.49 (dd, J = 7.4, 1.8 Hz, 2H), 4.88 (s, 4H), 4.64-4.29 (m, 8H), 3.90-3.60 (m, 4H), 2.97-2.72 (m, 8H), 1.39 (t, J = 7.5 Hz, 6H). |
| 84 | ¹H NMR (400 MHz, Methanol-d4) δ 8.77 (s, 2H), 7.68 (dd, J = 7.6, 1.7 Hz, 2H), 7.59 (t, J = 7.6 Hz, 2H), 7.50 (dd, J = 7.6, 1.7 Hz, 2H), 4.88 (s, 4H), 4.78-4.23 (m, 8H), 2.92 (q, J = 7.5 Hz, 4H), 2.58 (t, J = 7.9 Hz, 4H), 2.42 (t, J = 7.8 Hz, 4H), 1.40 (t, J = 7.5 Hz, 6H). |
| 88 | ¹H NMR (400 MHz, Methanol-d4) δ 8.60 (s, 2H), 7.73 (dd, J = 7.7, 1.8 Hz, 2H), 7.59 (t, J = 7.6 Hz, 2H), 7.50 (dd, J = 7.6, 1.7 Hz, 2H), 4.83-3.91 (m, 14), 2.69 (s, 6H). |

TABLE 2-continued

| No. | NMR |
|---|---|
| 89 | $^1$H NMR (400 MHz, Methanol-d4) δ 8.60 (s, 2H), 7.73 (dd, J = 7.7, 1.7 Hz, 2H), 7.59 (t, J = 7.6 Hz, 2H), 7.50 (dd, J = 7.6, 1.7 Hz, 2H), 4.73 (s, 4H), 4.68-4.27 (m, 8H), 3.88-3.55 (m, 4H), 2.93-2.71 (m, 4H), 2.70 (s, 6H). |
| 90 | $^1$H NMR (400 MHz, Methanol-d4) δ 8.60 (s, 2H), 7.73 (dd, J = 7.7, 1.7 Hz, 2H), 7.59 (t, J = 7.7 Hz, 2H), 7.50 (dd, J = 7.7, 1.7 Hz, 2H), 4.73 (s, 4H), 4.72-4.18 (m, 8H), 2.70 (s, 6H), 2.57 (t, J = 7.9 Hz, 4H), 2.42 (t, J = 7.9 Hz, 4H). |
| 93 | $^1$H NMR (400 MHz, Methanol-d4) δ 8.75 (s, 2H), 7.65 (dd, J = 7.7, 1.8 Hz, 2H), 7.58 (t, J = 7.6 Hz, 2H), 7.49 (dd, J = 7.6, 1.8 Hz, 2H), 4.85-4.63 (m, 8H), 4.46-4.22 (m, 4H), 4.09-4.00 (m, 2H), 2.63 (s, 6H). |
| 100 | $^1$H NMR (400 MHz, Methanol-d4) δ 8.94 (s, 1H), 8.34 (s, 1H), 7.74-7.64 (m, 2H), 7.64-7.49 (m, 3H), 7.45 (dd, J = 7.6, 1.7 Hz, 1H), 4.97-3.93 (m, 14H), 3.05 (s, 6H). |
| 101 | $^1$H NMR (400 MHz, Methanol-d4) δ 8.33 (s, 2H), 7.65 (dd, J = 7.7, 1.7 Hz, 2H), 7.53 (t, J = 7.6 Hz, 2H), 7.43 (dd, J = 7.6, 1.7 Hz, 2H), 4.81 (s, 4H), 4.57-4.17 (m, 8H), 3.86-3.59 (m, 4H), 3.05 (s, 12H), 2.90-2.66 (m, 4H). |
| 102 | $^1$H NMR (400 MHz, Methanol-d4) δ 8.94 (s, 1H), 8.34 (s, 1H), 7.73-7.65 (m, 2H), 7.65-7.48 (m, 3H), 7.45 (d, J = 6.6 Hz, 1H), 4.95 (s, 2H), 4.81 (s, 2H), 4.62-4.12 (m, 8H), 3.90-3.58 (m, 2H), 3.06 (s, 6H), 2.90-2.65 (m, 2H). |
| 103 | $^1$H NMR (400 MHz, Methanol-d4) δ 8.34 (s, 2H), 7.66 (dd, J = 7.7, 1.8 Hz, 2H), 7.54 (t, J = 7.6 Hz, 2H), 7.44 (dd, J = 7.6, 1.7 Hz, 2H), 4.82 (s, 4H), 4.75-4.11 (m, 8H), 3.06 (s, 12H), 2.60-2.49 (m, 4H), 2.47-2.32 (m, 4H). |
| 104 | $^1$H NMR (400 MHz, Methanol-d4) δ 8.94 (s, 1H), 8.35 (s, 1H), 7.73-7.66 (m, 2H), 7.65-7.49 (m, 3H), 7.49-7.41 (m, 1H), 4.95 (s, 2H), 4.87-4.17 (m, 10H), 3.06 (s, 6H), 2.61-2.51 (m, 4H), 2.46-2.35 (m, 4H). |
| 112 | $^1$H NMR (400 MHz, Methanol-d4) δ 8.43 (s, 2H), 7.63-7.57 (m, 4H), 7.43 (dd, J = 5.2, 4.1 Hz, 2H), 4.83-4.00 (m, 14H), 4.10 (s, 6H). |
| 113 | $^1$H NMR (400 MHz, Methanol-d4) δ 8.48 (s, 2H), 7.65-7.59 (m, 4H), 7.44 (dd, J = 5.8, 3.5 Hz, 2H), 4.60-4.43 (m, 4H), 4.18-4.05 (m, 2H), 4.12 (s, 6H), 3.37-3.30 (m, 4H), 2.54-2.34 (m, 6H), 2.06-1.93 (m, 2H). |
| 114 | $^1$H NMR (400 MHz, Methanol-d4) δ 8.48 (s, 1H), 8.27 (d, J = 8.0 Hz, 1H), 7.81-7.40 (m, 7H), 4.74 (s, 2H), 4.61-4.29 (m, 4H), 4.18 (s, 4H), 4.10 (s, 6H), 3.83-3.65 (m, 2H), 2.89-2.59 (m, 2H). |
| 116 | $^1$H NMR (400 MHz, Methanol-d4) δ 8.48 (s, 1H), 8.28 (d, J = 8.0 Hz, 1H), 7.81-7.40 (m, 7H), 4.83-4.21 (m, 7H), 4.18 (s, 4H), 4.10 (s, 6H). |
| 120 | $^1$H NMR (400 MHz, Methanol-d4) δ 8.48 (s, 2H), 7.70 (dd, J = 7.7, 1.7 Hz, 2H), 7.57 (t, J = 7.7 Hz, 2H), 7.47 (dd, J = 7.5, 1.7 Hz, 2H), 4.74 (s, 4H), 4.69-4.19 (m, 8H), 4.11 (s, 6H), 3.89-3.60 (m, 4H), 2.97-2.54 (m, 4H). |
| 121 | $^1$H NMR (400 MHz, Methanol-d4) δ 8.82 (s, 2H), 7.83 (dd, J = 7.6, 1.7 Hz, 2H), 7.65 (t, J = 7.7 Hz, 2H), 7.57 (dd, J = 7.6, 1.7 Hz, 2H), 4.64-4.51 (m, 2H), 4.32-4.23 (m, 2H), 4.26 (s, 6H), 3.73 (dd, J = 11.7, 8.0 Hz, 2H), 1.50 (d, J = 6.4 Hz, 6H). |
| 122 | $^1$H NMR (400 MHz, Methanol-d4) δ 8.47 (s, 1H), 7.79-7.03 (m, 9H), 4.56 (s, 2H), 4.15 (s, 2H), 4.10 (s, 3H), 3.95 (s, 3H). |
| 123 | $^1$H NMR (400 MHz, Methanol-d4) δ 8.47 (s, 1H), 7.68 (dd, J = 7.6, 1.7 Hz, 1H), 7.59-7.40 (m, 5H), 7.37 (dd, J = 7.4, 1.9 Hz, 1H), 7.18 (s, 1H), 7.16-7.10 (m, 1H), 4.74 (s, 2H), 4.61-4.19 (m, 10H), 4.11 (s, 3H), 3.96 (s, 3H), 3.85-3.60 (m, 4H), 2.92-2.66 (m, 4H). |
| 124 | $^1$H NMR (400 MHz, Methanol-d4) δ 8.48 (s, 1H), 7.68 (dd, J = 7.8, 1.8 Hz, 1H), 7.61-7.41 (m, 5H), 7.38 (dd, J = 7.3, 1.9 Hz, 1H), 7.20 (s, 1H), 7.14 (d, J = 7.7 Hz, 1H), 4.83-4.23 (m, 12H), 4.11 (s, 3H), 3.97 (s, 3H), 2.63-2.33 (m, 8H). |
| 125 | $^1$H NMR (400 MHz, Methanol-d4) δ 8.53 (s, 1H), 7.72-7.66 (m, 1H), 7.62-7.42 (m, 5H), 7.38 (dd, J = 7.4, 2.1 Hz, 1H), 7.20 (s, 1H), 7.14 (d, J = 7.8 Hz, 1H), 4.58-4.44 (m, 2H), 4.41-4.26 (m, 2H), 4.12 (s, 3H), 4.12-4.01 (m, 2H), 3.98 (s, 3H), 3.39-3.17 (m, 4H), 2.51-2.27 (m, 6H), 2.08-1.72 (m, 2H). |
| 126 | $^1$H NMR (400 MHz, Methanol-d4) δ 8.53 (s, 1H), 7.89 (d, J = 7.5 Hz, 1H), 7.70 (dd, J = 7.6, 1.7 Hz, 1H), 7.66 (dd, J = 7.6, 1.7 Hz, 1H), 7.60-7.50 (m, 2H), 7.47 (dd, J = 7.6, 1.7 Hz, 1H), 7.42 (dd, J = 7.6, 1.7 Hz, 1H), 7.37 (d, J = 7.4 Hz, 1H), 4.60-4.43 (m, 2H), 4.41-4.26 (m, 2H), 4.12-4.00 (m, 2H), 4.12 (s, 3H), 4.10 (s, 3H), 3.38-3.20 (m, 4H), 2.54-2.24 (m, 6H), 2.10-1.76 (m, 2H). |
| 130 | $^1$H NMR (400 MHz, Methanol-d4) δ 8.54 (s, 2H), 7.72 (dd, J = 7.7, 1.8 Hz, 2H), 7.58 (t, J = 7.7 Hz, 2H), 7.48 (dd, J = 7.6, 1.7 Hz, 2H), 4.75-4.55 (m, 6H), 4.11 (s, 6H), 4.06-3.28 (m, 8H), 2.49-2.00 (m, 4H). |
| 131 | $^1$H NMR (400 MHz, Methanol-d4) δ 8.48 (s, 2H), 7.70 (dd, J = 7.7, 1.7 Hz, 2H), 7.57 (t, J = 7.6 Hz, 2H), 7.47 (dd, J = 7.6, 1.7 Hz, 2H), 4.81-3.95 (m, 14H), 4.10 (s, 6H). |
| 133 | $^1$H NMR (400 MHz, Methanol-d4) δ 8.82 (s, 2H), 7.83 (dd, J = 7.7, 1.8 Hz, 2H), 7.65 (t, J = 7.6 Hz, 2H), 7.57 (dd, J = 7.6, 1.8 Hz, 2H), 4.59-4.49 (m, 2H), 4.26 (s, 6H), 4.22 (t, J = 11.9 Hz, 2H), 4.05 (dd, J = 11.8, 7.5 Hz, 2H), 3.85 (dd, J = 11.8, 3.6 Hz, 2H), 3.72 (dd, J = 11.8, 3.6 Hz, 2H). |
| 134 | $^1$H NMR (400 MHz, Methanol-d4) δ 8.82 (s, 2H), 7.83 (dd, J = 7.6, 1.8 Hz, 2H), 7.65 (t, J = 7.6 Hz, 2H), 7.57 (dd, J = 7.7, 1.8 Hz, 2H), 4.63-4.43 (m, 2H), 4.26 (s, 6H), 4.22 (t, J = 11.9 Hz, 2H), 4.11-4.01 (m, 2H), 3.85 (dd, J = 11.8, 3.7 Hz, 2H), 3.72 (dd, J = 11.8, 3.6 Hz, 2H). |
| 136 | $^1$H NMR (400 MHz, Methanol-d4) δ 8.49 (s, 2H), 7.70 (dd, J = 7.7, 1.8 Hz, 2H), 7.57 (t, J = 7.7 Hz, 2H), 7.48 (dd, J = 7.6, 1.7 Hz, 2H), 4.74 (s, 4H), 4.69-4.18 (m, 8H), 4.12 (s, 6H), 2.63-2.52 (m, 2H), 2.42 (t, J = 7.7 Hz, 2H). |
| 137 | $^1$H NMR (400 MHz, Methanol-d4) δ 8.52 (s, 2H), 7.71 (dd, J = 7.7, 1.8 Hz, 2H), 7.57 (t, J = 7.6 Hz, 2H), 7.48 (dd, J = 7.6, 1.7 Hz, 2H), 4.49 (s, 4H), 4.40 (ddd, J = 9.8, 6.3, 2.9 Hz, 2H), 4.11 (s, 6H), 3.41 (dd, J = 12.7, 3.1 Hz, 2H), 3.21 (dd, J = 12.6, 9.8 Hz, 2H), 2.59 (d, J = 6.3 Hz, 4H). |

TABLE 2-continued

| No. | NMR |
|---|---|
| 138 | $^1$H NMR (400 MHz, Methanol-d4) δ 8.53 (s, 2H), 7.72 (dd, J = 7.7, 1.8 Hz, 2H), 7.58 (t, J = 7.6 Hz, 2H), 7.48 (dd, J = 7.6, 1.7 Hz, 2H), 4.60-4.45 (m, 4H), 4.18-4.07 (m, 2H), 4.12 (s, 6H), 3.39-3.31 (m, 4H), 2.53-2.25 (m, 6H), 2.08-1.81 (m, 2H). |
| 139 | $^1$H NMR (400 MHz, Methanol-d4) δ 8.53 (s, 2H), 7.72 (dd, J = 7.6, 1.7 Hz, 2H), 7.58 (t, J = 7.6 Hz, 2H), 7.48 (dd, J = 7.6, 1.7 Hz, 2H), 4.58-4.47 (m, 4H), 4.18-4.07 (m, 2H), 4.12 (s, 6H), 3.42-3.27 (m, 4H), 2.54-2.25 (m, 6H), 2.08-1.83 (m, 2H). |
| 140 | $^1$H NMR (400 MHz, Methanol-d4) δ 8.52 (s, 2H), 7.71 (dd, J = 7.7, 1.7 Hz, 2H), 7.57 (t, J = 7.6 Hz, 2H), 7.48 (dd, J = 7.7, 1.7 Hz, 2H), 4.49 (s, 6H), 4.11 (s, 8H), 3.91-3.87 (m, 4H), 3.37-3.27 (m, 4H). |
| 141 | $^1$H NMR (400 MHz, Methanol-d4) δ 8.82 (s, 2H), 7.83 (dd, J = 7.7, 1.7 Hz, 2H), 7.65 (t, J = 7.7 Hz, 2H), 7.57 (dd, J = 7.7, 1.7 Hz, 2H), 4.26 (s, 6H), 4.15 (s, 8H). |
| 156 | $^1$H NMR (400 MHz, Methanol-d4) δ 8.56 (s, 1H), 7.89 (d, J = 7.5 Hz, 1H), 7.78-7.30 (m, 7H), 4.60-4.40 (m, 4H), 4.30-3.87 (m, 11H), 3.63-3.36 (m, 4H), 2.57-2.29 (m, 3H), 2.05-1.89 (m, 1H), 1.32 (d, J = 10.3 Hz, 3H). |
| 157 | $^1$H NMR (400 MHz, Methanol-d4) δ 8.56 (s, 1H), 7.90 (s, 1H), 7.78-7.34 (m, 7H), 4.62-4.04 (m, 15H), 3.38 (d, J = 4.3 Hz, 5H), 2.53-2.33 (m, 3H), 2.06-1.88 (m, 1H). |
| 158 | $^1$H NMR (400 MHz, Methanol-d4) δ 8.56 (s, 1H), 7.95 (d, J = 7.6 Hz, 1H), 7.81-7.34 (m, 7H), 4.63-4.44 (m, 2H), 4.41 (s, 2H), 4.20-4.05 (m, 7H), 3.50-3.35 (m, 6H), 2.53-2.31 (m, 3H), 2.10-1.72 (m, 5H), 1.31 (s, 3H). |
| 159 | $^1$H NMR (400 MHz, Methanol-d4) δ 8.56 (s, 1H), 7.95 (d, J = 7.6 Hz, 1H), 7.77-7.67 (m, 2H), 7.63-7.34 (m, 5H), 4.61-4.35 (m, 4H), 4.13 (d, J = 13.6 Hz, 7H), 3.92-3.11 (m, 6H), 2.52-1.92 (m, 6H), 1.48 (s, 3H). |
| 160 | $^1$H NMR (400 MHz, Methanol-d4) δ 8.56 (s, 1H), 7.94 (d, J = 7.6 Hz, 1H), 7.72 (ddd, J = 10.6, 7.7, 1.7 Hz, 2H), 7.65-7.36 (m, 5H), 4.62-4.49 (m, 2H), 4.39 (s, 2H), 4.20-4.04 (m, 7H), 3.62 (d, J = 11.8 Hz, 2H), 3.51-3.43 (m, 2H), 3.37 (dd, J = 6.2, 5.1 Hz, 2H), 3.21-3.07 (m, 2H), 2.55-2.34 (m, 3H), 2.12-1.44 (m, 6H). |
| 161 | $^1$H NMR (400 MHz, Methanol-d4) δ 8.56 (s, 1H), 7.91 (d, J = 7.6 Hz, 1H), 7.71 (ddd, J = 16.8, 7.7, 1.8 Hz, 2H), 7.66-7.31 (m, 5H), 4.64-4.50 (m, 2H), 4.46 (s, 2H), 4.37 (s, 2H), 4.20-4.04 (m, 7H), 3.37 (dd, J = 6.2, 5.0 Hz, 2H), 2.55-2.33 (m, 3H), 2.06-1.97 (m, 1H). |
| 162 | $^1$H NMR (400 MHz, Methanol-d4) δ 8.56 (s, 1H), 7.91 (d, J = 7.5 Hz, 1H), 7.79-7.32 (m, 7H), 4.63-4.46 (m, 2H), 4.33 (s, 2H), 4.13 (d, J = 12.1 Hz, 9H), 3.50 (td, J = 12.1, 2.1 Hz, 3H), 3.37 (dd, J = 6.2, 5.2 Hz, 2H), 2.60-2.32 (m, 3H), 2.15 (dd, J = 12.0, 3.9 Hz, 2H), 2.08-1.90 (m, 1H), 1.76 (qd, J = 12.2, 4.7 Hz, 2H). |
| 163 | $^1$H NMR (400 MHz, Methanol-d4) δ 8.56 (s, 1H), 7.94 (d, J = 7.6 Hz, 1H), 7.72 (ddd, J = 10.3, 7.7, 1.7 Hz, 2H), 7.66-7.35 (m, 5H), 4.62-4.48 (m, 2H), 4.43 (d, J = 21.3 Hz, 2H), 4.21-4.04 (m, 7H), 3.66 (d, J = 12.3 Hz, 2H), 3.50-3.35 (m, 2H), 3.23-3.10 (m, 2H), 2.75-1.85 (m, 9H). |
| 164 | $^1$H NMR (400 MHz, Methanol-d4) δ 8.56 (s, 1H), 7.91 (d, J = 7.6 Hz, 1H), 7.81-7.30 (m, 7H), 4.82-4.29 (m, 7H), 4.13 (d, J = 15.8 Hz, 9H), 3.44-3.36 (m, 2H), 2.57-2.30 (m, 3H), 2.07-1.87 (m, 1H). |
| 165 | $^1$H NMR (400 MHz, Methanol-d4) δ 8.56 (s, 1H), 7.93 (d, J = 7.5 Hz, 1H), 7.79-7.33 (m, 7H), 4.65-4.50 (m, 3H), 4.48-4.30 (m, 2H), 4.27-4.06 (m, 9H), 4.02 (dd, J = 11.0, 3.2 Hz, 1H), 3.73 (dt, J = 5.7, 2.8 Hz, 1H), 3.63 (dd, J = 9.8, 4.4 Hz, 1H), 3.37 (dd, J = 6.2, 5.2 Hz, 2H), 2.56-2.31 (m, 3H), 2.12-1.90 (m, 1H). |
| 166 | $^1$H NMR (400 MHz, Methanol-d4) δ 8.56 (s, 1H), 7.92 (d, J = 7.6 Hz, 1H), 7.77-7.33 (m, 7H), 4.63-4.48 (m, 2H), 4.35 (s, 2H), 4.26 (tt, J = 8.5, 4.4 Hz, 1H), 4.14 (d, J = 8.2 Hz, 7H), 3.90 (dd, J = 11.7, 7.6 Hz, 1H), 3.61 (dd, J = 11.7, 4.0 Hz, 1H), 3.37 (dd, J = 6.2, 5.1 Hz, 2H), 2.93 (dd, J = 17.8, 8.8 Hz, 1H), 2.59 (dd, J = 17.8, 4.7 Hz, 1H), 2.54-2.30 (m, 3H), 2.00 (ddd, J = 13.1, 5.7, 3.5 Hz, 1H). |
| 167 | $^1$H NMR (400 MHz, Methanol-d4) δ 8.56 (s, 1H), 7.92 (d, J = 7.6 Hz, 1H), 7.79-7.35 (m, 7H), 4.63-4.47 (m, 2H), 4.35 (s, 2H), 4.26 (dt, J = 8.2, 4.2 Hz, 1H), 4.14 (d, J = 8.2 Hz, 7H), 3.90 (dd, J = 11.6, 7.6 Hz, 1H), 3.61 (dd, J = 11.6, 3.9 Hz, 1H), 3.37 (dd, J = 6.2, 5.2 Hz, 2H), 2.93 (dd, J = 17.8, 8.8 Hz, 1H), 2.59 (dd, J = 17.8, 4.7 Hz, 1H), 2.54-2.36 (m, 3H), 2.07-1.94 (m, 1H). |
| 168 | $^1$H NMR (400 MHz, Methanol-d4) δ 8.56 (s, 1H), 7.90 (d, J = 7.6 Hz, 1H), 7.80-7.37 (m, 7H), 4.62-4.33 (m, 9H), 4.13 (d, J = 12.3 Hz, 6H), 3.83 (s, 2H), 3.37 (dd, J = 6.2, 5.1 Hz, 2H), 2.58-2.35 (m, 3H), 2.07-1.97 (m, 1H). |
| 169 | $^1$H NMR (400 MHz, Methanol-d4) δ 8.56 (s, 1H), 7.92 (d, J = 7.5 Hz, 1H), 7.79-7.30 (m, 7H), 4.61-4.48 (m, 3H), 4.38 (d, J = 13.2 Hz, 1H), 4.22 (dd, J = 10.6, 8.6 Hz, 1H), 4.13 (d, J = 11.1 Hz, 7H), 3.54-3.41 (m, 2H), 3.41-3.35 (m, 2H), 2.66 (ddt, J = 8.7, 6.5, 3.3 Hz, 1H), 2.54-2.35 (m, 3H), 2.33-2.18 (m, 1H), 2.06-1.96 (m, 1H). |
| 170 | $^1$H NMR (400 MHz, Methanol-d4) δ 8.56 (s, 1H), 7.92 (d, J = 7.6 Hz, 1H), 7.77-7.31 (m, 7H), 4.65-4.46 (m, 2H), 4.31 (s, 2H), 4.20-3.97 (m, 10H), 3.88 (dd, J = 10.8, 5.7 Hz, 1H), 3.84-3.71 (m, 1H), 3.38 (dd, J = 6.2, 5.3 Hz, 2H), 2.56-2.34 (m, 4H), 2.22-1.96 (m, 2H). |
| 171 | $^1$H NMR (400 MHz, Methanol-d4) δ 8.56 (s, 1H), 7.91 (d, J = 7.6 Hz, 1H), 7.71 (ddd, J = 19.1, 7.7, 1.7 Hz, 2H), 7.63-7.33 (m, 5H), 4.62-4.48 (m, 2H), 4.31 (s, 2H), 4.22-3.96 (m, 10H), 3.88 (dd, J = 10.8, 5.7 Hz, 1H), 3.83-3.70 (m, 1H), 3.37 (dd, J = 6.2, 5.2 Hz, 2H), 2.57-2.37 (m, 4H), 2.21-1.96 (m, 2H). |
| 172 | $^1$H NMR (400 MHz, Methanol-d4) δ 8.56 (d, J = 7.5 Hz, 2H), 7.74 (dt, J = 7.7, 1.6 Hz, 2H), 7.61 (td, J = 7.7, 1.1 Hz, 2H), 7.51 (dt, J = 7.6, 1.6 Hz, 2H), 4.62-4.48 (m, 2H), 4.45 (s, 2H), 4.24-4.05 (m, 8H), 3.43-3.35 (m, 2H), 3.27 (d, J = 7.4 Hz, 2H), 2.66-2.14 (m, 6H), 2.05-1.97 (m, 1H), 1.85-1.67 (m, 2H). |
| 173 | 1H NMR (400 MHz, Methanol-d4) δ 8.56 (s, 1H), 8.51 (s, 1H), 7.74 (ddd, J = 7.5, 5.6, 1.7 Hz, 2H), 7.60 (td, J = 7.7, 2.7 Hz, 2H), 7.51 (dt, J = 7.6, 1.7 Hz, 2H), 4.75 (d, J = 9.9 Hz, 4H), 4.64-4.49 (m, 2H), 4.41 (s, 3H), 4.27-4.03 (m, 7H), 3.39 (t, J = 5.3 Hz, 5H), 2.57-2.34 (m, 3H), 2.04-1.97 (m, 1H). |

TABLE 2-continued

| No. | NMR |
|---|---|
| 174 | 1H NMR (400 MHz, Methanol-d4) δ 8.56 (d, J = 2.2 Hz, 2H), 7.75 (dt, J = 7.7, 1.6 Hz, 2H), 7.61 (td, J = 7.6, 0.9 Hz, 2H), 7.51 (dt, J = 7.6, 1.5 Hz, 2H), 4.81 (d, J = 8.6 Hz, 1H), 4.71 (s, 1H), 4.62-4.47 (m, 2H), 4.19-4.04 (m, 7H), 4.07-3.47 (m, 3H), 3.42-3.34 (m, 2H), 3.29-3.11 (m, 1H), 2.57-1.97 (m, 6H), 1.49 (d, J = 1.6 Hz, 3H). |
| 175 | 1H NMR (400 MHz, Methanol-d4) δ 8.56 (s, 1H), 8.50 (d, J = 2.5 Hz, 1H), 7.73 (tt, J = 6.3, 1.6 Hz, 2H), 7.60 (td, J = 7.6, 3.0 Hz, 2H), 7.50 (dt, J = 7.6, 2.0 Hz, 2H), 4.70 (d, J = 19.7 Hz, 2H), 4.55 (d, J = 4.0 Hz, 2H), 4.53-4.43 (m, 1H), 4.26-4.06 (m, 9H), 4.02 (d, J = 10.7 Hz, 1H), 3.62 (s, 1H), 3.45 (s, 1H), 3.37 (dd, J = 6.2, 5.0 Hz, 2H), 2.60-2.35 (m, 3H), 2.13-1.93 (m, 1H), 1.35 (d, J = 32.2 Hz, 3H). |
| 176 | 1H NMR (400 MHz, Methanol-d4) δ 8.56 (s, 1H), 8.50 (s, 1H), 7.74 (ddd, J = 7.2, 5.3, 1.7 Hz, 2H), 7.60 (td, J = 7.7, 3.0 Hz, 2H), 7.50 (dt, J = 7.6, 2.0 Hz, 2H), 4.71 (d, J = 3.2 Hz, 2H), 4.59-4.22 (m, 6H), 4.19-4.07 (m, 7H), 3.79 (d, J = 4.3 Hz, 1H), 3.67 (d, J = 3.8 Hz, 1H), 3.43-3.37 (m, 2H), 3.27-3.03 (m, 1H), 2.60-2.33 (m, 3H), 2.04-1.94 (m, 1H). |
| 177 | 1H NMR (400 MHz, Methanol-d4) δ 8.56 (d, J = 4.4 Hz, 2H), 7.74 (d, J = 7.7 Hz, 2H), 7.61 (t, J = 7.7 Hz, 2H), 7.51 (d, J = 7.6 Hz, 2H), 5.25 (d, J = 53.4 Hz, 1H), 4.56 (d, J = 3.9 Hz, 2H), 4.50 (s, 2H), 4.22-4.10 (m, 7H), 4.03-3.85 (m, 1H), 3.45-3.35 (m, 2H), 2.71-1.78 (m, 10H). |
| 178 | 1H NMR (400 MHz, Methanol-d4) δ 8.56 (d, J = 2.5 Hz, 2H), 7.75 (dd, J = 7.9, 1.7 Hz, 2H), 7.61 (t, J = 7.6 Hz, 2H), 7.51 (d, J = 7.5 Hz, 2H), 5.14-4.97 (m, 1H), 4.63 (d, J = 5.9 Hz, 2H), 4.55 (d, J = 3.8 Hz, 2H), 4.15 (s, 7H), 3.45-3.35 (m, 2H), 3.11-2.99 (m, 1H), 2.44 (q, J = 11.9, 10.7 Hz, 3H), 1.99 (d, J = 8.9 Hz, 1H), 1.64-1.24 (m, 2H). |
| 179 | 1H NMR (400 MHz, Methanol-d4) δ 8.56 (d, J = 4.5 Hz, 2H), 7.75 (dd, J = 7.7, 1.7 Hz, 2H), 7.61 (t, J = 7.7 Hz, 2H), 7.51 (dt, J = 7.6, 1.7 Hz, 2H), 4.64-4.44 (m, 4H), 4.21-4.08 (m, 7H), 3.38 (t, J = 5.7 Hz, 2H), 3.13 (d, J = 7.6 Hz, 2H), 2.52-2.33 (m, 3H), 1.98 (dd, J = 11.8, 6.5 Hz, 1H), 1.29-1.12 (m, 1H), 0.84-0.71 (m, 2H), 0.49 (d, J = 5.0 Hz, 2H). |
| 185 | 1H NMR (400 MHz, Methanol-d4) δ 8.56 (s, 1H), 8.56 (s, 1H), 7.75 (t, J = 1.7 Hz, 1H), 7.73 (t, J = 1.7 Hz, 1H), 7.61 (t, J = 7.7 Hz, 2H), 7.52 (d, J = 1.7 Hz, 1H), 7.50 (d, J = 1.7 Hz, 1H), 4.61-4.49 (m, 2H), 4.36 (s, 2H), 4.15 (m, 7H), 3.83 (s, 2H), 3.47 (s, 3H), 3.40-3.34 (m, 2H), 2.53-2.36 (m, 5H), 2.29-2.17 (m, 2H), 2.03 (dtd, J = 23.7, 9.1, 4.9 Hz, 3H). |
| 186 | 1H NMR (400 MHz, Methanol-d4) δ 8.56 (s, 1H), 8.55 (s, 1H), 7.75 (d, J = 1.7 Hz, 1H), 7.73 (d, J = 1.7 Hz, 1H), 7.61 (td, J = 7.6, 1.3 Hz, 2H), 7.52 (t, J = 2.0 Hz, 1H), 7.50 (t, J = 1.9 Hz, 1H), 4.55 (d, J = 4.1 Hz, 2H), 4.50 (d, J = 2.0 Hz, 2H), 4.15 (s, 3H), 4.14 (s, 5H), 3.95 (q, J = 7.4 Hz, 1H), 3.43-3.35 (m, 2H), 3.25 (m, 2H), 2.53-2.36 (m, 3H), 2.17 (dq, J = 15.7, 7.8 Hz, 1H), 2.02 (ddtd, J = 17.9, 13.6, 9.8, 9.2, 4.4 Hz, 3H), 1.85 (ddd, J = 13.2, 9.4, 5.0 Hz, 1H), 1.78-1.68 (m, 1H), 1.68-1.55 (m, 1H), 1.45-1.33 (m, 1H). |
| 187 | 1H NMR (400 MHz, Methanol-d4) δ 8.56 (s, 1H), 8.55 (s, 1H), 7.75 (t, J = 1.4 Hz, 1H), 7.73 (d, J = 1.5 Hz, 1H), 7.61 (td, J = 7.7, 1.1 Hz, 2H), 7.52 (d, J = 1.7 Hz, 1H), 7.50 (d, J = 1.7 Hz, 1H), 4.74 (m, 1H), 4.66-4.49 (m, 2H), 4.19 (m, 1H), 4.15 (s, 3H), 4.13 (s, 3H), 4.00 (m, 2H), 3.84 (m, 1H), 3.69 (s, 1H), 3.41-3.34 (m, 2H), 2.53-2.36 (m, 3H), 1.99 (ddt, J = 14.3, 10.3, 4.7 Hz, 2H), 1.85 (td, J = 7.9, 4.2 Hz, 1H), 1.30 (m, 1H), 1.05 (m, 1H), 0.97 (m, 1H), 0.85 (m, 1H). |
| 188 | 1H NMR (400 MHz, Methanol-d4) δ 8.56 (s, 2H), 7.76 (t, J = 2.0 Hz, 1H), 7.74 (t, J = 2.0 Hz, 1H), 7.61 (t, J = 7.6 Hz, 2H), 7.52 (d, J = 1.7 Hz, 1H), 7.50 (d, J = 1.7 Hz, 1H), 4.73 (s, 2H), 4.61-4.49 (m, 2H), 4.38 (s, 1H), 4.15 (s, 3H), 4.14 (s, 4H), 4.12 (d, J = 9.8 Hz, 1H), 4.05 (m, 1H), 3.93 (d, J = 23.2 z, 1H), 3.69 (s, 3H), 3.4.5 (m, 1H), 3.41-3.36 (m, 2H), 2.56 (m, 1H), 2.53-2.35 (m, 3H), 2.17 (s, 1H), 2.06-1.91 (m, 1H). |
| 189 | 1H NMR (400 MHz, Methanol-d4) δ 8.56 (s, 2H), 7.78-7.72 (m, 2H), 7.61 (t, J = 7.7 Hz, 2H), 7.56-7.46 (m, 2H), 4.53 (s, 4H), 4.44 (t, J = 8.8 Hz, 2H), 4.20 (t, J = 9.4 Hz, 2H), 4.15 (s, 6H), 4.06 (dd, J = 9.1, 5.5 Hz, 2H), 3.86 (dd, J = 10.3, 5.6 Hz, 2H), 3.54 (d, J = 7.5 Hz, 4H), 3.21-3.08 (m, 2H), 1.89 (s, 6H). |
| 190 | 1H NMR (400 MHz, Methanol-d4) δ 8.54 (s, 2H), 7.74 (dd, J = 7.9, 1.8 Hz, 2H), 7.61 (t, J = 7.7 Hz, 2H), 7.51 (dd, J = 7.7, 1.7 Hz, 2H), 4.37 (s, 4H), 4.32 (s, 2H), 4.23 (s, 2H), 4.14 (s, 6H), 4.08 (s, 2H), 3.99 (s, 2H), 3.93 (q, J = 8.2 Hz, 2H), 2.74 (dt, J = 12.6, 9.9 Hz, 4H), 2.53 (t, J = 10.8 Hz, 4H), 1.92-1.84 (m, 6H). |
| 191 | 1H NMR (400 MHz, Methanol-d4) δ 8.57 (s, 1H), 8.56 (s, 1H), 7.75 (d, J = 7.7 Hz, 2H), 7.61 (t, J = 7.7 Hz, 2H), 7.52 (dd, J = 7.4, 1.7 Hz, 2H), 4.62 (d, J = 9.4 Hz, 2H), 4.56 (d, J = 3.9 Hz, 2H), 4.52 (s, 2H), 4.46-4.32 (m, 3H), 4.15 (s, 7H), 3.38 (d, J = 4.7 Hz, 2H), 2.44 (h, J = 7.4, 6.9 Hz, 3H), 2.06-1.97 (m, 1H), 1.95 (s, 3H). |
| 192 | 1H NMR (400 MHz, Methanol-d4) δ 8.56 (s, 1H), 8.51 (d, J = 7.7 Hz, 2H), 7.74 (t, J = 6.9 Hz, 2H), 7.61 (td, J = 7.6, 2.0 Hz, 2H), 7.56-7.47 (m, 2H), 4.73 (s, 2H), 4.62 (d, J = 17.1 Hz, 1H), 4.56 (d, J = 3.9 Hz, 2H), 4.49 (m, 2H), 4.28 (s, 1H), 4.15 (m, 5H), 4.14 (m, 5H), 3.39 (d, J = 4.7 Hz, 2H), 2.55-2.33 (m, 3H), 1.99 (q, J = 10.0 Hz, 1H), 1.89 (s, 3H). |
| 193 | 1H NMR (400 MHz, Methanol-d4) δ 8.57 (d, J = 2.3 Hz, 2H), 7.75 (d, J = 7.7 Hz, 2H), 7.61 (t, J = 7.7 Hz, 2H), 7.52 (d, J = 7.6 Hz, 2H), 4.78 (d, J = 4.7 Hz, 2H), 4.56 (d, J = 3.8 Hz, 2H), 4.15 (s, 7H), 4.00 (s, 2H), 3.54 (m, 3H), 3.38 (m, 2H), 2.63 (d, J = 17.4 Hz, 1H), 2.55-2.34 (m, 3H), 2.27 (m, 3H), 1.99 (d, J = 8.1 Hz, 1H). |
| 194 | 1H NMR (400 MHz, Methanol-d4) δ 8.56 (d, J = 2.8 Hz, 2H), 7.78-7.71 (m, 2H), 7.61 (t, J = 7.7 Hz, 2H), 7.51 (d, J = 7.6 Hz, 2H), 4.65-4.46 (m, 4H), 4.26-4.02 (m, 8H), 3.93 (dd, J = 13.1, 7.3 Hz, 1H), 3.79 (dd, J = 16.3, 10.4 Hz, 1H), 3.71 (t, J = 7.6 Hz, 1H), 3.37 (d, J = 2.5 Hz, 3H), 2.70-2.55 (m, 1H), 2.55-2.42 (m, 3H), 2.42-2.19 (m, 1H), 2.12 (d, J = 3.9 Hz, 3H), 1.99 (d, J = 9.4 Hz, 1H). |
| 195 | 1H NMR (400 MHz, Methanol-d4) δ 8.57 (s, 1H), 8.55 (s, 1H), 7.75 (d, J = 7.7 Hz, 2H), 7.61 (t, J = 7.7 Hz, 2H), 7.51 (d, J = 7.7 Hz, 2H), 4.56 (d, J = 3.9 Hz, 2H), 4.51 (s, 2H), 4.15 (s, 7H), 3.69 (s, 1H), 3.38 (d, J = 4.6 Hz, 2H), 2.44 (q, J = 11.8, 10.7 Hz, 3H), 2.31 (d, J = 12.5 Hz, 2H), 2.10 (d, J = 12.8 Hz, 2H), 1.99 (d, J = 8.0 Hz, 1H), 1.95 (s, 3H), 1.64 (q, J = 12.7 Hz, 2H), 1.39 (q, J = 15.5, 14.2 Hz, 3H). |

TABLE 2-continued

| No. | NMR |
|---|---|
| 196 | 1H NMR (400 MHz, Methanol-d4) δ 8.57 (s, 2H), 7.78-7.71 (m, 2H), 7.61 (t, J = 7.7 Hz, 2H), 7.51 (d, J = 7.6 Hz, 2H), 4.56 (d, J = 4.0 Hz, 2H), 4.54 (s, 2H), 4.15 (s, 7H), 3.67 (dd, J = 10.3, 8.1 Hz, 1H), 3.38 (d, J = 4.1 Hz, 2H), 3.30-3.21 (m, 1H), 3.01 (p, J = 7.4 Hz, 1H), 2.63 (dd, J = 16.9, 8.8 Hz, 1H), 2.47 (td, J = 17.7, 16.9, 9.4 Hz, 3H), 2.32 (dd, J = 16.9, 7.5 Hz, 1H), 1.99 (d, J = 8.4 Hz, 1H). |
| 197 | 1H NMR (400 MHz, Methanol-d4) δ 8.57 (d, J = 2.9 Hz, 2H), 7.75 (d, J = 7.6 Hz, 2H), 7.61 (t, J = 7.7 Hz, 2H), 7.52 (d, J = 7.7 Hz, 2H), 4.78 (s, 2H), 4.56 (d, J = 3.9 Hz, 2H), 4.21-4.11 (m, 7H), 4.02 (s, 5H), 3.38 (s, 1H), 2.46 (dd, J = 12.0, 7.4 Hz, 4H), 2.41-2.21 (m, 1H), 2.00 (d, J = 11.7 Hz, 1H). |
| 198 | 1H NMR (400 MHz, Methanol-d4) δ 8.57 (s, 2H), 7.75 (d, J = 7.8 Hz, 2H), 7.61 (t, J = 7.8 Hz, 2H), 7.52 (d, J = 7.6 Hz, 2H), 4.73 (s, 1H), 4.55 (d, J = 3.7 Hz, 2H), 4.15 (d, J = 2.1 Hz, 7H), 3.37 (s, 1H), 2.45 (s, 3H), 2.18 (s, 1H), 2.01 (m, 5H). |
| 199 | 1H NMR (400 MHz, Methanol-d4) δ 8.57 (s, 1H), 8.56 (s, 1H), 7.75 (d, J = 7.7 Hz, 2H), 7.61 (t, J = 7.7 Hz, 2H), 7.55-7.48 (m, 2H), 4.56 (d, J = 3.3 Hz, 4H), 4.35 (m, 1H), 4.21-4.04 (m, 7H), 3.92 (dd, J = 11.5, 7.7 Hz, 1H), 3.65 (dd, J = 11.6, 4.0 Hz, 1H), 3.38 (d, J = 4.6 Hz, 2H), 2.94 (dd, J = 17.7, 8.8 Hz, 1H), 2.66 (dd, J = 17.7, 4.9 Hz, 1H), 2.54-2.36 (m, 3H), 2.06-1.92 (m, 1H). |
| 200 | 1H NMR (400 MHz, Methanol-d4) δ 8.57 (s, 1H), 8.56 (s, 1H), 7.75 (d, J = 7.7 Hz, 2H), 7.61 (t, J = 7.7 Hz, 2H), 7.51 (d, J = 7.6 Hz, 2H), 4.62-4.50 (m, 4H), 4.35 (s, 1H), 4.15 (m, 7H), 3.92 (dd, J = 11.5, 7.7 Hz, 1H), 3.70-3.59 (m, 1H), 3.38 (d, J = 4.7 Hz, 2H), 2.93 (dd, J = 17.6, 8.7 Hz, 1H), 2.66 (dd, J = 17.7, 4.9 Hz, 1H), 2.55-2.34 (m, 3H), 2.00 (d, J = 12.4 Hz, 1H). |
| 201 | 1H NMR (400 MHz, Methanol-d4) δ 8.56 (s, 1H), 8.54 (s, 1H), 7.79-7.71 (m, 2H), 7.61 (t, J = 7.7 Hz, 2H), 7.57-7.48 (m, 4H), 4.58 (s, 2H), 4.56 (d, J = 4.0 Hz, 2H), 4.15 (d, J = 1.9 Hz, 7H), 3.72 (t, J = 7.7 Hz, 2H), 3.59 (t, J = 7.7 Hz, 2H), 3.38 (t, J = 5.8 Hz, 2H), 2.55-2.34 (m, 3H), 2.02 (dd, J = 19.7, 9.9 Hz, 1H). |
| 202 | 1H NMR (400 MHz, Methanol-d4) δ 8.56 (s, 1H), 8.55 (s, 1H), 7.75 (d, J = 7.7 Hz, 2H), 7.61 (t, J = 7.7 Hz, 2H), 7.51 (dd, J = 7.3, 1.7 Hz, 2H), 4.56 (d, J = 3.9 Hz, 2H), 4.48 (s, 2H), 4.15 (m, 7H), 3.92 (s, 1H), 3.47-3.35 (m, 5H), 2.53-2.40 (m, 5H), 2.35 (dd, J = 15.0, 6.8 Hz, 1H), 1.97 (q, J = 12.1, 10.3 Hz, 2H), 1.88 (dd, J = 13.0, 8.8 Hz, 1H). |
| 203 | 1H NMR (400 MHz, Methanol-d4) δ 8.61 (s, 1H), 8.57 (s, 1H), 7.76 (t, J = 6.8 Hz, 2H), 7.62 (t, J = 7.7 Hz, 2H), 7.52 (d, J = 7.6 Hz, 2H), 4.63 (s, 2H), 4.56 (d, J = 3.9 Hz, 2H), 4.15 (s, 6H), 3.77 (s, 2H), 3.38 (m, 2H), 2.53-2.37 (m, 5H), 2.21 (s, 1H), 2.09 (s, 8H), 1.98 (m, J = 9.0 Hz, 1H). |
| 204 | 1H NMR (400 MHz, Methanol-d4) δ 8.57 (s, 2H), 7.75 (d, J = 7.3 Hz, 2H), 7.61 (t, J = 7.7 Hz, 2H), 7.56-7.48 (m, 2H), 4.74 (s, 1H), 4.56 (d, J = 3.9 Hz, 2H), 4.45 (s, 1H), 4.15 (d, J = 2.0 Hz, 6H), 4.06 (m, 1H), 4.00-3.77 (m, 1H), 3.59 (m, 1H), 3.38 (t, J = 5.6 Hz, 2H), 2.60 (s, 1H), 2.44 (q, J = 11.7, 10.6 Hz, 3H), 2.19 (s, 1H), 2.06-1.93 (m, 4H). |
| 205 | 1H NMR (400 MHz, Methanol-d4) δ 8.56 (d, J = 3.3 Hz, 2H), 7.75 (dd, J = 7.7, 1.7 Hz, 2H), 7.61 (t, J = 7.7 Hz, 2H), 7.51 (d, J = 7.6 Hz, 2H), 4.61 (d, J = 5.0 Hz, 1H), 4.58 (s, 2H), 4.56 (d, J = 3.8 Hz, 2H), 4.44 (d, J = 11.1 Hz, 1H), 4.30 (t, J = 14.4 Hz, 1H), 4.15 (d, J = 2.0 Hz, 6H), 3.78 (d, J = 13.9 Hz, 1H), 3.48-3.36 (m, 3H), 2.54-2.40 (m, 3H), 2.36 (d, J = 18.0 Hz, 2H), 2.20 (s, 1H), 2.17 (s, 3H), 2.08-1.94 (m, 1H), 1.90 (d, J = 11.9 Hz, 3H), 1.78-1.55 (m, 1H). |
| 206 | 1H NMR (400 MHz, Methanol-d4) δ 8.56 (s, 1H), 8.56 (s, 1H), 7.75 (dd, J = 7.7, 1.7 Hz, 2H), 7.61 (t, J = 7.7 Hz, 2H), 7.51 (dd, J = 7.6, 1.7 Hz, 2H), 4.72 (d, J = 14.2 Hz, 1H), 4.64-4.48 (m, 4H), 4.15 (d, J = 1.8 Hz, 8H), 3.67-3.54 (m, 1H), 3.38 (t, J = 5.7 Hz, 2H), 3.24 (t, J = 13.2 Hz, 1H), 2.72 (dd, J = 14.4, 11.7 Hz, 1H), 2.55-2.36 (m, 3H), 2.30 (t, J = 15.4 Hz, 2H), 2.16 (s, 3H), 1.99 (q, J = 10.1 Hz, 1H), 1.73 (tt, J = 12.2, 6.1 Hz, 1H), 1.65-1.54 (m, 1H). |
| 207 | 1H NMR (400 MHz, Methanol-d4) δ 8.57 (s, 1H), 8.52 (s, 1H), 7.74 (t, J = 6.3 Hz, 2H), 7.66-7.58 (m, 2H), 7.51 (d, J = 7.6 Hz, 2H), 4.78 (s, 2H), 4.69 (s, 1H), 4.56 (d, J = 3.9 Hz, 2H), 4.39 (s, 1H), 4.15 (d, J = 1.8 Hz, 7H), 3.90 (s, 2H), 3.38 (d, J = 4.5 Hz, 2H), 2.53-2.32 (m, 3H), 2.06-1.93 (m, 1H). |
| 208 | 1H NMR (400 MHz, Methanol-d4) δ 8.57 (s, 1H), 8.54 (s, 1H), 7.74 (d, J = 7.5 Hz, 2H), 7.61 (t, J = 7.7 Hz, 2H), 7.51 (dd, J = 8.0, 1.7 Hz, 2H), 4.56 (d, J = 3.9 Hz, 2H), 4.38 (s, 2H), 4.32 (s, 1H), 4.23 (s, 1H), 4.15 (s, 3H), 4.14 (s, 4H), 4.08 (s, 1H), 3.99 (s, 1H), 3.98-3.88 (m, 1H), 3.38 (d, 1H), 2.74 (m, 2H), 2.59-2.47 (m, 1H), 2.47-2.37 (m, 2H), 2.01 (m, 1H), 1.90-1.84 (m, 3H). |
| 209 | 1H NMR (400 MHz, Methanol-d4) δ 8.51 (s, 2H), 7.73 (d, J = 7.7 Hz, 2H), 7.60 (t, J = 7.7 Hz, 2H), 7.51 (d, J = 7.6 Hz, 2H), 4.73 (s, 4H), 4.65 (s, 4H), 4.47 (m 8H), 4.23 (m, 4H), 4.14 (s, 6H), 1.89 (s, 6H). |
| 221 | $^1$H NMR (400 MHz, Methanol-$d_4$) δ 8.55 (d, J = 8.4 Hz, 2H), 7.74 (dt, J = 7.7, 1.8 Hz, 2H), 7.61 (td, J = 7.6, 1.1 Hz, 2H), 7.51 (dt, J = 7.6, 1.5 Hz, 2H), 4.62-4.48 (m, 2H), 4.36 (s, 2H), 4.14 (d, J = 3.9 Hz, 6H), 3.85 (q, J = 8.1 Hz, 1H), 3.47-3.33 (m, 7H), 2.58-2.33 (m, 5H), 2.17-2.07 (m, 4H), 2.05-1.93 (m, 1H). |
| 222 | $^1$H NMR (400 MHz, Methanol-$d_4$) δ 8.59-8.51 (m, 2H), 7.78-7.70 (m, 2H), 7.60 (td, J = 7.7, 1.5 Hz, 2H), 7.51 (dt, J = 7.6, 1.8 Hz, 2H), 4.62-4.45 (m, 4H), 4.15 (d, J = 1.2 Hz, 6H), 3.95 (q, J = 6.6, 6.1 Hz, 1H), 3.91-3.78 (m, 1H), 3.48-3.33 (m, 5H), 2.79-2.54 (m, 3H), 2.53-2.07 (m, 6H), 2.08-1.93 (m, 2H). |
| 224 | $^1$H NMR (400 MHz, Methanol-$d_4$) δ 8.58 (d, J = 9.2 Hz, 2H), 7.75 (ddd, J = 7.3, 5.4, 1.7 Hz, 2H), 7.61 (t, J = 7.7 Hz, 2H), 7.55-7.48 (m, 2H), 5.02 (d, J = 15.6 Hz, 1H), 4.69-4.58 (m, 1H), 4.55 (d, J = 4.0 Hz, 2H), 4.15 (d, J = 3.1 Hz, 7H), 4.06 (d, J = 12.4 Hz, 1H), 4.02-3.87 (m, 3H), 3.51-3.45 (m, 1H), 3.40-3.34 (m, 4H), 2.63-2.47 (m, 2H), 2.50-2.36 (m, 4H), 2.05-1.94 (m, 2H). |
| 225 | $^1$H NMR (400 MHz, Methanol-$d_4$) δ 8.56 (s, 1H), 8.50 (d, J = 1.8 Hz, 1H), 7.74 (ddd, J = 7.4, 5.5, 1.8 Hz, 2H), 7.60 (td, J = 7.6, 2.9 Hz, 2H), 7.50 (dt, J = 7.6, 1.8 Hz, 2H), 4.76 (s, 1H), 4.67 (s, 1H), 4.62-4.44 (m, 3H), 4.31-4.23 (m, 2H), 4.14 (d, J = 7.7 Hz, 7H), |

TABLE 2-continued

| No. | NMR |
|---|---|
| | 4.08-3.98 (m, 2H), 3.51-3.33 (m, 5H), 3.20-3.07 (m, 1H), 2.54-2.36 (m, 4H), 2.08-1.90 (m, 3H). |
| 227 | $^1$H NMR (400 MHz, Methanol-d$_4$) δ 8.56 (d, J = 1.0 Hz, 2H), 7.75 (dd, J = 7.7, 1.7 Hz, 2H), 7.61 (t, J = 7.6 Hz, 2H), 7.55-7.47 (m, 2H), 4.63-4.48 (m, 4H), 4.15 (d, J = 1.0 Hz, 6H), 3.90-3.53 (m, 4H), 3.49-3.33 (m, 3H), 3.28-3.18 (m, 1H), 2.85-2.65 (m, 1H), 2.54-2.36 (m, 4H), 2.28 (ddd, J = 24.7, 12.2, 5.2 Hz, 1H), 2.09 (d, J = 3.4 Hz, 3H), 2.08-1.96 (m, 1H), 1.99-1.76 (m, 1H). |
| 228 | $^1$H NMR (400 MHz, Methanol-d$_4$) δ 8.55 (d, J = 7.3 Hz, 2H), 7.74 (dt, J = 7.6, 1.4 Hz, 2H), 7.61 (td, J = 7.7, 1.1 Hz, 2H), 7.51 (dt, J = 7.6, 1.6 Hz, 2H), 4.62-4.48 (m, 2H), 4.46 (s, 2H), 4.14 (d, J = 3.3 Hz, 7H), 3.87 (p, J = 7.2 Hz, 1H), 3.44-3.33 (m, 2H), 3.28 (d, J = 10.8 Hz, 5H), 2.63-2.21 (m, 6H), 2.08-1.93 (m, 1H), 1.82-1.69 (m, 2H). |
| 229 | $^1$H NMR (400 MHz, Methanol-d$_4$) δ 8.58 (d, J = 13.1 Hz, 2H), 7.75 (ddd, J = 5.7, 4.6, 2.5 Hz, 2H), 7.61 (t, J = 7.7 Hz, 2H), 7.52 (dd, J = 7.6, 1.7 Hz, 2H), 4.63-4.52 (m, 3H), 4.50 (d, J = 15.9 Hz, 1H), 4.14 (d, J = 3.0 Hz, 6H), 3.93 (s, 1H), 3.70 (d, J = 12.2 Hz, 1H), 3.62 (d, J = 12.2 Hz, 1H), 3.44-3.33 (m, 3H), 3.27 (d, J = 12.3 Hz, 2H), 2.54-2.33 (m, 3H), 2.15-1.93 (m, 2H), 1.86 (s, 1H), 1.72 (d, J = 14.3 Hz, 1H), 1.08 (d, J = 6.7 Hz, 3H). |
| 231 | $^1$H NMR (400 MHz, Methanol-d$_4$) δ 8.58 (d, J = 15.0 Hz, 2H), 7.75 (ddd, J = 7.3, 5.4, 1.7 Hz, 2H), 7.61 (t, J = 7.6 Hz, 2H), 7.51 (ddd, J = 7.6, 1.8, 0.8 Hz, 2H), 4.63-4.48 (m, 4H), 4.14 (d, J = 2.8 Hz, 7H), 3.78 (d, J = 12.5 Hz, 1H), 3.67 (d, J = 12.6 Hz, 1H), 3.49-3.33 (m, 3H), 2.99 (t, J = 12.5 Hz, 1H), 2.54-2.36 (m, 4H), 2.23-2.15 (m, 1H), 2.08-1.80 (m, 3H), 1.11 (d, J = 6.5 Hz, 3H). |
| 232 | $^1$H NMR (400 MHz, Methanol-d$_4$) δ 8.57 (d, J = 4.2 Hz, 2H), 7.75 (dt, J = 7.6, 1.8 Hz, 2H), 7.61 (t, J = 7.7 Hz, 2H), 7.51 (dd, J = 7.7, 1.7 Hz, 2H), 4.82 (d, J = 9.3 Hz, 2H), 4.63-4.48 (m, 2H), 4.49-4.37 (m, 2H), 4.15 (s, 6H), 3.74-3.64 (m, 5H), 3.44-3.32 (m, 4H), 2.55-2.35 (m, 4H), 2.08-1.93 (m, 2H). |
| 234 | $^1$H NMR (400 MHz, Methanol-d$_4$) δ 8.56 (s, 1H), 8.51 (s, 1H), 7.74 (ddd, J = 7.5, 5.5, 1.8 Hz, 2H), 7.60 (td, J = 7.7, 2.2 Hz, 2H), 7.55-7.47 (m, 2H), 4.76 (d, J = 10.4 Hz, 3H), 4.62-4.45 (m, 4H), 4.34 (t, J = 10.9 Hz, 2H), 4.14 (d, J = 4.1 Hz, 6H), 4.03 (s, 1H), 3.94 (s, 1H), 3.90-3.82 (m, 2H), 3.41-3.33 (m, 3H), 2.52-2.36 (m, 3H), 2.31 (s, 1H), 2.05-1.93 (m, 1H). |
| 235 | $^1$H NMR (400 MHz, Methanol-d$_4$) δ 8.56 (d, J = 5.3 Hz, 2H), 7.74 (dd, J = 7.7, 1.7 Hz, 2H), 7.61 (t, J = 7.7 Hz, 2H), 7.51 (ddd, J = 7.6, 1.7, 0.8 Hz, 2H), 4.62-4.48 (m, 4H), 4.15 (d, J = 1.4 Hz, 6H), 3.61 (dd, J = 10.0, 7.7 Hz, 1H), 3.44-3.33 (m, 3H), 3.26 (t, J = 8.1 Hz, 2H), 3.13 (d, J = 10.0 Hz, 1H), 2.68-2.45 (m, 3H), 2.50-2.34 (m, 2H), 2.25-2.07 (m, 1H), 2.07-1.90 (m, 3H). |
| 236 | $^1$H NMR (400 MHz, Methanol-d$_4$) δ 8.55 (d, J = 9.4 Hz, 2H), 7.74 (ddd, J = 7.7, 1.7, 0.9 Hz, 2H), 7.61 (td, J = 7.6, 1.3 Hz, 2H), 7.51 (dt, J = 7.6, 1.8 Hz, 2H), 4.62-4.48 (m, 2H), 4.48 (d, J = 1.7 Hz, 2H), 4.14 (d, J = 2.5 Hz, 7H), 4.15-3.91 (m, 2H), 3.80 (td, J = 7.9, 6.4 Hz, 1H), 3.44-3.33 (m, 4H), 2.54-2.33 (m, 4H), 2.21-1.87 (m, 5H), 1.61 (dq, J = 12.1, 7.9 Hz, 1H) |
| 237 | $^1$H NMR (400 MHz, Methanol-d$_4$) δ 8.55 (d, J = 10.7 Hz, 2H), 7.74 (dd, J = 7.7, 1.7 Hz, 2H), 7.61 (td, J = 7.7, 1.2 Hz, 2H), 7.51 (dt, J = 7.6, 1.7 Hz, 2H), 4.69 (d, J = 16.2 Hz, 1H), 4.62-4.48 (m, 3H), 4.15 (d, J = 2.2 Hz, 6H), 3.97 (dt, J = 10.1, 5.0 Hz, 1H), 3.86 (ddd, J = 10.6, 8.3, 4.6 Hz, 1H), 3.45-3.33 (m, 2H), 2.94-2.83 (m, 1H), 2.68 (s, 1H), 2.54-2.33 (m, 3H), 2.18-2.03 (m, 1H), 2.05-1.93 (m, 1H), 1.18-1.05 (m, 1H), 0.86 (s, 2H), 0.91-0.75 (m, 1H), 0.67 (dq, J = 8.8, 4.7 Hz, 1H), 0.45 (dq, J = 10.2, 4.7 Hz, 1H). |
| 261 | 8.57 (s, 1H), 8.52 (s, 1H), 7.72 (td, J = 7.7, 1.7 Hz, 2H), 7.58 (td, J = 7.7, 1.5 Hz, 2H), 7.48 (dt, J = 7.6, 1.6 Hz, 2H), 4.63 (d, J = 7.3 Hz, 2H), 4.52 (d, J = 3.9 Hz, 2H), 4.12 (d, J = 1.2 Hz, 7H), 3.99 (s, 1H), 3.79-3.53 (m, 3H), 3.35 (t, J = 5.9 Hz, 2H), 2.52-1.64 (m, 7H), 1.37 (dd, J = 6.7, 3.6 Hz, 2H). |
| 265 | δ 8.53 (d, J = 7.1 Hz, 2H), 7.72 (ddd, J = 7.7, 3.0, 1.7 Hz, 2H), 7.58 (t, J = 7.6 Hz, 2H), 7.48 (dd, J = 7.6, 1.7 Hz, 2H), 5.20 (d, J = 50.4 Hz, 1H), 4.79 (d, J = 2.5 Hz, 2H), 4.63-4.45 (m, 4H), 4.11 (d, J = 2.2 Hz, 7H), 3.35 (t, J = 5.9 Hz, 2H), 2.56-2.30 (m, 3H), 2.03-1.88 (m, 1H). |
| 270 | 1H NMR (400 MHz, Methanol-d4) δ 8.57 (s, 1H), 8.52 (s, 1H), 7.72 (td, J = 7.5, 1.7 Hz, 2H), 7.58 (td, J = 7.6, 1.5 Hz, 2H), 7.48 (dt, J = 7.6, 1.8 Hz, 2H), 5.08 (d, J = 45.1 Hz, 1H), 4.71-4.55 (m, 2H), 4.52 (d, J = 3.9 Hz, 2H), 4.12 (d, J = 0.8 Hz, 8H), 3.93 (s, 0H), 3.67 (s, 1H), 3.35 (t, J = 5.9 Hz, 2H), 2.54-2.32 (m, 3H), 2.21 (dd, J = 30.9, 17.5 Hz, 2H), 2.03-1.81 (m, 3H). |
| 274 | 1H NMR (400 MHz, Methanol-d4) δ 8.52 (d, J = 5.6 Hz, 2H), 7.71 (dt, J = 7.7, 1.5 Hz, 2H), 7.57 (td, J = 7.7, 0.6 Hz, 2H), 7.48 (dt, J = 7.6, 1.7 Hz, 2H), 4.52 (d, J = 3.9 Hz, 2H), 4.35 (s, 2H), 4.11 (d, J = 2.3 Hz, 7H), 3.67-3.56 (m, 1H), 3.43-3.33 (m, 2H), 2.59-2.26 (m, 7H), 2.05-1.88 (m, 1H), 1.39 (s, 3H). |
| 275 | 1H NMR (400 MHz, Methanol-d4) δ 8.52 (d, J = 4.3 Hz, 2H), 7.71 (dd, J = 7.7, 1.7 Hz, 2H), 7.57 (td, J = 7.7, 0.7 Hz, 2H), 7.48 (ddd, J = 7.6, 1.7, 0.7 Hz, 2H), 4.52 (d, J = 3.9 Hz, 2H), 4.44 (s, 2H), 4.37 (td, J = 6.6, 6.1, 1.0 Hz, 1H), 4.11 (d, J = 2.1 Hz, 8H), 3.41-3.32 (m, 2H), 2.69 (tt, J = 8.6, 4.4 Hz, 1H), 2.51-2.33 (m, 3H), 2.31-2.12 (m, 4H), 2.03-1.89 (m, 1H), 1.36 (dd, J = 6.7, 3.5 Hz, 1H). |
| 283 | 1H NMR (400 MHz, Methanol-d4) δ 8.53 (d, J = 2H), 7.71 (dt, J = 7.7, 1.5 Hz, 2H), 7.58 (t, J = 7.7 Hz, 2H), 7.48 (dd, J = 7.6, 1.7 Hz, 2H), 5.35 (t, J = 4.7 Hz, 1H), 5.21 (t, J = 4.7 Hz, 1H), 4.52 (d, J = 3.9 Hz, 2H), 4.39 (s, 2H), 4.27-4.17 (m, 1H), 4.12 (d, J = 2.3 Hz, 6H), 3.35 (d, J = 4.6 Hz, 2H), 2.79-2.60 (m, 4H), 2.51-2.34 (m, 3H), 2.02-1.86 (m, 1H). |
| 286 | 1H NMR (400 MHz, Methanol-d4) δ 8.54 (d, J = 3.0 Hz, 2H), 7.72 (dd, J = 7.7, 1.7 Hz, 2H), 7.58 (t, J = 7.7 Hz, 2H), 7.48 (dd, J = 7.6, 1.7 Hz, 2H), 4.53 (t, J = 1.9 Hz, 4H), 4.12 (s, 6H), 3.55-3.24 (m, 10H), 2.52-2.31 (m, 4H), 2.03-1.90 (m, 2H). 19F NMR (376 MHz, Methanol-d4) δ −77.66 |
| 287 | 1H NMR (400 MHz, Methanol-d4) δ 8.54 (d, J = 9.1 Hz, 2H), 7.73 (ddd, J = 9.0, 7.7, 1.7 Hz, 2H), 7.58 (t, J = 7.6 Hz, 2H), 7.48 (dd, J = 7.6, 1.7 Hz, 2H), 4.80 (d, J = 14.9 Hz, 1H), |

TABLE 2-continued

| No. | NMR |
|---|---|
| | 4.69 (d, J = 9.2 Hz, 1H), 4.60-4.46 (m, 2H), 4.12 (d, J = 3.3 Hz, 6H), 3.78 (s, 1H), 3.67 (dd, J = 10.7, 7.4 Hz, 1H), 3.59 (s, 1H), 3.46-3.31 (m, 3H), 3.27 (dd, J = 10.6, 1.7 Hz, 1H), 2.64-2.50 (m, 1H), 2.52-2.31 (m, 3H), 2.07-1.90 (m, 2H). 19F NMR (376 MHz, Methanol-d4) δ −77.67 |
| 288 | 1H NMR (400 MHz, Methanol-d4) δ 8.56-8.47 (m, 2H), 7.71 (ddd, J = 7.7, 3.2, 1.7 Hz, 2H), 7.58 (td, J = 7.7, 2.2 Hz, 2H), 7.48 (ddd, J = 7.6, 2.9, 1.7 Hz, 2H), 4.60-4.44 (m, 3H), 4.34 (s, 2H), 4.12 (d, J = 3.4 Hz, 6H), 3.98 (s, 2H), 3.42-3.31 (m, 2H), 2.82 (s, 2H), 2.52-2.31 (m, 3H), 2.03-1.90 (m, 2H). 19F NMR (376 MHz, Methanol-d4) δ −77.60 (d, J = 5.2 Hz). |
| 289 | 1H NMR (400 MHz, Methanol-d4) δ 8.53 (s, 1H), 8.47 (s, 1H), 7.70 (ddd, J = 8.1, 6.6, 1.7 Hz, 2H), 7.57 (td, J = 7.7, 2.6 Hz, 2H), 7.51-7.44 (m, 2H), 4.65 (s, 2H), 4.60-4.36 (m, 4H), 4.27-4.15 (m, 2H), 4.18-4.07 (m, 7H), 3.42-3.31 (m, 3H), 2.79-2.71 (m, 2H), 2.65-2.57 (m, 2H), 2.52-2.31 (m, 3H), 2.28-2.12 (m, 2H), 2.05-1.90 (m, 2H). 19F NMR (376 MHz, Methanol-d4) δ −77.70 |
| 290 | 1H NMR (400 MHz, Methanol-d4) δ 8.56 (d, J = 19.7 Hz, 2H), 7.73 (ddd, J = 8.4, 6.8, 1.7 Hz, 2H), 7.59 (td, J = 7.7, 1.9 Hz, 2H), 7.49 (dt, J = 7.6, 2.0 Hz, 2H), 4.63 (s, 2H), 4.60-4.46 (m, 4H), 4.13 (d, J = 3.4 Hz, 4H), 3.89 (dd, J = 12.6, 5.0 Hz, 2H), 3.42-3.31 (m, 2H), 2.52-2.33 (m, 4H), 2.14 (s, 2H), 2.03-1.90 (m, 2H), 0.09 (s, 2H). 19F NMR (376 MHz, Methanol-d4) δ −77.55. |
| 291 | 1H NMR (400 MHz, Methanol-d4) δ 8.53 (d, J = 6.2 Hz, 2H), 7.72 (dt, J = 7.7, 2.0 Hz, 2H), 7.58 (td, J = 7.7, 1.9 Hz, 2H), 7.48 (dt, J = 7.5, 1.4 Hz, 2H), 4.51 (dd, J = 14.8, 5.7 Hz, 4H), 4.11 (d, J = 8.2 Hz, 7H), 3.55 (d, J = 12.4 Hz, 1H), 3.45-3.31 (m, 4H), 2.52-2.33 (m, 3H), 2.30 (d, J = 18.8 Hz, 2H), 2.22 (d, J = 12.3 Hz, 2H), 2.11 (s, 2H), 2.03-1.88 (m, 2H), 1.78 (d, J = 13.5 Hz, 2H). 19F NMR (376 MHz, Methanol-d4) δ −77.66 |
| 292 | 1H NMR (400 MHz, Methanol-d4) δ 8.54 (d, J = 2.4 Hz, 2H), 7.72 (dt, J = 7.7, 1.8 Hz, 2H), 7.58 (t, J = 7.7 Hz, 2H), 7.48 (dd, J = 7.6, 1.7 Hz, 2H), 4.79 (d, J = 1.4 Hz, 2H), 4.64-4.46 (m, 2H), 4.12 (d, J = 0.7 Hz, 6H), 4.02 (s, 1H), 3.87 (s, 2H), 3.78 (s, 1H), 3.65 (s, 1H), 3.42-3.31 (m, 2H), 2.66 (dt, J = 14.3, 7.2 Hz, 1H), 2.52-2.31 (m, 4H), 2.05-1.90 (m, 1H). $^{19}$F NMR (376 MHz, Methanol-d$_4$) δ −77.66. |
| 293 | 1H NMR (400 MHz, Methanol-d4) δ 8.53 (d, J = 3.2 Hz, 2H), 7.72 (ddd, J = 7.6, 4.6, 1.7 Hz, 2H), 7.58 (td, J = 7.7, 1.8 Hz, 2H), 7.48 (dt, J = 7.6, 2.1 Hz, 2H), 4.53 (d, J = 3.9 Hz, 3H), 4.12 (d, J = 4.6 Hz, 7H), 3.67 (s, 2H), 3.45-3.31 (m, 5H), 2.52-2.31 (m, 3H), 2.09 (s, 3H), 2.03-1.89 (m, 2H). $^{19}$F NMR (376 MHz, Methanol-d4) δ −77.60 |
| 294 | 1H NMR (400 MHz, Methanol-d4) δ 8.53 (d, J = 1.2 Hz, 2H), 7.72 (dt, J = 7.7, 1.4 Hz, 2H), 7.58 (t, J = 7.6 Hz, 2H), 7.48 (dd, J = 7.7, 1.7 Hz, 2H), 4.79 (s, 2H), 4.60-4.46 (m, 2H), 4.12 (d, J = 1.0 Hz, 7H), 4.00 (s, 1H), 3.88 (s, 2H), 3.75 (s, 2H), 3.42-3.31 (m, 3H), 2.99 (s, 3H), 2.64 (dt, J = 14.3, 7.2 Hz, 1H), 2.52-2.31 (m, 3H), 2.03-1.90 (m, 2H). $^{19}$F NMR (376 MHz, Methanol-d4) δ −77.57 |
| 295 | 1H NMR (400 MHz, Methanol-d4) δ 8.53 (s, 2H), 7.72 (dd, J = 7.7, 1.7 Hz, 2H), 7.58 (t, J = 7.6 Hz, 2H), 7.48 (dd, J = 7.6, 1.7 Hz, 2H), 4.60-4.49 (m, 3H), 4.51-4.40 (m, 1H), 4.12 (d, J = 2.8 Hz, 7H), 4.12-4.00 (m, 1H), 3.97 (dq, J = 8.6, 4.7, 3.8 Hz, 1H), 3.82-3.68 (m, 1H), 3.42-3.31 (m, 3H), 2.56-2.31 (m, 2H), 2.30-2.16 (m, 1H), 2.03-1.90 (m, 1H), 1.47 (d, J = 6.6 Hz, 2H). 19F NMR (376 MHz, Methanol-d4) δ −77.55. |
| 296 | 1H NMR (400 MHz, Methanol-d4) δ 8.53 (d, J = 2.4 Hz, 2H), 7.75-7.68 (m, 2H), 7.58 (t, J = 7.6 Hz, 2H), 7.48 (ddd, J = 7.6, 2.0, 0.8 Hz, 2H), 4.60-4.43 (m, 4H), 4.12 (dd, J = 1.3, 0.6 Hz, 7H), 3.97-3.87 (m, 2H), 3.84-3.73 (m, 1H), 3.62 (dd, J = 9.0, 5.7 Hz, 1H), 3.42-3.15 (m, 4H), 2.71 (hept, J = 7.0 Hz, 1H), 2.52-2.31 (m, 3H), 2.23 (dtd, J = 12.9, 7.9, 5.0 Hz, 1H), 2.03-1.90 (m, 1H), 1.76 (dq, J = 14.0, 7.3 Hz, 1H). 19F NMR (376 MHz, Methanol-d4) δ −77.54. |
| 297 | 1H NMR (400 MHz, Methanol-d4) δ 8.55 (d, J = 14.9 Hz, 2H), 7.73 (ddd, J = 7.6, 5.8, 1.7 Hz, 2H), 7.58 (td, J = 7.7, 1.6 Hz, 2H), 7.49 (dt, J = 7.6, 2.0 Hz, 2H), 4.59 (d, J = 9.5 Hz, 2H), 4.55-4.46 (m, 3H), 4.29 (ddt, J = 12.0, 8.7, 2.7 Hz, 2H), 4.22-4.06 (m, 5H), 3.92-3.80 (m, 2H), 3.73 (q, J = 8.4 Hz, 2H), 3.42-3.31 (m, 4H), 2.99 (s, 3H), 2.52-2.27 (m, 3H), 2.03-1.90 (m, 1H). Multiplet Report 19F NMR (376 MHz, Methanol-d4) δ −77.54. |
| 298 | 1H NMR (400 MHz, Methanol-d4) δ 8.54 (d, J = 4.5 Hz, 2H), 7.72 (dt, J = 7.6, 2.0 Hz, 2H), 7.58 (t, J = 7.7 Hz, 2H), 7.49 (dd, J = 7.5, 1.7 Hz, 2H), 4.70-4.57 (m, 2H), 4.53 (d, J = 3.9 Hz, 2H), 4.38 (dd, J = 11.0, 6.4 Hz, 1H), 4.18-4.06 (m, 6H), 3.96 (d, J = 11.8 Hz, 1H), 3.90-3.73 (m, 1H), 3.52 (dd, J = 11.2, 6.1 Hz, 2H), 3.42-3.32 (m, 1H), 3.36-3.20 (m, 3H), 2.54-2.38 (m, 1H), 2.40-2.19 (m, 1H), 2.18-2.07 (m, 0H), 2.07-1.91 (m, 2H). 19F NMR (376 MHz, Methanol-d4) δ −77.31 (d, J = 7.5 Hz), −77.59 |
| 299 | 1H NMR (400 MHz, Methanol-d4) δ 8.53 (d, J = 2.4 Hz, 2H), 7.75-7.68 (m, 2H), 7.58 (t, J = 7.6 Hz, 2H), 7.48 (ddd, J = 7.6, 2.0, 0.8 Hz, 2H), 4.60-4.43 (m, 4H), 4.12 (dd, J = 1.3, 0.6 Hz, 7H), 3.97-3.87 (m, 2H), 3.84-3.73 (m, 1H), 3.62 (dd, J = 9.0, 5.7 Hz, 1H), 3.42-3.15 (m, 4H), 2.71 (hept, J = 7.0 Hz, 1H), 2.52-2.31 (m, 3H), 2.23 (dtd, J = 12.9, 7.9, 5.0 Hz, 1H), 2.03-1.90 (m, 1H), 1.76 (dq, J = 14.0, 7.3 Hz, 1H). 19F NMR (376 MHz, Methanol-d4) δ −77.54. |
| 300 | 1H (400 MHz, Methanol-d4) δ 8.55 (d, J = 14.9 Hz, 2H), 7.73 (ddd, J = 7.6, 5.8, 1.7 Hz, 2H), 7.58 (td, J = 7.7, 1.6 Hz, 2H), 7.49 (dt, J = 7.6, 2.0 Hz, 2H), 4.59 (d, J = 9.5 Hz, 2H), 4.55-4.46 (m, 2H), 4.29 (ddt, J = 12.0, 8.7, 2.7 Hz, 2H), 4.22-4.06 (m, 5H), 3.92-3.80 (m, 4H), 3.73 (q, J = 8.4 Hz, 3H), 3.42-3.31 (m, 2H), 2.99 (s, 3H), 2.52-2.27 (m, 2H), 2.03-1.90 (m, 1H). 19F NMR (376 MHz, Methanol-d4) δ −77.54. |
| 301 | 1H NMR (400 MHz, Methanol-d4) δ 8.51 (d, J = 16.6 Hz, 2H), 7.71 (ddd, J = 7.7, 4.2, 1.7 Hz, 2H), 7.58 (td, J = 7.7, 2.0 Hz, 2H), 7.48 (ddd, J = 7.6, 1.7, 0.7 Hz, 2H), 4.89 (d, J = 12.5 Hz, 2H), 4.76 (s, 2H), 4.65 (d, J = 12.5 Hz, 2H), 4.60-4.46 (m, 2H), 4.17-4.06 (m, 8H), 3.42-3.31 (m, 3H), 2.57-2.48 (m, 2H), 2.52-2.31 (m, 3H), 2.03-1.90 (m, 1H). 19F NMR (376 MHz, Methanol-d4) δ −77.56. |
| 302 | 1H NMR (400 MHz, Methanol-d4) δ 8.53 (d, J = 5.5 Hz, 2H), 7.72 (ddd, J = 7.6, 1.8, 0.8 Hz, 2H), 7.58 (td, J = 7.7, 1.2 Hz, 2H), 7.48 (dt, J = 7.6, 1.7 Hz, 2H), 4.59-4.45 (m, 4H), |

TABLE 2-continued

| No. | NMR |
|---|---|
| | 4.12 (d, J = 3.9 Hz, 6H), 4.01 (s, 2H), 3.65 (s, 2H), 3.34 (s, 2H), 2.49-2.35 (m, 2H), 1.29 (s, 0H). 19F NMR (376 MHz, Methanol-d4) δ −77.47. |
| 303 | 1H NMR (400 MHz, Methanol-d4) δ 8.54 (d, J = 2.0 Hz, 2H), 7.72 (dt, J = 7.7, 1.8 Hz, 2H), 7.58 (t, J = 7.6 Hz, 2H), 7.49 (dd, J = 7.6, 1.7 Hz, 2H), 4.60-4.46 (m, 4H), 4.13 (d, J = 1.4 Hz, 7H), 3.53 (dd, J = 12.9, 3.2 Hz, 1H), 3.46-3.31 (m, 4H), 2.90 (s, 3H), 2.58-2.45 (m, 1H), 2.42 (ddtt, J = 17.2, 13.8, 6.8, 3.2 Hz, 5H), 2.14-1.90 (m, 2H), 1.31 (d, J = 16.8 Hz, 1H). Multiplet Report 19F NMR (376 MHz, Methanol-d4) δ −77.60. |
| 304 | 1H NMR (400 MHz, Methanol-d4) δ 8.53 (d, J = 5.8 Hz, 2H), 7.72 (dd, J = 7.7, 1.7 Hz, 2H), 7.58 (td, J = 7.6, 1.5 Hz, 2H), 7.48 (dt, J = 7.7, 2.1 Hz, 2H), 4.53 (d, J = 3.9 Hz, 3H), 4.28-4.17 (m, 1H), 4.12 (d, J = 4.7 Hz, 6H), 4.02 (dd, J = 12.0, 5.6 Hz, 1H), 3.41-3.31 (m, 3H), 2.50-2.33 (m, 3H), 2.03-1.90 (m, 1H), 1.29 (s, 1H). 19F NMR (376 MHz, Methanol-d4) δ −77.58. |
| 305 | 1H NMR (400 MHz, Methanol-d4) δ 8.53 (d, J = 9.4 Hz, 2H), 7.81-7.67 (m, 2H), 7.58 (td, J = 7.7, 1.4 Hz, 2H), 7.48 (dt, J = 7.7, 2.0 Hz, 4H), 6.43 (t, J = 6.9 Hz, 2H), 4.60-4.45 (m, 2H), 4.31 (s, 3H), 4.12 (d, J = 6.7 Hz, 9H), 3.61 (s, 4H), 3.35 (q, J = 3.7, 3.3 Hz, 4H), 2.50-2.33 (m, 4H), 2.03-1.90 (m, 3H). Multiplet Report 19F NMR (376 MHz, Methanol-d4) δ −77.58. |
| 306 | 1H NMR (400 MHz, Methanol-d4) δ 8.53 (d, J = 5.0 Hz, 2H), 7.72 (dd, J = 7.7, 1.7 Hz, 2H), 7.58 (td, J = 7.7, 1.0 Hz, 2H), 7.48 (dt, J = 7.6, 1.7 Hz, 2H), 4.60-4.44 (m, 4H), 4.12 (d, J = 0.9 Hz, 8H), 3.44-3.31 (m, 4H), 3.28 (d, J = 2.5 Hz, 1H), 3.05 (ddd, J = 12.8, 11.0, 9.0 Hz, 1H), 2.73 (dtd, J = 13.5, 8.8, 2.5 Hz, 1H), 2.52-2.33 (m, 3H), 2.21-2.04 (m, 1H), 2.03-1.90 (m, 1H). 19F NMR (376 MHz, Methanol-d4) δ −77.57. |
| 307 | 1H NMR (400 MHz, Methanol-d4) δ 8.53 (s, 1H), 8.48 (s, 1H), 7.71 (ddd, J = 8.1, 6.5, 1.7 Hz, 2H), 7.58 (td, J = 7.7, 2.8 Hz, 2H), 7.48 (dt, J = 7.6, 1.5 Hz, 2H), 4.66 (s, 2H), 4.55 (d, J = 16.5 Hz, 1H), 4.55-4.41 (m, 3H), 4.31-4.22 (m, 4H), 4.11 (d, J = 8.0 Hz, 8H), 3.42-3.31 (m, 3H), 2.52-2.27 (m, 6H), 2.05-1.90 (m, 2H). 19F NMR (376 MHz, Methanol-d4) δ −77.81. |
| 308 | 1H NMR (400 MHz, Methanol-d4) δ 8.53 (s, 1H), 8.48 (s, 1H), 7.71 (ddd, J = 7.7, 6.1, 1.7 Hz, 2H), 7.58 (td, J = 7.7, 2.7 Hz, 2H), 7.48 (ddd, J = 7.6, 1.8, 1.0 Hz, 2H), 4.67 (s, 2H), 4.60-4.43 (m, 4H), 4.33 (d, J = 10.4 Hz, 1H), 4.11 (d, J = 7.8 Hz, 6H), 3.42-3.31 (m, 2H), 2.86 (d, J = 13.7 Hz, 1H), 2.77 (d, J = 14.0 Hz, 2H), 2.55 (d, J = 13.9 Hz, 2H), 2.52-2.32 (m, 3H), 2.05-1.90 (m, 2H). 19F NMR (376 MHz, Methanol-d4) δ −77.81, −86.45. |
| 309 | 1H NMR (400 MHz, Methanol-d4) δ 8.52 (d, J = 13.9 Hz, 2H), 7.71 (ddd, J = 7.7, 3.2, 1.8 Hz, 2H), 7.58 (td, J = 7.7, 1.3 Hz, 2H), 7.48 (dt, J = 7.6, 1.2 Hz, 2H), 4.79-4.61 (m, 2H), 4.60-4.46 (m, 2H), 4.35 (td, J = 10.0, 5.4 Hz, 1H), 4.12 (d, J = 3.9 Hz, 7H), 3.82-3.66 (m, 2H), 3.42 (s, 3H), 3.42-3.31 (m, 2H), 2.63-2.52 (m, 1H), 2.54-2.41 (m, 2H), 2.45-2.31 (m, 2H), 2.05-1.90 (m, 2H). Multiplet Report 19F NMR (376 MHz, Methanol-d4) δ −77.82. |
| 310 | 1H NMR (400 MHz, Methanol-d4) δ 8.52 (d, J = 13.9 Hz, 2H), 7.71 (ddd, J = 7.7, 3.2, 1.8 Hz, 2H), 7.58 (td, J = 7.7, 1.3 Hz, 2H), 7.48 (dt, J = 7.6, 1.2 Hz, 2H), 4.79-4.61 (m, 2H), 4.60-4.46 (m, 2H), 4.35 (td, J = 10.0, 5.4 Hz, 1H), 4.12 (d, J = 3.9 Hz, 7H), 3.82-3.66 (m, 2H), 3.42 (s, 3H), 3.42-3.31 (m, 2H), 2.63-2.52 (m, 1H), 2.54-2.41 (m, 2H), 2.45-2.31 (m, 2H), 2.05-1.90 (m, 2H). Multiplet Report 19F NMR (376 MHz, Methanol-d4) δ −77.82. |
| 311 | 1H NMR (400 MHz, Methanol-d4) δ 8.53 (d, J = 2.0 Hz, 2H), 7.72 (dd, J = 7.7, 1.7 Hz, 2H), 7.58 (t, J = 7.6 Hz, 2H), 7.48 (dd, J = 7.6, 1.8 Hz, 2H), 4.60-4.46 (m, 4H), 4.45-4.34 (m, 2H), 4.15-4.03 (m, 8H), 3.58 (d, J = 7.5 Hz, 2H), 3.42-3.31 (m, 2H), 3.12-2.99 (m, 2H), 2.50-2.33 (m, 2H), 2.05-1.90 (m, 2H). 19F NMR (376 MHz, Methanol-d4) δ −77.83 |
| 312 | 1H NMR (400 MHz, Methanol-d4) δ 8.54 (d, J = 5.1 Hz, 2H), 7.72 (dt, J = 7.7, 2.0 Hz, 2H), 7.58 (t, J = 7.6 Hz, 2H), 7.49 (dt, J = 7.6, 1.5 Hz, 2H), 4.71 (s, 2H), 4.53 (d, J = 3.9 Hz, 2H), 4.12 (d, J = 2.5 Hz, 7H), 3.73 (s, 2H), 3.44 (s, 1H), 3.35 (d, J = 6.2, 5.1 Hz, 2H), 2.78 (dd, J = 18.0, 10.2 Hz, 1H), 2.52-2.40 (m, 1H), 2.42 (s, 2H), 2.44-2.32 (m, 2H), 2.05-1.90 (m, 2H). 19F NMR (376 MHz, Methanol-d4) δ −77.71. |
| 313 | 1H NMR (400 MHz, Methanol-d4) δ 8.51 (d, J = 18.6 Hz, 2H), 7.71 (ddd, J = 7.7, 4.0, 1.7 Hz, 2H), 7.58 (td, J = 7.7, 1.7 Hz, 2H), 7.48 (dd, J = 7.6, 1.7 Hz, 2H), 4.84 (s, 6H), 4.60-4.46 (m, 2H), 4.12 (d, J = 2.0 Hz, 4H), 3.35 (dd, J = 6.2, 5.2 Hz, 1H), 2.52-2.31 (m, 2H), 2.05-1.90 (m, 1H). Multiplet Report 19F NMR (376 MHz, Methanol-d4) δ −77.85. |
| 314 | 1H NMR (400 MHz, Methanol-d4) δ 8.53 (d, J = 4.4 Hz, 2H), 7.72 (ddd, J = 7.7, 1.7, 0.7 Hz, 2H), 7.58 (t, J = 7.6 Hz, 2H), 7.48 (dd, J = 7.7, 1.7 Hz, 2H), 4.60-4.46 (m, 4H), 4.12 (d, J = 0.8 Hz, 2H), 3.78 (q, J = 6.6 Hz, 2H), 3.42-3.31 (m, 2H), 3.26 (dd, J = 10.2, 6.4 Hz, 4H), 2.52-2.28 (m, 4H), 2.09-1.90 (m, 4H), 1.87-1.76 (m, 2H), 1.28 (s, 1H). Multiplet Report 19F NMR (376 MHz, Methanol-d4) δ −77.68. |
| 315 | $^1$H NMR (400 MHz, Methanol-$d_4$) δ 8.55 (d, J = 7.1 Hz, 2H), 7.74 (dt, J = 7.8, 1.7 Hz, 2H), 7.60 (td, J = 7.6, 1.3 Hz, 2H), 7.51 (dt, J = 7.6, 1.7 Hz, 2H), 4.82 (d, J = 6.8 Hz, 1H), 4.54 (d, J = 4.0 Hz, 2H), 4.15 (s, 6H), 3.36 (s, 1H), 2.51-2.32 (m, 5H), 1.99 (d, J = 7.8 Hz, 1H), 1.66 (d, J = 6.8 Hz, 3H). |
| 316 | 1H NMR (400 MHz, Methanol-d4) δ 8.56 (d, J = 7.0 Hz, 2H), 7.74 (dt, J = 7.8, 1.7 Hz, 2H), 7.58 (td, J = 7.6, 1.3 Hz, 2H), 7.50 (dt, J = 7.6, 1.8 Hz, 2H), 4.82 (d, J = 6.8 Hz, 1H), 4.54 (d, J = 4.0 Hz, 2H), 4.16 (s, 6H), 3.37 (s, 1H), 2.51-2.31 (m, 5H), 2.01 (d, J = 7.7 Hz, 1H), 1.66 (d, J = 6.8 Hz, 3H). |
| 317 | $^1$H NMR (400 MHz, Methanol-$d_4$) δ 8.54 (s, 2H), 7.74 (dd, J = 7.7, 1.7 Hz, 2H), 7.60 (t, J = 7.6 Hz, 2H), 7.50 (dd, J = 7.6, 1.8 Hz, 2H), 4.15-4.06 (m, 6H), 3.50 (t, J = 1.7 Hz, 2H), 3.37 (s, 6H), 3.15 (t, J = 1.7 Hz, 2H), 2.44-2.36 (m, 4H), 2.03 (s, 4H), 1.35 (d, J = 6.6 Hz, 4H). |
| 318 | $^1$H NMR (400 MHz, Methanol-$d_4$) δ 8.54 (d, J = 14.3 Hz, 2H), 7.74 (ddd, J = 7.7, 3.4, 1.7 Hz, 2H), 7.60 (td, J = 7.7, 2.3 Hz, 2H), 7.50 (ddd, J = 7.6, 3.3, 1.7 Hz, 2H), 4.55 (d, J = 4.1 Hz, |

TABLE 2-continued

| No. | NMR |
|---|---|
| | 2H), 4.37 (s, 2H), 4.14 (d, J = 3.7 Hz, 6H), 3.37 (d, J = 6.7 Hz, 1H), 3.01 (s, 1H), 2.88 (d, J = 0.7 Hz, 1H), 2.72 (s, 1H), 2.46-2.42 (m, 2H), 1.99 (d, J = 7.9 Hz, 1H). |
| 319 | 1H NMR (400 MHz, Methanol-d4) δ 8.07 (s, 2H), 7.69 (dd, J = 7.7, 1.8 Hz, 2H), 7.52 (t, J = 7.6 Hz, 2H), 7.40 (dd, J = 7.6, 1.8 Hz, 2H), 4.39-4.26 (m, 4H), 4.19-3.99 (m, 2H), 3.38-3.26 (m, 4H), 3.15 (s, 6H), 3.03 (s, 6H), 2.52-2.29 (m, 6H), 2.07-1.92 (m, 2H). |
| 320 | 1H NMR (400 MHz, Methanol-d4) δ 8.07 (s, 2H), 7.64 (dd, J = 7.7, 1.8 Hz, 2H), 7.52 (t, J = 7.6 Hz, 2H), 7.42 (dd, J = 7.6, 1.8 Hz, 2H), 4.39-4.24 (m, 4H), 4.19-3.99 (m, 2H), 3.38-3.26 (m, 4H), 3.03 (s, 6H), 2.52-2.29 (m, 6H), 2.07-1.92 (m, 2H). |
| 321 | $^1$H NMR (400 MHz, Methanol-$d_4$) δ 8.55 (s, 2H), 7.74 (dd, J = 7.7, 1.8 Hz, 2H), 7.60 (t, J = 7.7 Hz, 2H), 7.51 (dd, J = 7.6, 1.7 Hz, 2H), 4.52 (d, J = 3.4 Hz, 4H), 4.15 (s, 7H), 3.77 (dd, J = 11.2, 6.8 Hz, 2H), 3.68-3.57 (m, 4H), 3.44 (dt, J = 10.1, 7.7 Hz, 3H), 2.98 (s, 6H), 2.61-2.52 (m, 2H), 2.27 (dd, J = 13.8, 6.7 Hz, 2H). |
| 322 | $^1$H NMR (400 MHz, Methanol-$d_4$) δ 8.58-8.50 (m, 2H), 7.75-7.69 (m, 2H), 7.61-7.55 (m, 2H), 7.48 (d, J = 7.4 Hz, 2H), 4.50 (d, J = 12.2 Hz, 2H), 4.20-4.09 (m, 7H), 3.96 (s, 2H), 3.89 (t, J = 5.2 Hz, 2H), 3.49-3.45 (m, 1H), 3.33 (d, J = 8.2 Hz, 3H), 3.12 (d, J = 1.7 Hz, 1H), 3.08 (s, 2H), 2.44-2.31 (m, 4H), 2.01-1.80 (m, 3H). |
| 323 | $^1$H NMR (400 MHz, Methanol-$d_4$) δ 8.55 (d, J = 12.2 Hz, 2H), 7.72 (ddd, J = 7.7, 6.0, 1.7 Hz, 2H), 7.62-7.55 (m, 2H), 7.52-7.46 (m, 2H), 4.76 (s, 2H), 4.52 (d, J = 3.9 Hz, 2H), 4.12 (s, 6H), 4.11-4.05 (m, 1H), 4.00-3.93 (m, 2H), 3.53 (d, J = 8.2 Hz, 1H), 3.37-3.32 (m, 2H), 3.09 (s, 3H), 2.50-2.33 (m, 4H), 1.96 (d, J = 7.8 Hz, 1H). |
| 324 | $^1$H NMR (400 MHz, Methanol-$d_4$) δ 8.56 (s, 1H), 7.75 (dd, J = 7.7, 1.7 Hz, 1H), 7.61 (t, J = 7.7 Hz, 1H), 7.51 (dd, J = 7.6, 1.7 Hz, 1H), 4.59-4.54 (m, 2H), 4.15 (s, 3H), 3.98 (t, J = 5.4 Hz, 1H), 3.47-3.36 (m, 2H), 2.13-2.08 (m, 1H), 2.00-1.95 (m, 1H), 1.33 (td, J = 8.1, 4.7 Hz, 1H), 0.77 (q, J = 4.1 Hz, 1H). |
| 325 | $^1$H NMR (400 MHz, Methanol-$d_4$) δ 8.57 (s, 1H), 8.49 (s, 1H), 7.73 (ddd, J = 12.7, 7.7, 1.7 Hz, 2H), 7.63-7.56 (m, 2H), 7.55-7.26 (m, 7H), 4.55 (d, J = 4.0 Hz, 2H), 4.30-4.19 (m, 2H), 4.15 (s, 4H), 4.05 (s, 2H), 3.50 (t, J = 1.7 Hz, 1H), 3.42-3.34 (m, 4H), 3.15 (t, J = 1.7 Hz, 1H), 2.51-2.39 (m, 3H), 2.32 (s, 3H), 2.04-1.90 (m, 2H), 1.87-1.72 (m, 2H). |
| 326 | $^1$H NMR (400 MHz, Methanol-$d_4$) δ 8.56 (s, 1H), 7.74 (dd, J = 7.7, 1.7 Hz, 1H), 7.61 (t, J = 7.7 Hz, 1H), 7.51 (dd, J = 7.6, 1.7 Hz, 1H), 4.54 (d, J = 4.2 Hz, 2H), 4.15 (s, 3H), 4.06 (dq, J = 8.0, 2.6 Hz, 1H), 3.36 (d, J = 5.1 Hz, 2H), 2.69-2.59 (m, 1H), 2.30-2.23 (m, 1H), 2.14-2.06 (m, 1H), 1.22 (d, J = 7.2 Hz, 3H). |
| 327 | $^1$H NMR (400 MHz, Methanol-$d_4$) δ 8.60 (s, 1H), 7.76 (dd, J = 7.7, 1.7 Hz, 1H), 7.62 (t, J = 7.7 Hz, 1H), 7.52 (dd, J = 7.6, 1.8 Hz, 1H), 4.70 (s, 2H), 4.26 (q, J = 6.4 Hz, 1H), 4.15 (s, 3H), 3.45 (s, 2H), 3.15 (s, 3H), 2.52-2.33 (m, 3H), 1.96 (s, 1H). |
| 328 | 1H NMR (400 MHz, Methanol-d4) δ 8.59 (s, 1H), 7.76 (dd, J = 7.7, 1.7 Hz, 1H), 7.65 (t, J = 7.7 Hz, 1H), 7.51 (dd, J = 7.6, 1.8 Hz, 1H), 4.70 (s, 2H), 4.26 (q, J = 6.4 Hz, 1H), 4.12 (s, 3H), 3.45 (s, 2H), 3.15 (s, 3H), 2.52-2.33 (m, 3H), 2.01-1.97 (m, 4H), 1.96 (s, 1H). |
| 329 | $^1$H NMR (400 MHz, Methanol-$d_4$) δ 8.60 (s, 1H), 8.56 (s, 1H), 7.76 (td, J = 7.8, 1.7 Hz, 2H), 7.61 (td, J = 7.7, 1.4 Hz, 2H), 7.51 (dt, J = 7.6, 1.6 Hz, 2H), 4.84-4.70 (m, 2H), 4.55 (d, J = 4.1 Hz, 2H), 4.31-4.23 (m, 1H), 4.15 (d, J = 4.5 Hz, 7H), 3.58-3.35 (m, 6H), 2.52-2.36 (m, 6H), 2.04-1.91 (m, 2H), 1.24 (s, 1H), 0.82 (d, J = 7.7 Hz, 2H), 0.52 (s, 2H). |
| 330 | HPLC retention time = 4.89 min. |
| 331 | 1H NMR (400 MHz, Methanol-d4) δ 8.56 (s, 1H), 7.75 (dd, J = 7.7, 1.7 Hz, 1H), 7.63 (t, J = 7.7 Hz, 1H), 7.51 (dd, J = 7.6, 1.7 Hz, 1H), 4.57-4.55 (m, 2H), 4.15 (s, 3H), 3.98 (t, J = 5.4 Hz, 1H), 3.47-3.36 (m, 2H), 2.13-1.95 (m, 2H), 1.35 (td, J = 8.1, 4.7 Hz, 1H), 0.77 (q, J = 4.1 Hz, 1H). |
| 332 | $^1$H NMR (400 MHz, Methanol-$d_4$) δ 8.61 (s, 1H), 8.56 (s, 1H), 7.76 (t, J = 7.3 Hz, 2H), 7.61 (t, J = 7.6 Hz, 2H), 7.52 (d, J = 7.6 Hz, 2H), 4.53 (s, 2H), 4.16 (d, J = 6.1 Hz, 7H), 4.05-3.71 (m, 7H), 3.50 (s, 1H), 3.15 (s, 1H), 2.45 (s, 4H), 1.99 (d, J = 17.9 Hz, 2H), 1.45 (s, 5H). |
| 333 | $^1$H NMR (400 MHz, Methanol-$d_4$) δ 8.56 (d, J = 7.2 Hz, 2H), 7.75 (d, J = 7.5 Hz, 2H), 7.61 (t, J = 7.6 Hz, 2H), 7.51 (d, J = 8.0 Hz, 2H), 4.80 (t, J = 6.7 Hz, 2H), 4.65 (d, J = 6.6 Hz, 2H), 4.56 (d, J = 4.0 Hz, 2H), 4.49 (d, J = 4.2 Hz, 2H), 4.11-4.00 (m, 2H), 3.83 (s, 2H), 3.50 (d, J = 3.4 Hz, 3H), 3.17-3.06 (m, 3H), 2.85 (d, J = 7.2 Hz, 2H), 2.62-2.52 (m, 2H), 2.47-2.38 (m, 3H), 2.19-2.07 (m, 2H), 2.06-1.96 (m, 2H). |
| 334 | $^1$H NMR (400 MHz, Methanol-$d_4$) δ 8.56 (s, 2H), 7.75 (d, J = 7.7 Hz, 2H), 7.61 (t, J = 7.7 Hz, 2H), 7.51 (d, J = 7.6 Hz, 2H), 4.61 (s, 2H), 4.51 (s, 2H), 4.15 (s, 7H), 4.00 (dd, J = 10.8, 5.1 Hz, 2H), 3.81 (d, J = 5.1 Hz, 2H), 3.52-3.37 (m, 3H), 3.17 (t, J = 10.2 Hz, 2H), 2.45 (t, J = 9.6 Hz, 3H), 2.24 (d, J = 13.2 Hz, 1H), 2.02-1.96 (m, 1H). |
| 335 | $^1$H NMR (400 MHz, Methanol-$d_4$) δ 8.56 (s, 2H), 7.75 (d, J = 7.7 Hz, 2H), 7.61 (t, J = 7.7 Hz, 2H), 7.51 (d, J = 7.6 Hz, 2H), 4.61 (s, 2H), 4.51 (s, 2H), 4.15 (s, 7H), 4.00 (dd, J = 10.8, 5.1 Hz, 2H), 3.81 (d, J = 5.1 Hz, 2H), 3.52-3.37 (m, 3H), 3.17 (t, J = 10.2 Hz, 2H), 2.45 (t, J = 9.6 Hz, 3H), 2.24 (d, J = 13.2 Hz, 1H), 2.02-1.96 (m, 1H). |
| 336 | $^1$H NMR (400 MHz, Methanol-$d_4$) δ 8.56 (s, 2H), 7.75 (d, J = 7.7 Hz, 2H), 7.61 (t, J = 7.7 Hz, 2H), 7.51 (d, J = 7.6 Hz, 2H), 4.61 (s, 2H), 4.51 (s, 2H), 4.15 (s, 7H), 4.00 (dd, J = 10.8, 5.1 Hz, 2H), 3.81 (d, J = 5.1 Hz, 2H), 3.52-3.37 (m, 3H), 3.17 (t, J = 10.2 Hz, 2H), 2.45 (t, J = 9.6 Hz, 3H), 2.24 (d, J = 13.2 Hz, 1H), 2.02-1.96 (m, 1H). |
| 337 | $^1$H NMR (400 MHz, Methanol-$d_4$) δ 8.55 (d, J = 6.2 Hz, 2H), 7.74 (d, J = 7.9 Hz, 2H), 7.61 (t, J = 7.0 Hz, 3H), 7.51 (d, J = 7.6 Hz, 2H), 7.32 (s, 1H), 4.64 (s, 2H), 4.53 (s, 2H), 4.47 (s, 2H), 4.14 (d, J = 7.7 Hz, 6H), 3.50 (s, 1H), 3.15 (s, 1H), 2.44 (d, J = 6.7 Hz, 3H), 2.18 (s, 1H), 2.08-1.96 (m, 2H). |
| 338 | 1H NMR (400 MHz, Methanol-d4) δ 8.55 (d, J = 6.2 Hz, 2H), 7.74 (d, J = 7.9 Hz, 2H), 7.61 (t, J = 7.0 Hz, 4H), 7.49 (d, J = 7.4 Hz, 2H), 7.32 (s, 1H), 4.60 (s, 2H), 4.53 (s, 2H), 4.47 (s, 2H), 4.13 (d, J = 7.4 Hz, 6H), 3.50 (s, 1H), 3.15 (s, 1H), 2.44 (d, J = 6.7 Hz, 3H), 2.18 (s, 1H), 2.08-1.96 (m, 2H). |
| 339 | $^1$H NMR (400 MHz, Methanol-$d_4$) δ 8.56 (s, 2H), 7.75 (d, J = 7.7 Hz, 2H), 7.61 (t, J = 7.7 Hz, 2H), 7.51 (d, J = 7.6 Hz, 2H), 4.61 (s, 2H), 4.51 (s, 2H), 4.15 (s, 7H), 4.00 (dd, J = 10.8, |

TABLE 2-continued

| No. | NMR |
|---|---|
| | 5.1 Hz, 2H), 3.81 (d, J = 5.1 Hz, 2H), 3.52-3.37 (m, 3H), 3.17 (t, J = 10.2 Hz, 2H), 2.45 (t, J = 9.6 Hz, 3H), 2.24 (d, J = 13.2 Hz, 1H), 2.02-1.96 (m, 1H). |
| 340 | 1H NMR (400 MHz, Methanol-d4) δ 8.58-8.50 (m, 2H), 7.75-7.69 (m, 2H), 7.61-7.55 (m, 2H), 7.48 (d, J = 7.4 Hz, 2H), 4.50 (d, J = 12.2 Hz, 2H), 4.20-4.09 (m, 7H), 3.96 (s, 2H), 3.89 (t, J = 5.2 Hz, 2H), 3.49-3.45 (m, 1H), 3.35-3.21 (m, 3H), 3.18 (d, J = 1.7 Hz, 1H), 3.16 (s, 2H), 2.44-2.23 (m, 4H). |
| 341 | 1H NMR (400 MHz, Methanol-d4) δ 8.55 (d, J = 2.9 Hz, 2H), 7.74 (dt, J = 7.7, 1.6 Hz, 2H), 7.60 (t, J = 7.7 Hz, 2H), 7.51 (dd, J = 7.4, 1.7 Hz, 2H), 4.52 (dd, J = 16.1, 3.8 Hz, 3H), 4.38 (s, 2H), 4.17-4.07 (m, 7H), 3.54-3.46 (m, 1H), 3.19-3.10 (m, 1H), 2.60 (dd, J = 13.8, 6.9 Hz, 2H), 2.56-2.49 (m, 2H) 2.46-2.38 (m, 4H), 2.17 (s, 2H), 2.04-1.91 (m, 2H). |
| 342 | $^1$H NMR (400 MHz, Methanol-$d_4$) δ 8.55 (d, J = 2.9 Hz, 2H), 7.74 (dt, J = 7.7, 1.6 Hz, 2H), 7.60 (t, J = 7.7 Hz, 2H), 7.51 (dd, J = 7.4, 1.7 Hz, 2H), 4.52 (dd, J = 16.1, 3.8 Hz, 3H), 4.38 (s, 2H), 4.17-4.07 (m, 7H), 3.54-3.46 (m, 1H), 3.19-3.10 (m, 1H), 2.60 (dd, J = 13.8, 6.9 Hz, 2H), 2.46-2.38 (m, 4H), 2.17 (s, 2H), 2.04-1.91 (m, 2H). |
| 343 | $^1$H NMR (400 MHz, Methanol-$d_4$) δ 8.55 (d, J = 2.9 Hz, 2H), 7.74 (dt, J = 7.7, 1.6 Hz, 2H), 7.60 (t, J = 7.7 Hz, 2H), 7.51 (dd, J = 7.4, 1.7 Hz, 2H), 4.52 (dd, J = 16.1, 3.8 Hz, 3H), 4.38 (s, 2H), 4.17-4.07 (m, 7H), 3.54-3.46 (m, 1H), 3.19-3.10 (m, 1H), 2.60 (dd, J = 13.8, 6.9 Hz, 2H), 2.46-2.38 (m, 4H), 2.17 (s, 2H), 2.04-1.91 (m, 2H). |
| 344 | 1H NMR (400 MHz, Methanol-d4) δ 8.51 (d, J = 5.9 Hz, 2H), 7.71 (dd, J = 7.7, 1.7 Hz, 2H), 7.62-7.54 (m, 2H), 7.48 (dt, J = 7.5, 1.7 Hz, 2H), 4.54-4.45 (m, 4H), 4.12 (d, J = 2.0 Hz, 7H), 3.93-3.34 (m, 5H), 2.48-2.39 (m, 5H), 2.00-1.92 (m, 2H). |
| 345 | 1H NMR (400 MHz, Methanol-d4) δ 8.51 (d, J = 5.9 Hz, 2H), 7.71 (dd, J = 7.7, 1.7 Hz, 2H), 7.62-7.54 (m, 2H), 7.48 (dt, J = 7.5, 1.7 Hz, 2H), 4.54-4.45 (m, 4H), 4.12 (d, J = 2.0 Hz, 7H), 3.93-3.34 (m, 5H), 2.48-2.39 (m, 5H), 2.00-1.92 (m, 2H). |
| 346 | 1H NMR (400 MHz, Methanol-d4) δ 8.51 (d, J = 5.9 Hz, 2H), 7.71 (dd, J = 7.7, 1.7 Hz, 2H), 7.62-7.54 (m, 2H), 7.48 (dt, J = 7.5, 1.7 Hz, 2H), 4.54-4.45 (m, 4H), 4.06 (d, J = 2.0 Hz, 7H), 3.92-3.34 (m, 5H), 2.48-2.39 (m, 5H), 2.00-1.92 (m, 2H). |
| 347 | 1H NMR (400 MHz, Methanol-d4) δ 8.51 (d, J = 5.9 Hz, 2H), 7.71 (dd, J = 7.7, 1.7 Hz, 2H), 7.62-7.54 (m, 2H), 7.48 (dt, J = 7.5, 1.7 Hz, 2H), 4.54-4.45 (m, 4H), 4.06 (d, J = 2.0 Hz, 7H), 3.92-3.34 (m, 5H), 2.48-2.39 (m, 5H), 2.00-1.92 (m, 2H). |
| 348 | HPLC retention time = 3.81 min. |
| 349 | $^1$H NMR (400 MHz, Methanol-$d_4$) δ 8.74 (s, 1H), 8.54 (d, J = 12.9 Hz, 2H), 7.82 (d, J = 8.0 Hz, 1H), 7.74 (d, J = 7.9 Hz, 2H), 7.60 (t, J = 7.7 Hz, 2H), 7.51 (d, J = 7.5 Hz, 2H), 7.38 (d, J = 8.3 Hz, 2H), 4.52 (s, 4H), 4.33 (s, 2H), 4.15 (d, J = 5.4 Hz, 7H), 3.50 (s, 1H), 3.44-3.35 (m, 2H), 3.15 (s, 1H), 2.43 (d, J = 6.9 Hz, 2H), 2.06-1.94 (m, 2H). |
| 350 | $^1$H NMR (400 MHz, Methanol-$d_4$) δ 8.54 (d, J = 4.6 Hz, 2H), 7.74 (d, J = 7.5 Hz, 2H), 7.60 (t, J = 7.6 Hz, 2H), 7.53-7.48 (m, 2H), 7.45 (d, J = 4.4 Hz, 3H), 7.37 (s, 2H), 4.72 (d, J = 16.1 Hz, 2H), 4.50-4.33 (m, 5H), 4.17-3.98 (m, 7H), 3.50 (s, 1H), 3.16 (s, 1H), 2.42 (d, J = 5.5 Hz, 3H), 2.05 (d, J = 8.7 Hz, 3H). |
| 351 | $^1$H NMR (400 MHz, Methanol-$d_4$) δ 8.54 (d, J = 19.5 Hz, 2H), 7.73 (d, J = 7.2 Hz, 2H), 7.61 (t, J = 8.0 Hz, 2H), 7.51 (d, J = 7.8 Hz, 2H), 4.75 (s, 2H), 4.54 (s, 2H), 4.41-4.29 (m, 2H), 4.14 (d, J = 3.5 Hz, 6H), 3.75 (s, 3H), 3.50 (s, 1H), 3.15 (s, 1H), 2.43 (d, J = 20.9 Hz, 7H), 2.01 (d, J = 23.5 Hz, 3H), 1.35-1.20 (m, 2H). |
| 352 | $^1$H NMR (400 MHz, Methanol-$d_4$) δ 8.57 (s, 2H), 7.78 (d, J = 29.3 Hz, 4H), 7.57 (d, J = 35.0 Hz, 4H), 4.55 (s, 3H), 4.18 (d, J = 19.1 Hz, 8H), 3.50 (s, 1H), 3.15 (s, 1H), 2.44 (s, 4H), 2.06-1.90 (m, 4H), 1.51 (d, J = 6.6 Hz, 2H). |
| 353 | $^1$H NMR (400 MHz, Methanol-$d_4$) δ 8.54 (s, 2H), 7.74 (d, J = 7.6 Hz, 2H), 7.60 (t, J = 7.7 Hz, 2H), 7.51 (d, J = 7.7 Hz, 2H), 4.50-4.39 (m, 5H), 4.15 (d, J = 3.8 Hz, 7H), 3.90-3.85 (m, 1H), 3.50 (s, 1H), 3.26 (d, J = 16.0 Hz, 2H), 3.16 (s, 1H), 2.42 (d, J = 5.4 Hz, 3H), 2.27 (s, 2H), 1.96 (d, J = 25.8 Hz, 3H). |
| 354 | $^1$H NMR (400 MHz, Methanol-$d_4$) δ 8.54 (s, 2H), 7.74 (d, J = 7.6 Hz, 2H), 7.60 (t, J = 7.7 Hz, 2H), 7.51 (d, J = 7.7 Hz, 2H), 4.50-4.39 (m, 5H), 4.15 (d, J = 3.8 Hz, 7H), 3.90-3.85 (m, 1H), 3.50 (s, 1H), 3.26 (d, J = 16.0 Hz, 2H), 3.19 (s, 1H), 2.42 (d, J = 5.4 Hz, 3H), 2.27 (s, 2H), 1.96 (d, J = 25.8 Hz, 3H). |
| 355 | $^1$H NMR (400 MHz, Methanol-$d_4$) δ 8.54 (s, 2H), 7.74 (d, J = 7.6 Hz, 2H), 7.61 (t, J = 7.7 Hz, 2H), 7.51 (d, J = 7.7 Hz, 2H), 4.50-4.39 (m, 5H), 4.15 (d, J = 3.8 Hz, 7H), 3.90-3.85 (m, 1H), 3.50 (s, 1H), 3.26 (d, J = 16.0 Hz, 2H), 3.17 (s, 1H), 2.42 (d, J = 5.4 Hz, 3H), 2.27 (s, 2H), 1.96 (d, J = 25.8 Hz, 3H). |
| 356 | $^1$H NMR (400 MHz, Methanol-$d_4$) δ 8.54 (s, 2H), 7.74 (d, J = 7.6 Hz, 2H), 7.60 (t, J = 7.7 Hz, 2H), 7.51 (d, J = 7.7 Hz, 2H), 4.50-4.39 (m, 5H), 4.15 (d, J = 3.8 Hz, 7H), 3.90-3.83 (m, 1H), 3.49 (s, 1H), 3.26 (d, J = 16.0 Hz, 2H), 3.16 (s, 1H), 2.42 (d, J = 5.4 Hz, 3H), 2.27 (s, 2H), 1.96 (d, J = 25.8 Hz, 3H). |
| 357 | $^1$H NMR (400 MHz, Methanol-$d_4$) δ 8.55 (d, J = 6.9 Hz, 2H), 7.74 (d, J = 7.6 Hz, 2H), 7.61 (t, J = 7.7 Hz, 2H), 7.51 (d, J = 7.7 Hz, 2H), 4.52 (d, J = 3.6 Hz, 2H), 4.40 (s, 2H), 4.15 (d, J = 2.1 Hz, 7H), 3.97 (d, J = 11.0 Hz, 1H), 3.50 (s, 1H), 3.16 (s, 1H), 3.00 (s, 3H), 2.92 (s, 2H), 2.80 (s, 2H), 2.43 (d, J = 6.9 Hz, 2H). |
| 358 | $^1$H NMR (400 MHz, Methanol-$d_4$) δ 8.55 (d, J = 6.9 Hz, 2H), 7.74 (d, J = 7.6 Hz, 2H), 7.61 (t, J = 7.7 Hz, 2H), 7.51 (d, J = 7.7 Hz, 2H), 4.52 (d, J = 3.6 Hz, 2H), 4.40 (s, 2H), 4.15 (d, J = 2.1 Hz, 7H), 3.97 (d, J = 11.0 Hz, 1H), 3.50 (s, 1H), 3.16 (s, 1H), 3.00 (s, 3H), 2.92 (s, 2H), 2.80 (s, 2H), 2.43 (d, J = 6.9 Hz, 2H). |
| 359 | $^1$H NMR (400 MHz, Methanol-$d_4$) δ 8.55 (s, 2H), 7.74 (dd, J = 7.7, 1.7 Hz, 2H), 7.60 (t, J = 7.6 Hz, 2H), 7.53-7.48 (m, 2H), 4.49 (d, J = 1.5 Hz, 3H), 4.15-4.07 (m, 8H), 3.94-3.88 (m, 2H), 3.84-3.75 (m, 2H), 3.50 (t, J = 1.7 Hz, 1H), 3.15 (d, J = 1.7 Hz, 1H), 2.46-2.38 (m, 3H), 2.17 (s, 2H), 2.04-1.95 (m, 2H). |
| 360 | $^1$H NMR (400 MHz, Methanol-$d_4$) δ 8.55 (s, 2H), 7.74 (dd, J = 7.7, 1.7 Hz, 2H), 7.60 (t, J = 7.6 Hz, 2H), 7.53-7.48 (m, 2H), 4.49 (d, J = 1.5 Hz, 3H), 4.15-4.07 (m, 8H), |

TABLE 2-continued

| No. | NMR |
|---|---|
| | 3.94-3.88 (m, 2H), 3.84-3.75 (m, 2H), 3.50 (t, J = 1.7 Hz, 1H), 3.15 (d, J = 1.7 Hz, 1H), 2.46-2.38 (m, 3H), 2.17 (s, 2H), 2.04-1.95 (m, 2H). |
| 361 | $^1$H NMR (400 MHz, Methanol-$d_4$) δ 8.55 (s, 2H), 7.74 (d, J = 8.0 Hz, 2H), 7.61 (t, J = 7.7 Hz, 2H), 7.51 (d, J = 7.4 Hz, 2H), 4.45 (s, 2H), 4.39 (s, 2H), 4.14 (s, 7H), 3.51 (s, 1H), 3.15 (s, 1H), 2.69 (s, 2H), 2.47 (d, J = 31.2 Hz, 5H), 2.05 (d, J = 8.8 Hz, 3H), 1.98 (s, 3H). |
| 362 | $^1$H NMR (400 MHz, Methanol-$d_4$) δ 8.55 (s, 2H), 7.74 (d, J = 8.0 Hz, 2H), 7.61 (t, J = 7.7 Hz, 2H), 7.51 (d, J = 7.4 Hz, 2H), 4.45 (s, 2H), 4.39 (s, 2H), 4.14 (s, 7H), 3.51 (s, 1H), 3.15 (s, 1H), 2.69 (s, 2H), 2.47 (d, J = 31.2 Hz, 5H), 2.05 (d, J = 8.8 Hz, 3H), 1.98 (s, 3H). |
| 363 | $^1$H NMR (400 MHz, Methanol-$d_4$) δ 8.54 (d, J = 4.2 Hz, 2H), 7.74 (d, J = 7.6 Hz, 2H), 7.61 (t, J = 7.7 Hz, 2H), 7.51 (d, J = 7.8 Hz, 2H), 4.48 (s, 2H), 4.36 (s, 2H), 4.29 (s, 2H), 4.24 (s, 2H), 4.14 (s, 6H), 4.04-3.94 (m, 2H), 3.16 (s, 1H), 2.81 (t, J = 10.0 Hz, 2H), 2.64 (t, J = 10.8 Hz, 2H), 2.43 (d, J = 6.7 Hz, 2H), 2.39 (s, 1H), 2.05 (d, J = 8.5 Hz, 1H), 1.97 (s, 1H). |
| 364 | $^1$H NMR (400 MHz, Methanol-$d_4$) δ 8.52 (d, J = 9.1 Hz, 2H), 7.71 (dt, J = 7.6, 2.2 Hz, 2H), 7.61-7.54 (m, 2H), 7.50-7.45 (m, 2H), 4.52 (d, J = 3.9 Hz, 2H), 4.36 (s, 2H), 4.12 (d, J = 3.4 Hz, 7H), 3.80 (t, J = 7.0 Hz, 1H), 3.59 (d, J = 8.1 Hz, 1H), 3.48 (d, J = 7.0 Hz, 1H), 3.38-3.32 (m, 2H), 2.84-2.75 (m, 2H), 2.41 (dd, J = 7.8, 4.4 Hz, 2H), 2.19-2.11 (m, 2H), 2.00 (s, 4H). |
| 365 | $^1$H NMR (400 MHz, Methanol-$d_4$) δ 8.52 (d, J = 9.1 Hz, 2H), 7.71 (dt, J = 7.6, 2.2 Hz, 2H), 7.63-7.54 (m, 2H), 7.50-7.45 (m, 2H), 4.52 (d, J = 3.9 Hz, 2H), 4.36 (s, 2H), 4.12 (d, J = 3.4 Hz, 7H), 3.80 (t, J = 7.0 Hz, 1H), 3.59 (d, J = 8.1 Hz, 1H), 3.48 (d, J = 7.0 Hz, 1H), 3.38-3.32 (m, 2H), 2.84-2.75 (m, 2H), 2.42 (dd, J = 7.8, 4.4 Hz, 2H), 2.19-2.10 (m, 2H), 2.00 (s, 4H). |
| 366 | $^1$H NMR (400 MHz, Methanol-$d_4$) δ 8.52 (d, J = 7.6 Hz, 2H), 7.71 (dt, J = 7.7, 1.9 Hz, 2H), 7.61-7.54 (m, 2H), 7.51-7.45 (m, 2H), 4.52 (d, J = 3.9 Hz, 2H), 4.33 (s, 2H), 4.12 (d, J = 3.2 Hz, 7H), 3.92-3.84 (m, 1H), 3.34 (d, J = 6.7 Hz, 2H), 2.52-2.28 (m, 9H), 1.99-1.93 (m, 1H), 1.16 (s, 6H). |
| 367 | $^1$H NMR (400 MHz, Methanol-$d_4$) δ 8.53 (s, 1H), 8.47 (s, 1H), 7.71 (ddd, J = 7.3, 5.4, 1.7 Hz, 2H), 7.57 (td, J = 7.7, 2.2 Hz, 2H), 7.48 (ddd, J = 7.6, 1.8, 0.9 Hz, 2H), 4.70 (s, 2H), 4.58 (s, 3H), 4.51 (d, J = 8.5 Hz, 6H), 4.11 (d, J = 6.2 Hz, 6H), 3.34 (d, J = 4.6 Hz, 2H), 2.48-2.31 (m, 4H), 2.01-1.90 (m, 2H), 1.28 (s, 1H), 1.23 (t, J = 7.1 Hz, 1H), 0.93-0.82 (m, 2H). |
| 368 | $^1$H NMR (400 MHz, Methanol-$d_4$) δ 8.51 (d, J = 20.3 Hz, 2H), 7.71 (ddd, J = 7.5, 5.7, 1.7 Hz, 2H), 7.57 (td, J = 7.7, 2.0 Hz, 2H), 7.48 (dd, J = 7.6, 1.7 Hz, 2H), 4.74 (s, 2H), 4.52 (d, J = 3.8 Hz, 3H), 4.38 (s, 1H), 4.11 (d, J = 3.8 Hz, 7H), 3.82-3.64 (m, 3H), 3.37-3.32 (m, 2H), 2.87-2.69 (m, 3H), 2.45-2.32 (m, 3H), 1.96 (d, J = 8.1 Hz, 1H). |
| 369 | $^1$H NMR (400 MHz, Methanol-$d_4$) δ 8.50 (d, J = 19.8 Hz, 2H), 7.73-7.68 (m, 2H), 7.57 (td, J = 7.6, 2.2 Hz, 2H), 7.47 (d, J = 7.6 Hz, 2H), 4.73 (s, 2H), 4.48 (s, 2H), 4.11 (d, J = 2.8 Hz, 7H), 2.40 (d, J = 6.6 Hz, 3H), 2.00 (s, 4H), 1.28 (s, 4H), 0.90 (d, J = 6.6 Hz, 4H). |
| 370 | $^1$H NMR (400 MHz, Methanol-$d_4$) δ 8.53 (s, 1H), 8.47 (s, 1H), 7.73-7.65 (m, 3H), 7.63-7.54 (m, 4H), 7.50-7.45 (m, 2H), 6.63 (d, J = 9.1 Hz, 1H), 6.47 (t, J = 6.6 Hz, 1H), 4.49 (s, 4H), 4.46-4.42 (m, 2H), 4.11 (d, J = 5.0 Hz, 8H), 3.62-3.57 (m, 2H), 2.43-2.36 (m, 3H), 1.98-1.90 (m, 2H). |
| 371 | $^1$H NMR (400 MHz, Methanol-$d_4$) δ 8.50 (d, J = 19.0 Hz, 2H), 7.72-7.68 (m, 2H), 7.60-7.54 (m, 2H), 7.47 (d, J = 8.4 Hz, 2H), 4.48 (s, 2H), 4.11 (d, J = 3.3 Hz, 7H), 3.47 (d, J = 1.9 Hz, 1H), 3.39-3.31 (m, 4H), 3.12 (s, 1H), 2.53 (d, J = 8.1 Hz, 3H), 2.41 (t, J = 6.7 Hz, 5H), 1.96 (d, J = 17.8 Hz, 2H). |
| 372 | $^1$H NMR (400 MHz, Methanol-$d_4$) δ 8.52 (d, J = 6.9 Hz, 2H), 7.74-7.68 (m, 2H), 7.61-7.54 (m, 2H), 7.48 (d, J = 7.6 Hz, 2H), 4.50 (d, J = 5.1 Hz, 4H), 4.12 (d, J = 1.2 Hz, 7H), 3.71 (t, J = 5.6 Hz, 2H), 3.55 (t, J = 7.1 Hz, 2H), 3.48 (d, J = 6.9 Hz, 1H), 3.42 (t, J = 5.6 Hz, 2H), 2.45-2.34 (m, 5H), 2.15-2.09 (m, 2H), 1.96 (t, J = 11.3 Hz, 2H). |
| 373 | $^1$H NMR (400 MHz, Methanol-$d_4$) δ 8.52 (d, J = 9.9 Hz, 2H), 7.74-7.68 (m, 2H), 7.58 (td, J = 7.7, 1.3 Hz, 2H), 7.51-7.46 (m, 2H), 4.52 (d, J = 3.9 Hz, 2H), 4.48 (s, 2H), 4.12 (d, J = 2.9 Hz, 7H), 3.58 (t, J = 5.7 Hz, 2H), 3.38-3.32 (m, 4H), 2.48-2.38 (m, 3H), 2.00 (s, 4H). |
| 374 | $^1$H NMR (400 MHz, Methanol-$d_4$) δ 8.52 (d, J = 5.9 Hz, 2H), 7.71 (dd, J = 7.7, 1.7 Hz, 2H), 7.61-7.54 (m, 2H), 7.48 (dt, J = 7.5, 1.7 Hz, 2H), 4.54-4.46 (m, 4H), 4.12 (d, J = 2.0 Hz, 7H), 3.93-3.86 (m, 2H), 3.34 (s, 3H), 2.48-2.38 (m, 3H), 2.00-1.92 (m, 2H). |
| 375 | $^1$H NMR (400 MHz, Methanol-$d_4$) δ 8.51 (d, J = 3.7 Hz, 2H), 7.71 (d, J = 7.7 Hz, 2H), 7.57 (t, J = 7.8 Hz, 2H), 7.50-7.45 (m, 2H), 4.50 (s, 2H), 4.11 (d, J = 6.6 Hz, 6H), 3.51 (s, 2H), 3.47 (s, 2H), 3.32 (d, J = 2.3 Hz, 3H), 3.12 (s, 1H), 2.39 (d, J = 3.6 Hz, 3H), 2.01 (d, J = 3.2 Hz, 3H), 1.45 (s, 6H). |
| 376 | $^1$H NMR (400 MHz, Methanol-$d_4$) δ 8.52 (d, J = 4.8 Hz, 2H), 7.74-7.68 (m, 2H), 7.58 (dd, J = 8.0, 7.3 Hz, 2H), 7.51-7.45 (m, 2H), 4.49 (d, J = 3.9 Hz, 2H), 4.45 (s, 2H), 4.12 (d, J = 1.5 Hz, 7H), 3.43 (s, 2H), 3.39-3.32 (m, 2H), 2.44-2.35 (m, 3H), 1.99 (s, 4H), 1.45 (s, 6H). |
| 377 | $^1$H NMR (400 MHz, Methanol-$d_4$) δ 8.52 (d, J = 5.2 Hz, 2H), 7.71 (dd, J = 7.6, 1.7 Hz, 2H), 7.61-7.55 (m, 2H), 7.47 (dd, J = 7.5, 1.7 Hz, 2H), 4.43 (s, 4H), 4.12 (d, J = 5.3 Hz, 7H), 3.68 (s, 2H), 2.39 (d, J = 5.5 Hz, 4H), 1.97-1.87 (m, 2H), 1.43 (s, 6H). |
| 378 | $^1$H NMR (400 MHz, Methanol-$d_4$) δ 8.52 (d, J = 7.1 Hz, 2H), 7.71 (d, J = 7.9 Hz, 2H), 7.57 (t, J = 7.7 Hz, 2H), 7.50-7.45 (m, 2H), 4.47 (s, 2H), 4.41 (s, 2H), 4.11 (d, J = 2.5 Hz, 7H), 3.22 (s, 1H), 3.17 (s, 2H), 2.42-2.33 (m, 3H), 1.97-1.86 (m, 2H), 1.35 (s, 6H). |
| 379 | $^1$H NMR (400 MHz, Methanol-$d_4$) δ 8.49 (d, J = 9.1 Hz, 2H), 7.72-7.67 (m, 2H), 7.60-7.53 (m, 2H), 7.47 (d, J = 7.6 Hz, 2H), 4.71 (d, J = 17.2 Hz, 4H), 4.53 (s, 1H), 4.39 (d, J = 11.7 Hz, 2H), 4.10 (s, 8H), 3.23-3.15 (m, 2H), 2.39 (d, J = 18.4 Hz, 3H), 1.90 (s, 2H). |
| 380 | 1H NMR (400 MHz, Methanol-d4) δ 8.50 (d, J = 9.1 Hz, 2H), 7.72-7.67 (m, 2H), 7.60-7.53 (m, 2H), 7.48 (d, J = 7.6 Hz, 2H), 4.71 (d, J = 17.2 Hz, 4H), 4.52 (s, 1H), 4.39 (d, J = 11.7 Hz, 2H), 4.10 (s, 8H), 3.20-3.15 (m, 4H), 2.39 (d, J = 18.4 Hz, 3H), 1.90 (s, 2H). |

TABLE 2-continued

| No. | NMR |
|---|---|
| 381 | ¹H NMR (400 MHz, Methanol-d₄) δ 8.52 (s, 2H), 7.71 (dd, J = 7.7, 1.7 Hz, 2H), 7.57 (t, J = 7.7 Hz, 2H), 7.48 (dd, J = 7.5, 1.7 Hz, 2H), 4.53-4.37 (m, 5H), 4.12 (s, 7H), 3.61 (d, J = 5.0 Hz, 1H), 3.48 (q, J = 7.1 Hz, 1H), 2.46-2.36 (m, 3H), 2.17 (d, J = 14.5 Hz, 1H), 1.94-1.69 (m, 4H), 1.20 (dt, J = 24.4, 7.1 Hz, 3H). |
| 382 | ¹H NMR (400 MHz, Methanol-d₄) δ 8.53 (s, 1H), 7.72 (dd, J = 7.7, 1.7 Hz, 1H), 7.57 (t, J = 7.7 Hz, 1H), 7.48 (dd, J = 7.6, 1.7 Hz, 1H), 4.48 (s, 2H), 4.11 (s, 3H), 3.18 (s, 2H), 1.35 (s, 6H). |
| 383 | ¹H NMR (400 MHz, Methanol-d₄) δ 8.52 (s, 1H), 7.71 (dd, J = 7.7, 1.7 Hz, 1H), 7.57 (t, J = 7.7 Hz, 1H), 7.48 (dd, J = 7.6, 1.7 Hz, 1H), 4.46 (d, J = 5.5 Hz, 2H), 4.40 (d, J = 6.4 Hz, 1H), 4.11 (s, 3H), 3.60 (d, J = 5.0 Hz, 1H), 2.16 (d, J = 8.4 Hz, 1H), 1.98-1.78 (m, 4H), 1.73-1.64 (m, 1H). |
| 384 | ¹H NMR (400 MHz, Methanol-d₄) δ 8.52 (s, 1H), 7.71 (dd, J = 7.7, 1.7 Hz, 1H), 7.57 (t, J = 7.6 Hz, 1H), 7.48 (dd, J = 7.6, 1.7 Hz, 1H), 4.43 (s, 2H), 4.12 (s, 3H), 3.68 (s, 2H), 1.43 (s, 6H). |
| 385 | ¹H NMR (400 MHz, Methanol-d₄) δ 8.51 (s, 1H), 7.71 (dd, J = 7.8, 1.7 Hz, 1H), 7.57 (t, J = 7.7 Hz, 1H), 7.48 (dd, J = 7.6, 1.7 Hz, 1H), 4.79 (t, J = 6.8 Hz, 1H), 4.12 (s, 3H), 1.63 (d, J = 6.8 Hz, 3H). |
| 386 | ¹H NMR (400 MHz, Methanol-d₄) δ 8.51 (s, 1H), 7.71 (dd, J = 7.8, 1.7 Hz, 1H), 7.57 (t, J = 7.7 Hz, 1H), 7.48 (dd, J = 7.6, 1.7 Hz, 1H), 4.79 (t, J = 6.8 Hz, 1H), 4.12 (s, 3H), 1.63 (d, J = 6.8 Hz, 3H). |
| 387 | 1H NMR (400 MHz, Methanol-d4) δ 8.53 (s, 2H), 7.71 (d, J = 7.5 Hz, 2H), 7.58 (t, J = 7.6 Hz, 2H), 7.48 (d, J = 7.9 Hz, 2H), 4.50 (s, 4H), 4.37 (s, 1H), 4.12 (d, J = 3.0 Hz, 7H), 3.34 (s, 2H), 2.72 (dd, J = 17.9, 10.6 Hz, 1H), 2.46-2.35 (m, 2H), 2.15 (s, 2H), 2.08-1.87 (m, 2H), 1.28 (s, 1H). |
| 389 | 1H NMR (400 MHz, Methanol-d4) δ 8.53 (s, 1H), 8.48 (s, 1H), 7.78-7.71 (m, 1H), 7.65 (d, J = 4.6 Hz, 1H), 7.64-7.58 (m, 1H), 7.55-7.46 (m, 2H), 4.79 (s, 4H), 4.55 (s, 3H), 4.41 (s, 4H), 4.16 (d, J = 1.9 Hz, 5H), 3.78 (d, J = 39.5 Hz, 4H), 2.83 (d, J = 40.2 Hz, 4H). |
| 390 | 1H NMR (400 MHz, Methanol-d4) δ 8.54 (s, 1H), 8.48 (s, 1H), 7.75 (dd, J = 7.7, 1.7 Hz, 1H), 7.65 (d, J = 4.7 Hz, 1H), 7.62 (td, J = 7.7, 2.2 Hz, 1H), 7.55-7.47 (m, 2H), 4.78 (s, 4H), 4.64 (s, 2H), 4.39 (s, 3H), 4.16 (d, J = 1.9 Hz, 5H), 2.61 (t, J = 7.8 Hz, 4H), 2.47 (t, J = 7.8 Hz, 4H). |
| 391 | 1H NMR (400 MHz, Methanol-d4) δ 8.53 (s, 1H), 8.48 (s, 1H), 7.75 (dd, J = 7.7, 1.7 Hz, 1H), 7.65 (d, J = 4.7 Hz, 1H), 7.61 (td, J = 7.7, 2.3 Hz, 1H), 7.54-7.48 (m, 2H), 4.76 (s, 9H), 4.39 (d, J = 43.4 Hz, 2H), 4.15 (d, J = 1.9 Hz, 6H), 4.09 (s, 2H). |
| 392 | 1H NMR (400 MHz, Methanol-d4) δ 8.58 (s, 1H), 8.53 (s, 1H), 7.80-7.45 (m, 6H), 4.57 (d, J = 3.9 Hz, 3H), 4.17 (d, J = 1.9 Hz, 6H), 3.40 (t, J = 5.7 Hz, 3H), 2.61-2.36 (m, 5H), 2.02 (dt, J = 13.3, 4.9 Hz, 2H). |
| 397 | 1H NMR (400 MHz, Methanol-d4) δ 8.62 (s, 1H), 7.62 (dd, J = 8.5, 3.1 Hz, 1H), 7.42 (dd, J = 8.1, 2.9 Hz, 1H), 4.58 (s, 2H), 4.18 (s, 3H), 2.46 (d, J = 7.0 Hz, 3H), 1.98 (s, 2H), 1.33 (s, 2H). |
| 398 | 1H NMR (400 MHz, Methanol-d4) δ 8.58 (s, 1H), 8.54 (s, 1H), 7.74 (dd, J = 7.6, 1.7 Hz, 1H), 7.60 (t, J = 7.7 Hz, 1H), 7.55 (dd, J = 8.6, 3.0 Hz, 1H), 7.50 (dd, J = 7.7, 1.7 Hz, 1H), 7.33 (dd, J = 8.1, 3.1 Hz, 1H), 4.53 (dd, J = 4.1, 1.5 Hz, 4H), 4.13 (s, 4H), 4.12 (s, 3H), 3.36-3.32 (m, 8H), 2.49-2.36 (m, 6H), 1.96 (dd, J = 17.9, 9.9 Hz, 2H). |
| 399 | 1H NMR (400 MHz, Methanol-d4) δ 8.57 (s, 1H), 8.53 (s, 1H), 7.77 (dd, J = 7.7, 1.6 Hz, 1H), 7.64 (t, J = 7.6 Hz, 1H), 7.58 (dd, J = 8.7, 3.1 Hz, 1H), 7.54 (dd, J = 7.6, 1.7 Hz, 1H), 7.37 (dd, J = 8.2, 3.1 Hz, 1H), 4.82-4.66 (m, 8H), 4.43 (s, 1H), 4.34 (s, 1H), 4.16 (s, 4H), 4.15 (s, 3H), 4.09 (s, 2H). |
| 400 | 1H NMR (400 MHz, Methanol-d4) δ 8.52 (d, J = 3.6 Hz, 1H), 7.75 (dd, J = 7.7, 1.8 Hz, 1H), 7.62 (t, J = 7.7 Hz, 1H), 7.52 (dd, J = 7.6, 1.7 Hz, 1H), 4.77 (s, 3H), 4.43 (s, 3H), 4.16 (s, 3H), 3.42 (s, 4H). |
| 401 | 1H NMR (400 MHz, Methanol-d4) δ 8.60 (s, 1H), 7.77 (dd, J = 7.7, 1.7 Hz, 1H), 7.62 (t, J = 7.6 Hz, 1H), 7.53 (dd, J = 7.6, 1.7 Hz, 1H), 4.64 (s, 2H), 4.16 (s, 3H), 3.09 (s, 7H). |
| 402 | 1H NMR (400 MHz, Methanol-d4) δ 8.51 (s, 1H), 7.71 (dd, J = 7.7, 1.5 Hz, 1H), 7.57 (t, J = 7.8 Hz, 1H), 7.48 (dd, J = 7.5, 1.9 Hz, 1H), 4.44 (s, 2H), 4.11 (s, 3H), 2.88 (s, 3H). |
| 404 | 1H NMR (400 MHz, Methanol-d4) δ 8.70-8.59 (m, 2H), 8.57-8.47 (m, 3H), 7.72 (ddd, J = 7.7, 4.1, 1.7 Hz, 2H), 7.58 (t, J = 7.7 Hz, 2H), 7.48 (dd, J = 7.6, 1.7 Hz, 2H), 4.52 (d, J = 3.8 Hz, 2H), 4.27 (d, J = 36.3 Hz, 2H), 4.12 (d, J = 5.3 Hz, 6H), 3.97 (d, J = 31.8 Hz, 2H), 3.84-3.45 (m, 5H), 3.35 (dd, J = 6.2, 5.2 Hz, 2H), 2.65 (s, 2H), 2.52-2.24 (m, 5H), 2.03-1.88 (m, 2H). |
| 405 | 1H NMR (400 MHz, Methanol-d4) δ 8.79 (d, J = 2.1 Hz, 1H), 8.69 (dd, J = 5.4, 1.4 Hz, 1H), 8.53 (d, J = 7.3 Hz, 2H), 8.39 (dt, J = 8.1, 1.8 Hz, 1H), 7.86 (ddd, J = 8.1, 5.4, 0.8 Hz, 1H), 7.72 (ddd, J = 7.7, 2.8, 1.7 Hz, 2H), 7.63-7.54 (m, 2H), 7.48 (ddd, J = 7.6, 1.7, 0.9 Hz, 2H), 4.52 (d, J = 3.8 Hz, 2H), 4.12 (d, J = 4.0 Hz, 6H), 4.04-3.46 (m, 5H), 3.42-3.32 (m, 2H), 2.76-2.60 (m, 2H), 2.53-2.28 (m, 5H), 2.03-1.87 (m, 2H). |
| 406 | 1H NMR (400 MHz, Methanol-d4) δ 8.60 (ddd, J = 5.0, 1.8, 1.0 Hz, 1H), 8.54 (d, J = 7.0 Hz, 2H), 7.83 (td, J = 7.7, 1.8 Hz, 1H), 7.72 (ddd, J = 7.7, 4.8, 1.7 Hz, 2H), 7.58 (t, J = 7.6 Hz, 2H), 7.48 (dd, J = 7.6, 1.7 Hz, 2H), 7.43 (d, J = 7.8 Hz, 1H), 7.35 (ddd, J = 7.6, 4.9, 1.1 Hz, 1H), 4.52 (d, J = 3.8 Hz, 2H), 4.12 (d, J = 6.2 Hz, 6H), 3.94 (s, 3H), 3.87-3.51 (m, 3H), 3.35 (dd, J = 6.2, 5.1 Hz, 2H), 2.65 (s, 2H), 2.51-2.36 (m, 3H), 2.34 (d, J = 10.0 Hz, 2H), 2.03-1.89 (m, 2H). |
| 407 | 1H NMR (400 MHz, Methanol-d4) δ 8.53 (d, J = 3.7 Hz, 2H), 7.72 (ddd, J = 7.7, 2.5, 1.7 Hz, 2H), 7.58 (t, J = 7.7 Hz, 2H), 7.48 (dd, J = 7.6, 1.7 Hz, 2H), 4.76 (s, 2H), 4.52 (d, J = 4.0 Hz, 2H), 4.16-4.08 (m, 7H), 3.34 (d, J = 4.5 Hz, 4H), 2.97 (s, 2H), 2.53-2.35 (m, 4H), 2.33 (d, J = 21.4 Hz, 2H), 2.04-1.89 (m, 2H). |
| 408 | 1H NMR (400 MHz, Methanol-d4) δ 8.80 (d, J = 4.9 Hz, 2H), 8.54 (d, J = 7.9 Hz, 2H), 7.72 (ddd, J = 7.6, 5.2, 1.7 Hz, 2H), 7.58 (t, J = 7.7 Hz, 2H), 7.48 (dd, J = 7.6, 1.7 Hz, 2H), 7.41 (t, J = 5.0 Hz, 1H), 4.52 (d, J = 3.9 Hz, 2H), 4.37 (s, 1H), 4.33-4.20 (m, 1H), 4.12 (d, |

TABLE 2-continued

| No. | NMR |
|---|---|
| | J = 4.4 Hz, 6H), 4.06 (d, J = 20.5 Hz, 2H), 3.84 (s, 1H), 3.55 (s, 1H), 3.39-3.32 (m, 2H), 2.75 (s, 1H), 2.64 (s, 1H), 2.54-2.31 (m, 4H), 2.05-1.89 (m, 2H). |
| 409 | $^1$H NMR (400 MHz, Methanol-d4) δ 8.53 (d, J = 1.1 Hz, 2H), 7.72 (ddd, J = 7.7, 2.5, 1.7 Hz, 2H), 7.58 (t, J = 7.7 Hz, 2H), 7.48 (dd, J = 7.6, 1.7 Hz, 2H), 4.68 (d, J = 9.0 Hz, 2H), 4.52 (d, J = 3.9 Hz, 2H), 4.12 (d, J = 2.9 Hz, 6H), 3.88 (dd, J = 22.3, 9.7 Hz, 4H), 3.76 (q, J = 7.5 Hz, 2H), 3.40-3.32 (m, 3H), 2.51-2.32 (m, 4H), 2.13-1.89 (m, 5H), 1.57 (s, 2H), 1.30 (t, J = 7.4 Hz, 1H). |
| 410 | $^1$H NMR (400 MHz, Methanol-d4) δ 8.77-8.71 (m, 2H), 8.54 (d, J = 7.4 Hz, 2H), 7.92-7.83 (m, 2H), 7.72 (ddd, J = 7.7, 2.8, 1.7 Hz, 2H), 7.58 (td, J = 7.6, 0.8 Hz, 2H), 7.48 (ddd, J = 7.6, 1.7, 1.0 Hz, 2H), 4.52 (d, J = 4.0 Hz, 2H), 4.12 (d, J = 3.7 Hz, 6H), 3.97 (d, J = 28.1 Hz, 2H), 3.88 (d, J = 39.6 Hz, 4H), 3.42-3.33 (m, 2H), 2.73 (dt, J = 11.9, 6.3 Hz, 2H), 2.50-2.30 (m, 4H), 2.06-1.87 (m, 2H). |
| 411 | $^1$H NMR (400 MHz, Methanol-d4) δ 8.57-8.49 (m, 2H), 7.72 (dt, J = 7.7, 1.9 Hz, 2H), 7.58 (t, J = 7.7 Hz, 2H), 7.48 (dd, J = 7.6, 1.7 Hz, 2H), 4.70 (s, 2H), 4.52 (d, J = 3.9 Hz, 2H), 4.16-4.06 (m, 6H), 3.86 (ddd, J = 17.9, 8.2, 5.2 Hz, 3H), 3.75 (q, J = 7.9 Hz, 1H), 3.56-3.33 (m, 5H), 3.13-2.96 (m, 1H), 2.49-2.24 (m, 5H), 2.22-2.01 (m, 2H), 2.03-1.88 (m, 2H), 1.65 (ddd, J = 29.0, 12.6, 7.4 Hz, 2H). |
| 412 | $^1$H NMR (400 MHz, Methanol-d4) δ 8.52 (d, J = 7.0 Hz, 2H), 8.27 (d, J = 1.6 Hz, 1H), 8.22 (d, J = 2.5 Hz, 1H), 7.83-7.79 (m, 1H), 7.71 (dt, J = 7.7, 1.6 Hz, 2H), 7.58 (td, J = 7.7, 0.8 Hz, 2H), 7.48 (dd, J = 7.6, 1.7 Hz, 2H), 4.52 (d, J = 3.3 Hz, 4H), 4.11 (d, J = 2.8 Hz, 6H), 3.56 (dd, J = 8.9, 6.8 Hz, 2H), 3.40-3.32 (m, 2H), 3.27 (t, J = 7.8 Hz, 2H), 2.50-2.30 (m, 4H), 2.04-1.88 (m, 2H). |
| 413 | $^1$H NMR (400 MHz, Methanol-d4) δ 8.52 (d, J = 6.9 Hz, 2H), 7.71 (dt, J = 7.8, 1.9 Hz, 2H), 7.58 (td, J = 7.6, 0.7 Hz, 2H), 7.48 (ddd, J = 7.6, 1.7, 0.7 Hz, 2H), 4.52 (d, J = 4.4 Hz, 4H), 4.49-4.37 (m, 1H), 4.17-4.06 (m, 7H), 3.43-3.31 (m, 6H), 3.24 (dd, J = 12.9, 9.2 Hz, 2H), 2.52-2.30 (m, 4H), 2.12 (s, 4H), 2.05-1.87 (m, 2H). |
| 414 | $^1$H NMR (400 MHz, Methanol-d4) δ 8.57 (s, 1H), 8.53 (d, J = 2.7 Hz, 1H), 7.73 (ddd, J = 7.6, 6.9, 1.7 Hz, 2H), 7.59 (td, J = 7.7, 2.2 Hz, 2H), 7.53-7.43 (m, 3H), 4.97 (d, J = 11.8 Hz, 6H), 4.53 (d, J = 3.9 Hz, 2H), 4.12 (d, J = 2.7 Hz, 7H), 3.90 (s, 3H), 3.41-3.32 (m, 2H), 2.51-2.33 (m, 3H), 2.06-1.89 (m, 1H). |
| 415 | $^1$H NMR (400 MHz, Methanol-d4) δ 8.52 (d, J = 1.7 Hz, 2H), 7.90 (d, J = 1.6, 0.9 Hz, 1H), 7.71 (dd, J = 7.7, 1.7 Hz, 2H), 7.65-7.54 (m, 3H), 7.48 (dd, J = 7.6, 1.7 Hz, 2H), 6.64 (dd, J = 1.9, 0.9 Hz, 1H), 4.52 (d, J = 4.2 Hz, 4H), 4.12 (d, J = 2.1 Hz, 6H), 3.63 (tt, J = 11.7, 4.1 Hz, 1H), 3.42-3.32 (m, 2H), 3.12 (t, J = 1.7 Hz, 4H), 2.51-2.35 (m, 3H), 2.35-2.22 (m, 2H), 2.04-1.89 (m, 2H), 1.69 (qd, J = 12.4, 4.5 Hz, 2H). |
| 416 | $^1$H NMR (400 MHz, Methanol-d4) δ 8.52 (d, J = 1.2 Hz, 2H), 7.71 (dd, J = 7.7, 1.7 Hz, 2H), 7.57 (t, J = 7.6 Hz, 2H), 7.48 (dd, J = 7.6, 1.7 Hz, 2H), 4.57-4.47 (m, 4H), 4.12 (d, J = 2.9 Hz, 6H), 3.89-3.76 (m, 1H), 3.53-3.41 (m, 2H), 3.41-3.32 (m, 2H), 3.04-2.89 (m, 4H), 2.58 (dd, J = 16.9, 10.6 Hz, 1H), 2.53-2.31 (m, 4H), 2.16-1.89 (m, 3H). |
| 417 | $^1$H NMR (400 MHz, Methanol-d4) δ 8.61 (ddd, J = 5.1, 1.8, 0.9 Hz, 1H), 8.52 (d, J = 6.6 Hz, 2H), 8.00 (td, J = 7.8, 1.8 Hz, 1H), 7.71 (dd, J = 7.7, 1.7 Hz, 2H), 7.62-7.54 (m, 3H), 7.53-7.43 (m, 3H), 4.58-4.48 (m, 4H), 4.12 (s, 7H), 3.67 (t, J = 7.0 Hz, 2H), 3.44-3.32 (m, 4H), 2.51-2.33 (m, 3H), 2.03-1.89 (m, 1H). |
| 418 | $^1$H NMR (400 MHz, Methanol-d4) δ 8.66 (ddd, J = 4.9, 1.7, 0.9 Hz, 1H), 8.53 (d, J = 0.9 Hz, 2H), 7.88 (td, J = 7.7, 1.8 Hz, 1H), 7.71 (dd, J = 7.7, 1.7 Hz, 2H), 7.62-7.54 (m, 2H), 7.48 (dt, J = 7.6, 1.6 Hz, 3H), 7.43 (ddd, J = 7.6, 4.9, 1.1 Hz, 1H), 4.57 (d, J = 3.7 Hz, 4H), 4.52 (d, J = 3.9 Hz, 2H), 4.11 (d, J = 5.4 Hz, 6H), 3.38-3.33 (m, 2H), 2.50-2.32 (m, 4H), 2.01-1.91 (m, 1H). |
| 419 | $^1$H NMR (400 MHz, Methanol-d4) δ 8.52 (s, 1H), 8.47 (s, 1H), 7.80-7.73 (m, 2H), 7.70 (td, J = 7.5, 1.7 Hz, 2H), 7.61-7.54 (m, 4H), 7.48 (dt, J = 7.5, 1.5 Hz, 2H), 4.59-4.46 (m, 4H), 4.11 (m, 7H), 3.47-3.33 (m, 6H), 2.52-2.34 (m, 5H), 2.03-1.90 (m, 1H). |
| 420 | $^1$H NMR (400 MHz, Methanol-d4) δ 8.87 (d, J = 4.9 Hz, 2H), 8.54 (s, 2H), 7.72 (ddd, J = 7.6, 3.4, 1.7 Hz, 2H), 7.58 (t, J = 7.7 Hz, 2H), 7.53-7.46 (m, 3H), 4.70 (s, 2H), 4.65 (s, 2H), 4.52 (d, J = 3.9 Hz, 2H), 4.12 (d, J = 0.9 Hz, 6H), 3.38-3.33 (m, 2H), 2.51-2.35 (m, 4H), 1.98-1.92 (m, 1H). |
| 421 | $^1$H NMR (400 MHz, Methanol-d4) δ 8.56 (ddd, J = 5.0, 1.7, 0.9 Hz, 1H), 8.52 (d, J = 5.5 Hz, 2H), 7.87 (td, J = 7.9, 1.8 Hz, 1H), 7.71 (ddd, J = 7.7, 4.2, 1.7 Hz, 2H), 7.58 (td, J = 7.6, 0.7 Hz, 2H), 7.48 (dt, J = 7.6, 1.5 Hz, 2H), 7.36 (ddd, J = 7.6, 4.9, 1.0 Hz, 1H), 7.21 (dt, J = 8.2, 1.0 Hz, 1H), 4.60 (s, 2H), 4.53 (d, J = 3.9 Hz, 2H), 4.19-4.08 (m, 4H), 4.06 (s, 3H), 3.41-3.33 (m, 2H), 2.53-2.31 (m, 4H), 2.03-1.90 (m, 1H), 1.84-1.74 (m, 2H), 1.64-1.53 (m, 2H). |
| 422 | $^1$H NMR (400 MHz, Methanol-d4) δ 8.80-8.72 (m, 2H), 8.53 (d, J = 1.4 Hz, 2H), 7.83-7.76 (m, 2H), 7.71 (ddd, J = 7.6, 1.7, 0.6 Hz, 2H), 7.58 (t, J = 7.7 Hz, 2H), 7.48 (dd, J = 7.6, 1.7 Hz, 2H), 4.57 (d, J = 2.6 Hz, 4H), 4.52 (d, J = 3.9 Hz, 2H), 4.11 (d, J = 3.5 Hz, 6H), 3.42-3.32 (m, 2H), 2.55-2.32 (m, 4H), 2.03-1.89 (m, 2H). |
| 423 | $^1$H NMR (400 MHz, Methanol-d4) δ 8.53 (d, J = 7.5 Hz, 2H), 7.72 (ddd, J = 7.7, 4.5, 1.7 Hz, 2H), 7.58 (t, J = 7.7 Hz, 2H), 7.48 (dd, J = 7.6, 1.7 Hz, 2H), 5.03 (d, J = 15.5 Hz, 1H), 4.69 (d, J = 15.4 Hz, 1H), 4.57 (s, 1H), 4.52 (d, J = 3.9 Hz, 2H), 4.12 (s, 7H), 4.02 (dd, J = 12.3, 3.6 Hz, 1H), 3.84 (ddd, J = 26.3, 12.5, 5.0 Hz, 2H), 3.49-3.32 (m, 3H), 2.53-2.32 (m, 3H), 2.23 (dd, J = 13.7, 6.7 Hz, 1H), 2.18-2.04 (m, 1H), 2.06-1.88 (m, 2H). |
| 424 | $^1$H NMR (400 MHz, Methanol-d4) δ 8.93 (dd, J = 2.3, 0.8 Hz, 1H), 8.67 (dd, J = 5.2, 1.5 Hz, 1H), 8.52 (s, 1H), 8.42 (s, 1H), 8.33 (ddd, J = 8.0, 2.2, 1.5 Hz, 1H), 7.75-7.61 (m, 3H), 7.56 (td, J = 7.7, 4.8 Hz, 2H), 7.46 (dd, J = 7.6, 1.7 Hz, 2H), 4.52 (d, J = 3.9 Hz, 2H), 4.45 (s, 2H), 4.11 (s, 4H), 4.04 (s, 3H), 3.43-3.32 (m, 2H), 2.54-2.31 (m, 3H), 2.05-1.88 (m, 1H), 1.74-1.61 (m, 2H), 1.52-1.39 (m, 2H). |
| 425 | $^1$H NMR (400 MHz, Methanol-d4) δ 8.88 (d, J = 2.5 Hz, 1H), 8.77 (dd, J = 5.3, 1.5 Hz, 1H), 8.52 (s, 2H), 8.34 (dt, J = 8.0, 1.9 Hz, 1H), 7.79 (ddd, J = 8.0, 5.3, 0.8 Hz, 1H), 7.71 (dt, J = 7.7, 1.5 Hz, 2H), 7.57 (t, J = 7.6 Hz, 2H), 7.48 (dd, J = 7.6, 1.7 Hz, 2H), 4.57 (d, J = 4.7 Hz, |

TABLE 2-continued

| No. | NMR |
|---|---|
| | 4H), 4.52 (d, J = 3.9 Hz, 2H), 4.11 (d, J = 2.9 Hz, 6H), 3.44-3.31 (m, 2H), 2.56-2.31 (m, 3H), 2.06-1.88 (m, 2H). |
| 426 | ¹H NMR (400 MHz, Methanol-d4) δ 8.52 (d, J = 3.8 Hz, 2H), 7.71 (dd, J = 7.7, 1.7 Hz, 2H), 7.58 (td, J = 7.6, 0.9 Hz, 2H), 7.48 (dt, J = 7.6, 1.6 Hz, 2H), 4.58-4.48 (m, 4H), 4.12 (d, J = 1.2 Hz, 6H), 3.41-3.31 (m, 5H), 2.51-2.32 (m, 3H), 2.03-1.88 (m, 1H), 0.96-0.88 (m, 2H), 0.83-0.70 (m, 2H). |
| 427 | ¹H NMR (400 MHz, Methanol-d4) δ 8.53 (d, J = 4.0 Hz, 2H), 7.72 (ddd, J = 7.7, 2.5, 1.7 Hz, 2H), 7.58 (t, J = 7.6 Hz, 2H), 7.48 (dd, J = 7.6, 1.7 Hz, 2H), 4.69 (s, 2H), 4.52 (d, J = 3.9 Hz, 2H), 4.22 (s, 1H), 4.11 (d, J = 3.0 Hz, 6H), 3.93 (d, J = 3.0 Hz, 2H), 3.36 (d, J = 8.6 Hz, 6H), 2.53-2.32 (m, 4H), 2.19 (d, J = 34.8 Hz, 2H), 2.07-1.84 (m, 2H). |
| 428 | ¹H NMR (400 MHz, Methanol-d4) δ 8.52 (d, J = 1.5 Hz, 2H), 7.71 (dt, J = 7.7, 1.7 Hz, 2H), 7.57 (t, J = 7.7 Hz, 2H), 7.48 (ddd, J = 7.6, 1.7, 0.8 Hz, 2H), 4.64 (s, 2H), 4.52 (d, J = 3.9 Hz, 2H), 4.12 (d, J = 2.5 Hz, 7H), 3.86 (s, 6H), 3.40-3.32 (m, 2H), 2.54-2.32 (m, 3H), 2.01-1.89 (m, 1H). |
| 429 | ¹H NMR (400 MHz, Methanol-d4) δ 8.53 (d, J = 3.6 Hz, 2H), 7.71 (ddd, J = 7.7, 1.7, 1.1 Hz, 2H), 7.57 (t, J = 7.7 Hz, 2H), 7.48 (dd, J = 7.6, 1.7 Hz, 2H), 4.55 (s, 2H), 4.52 (d, J = 3.8 Hz, 2H), 4.18-4.06 (m, 7H), 3.43 (s, 2H), 3.40-3.32 (m, 2H), 2.52-2.31 (m, 3H), 2.04-1.91 (m, 1H), 1.57-1.48 (m, 2H), 1.39-1.29 (m, 2H). |
| 430 | ¹H NMR (400 MHz, Methanol-d4) δ 8.53 (d, J = 4.2 Hz, 2H), 7.72 (ddd, J = 7.7, 2.6, 1.8 Hz, 2H), 7.58 (t, J = 7.7 Hz, 2H), 7.48 (dd, J = 7.6, 1.8 Hz, 2H), 4.69 (s, 2H), 4.52 (d, J = 3.9 Hz, 2H), 4.22 (s, 1H), 4.11 (d, J = 2.9 Hz, 6H), 4.05-3.83 (m, 2H), 3.36 (d, J = 8.4 Hz, 6H), 2.52-2.32 (m, 4H), 2.24 (s, 2H), 2.04-1.90 (m, 2H). |
| 431 | ¹H NMR (400 MHz, Methanol-d4) δ 8.53 (d, J = 4.2 Hz, 2H), 7.72 (ddd, J = 7.7, 3.0, 1.7 Hz, 2H), 7.58 (t, J = 7.6 Hz, 2H), 7.48 (dd, J = 7.6, 1.7 Hz, 2H), 4.72 (d, J = 34.7 Hz, 2H), 4.61 (s, 1H), 4.52 (d, J = 3.9 Hz, 2H), 4.11 (d, J = 2.5 Hz, 6H), 4.08-3.75 (m, 3H), 3.54 (s, 1H), 3.37 (tt, J = 12.6, 7.7 Hz, 3H), 2.51-2.35 (m, 3H), 2.14 (d, J = 34.6 Hz, 2H), 2.02-1.91 (m, 1H). |
| 432 | ¹H NMR (400 MHz, DMSO-d6) δ 9.50 (s, 2H), 9.25 (s, 2H), 9.15 (s, 2H), 8.60 (d, J = 5.8 Hz, 2H), 7.78 (d, J = 7.5 Hz, 2H), 7.68-7.65 (m, 2H), 7.59 (d, J = 7.6 Hz, 2H), 4.49 (s, 3H), 4.31 (d, J = 6.0 Hz, 2H), 4.05 (d, J = 3.8 Hz, 5H), 3.97 (s, 2H), 3.22 (s, 4H), 2.29 (s, 2H), 2.21 (q, J = 7.4, 6.5 Hz, 3H), 1.82 (d, J = 8.4 Hz, 2H). |
| 433 | ¹H NMR (400 MHz, DMSO-d6) δ 9.32 (s, 3H), 9.15 (s, 2H), 8.60 (d, J = 6.5 Hz, 2H), 7.78 (d, J = 7.8 Hz, 2H), 7.69-7.65 (m, 2H), 7.59 (d, J = 7.7 Hz, 2H), 5.77 (s, 5H), 5.28-5.21 (m, 1H), 4.48 (d, J = 13.6 Hz, 4H), 4.04 (t, J = 4.2 Hz, 7H), 4.00-3.90 (m, 4H), 2.26-2.14 (m, 3H), 1.82 (d, J = 8.8 Hz, 2H). |
| 434 | ¹H NMR (400 MHz, Methanol-d4) δ 8.52 (s, 2H), 7.71 (dd, J = 7.7, 1.7 Hz, 2H), 7.58 (t, J = 7.6 Hz, 2H), 7.48 (dd, J = 7.6, 1.7 Hz, 2H), 4.84 (s, 2H), 4.48 (s, 4H), 4.12 (s, 6H), 3.85-3.73 (m, 2H), 3.26 (dd, J = 10.2, 6.4 Hz, 2H), 2.44-2.26 (m, 6H), 2.11-1.92 (m, 4H), 1.90-1.73 (m, 2H) |
| 435 | ¹H NMR (400 MHz, Methanol-d4) δ 8.55 (s, 2H), 7.74 (dd, J = 7.7, 1.7 Hz, 2H), 7.60 (t, J = 7.7 Hz, 2H), 7.51 (dd, J = 7.6, 1.7 Hz, 2H), 4.60-4.46 (m, 4H), 4.14 (s, 7H), 3.67 (dd, J = 10.2, 8.0 Hz, 1H), 3.46-3.35 (m, 4H), 3.27 (dd, J = 10.2, 6.5 Hz, 1H), 3.10-2.95 (m, 1H), 2.70-2.56 (m, 1H), 2.56-2.40 (m, 3H), 2.32 (dd, J = 16.9, 7.6 Hz, 1H), 2.07-1.91 (m, 1H) |
| 436 | 1H NMR (400 MHz, Methanol-d4) δ 8.50 (s, 1H), 7.82 (d, J = 7.7 Hz, 1H), 7.73-7.60 (m, 2H), 7.60-7.49 (m, 2H), 7.47 (s, 1H), 7.41 (d, J = 5.9 Hz, 1H), 7.33 (d, J = 7.6 Hz, 1H), 4.34 (s, 2H), 4.16 (s, 2H), 4.11 (s, 3H), 4.08 (s, 3H). |
| 437 | 1H NMR (400 MHz, Methanol-d4) δ 8.48 (s, 1H), 7.88 (d, J = 7.6 Hz, 1H), 7.69 (dd, J = 7.6, 1.7 Hz, 1H), 7.65 (dd, J = 7.7, 1.7 Hz, 1H), 7.61-7.48 (m, 2H), 7.46 (dd, J = 7.6, 1.7 Hz, 1H), 7.41 (dd, J = 7.6, 1.7 Hz, 1H), 7.36 (d, J = 7.5 Hz, 2H), 4.57-4.21 (m, 10H), 4.11 (s, 3H), 4.08 (s, 3H), 3.86-3.60 (m, 4H), 2.95-2.67 (m, 4H). |
| 439 | 1H NMR (400 MHz, Methanol-d4) δ 8.53 (d, J = 1.8 Hz, 1H), 7.92 (s, 2H), 7.72 (dd, J = 12.1, 7.4 Hz, 3H), 7.64-7.38 (m, 7H), 4.77 (s, 1H), 4.53 (s, 1H), 4.15 (s, 3H), 4.13 (s, 5H). |
| 440 | 1H NMR (400 MHz, DMSO-d6) δ 9.00 (d, J = 43.2 Hz, 2H), 8.15 (s, 2H), 7.84 (s, 4H), 7.74-7.64 (m, 2H), 7.56 (d, J = 31.3 Hz, 3H), 6.54 (s, 4H), 4.55 (s, 1H), 4.23 (s, 1H), 3.99 (s, 1H), 2.88 (dq, J = 11.1, 6.4 Hz, 3H), 2.17 (td, J = 12.3, 6.5 Hz, 6H), 1.87-1.67 (m, 3H). |
| 629 | ¹H NMR (400 MHz, Acetonitrile-d₃) δ 8.43 (s, 2H), 7.71 (dd, J = 7.7, 1.8 Hz, 2H), 7.59 (t, J = 7.7 Hz, 2H), 7.50 (dd, J = 7.6, 1.7 Hz, 2H), 4.61 (m, 4H), 4.37 (m, 2H), 4.25 (m, 3H), 4.03 (s, 6H), 3.97 (m, 3H), 1.52 (s, 3H). |
| 630 | ¹H NMR (400 MHz, Methanol-d₄) δ 8.50 (s, 1H), 7.90 (d, J = 7.6 Hz, 1H), 7.70 (dd, J = 7.7, 1.7 Hz, 1H), 7.67 (dd, J = 7.7, 1.7 Hz, 1H), 7.55 (dt, J = 14.2, 7.7 Hz, 2H), 7.47 (dd, J = 7.6, 1.7 Hz, 1H), 7.43 (dd, J = 7.6, 1.7 Hz, 1H), 7.38 (d, J = 7.6 Hz, 1H), 4.35 (d, J = 2.7 Hz, 4H), 4.11 (d, J = 4.8 Hz, 6H), 4.09-4.02 (m, 1H), 3.26 (dd, J = 6.2, 4.2 Hz, 2H), 2.48-2.33 (m, 3H), 1.98-1.86 (m, 1H). |
| 631 | ¹H NMR (400 MHz, Methanol-d₄) δ 8.48 (s, 1H), 7.89 (dd, J = 7.6, 1.2 Hz, 1H), 7.74-7.61 (m, 2H), 7.59-7.48 (m, 2H), 7.48-7.38 (m, 2H), 7.35 (d, J = 7.5 Hz, 1H), 4.72 (d, J = 22.2 Hz, 2H), 4.51-4.24 (m, 4H), 4.09 (d, J = 5.0 Hz, 8H), 3.28-3.18 (m, 2H), 2.54-2.27 (m, 4H), 2.02-1.83 (m, 1H), 1.58 (s, 3H). |
| 632 | ¹H NMR (400 MHz, Methanol-d₄) δ 8.47 (s, 1H), 7.89 (dd, J = 7.6, 1.1 Hz, 1H), 7.74-7.61 (m, 2H), 7.60-7.48 (m, 2H), 7.46 (dd, J = 7.6, 1.7 Hz, 1H), 7.40 (ddd, J = 7.6, 3.1, 1.7 Hz, 1H), 7.35 (d, J = 7.5 Hz, 1H), 4.69 (s, 2H), 4.54 (d, J = 64.1 Hz, 5H), 4.34 (d, J = 2.5 Hz, 2H), 4.24 (d, J = 26.8 Hz, 2H), 4.09 (d, J = 4.0 Hz, 7H), 4.08-4.03 (m, 1H), 3.28-3.19 (m, 2H), 2.48-2.28 (m, 3H), 1.98-1.87 (m, 1H), 1.85 (s, 3H). |
| 633 | ¹H NMR (400 MHz, Methanol-d₄) δ 8.48 (s, 1H), 7.89 (d, J = 7.6 Hz, 1H), 7.73-7.62 (m, 2H), 7.61-7.50 (m, 2H), 7.44 (ddd, J = 20.5, 7.6, 1.8 Hz, 2H), 7.36 (d, J = 7.5 Hz, 1H), |

TABLE 2-continued

| No. | NMR |
|---|---|
| | 4.74 (s, 2H), 4.49 (s, 4H), 4.34 (d, J = 2.6 Hz, 2H), 4.10 (d, J = 4.6 Hz, 7H), 4.05 (q, J = 6.5 Hz, 1H), 3.72 (s, 1H), 3.29-3.16 (m, 2H), 2.80 (s, 2H), 2.50-2.29 (m, 3H), 2.01-1.84 (m, 1H). |
| 634 | 1H NMR (400 MHz, Methanol-d4) δ 8.56 (s, 2H), 7.75 (dd, J = 7.7, 1.7 Hz, 2H), 7.60 (t, J = 7.6 Hz, 2H), 7.51 (dd, J = 7.6, 1.7 Hz, 2H), 4.70 (s, 4H), 4.14 (s, 6H), 3.92 (t, J = 11.0 Hz, 4H), 3.73-3.53 (m, 8H), 3.45 (q, J = 9.9 Hz, 2H), 3.25 (d, J = 11.9 Hz, 2H), 2.28-2.14 (m, 2H), 2.08 (q, J = 13.2, 11.0 Hz, 2H). |
| 635 | 1H NMR (400 MHz, Methanol-d4) δ 8.54 (s, 1H), 7.90 (d, J = 7.6 Hz, 1H), 7.73 (dd, J = 7.6, 1.7 Hz, 1H), 7.68 (dd, J = 7.7, 1.8 Hz, 1H), 7.59 (t, J = 7.9 Hz, 1H), 7.54 (d, J = 7.7 Hz, 1H), 7.49 (dd, J = 7.6, 1.7 Hz, 1H), 7.44 (dd, J = 7.6, 1.7 Hz, 1H), 7.39 (dd, J = 7.5, 2.7 Hz, 1H), 4.61 (d, J = 9.5 Hz, 2H), 4.55-4.41 (m, 4H), 4.33 (dd, J = 10.7, 6.2 Hz, 1H), 4.18 (dt, J = 18.4, 9.3 Hz, 5H), 4.10 (d, J = 1.3 Hz, 3H), 2.94 (dp, J = 26.4, 8.7 Hz, 2H), 1.18 (d, J = 23.4 Hz, 13H), 0.94-0.79 (m, 4H). |
| 636 | 1H NMR (400 MHz, Methanol-d4) δ 8.54 (s, 1H), 7.90 (d, J = 7.6 Hz, 1H), 7.73 (dd, J = 7.7, 1.8 Hz, 1H), 7.68 (dd, J = 7.7, 1.8 Hz, 1H), 7.59 (t, J = 7.7 Hz, 1H), 7.55 (t, J = 7.8 Hz, 1H), 7.50 (dd, J = 7.6, 1.7 Hz, 1H), 7.45 (dd, J = 7.6, 1.7 Hz, 1H), 7.40 (d, J = 7.5 Hz, 1H), 4.71 (s, 2H), 4.63 (s, 4H), 4.51 (dp, J = 6.3, 3.0 Hz, 3H), 4.41 (q, J = 12.2, 11.4 Hz, 6H), 4.11 (s, 3H), 2.56 (dt, J = 23.8, 7.6 Hz, 4H), 2.48-2.34 (m, 4H), 1.02-0.78 (m, 4H). |
| 637 | 1H NMR (400 MHz, Methanol-d4) δ 8.54 (s, 1H), 7.91 (d, J = 7.6 Hz, 1H), 7.73 (dd, J = 7.7, 1.7 Hz, 1H), 7.68 (dd, J = 7.7, 1.7 Hz, 1H), 7.64-7.56 (m, 1H), 7.54 (d, J = 7.6 Hz, 1H), 7.49 (dd, J = 7.6, 1.8 Hz, 1H), 7.44 (dd, J = 7.6, 1.8 Hz, 1H), 7.39 (d, J = 7.5 Hz, 1H), 4.70 (s, 2H), 4.64-4.44 (m, 4H), 4.35 (s, 6H), 4.11 (s, 3H), 3.72 (s, 3H), 2.77 (s, 3H), 0.96-0.74 (m, 2H). |
| 638 | 1H NMR (400 MHz, Methanol-d4) δ 8.59 (s, 1H), 7.92 (d, J = 7.6 Hz, 1H), 7.74 (dd, J = 7.7, 1.7 Hz, 1H), 7.69 (dd, J = 7.7, 1.8 Hz, 1H), 7.60 (t, J = 7.7 Hz, 1H), 7.55 (t, J = 7.7 Hz, 1H), 7.50 (dd, J = 7.7, 1.7 Hz, 1H), 7.45 (dd, J = 7.6, 1.7 Hz, 1H), 7.39 (d, J = 7.5 Hz, 1H), 4.53 (dt, J = 6.1, 3.2 Hz, 1H), 4.48 (d, J = 4.1 Hz, 2H), 4.37 (d, J = 2.6 Hz, 2H), 4.12 (s, 5H), 3.47-3.35 (m, 2H), 3.29-3.17 (m, 2H), 2.54-2.25 (m, 6H), 1.96 (dddd, J = 18.9, 11.6, 6.1, 3.2 Hz, 2H), 0.94-0.77 (m, 5H). |
| 639 | 1H NMR (400 MHz, Methanol-d4) δ 8.54 (s, 1H), 7.91 (d, J = 7.5 Hz, 1H), 7.73 (dd, J = 7.7, 1.7 Hz, 1H), 7.68 (dd, J = 7.7, 1.7 Hz, 1H), 7.57 (dt, J = 15.7, 7.6 Hz, 2H), 7.49 (dd, J = 7.6, 1.7 Hz, 1H), 7.45 (dd, J = 7.6, 1.7 Hz, 1H), 7.39 (d, J = 7.5 Hz, 1H), 4.39 (s, 2H), 4.34 (s, 2H), 4.14 (s, 3H), 4.12 (s, 3H), 3.93 (p, J = 7.8 Hz, 1H), 3.64 (dd, J = 10.2, 8.0 Hz, 1H), 3.31-3.26 (m, 1H), 3.21 (dd, J = 10.1, 6.6 Hz, 1H), 3.07 (q, J = 8.4 Hz, 1H), 3.02-2.91 (m, 1H), 2.75-2.63 (m, 2H), 2.58 (dd, J = 16.8, 8.8 Hz, 1H), 2.53-2.40 (m, 2H), 2.26 (dd, J = 16.8, 7.8 Hz, 1H). |
| 640 | 1H NMR (400 MHz, Methanol-d4) δ 8.55 (s, 1H), 7.91 (d, J = 7.5 Hz, 1H), 7.73 (dd, J = 7.7, 1.7 Hz, 1H), 7.68 (dd, J = 7.7, 1.8 Hz, 1H), 7.57 (dt, J = 15.6, 7.7 Hz, 2H), 7.49 (dd, J = 7.6, 1.7 Hz, 1H), 7.44 (dd, J = 7.6, 1.7 Hz, 1H), 7.39 (d, J = 7.5 Hz, 1H), 4.49 (d, J = 5.8 Hz, 2H), 4.43 (td, J = 4.6, 2.2 Hz, 1H), 4.34 (s, 2H), 4.14 (s, 3H), 3.70-3.58 (m, 2H), 3.31-3.26 (m, 1H), 3.22 (dd, J = 10.2, 6.6 Hz, 1H), 2.97 (dt, J = 15.3, 7.8 Hz, 1H), 2.58 (dd, J = 16.9, 8.8 Hz, 1H), 2.34-2.23 (m, 1H), 2.18 (dddd, J = 12.4, 8.3, 3.9, 1H), 2.11-1.89 (m, 2H), 1.89-1.80 (m, 1H), 1.80-1.66 (m, 1H). |
| 641 | 1H NMR (400 MHz, Methanol-d4) δ 8.84 (s, 1H), 7.97-7.78 (m, 2H), 7.78-7.52 (m, 4H), 7.52-7.34 (m, 2H), 4.61-4.32 (m, 6H), 4.29 (s, 3H), 4.18 (s, 4H), 4.12 (s, 3H), 2.64-2.32 (m, 4H). |
| 642 | 1H NMR (400 MHz, Methanol-d4) δ 8.84 (s, 1H), 7.97-7.78 (m, 2H), 7.73-7.52 (m, 4H), 7.50-7.31 (m, 2H), 4.51 (d, J = 28.6 Hz, 2H), 4.32-4.02 (m, 14H), 1.56 (s, 3H). |
| 643 | 1H NMR (400 MHz, Methanol-d4) δ 8.84 (s, 1H), 7.92 (d, J = 7.6 Hz, 1H), 7.84 (dd, J = 7.7, 1.7 Hz, 1H), 7.74-7.50 (m, 4H), 7.46 (dd, J = 7.6, 1.7 Hz, 1H), 7.40 (d, J = 7.5 Hz, 1H), 4.60 (ddd, J = 11.3, 7.9, 6.2 Hz, 1H), 4.37 (d, J = 2.8 Hz, 2H), 4.34-4.21 (m, 3H), 4.18-4.03 (m, 4H), 3.75 (dd, J = 11.7, 8.0 Hz, 1H), 3.28 (dd, J = 6.2, 4.0 Hz, 2H), 2.51-2.30 (m, 3H), 2.01-1.83 (m, 1H), 1.52 (d, J = 6.4 Hz, 3H). |
| 644 | 1H NMR (400 MHz, Methanol-d4) δ 8.84 (s, 1H), 7.92 (d, J = 7.6 Hz, 1H), 7.84 (dd, J = 7.7, 1.8 Hz, 1H), 7.75-7.50 (m, 5H), 7.51-7.30 (m, 2H), 4.60 (ddd, J = 11.5, 7.9, 6.3 Hz, 1H), 4.37 (d, J = 2.8 Hz, 2H), 4.36-4.22 (m, 3H), 4.16-4.02 (m, 4H), 3.75 (dd, J = 11.7, 8.0 Hz, 1H), 3.28 (dd, J = 6.2, 4.0 Hz, 2H), 2.52-2.31 (m, 3H), 1.94 (ddt, J = 8.8, 5.4, 2.9 Hz, 1H), 1.52 (d, J = 6.3 Hz, 3H). |
| 645 | 1H NMR (400 MHz, Methanol-d4) δ 8.84 (s, 1H), 7.92 (d, J = 7.6 Hz, 1H), 7.84 (dd, J = 7.7, 1.8 Hz, 1H), 7.74-7.50 (m, 4H), 7.51-7.32 (m, 2H), 4.37 (d, J = 2.8 Hz, 2H), 4.29 (s, 3H), 4.21-3.99 (d, J = 19.3 Hz, 8H), 3.29-3.23 (m, 2H), 2.53-2.30 (m, 3H), 2.02-1.82 (m, 1H). |
| 646 | 1H NMR (400 MHz, Methanol-d4) δ 8.84 (s, 1H), 8.57 (s, 1H), 7.85 (dd, J = 7.7, 1.7 Hz, 1H), 7.76 (dd, J = 7.7, 1.7 Hz, 1H), 7.74-7.45 (m, 4H), 4.57 (dd, J = 16.5, 4.2 Hz, 3H), 4.34-4.21 (m, 4H), 4.17-4.06 (m, 4H), 3.75 (dd, J = 11.7, 8.0 Hz, 1H), 3.37 (t, J = 5.6 Hz, 2H), 2.57-2.32 (m, 3H), 2.09-1.85 (m, 1H), 1.52 (d, J = 6.4 Hz, 3H). |
| 647 | 1H NMR (400 MHz, Methanol-d4) δ 8.84 (s, 1H), 8.57 (s, 1H), 7.85 (dd, J = 7.7, 1.7 Hz, 1H), 7.76 (dd, J = 7.7, 1.8 Hz, 1H), 7.72-7.40 (m, 4H), 4.67-4.48 (m, 3H), 4.38-4.22 (m, 4H), 4.15 (s, 4H), 3.75 (dd, J = 11.7, 8.0 Hz, 1H), 3.37 (t, J = 5.7 Hz, 2H), 2.58-2.32 (m, 3H), 2.08-1.87 (m, 1H), 1.52 (d, J = 6.4 Hz, 3H). |
| 648 | 1H NMR (400 MHz, Methanol-d4) δ 8.55 (d, J = 11.6 Hz, 2H), 7.74 (dt, J = 7.7, 2.0 Hz, 2H), 7.61 (td, J = 7.7, 1.3 Hz, 2H), 7.51 (dt, J = 7.6, 1.7 Hz, 2H), 4.62-4.33 (m, 4H), 4.20-4.07 (m, 7H), 3.93-3.73 (m, 1H), 3.69-3.51 (m, 2H), 3.37 (dd, J = 6.2, 5.1 Hz, 2H), 2.59-1.52 (m, 11H). |
| 649 | 1H NMR (400 MHz, Methanol-d4) δ 8.51 (s, 1H), 8.24-8.13 (m, 1H), 7.88 (d, J = 7.7 Hz, 1H), 7.79-7.36 (m, 6H), 4.82-4.24 (m, 12H), 4.16 (d, J = 11.4 Hz, 6H), 2.69-2.29 (m, 8H). |

TABLE 2-continued

| No. | NMR |
|---|---|
| 650 | 1H NMR (400 MHz, Methanol-d4) δ 8.52 (s, 1H), 8.21-8.09 (m, 1H), 7.72 (dd, J = 7.4, 2.1 Hz, 1H), 7.67-7.52 (m, 2H), 7.52-7.36 (m, 3H), 4.81-4.25 (m, 12H), 4.15 (d, J = 4.4 Hz, 6H), 2.69-2.35 (m, 11H). |
| 651 | 1H NMR (400 MHz, Methanol-d4) δ 8.51 (s, 1H), 8.16 (td, J = 7.2, 3.1 Hz, 1H), 7.72 (dd, J = 7.4, 2.0 Hz, 1H), 7.66-7.51 (m, 2H), 7.51-7.36 (m, 3H), 4.80-4.07 (m, 18H), 3.87-3.64 (m, 4H), 2.82 (d, J = 34.6 Hz, 4H), 2.53 (s, 3H). |
| 652 | 1H NMR (400 MHz, Methanol-d4) δ 8.56 (s, 1H), 7.73 (dd, J = 7.7, 1.7 Hz, 1H), 7.65 (dd, J = 7.7, 1.7 Hz, 1H), 7.59 (t, J = 7.6 Hz, 1H), 7.54 (t, J = 7.6 Hz, 1H), 7.49 (dd, J = 7.6, 1.8 Hz, 1H), 7.43 (dd, J = 7.6, 1.7 Hz, 1H), 7.25 (m, 1H), 4.60-4.50 (m, 2H), 4.42 (q, J = 6.7 Hz, 1H), 4.38-4.28 (m, 2H), 4.15 (s, 4H), 4.10 (d, J = 2.0 Hz, 3H), 3.42-3.35 (m, 2H), 3.28 (m, 3H), 2.81-2.66 (m, 2H), 2.52 (s, 3H), 2.50-2.38 (m, 3H), 2.27-2.19 (m, 4H), 2.04-1.94 (m, 1H). |
| 653 | 1H NMR (400 MHz, Methanol-d4) δ 8.56 (s, 1H), 7.73 (dd, J = 7.7, 1.7 Hz, 1H), 7.65 (dd, J = 7.7, 1.7 Hz, 1H), 7.59 (t, J = 7.7 Hz, 1H), 7.54 (t, J = 7.6 Hz, 1H), 7.49 (dd, J = 7.6, 1.7 Hz, 1H), 7.43 (dd, J = 7.6, 1.7 Hz, 1H), 7.27 (s, 1H), 4.55 (t, J = 2.0 Hz, 4H), 4.43 (d, J = 24.3 Hz, 2H), 4.22 (s, 1H), 4.17 (s, 1H), 4.15 (m, 4H), 4.10 (s, 3H), 3.41-3.35 (m, 2H), 2.55 (s, 3H), 2.51-2.36 (m, 3H), 2.06-1.93 (m, 1H), 1.87 (s, 3H). |
| 654 | 1H NMR (400 MHz, Methanol-d4) δ 8.56 (s, 1H), 7.73 (dd, J = 7.7, 1.7 Hz, 1H), 7.67 (dd, J = 7.7, 1.7 Hz, 1H), 7.59 (t, J = 7.7 Hz, 1H), 7.54 (t, J = 7.7 Hz, 1H), 7.49 (dd, J = 7.6, 1.7 Hz, 1H), 7.44 (dd, J = 7.6, 1.8 Hz, 1H), 7.29 (s, 1H), 4.69 (s, 1H), 4.55 (d, J = 3.9 Hz, 2H), 4.15 (s, 3H), 4.12 (s, 3H), 4.09 (s, 1H), 4.02-3.83 (m, 1H), 3.76 (s, 7H), 3.62-3.50 (m, 1H), 3.43-3.35 (m, 3H), 2.57 (s, 3H), 2.53 (s, 1H), 2.52-2.36 (m, 3H), 2.21 (s, 1H), 2.10-1.91 (m, 1H). |
| 655 | 1H NMR (400 MHz, Methanol-d4) δ 8.56 (s, 1H), 7.73 (dd, J = 7.7, 1.8 Hz, 1H), 7.67 (dd, J = 7.7, 1.8 Hz, 1H), 7.59 (t, J = 7.6 Hz, 1H), 7.54 (t, J = 7.7 Hz, 1H), 7.49 (dd, J = 7.6, 1.7 Hz, 1H), 7.44 (dd, J = 7.6, 1.7 Hz, 1H), 7.28 (s, 1H), 4.57 (d, J = 3.0 Hz, 2H), 4.55 (d, J = 4.0 Hz, 2H), 4.28 (d, J = 11.6 Hz, 1H), 4.15 (m, 4H), 4.11 (s, 3H), 3.88 (t, J = 9.7 Hz, 1H), 3.37 (m, 3H), 3.15 (p, J = 1.6 Hz, 1H), 3.08 (d, J = 11.7 Hz, 1H), 3.00 (t, J = 10.6 Hz, 1H), 2.54 (s, 3H), 2.52-2.32 (m, 3H), 2.08 (d, J = 9.9 Hz, 1H), 2.05-1.87 (m, 2H), 1.79 (s, 1H). |
| 656 | 1H NMR (400 MHz, Methanol-d4) δ 8.54 (s, 1H), 7.92 (d, J = 7.6 Hz, 1H), 7.73 (dd, J = 7.7, 1.7 Hz, 1H), 7.59 (t, J = 7.8 Hz, 1H), 7.54 (d, J = 7.6 Hz, 1H), 7.49 (dd, J = 7.6, 1.7 Hz, 1H), 7.44 (dd, J = 7.6, 1.7 Hz, 1H), 7.39 (d, J = 7.5 Hz, 1H), 4.47 (s, 2H), 4.43-4.32 (m, 3H), 4.14 (s, 3H), 4.12 (s, 3H), 4.11-4.05 (m, 1H), 3.31-3.23 (m, 2H), 2.72 (qp, J = 8.5, 4.5 Hz, 1H), 2.51-2.33 (m, 3H), 2.33-2.16 (m, 4H), 2.01-1.87 (m, 1H). |
| 657 | 1H NMR (400 MHz, Methanol-d4) δ 8.51 (s, 2H), 7.73 (m, 2H), 7.59 (t, J = 7.6 Hz, 2H), 7.50 (dd, J = 7.6, 1.7 Hz, 2H), 4.78 (s, 6H), 4.69-4.19 (m, 6H), 4.13 (s, 6H), 4.08 (s, 4H). |
| 658 | 1H NMR (400 MHz, Methanol-d4) δ 8.53 (dd, J = 5.3, 0.7 Hz, 2H), 7.72 (ddt, J = 7.7, 1.7, 0.8 Hz, 2H), 7.58 (tt, J = 7.6, 0.7 Hz, 2H), 7.48 (dtd, J = 7.6, 1.8, 0.7 Hz, 2H), 4.60-4.45 (m, 4H), 4.12 (d, J = 0.7 Hz, 7H), 3.54-3.38 (m, 5H), 3.38-3.27 (m, 6H), 3.04-2.91 (m, 2H), 2.52-2.31 (m, 5H), 2.05-1.86 (m, 3H). 19F NMR (376 MHz, Methanol-d4) δ −77.75. |
| 659 | 1H NMR (400 MHz, Methanol-d4) δ 8.53 (t, J = 0.8 Hz, 2H), 7.72 (ddt, J = 7.6, 1.6, 0.8 Hz, 2H), 7.58 (td, J = 7.6, 0.7 Hz, 2H), 7.48 (dd, J = 7.7, 1.5 Hz, 2H), 4.60-4.46 (m, 4H), 4.12 (d, J = 0.7 Hz, 6H), 3.40 (ddd, J = 12.6, 5.7, 3.2 Hz, 1H), 3.39-3.28 (m, 3H), 3.33-3.20 (m, H), 3.19 (dd, J = 12.7, 6.9 Hz, 1H), 2.57 (ddd, J = 17.2, 5.3, 1.9 Hz, 1H), 2.52-2.33 (m, 4H), 2.17 (dd, J = 17.3, 10.8 Hz, 1H), 2.07 (d, J = 13.7 Hz, 1H), 2.03-1.90 (m, 1H), 1.59 (ddt, J = 17.0, 11.2, 5.6 Hz, 1H). 19F NMR (376 MHz, Methanol-d4) δ −77.73 (d, J = 2.3 Hz). |
| 660 | 1H NMR (400 MHz, Methanol-d4) δ 8.53 (d, J = 0.6 Hz, 2H), 7.72 (ddd, J = 7.6, 1.7, 0.6 Hz, 2H), 7.58 (td, J = 7.6, 0.6 Hz, 2H), 7.48 (ddd, J = 7.6, 1.7, 0.6 Hz, 2H), 4.51 (s, 4H), 4.12 (d, J = 0.7 Hz, 6H), 3.45-3.14 (m, 5H), 2.57 (ddd, J = 17.3, 5.2, 1.9 Hz, 2H), 2.40 (t, J = 11.3 Hz, 2H), 2.17 (dd, J = 17.2, 10.8 Hz, 2H), 2.12-2.02 (m, 2H), 1.59 (dtd, J = 13.2, 11.1, 5.6 Hz, 2H). 19F NMR (376 MHz, Methanol-d4) δ −77.84. |
| 661 | 1H NMR (400 MHz, Methanol-d4) δ 8.52 (d, J = 0.7 Hz, 2H), 7.72 (ddd, J = 7.7, 1.7, 0.7 Hz, 2H), 7.58 (td, J = 7.7, 0.7 Hz, 2H), 7.48 (ddd, J = 7.6, 1.8, 0.7 Hz, 2H), 4.60-4.45 (m, 5H), 4.12 (d, J = 0.7 Hz, 6H), 3.52-3.36 (m, 9H), 3.30 (p, J = 1.7 Hz, 5H), 2.98 (dtd, J = 10.5, 8.8, 6.9 Hz, 3H), 2.49-2.35 (m, 3H), 2.05-1.86 (m, 3H). Multiplet Report 19F NMR (376 MHz, Methanol-d4) δ −77.63--77.74 (m), −77.76, −77.77--77.95 (m). |
| 662 | 1H NMR (400 MHz, Methanol-d$_4$) δ 8.48 (s, 1H), 8.33 (d, J = 1.9 Hz, 1H), 7.66 (d, J = 7.8 Hz, 1H), 7.56 (t, J = 7.7 Hz, 1H), 7.50 (d, J = 7.7 Hz, 1H), 7.45 (d, J = 1.9 Hz, 1H), 7.42 (s, 1H), 7.30 (d, J = 7.4 Hz, 1H), 4.69 (s, 3H), 4.68 (s, 2H), 4.62 (s, 2H), 4.49 (s, 1H), 4.44 (s, 2H), 4.26 (s, 1H), 4.15 (s, 1H), 4.11 (d, J = 1.9 Hz, 4H), 4.08 (s, 3H), 2.16 (s, 4H), 2.03 (d, J = 1.9 Hz, 2H), 1.86 (s, 8H). |
| 663 | 1H NMR (400 MHz, Methanol-d4) δ 8.53 (s, 2H), 7.72 (dd, J = 7.7, 1.7 Hz, 2H), 7.58 (t, J = 7.7 Hz, 2H), 7.48 (dd, J = 7.6, 1.7 Hz, 2H), 4.69 (s, 4H), 4.11 (s, 6H), 3.90 (d, J = 15.1 Hz, 4H), 3.61 (s, 1H), 3.41 (d, J = 9.7 Hz, 4H), 3.00 (d, J = 10.1 Hz, 1H), 2.72 (d, J = 48.1 Hz, 3H), 2.27 (d, J = 35.2 Hz, 3H), 1.95 (s, 6H), 1.81 (d, J = 16.7 Hz, 2H). |

Biological Example 1

PD-1/PD-L1 & CTLA/CD80 Biochemical Protein-Protein Interaction Assay

Compounds were tested in biochemical protein-protein interaction assays to determine if they can specifically block the interaction between the extracellular domains of PD-1/PD-L1 or CTLA/CD80. Binding of the protein pairs is measured using a bead based Amplified Luminescent Proximity Homogeneous Assay (ALPHA) platform. Binding of each protein pair results in proximity of the donor and acceptor beads which leads to an increase in ALPHA signal. Disruption of the protein-protein interaction with a test compound results in a decrease in ALPHA signal. Assays are performed in 25 mM Hepes (pH 7.4), 150 mM NaCl, 3.4 mM EDTA, 0.005% Tween 20, and 0.01% BSA. Final protein concentration in the assays were 0.3 nM (His tagged PD-L1), 2.5 nM (biotinylated Fc-PD-1), 1 nM (His tagged CTLA4) and 1 nM (biotinylated CD80). After an assay reaction time of 60 minutes at 25° C., binding was measured with addition of 20 μg/mL ALPHA assay acceptor beads (anti-His coated) and 20 g/mL ALPHA assay donor beads (streptavidin coated). $IC_{50}$ values were calculated from the fit of the dose-response curves to a four-parameter equation. Representative data are shown below in Table 3.

TABLE 3

| No. | $IC_{50}$ PD-L1-PD1 (nM) |
|---|---|
| 1 | 0.080 |
| 2 | 0.135 |
| 3 | 0.318 |
| 4 | 0.086 |
| 5 | 0.213 |
| 6 | 0.099 |
| 7 | 0.430 |
| 8 | 0.590 |
| 9 | 0.490 |
| 10 | 0.270 |
| 11 | 0.172 |
| 12 | 1.492 |
| 13 | 0.482 |
| 14 | 0.224 |
| 15 | 7.508 |
| 16 | 0.173 |
| 17 | 0.163 |
| 18 | 0.266 |
| 19 | 0.199 |
| 20 | 0.546 |
| 21 | 0.525 |
| 22 | 0.506 |
| 23 | 0.221 |
| 24 | 0.179 |
| 25 | 0.080 |
| 26 | 0.060 |
| 27 | 0.090 |
| 28 | 0.436 |
| 29 | 1.091 |
| 30 | 0.475 |
| 31 | 0.334 |
| 32 | 0.187 |
| 33 | 0.138 |
| 34 | 0.231 |
| 35 | 0.191 |
| 36 | 1.290 |
| 37 | 1.697 |
| 38 | 0.660 |
| 39 | 0.390 |
| 40 | 0.238 |
| 41 | 0.083 |
| 42 | 3.419 |
| 43 | 0.083 |
| 44 | 0.113 |
| 45 | 0.064 |
| 46 | 0.081 |
| 47 | 0.160 |
| 48 | 0.822 |
| 49 | 0.356 |
| 50 | 0.259 |
| 51 | 0.301 |
| 52 | 0.170 |
| 53 | 0.100 |
| 54 | 0.180 |
| 55 | 0.260 |
| 56 | 0.090 |
| 57 | 8.780 |
| 58 | 6.760 |
| 59 | 0.100 |
| 60 | 0.140 |
| 61 | 0.070 |
| 62 | 0.160 |
| 63 | 2.990 |
| 65 | 0.165 |
| 66 | 0.610 |
| 67 | 0.292 |
| 68 | 0.403 |
| 69 | 2.622 |
| 70 | 0.784 |
| 71 | 0.081 |
| 72 | 0.198 |
| 73 | 0.370 |
| 74 | 1.340 |
| 75 | 0.877 |
| 76 | 0.090 |
| 77 | 0.192 |
| 78 | 0.064 |
| 79 | 0.292 |
| 80 | 0.360 |
| 81 | 4.176 |
| 82 | 0.335 |
| 83 | 0.560 |
| 84 | 0.189 |
| 85 | 0.976 |
| 86 | 3.050 |
| 87 | 5.883 |
| 88 | 0.217 |
| 89 | 0.286 |
| 90 | 0.156 |
| 91 | 0.978 |
| 92 | 1.026 |
| 93 | 0.566 |
| 94 | 0.862 |
| 95 | 0.233 |
| 96 | 1.495 |
| 97 | 0.701 |
| 98 | 0.647 |
| 99 | 0.407 |
| 100 | 0.146 |
| 101 | 0.130 |
| 102 | 0.223 |
| 103 | 0.071 |
| 104 | 0.077 |
| 105 | 0.302 |
| 106 | 0.360 |
| 107 | 1.540 |
| 108 | 0.474 |
| 109 | 0.586 |
| 110 | 0.327 |
| 111 | 0.297 |
| 112 | 0.076 |
| 113 | 0.211 |
| 114 | 0.064 |
| 115 | 0.115 |
| 116 | 0.064 |
| 117 | 0.281 |
| 118 | 0.715 |
| 119 | 0.115 |
| 120 | 0.320 |
| 121 | 0.064 |
| 122 | 1.692 |
| 123 | 0.112 |
| 124 | 0.190 |
| 125 | 0.225 |
| 126 | 0.272 |
| 127 | 0.064 |
| 128 | 0.557 |
| 129 | 0.064 |
| 130 | 0.185 |
| 131 | 0.309 |
| 132 | 0.753 |
| 133 | 0.064 |
| 134 | 0.064 |
| 135 | 0.733 |
| 136 | 0.147 |
| 137 | 0.168 |
| 138 | 0.161 |
| 139 | 0.213 |

TABLE 3-continued

| No. | IC$_{50}$ PD-L1-PD1 (nM) |
|---|---|
| 140 | 0.260 |
| 141 | 0.064 |
| 142 | 0.200 |
| 143 | 0.410 |
| 144 | 0.240 |
| 145 | 0.100 |
| 146 | 0.130 |
| 147 | 0.060 |
| 148 | 0.060 |
| 149 | 0.270 |
| 150 | 0.200 |
| 151 | 0.684 |
| 152 | 0.073 |
| 153 | 0.396 |
| 154 | 0.126 |
| 155 | 1.647 |
| 156 | 0.084 |
| 157 | 0.064 |
| 158 | 0.162 |
| 159 | 0.150 |
| 160 | 0.128 |
| 161 | 0.167 |
| 162 | 0.116 |
| 163 | 0.177 |
| 164 | 0.122 |
| 165 | 0.187 |
| 166 | 0.233 |
| 167 | 0.262 |
| 168 | 0.196 |
| 169 | 0.344 |
| 170 | 0.227 |
| 171 | 0.208 |
| 172 | 0.222 |
| 173 | 0.209 |
| 174 | 0.219 |
| 175 | 0.110 |
| 176 | 0.111 |
| 177 | 0.330 |
| 178 | 0.553 |
| 179 | 0.211 |
| 180 | 1.032 |
| 181 | 1.510 |
| 182 | 0.547 |
| 183 | 0.888 |
| 184 | 0.763 |
| 185 | 0.480 |
| 186 | 0.100 |
| 187 | 0.280 |
| 188 | 0.120 |
| 189 | 0.094 |
| 190 | 0.200 |
| 191 | 0.143 |
| 192 | 0.156 |
| 193 | 0.133 |
| 194 | 0.149 |
| 195 | 0.064 |
| 196 | 0.170 |
| 197 | 0.230 |
| 198 | 0.121 |
| 199 | 0.126 |
| 200 | 0.132 |
| 201 | 0.280 |
| 202 | 0.144 |
| 203 | 0.129 |
| 204 | 0.110 |
| 205 | 0.079 |
| 206 | 0.113 |
| 207 | 0.104 |
| 208 | 0.223 |
| 209 | 0.175 |
| 210 | 0.30 |
| 211 | 0.095 |
| 212 | 0.48 |
| 213 | 0.840 |
| 214 | 0.260 |
| 215 | 0.110 |
| 216 | 0.210 |
| 217 | 0.140 |
| 218 | 0.140 |
| 219 | 0.190 |
| 220 | 0.360 |
| 221 | 0.227 |
| 222 | 0.291 |
| 223 | 0.584 |
| 224 | 0.393 |
| 225 | 0.288 |
| 226 | 0.474 |
| 227 | 0.136 |
| 228 | 0.168 |
| 229 | 0.229 |
| 230 | 0.331 |
| 231 | 0.064 |
| 232 | 0.312 |
| 233 | 0.451 |
| 234 | 0.088 |
| 235 | 0.106 |
| 236 | 0.064 |
| 237 | 0.064 |
| 238 | 0.297 |
| 239 | 0.300 |
| 240 | 0.090 |
| 241 | 0.270 |
| 242 | 0.140 |
| 243 | 0.110 |
| 244 | 0.080 |
| 245 | 0.150 |
| 246 | 0.210 |
| 247 | 0.130 |
| 248 | 0.180 |
| 249 | 2.670 |
| 250 | 0.120 |
| 251 | 0.070 |
| 252 | 0.060 |
| 253 | 0.090 |
| 254 | 0.110 |
| 255 | 0.080 |
| 256 | 0.160 |
| 257 | 0.426 |
| 258 | 0.673 |
| 259 | 0.273 |
| 260 | 0.295 |
| 261 | 0.128 |
| 262 | 0.465 |
| 263 | 0.379 |
| 264 | 0.407 |
| 265 | 0.225 |
| 266 | 0.243 |
| 267 | 0.606 |
| 268 | 0.352 |
| 269 | 0.230 |
| 270 | 0.378 |
| 271 | 1.704 |
| 272 | 2.426 |
| 273 | 0.265 |
| 274 | 0.117 |
| 275 | 0.064 |
| 276 | 0.270 |
| 277 | 0.652 |
| 278 | 0.538 |
| 279 | 0.343 |
| 280 | 0.180 |
| 281 | 1.194 |
| 282 | 1.573 |
| 283 | 0.711 |
| 284 | 0.816 |
| 285 | 0.358 |
| 286 | 0.060 |
| 287 | 0.340 |
| 288 | 0.260 |
| 289 | 0.060 |
| 290 | 0.259 |
| 291 | 0.216 |
| 292 | 0.229 |
| 293 | 0.516 |

TABLE 3-continued

| No. | IC$_{50}$ PD-L1-PD1 (nM) |
|---|---|
| 294 | 0.298 |
| 295 | 0.414 |
| 296 | 0.222 |
| 297 | 0.254 |
| 298 | 0.181 |
| 299 | 0.260 |
| 300 | 0.299 |
| 301 | 0.250 |
| 302 | 0.089 |
| 303 | 0.256 |
| 304 | 0.290 |
| 305 | 0.244 |
| 306 | 0.245 |
| 307 | 0.167 |
| 308 | 0.337 |
| 309 | 0.178 |
| 310 | 0.216 |
| 311 | 0.240 |
| 312 | 0.295 |
| 313 | 0.327 |
| 314 | 0.142 |
| 315 | 0.18 |
| 316 | 0.17 |
| 317 | 0.220 |
| 318 | 0.150 |
| 319 | 3.870 |
| 320 | 3.720 |
| 321 | 0.460 |
| 322 | 0.230 |
| 323 | 0.120 |
| 324 | 0.358 |
| 325 | 1.860 |
| 326 | 0.180 |
| 327 | 0.238 |
| 328 | 4.042 |
| 329 | 0.955 |
| 330 | 5.676 |
| 331 | 0.669 |
| 332 | 0.743 |
| 333 | 0.171 |
| 334 | 0.246 |
| 335 | 0.172 |
| 336 | 0.137 |
| 337 | 1.102 |
| 338 | 0.565 |
| 339 | 0.192 |
| 340 | 0.118 |
| 341 | 0.094 |
| 342 | 0.107 |
| 343 | 0.126 |
| 344 | 0.114 |
| 345 | 0.313 |
| 346 | 0.323 |
| 347 | 0.245 |
| 348 | 0.138 |
| 349 | 0.389 |
| 350 | 0.737 |
| 351 | 0.283 |
| 352 | 4.633 |
| 353 | 0.064 |
| 354 | 0.133 |
| 355 | 0.129 |
| 356 | 0.102 |
| 357 | 0.096 |
| 358 | 0.141 |
| 359 | 0.132 |
| 360 | 0.401 |
| 361 | 0.130 |
| 362 | 0.074 |
| 363 | 0.424 |
| 364 | 0.244 |
| 365 | 0.070 |
| 366 | 0.115 |
| 367 | 0.064 |
| 368 | 0.064 |
| 369 | 0.078 |
| 370 | 0.064 |
| 371 | 0.213 |
| 372 | 0.104 |
| 373 | 0.130 |
| 374 | 0.183 |
| 375 | 0.459 |
| 376 | 0.208 |
| 377 | 0.098 |
| 378 | 0.396 |
| 379 | 0.155 |
| 380 | 0.203 |
| 381 | 0.085 |
| 382 | 0.289 |
| 383 | 0.887 |
| 384 | 0.154 |
| 385 | 0.292 |
| 386 | 0.879 |
| 387 | 0.625 |
| 388 | 1.223 |
| 389 | 0.211 |
| 390 | 0.146 |
| 391 | 0.232 |
| 392 | 0.246 |
| 393 | 2.229 |
| 394 | 1.782 |
| 395 | 9.235 |
| 396 | 2.015 |
| 397 | 0.561 |
| 398 | 0.195 |
| 399 | 0.324 |
| 400 | 0.173 |
| 401 | 0.295 |
| 402 | 0.175 |
| 403 | 0.070 |
| 404 | 0.070 |
| 405 | 0.160 |
| 406 | 0.280 |
| 407 | 0.186 |
| 408 | 0.139 |
| 409 | 0.124 |
| 410 | 0.316 |
| 411 | 0.321 |
| 412 | 0.187 |
| 413 | 0.162 |
| 414 | 0.559 |
| 415 | 0.195 |
| 416 | 0.140 |
| 417 | 0.196 |
| 418 | 0.219 |
| 419 | 0.542 |
| 420 | 0.449 |
| 421 | 0.603 |
| 422 | 0.554 |
| 423 | 0.237 |
| 424 | 0.617 |
| 425 | 0.414 |
| 426 | 0.273 |
| 427 | 0.136 |
| 428 | 0.272 |
| 429 | 0.349 |
| 430 | 0.071 |
| 431 | 0.124 |
| 432 | 0.084 |
| 433 | 0.259 |
| 434 | 0.064 |
| 435 | 0.064 |
| 436 | 5.463 |
| 437 | 0.086 |
| 438 | 1.34 |
| 439 | 0.646 |
| 440 | 1.873 |
| 441 | 0.064 |
| 442 | 0.146 |
| 443 | 0.246 |
| 444 | 0.074 |
| 445 | 0.069 |
| 446 | 0.138 |
| 447 | 0.064 |

TABLE 3-continued

| No. | IC$_{50}$ PD-L1-PD1 (nM) |
|---|---|
| 448 | 0.064 |
| 449 | 0.285 |
| 450 | 0.064 |
| 451 | 0.101 |
| 452 | 0.086 |
| 453 | 0.139 |
| 454 | 0.064 |
| 455 | 0.145 |
| 456 | 0.186 |
| 457 | 0.172 |
| 458 | 0.087 |
| 459 | 0.344 |
| 460 | 0.157 |
| 461 | 0.159 |
| 462 | 0.346 |
| 463 | 0.076 |
| 464 | 0.11 |
| 465 | 0.158 |
| 466 | 0.073 |
| 467 | 0.146 |
| 468 | 0.123 |
| 469 | 0.26 |
| 470 | 0.094 |
| 471 | 0.119 |
| 472 | 0.066 |
| 473 | 0.093 |
| 474 | 0.219 |
| 475 | 0.162 |
| 476 | 0.622 |
| 477 | 0.246 |
| 478 | 0.064 |
| 479 | 0.239 |
| 480 | 0.064 |
| 481 | 0.227 |
| 482 | 0.108 |
| 483 | 0.341 |
| 484 | 0.122 |
| 485 | 0.229 |
| 486 | 0.29 |
| 487 | 0.123 |
| 488 | 0.064 |
| 489 | 0.332 |
| 490 | 0.565 |
| 491 | 0.064 |
| 492 | 0.092 |
| 493 | 0.109 |
| 494 | 0.139 |
| 495 | 0.247 |
| 496 | 0.386 |
| 497 | 0.276 |
| 498 | 0.169 |
| 499 | 0.203 |
| 500 | 0.232 |
| 501 | 0.087 |
| 502 | 0.064 |
| 508 | 0.084 |
| 509 | 0.106 |
| 510 | 0.192 |
| 511 | 0.197 |
| 512 | 0.101 |
| 513 | 0.064 |
| 514 | 0.09 |
| 515 | 0.342 |
| 516 | 0.064 |
| 517 | 0.106 |
| 518 | 0.144 |
| 519 | 0.277 |
| 520 | 0.072 |
| 521 | 0.071 |
| 522 | 0.064 |
| 523 | 0.181 |
| 524 | 0.115 |
| 525 | 0.105 |
| 526 | 0.168 |
| 527 | 0.089 |
| 528 | 0.064 |
| 529 | 0.091 |
| 530 | 0.212 |
| 531 | 0.225 |
| 532 | 0.273 |
| 533 | 0.096 |
| 534 | 0.299 |
| 535 | 0.095 |
| 536 | 0.276 |
| 537 | 0.064 |
| 538 | 0.199 |
| 539 | 0.171 |
| 540 | 0.072 |
| 541 | 0.094 |
| 542 | 0.392 |
| 543 | 0.2 |
| 544 | 0.238 |
| 545 | 0.214 |
| 546 | 0.089 |
| 547 | 0.064 |
| 548 | 0.665 |
| 549 | 0.194 |
| 550 | 0.593 |
| 551 | 0.464 |
| 552 | 0.144 |
| 553 | 0.118 |
| 554 | 0.099 |
| 555 | 0.345 |
| 556 | 0.176 |
| 557 | 0.09 |
| 558 | 0.064 |
| 559 | 0.12 |
| 560 | 0.144 |
| 561 | 0.164 |
| 562 | 0.151 |
| 563 | 0.431 |
| 564 | 0.2 |
| 565 | 0.43 |
| 566 | 0.13 |
| 567 | 0.064 |
| 568 | 0.293 |
| 569 | 0.59 |
| 570 | 0.414 |
| 571 | 0.064 |
| 572 | 0.064 |
| 573 | 0.089 |
| 574 | 0.133 |
| 575 | 0.064 |
| 576 | 0.641 |
| 577 | 0.064 |
| 578 | 0.182 |
| 579 | 0.782 |
| 580 | 0.359 |
| 581 | 0.201 |
| 582 | 0.19 |
| 583 | 0.064 |
| 584 | 0.118 |
| 585 | 0.442 |
| 586 | 0.29 |
| 587 | 0.515 |
| 588 | 0.17 |
| 589 | 0.291 |
| 590 | 0.131 |
| 591 | 0.138 |
| 592 | 0.151 |
| 593 | 0.346 |
| 594 | 0.12 |
| 595 | 0.064 |
| 596 | 0.181 |
| 597 | 0.129 |
| 598 | 0.178 |
| 599 | 0.174 |
| 600 | 0.064 |
| 601 | 0.196 |
| 602 | 0.145 |
| 603 | 0.073 |
| 604 | 0.064 |
| 605 | 0.113 |
| 606 | 0.077 |

TABLE 3-continued

| No. | IC$_{50}$ PD-L1-PD1 (nM) |
|---|---|
| 607 | 0.064 |
| 608 | 0.064 |
| 609 | 0.079 |
| 610 | 0.313 |
| 611 | 0.21 |
| 612 | 0.064 |
| 613 | 0.182 |
| 614 | 0.079 |
| 615 | 0.291 |
| 616 | 0.069 |
| 617 | 0.064 |
| 618 | 0.064 |
| 619 | 0.178 |
| 620 | 0.101 |
| 621 | 1.054 |
| 622 | 0.26 |
| 623 | 0.064 |
| 624 | 0.152 |
| 625 | 0.074 |
| 626 | 0.064 |
| 627 | 0.081 |
| 628 | 0.064 |
| 629 | 0.083 |
| 630 | 0.437 |
| 631 | 0.064 |
| 632 | 0.172 |
| 633 | 0.064 |
| 634 | 0.064 |
| 635 | 0.098 |
| 636 | 0.12 |
| 637 | 0.134 |
| 638 | 0.079 |
| 639 | 0.066 |
| 640 | 0.167 |
| 641 | 0.064 |
| 642 | 0.064 |
| 643 | 0.064 |
| 644 | 0.093 |
| 645 | 0.064 |
| 646 | 0.064 |
| 647 | 0.064 |
| 648 | 0.08 |
| 649 | 0.128 |
| 650 | 0.064 |
| 651 | 0.064 |
| 652 | 0.12 |
| 653 | 0.064 |
| 654 | 0.071 |
| 655 | 0.064 |
| 656 | 0.167 |
| 657 | 0.064 |
| 658 | 0.196 |
| 659 | 0.121 |
| 660 | 0.135 |
| 661 | 0.064 |
| 662 | 0.082 |
| 663 | 0.281 |

The above data shows that compounds of the present disclosure are generally effective at blocking the PD-1/PD-L1 interaction.

PD-1/PD-L1 NFAT Reporter Assay:

Compounds were tested in a functional co-culture reporter assay in which TCR-mediated NFAT activity is inhibited by the engagement of PD-1 with PD-L1. Blocking the PD-1/PD-L1 interaction impairs PD-1 mediated blunting of TCR signaling and significantly increases NFAT-mediated transcription of luciferase. CHO cells expressing surface-bound anti-CD3 antibodies and PD-L1 (artificial antigen presenting cells, aAPC-PD-L1) were first seeded overnight. Jurkat cells overexpressing PD-1 and expressing a luciferase construct under NFAT control are diluted in RPMI assay medium (RPMI 1640 with 2% FBS), mixed with compounds, and immediately seeded on the monolayer of aAPC-PD-L1. The co-culture is then incubated for 6 hrs at 37° C. Luciferase activity is assessed by adding the ONE-Glo reagent and measuring luminescence with a plate reader. EC$_{50}$ values are calculated from the fit of the dose-response curves to a four-parameter equation (Table 4).

PD-L1/PD-L1 Dimerization Biochemical Protein-Protein Interaction Assay:

Compounds were tested in biochemical protein-protein interaction assays to determine if they can specifically dimerize the extracellular domains of PD-L1. Dimerization of the proteins (His-tagged PD-L1 and FLAG-tagged PD-L1) is measured using a bead based Amplified Luminescent Proximity Homogeneous Assay (ALPHA) platform. Compound induced dimerization of PD-L1 results in proximity of the donor and acceptor beads which leads to an increase in ALPHA signal. Assays are performed in 25 mM Hepes (pH 7.4), 150 mM NaCl, 3.4 mM EDTA, 0.005% Tween 20, and 0.01% BSA. Final protein concentration in the assays were 0.5 nM (His tagged PD-L1) and 0.5 nM (FLAG tagged PD-L1). After an assay reaction time of 2 hours at 25° C., 20 µg/mL (final assay concentration) ALPHA assay acceptor beads (anti-His coated) were added and incubated for 60 minutes at 25° C. Binding was measured following a final 60 minute incubation with 40 µg/mL (final assay concentration) ALPHA assay donor beads (anti-FLAG coated). AC$_{50}$ values were calculated from the fit of the dose-response curves to a four-parameter equation (Table 4).

TABLE 4

| No. | AC$_{50}$ PDL1 Dimer | EC$_{50}$ NFAT Luciferase |
|---|---|---|
| 1 | 240.33 | 66 |
| 2 | 202.6 | 90 |
| 3 | 392.74 | 218 |
| 4 | 335.51 | 59 |
| 5 | 393.97 | 274 |
| 6 | 305.57 | 126 |
| 7 | 583.46 | 3442 |
| 8 | 644.47 | 5852 |
| 9 | 607.65 | 375 |
| 10 | 403.62 | 142 |
| 11 | 462.83 | 163 |
| 12 | 757.1 | 299 |
| 13 | 347.99 | 403 |
| 14 | 353.78 | 87 |
| 15 | 10000 | 50000 |
| 16 | 282.19 | 49 |
| 17 | 408.39 | 99 |
| 18 | 426.95 | 391 |
| 19 | 611.82 | 50000 |
| 20 | 10000 | 1164 |
| 21 | 731.29 | 193 |
| 22 | 685.61 | 252 |
| 23 | 335.84 | 108 |
| 24 | 338.33 | 89 |
| 25 | 229.05 | 76 |
| 26 | 215.35 | 78 |
| 27 | 205.5 | 157 |
| 28 | 530.34 | 156 |
| 29 | 1357.1 | 50000 |
| 30 | 446.13 | 181 |
| 31 | 247.95 | 325 |
| 32 | 252.14 | 242 |
| 33 | 527.94 | 138 |
| 34 | 668.28 | 271 |
| 35 | 371.63 | 40 |
| 36 | 10000 | 1608 |
| 37 | 516.49 | 667 |
| 38 | 1702.4 | 1607 |
| 39 | 282.95 | 291 |

TABLE 4-continued

| No. | AC$_{50}$ PDL1 Dimer | EC$_{50}$ NFAT Luciferase |
|---|---|---|
| 40 | 694.13 | 3977 |
| 41 | 840.99 | 1206 |
| 42 | 10000 | 3046 |
| 43 | 372.8 | 214 |
| 44 | 369.96 | 145 |
| 45 | 325.08 | 68 |
| 46 | 311.32 | 55 |
| 47 | 694.52 | 215 |
| 48 | 2569.1 | 332 |
| 49 | 402.54 | 123 |
| 50 | 578.04 | 77 |
| 51 | 653.49 | 3264 |
| 52 | 586.85 | 220 |
| 53 | 353.66 | 104 |
| 54 | 201.78 | 131 |
| 55 | 421.05 | 211 |
| 56 | 259.11 | 104 |
| 57 | 319.44 | 277 |
| 58 | 728.88 | 711 |
| 59 | 291.2 | 56 |
| 60 | 260.45 | 59 |
| 61 | 211.47 | 50 |
| 62 | 311.93 | 201 |
| 63 | 387.65 | 314 |
| 65 | 167.34 | 957 |
| 66 | 306.4 | 1717 |
| 67 | 509.76 | 1806 |
| 68 | 769.42 | 50000 |
| 69 | 1489.1 | 50000 |
| 70 | 356.8 | 1131 |
| 71 | 298.23 | 842 |
| 72 | 144.68 | 175 |
| 73 | 141.66 | 222 |
| 74 | 120.4 | 128 |
| 75 | 733.44 | 606 |
| 76 | 364.58 | 81 |
| 77 | 243.78 | 44 |
| 78 | 276.77 | 55 |
| 79 | 428.2 | 221 |
| 80 | 481.52 | 286 |
| 81 | 10000 | 50000 |
| 82 | 1287.4 | 193 |
| 83 | 2505.1 | 94 |
| 84 | 749.38 | 75 |
| 85 | 1984.9 | 1027 |
| 86 | 10000 | 50000 |
| 87 | 10000 | 314 |
| 88 | 443.98 | 209 |
| 89 | 984.05 | 145 |
| 90 | 459.79 | 90 |
| 91 | 1327.2 | 579 |
| 92 | 10000 | 906 |
| 93 | 3077.7 | 234 |
| 94 | 7667.6 | 844 |
| 95 | 935.74 | 1008 |
| 96 | 6153.3 | 10199 |
| 97 | 755 | 50000 |
| 98 | 4099.2 | 296 |
| 99 | 694.66 | 568 |
| 100 | 733.69 | 94 |
| 101 | 319.17 | 250 |
| 102 | 916.48 | 194 |
| 103 | 273.94 | 63 |
| 104 | 762.09 | 108 |
| 105 | 631.44 | 630 |
| 106 | 766.54 | 6565 |
| 107 | 10000 | 922 |
| 108 | 3331.7 | 105 |
| 109 | 9105.7 | 11321 |
| 110 | 3779.4 | 893 |
| 111 | 2805.9 | 1010 |
| 112 | 334.96 | 92 |
| 113 | 345.93 | 121 |
| 114 | 128.97 | 169 |
| 115 | 215.77 | 251 |
| 116 | 182.89 | 221 |
| 117 | 208.11 | 281 |
| 118 | 10000 | 75 |
| 119 | 199.58 | 684 |
| 120 | 445.1 | 54 |
| 121 | 49.136 | 118 |
| 122 | 273.52 | 178 |
| 123 | 162.4 | 66 |
| 124 | 141.41 | 189 |
| 125 | 75.808 | 96 |
| 126 | 149.37 | 89 |
| 127 | 147.82 | 573 |
| 128 | 850.98 | 597 |
| 129 | 138.43 | 412 |
| 130 | 362.76 | 90 |
| 131 | 380.73 | 51 |
| 132 | 1987.6 | 335 |
| 133 | 80.854 | 73 |
| 134 | 93.585 | 121 |
| 135 | 893.64 | 323 |
| 136 | 497.22 | 64 |
| 137 | 911.52 | 185 |
| 138 | 478.77 | 74 |
| 139 | 316.16 | 119 |
| 140 | 523.32 | 40 |
| 141 | 61.477 | 83 |
| 142 | 444.64 | 86 |
| 143 | 935.68 | 218 |
| 144 | 821.08 | 160 |
| 145 | 284.53 | 62 |
| 146 | 376.2 | 84 |
| 147 | 219.91 | 21 |
| 148 | 240.84 | 50 |
| 149 | 644.02 | 174 |
| 150 | 555.04 | 198 |
| 151 | 10000 | 3920 |
| 152 | 193.3 | 2405 |
| 153 | 10000 | 50000 |
| 154 | 10000 | 6236 |
| 155 | 354.32 | 461 |
| 156 | 198.61 | 57 |
| 157 | 199.71 | 35 |
| 158 | 195.23 | 103 |
| 159 | 242.49 | 86 |
| 160 | 257.43 | 98 |
| 161 | 447.76 | 217 |
| 162 | 220.19 | 60 |
| 163 | 178.77 | 92 |
| 164 | 169.19 | 52 |
| 165 | 363.23 | 116 |
| 166 | 396.99 | 137 |
| 167 | 416.64 | 188 |
| 168 | 328.93 | 91 |
| 169 | 614.81 | 144 |
| 170 | 289.16 | 114 |
| 171 | 332.93 | 88 |
| 172 | 352.96 | 107 |
| 173 | 344.94 | 87 |
| 174 | 418.66 | 75 |
| 175 | 301.88 | 89 |
| 176 | 255.56 | 71 |
| 177 | 458.57 | 126 |
| 178 | 342.2 | 181 |
| 179 | 243.89 | 133 |
| 180 | 7553.7 | 610 |
| 181 | 10000 | 50000 |
| 182 | 734.41 | 315 |
| 183 | 838.01 | 360 |
| 184 | 502.06 | 271 |
| 185 | 368.99 | 617 |
| 186 | 253.73 | 124 |
| 187 | 498.41 | 232 |
| 188 | 290.06 | 129 |
| 189 | 489.49 | 41 |
| 190 | 704.99 | 41 |
| 191 | 602.43 | 279 |
| 192 | 473.83 | 64 |
| 193 | 513.8 | 92 |
| 194 | 593.95 | 169 |

TABLE 4-continued

| No. | AC$_{50}$ PDL1 Dimer | EC$_{50}$ NFAT Luciferase |
|---|---|---|
| 195 | 437.96 | 48 |
| 196 | 434.26 | 95 |
| 197 | 412.83 | 68 |
| 198 | 331.55 | 125 |
| 199 | 361.43 | 61 |
| 200 | 593.43 | 100 |
| 201 | 250.63 | 181 |
| 202 | 330.42 | 47 |
| 203 | 602.8 | 121 |
| 204 | 415.43 | 70 |
| 205 | 423.98 | 73 |
| 206 | 509 | 59 |
| 207 | 367.58 | 52 |
| 208 | 446.16 | 41 |
| 209 | 442.05 | 18 |
| 210 | 250.74 | 123 |
| 211 | 161.64 | 74 |
| 212 | 284.89 | 189 |
| 213 | 942.18 | 458 |
| 214 | 345.44 | 536 |
| 215 | 287.86 | 154 |
| 216 | 566.87 | 191 |
| 217 | 295.45 | 98 |
| 218 | 267.04 | 154 |
| 219 | 136.53 | 144 |
| 220 | 443.54 | 180 |
| 221 | 425.01 | 186 |
| 222 | 567.51 | 134 |
| 223 | 667.4 | 305 |
| 224 | 613.37 | 245 |
| 225 | 299.81 | 117 |
| 226 | 559.43 | 368 |
| 227 | 318.49 | 65 |
| 228 | 337.06 | 96 |
| 229 | 320.33 | 201 |
| 230 | 627.52 | 284 |
| 231 | 317.88 | 49 |
| 232 | 377.77 | 117 |
| 233 | 472.96 | 353 |
| 234 | 212.85 | 37 |
| 235 | 306.18 | 45 |
| 236 | 213.57 | 54 |
| 237 | 301.81 | 52 |
| 238 | 363.63 | 337 |
| 239 | 1266 | 250 |
| 240 | 301.58 | 121 |
| 241 | 912.47 | 274 |
| 242 | 424.01 | 81 |
| 243 | 396.89 | 83 |
| 244 | 255.87 | 130 |
| 245 | 309.98 | 202 |
| 246 | 724.79 | 2078 |
| 247 | 366.02 | 156 |
| 248 | 408.37 | 138 |
| 249 | 10000 | 50000 |
| 250 | 253.1 | 929 |
| 251 | 261.95 | 50000 |
| 252 | 357.76 | 82 |
| 253 | 255.07 | 78 |
| 254 | 202.9 | 633 |
| 255 | 138.35 | 172 |
| 256 | 613.08 | 263 |
| 257 | 528.03 | 268 |
| 258 | 10000 | 3534 |
| 259 | 372.54 | 1977 |
| 260 | 869.26 | 1872 |
| 261 | 494.43 | 117 |
| 262 | 1383.3 | 1409 |
| 263 | 796.17 | 1060 |
| 264 | 806.91 | 1136 |
| 265 | 579.77 | 238 |
| 266 | 606.61 | 640 |
| 267 | 416.46 | 484 |
| 268 | 405.02 | 275 |
| 269 | 455.1 | 347 |
| 270 | 490.29 | 208 |
| 271 | 10000 | 50000 |
| 272 | 2199.5 | 1519 |
| 273 | 299.55 | 261 |
| 274 | 374.67 | 94 |
| 275 | 177.21 | 27 |
| 276 | 558.56 | 278 |
| 277 | 2992.8 | 616 |
| 278 | 1886.1 | 923 |
| 279 | 996.73 | 423 |
| 280 | 577.23 | 1093 |
| 281 | 1110.6 | 256 |
| 282 | 10000 | 352 |
| 283 | 810.85 | 203 |
| 284 | 928.54 | 520 |
| 285 | 636.77 | 156 |
| 286 | 233.86 | 101 |
| 287 | 911.62 | 5209 |
| 288 | 221.54 | 132 |
| 289 | 253.52 | 61 |
| 290 | 757.43 | 234 |
| 291 | 431.8 | 10913 |
| 292 | 329.88 | 205 |
| 293 | 768.18 | 243 |
| 294 | 510.87 | 267 |
| 295 | 528.13 | 217 |
| 296 | 351.75 | 95 |
| 297 | 404.21 | 223 |
| 298 | 343.89 | 126 |
| 299 | 320.99 | 122 |
| 300 | 509.06 | 175 |
| 301 | 852.36 | 311 |
| 302 | 351.12 | 156 |
| 303 | 564.3 | 173 |
| 304 | 589.38 | 391 |
| 305 | 390.28 | 102 |
| 306 | 417.73 | 138 |
| 307 | 366.17 | 70 |
| 308 | 376.22 | 152 |
| 309 | 392.45 | 84 |
| 310 | 391.31 | 173 |
| 311 | 318.45 | 158 |
| 312 | 476.32 | 176 |
| 313 | 637.34 | 426 |
| 314 | 311.4 | 77 |
| 315 | 110.9 | 52 |
| 316 | 219.01 | 85 |
| 317 | 625.74 | 169 |
| 318 | 197.44 | 87 |
| 319 | 10000 | 50000 |
| 320 | 186.69 | 111 |
| 321 | 934.73 | 1025 |
| 322 | 596.63 | 276 |
| 323 | 187.05 | 87 |
| 324 | 443 | 195 |
| 325 | 1664.9 | 50000 |
| 326 | 235.57 | 135 |
| 327 | 1194.4 | 150 |
| 328 | 10000 | 50000 |
| 329 | 647.48 | 223 |
| 330 | 10000 | 286 |
| 331 | 332.12 | 236 |
| 332 | 1070.4 | 50000 |
| 333 | 355.27 | 100 |
| 334 | 484.05 | 120 |
| 335 | 397.45 | 146 |
| 336 | 328.96 | 200 |
| 337 | 419.55 | 238 |
| 338 | 393.49 | 344 |
| 339 | 392.15 | 204 |
| 340 | 542.53 | 91 |
| 341 | 669.95 | 83 |
| 342 | 459.66 | 54 |
| 343 | 519.17 | 92 |
| 344 | 403.75 | 57 |
| 345 | 423.04 | 80 |
| 346 | 452.36 | 95 |
| 347 | 567.07 | 84 |
| 348 | 407.79 | 64 |

TABLE 4-continued

| No. | AC$_{50}$ PDL1 Dimer | EC$_{50}$ NFAT Luciferase |
|---|---|---|
| 349 | 268.4 | 151 |
| 350 | 5440.8 | 550 |
| 351 | 566.15 | 83 |
| 352 | 10000 | 2822 |
| 353 | 262.56 | 47 |
| 354 | 392.78 | 58 |
| 355 | 336.38 | 68 |
| 356 | 345.82 | 44 |
| 357 | 316.85 | 77 |
| 358 | 445.56 | 69 |
| 359 | 398.4 | 52 |
| 360 | 636.01 | 115 |
| 361 | 380.23 | 56 |
| 362 | 273.29 | 51 |
| 363 | 419.83 | 162 |
| 364 | 562.57 | 126 |
| 365 | 395.18 | 88 |
| 366 | 418.51 | 136 |
| 367 | 401.17 | 34 |
| 368 | 494.92 | 46 |
| 369 | 451.56 | 193 |
| 370 | 246.32 | 48 |
| 371 | 423.53 | 68 |
| 372 | 375.51 | 47 |
| 373 | 396.81 | 159 |
| 374 | 310.58 | 46 |
| 375 | 810.72 | 179 |
| 376 | 455.77 | 88 |
| 377 | 461.33 | 83 |
| 378 | 492.68 | 124 |
| 379 | 304.77 | 24 |
| 380 | 903.67 | 86 |
| 381 | 220.58 | 35 |
| 382 | 1018.8 | 173 |
| 383 | 438.4 | 321 |
| 384 | 1529.5 | 87 |
| 385 | 246.71 | 143 |
| 386 | 1139 | 1070 |
| 387 | 658.16 | 233 |
| 388 | 831.08 | 5277 |
| 389 | 711.54 | 98 |
| 390 | 537.01 | 110 |
| 391 | 412.01 | 64 |
| 392 | 418.26 | 116 |
| 393 | 10000 | 50000 |
| 394 | 10000 | 50000 |
| 395 | 10000 | 50000 |
| 396 | 10000 | 50000 |
| 397 | 3410.2 | 291 |
| 398 | 434.16 | 139 |
| 399 | 589.87 | 60 |
| 400 | 601.31 | 47 |
| 401 | 652.27 | 121 |
| 402 | 256.72 | 147 |
| 403 | 223.08 | 68 |
| 404 | 206.21 | 107 |
| 405 | 371.33 | 186 |
| 406 | 348.29 | 255 |
| 407 | 320.76 | 92 |
| 408 | 245.75 | 89 |
| 409 | 276.42 | 68 |
| 410 | 265.76 | 94 |
| 411 | 220.22 | 109 |
| 412 | 177.99 | 121 |
| 413 | 190.09 | 159 |
| 414 | 477.79 | 410 |
| 415 | 463.96 | 227 |
| 416 | 297.81 | 102 |
| 417 | 254.17 | 339 |
| 418 | 353.69 | 134 |
| 419 | 154.71 | 304 |
| 420 | 648.16 | 188 |
| 421 | 10000 | 50000 |
| 422 | 360.44 | 132 |
| 423 | 1137.7 | 216 |
| 424 | 5708.9 | 50000 |
| 425 | 689.58 | 230 |
| 426 | 465.34 | 98 |
| 427 | 567.52 | 107 |
| 428 | 533.99 | 178 |
| 429 | 539.48 | 133 |
| 430 | 426.93 | 76 |
| 431 | 301.45 | 56 |
| 432 | 221.18 | 249 |
| 433 | 411.65 | 95 |
| 434 | 138.15 | 31 |
| 435 | 119.7 | 27 |
| 436 | 252.11 | 114 |
| 437 | 248.47 | 41 |
| 438 | 1067.7 | 446 |
| 439 | 639.68 | 158 |
| 440 | 3589.1 | 1357 |
| 441 | 354.66 | 112 |
| 442 | 205.36 | 88 |
| 443 | 267.4 | 57 |
| 444 | 336.13 | 32 |
| 445 | 249.34 | 35 |
| 446 | 309.41 | 54 |
| 447 | 354.48 | 24 |
| 448 | 388.09 | 28 |
| 449 | 420.34 | 46 |
| 450 | 83.295 | 153 |
| 451 | 246.61 | 131 |
| 452 | 197.92 | 95 |
| 453 | 208.68 | 98 |
| 454 | 548.84 | 140 |
| 455 | 307.89 | 79 |
| 456 | 220.61 | 55 |
| 457 | 350.98 | 120 |
| 458 | 291.36 | 169 |
| 459 | 467.3 | 146 |
| 460 | 422.41 | 198 |
| 461 | 280.93 | 130 |
| 462 | 313.97 | 165 |
| 463 | 250.21 | 88 |
| 464 | 394.11 | 139 |
| 465 | 276.08 | 84 |
| 466 | 328.83 | 97 |
| 467 | 293.02 | 90 |
| 468 | 148.43 | 44 |
| 469 | 377.61 | 166 |
| 470 | 251.52 | 121 |
| 471 | 141.95 | 49 |
| 472 | 159.64 | 40 |
| 473 | 178.06 | 57 |
| 474 | 637.08 | 95 |
| 475 | 338.67 | 50 |
| 476 | 384.96 | 171 |
| 477 | 393.47 | 66 |
| 478 | 209.93 | 16 |
| 479 | 517.18 | 109 |
| 480 | 218.25 | 29 |
| 481 | 245.05 | 72 |
| 482 | 309.56 | 56 |
| 483 | 304.7 | 153 |
| 484 | 195.44 | 72 |
| 485 | 293.8 | 63 |
| 486 | 234.14 | 148 |
| 487 | 180.17 | 65 |
| 488 | 321.37 | 67 |
| 489 | 1160.7 | 43 |
| 490 | 1365.8 | 104 |
| 491 | 225.05 | 43 |
| 492 | 127.28 | 65 |
| 493 | 165.61 | 40 |
| 494 | 139.69 | 57 |
| 495 | 373.48 | 180 |
| 496 | 450.5 | 176 |
| 497 | 242.05 | 158 |
| 498 | 179.03 | 80 |
| 499 | 455.99 | 110 |
| 500 | 324.11 | 89 |
| 501 | 262.7 | 76 |
| 502 | 209.05 | 40 |

TABLE 4-continued

| No. | AC$_{50}$ PDL1 Dimer | EC$_{50}$ NFAT Luciferase |
|---|---|---|
| 508 | 193.02 | 80 |
| 509 | 179.77 | 81 |
| 510 | 161 | 41 |
| 511 | 198.59 | 60 |
| 512 | 255.73 | 127 |
| 513 | 155.63 | 141 |
| 514 | 187.1 | 135 |
| 515 | 326.79 | 162 |
| 516 | 277.85 | 68 |
| 517 | 282.44 | 100 |
| 518 | 318.12 | 151 |
| 519 | 438.99 | 71 |
| 520 | 179.81 | 82 |
| 521 | 126.14 | 50 |
| 522 | 209.96 | 79 |
| 523 | 268.2 | 84 |
| 524 | 274.9 | 54 |
| 525 | 322.25 | 43 |
| 526 | 307.95 | 155 |
| 527 | 238.19 | 92 |
| 528 | 187.07 | 76 |
| 529 | 157.29 | 104 |
| 530 | 392.15 | 100 |
| 531 | 449.69 | 74 |
| 532 | 271.56 | 68 |
| 533 | 156.78 | 37 |
| 534 | 153.8 | 46 |
| 535 | 156.47 | 60 |
| 536 | 234.37 | 99 |
| 537 | 160.28 | 46 |
| 538 | 559.01 | 99 |
| 539 | 314.53 | 63 |
| 540 | 401.53 | 46 |
| 541 | 345.59 | 80 |
| 542 | 275.46 | 83 |
| 543 | 199.23 | 62 |
| 544 | 1741.3 | 111 |
| 545 | 493.12 | 124 |
| 546 | 373.32 | 125 |
| 547 | 248.97 | 73 |
| 548 | 353.21 | 142 |
| 549 | 393.57 | 96 |
| 550 | 1165.1 | 148 |
| 551 | 358.35 | 92 |
| 552 | 352.37 | 169 |
| 553 | 425.98 | 122 |
| 554 | 240.08 | 130 |
| 555 | 379.07 | 106 |
| 556 | 513.98 | 74 |
| 557 | 313.91 | 115 |
| 558 | 210.24 | 50 |
| 559 | 261.43 | 66 |
| 560 | 433.11 | 162 |
| 561 | 203.15 | 31 |
| 562 | 473.43 | 58 |
| 563 | 545.94 | 98 |
| 564 | 330.63 | 58 |
| 565 | 326.42 | 90 |
| 566 | 293.18 | 63 |
| 567 | 227.96 | 21 |
| 568 | 646.29 | 164 |
| 569 | 593.64 | 153 |
| 570 | 427.87 | 184 |
| 571 | 259.53 | 96 |
| 572 | 351.82 | 130 |
| 573 | 257.44 | 75 |
| 574 | 310.5 | 150 |
| 575 | 227.13 | 73 |
| 576 | 432.38 | 187 |
| 577 | 90.285 | 63 |
| 578 | 267.8 | 198 |
| 579 | 448.31 | 165 |
| 580 | 306.36 | 194 |
| 581 | 187.05 | 149 |
| 582 | 135.62 | 121 |
| 583 | 53.288 | 65 |
| 584 | 84.945 | 115 |
| 585 | 492.38 | 129 |
| 586 | 469.53 | 85 |
| 587 | 496.67 | 105 |
| 588 | 390.01 | 58 |
| 589 | 307.89 | 99 |
| 590 | 676.48 | 56 |
| 591 | 195.23 | 28 |
| 592 | 246.23 | 43 |
| 593 | 246.65 | 82 |
| 594 | 239.11 | 21 |
| 595 | 117.9 | 17 |
| 596 | 215.39 | 32 |
| 597 | 281.77 | 31 |
| 598 | 174.83 | 60 |
| 599 | 189.42 | 99 |
| 600 | 137.66 | 34 |
| 601 | 268.53 | 88 |
| 602 | 217.64 | 73 |
| 603 | 195.39 | 159 |
| 604 | 254.67 | 34 |
| 605 | 256.04 | 60 |
| 606 | 203.59 | 74 |
| 607 | 142.37 | 36 |
| 608 | 379.95 | 18 |
| 609 | 396.2 | 56 |
| 610 | 227.28 | 73 |
| 611 | 233.34 | 145 |
| 612 | 282.68 | 19 |
| 613 | 377.69 | 92 |
| 614 | 169.8 | 63 |
| 615 | 294.52 | 144 |
| 616 | 188.86 | 60 |
| 617 | 309.56 | 74 |
| 618 | 205.79 | 27 |
| 619 | 223.42 | 102 |
| 620 | 154.07 | 143 |
| 621 | 224.96 | 71 |
| 622 | 231.74 | 79 |
| 623 | 192.23 | 94 |
| 624 | 163.79 | 39 |
| 625 | 129.55 | 32 |
| 626 | 263.43 | 25 |
| 627 | 189.61 | 58 |
| 628 | 171.09 | 53 |
| 629 | 157.06 | 14 |
| 630 | 200.17 | 40 |
| 631 | 130.42 | 25 |
| 632 | 229.73 | 47 |
| 633 | 233.21 | 46 |
| 634 | 232.31 | 14 |
| 635 | 134.19 | 50 |
| 636 | 180.16 | 25 |
| 637 | 243.34 | 42 |
| 638 | 98.219 | 42 |
| 639 | 563.95 | 31 |
| 640 | 525.75 | 50 |
| 641 | 64.437 | 44 |
| 642 | 60.016 | 31 |
| 643 | 44.34 | 48 |
| 644 | 35.75 | 48 |
| 645 | 36.462 | 49 |
| 646 | 66.651 | 48 |
| 647 | 51.449 | 37 |
| 648 | 287.34 | 38 |
| 649 | 220.43 | 21 |
| 650 | 76.27 | 35 |
| 651 | 68.737 | 26 |
| 652 | 104.79 | 46 |
| 653 | 64.175 | 15 |
| 654 | 142.04 | 39 |
| 655 | 154.84 | 50 |
| 656 | 199.94 | 43 |
| 657 | 274.75 | 21 |
| 658 | 253.78 | 49 |
| 659 | 306.76 | 39 |
| 660 | 663.58 | 39 |
| 661 | 356.06 | 30 |

TABLE 4-continued

| No. | AC$_{50}$ PDL1 Dimer | EC$_{50}$ NFAT Luciferase |
|---|---|---|
| 662 | 688.81 | 36 |
| 663 | 618.38 | 49 |

Biological Example 2

In Vitro Activity of Compound 139 on HBV-Specific T Cells from CHB Patient PBMCs This example shows the effect of compound 139 on HBV-specific T cell function in peripheral blood mononuclear cells obtained from chronic hepatitis B (CHB) patients. Inhibition of the interaction between programmed death 1 (PD-1) with its ligand (PD-L1) with specific monoclonal antibodies has been reported to enhance the antiviral function of HBV-specific T cells. This study evaluated the ability of a PD-L1 inhibitor described herein (i.e., compound 139), to enhance HBV-specific T cell functions in peripheral blood mononuclear cells (PBMC) isolated from chronic hepatitis B (CHB) patients. PBMCs from CHB patients were treated for 6 days with compound 139 or DMSO in the presence of HBV core peptides, followed by re-stimulation for 16 hours before analysis of CD8$^+$ and CD4$^+$ T cells by flow cytometry. Compared to DMSO-treated controls, treatment with compound 139 increased the percentage of interferon-γ (IFN-γ)$^+$ CD8$^+$ T cells by 2.5 fold (p=0.01) and IFN-γ+CD4$^+$ T cells by 2.5 fold (p=0.003). Compound 139 also significantly increased the expression of granzyme B (GrB) in HBV-specific CD8$^+$ T cells by 1.2 fold (p=0.015) and in CD4$^+$ T cells by 1.8 fold (p=0.045). The increases in IFN-γ and GrB production in CD8$^+$ T cells following treatment with compound 139 was comparable to those induced by durvalumab, a marketed anti-PD-L1 monoclonal antibody. These data demonstrate that compound 139 enhances the antiviral function of HBV-specific CD8$^+$ and CD4$^+$ T cells from CHB patients in vitro to a degree comparable to anti-PD-L1 monoclonal antibodies.

Materials and Methods

Compounds

Compound 139 was dissolved in 100% DMSO to prepare a 10 mM stock solution and stored at −20° C. The anti-PD-L1 Ab durvalumab was produced and purified at Gilead Sciences. In all assays, compound 139 was evaluated at the dose of 650 nM, which is 2× concentration above the EC$_{90}$ value as determined in a human blood polyclonal activation assay. Durvalumab (durva) was used at 10 μg/mL concentration as per previously reported studies (Boni et al. *J Virol*, 2007; 81(8); 4215-4225).

Whole Blood from CHB Donors

CHB donors were sourced by C&M LabPro, LLC (San Francisco, Calif.), MT Group, Inc. (Van Nuys, Calif.), and BioIVT (Westbury, N.Y.). Whole blood from CHB donors was drawn into K2 EDTA Tubes (Becton Dickinson, Franklin Lakes, N.J.) and shipped overnight to Gilead Sciences, Inc. PBMCs from the blood samples were isolated at Gilead Sciences using the protocol described below. Table 5 summarizes HBV s antigen (HBsAg) and HBV e antigen (HBeAg) reactivity as well as demographic data for the CHB patients in this study.

TABLE 5

CHB Patient Demographics.

| Donor ID# | HBsAg | HBeAg | Age | Sex |
|---|---|---|---|---|
| 1 | + | + | 74 | M |
| 2 | + | − | 59 | M |
| 3 | + | n/a | 36 | F |
| 4 | + | − | 65 | M |
| 5 | + | + | 63 | F |
| 6 | + | n/a | 67 | F |
| 7 | + | − | 53 | F |
| 8 | + | + | 59 | M |
| 9 | + | − | 44 | F |
| 10 | + | − | 69 | M |
| 11 | + | − | 48 | M |
| 12 | + | − | 55 | M |
| 13 | + | + | 49 | F |
| 14 | + | n/a | 48 | M | n/a = not available

Assays

PBMC Isolation from Whole Blood

PBMCs were isolated from whole blood using a standard Ficoll® Paque gradient. Briefly, 25-30 mL of blood was gently overlaid on top of 15 mL Ficoll® Paque Plus solution (GE Healthcare, Chicago, Ill.) in a 50 mL Falcon tube, and centrifuged in an Allegra X-14R (Beckman Coulter, Indianapolis, Ind.) at 520 g for 20 minutes at 25° C. The mononuclear cell layer was washed twice with PBMC wash buffer (RPMI Medium 1640-GlutaMAX-I (Life Technologies, Carlsbad, Calif.)) supplemented with 10% heat-inactivated Fetal Bovine Serum (FBS; Hyclone, Logan, Utah). Next, the cells were centrifuged at 520 g for 5 minutes and red blood cells (RBC) lysed for 5 minutes at room temperature using RBC Lysis Buffer (eBioscience, San Diego, Calif.). After a final wash with PBMC wash buffer, the cells were resuspended in cell culture medium consisting of RPMI 1640 culture medium supplemented with 25 mM HEPES (Life Technologies), 100 U/mL Penicillin/Streptomycin (Sigma Aldrich, St Louis, Mo.), lx non-essential amino acids (Life Technologies, Carlsbad, Calif.), 10% FBS, and 20 U/mL interleukin-2 (IL-2) (Miltenyi Biotec, Sunnyvale, Calif.) before cell number and viability were determined using trypan blue (VWR, Radnor, Pa.) exclusion. PBMCs were either subsequently used for the T cell expansion assay, or were cryopreserved with 10% DMSO in FBS before further use.

CD8$^+$ and CD4$^+$ T Cell 7-Day Expansion and Recall Response Assay

PBMCs were seeded at 2-4×10$^5$ cells/well in 96-well round bottom plates (Corning, N.Y.). A pool of 15-mer 11-amino acid (AA) overlapping peptides spanning the entire HBV core sequence was added at 100-300 ng/mL concentration in the presence of 650 nM compound 139, or 10 μg/mL durvalumab, or the equivalent volume of DMSO (Sigma Aldrich). PBMCs were incubated for 7 days at 37° C. with 5% CO$_2$ in a humidified incubator. Cell culture medium (as described above) was replenished with fresh medium containing IL-2 (without peptides, compound 139, or durvalumab) after 4 days. On Day 6, PBMCs were re-stimulated by the addition of 100-300 ng/mL HBV core peptides, or DMSO. Compound 139 or durvalumab was also added during the re-stimulation. To inhibit protein transport, 1 μg/mL brefeldin. A solution (Sigma) was added to each well. After overnight incubation, cells were processed for immunostaining and flow cytometry as described herein.

Immunostaining and Flow Cytometry

After re-stimulation overnight with the peptide pool and compound 139 or durvalumab, PBMCs were pelleted by centrifugation on Day 7 and washed twice with PBS. Washed cells were resuspended in Live/Dead Aquamine Stain (Invitrogen) per manufacturer's instructions to determine the viability of the cells by flow cytometry. Live/Dead Aqua stained PBMCs were washed twice with FACS staining buffer (1% FBS in PBS), and then incubated with 50 µL of Fc blocking reagent (BD Biosciences, Franklin Lakes, N.J.) for 10 minutes at room temperature. A mixture of antibodies (50 µL/well) described in Table 6 were added to the blocking solution for surface staining, and PBMCs were incubated with the antibodies for 40 minutes at 4° C. PBMCs were pelleted by centrifugation as described above and washed twice with FACS buffer, followed by fixation with 1× FoxP3 Fix/Perm buffer (eBioscience) for 1 hour. Cells were washed twice with the permeabilization reagent included in the FoxP3 staining kit and incubated with antibodies for intracellular staining of IFN-γ and GrB (Table 6) at 1.0 µg/mL. After 1 hour incubation at 4° C., PBMCs were centrifuged and washed twice before being resuspended in FACS buffer. Stained PBMCs were analyzed by flow cytometry using a BD LSRFortessa X-20 Cell Analyzer (Becton Dickinson). BD Comp Beads (BD Biosciences) were used as compensation controls. $CD8^+$ and $CD4^+$ T cells were identified by gating on the live Aquamine $^-CD3^+CD8^+$ and Aquamine-$CD3^+CD4^+$ PBMC population respectively.

TABLE 6

Flow Cytometry Antibodies

| Antibody | Fluorophore | Clone | Supplier |
|---|---|---|---|
| CD3 | Percp-Cy5.5 | UCHT1 | BD Biosciences |
| CD4 | BV650 | SK3 | BD Biosciences |
| CD8 | BV605 | SK1 | BD Biosciences |
| Granzyme B | Alexa Fluor ® 647 | GB11 | BD Biosciences |
| IFN-γ | APC-Cy7 | B27 | BioLegend ® |

Data Analysis

Flow cytometry data was analyzed using FlowJo Flow Cytometry Analysis Software v10 (TreeStar, Ashland, Oreg.). Data was exported and statistical analysis was performed using GraphPad Prism v6 (GraphPad Software, La Jolla, Calif.). Statistical significance relative to the DMSO control was calculated by two-tailed, paired t-test.

Results

To evaluate the effects of compound 139 on the activation of HBV-specific T cells, PBMCs isolated from 14 CHB donors were stimulated with a pool of 15-mer peptides spanning the HBV core sequence. During peptide stimulation, PBMCs were treated with compound 139 (650 nM) or vehicle control (DMSO) for 6 days. After 6 days of peptide stimulation and treatment with compound 139, PBMCs were re-stimulated for 16 hours with fresh peptides and compound 139 or DMSO. As surrogates of effector function, intracellular levels of IFN-γ (antiviral cytokine) and GrB (a marker of cytotoxic function) were measured by flow cytometry in CD3+CD8$^+$ and CD3+CD4$^+$ T cell populations.

In HBV core peptide-stimulated PBMCs isolated from 14 CHB donors, compound 139 significantly increased the frequencies of both IFN-γ$^+$ (2.5-fold, p=0.01) and GrB$^+$ (1.2-fold, p=0.015) CD8$^+$ T cells, as compared with DMSO treated PBMCs (FIG. 1A and Table 7). For control purposes, durvalumab, a marketed monoclonal α-PD-L1 antibody, was also tested in PBMCs isolated from 9 out of the 14 CHB donors. We found that both compound 139 and durvalumab induced a comparable increase of IFN-γ$^+$ CD8$^+$ T cells (2.5-fold versus 2.7-fold, respectively, p=0.21) and GrB$^+$ CD8$^+$ T cells (1.2-fold versus 1.1-fold, respectively, p=0.53) (FIG. 1B and Table 7). These data agree with a previous report where IFN-γ$^+$ cells in CD8$^+$ T and CD4+ T cells were enhanced by 1.8- to 8.2-fold (p=0.028) and 2.2- to 4.3-fold (p=0.01) respectively in 8 responsive patients out of 24 total patients after in vitro treatment with an α-PD-L1 antibody (Fisicaro et al., Gastroenterology, 2010; 138(2): 682-693, 93 e1-4).

TABLE 7

Compound 139 Enhances IFN-γ and Granzyme B Production in CHB CD8$^+$ T Cells.

| | IFN-γ$^+$ CD8$^+$ T cells | | | | | GrB$^+$ CD8$^+$ T cells | | | | |
|---|---|---|---|---|---|---|---|---|---|---|
| | % IFN-γ$^+$ | | | Fold change over DMSO | | % GrB$^+$ | | | Fold change over DMSO | |
| Donor ID# | DMSO | Cmpd 139 | Durva[1] | Cmpd 139 | Durva | DMSO | Cmpd 139 | Durva | Cmpd 139 | Durva |
| 1 | 0.94 | 1.53 | n.d.[2] | 1.63 | n.d. | 33.40 | 32.30 | n.d. | 0.97 | n.d. |
| 2 | 1.85 | 2.63 | n.d. | 1.42 | n.d. | 47.30 | 47.80 | n.d. | 1.01 | n.d. |
| 3 | 0.26 | 0.94 | n.d. | 3.62 | n.d. | 5.27 | 8.78 | n.d. | 1.67 | n.d. |
| 4 | 0.04 | 0.41 | 0.36 | 11.08 | 9.73 | 38.80 | 50.30 | 47.20 | 1.30 | 1.22 |
| 5 | 0.20 | 0.61 | n.d. | 3.00 | n.d. | 14.31 | 30.67 | n.d. | 2.14 | n.d. |
| 6 | 1.45 | 3.06 | 3.99 | 2.12 | 2.76 | 24.80 | 28.15 | 17.70 | 1.14 | 0.71 |
| 7 | 0.94 | 0.90 | 1.20 | 0.95 | 1.27 | 23.93 | 24.10 | 22.93 | 1.01 | 0.96 |
| 8 | 0.79 | 3.28 | 0.85 | 4.13 | 1.07 | 38.02 | 45.05 | 47.23 | 1.18 | 1.24 |
| 9 | 3.90 | 4.69 | n.d. | 1.20 | n.d. | 19.30 | 20.20 | n.d. | 1.05 | n.d. |
| 10 | 0.20 | 0.30 | 0.73 | 1.46 | 3.61 | 30.07 | 33.50 | 31.77 | 1.11 | 1.06 |
| 11 | 6.69 | 7.74 | 8.18 | 1.16 | 1.22 | 50.83 | 52.67 | 56.20 | 1.04 | 1.11 |
| 12 | 1.56 | 1.86 | 2.98 | 1.19 | 1.91 | 18.70 | 18.93 | 27.25 | 1.01 | 1.46 |
| 13 | 5.60 | 4.69 | 7.58 | 0.84 | 1.35 | 22.17 | 23.23 | 28.40 | 1.05 | 1.28 |
| 14 | 8.42 | 11.17 | 14.16 | 1.33 | 1.68 | 35.83 | 55.80 | 35.80 | 1.56 | 1.00 |
| Average ± SD | 2.35 ± 2.71 | 3.13 ± 3.12 | 4.45 ± 4.67 | 2.51 ± 2.67 | 2.73 ± 2.75 | 28.77 ± 12.78 | 33.68 ± 14.46 | 34.94 ± 12.78 | 1.23 ± 0.34 | 1.11 ± 0.22 |

[1] Durva = Durvalumab
[2] n.d. = not done

Additionally, treatment of CD4+ T cells with compound 139 significantly enhanced the frequency of HBV-specific IFN-γ+ cells (2.5 fold, p=0.003) and GrB+ cells (1.8 fold, p=0.045) over DMSO-treated PBMCs (FIG. 2A and Table 8). The frequencies of CD4+ IFN-γ+ T cells between compound 139 and durvalumab treated PBMCs were not statistically significant (2.5% versus 3.1% respectively; p=0.2018). Compound 139 and durvalumab also enhanced the frequency of GrB+ CD4+ T cells to similar levels (4.7% versus 4.3% respectively, p=0.07) (FIG. 2B), as compared with DMSO treatment (3.5%) (Table 8).

139 blocks the interaction between mouse PD-1 and human PD-L1 as determined by a biochemical binding assay. Therefore, a human PD-L1-expressing MC38 mouse colorectal tumor model was utilized to evaluate the activity of compound 139 in vivo. An α-PD-L1 antibody that is unable to bind to murine PD-L1 was included as a positive control.

At 10, 25, and 50 mg/kg compound 139 or 10 mg/kg PD-L1 antibody, >90% PD-L1 target occupancy (TO) on the tumor cells was observed for at least 24 hours. This result translated to similar tumor growth inhibition (TGI) of 32% to 38% for both compound 139 and PD-L1 antibody at

TABLE 8

Compound 139 Enhances IFN-γ and Granzyme B Production in CHB CD4+ T Cells.

| | IFN-γ+ CD4+ T cells | | | | | GrB+ CD4+ T cells | | | | |
|---|---|---|---|---|---|---|---|---|---|---|
| | % IFN-γ+ | | | Fold change over DMSO | | % GrB+ | | | Fold change over DMSO | |
| Donor ID# | DMSO | Cmpd 139 | Durva[1] | Cmpd 139 | Durva | DMSO | Cmpd 139 | Durva | Cmpd 139 | Durva |
| 1 | 0.94 | 1.53 | n.d.[2] | 1.63 | n.d. | 5.79 | 4.91 | n.d. | 0.85 | n.d. |
| 2 | 7.78 | 9.22 | n.d. | 1.19 | n.d. | 12.8 | 15.2 | n.d. | 1.19 | n.d. |
| 3 | 0.56 | 1.39 | n.d. | 2.48 | n.d. | 0.60 | 3.80 | n.d. | 6.33 | n.d. |
| 4 | 0.29 | 1.42 | 5.38 | 4.90 | 18.55 | 2.27 | 5.63 | 7.88 | 2.48 | 3.47 |
| 5 | 0.11 | 0.79 | n.d. | 7.48 | n.d. | 4.05 | 7.76 | n.d. | 1.92 | n.d. |
| 6 | 0.24 | 0.41 | 3.41 | 1.73 | 14.39 | 0.74 | 0.93 | 0.55 | 1.25 | 0.74 |
| 7 | 0.23 | 1.40 | 0.44 | 6.18 | 1.95 | 0.82 | 0.88 | 1.53 | 1.07 | 1.87 |
| 8 | 0.85 | 0.94 | 1.18 | 1.11 | 1.39 | 1.28 | 2.43 | 1.25 | 1.89 | 0.97 |
| 9 | 1.01 | 1.76 | n.d. | 1.74 | n.d. | 2.96 | 3.72 | n.d. | 1.26 | n.d. |
| 10 | 3.09 | 2.83 | 2.94 | 0.92 | 0.95 | 5.83 | 3.27 | 3.74 | 0.56 | 0.64 |
| 11 | 0.45 | 0.61 | 0.60 | 1.37 | 1.33 | 2.27 | 3.98 | 3.89 | 1.75 | 1.72 |
| 12 | 0.29 | 0.54 | 0.51 | 1.86 | 1.74 | 3.84 | 6.04 | 9.17 | 1.57 | 2.38 |
| 13 | 6.33 | 6.83 | 8.24 | 1.08 | 1.30 | 4.51 | 5.21 | 7.60 | 1.16 | 1.69 |
| 14 | 4.03 | 5.64 | 4.97 | 1.40 | 1.23 | 0.72 | 1.44 | 3.49 | 2.01 | 4.86 |
| Average ± SD | 1.87 ± 2.49 | 2.52 ± 2.72 | 3.07 ± 2.71 | 2.51 ± 2.10 | 4.76 ± 6.73 | 3.46 ± 3.25 | 4.66 ± 3.63 | 4.34 ± 3.15 | 1.81 ± 1.40 | 2.04 ± 1.38 |

[1]Durva = durvalumab;
[2]n.d. = not done

Conclusion

Compound 139 significantly increased the frequencies of HBV-specific IFN-γ+ cells in both CD4+ (2.5-fold, p=0.01) and CD8+ T cells (2.5-fold, p=0.003). Compound 139 also enhanced the frequency of GrB+ cells among HBV-specific CD8+ (1.2 fold, p=0.015) and CD4+ T cells (1.8 fold, p=0.045). Furthermore, the ability of compound 139 to enhance the antiviral functions of HBV-specific CD8+ and CD4+ T cells in vitro was comparable to those of durvalumab, a marketed α-PD-L1 antibody. Taken together, these data indicate that compound 139 enhances the antiviral/effector functions of HBV-specific CD8+ and CD4+ T cells from CHB patients in vitro.

Biological Example 3

Pharmacologic Assessment in Mouse Tumor Model

The compounds described herein are small molecule PD-L1 inhibitors that block the PD-1/PD-L1 interaction through a mechanism of action that is distinct from the clinically approved monoclonal antibodies The objective of this study was to assess the relationship of pharmacokinetics (PK), TO and anti-tumor activity of compound 139 in a human PD-L1 expressing MC38 mouse colorectal tumor model.

Compound 139 does not bind murine PD-L1, precluding the use of traditional syngeneic murine tumor models to assess compound 139 activity in vivo. However, compound indicated dose groups. In parallel, compound 139 plasma concentrations were determined at the same time points used to determine intratumoral TO. At 10 mg/kg, compound 139 plasma concentrations dropped below the whole blood $EC_{90}$ value for compound 139 but >90% TO was retained, indicating that compound 139 TO on the tumor extended beyond plasma exposure. Moreover, there was no treatment-related effect on body weight, indicating compound 139 was well-tolerated at all doses for the entire study.

Materials and Methods

Test Articles

Compound 139 was synthesized at Gilead Sciences, Inc. (Foster City, Calif.). Durvalumab; α-PD-L1 antibody and Isotype control antibody (human IgG1, hIgG1) were produced and purified at Gilead Sciences.

In Vivo Formulation of Compound 139

The vehicle formulation for compound 139 was 10% ethanol, 40% PEG 300 and 50% DI water and was formulated in a single batch for the entire study. Compound 139 formulations were prepared weekly and stored under refrigerated conditions (4° C.-8° C.). Before dosing, the solution was warmed to room temperature while stirring. Solution was stirred constantly during the whole process of dosing. Compound 139 was formulated as a 2 mg/mL and 5 mg/mL solution in the vehicle. Compound 139 powder was brought to room temperature before use, weighed and added to a suitable container. Appropriate volume of ethanol was dispensed into the container. Next, an appropriate volume of PEG-300 was added to the container while stirring. Once the powder was fully dissolved, an appropriate volume of water was slowly added while stirring. The powder was allowed to fully dissolve in solution and the pH was adjusted to 3 using 1 N NaOH. The solution was sterile filtered using a nylon syringe filter before administration.

In Vivo Formulation of Durvalumaband Isotype Control Antibody

The isotype control antibody (hIgG1) contains the same mutation in the Fc domain as durvalumab α-PD-L1 antibody. Isotype control antibody and durvalumab stock solutions (20 mM Histidine-HCl pH 5.8, 9% Sucrose and 0.05% Tween-80) were diluted in PBS to 2 mg/mL. The dosing volume was 5 mL/kg.

Animals

Female C57BL/6 mice were purchased from Shanghai Lingchang Bio-Technology. Animals were between 8 to 10 weeks when tumors were inoculated. Mice were acclimated for 1 week before tumor inoculation.

Human PD-L1-Expressing MC38 Colorectal Tumor Model

To create a human PD-L1-expressing MC38 tumor cell line (Crown Bioscience), murine PD-L1 knockout cells were generated by using the CRISPR-Cas9 system (FIG. 3). Stable clones expressing human PD-L1 (driven by a cytomegalovirus promoter) were then generated from knockout cells by lipofectamine (Thermo Fisher Scientific) transfection.

Cell Culture

Human PD-L1-expressing MC38 tumor cells were cultured in DMEM medium (GE Healthcare) supplemented with 10% heat-inactivated fetal bovine serum (ExCell Biology) and 50 µg/mL hygromycin B at 37° C. in an atmosphere of 5% $CO_2$ in air.

Tumor Inoculation

Before inoculation, human PD-L1-expressing MC38 tumor cells were measured by trypan blue staining to assess viability. Cells with viability greater than 90% were used for inoculation. Each mouse was inoculated subcutaneously (SC) at the right hind flank with the tumor cells ($1\times10^6$ cells suspended in 100 µL PBS for each mouse). After inoculation, the remaining cells were measured by trypan blue staining again for viability to confirm viability did not drop below 90%.

Group Randomization 108 mice were enrolled in the study. All animals were randomly allocated to the study groups. Day 0 was defined as the time when mean tumor size at randomization was approximately 50 mm$^3$ and mice weighted between 17 to 20 grams. Randomization was performed based on "Matched Distribution" randomization method using multi-task method (StudyDirector™ software, version 3.1.399.19).

Animal Observation and Tumor Measurement

After tumor cell inoculation, the animals were checked daily for morbidity and mortality. During routine monitoring, the animals were checked for any effects of tumor growth, changes with behavior such as mobility, food and water consumption, body weight gain/loss (body weights were measured twice per week), and any gross abnormalities. Mortality and observed clinical signs were recorded for individual animals. Body weight was measured twice per week.

Tumor volumes were measured twice weekly in two dimensions using a caliper, and the volume was expressed in mm$^3$ using the formula: $V=(L\times W\times W)/2$, where V is tumor volume, L is tumor length (the longest tumor dimension) and W is tumor width (the longest tumor dimension perpendicular to L).

Termination

Any animal with tumor size exceeding 2500 mm$^3$ (or group of mice with mean tumor size exceeding 2000 mm$^3$) was euthanized.

In Vivo TO on Human PD-L1-Expressing MC38 Tumor Cells

Tumor Dissociation

Tumors were collected from mice, washed in PBS with extra tissues removed (i.e. blood vessel, fat and fascia). In each well of a sterile 6-well plate (Corning), the tumor was placed in 3 mL of dissociation media (Murine Tumor Dissociation Kit, Miltenyi). Tumors were held in place with sterile tweezers and forceps and sliced with a scalpel until small tumor pieces of ~1 mm$^3$ were obtained. Tumor pieces were then transferred to gentleMACS C tubes (Miltenyi) and placed on ice until digestion. Once all the tumors had been sliced, C tubes were transferred to gentleMACS Octo Dissociator with Heaters (Miltenyi). Dissociation program (37_c m_TDK_1) was selected for tumor digestion. After completion of the program, C tubes were spun down at 300×g. Samples were re-suspended and added to a cell strainer (Corning) placed above a 50 mL centrifuge tube (Corning). Cells were washed through the cell strainer with 10 mL of wash buffer (10% FBS, Gibco; 40 mM EDTA, Boston BioProducts; PBS without calcium and magnesium, GE Healthcare) to obtain single cell suspensions. The tubes were then centrifuged at 300 g for 5 minutes. Supernatants were removed and cells were counted and adjusted to $1\times10^6$ per tube in Staining Buffer (BD Biosciences).

Assessment of TO on Tumor $1\times10^6$ cells from tumor were re-suspended in 15 mL centrifuge tubes (Corning) with 200 µL of Staining Buffer (BD Biosciences) and 1 µg/mL Mouse Fc Block (Purified rat α-mouse CD16/CD32, BD Biosciences). Tubes were incubated for 15 mins in the dark at 4° C. Antibody cocktail (Table 9) was added to each tube and further incubated for 30 mins in the dark at 4° C. 2 mL of ice cold PBS was added and tubes were centrifuged at 300×g for 5 mins. The wash step was performed twice. After discarding the supernatants from the last wash, cell pellets were re-suspended in 200 µL of Fixation/Permeabilization working solution (Thermo Fisher Scientific) for 10 minutes at room temperature in the dark. Tubes were centrifuged at 300×g for 5 minutes and supernatants were removed. Cells were resuspended with 150 µL of Staining Buffer and data was acquired on LSR-Fortessa X-20 (BD Biosciences).

TABLE 9

Flow Cytometry Reagents to Determine TO

| Markers | Fluorochrome | Clone | Catalogue # | Isotype | Vender |
|---|---|---|---|---|---|
| Mouse BD Fc Block | | 2.4G2 | 553141 | Rat IgG2b, κ | BD |

TABLE 9-continued

Flow Cytometry Reagents to Determine TO

| Markers | Fluorochrome | Clone | Catalogue # | Isotype | Vender |
|---|---|---|---|---|---|
| CD45 | BUV661 | 30-F11 | 565079 | Rat IgG2b,κ | BD |
| CD3 | BUV395 | 145-2C11 | 563565 | Hamster IgG1, κ | BD |
| CD11b | BV605 | M1/70 | 101257 | Rat IgG2b,κ | Biolegend |
| Human PD-L1 | PE-Cyanine7 | MIH1 | 25-5983-42 | Mouse IgG1,κ | Thermo Fisher |
| Fixable Viability Dye | eFluor-506 (BV510) | NA | 65-0866-14 | NA | Thermo Fisher |

Plasma Concentration Analysis of Compound 139

In parallel to the assessment of TO on tumor cells at the pre-determined time points, 100 μL of WB was collected into K$_2$EDTA lavender tubes (BD Biosciences), mixed by inverting and subjected to centrifugation. Plasma was transferred to labeled microcentrifuge tubes and stored at −80° C. until analysis.

To a 10 μL aliquot of each plasma sample with exception of the matrix blanks, 60 μL of 100 ng/mL Carbutamide in acetonitrile (ACN) was added. The matrix blank samples received 60 μL of acetonitrile only. The precipitated proteins were removed by centrifugation and 50 μL of supernatant was transferred into a clean 96 deep-well plate (Thermo Fisher Scientific). A 50 μL aliquot of water was added to each sample. An aliquot of 5 μL was injected into a Sciex API-5500 LC/MS/MS system.

Data Analysis

Calculation of Compound 139 TO on Tumor

TO of compound 139 or durvalumab, α-PD-L1, antibody was calibrated using tumor-bearing mice treated with either vehicle or isotype control antibody using the following equation:

$$TO = \frac{(\text{Average Control Group } MFI - \text{Average Sample } MFI) * 100}{(\text{Average Control Group } MFI)}$$

where:

TO is the Target occupancy (i.e., % PD-L1 occupied);

Average Sample MFI is the Mean fluorescence intensity averaged from tumors treated with either compound 139 or durvalumab, α-PD-L1 antibody (n=3); and Average Control Group MFI is the Mean fluorescence intensity averaged from tumors treated either with vehicle or isotype control antibody (n=3).

Calculation of Compound 139 TGI in Human PD-L1-Expressing MC38 Tumor Model

TGI of compound 139 or durvalumab α-PD-L1 antibody groups was calibrated using tumor volumes obtained from either vehicle or isotype control antibody groups on day 15 post dosing using the following equation:

$$TGI = \frac{(\text{Average Control Group Tumor Volume} - \text{Average Sample Tumor Volume}) * 100}{(\text{Average Control Group Tumor Volume})}$$

where:

TGI is the % of tumor growth inhibition;

Average Control Group Tumor Volume is the Mean tumor volume averaged from vehicle or isotype control antibody treated groups (n=12); and Average Sample Tumor Volume is the Mean tumor volume averaged from compound 139 or durvalumab α-PD-L1 antibody treated groups (n=12).

Results

This example demonstrated that compound 139 can block the interaction between mouse PD-1 and human PD-L1 in a functional biochemical binding assay with a potency of <0.75 nM (Table 10). Therefore, a human PD-L1-expressing MC38 colorectal tumor model was utilized to demonstrate the activity of compound 139 in vivo.

TABLE 10

Activity of Compound 139 and durvalumab Against Mouse PD-1/Human PD-L1 Interaction

| | Blockade of PD-1 and PD-L1 binding (IC$_{50}$) | | |
|---|---|---|---|
| | Human (nM) | Mouse (μM) | Mouse PD-1/ Human PD-L1 (nM) |
| Compound 139 | <0.15$^a$ | 61 | <0.75$^a$ |
| durvalumab α-PD-L1 antibody | <0.15$^a$ | >1 | <0.75$^a$ |

$^a$Values have been rounded to the theoretical bottom of the assay.

Relationship Between PK, Target Occupancy and Anti-Tumor Activity

The objective of this study was to assess the relationship between PK and TO of compound 139, as well as changes in body weight and tumor volume. Human PD-L1 MC38 tumor cells were implanted sSC) into the right flank of female C57BL/6 mice. Once tumors reached a mean volume of about 50 mm$^3$, mice were randomized and treatment administered as an IP injection.

Figure 4B:
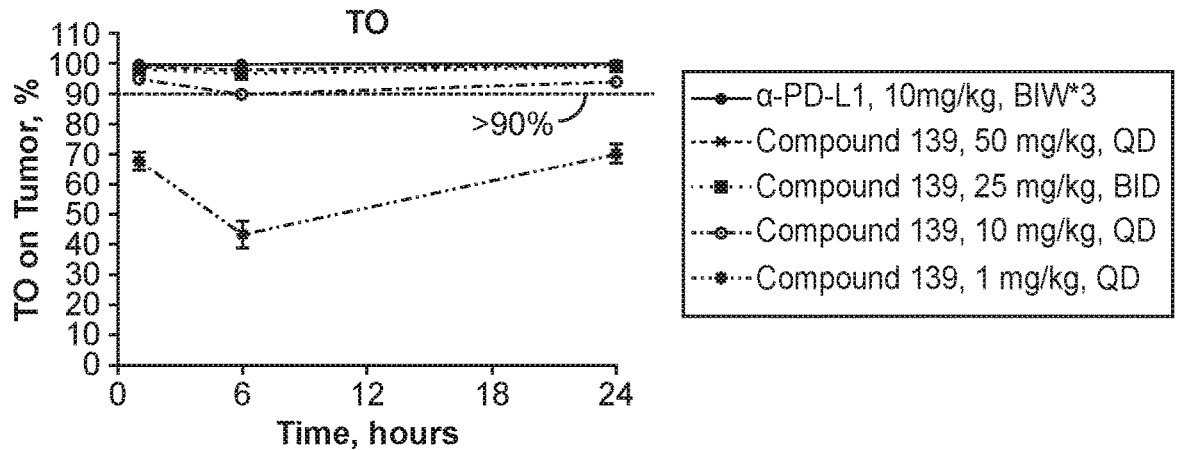

Compound 139 plasma concentration was determined at 1, 6 and 24 hours post dosing on day 6 when tumors were ~250 mm$^3$ in size (Table 12). In parallel, TO was measured at those same time points and evaluated by flow cytometry, measured as a reduction in PD-L1 MFI and normalized to either vehicle or isotype control. At 10, 25, and 50 mg/kg, compound 139 or 10 mg/kg durvalumab, a α-PD-L1 antibody, greater than 90% TO was observed for the duration of 24 hours post dosing (Table 13). For the 10 mg/kg dose (FIG. 4A), when compound 139 plasma concentration dropped below the whole blood EC$_{90}$ value, greater than 90% TO was retained (FIG. 4B).

Figure 5:
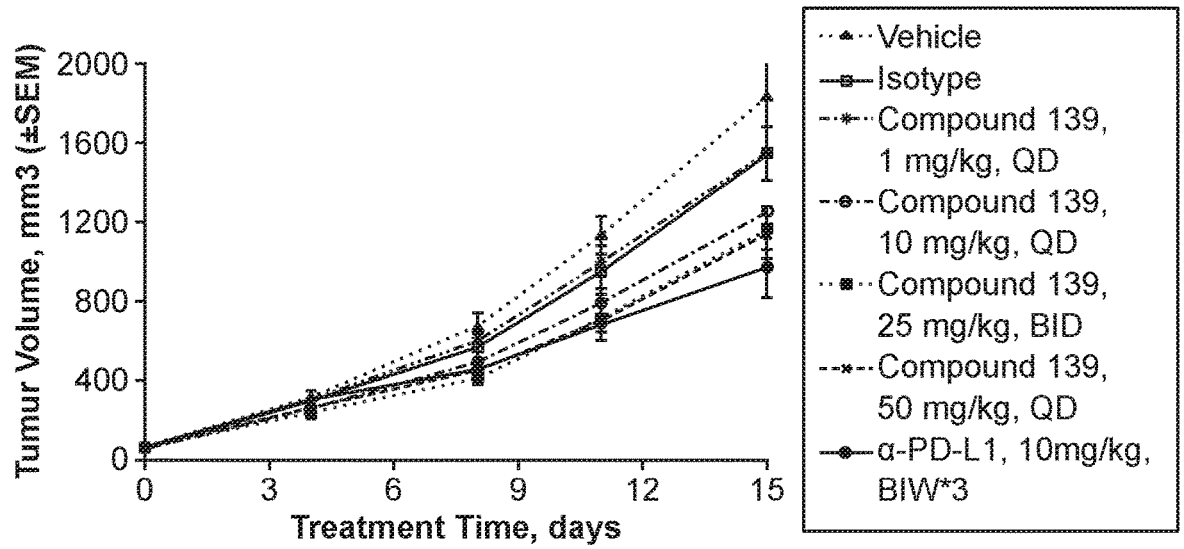
FIG. 5 shows the anti-tumor activity of compound 139 in a human PD-L1 MC38 mouse model.

With greater than 90% TO observed, comparable TGI between 31.8% and 37.9% was obtained at 10, 25, and 50 mg/kg compound 139 (Table 13 and 14), which was similar to the TGI of 37.3% achieved with the α-PD-L1 antibody dosed at 10 mg/kg twice weekly (FIG. 5). Compound 139 was well tolerated at all doses for the entire study with no effect on body weights.

TABLE 11

PK and TO Experimental Groups with Compound 139

| Test Articles | Schedule | Time Points After Last Dose on Day 6 (N[d]) | | |
|---|---|---|---|---|
| | | 1 hr | 6 hr | 24 hr |
| Human IgG1 isotype | BIW[a] (days 1,4, 6) | 3 | 3 | 3 |
| Vehicle | BID[b] * 6 (days 1-6) | 3 | 3 | 3 |
| 50 mg/kg (compound 139) | QD[c] * 6 (days 1-6) | 3 | 3 | 3 |
| 25 mg/kg (compound 139) | BID * 6 (days 1-6) | 3 | 3 | 3 |
| 10 mg/kg (compound 139) | QD * 6 (days 1-6) | 3 | 3 | 3 |
| 1 mg/kg (compound 139) | QD * 6 (days 1-6) | 3 | 3 | 3 |
| α-PD-L1 antibody (durvalumab) | BIW (days 1, 4, 6) | 3 | 3 | 3 |

[a]BIW, Twice a week.
[b]BID, Twice a day.
[c]QD, Once a day.
[d]N, Number of animals.

TABLE 12

PK Parameters of Compound 139 on Day 6 (Mean ± SD)[a]

| | 1 mg/kg QD | 10 mg/kg QD | 25 mg/kg BID | 50 mg/kg QD | α-PDL1 |
|---|---|---|---|---|---|
| $AUC_{0-24/0-12\ hr}$ (μM · h)[b] | 4.9 ± 1.3 | 18.6 ± 2.7 | 47.1 ± 9.0 | 152 ± 51 | ND[c] |
| $C_{max}$ (μM) | 0.41 ± 0.05 | 3.2 ± 0.5 | 7.3 ± 1.0 | 15.9 ± 2.4 | 16.8 ± 5.9 |
| $T_{max}$ (hour) | 2.7 ± 2.9 | 1.0 ± 0.0 | 1.0 ± 0.0 | 1.0 ± 0.0 | ND |

[a]n = 3 animals per time point.
[b]AUC was estimated based on a sparse sampling method.
[c]ND, not determined.

TABLE 13

TO of Compound 139 on Day 6 (Mean ± SD)[a]

| Time (hours) | 1 mg/kg QD | 10 mg/kg QD | 25 mg/kg BID | 50 mg/kg QD | α-PDL1 |
|---|---|---|---|---|---|
| 1 | 67.8 ± 2.9 | 94.7 ± 1.6 | 98.4 ± 0.4 | 98.8 ± 0.2 | 99.6 ± 0.5 |
| 6 | 43.2 ± 4.6 | 89.6 ± 0.9 | 96.6 ± 0.3 | 98.1 ± 0.3 | 99.9 ± 0.1 |
| 24 | 70.4 ± 3.2 | 93.9 ± 2.1 | 99.3 ± 0.0 | 99.4 ± 0.2 | 99.9 ± 0.3 |

[a]n = 3 animals per time point.

TABLE 14

Tumor Volumes (TV) and Percentage of Tumor Growth Inhibition (TGI)

| | Vehicle | 50 mg/kg QD | 25 mg/kg BID | 10 mg/kg QD | 1 mg/kg QD | 10 mg/kg isotype control antibody (hIgG1) BIW * 3 | 10 mg/kg durvalumab (α-PD-L1 antibody) BIW * 3 |
|---|---|---|---|---|---|---|---|
| TV (mm³ ± SEM[b]) | 1842.2 ± 167.1 | 1143.7 ± 132.7 | 1169.2 ± 109.6 | 1255.7 ± 104.8 | 1546.3 ± 137.0 | 1549.5 ± 132.7 | |
| % TGI (Mean ± SEM) | | 37.9 ± 5.4 | 36.5 ± 5.9 | 31.8 ± 5.2 | 16.1 ± 6.3 | | 37.3 ± 7.9 |
| P value[c] | | 0.001 | 0.001 | 0.003 | 0.128 | | 0.004 |

[a]% TGI of compound 139 (normalized to vehicle) and α-PD-L1 mAb (normalized to isotype) on day 15, the last day both controls groups (vehicle and isotype) were on study.
[b]Standard error of the mean.
[c]All data were analyzed with SPSS (Statistical Product and Service Solutions) version 18.0 (IBM, Armonk, NY, U.S.) and were two-sided. P < 0.05 was considered to be statistically significant. Compound 139 groups were compared to vehicle. Durvalumab group was compared to isotype.

CONCLUSION

The in vivo activity of compound 139 was assessed in a human PD-L1-expressing MC38 mouse colorectal tumor model. Intraperitoneal administration of 10 (QD), 25 (BID), and 50 mg/kg (QD) compound 139 showed greater than 90% TO on the tumors for the duration of at least 24 hours post dosing and resulted in anti-tumor activity comparable to the PD-L1 antibody.

The invention claimed is:
1. A compound which is:

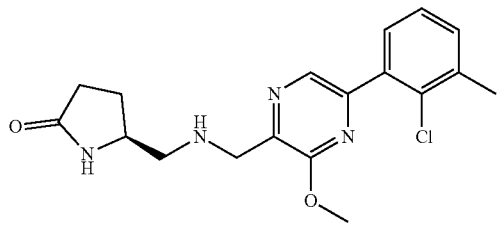

-continued

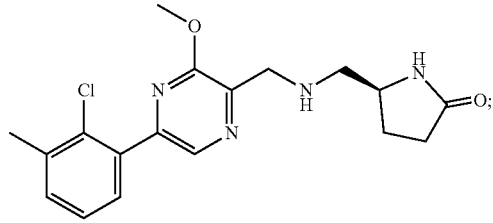

or a pharmaceutically acceptable salt thereof.

2. A pharmaceutical composition comprising the compound of claim 1, or a pharmaceutically acceptable salt thereof, and a pharmaceutically acceptable excipient.

3. The pharmaceutical composition of claim 2, further comprising one or more additional therapeutic agents.

4. The pharmaceutical composition of claim 3, wherein the additional therapeutic agent is an anticancer agent selected from nivolumab, pembrolizumab, atezolizumab, and ipilimumab.

5. A method for treating hepatitis B virus comprising administering a therapeutically effective amount of the compound of claim 1, or a pharmaceutically acceptable salt thereof, to a patient in need thereof.

* * * * *

UNITED STATES PATENT AND TRADEMARK OFFICE
CERTIFICATE OF CORRECTION

PATENT NO. : 10,710,986 B2  
APPLICATION NO. : 16/274106  
DATED : July 14, 2020  
INVENTOR(S) : Evangelos Aktoudianakis et al.

Page 1 of 2

It is certified that error appears in the above-identified patent and that said Letters Patent is hereby corrected as shown below:

In the Specification

In Column 134, Line 41, please replace "(0.5M) at room temperature, and sodium azide" with --(0.5 M) at room temperature, and sodium azide--.

In Column 135, Line 34, please replace "The reaction mixture warm to 23° C., and then stirred" with --The reaction mixture was warmed to 23° C., and then stirred--.

In Column 135, Line 41, please replace "column chromatography on silica gel ($CH_2Cl$/hexanes=1:1)" with --column chromatography on silica gel ($CH_2Cl_2$/hexanes=1:1)--.

In Column 137, Line 5, please replace "$Bin_2Pin_2$ (180 g, 0.722 mol, 2.5 eq)" with --$B_2Pin_2$ (180 g, 0.722 mol, 2.5 eq)--.

In Column 139, Line 23, please replace "Procedure 1" with --Procedure 1: 2,2'-(((2-chloro-2'-fluoro-[1,1'-biphenyl]-3,3'-diyl)bis(3-methoxypyrazine-5,2-diyl))bis(methylene))bis(2,5-diazaspiro[3.4]octan-6-one)--.

In Column 146, Line 36, please replace "to give (5 S,5'S)-5,5'-(((((2,2'-dichloro" with --to give (5S,5'S)-5,5'-(((((2,2'-dichloro--.

In Column 158, Line 64, please replace "to give (5 S,5'S)-5,5'-(((((2,2'-dichloro" with --to give (5S,5'S)-5,5'-(((((2,2'-dichloro--.

Signed and Sealed this  
First Day of December, 2020

Andrei Iancu  
*Director of the United States Patent and Trademark Office*

CERTIFICATE OF CORRECTION (continued)
U.S. Pat. No. 10,710,986 B2

In the Claims

In Claim 1, Column 604, Lines 13-47, please replace

"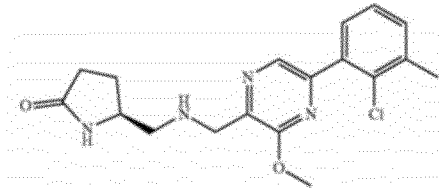

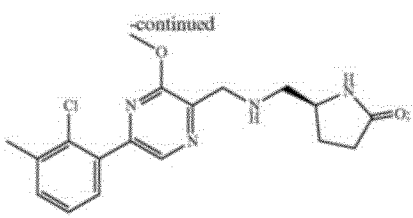

" with

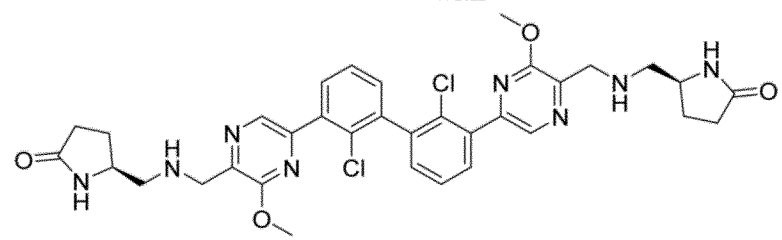

-- ;--.